US012565484B2

(12) United States Patent
Lee et al.

(10) Patent No.: US 12,565,484 B2
(45) Date of Patent: Mar. 3, 2026

(54) HETEROCYCLIC COMPOUND AND ORGANIC LIGHT-EMITTING DEVICE COMPRISING SAME

(71) Applicant: LT MATERIALS CO., LTD., Yongin-si (KR)

(72) Inventors: Gi-Back Lee, Yongin-si (KR); Seong-Jong Park, Yongin-si (KR); Won-Jang Jeong, Yongin-si (KR); Dong-Jun Kim, Yongin-si (KR)

(73) Assignee: LT MATERIALS CO., LTD., Yongin-Si (KR)

( * ) Notice: Subject to any disclaimer, the term of this patent is extended or adjusted under 35 U.S.C. 154(b) by 969 days.

(21) Appl. No.: 17/775,369

(22) PCT Filed: Nov. 16, 2020

(86) PCT No.: PCT/KR2020/016064

§ 371 (c)(1),
(2) Date: May 9, 2022

(87) PCT Pub. No.: WO2021/112444

PCT Pub. Date: Jun. 10, 2021

(65) Prior Publication Data

US 2023/0002350 A1 Jan. 5, 2023

(30) Foreign Application Priority Data

Dec. 2, 2019 (KR) ........................ 10-2019-0158377

(51) Int. Cl.

| | |
|---|---|
| ***H01L 51/54*** | (2006.01) |
| ***C07D 215/06*** | (2006.01) |
| ***C07D 401/04*** | (2006.01) |
| ***C07D 401/10*** | (2006.01) |
| ***C07D 401/14*** | (2006.01) |
| ***C07D 471/04*** | (2006.01) |
| ***H10K 85/60*** | (2023.01) |
| *H10K 50/16* | (2023.01) |
| *H10K 50/18* | (2023.01) |
| *H10K 50/19* | (2023.01) |

(52) U.S. Cl.

CPC ......... *C07D 401/10* (2013.01); *C07D 215/06* (2013.01); *C07D 401/04* (2013.01); *C07D 401/14* (2013.01); *C07D 471/04* (2013.01); *H10K 85/615* (2023.02); *H10K 85/654* (2023.02); *H10K 85/6572* (2023.02); *H10K 50/16* (2023.02); *H10K 50/18* (2023.02); *H10K 50/19* (2023.02)

(58) Field of Classification Search

None

See application file for complete search history.

(56) References Cited

U.S. PATENT DOCUMENTS

| | | | | |
|---|---|---|---|---|
| 2011/0156017 A1* | 6/2011 | Lee | ...................... | C07D 221/12 546/101 |
| 2012/0280613 A1* | 11/2012 | Kang | ................. | H10K 85/6572 546/101 |
| 2013/0256637 A1 | 10/2013 | Seo et al. | | |
| 2017/0324046 A1 | 11/2017 | Kim et al. | | |
| 2019/0319195 A1 | 10/2019 | Lee et al. | | |
| 2020/0308150 A1 | 10/2020 | Lee et al. | | |

FOREIGN PATENT DOCUMENTS

| | | | |
|---|---|---|---|
| CN | 107778309 | A | 3/2018 |
| CN | 109705148 | A | 5/2019 |
| CN | 109942637 | A | 6/2019 |
| CN | 109988160 | A | 7/2019 |
| JP | 2014-508130 | A | 4/2014 |
| KR | 10-2014-0046975 | A | 4/2014 |
| KR | 10-2015-0103967 | A | 9/2015 |
| KR | 10-2018-0005534 | A | 1/2018 |
| KR | 10-2019-0037925 | A | 4/2019 |
| TW | 201627306 | A | 8/2016 |

OTHER PUBLICATIONS

International Search Report (PCT/ISA/210) issued in PCT/KR2020/016064, dated Mar. 18, 2021.

* cited by examiner

*Primary Examiner* — Andrew K Bohaty
(74) *Attorney, Agent, or Firm* — Birch, Stewart, Kolasch & Birch, LLP

(57) ABSTRACT

The present application provides a heterocyclic compound capable of significantly enhancing lifetime, efficiency, electrochemical stability and thermal stability of an organic light emitting device, and an organic light emitting device comprising the heterocyclic compound in an organic material layer.

9 Claims, 3 Drawing Sheets

【FIG. 1】
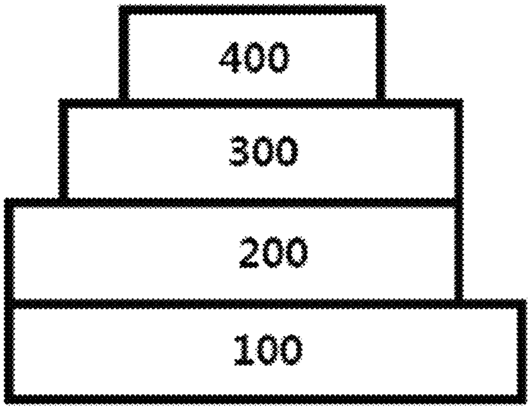
【FIG. 2】
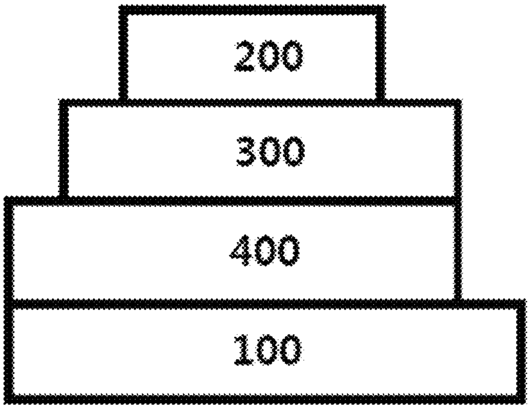

【FIG. 3】
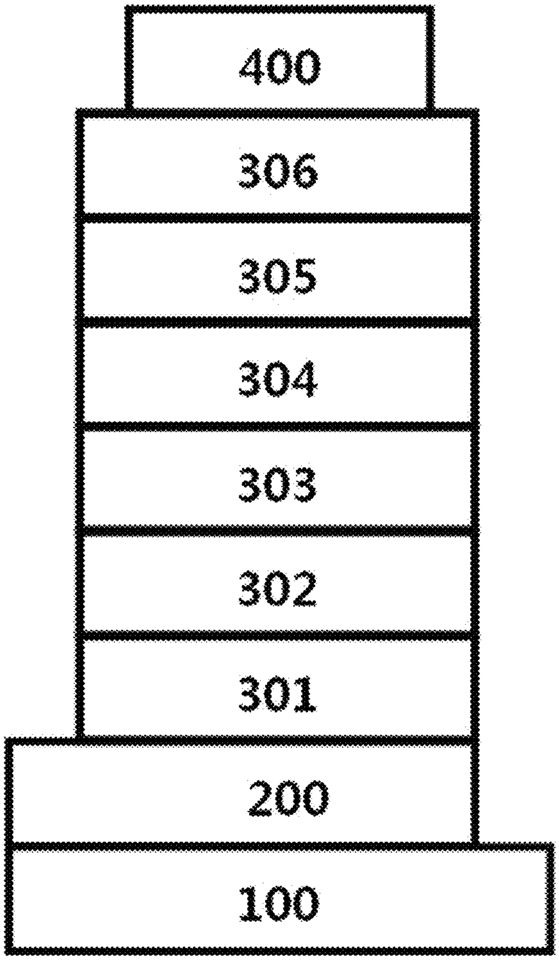

【FIG. 4】
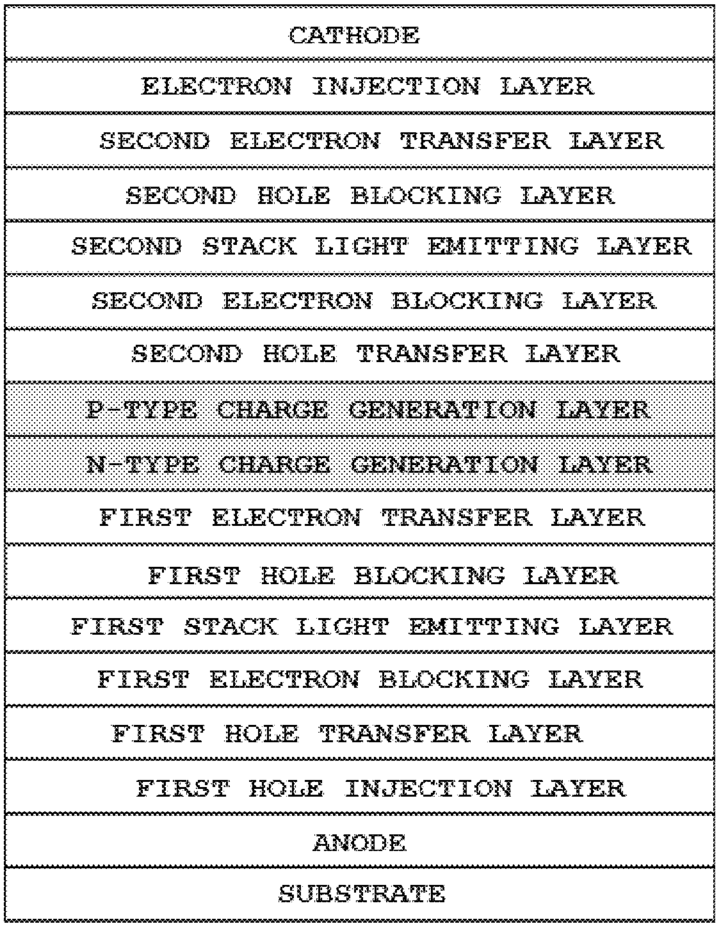

HETEROCYCLIC COMPOUND AND ORGANIC LIGHT-EMITTING DEVICE COMPRISING SAME

TECHNICAL FIELD

This application claims priority to and the benefits of Korean Patent Application No. 10-2019-0158377, filed with the Korean Intellectual Property Office on Dec. 2, 2019, the entire contents of which are incorporated herein by reference. The present specification relates to a heterocyclic compound, and an organic light emitting device comprising the same.

BACKGROUND ART

An organic electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents (Patent Document 1) U.S. Pat. No. 4,356,429

DISCLOSURE

Technical Problem

The present specification is directed to providing a heterocyclic compound, and an organic light emitting device comprising the same.

Technical Solution

One embodiment of the present application provides a heterocyclic compound represented by the following Chemical Formula 1.

[Chemical Formula 1]

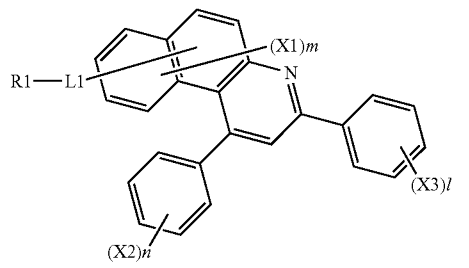

In Chemical Formula 1,

L1 is a direct bond; a substituted or unsubstituted arylene group having 6 to 60 carbon atoms; or a substituted or unsubstituted heteroarylene group having 2 to 60 carbon atoms, R1 is a substituted or unsubstituted aryl group having 6 to 60 carbon atoms; a substituted or unsubstituted heteroaryl group having 2 to 60 carbon atoms; or a substituted or unsubstituted phosphine oxide group, X1 to X3 are each independently hydrogen; deuterium; or a cyano group, or groups adjacent to each other bond to each other to form a substituted or unsubstituted C6 to C60 aromatic hydrocarbon ring or a substituted or unsubstituted C2 to C60 heteroring, m, n and 1 are each independently an integer of 1 to 5, and when m, n and 1 are each 2 or greater, substituents in the parentheses are the same as or different from each other.

Another embodiment of the present application provides an organic light emitting device comprising a first electrode; a second electrode; and one or more organic material layers provided between the first electrode and the second electrode, wherein one or more layers of the organic material layers comprise the heterocyclic compound represented by Chemical Formula 1.

Advantageous Effects

A heterocyclic compound described in the present specification can be used as a material of an organic material layer of an organic light emitting device. In the organic light emitting device, the heterocyclic compound is capable of performing a role of a hole injection material, a hole transfer material, a light emitting material, an electron transfer material, an electron injection material or the like. Particularly, the heterocyclic compound can be used as an electron transfer layer material, a hole blocking layer material or a charge generation layer material of the organic light emitting device.

Specifically, when using the heterocyclic compound represented by Chemical Formula 1 in the organic material layer, a driving voltage of the device can be lowered, light efficiency can be enhanced, and lifetime properties of the device can be enhanced.

DESCRIPTION OF DRAWINGS

FIG. 1 to FIG. 4 are diagrams each illustrating a lamination structure of an organic light emitting device according to one embodiment of the present application.

MODE FOR DISCLOSURE

Hereinafter, the present specification will be described in more detail. In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0% or a hydrogen content being 100%. In other words, an expression of "substituent X is hydrogen" does not exclude deuterium such as a hydrogen content being 100% or a deuterium content being 0%, and therefore, may mean a state in which hydrogen and deuterium are mixed.

In one embodiment of the present application, deuterium is one of isotopes of hydrogen, is an element having deuteron formed with one proton and one neutron as a nucleus, and may be expressed as hydrogen-2, and the elemental symbol may also be written as D or 2H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

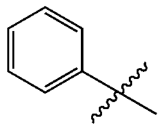 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

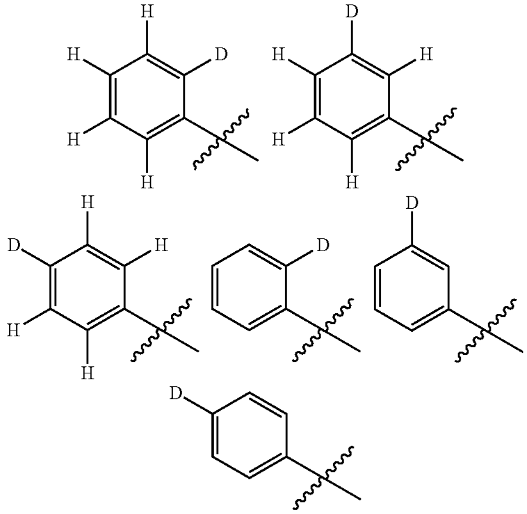

In addition, in one embodiment of the present application, "a phenyl group having a deuterium content of 0%" may mean a phenyl group that does not comprise a deuterium atom, that is, a phenyl group that has 5 hydrogen atoms.

In the present specification, a certain part "including" certain constituents means capable of further including other constituents, and does not exclude other constituents unless particularly stated on the contrary.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of a linear or branched alkyl group having 1 to 60 carbon atoms; a linear or branched alkenyl group having 2 to 60 carbon atoms; a linear or branched alkynyl group having 2 to 60 carbon atoms; a monocyclic or polycyclic cycloalkyl group having 3 to 60 carbon atoms; a monocyclic or polycyclic heterocycloalkyl group having 2 to 60 carbon atoms; a monocyclic or polycyclic aryl group having 6 to 60 carbon atoms; a monocyclic or polycyclic heteroaryl group having 2 to 60 carbon atoms; a silyl group; a phosphine oxide group; and an amine group, or being unsubstituted, or being substituted with a substituent linking two or more substituents selected from among the substituents illustrated above, or being unsubstituted.

More specifically, "substituted or unsubstituted" in the present specification means being substituted with one or more substituents selected from the group consisting of a monocyclic or polycyclic aryl group having 6 to 60 carbon atoms; or a monocyclic or polycyclic heteroaryl group having 2 to 60 carbon atoms.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20.

Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a terphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P(=O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR104R105R106. R104 to R106 are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

In the present specification, the spiro group is a group comprising a spiro structure, and may have 15 to 60 carbon atoms. For example, the spiro group may comprise a structure in which a 2,3-dihydro-1H-indene group or a cyclohexane group spiro bonds to a fluorenyl group. Specifically, the following spiro group may comprise any one of groups of the following structural formulae.

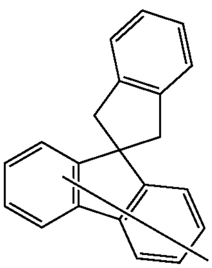
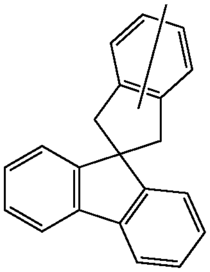
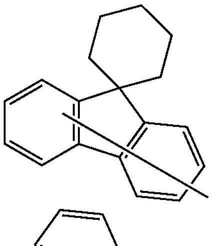
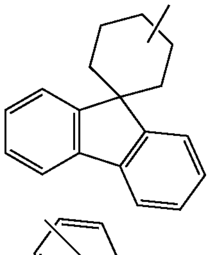
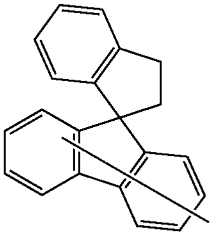
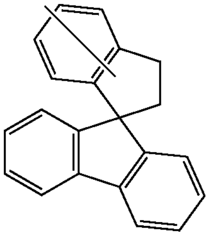
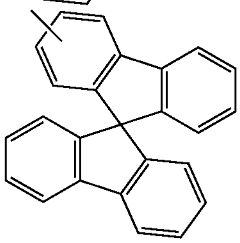

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; $-NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, an "energy level" means a magnitude of energy. Accordingly, the energy level is interpreted to mean an absolute value of the corresponding energy value. For example, the energy level being low or deep means the absolute value increasing in a negative direction from a vacuum level.

In the present specification, a highest occupied molecular orbital (HOMO) means a molecular orbital function in a region with the highest energy in a region where electrons may participate in bonding (highest occupied molecular orbital), and a lowest unoccupied molecular orbital (LUMO) means a molecular orbital function in a region with the lowest energy in an anti-bonding region of electrons (lowest unoccupied molecular orbital). A HOMO energy level means a distance from a vacuum level to the HOMO, and a LUMO energy level means a distance from a vacuum level to the LUMO.

In the present specification, a bandgap means a difference between the energy levels of HOMO and LUMO, that is, a HOMO-LUMO gap.

One embodiment of the present application provides a heterocyclic compound represented by the following Chemical Formula 1.

[Chemical Formula 1]

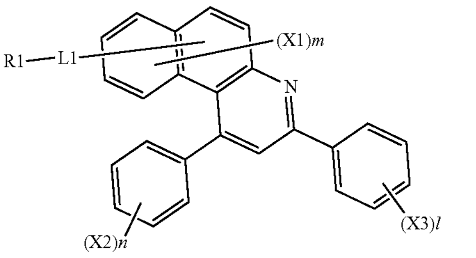

In Chemical Formula 1,

L1 is a direct bond; a substituted or unsubstituted arylene group having 6 to 60 carbon atoms; or a substituted or unsubstituted heteroarylene group having 2 to 60 carbon atoms, R1 is a substituted or unsubstituted aryl group having 6 to 60 carbon atoms; a substituted or unsubstituted heteroaryl group having 2 to 60 carbon atoms; or a substituted or unsubstituted phosphine oxide group, X1 to X3 are each independently hydrogen; deuterium; or a cyano group, or groups adjacent to each other bond to each other to form a substituted or unsubstituted C6 to C60 aromatic hydrocarbon ring or a substituted or unsubstituted C2 to C60 heteroring, m, n and 1 are each independently an integer of 1 to 5, and when m, n and 1 are each 2 or greater, substituents in the parentheses are the same as or different from each other.

The heterocyclic compound represented by Chemical Formula 1 is capable of adjusting bandgap and T1 values by using a specific substituent in the phenanthridine skeleton.

In addition, when the heterocyclic compound has a substituent with strengthened hole properties, the compound in an excited state by receiving electrons under a specific condition may be stabilized. When the excited state of the hetero-skeleton site of the compound is formed as above, the excited energy moves to a stable state by the substituent with strengthened hole properties before the excited hetero-skeleton site goes through other reactions, and the relatively stabilized compound is capable of efficiently transferring electrons without the compound being decomposed or destroyed.

Accordingly, when using the heterocyclic compound represented by Chemical Formula 1 as a material of an organic material layer of an organic light emitting device, a device with excellent efficiency and lifetime may be obtained. Herein, the T1 value means an energy level value in a triplet state.

In the heterocyclic compound provided in one embodiment of the present application, Chemical Formula 1 is represented by any one of the following Chemical Formula 2 to Chemical Formula 6.

[Chemical Formula 2]

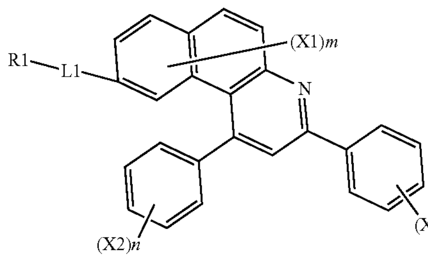

[Chemical Formula 3]

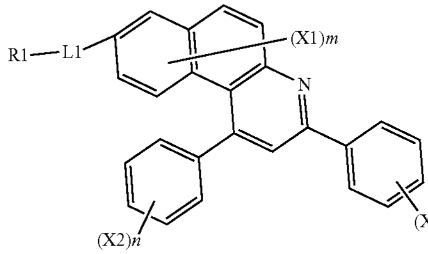

[Chemical Formula 4]

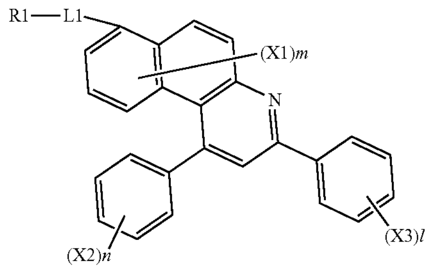

[Chemical Formula 5]

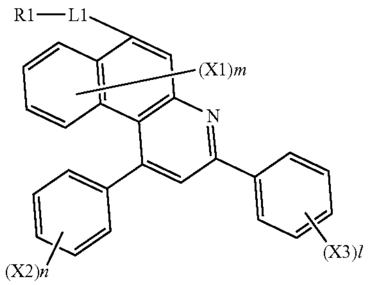

[Chemical Formula 6]

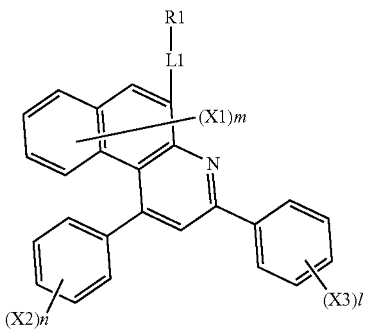

In Chemical Formula 2 to Chemical Formula 6, each substituent has the same definition as in Chemical Formula 1.

In one embodiment of the present application, L1 may be a direct bond; a substituted or unsubstituted arylene group having 6 to 60 carbon atoms; or a substituted or unsubstituted heteroarylene group having 2 to 60 carbon atoms.

In another embodiment, L1 may be a direct bond; a substituted or unsubstituted arylene group having 6 to 40 carbon atoms; or a substituted or unsubstituted heteroarylene group having 2 to 40 carbon atoms.

In another embodiment, L1 may be a direct bond; a substituted or unsubstituted arylene group having 6 to 20 carbon atoms; or a substituted or unsubstituted heteroarylene group having 2 to 20 carbon atoms.

In one embodiment of the present specification, L1 is a direct bond; or a substituted or unsubstituted arylene group having 6 to 60 carbon atoms.

In one embodiment of the present specification, L1 is a direct bond; or a substituted or unsubstituted arylene group having 6 to 40 carbon atoms.

In one embodiment of the present specification, L1 is a direct bond; or a substituted or unsubstituted arylene group having 6 to 20 carbon atoms.

In one embodiment of the present specification, L1 is a direct bond; a substituted or unsubstituted phenylene group; a substituted or unsubstituted biphenylene group; a substituted or unsubstituted naphthylene group; or a substituted or unsubstituted anthracene group.

In one embodiment of the present specification, L1 is a direct bond; a phenylene group; a biphenylene group; a naphthylene group; or an anthracene group.

In one embodiment of the present specification, L1 is a direct bond.

In one embodiment of the present specification, L1 is a substituted or unsubstituted arylene group having 6 to 60 carbon atoms.

In one embodiment of the present specification, L1 is a substituted or unsubstituted arylene group having 6 to 40 carbon atoms.

In one embodiment of the present specification, L1 is a substituted or unsubstituted arylene group having 6 to 20 carbon atoms.

In one embodiment of the present specification, L1 is a substituted or unsubstituted phenylene group; a biphenylene group; a naphthylene group; or an anthracene group.

In another embodiment, L1 is a phenylene group; a biphenylene group; a naphthylene group; or an anthracene group.

In another embodiment, L1 is a phenylene group.

In another embodiment, L1 is a biphenylene group.

In another embodiment, L1 is a naphthylene group.

In another embodiment, L1 is an anthracene group.

In one embodiment of the present specification, R1 may be a substituted or unsubstituted aryl group having 6 to 60 carbon atoms; a substituted or unsubstituted heteroaryl group having 2 to 60 carbon atoms; or a substituted or unsubstituted phosphine oxide group.

In one embodiment of the present specification, R1 may be a substituted or unsubstituted aryl group having 6 to 40 carbon atoms; a substituted or unsubstituted heteroaryl group having 2 to 40 carbon atoms; or a substituted or unsubstituted phosphine oxide group.

In one embodiment of the present specification, R1 may be a substituted or unsubstituted aryl group having 6 to 20 carbon atoms; a substituted or unsubstituted heteroaryl group having 2 to 20 carbon atoms; or a substituted or unsubstituted phosphine oxide group.

In one embodiment of the present specification, R1 may be a substituted or unsubstituted phenyl group; a substituted or unsubstituted biphenyl group; a substituted or unsubstituted naphthyl group; a substituted or unsubstituted anthracene group; a substituted or unsubstituted pyridine group; a substituted or unsubstituted pyrimidine group; a substituted or unsubstituted triazine group; a substituted or unsubstituted phenanthridine group; a substituted or unsubstituted phenanthroline group; or a substituted or unsubstituted phosphine oxide group.

In one embodiment of the present specification, R1 may be a substituted or unsubstituted phenyl group; a substituted or unsubstituted biphenyl group; a substituted or unsubstituted naphthyl group; a substituted or unsubstituted anthracene group; a group represented by the following Chemical Formula A1; a group represented by the following Chemical Formula A2; or a substituted or unsubstituted phosphine oxide group.

[Chemical Formula A1]

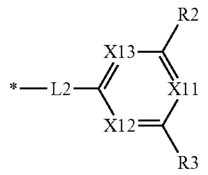

[Chemical Formula A2]

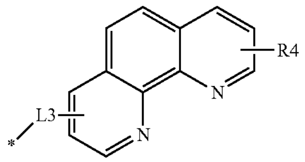

In Chemical Formulae A1 and A2,

L2 and L3 are each independently a direct bond; or a substituted or unsubstituted arylene group having 6 to 60 carbon atoms, X11 to X13 are each independently N or CH, and at least one of X11 to X13 is N, R2 to R4 are the same as or different from each other, and each independently hydrogen; deuterium; or a substituted or unsubstituted aryl group having 6 to 60 carbon atoms, and

* means a position bonding to L1.

In one embodiment of the present specification, L2 and L3 are each independently a direct bond; or a substituted or unsubstituted arylene group having 6 to 60 carbon atoms.

In one embodiment of the present specification, L2 and L3 are each independently a direct bond; or a substituted or unsubstituted arylene group having 6 to 40 carbon atoms.

In one embodiment of the present specification, L2 and L3 are each independently a direct bond; or a substituted or unsubstituted arylene group having 6 to 20 carbon atoms.

In one embodiment of the present specification, L2 and L3 are each independently a direct bond; a substituted or unsubstituted phenylene group; a substituted or unsubstituted biphenylene group; a substituted or unsubstituted naphthylene group; or a substituted or unsubstituted anthracene group.

In one embodiment of the present specification, L2 and L3 are each independently a direct bond; a phenylene group; a biphenylene group; a naphthylene group; or an anthracene group.

In one embodiment of the present specification, L2 is a direct bond; a phenylene group; a biphenylene group; a naphthylene group; or an anthracene group.

In one embodiment of the present specification, L2 is a direct bond.

In one embodiment of the present specification, L2 is a phenylene group.

In one embodiment of the present specification, L2 is a biphenylene group.

In one embodiment of the present specification, L2 is a naphthylene group.

In one embodiment of the present specification, L2 is an anthracene group.

In one embodiment of the present specification, L3 is a direct bond; a phenylene group; a biphenylene group; a naphthylene group; or an anthracene group.

In one embodiment of the present specification, L3 is a direct bond.

In one embodiment of the present specification, L3 is a phenylene group.

In one embodiment of the present specification, L3 is a biphenylene group.

In one embodiment of the present specification, L3 is a naphthylene group.

In one embodiment of the present specification, L3 is an anthracene group.

In one embodiment of the present specification, X11 to X13 are each independently N or CH, and at least one of X11 to X13 is N.

In one embodiment of the present specification, X11 is N, and X12 and X13 are CH.

In one embodiment of the present specification, X12 is N, and X11 and X13 are CH.

In one embodiment of the present specification, X13 is N, and X11 and X12 are CH.

In one embodiment of the present specification, X11 and X12 are N, and X13 is CH.

In one embodiment of the present specification, X11 and X13 are N, and X12 is CH.

In one embodiment of the present specification, X12 and X13 are N, and X11 is CH.

In one embodiment of the present specification, X11 to X13 are all N.

In one embodiment of the present specification, R2 to R4 are the same as or different from each other, and each independently hydrogen; deuterium; or a substituted or unsubstituted aryl group having 6 to 60 carbon atoms.

In one embodiment of the present specification, R2 to R4 are the same as or different from each other, and each independently hydrogen; deuterium; a substituted or unsubstituted phenyl group; a substituted or unsubstituted biphenyl group; a substituted or unsubstituted naphthyl group; or a substituted or unsubstituted anthracene group.

In one embodiment of the present specification, R2 to R4 are the same as or different from each other, and each independently hydrogen; deuterium; a phenyl group unsubstituted or substituted with a phenyl group or a carbazole group; a substituted or unsubstituted biphenyl group; a substituted or unsubstituted naphthyl group; or a substituted or unsubstituted anthracene group.

In one embodiment of the present specification, R2 to R4 are the same as or different from each other, and each independently hydrogen; deuterium; a phenyl group unsubstituted or substituted with a phenyl group or a carbazole group; a biphenyl group; a naphthyl group; or an anthracene group.

In one embodiment of the present application, X1 to X3 are each independently hydrogen; deuterium; or a cyano group, or groups adjacent to each other may bond to each other to form a substituted or unsubstituted C6 to C60 aromatic hydrocarbon ring or a substituted or unsubstituted C2 to C60 heteroring.

In one embodiment of the present application, X1 may be hydrogen; deuterium; or a cyano group.

In one embodiment of the present application, X1 is hydrogen.

In one embodiment of the present application, X1 is deuterium.

In one embodiment of the present application, X1 is a cyano group.

In one embodiment of the present application, X2 may be hydrogen; deuterium; or a cyano group.

In one embodiment of the present application, X2 is hydrogen.

In one embodiment of the present application, X2 is deuterium.

In one embodiment of the present application, X2 is a cyano group.

In one embodiment of the present application, adjacent X2s may bond to each other to form a substituted or unsubstituted C6 to C60 aromatic hydrocarbon ring.

In one embodiment of the present application, adjacent X2s may bond to each other to form a substituted or unsubstituted C6 to C40 aromatic hydrocarbon ring.

In one embodiment of the present application, adjacent X2s may bond to each other to form a substituted or unsubstituted C6 to C20 aromatic hydrocarbon ring.

In one embodiment of the present application, adjacent X2s may bond to each other to form a C6 to C20 aromatic hydrocarbon ring.

In one embodiment of the present application, adjacent X2s may bond to each other to form a benzene ring.

In one embodiment of the present application, X3 may be hydrogen; deuterium; or a cyano group.

In one embodiment of the present application, X3 is hydrogen.

In one embodiment of the present application, X3 is deuterium.

In one embodiment of the present application, X3 is a cyano group.

In one embodiment of the present application, adjacent X3s may bond to each other to form a substituted or unsubstituted C6 to C60 aromatic hydrocarbon ring.

In one embodiment of the present application, adjacent X3s may bond to each other to form a substituted or unsubstituted C6 to C40 aromatic hydrocarbon ring.

In one embodiment of the present application, adjacent X3s may bond to each other to form a substituted or unsubstituted C6 to C20 aromatic hydrocarbon ring.

In one embodiment of the present application, adjacent X3s may bond to each other to form a C6 to C20 aromatic hydrocarbon ring.

In one embodiment of the present application, adjacent X3s may bond to each other to form a benzene ring.

In one embodiment of the present application, X1 to X3 are hydrogen.

In one embodiment of the present application, m, n and 1 are each independently an integer of 1 to 5, and when m, n and 1 are 2 or greater, substituents in the parentheses are the same as or different from each other.

In one embodiment of the present application, m is an integer of 1 to 5.

In one embodiment of the present application, m is 5.

In one embodiment of the present application, m is 4.

In one embodiment of the present application, m is 3.

In one embodiment of the present application, m is 2.

In one embodiment of the present application, m is 1.

In one embodiment of the present application, when m is 2 or greater, substituents in the parentheses are the same as or different from each other.

In one embodiment of the present application, n is an integer of 1 to 5.

In one embodiment of the present application, n is 5.

In one embodiment of the present application, n is 4.

In one embodiment of the present application, n is 3.

In one embodiment of the present application, n is 2.

In one embodiment of the present application, n is 1.

In one embodiment of the present application, when n is 2 or greater, substituents in the parentheses are the same as or different from each other.

In one embodiment of the present application, 1 is an integer of 1 to 5.

In one embodiment of the present application, 1 is 5.

In one embodiment of the present application, 1 is 4.

In one embodiment of the present application, 1 is 3.

In one embodiment of the present application, 1 is 2.

In one embodiment of the present application, 1 is 1.

In one embodiment of the present application, when 1 is 2 or greater, substituents in the parentheses are the same as or different from each other.

In the heterocyclic compound provided in one embodiment of the present application, Chemical Formula 1 is represented by any one of the following compounds.

1

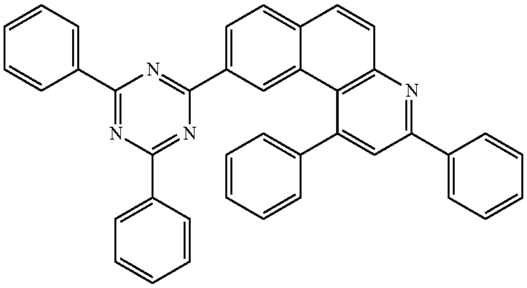

2

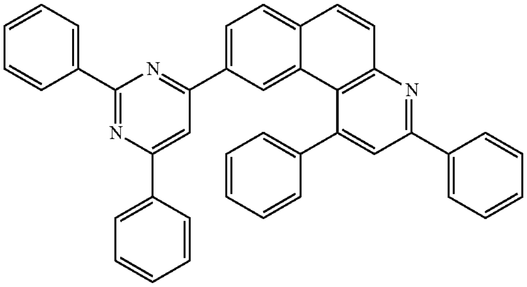

3

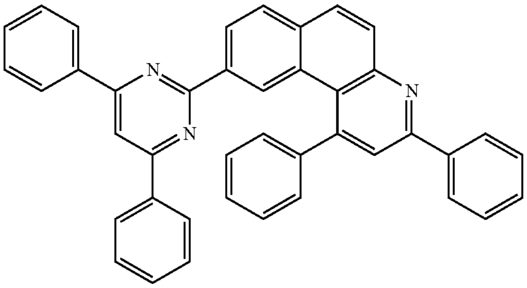

-continued

4

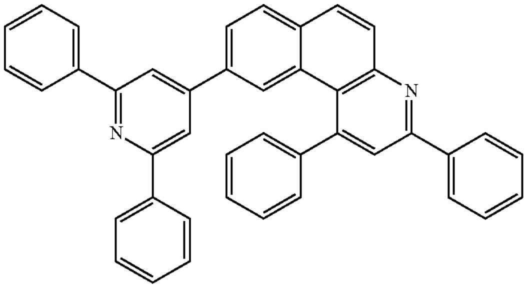

5

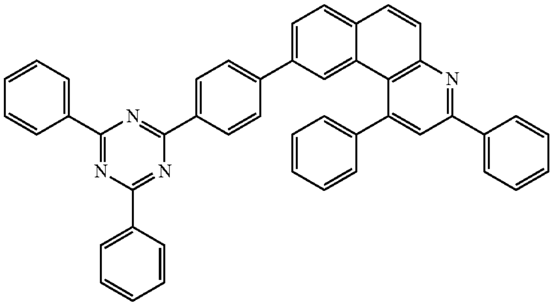

6

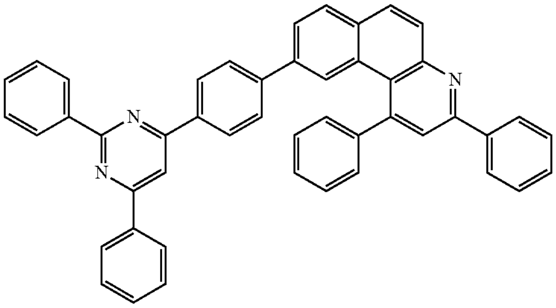

7

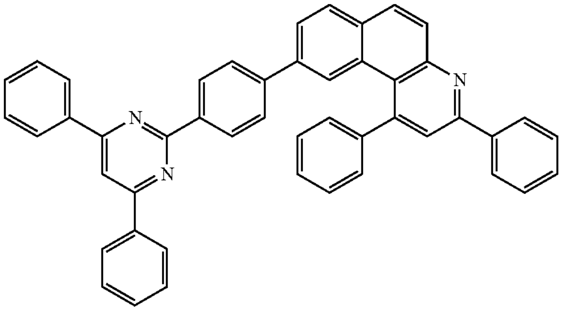

8

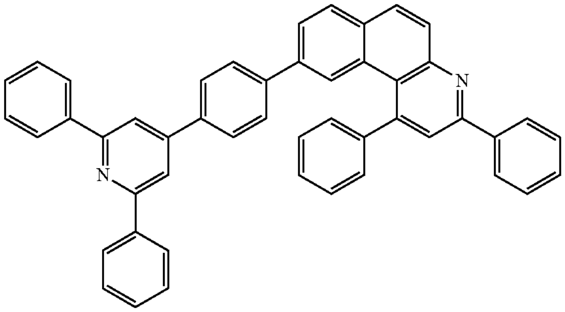

-continued
9
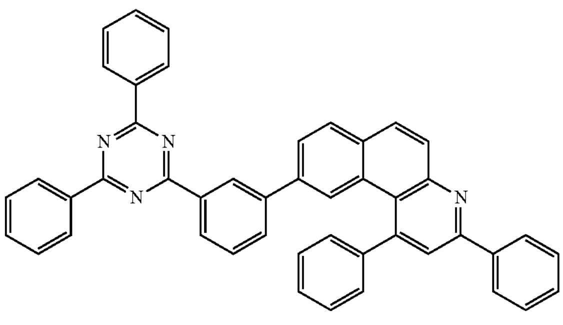
10
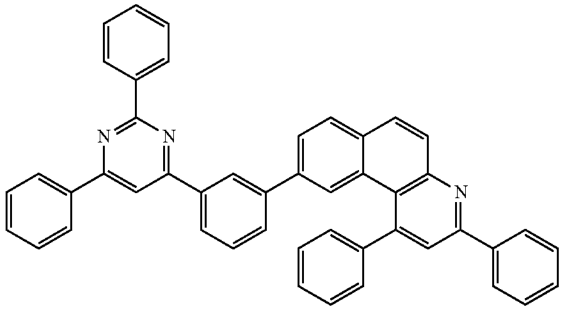
11
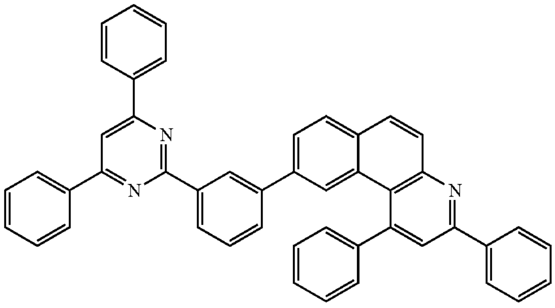
12
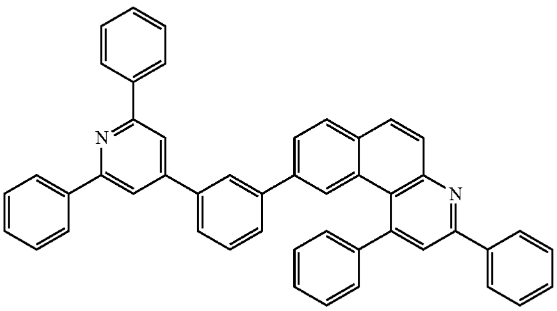
-continued
13
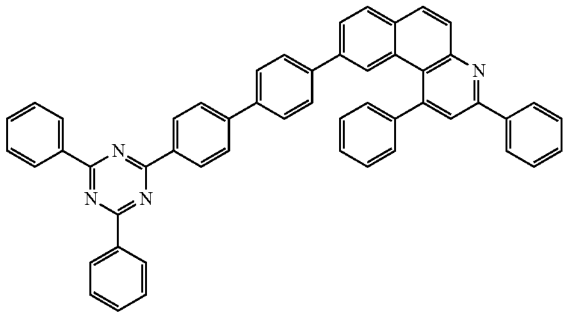
14
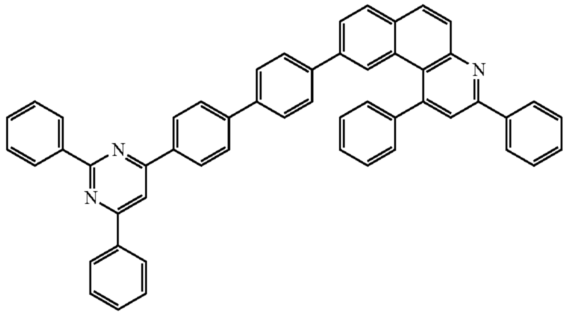
15
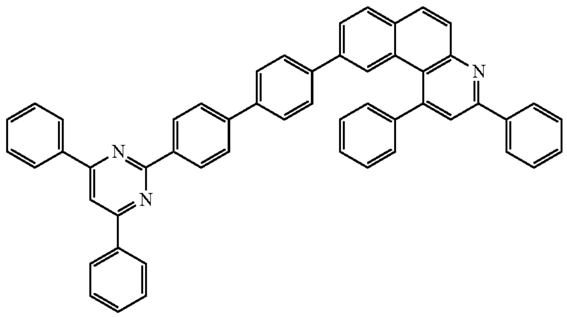
16
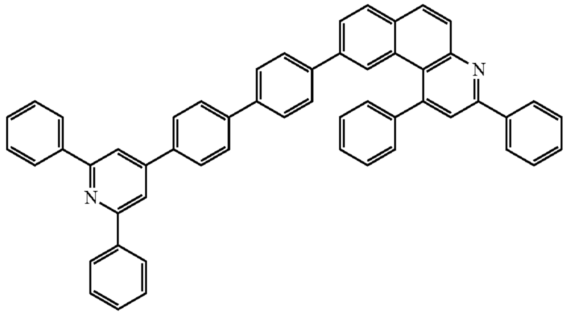
17
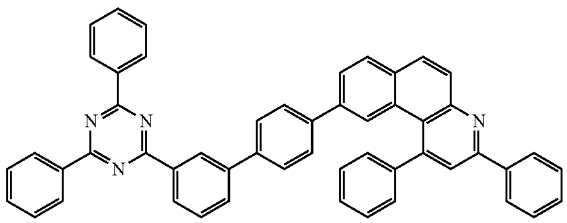

-continued
18
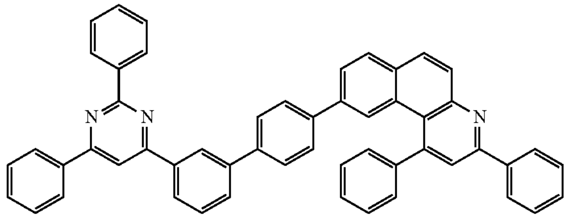
19
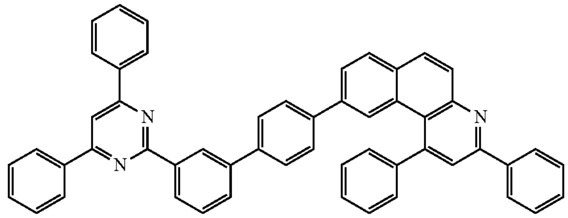
20
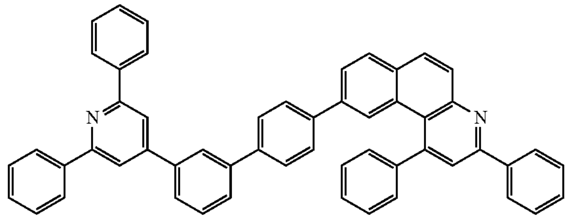
21
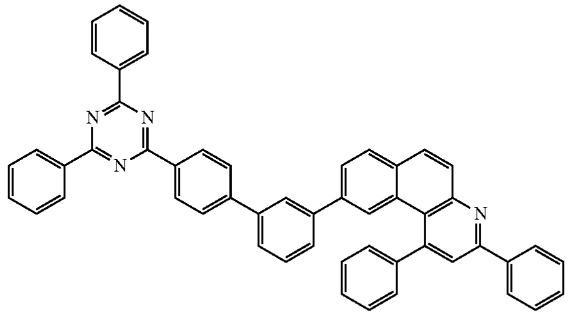
22
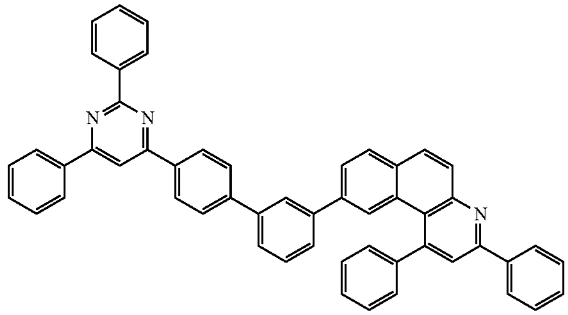
-continued
23
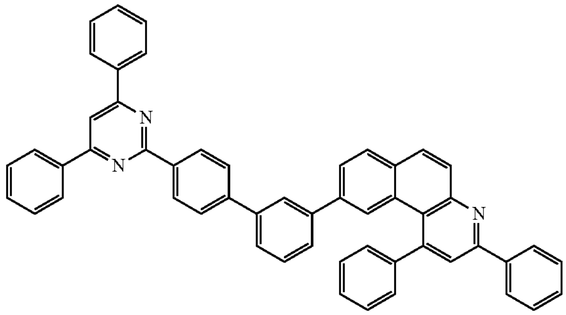
24
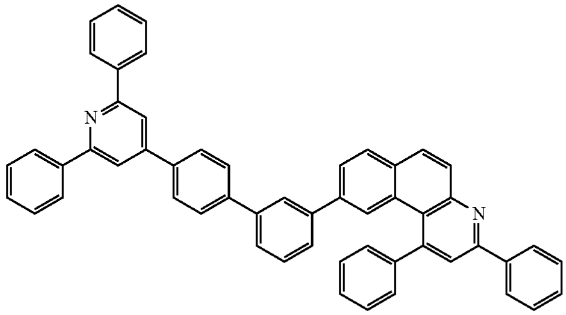
25
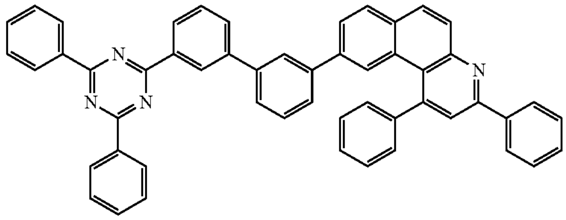
26
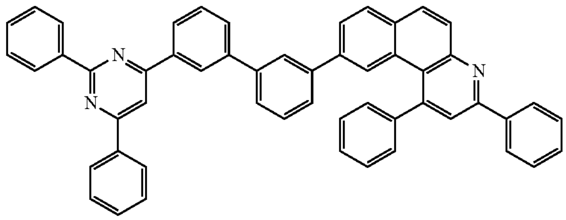
27
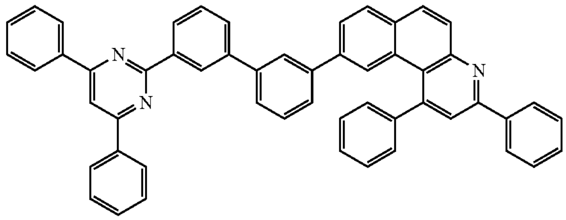

-continued
28
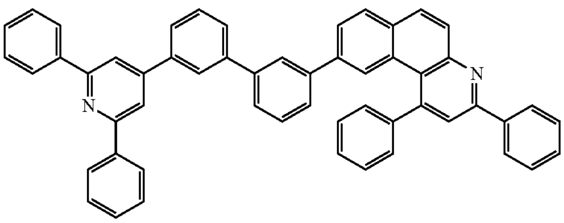
29
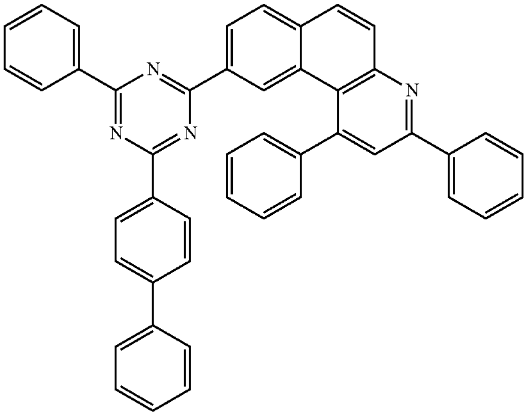
30
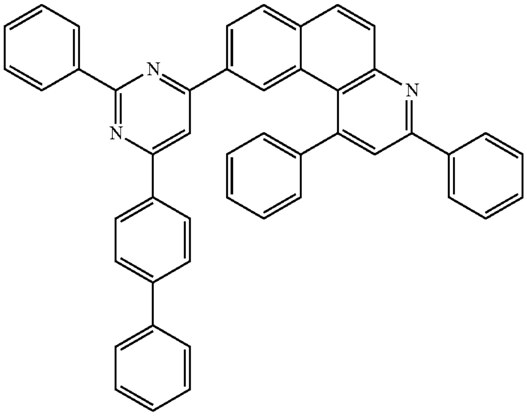
31
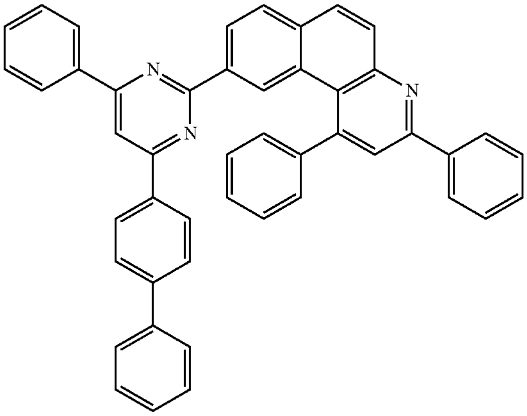
-continued
32
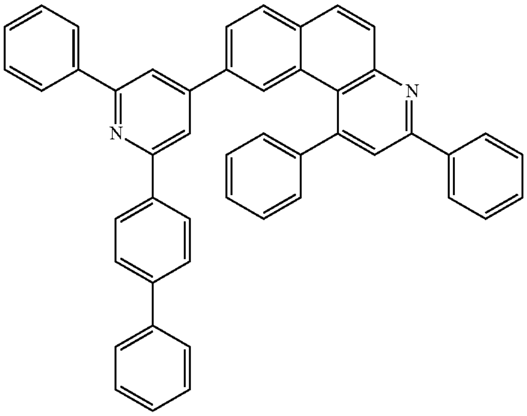
33
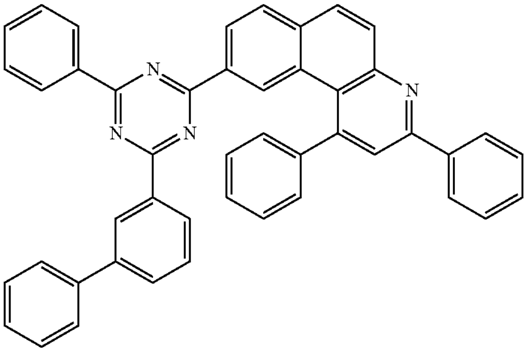
34
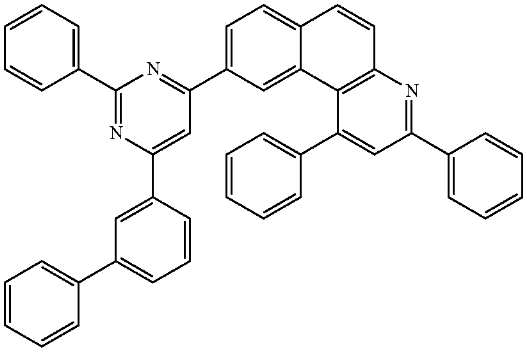
35
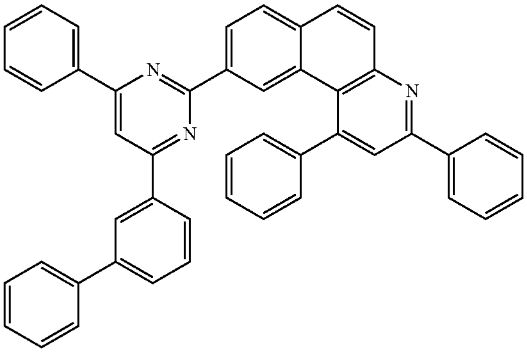

-continued
36
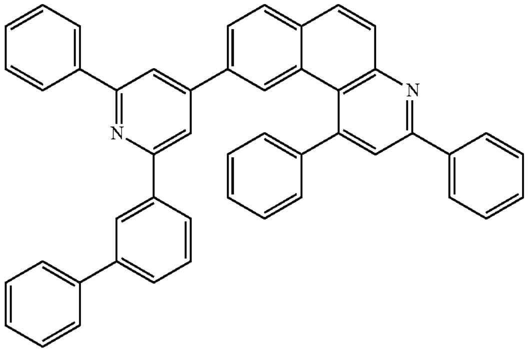
37
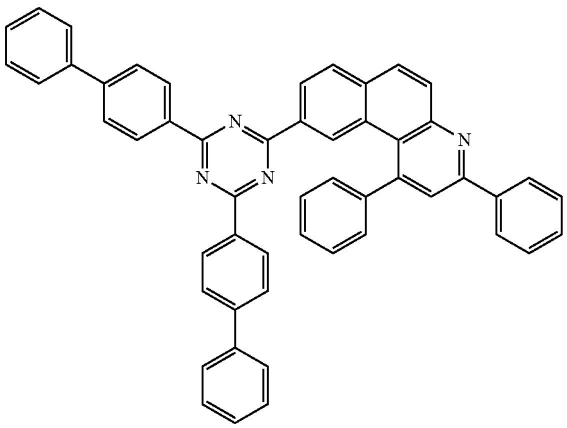
38
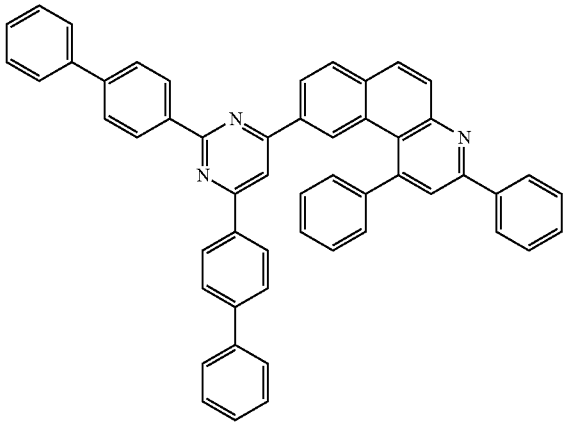
-continued
39
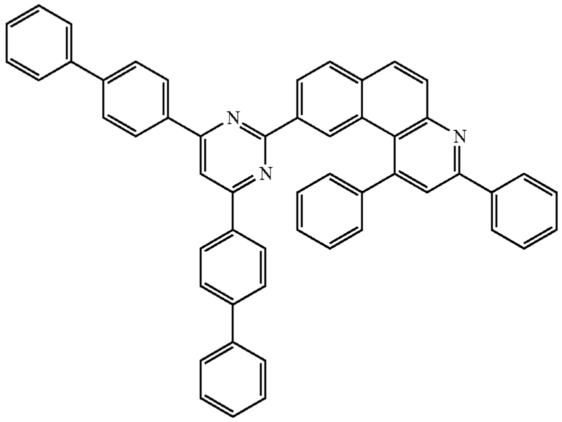
40
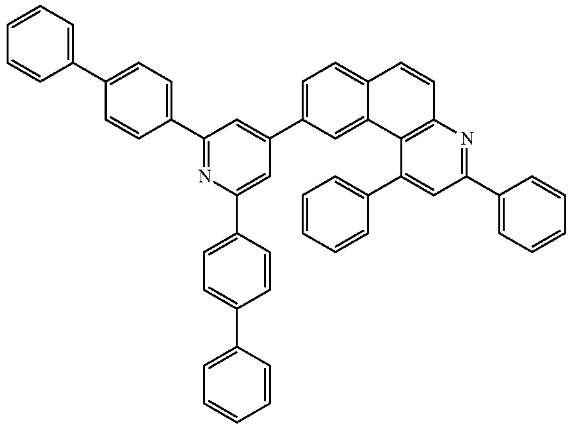
41
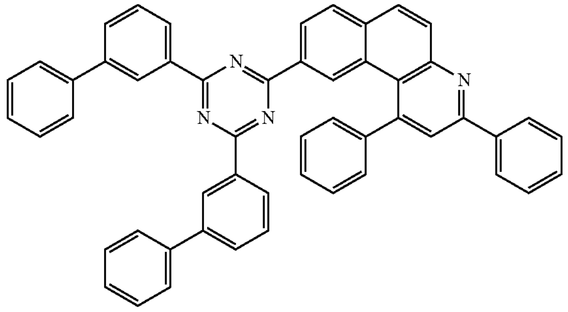
42
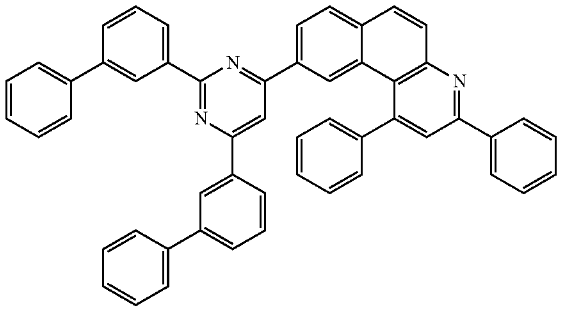

43
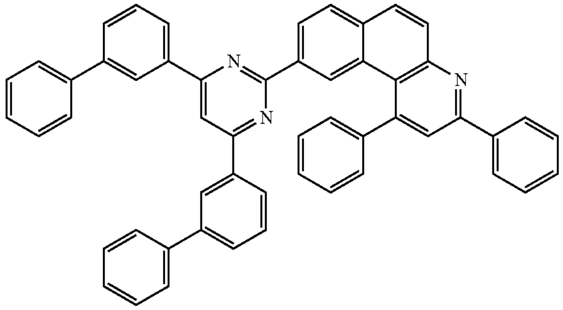
44
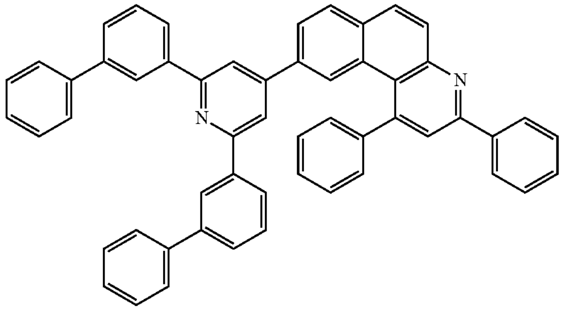
45
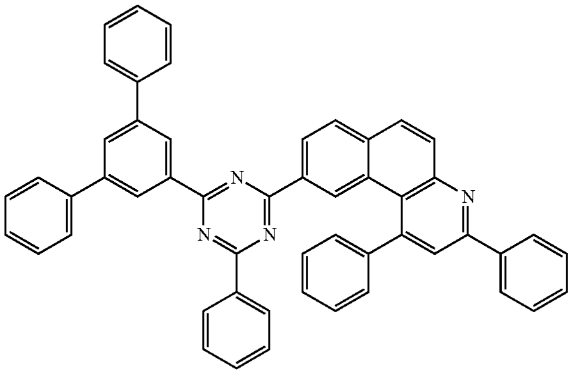
46
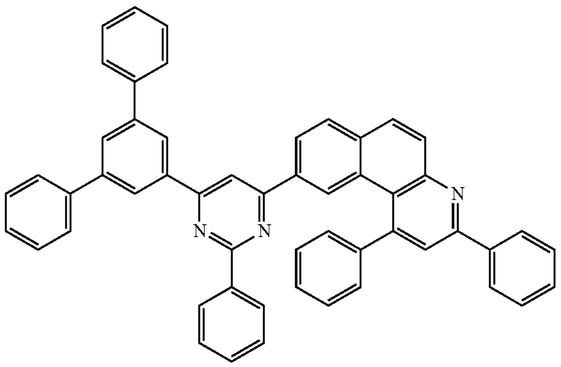
47
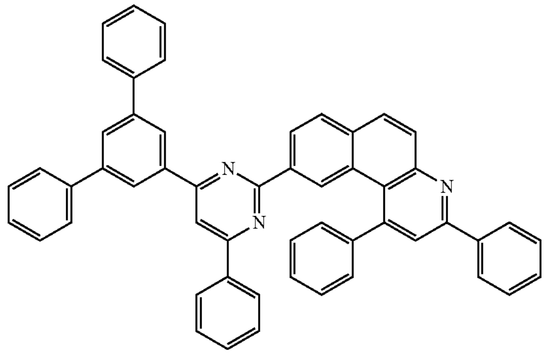
48
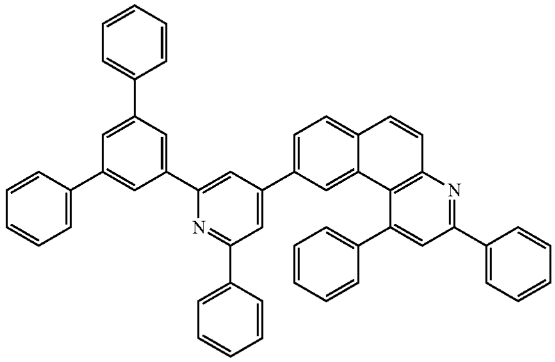
49
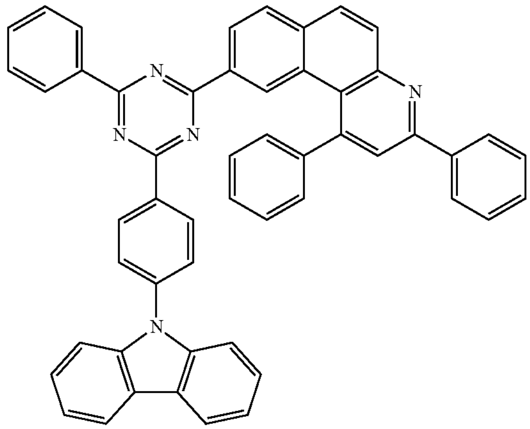
50
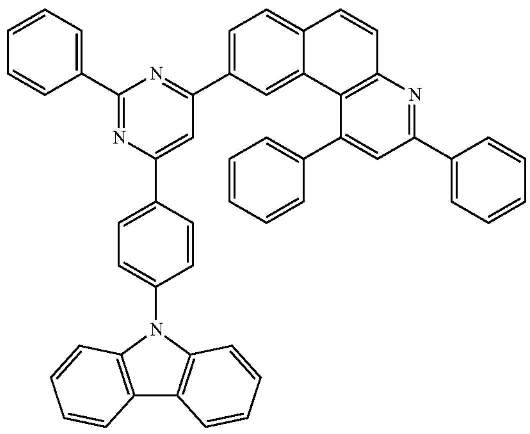

-continued
51
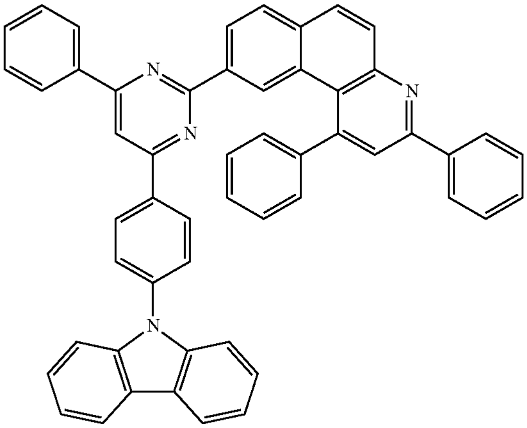
52
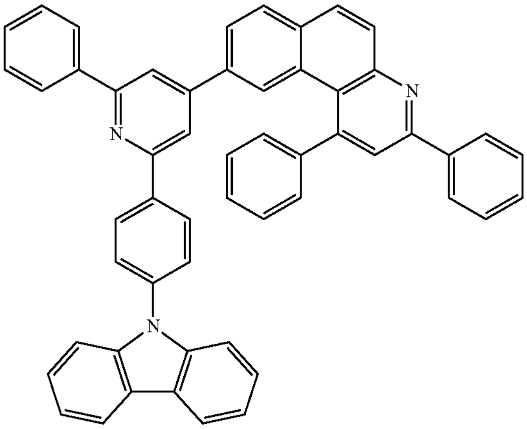
53
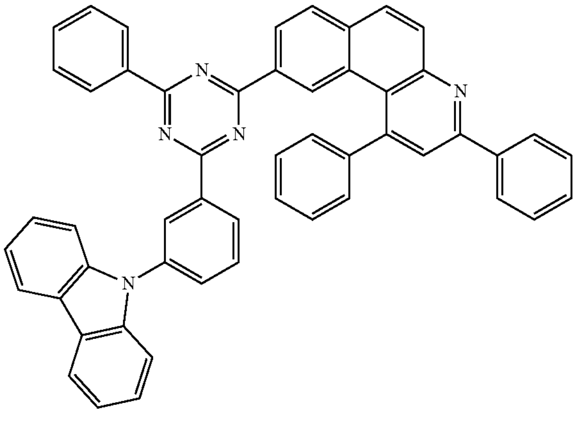
-continued
54
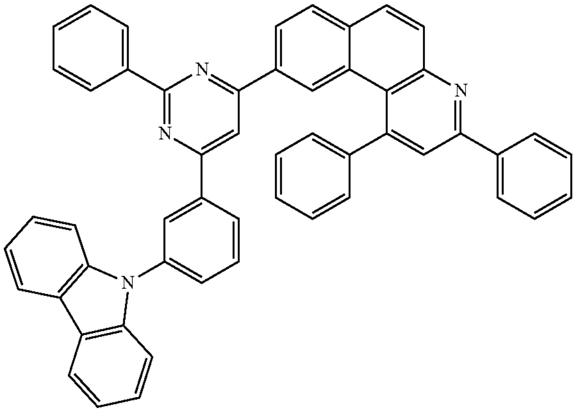
55
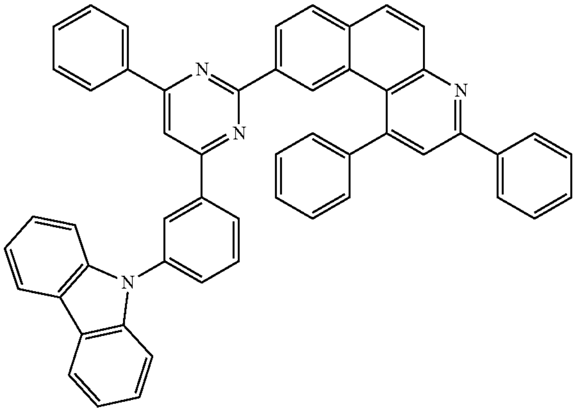
56
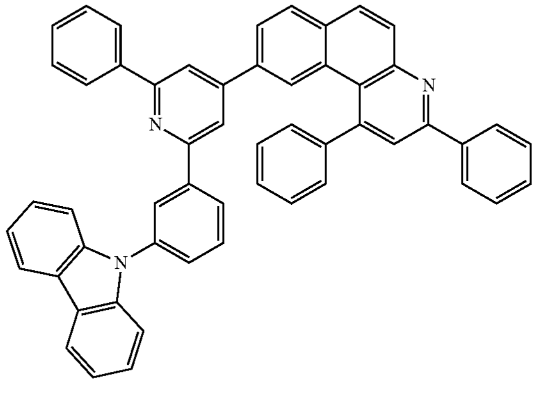

-continued
57
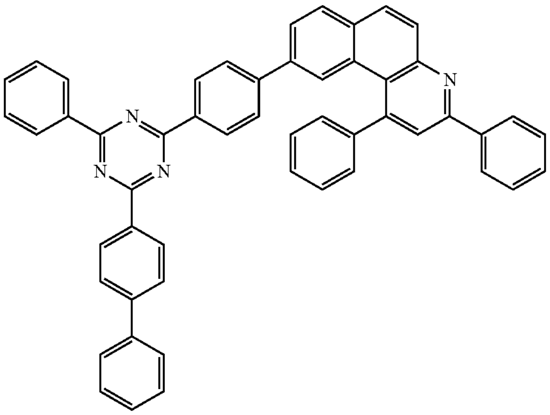
58
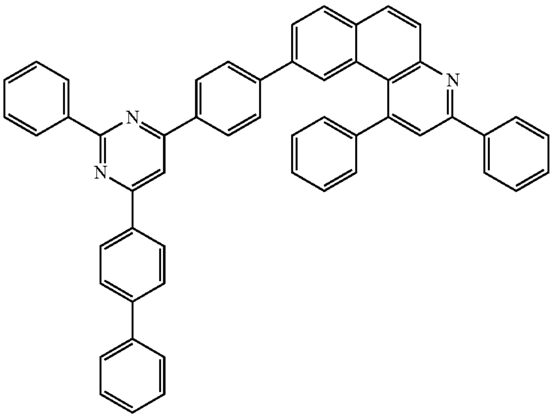
59
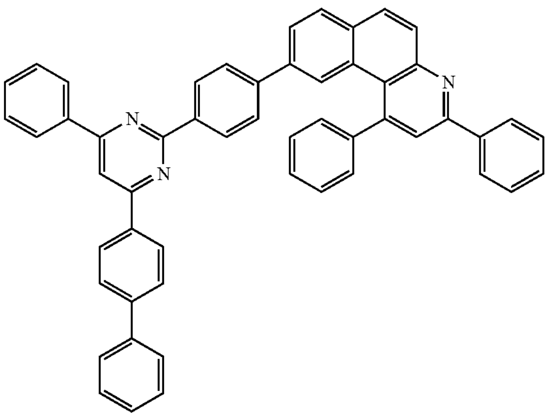
-continued
60
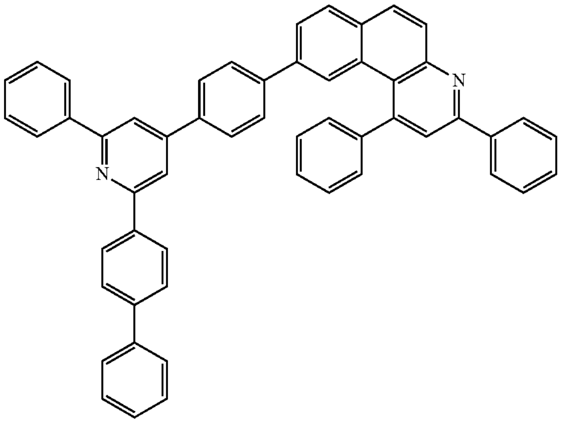
61
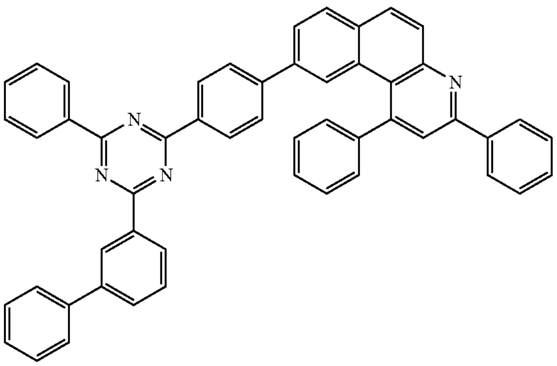
62
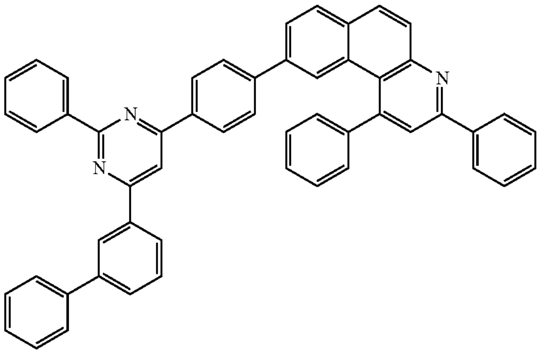
63
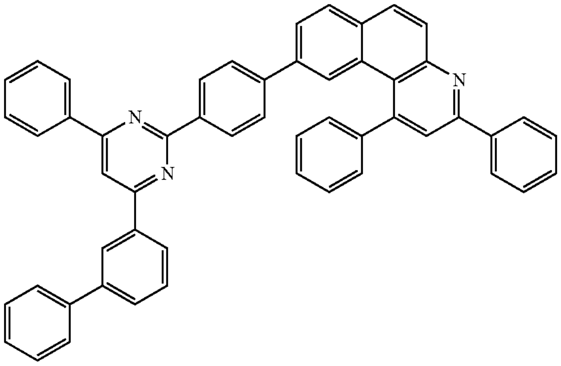

-continued
64
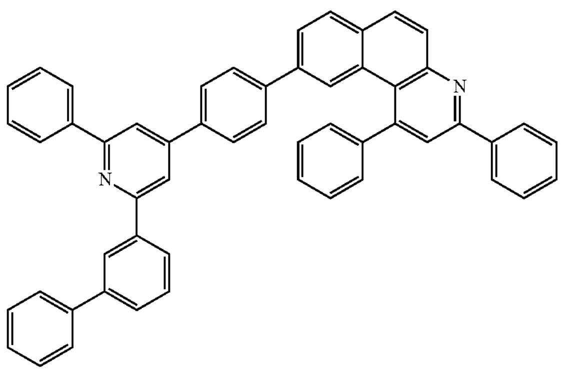
65
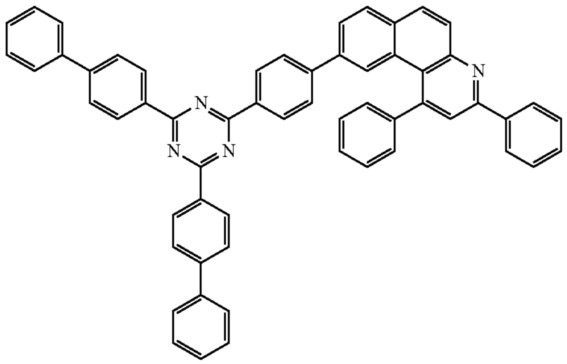
66
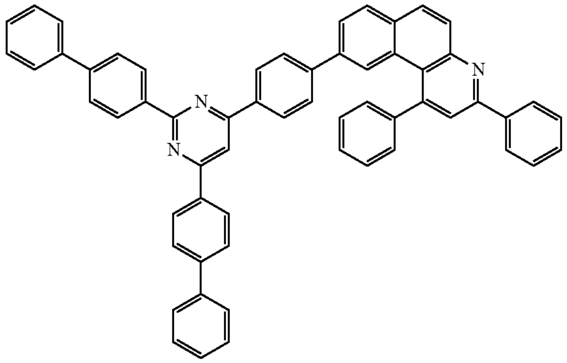
67
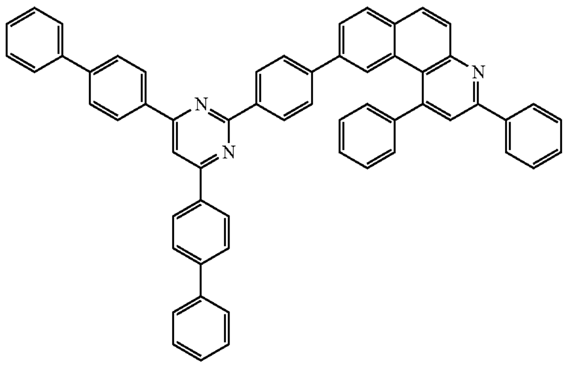
-continued
68
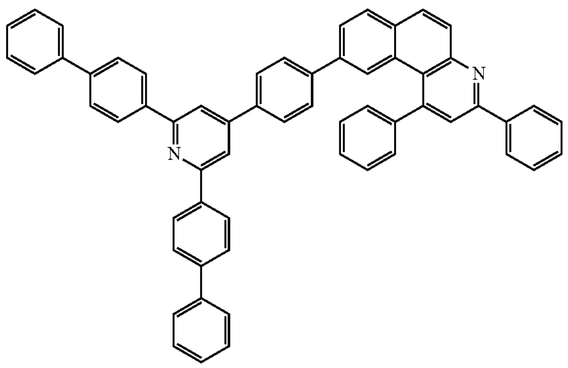
69
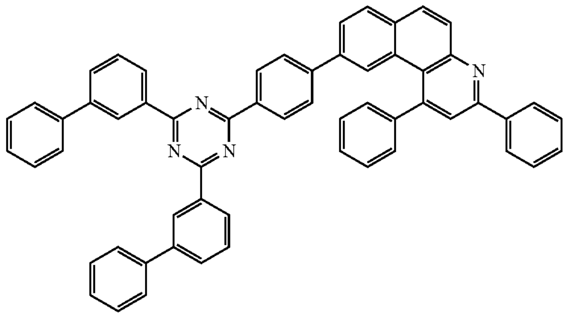
70
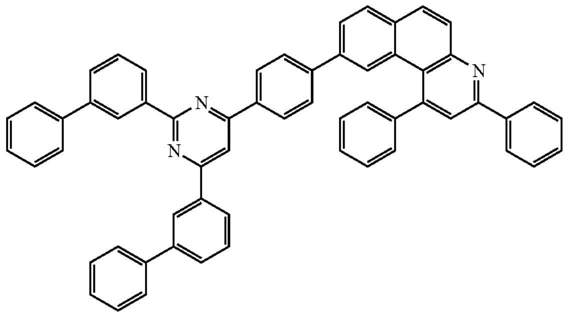
71
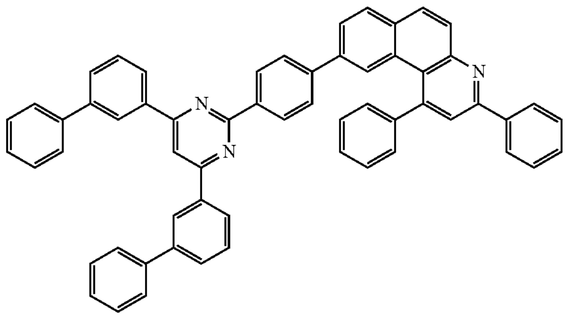

-continued
72
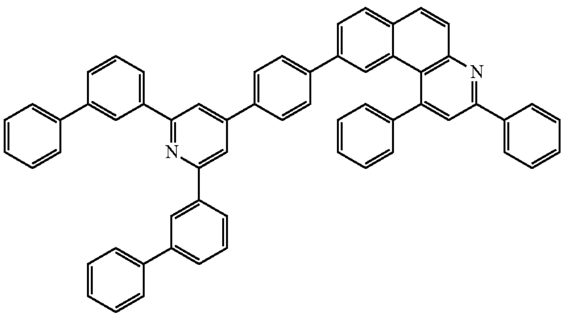
73
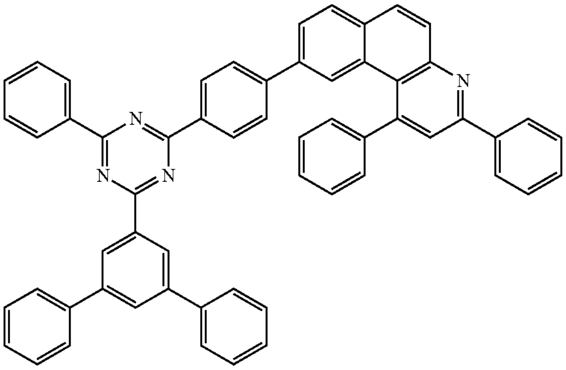
74
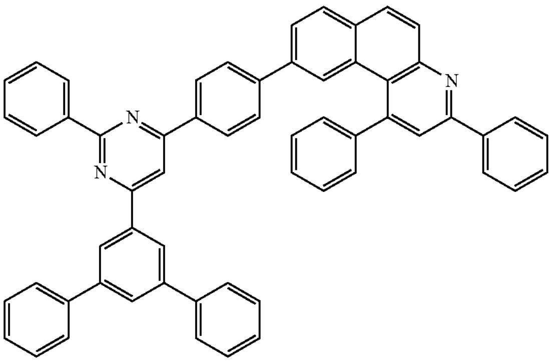
75
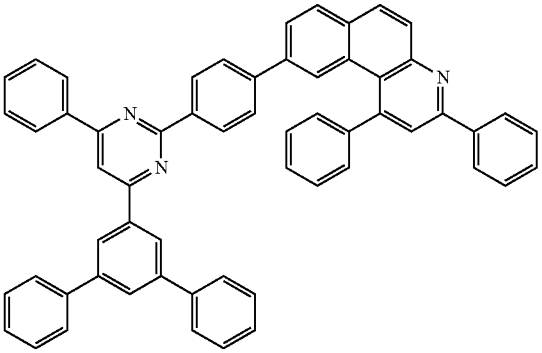
-continued
76
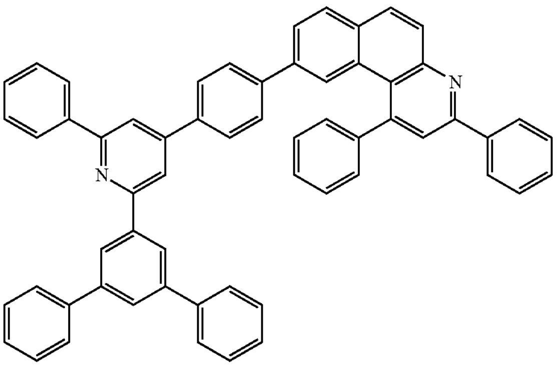
77
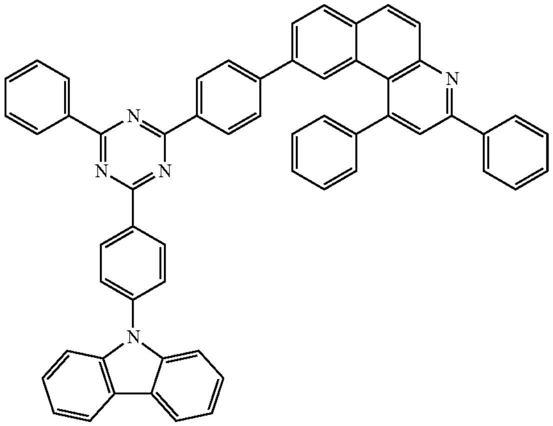
78
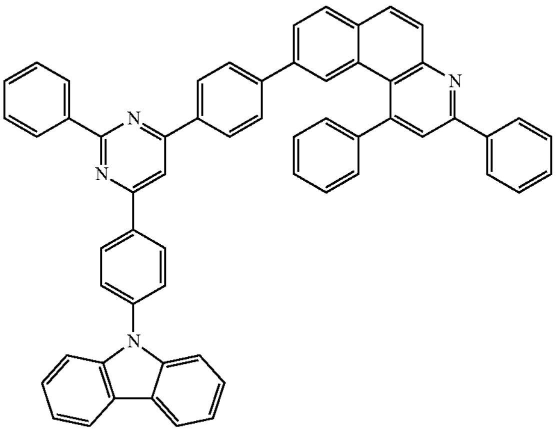

-continued
79
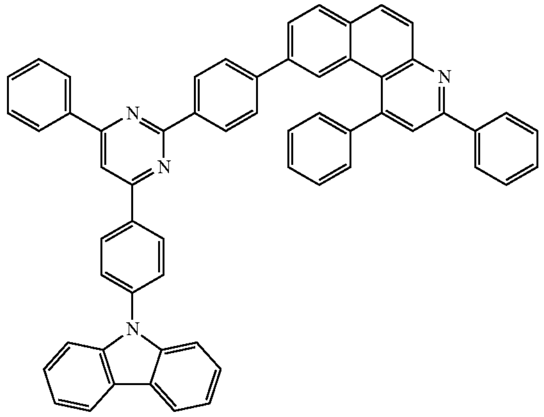
80
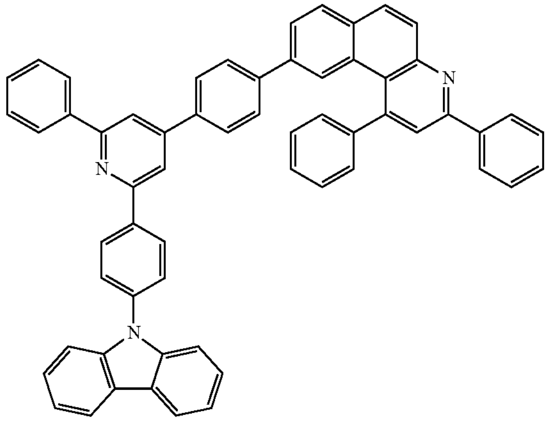
81
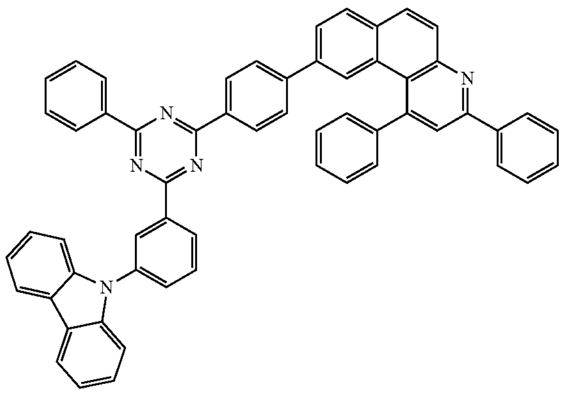
-continued
82
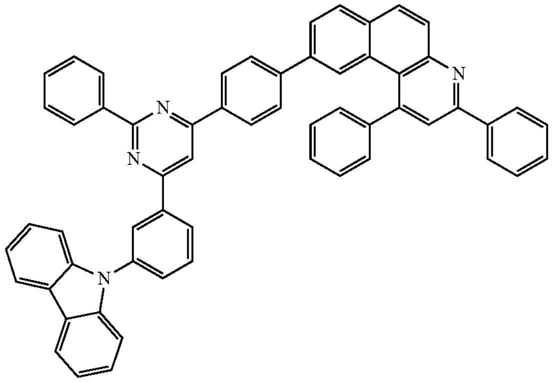
83
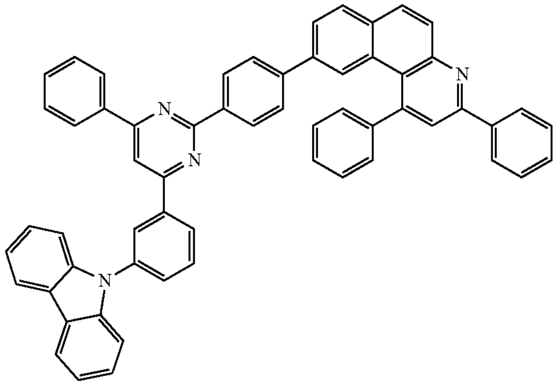
84
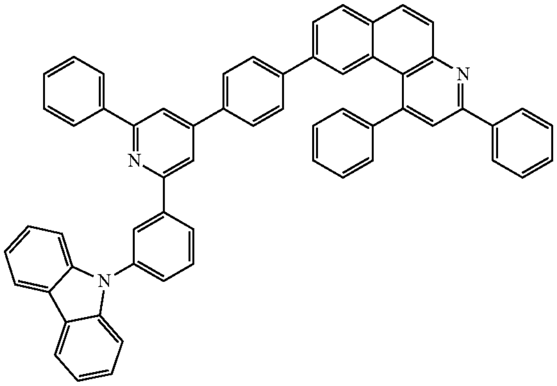
85
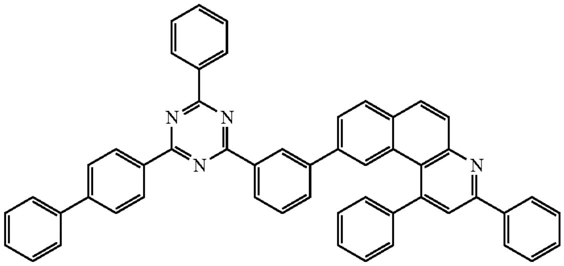

-continued
86
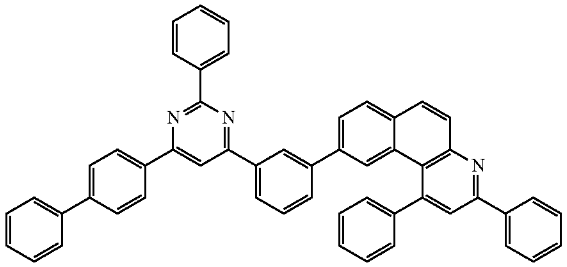
87
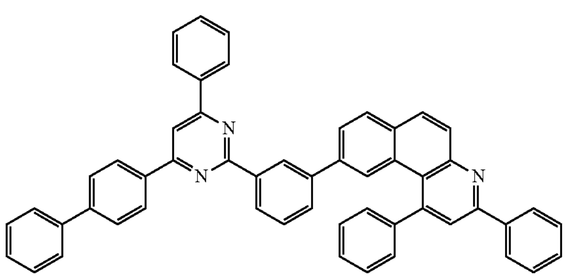
88
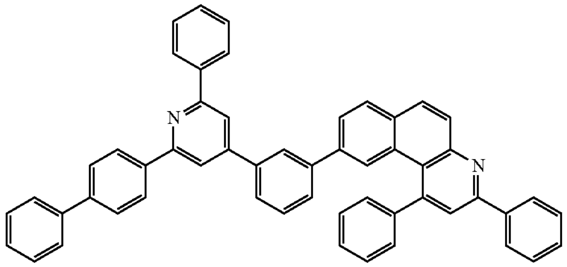
89
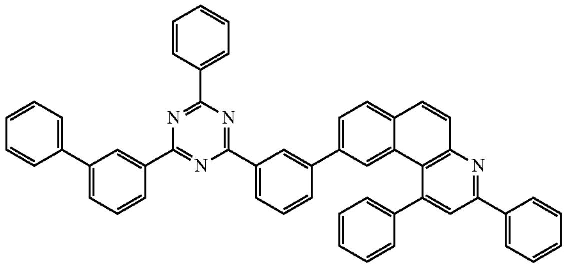
90
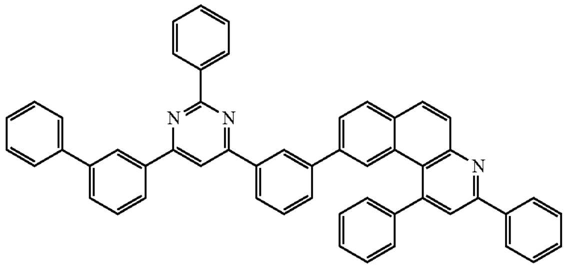
-continued
91
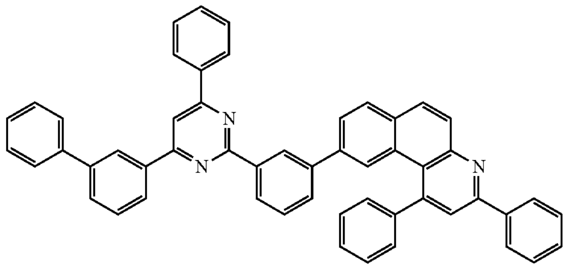
92
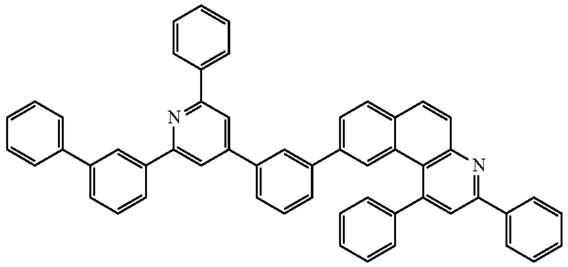
93
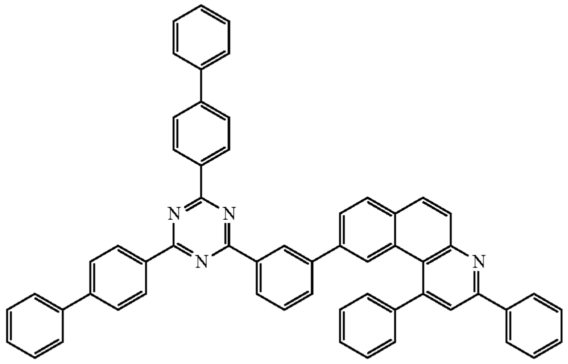
94
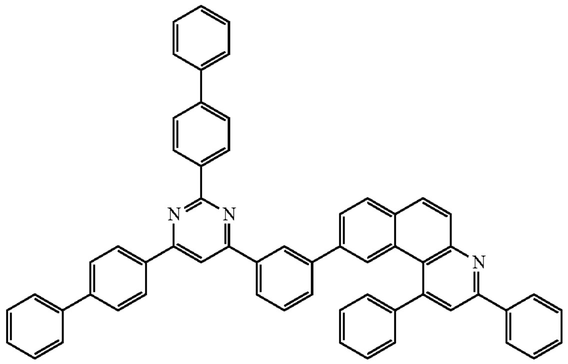

-continued
95
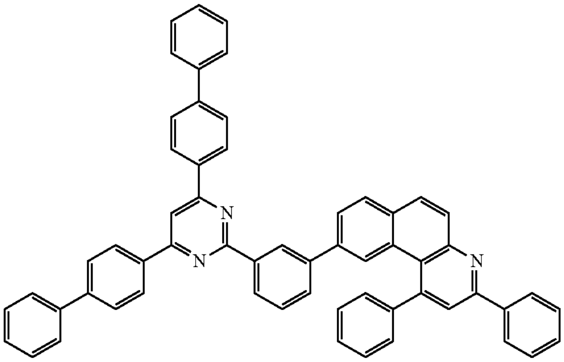
96
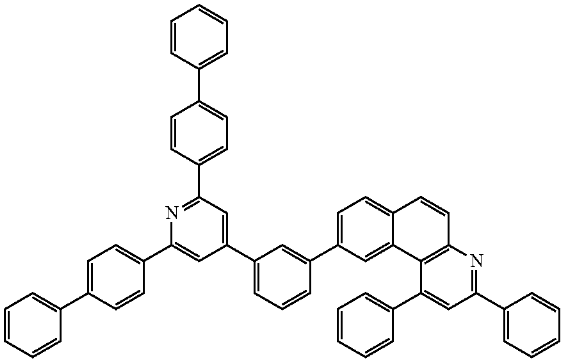
97
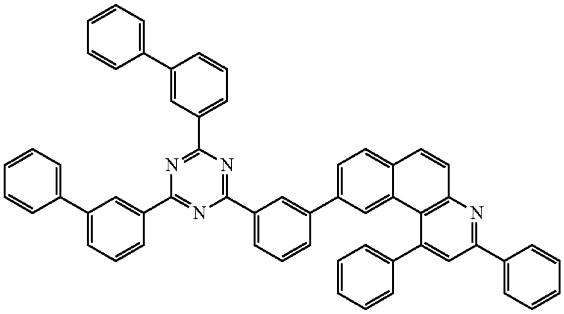
98
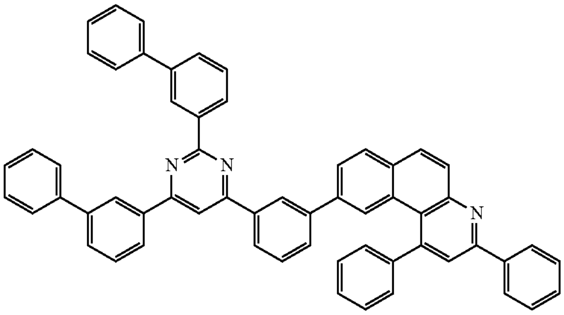
-continued
99
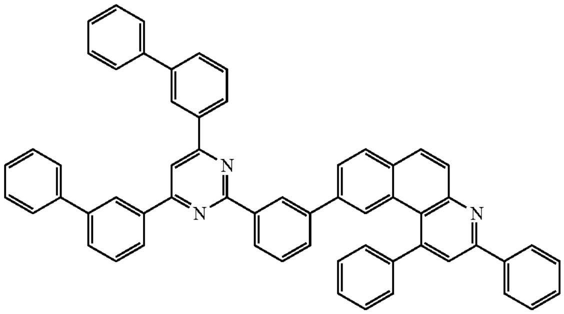
100
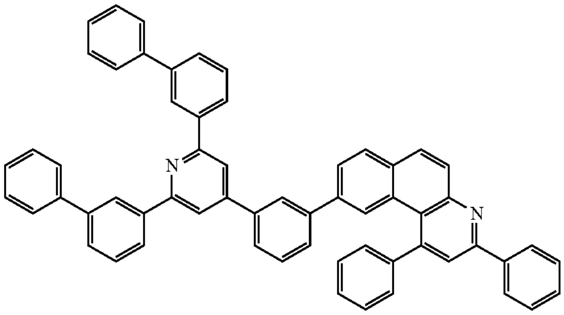
101
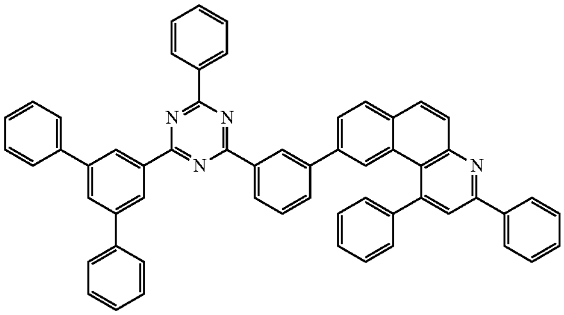
102
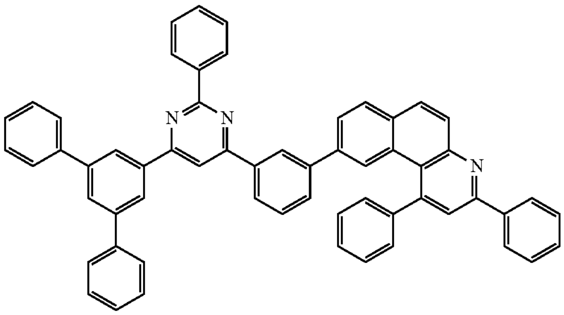

-continued
103
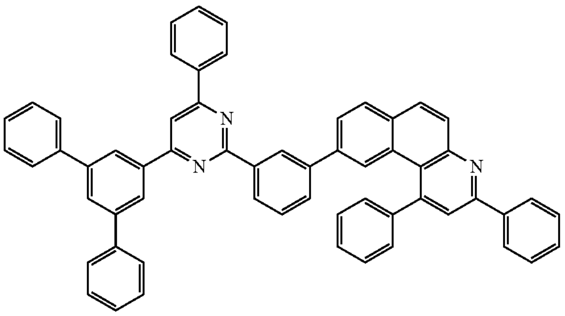
104
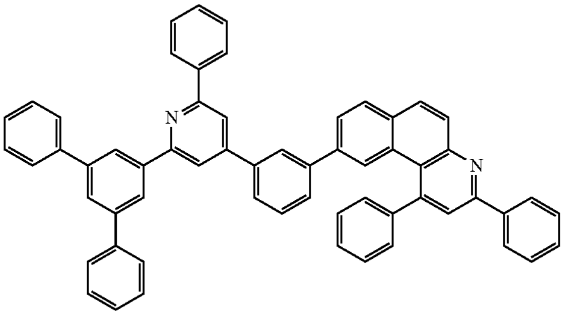
105
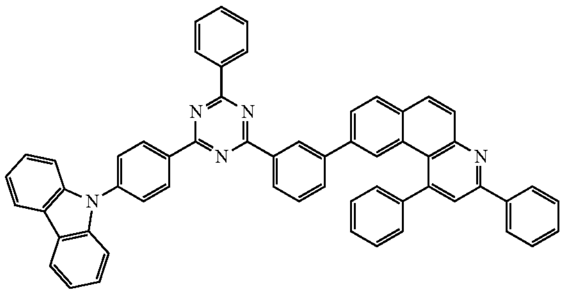
106
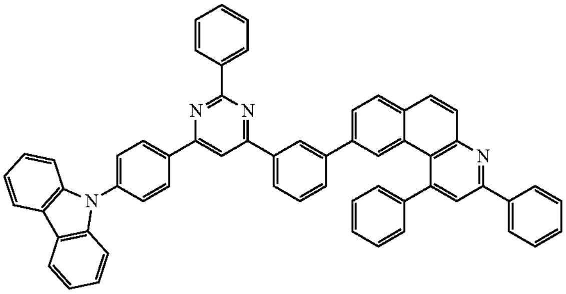
107
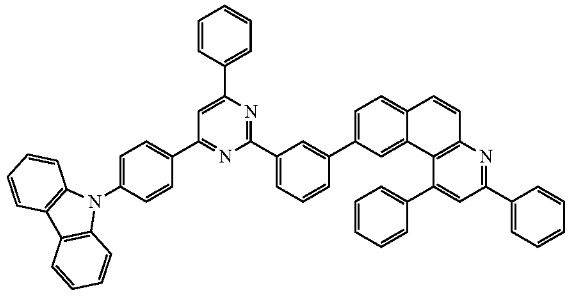
-continued
108
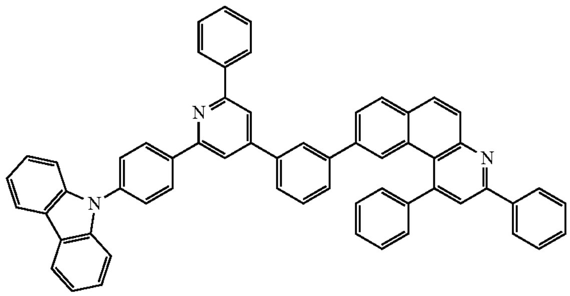
109
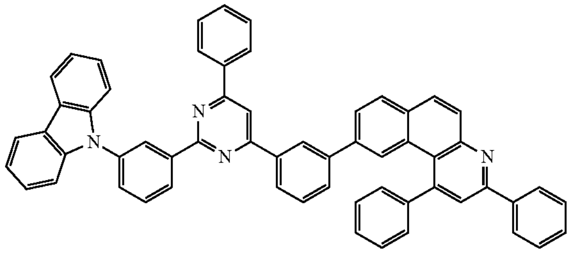
110
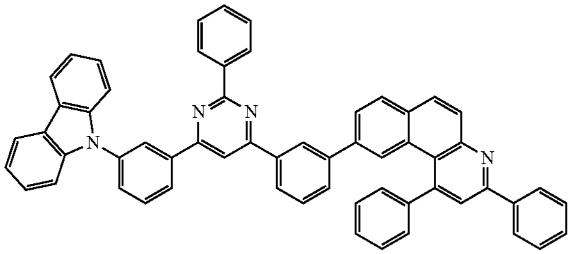
111
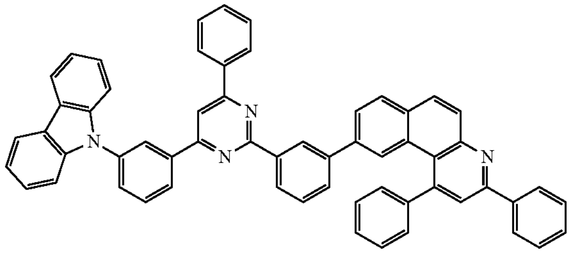
112
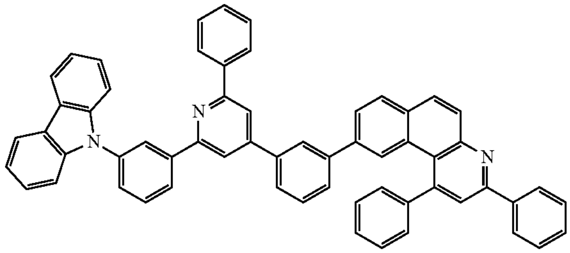

-continued
113
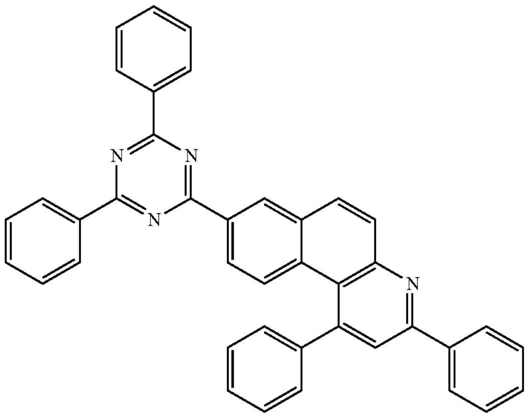
114
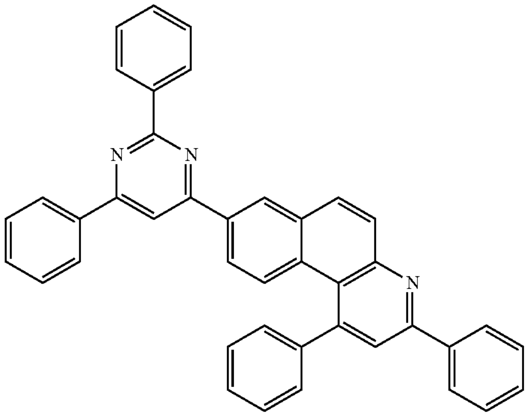
115
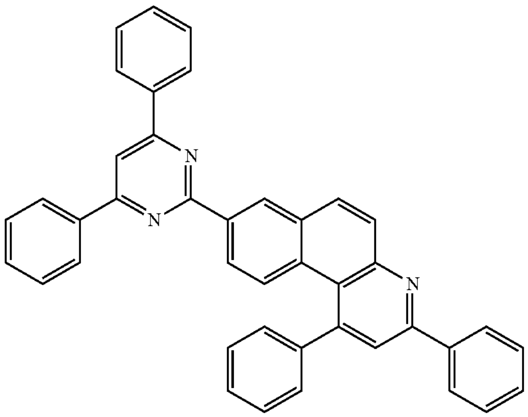
116
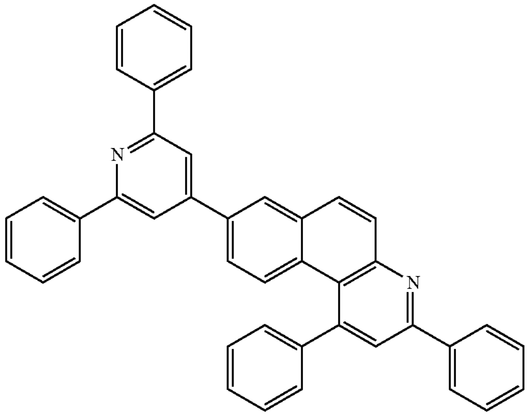
117
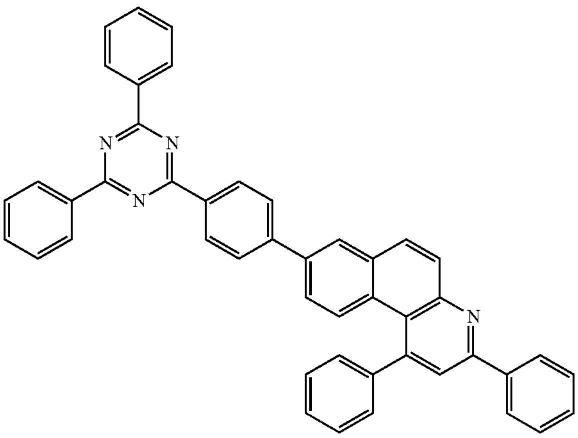
118
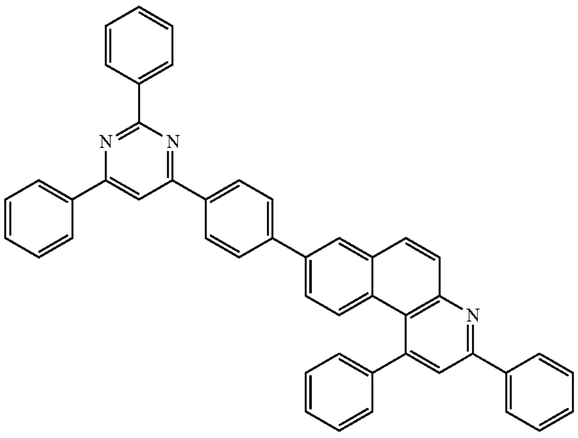

-continued
119
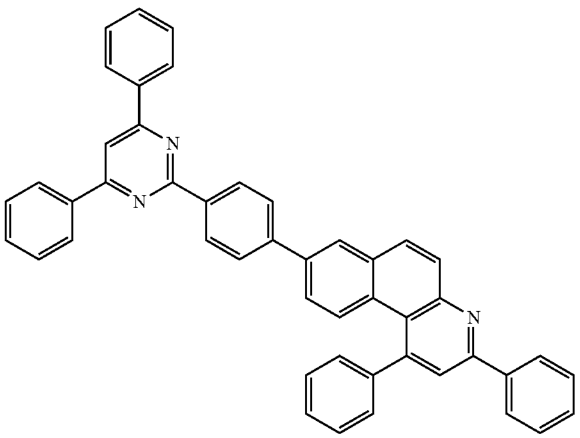
120
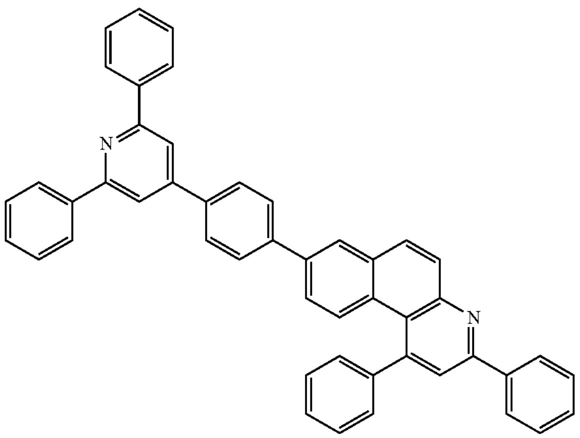
121
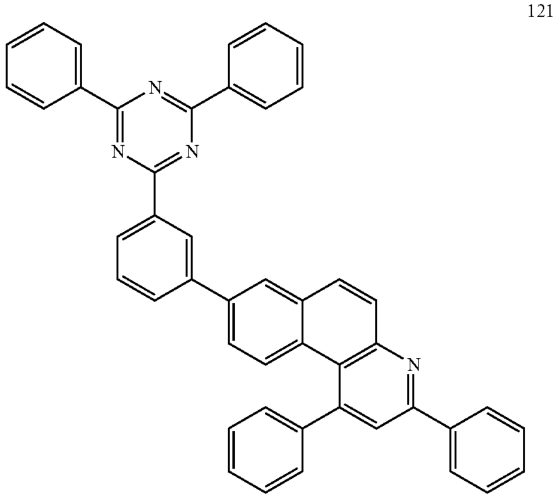
-continued
122
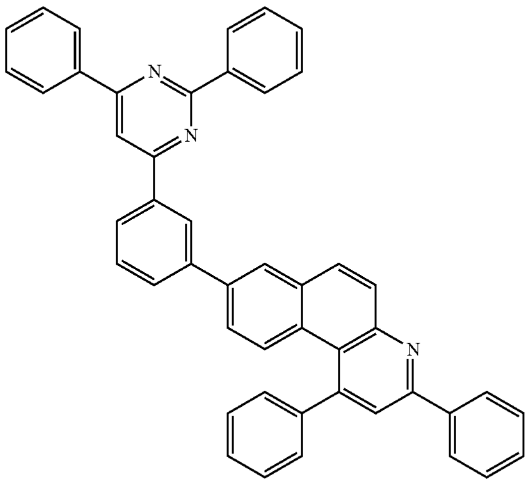
123
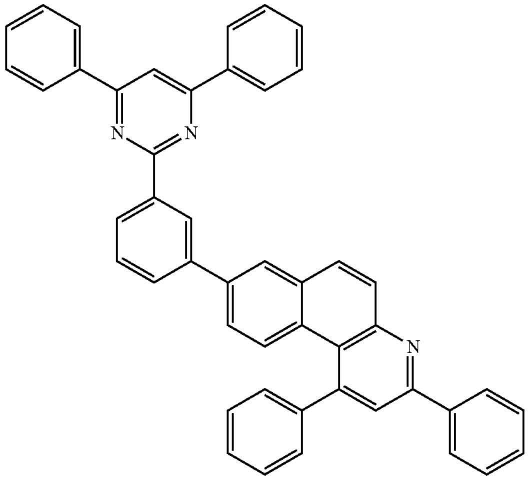
124
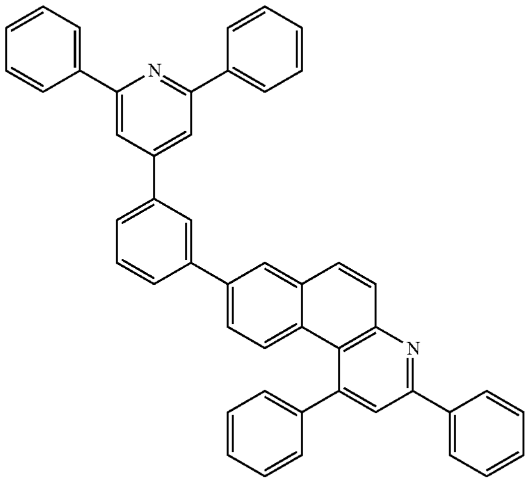

125
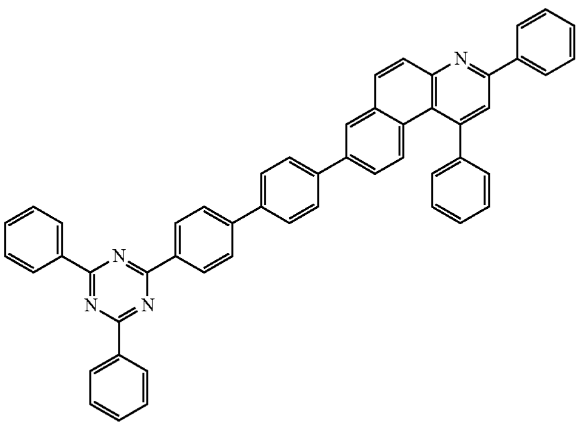
126
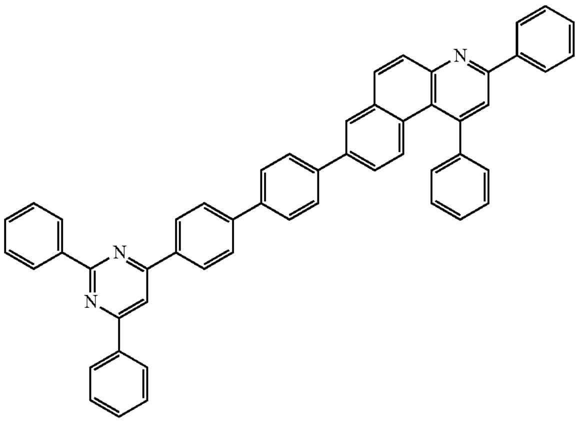
127
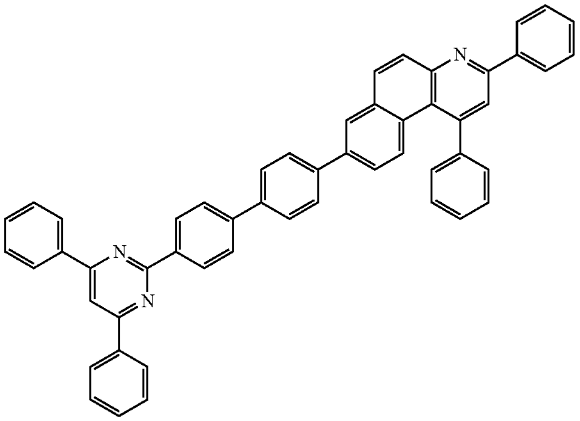
128
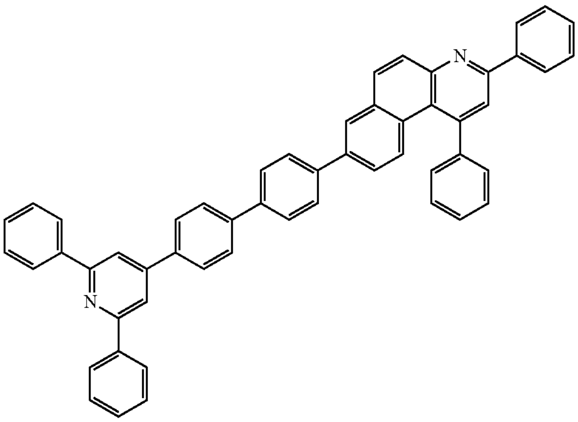
129
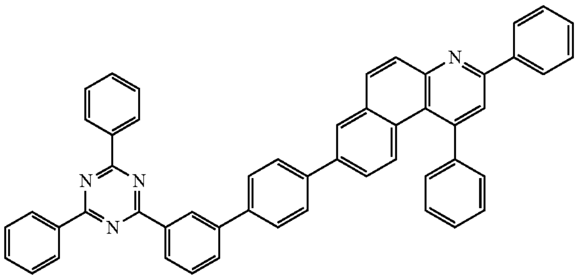
130
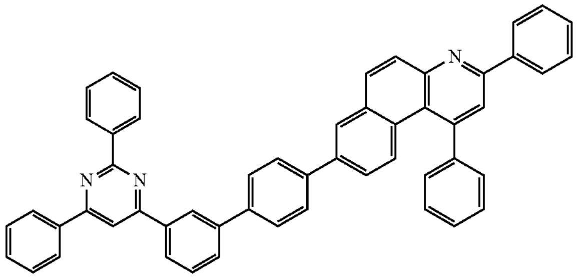
131
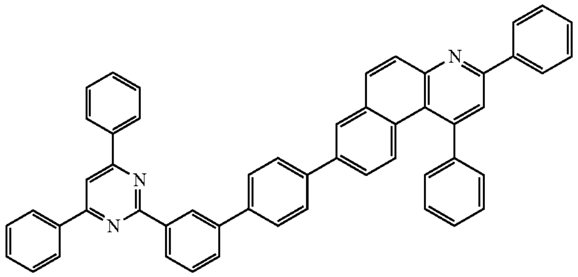

-continued
132
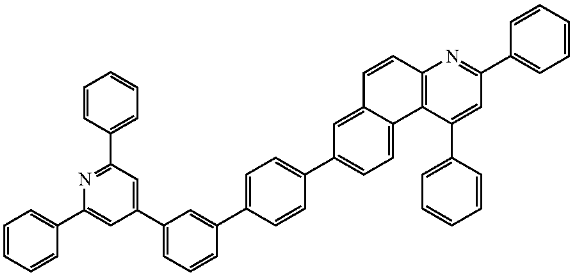
133
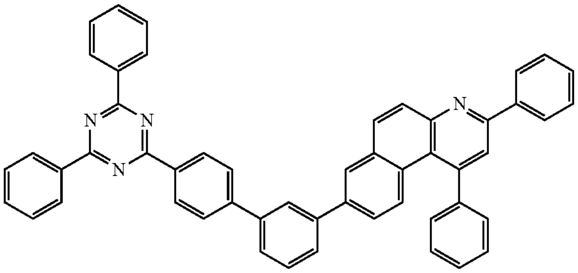
134
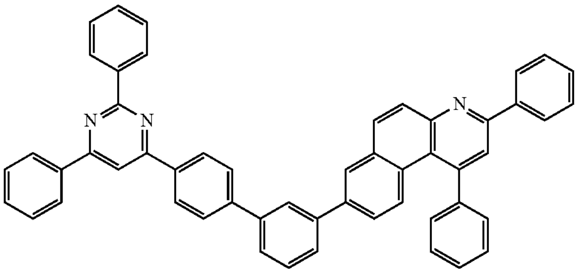
135
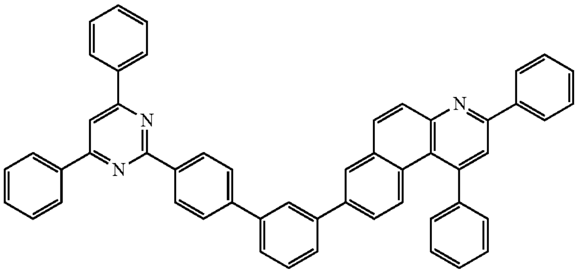
136
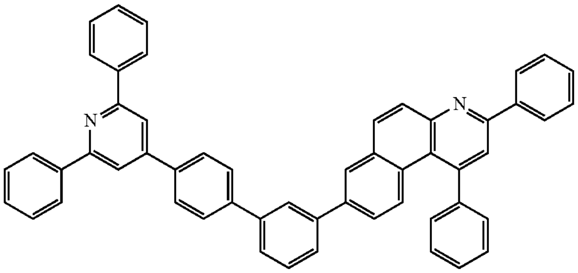
-continued
137
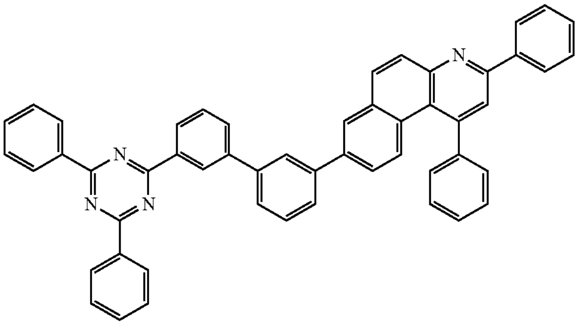
138
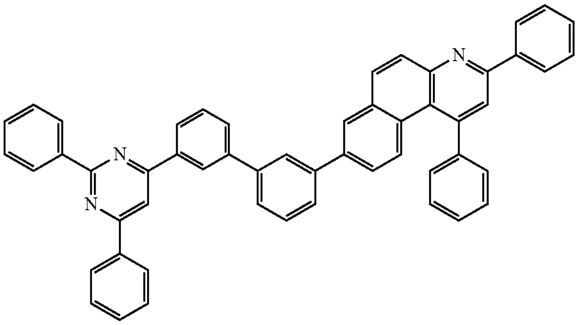
139
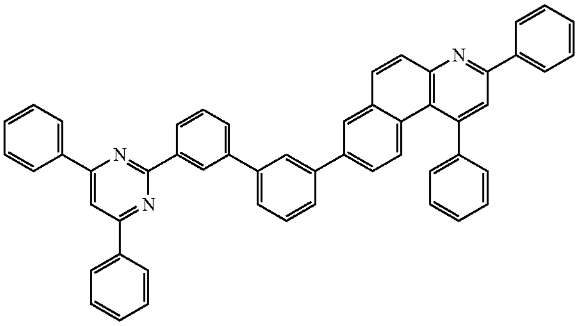
140
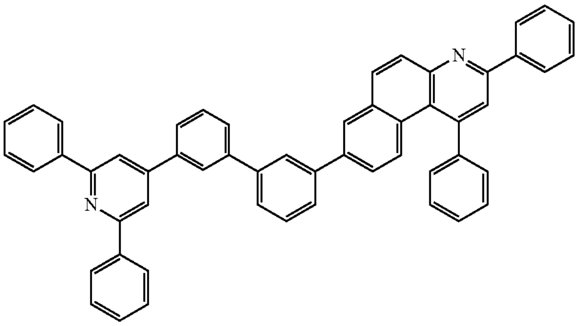

-continued
141
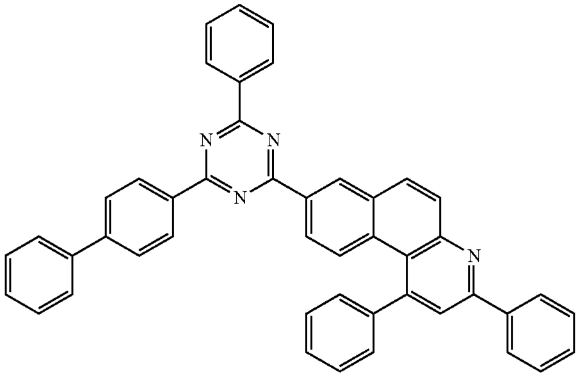
142
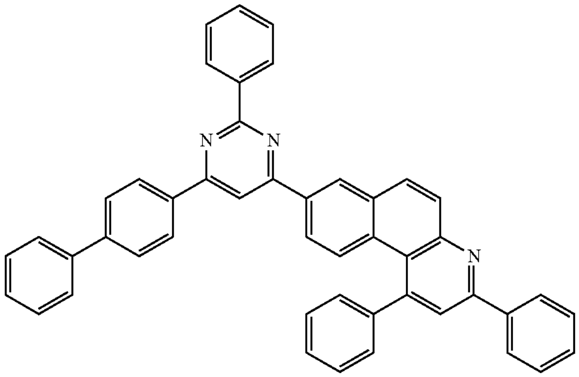
143
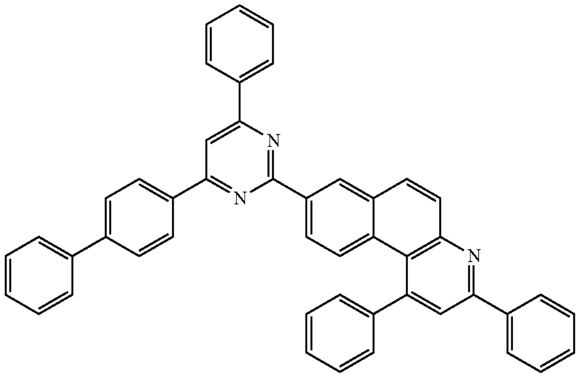
144
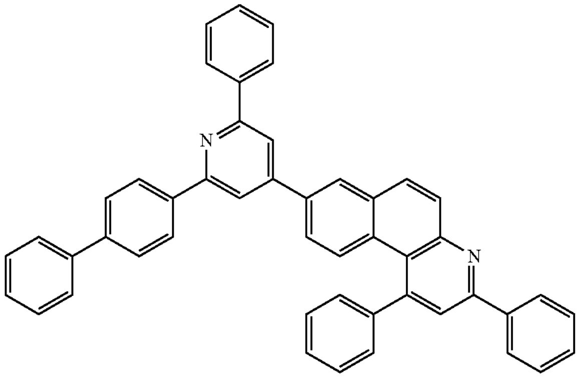
-continued
145
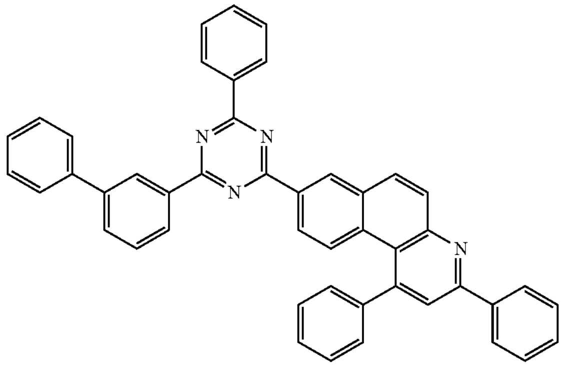
146
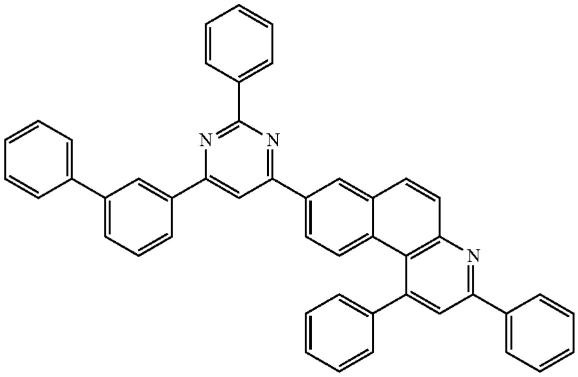
147
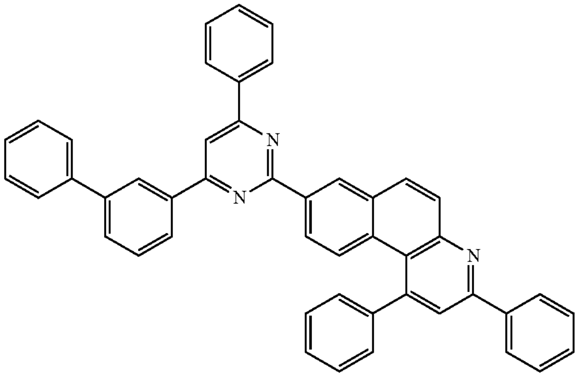
148
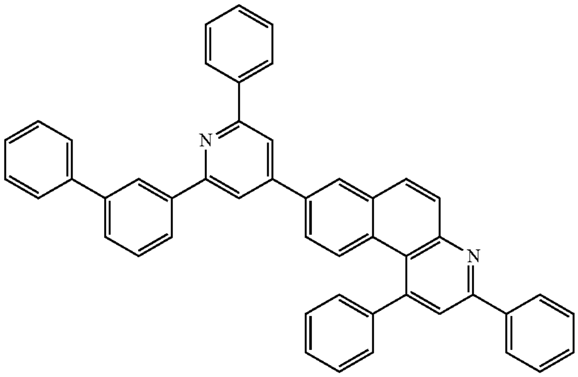

-continued
149
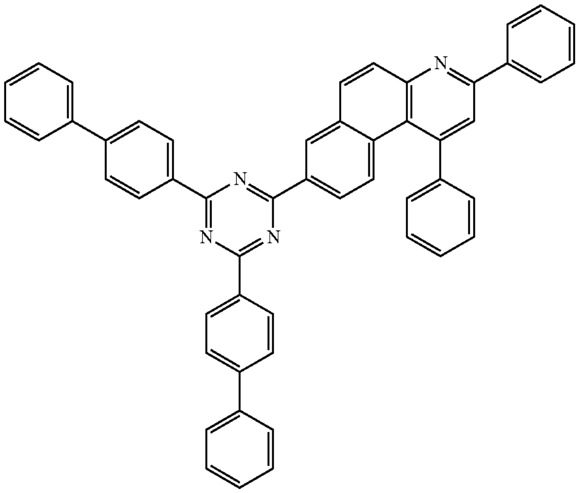
150
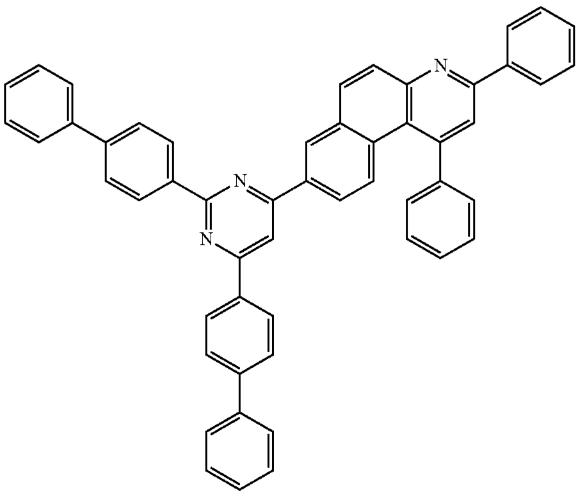
151
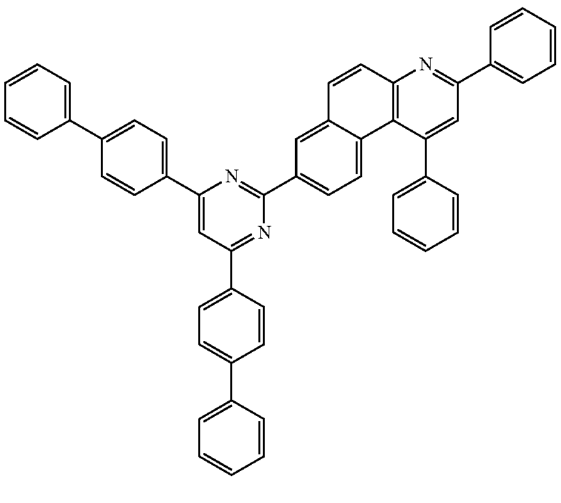
-continued
152
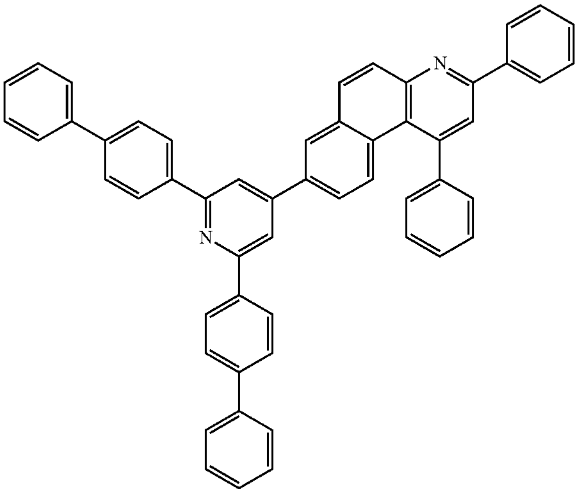
153
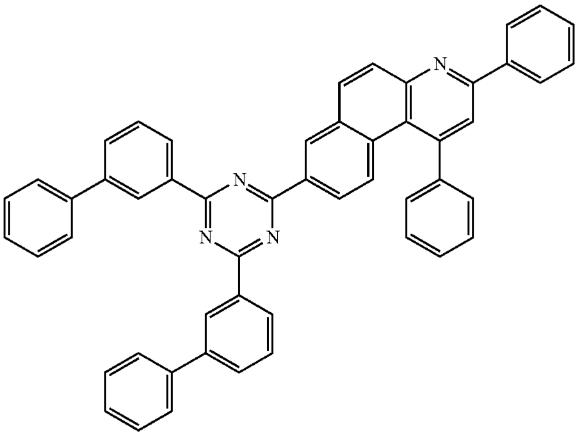
154
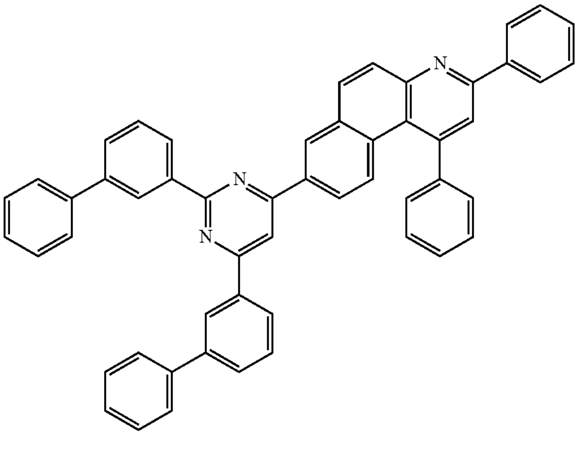

-continued
155
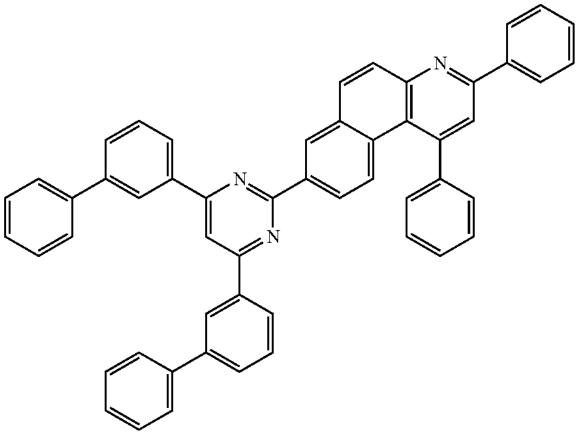
156
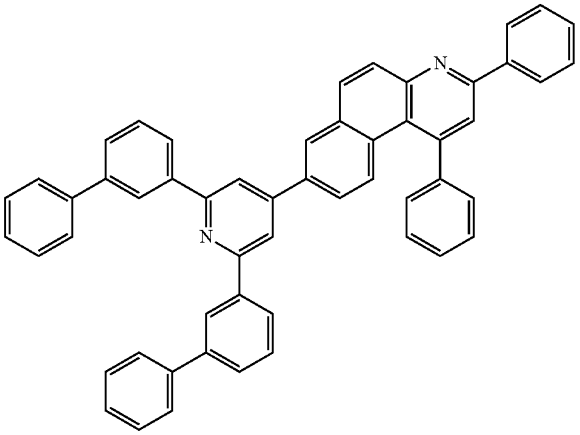
157
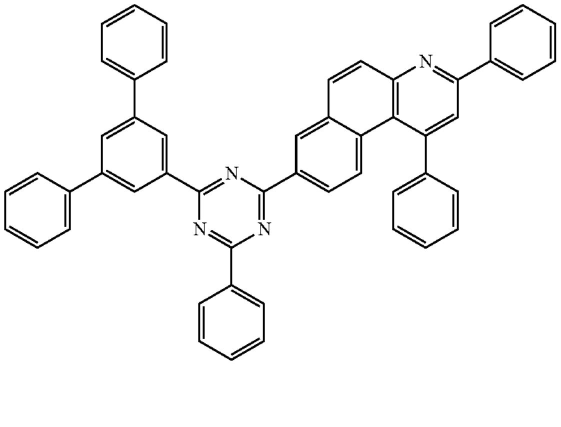
-continued
158
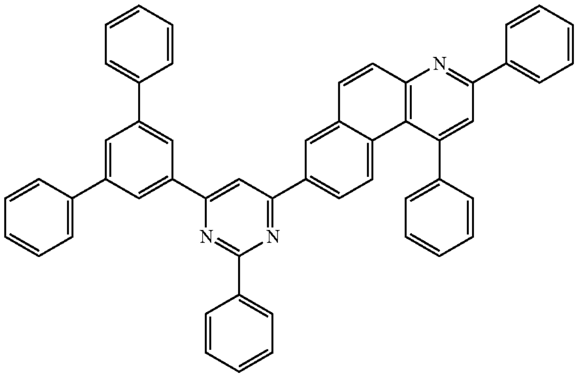
159
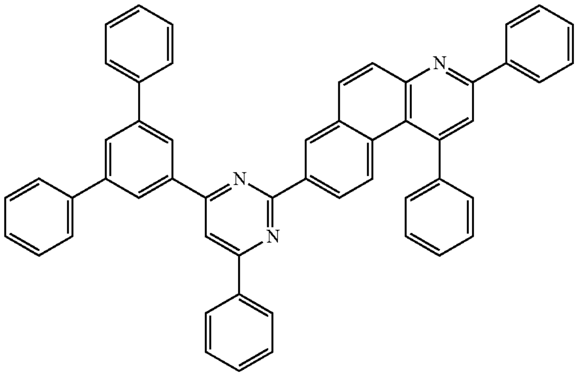
160
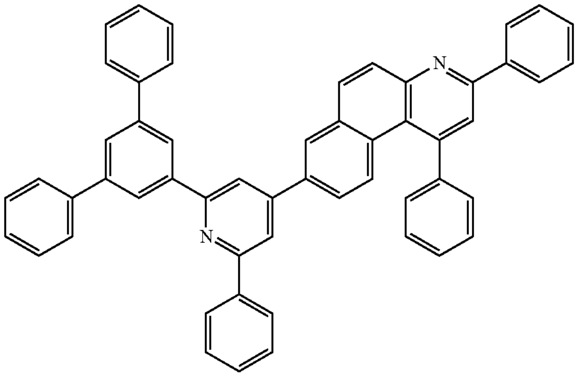

-continued
161
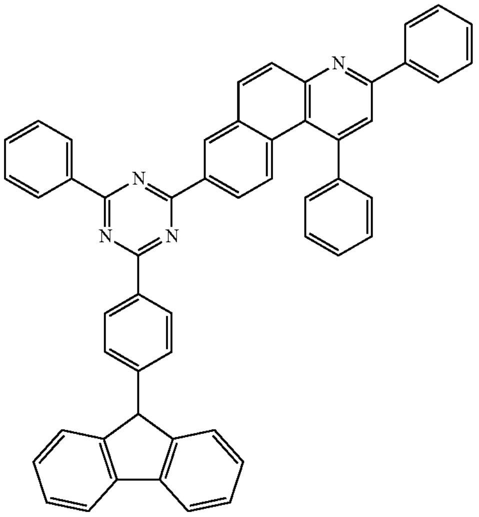
162
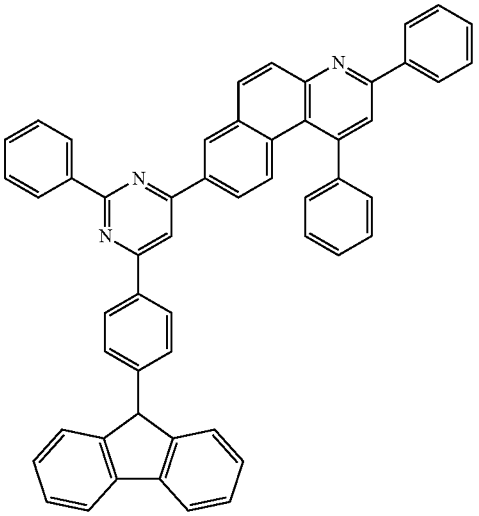
163
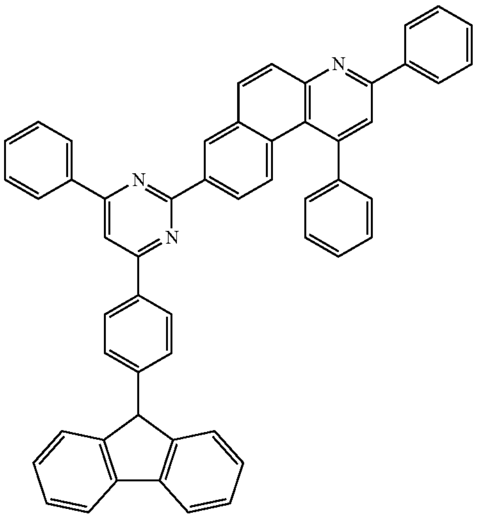
-continued
164
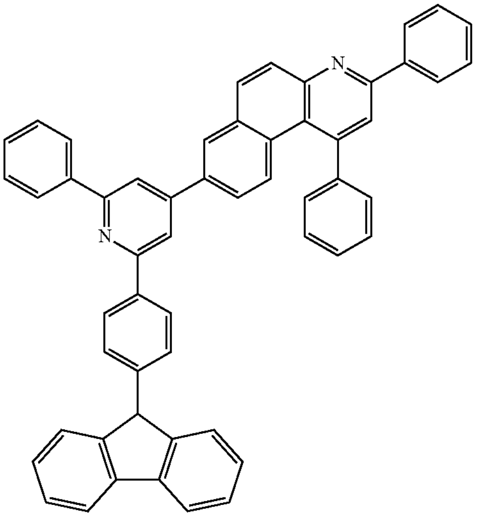
165
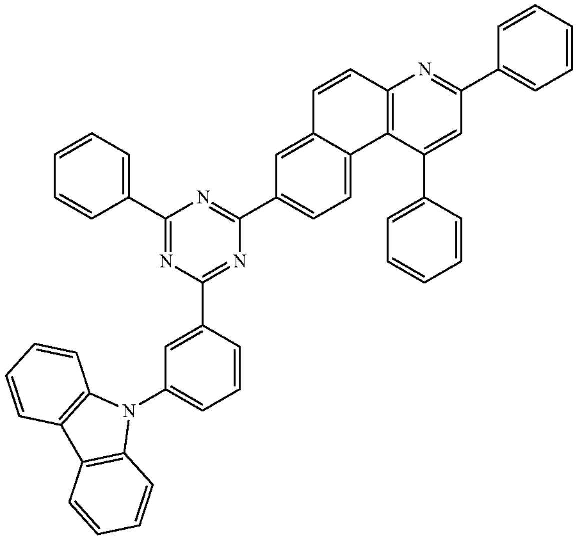
166
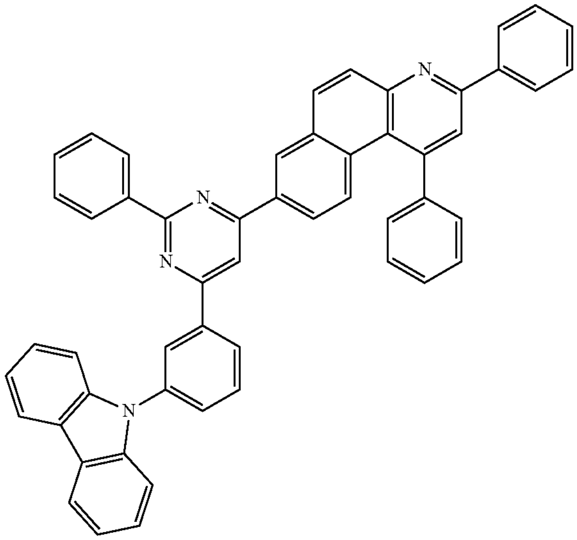

167
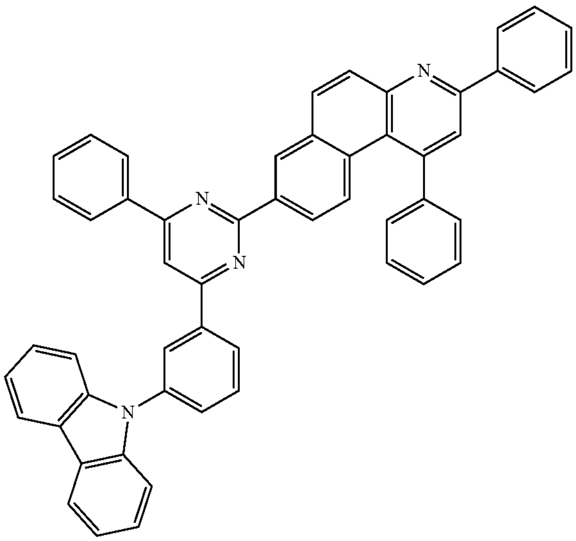
168
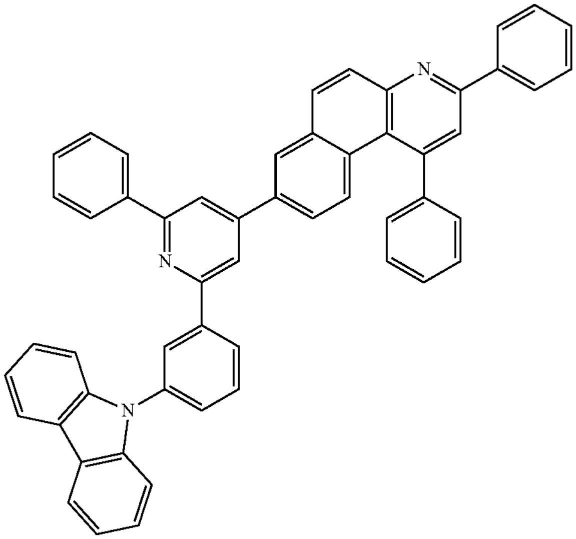
169
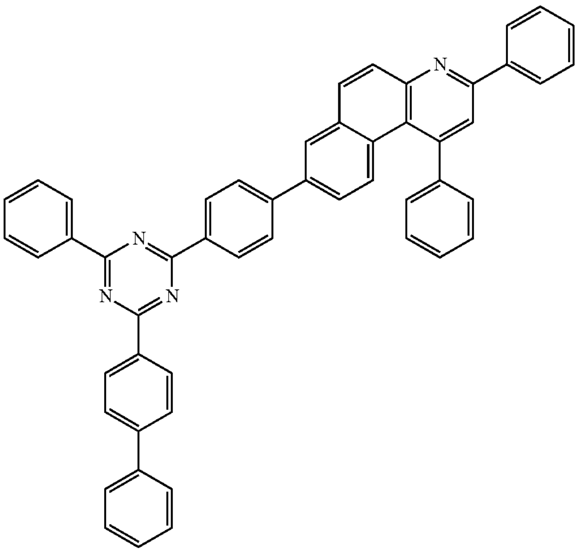
170
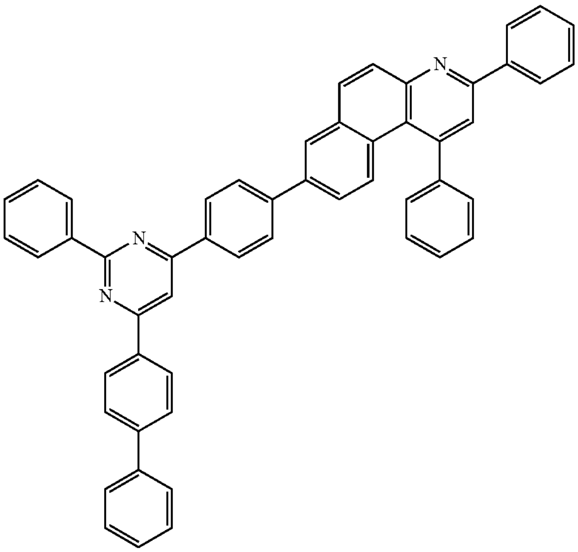

171
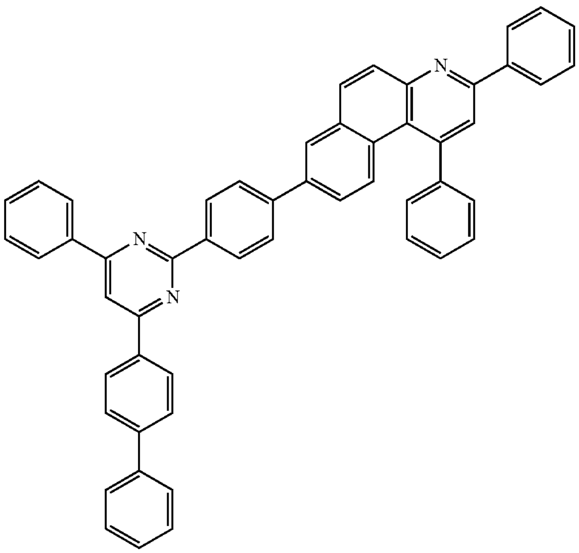
172
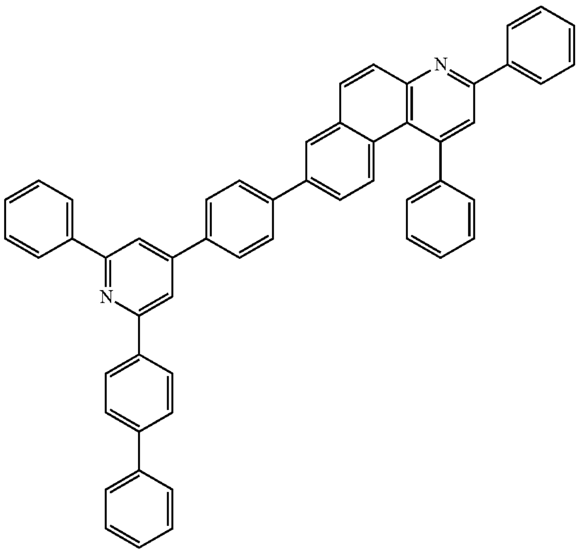
173
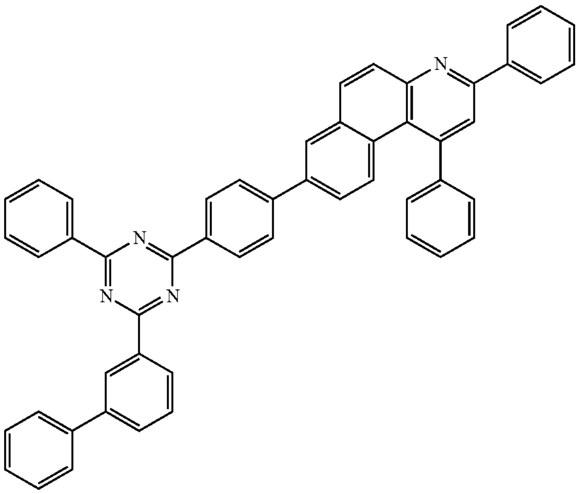
174
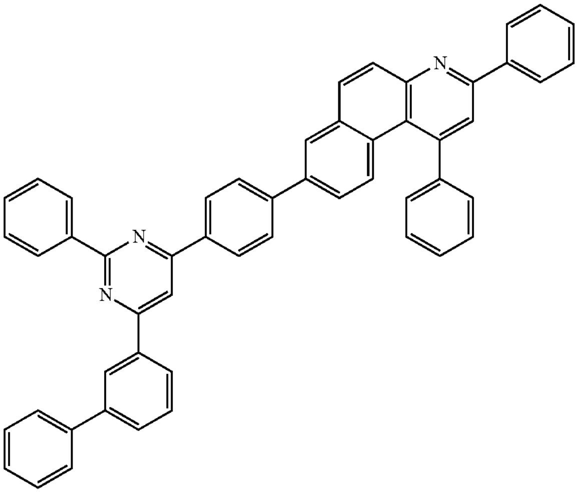
175
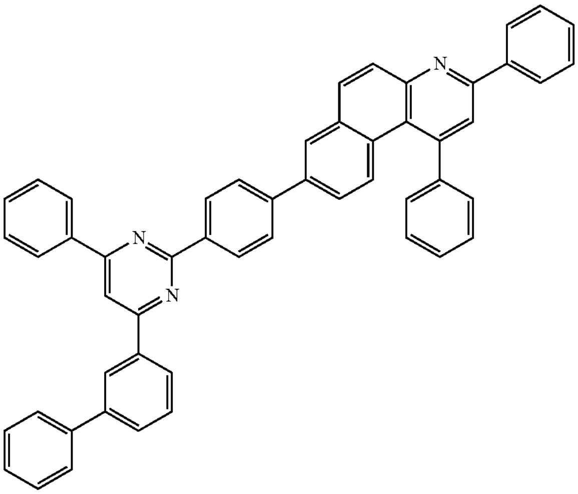
176
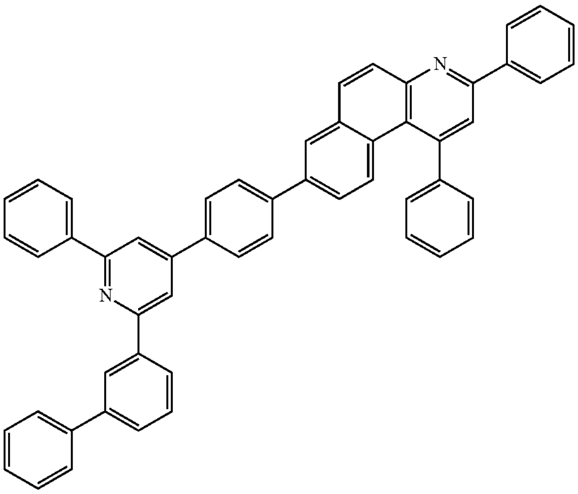

-continued
177
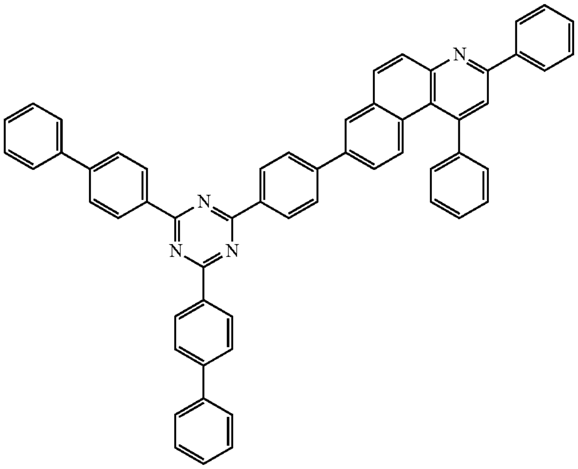
178
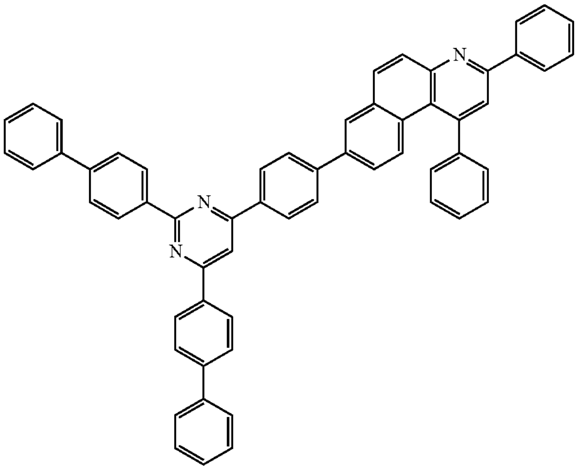
179
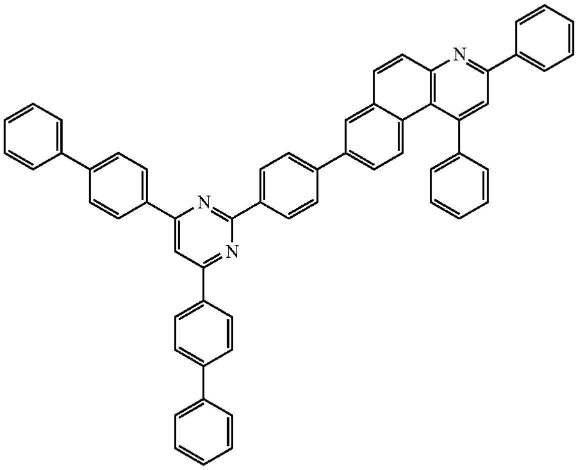
-continued
180
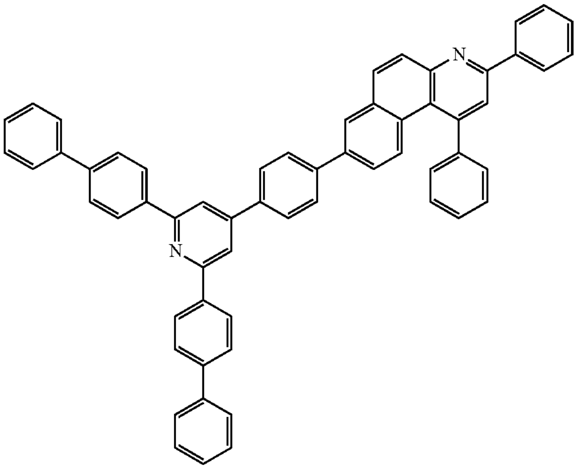
181
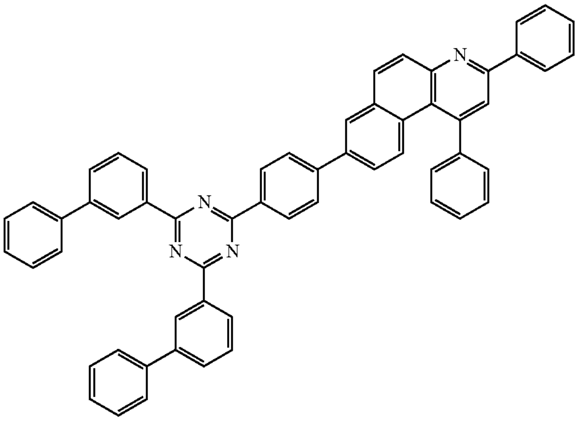
182
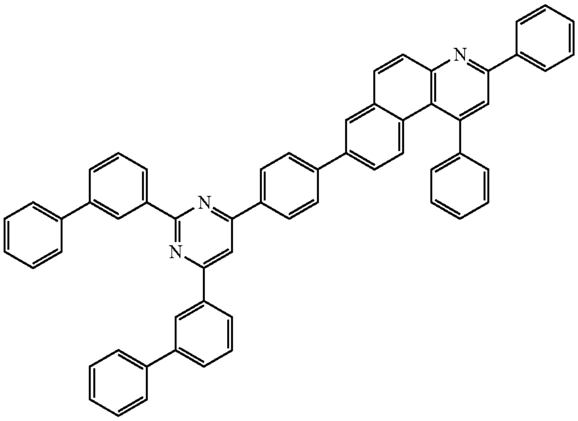

-continued
183
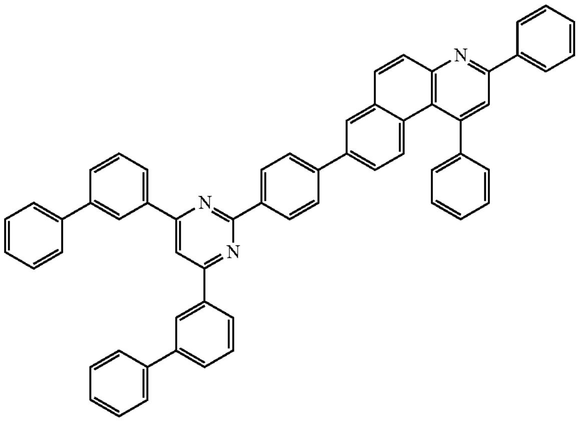
184
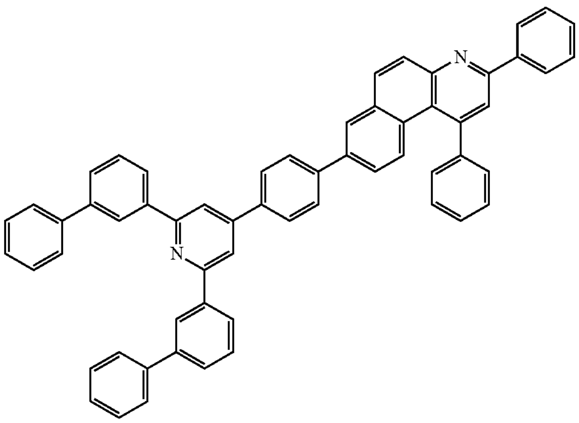
185
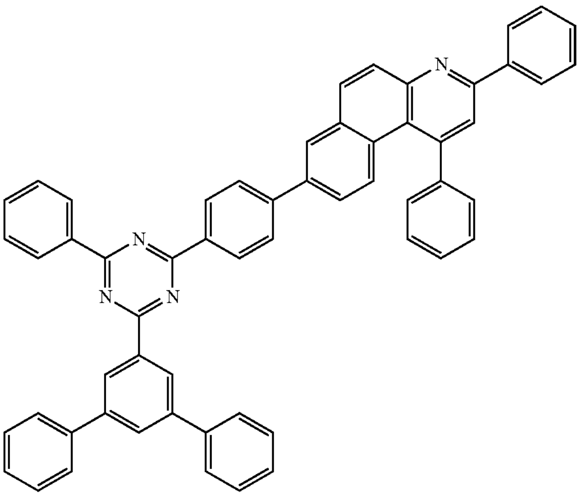
-continued
186
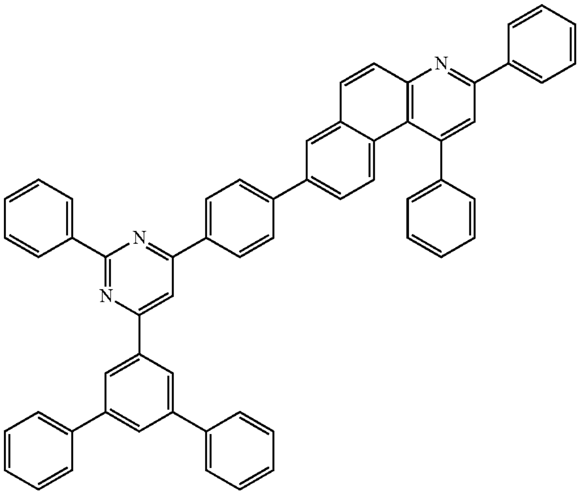
187
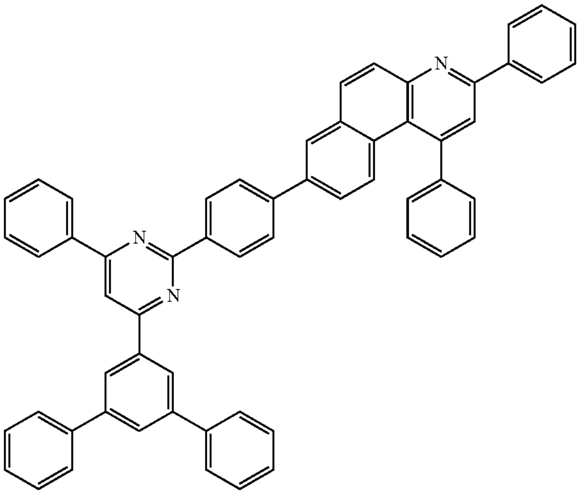
188
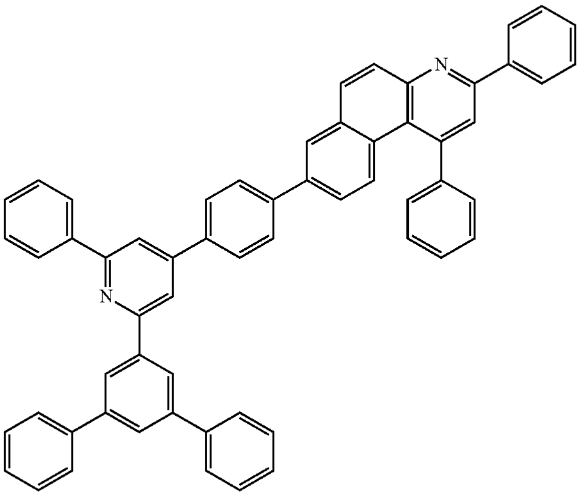

-continued
189
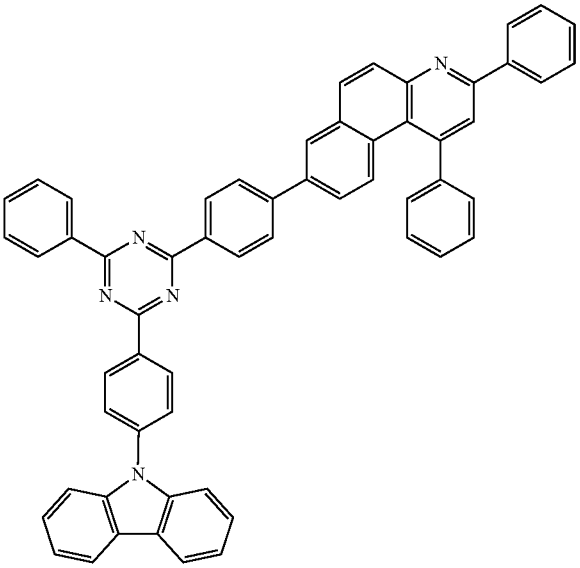
190
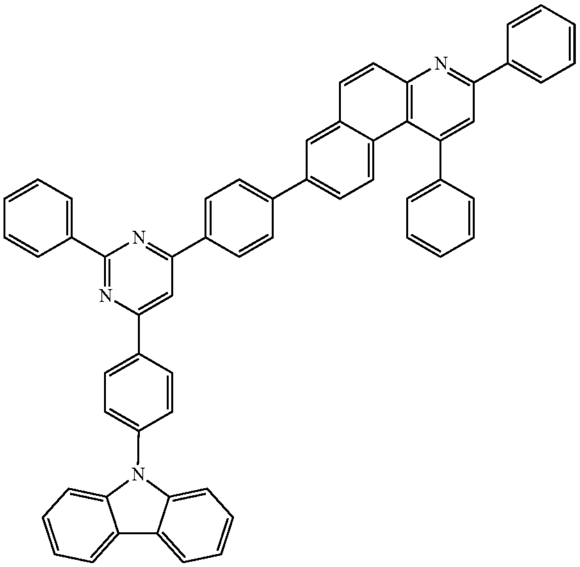
-continued
191
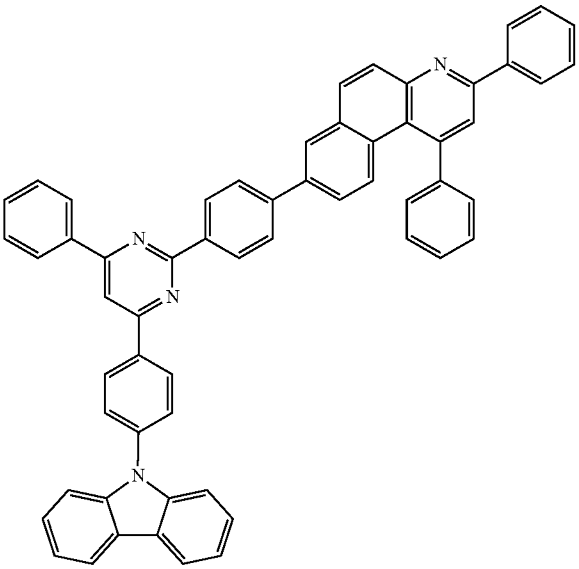
192
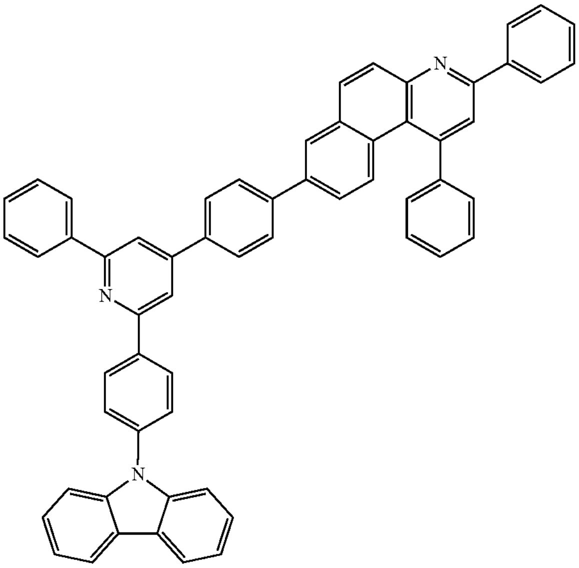

-continued
193
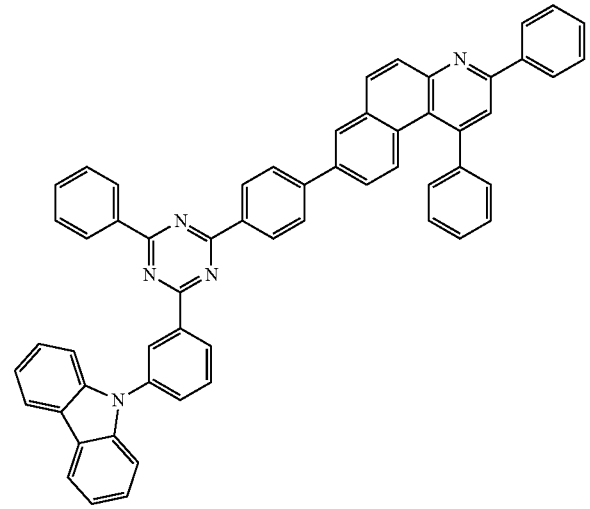
194
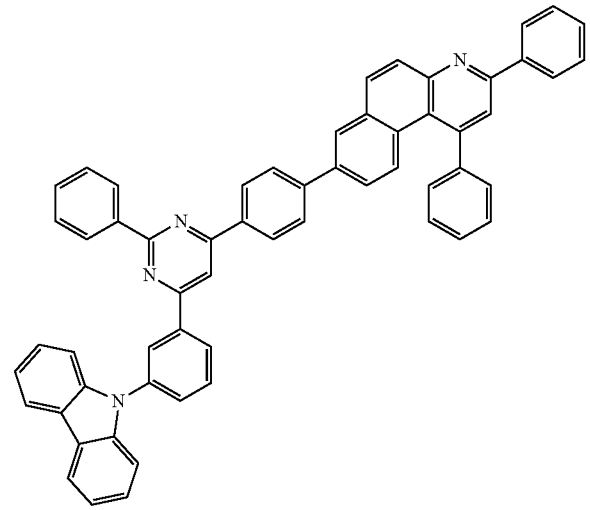
195
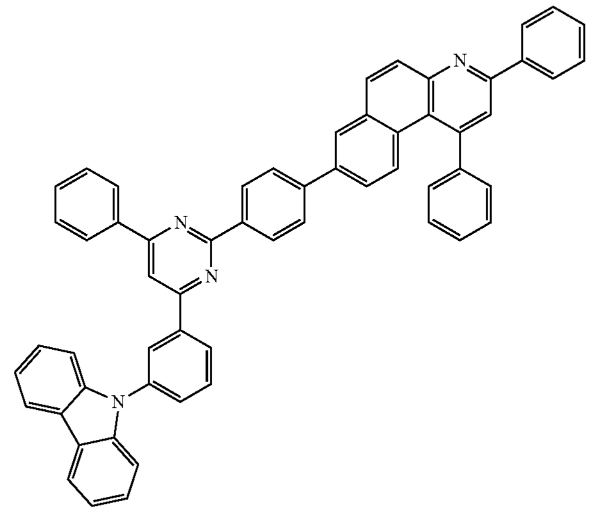
-continued
196
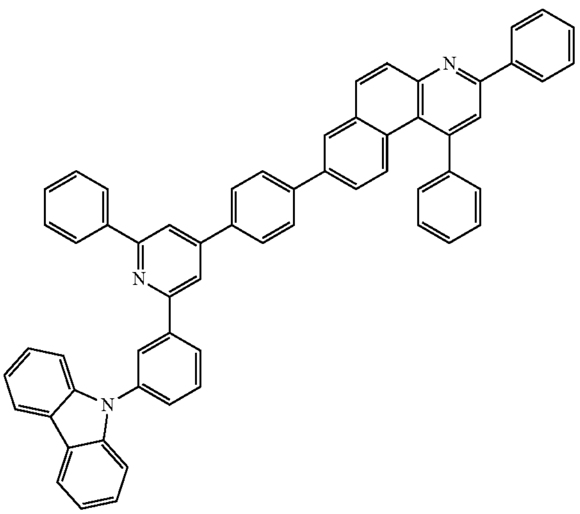
197
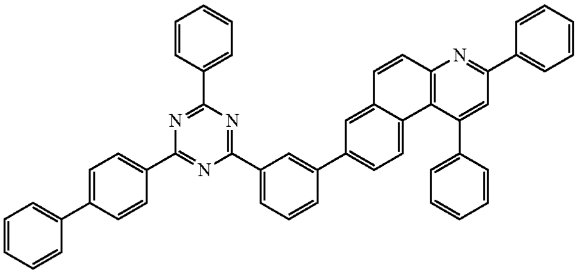
198
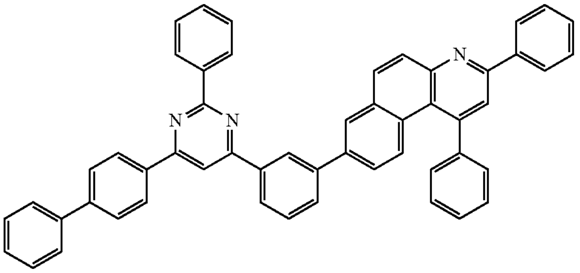
199
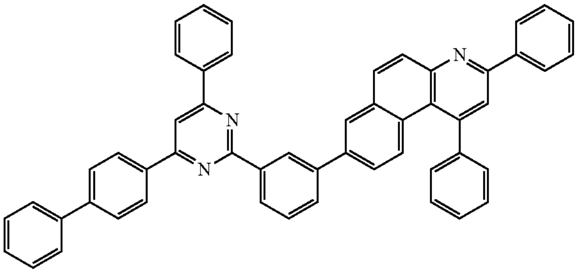

-continued
200
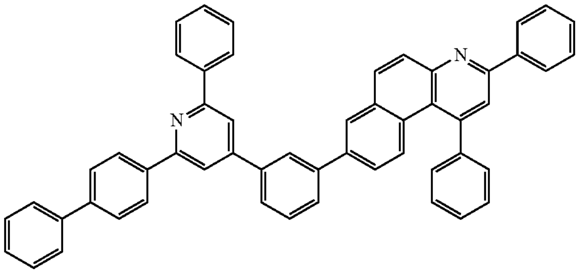
201
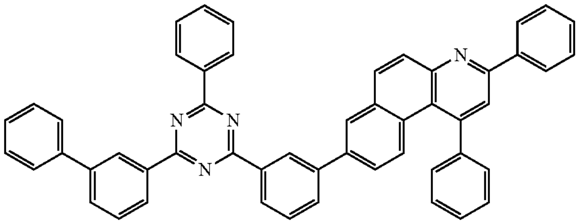
202
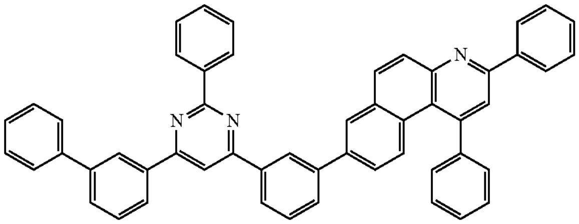
203
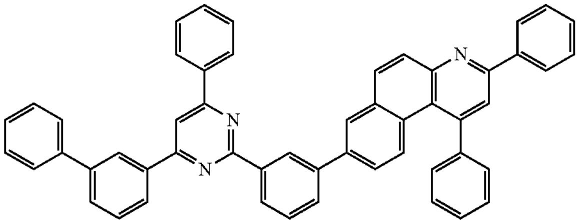
204
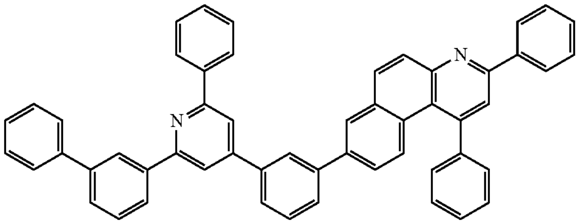
-continued
205
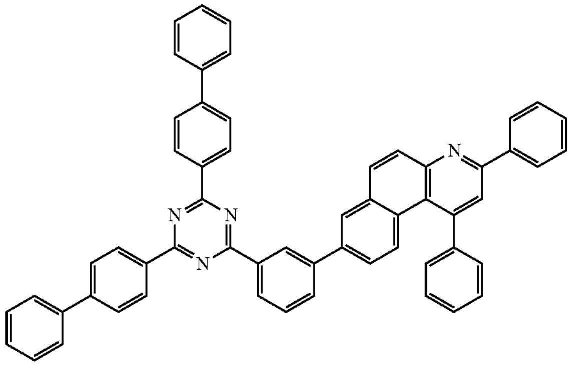
206
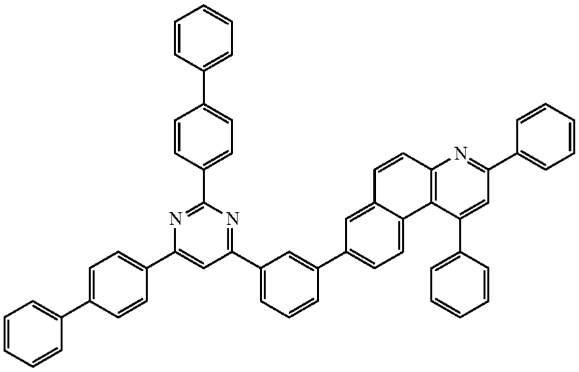
207
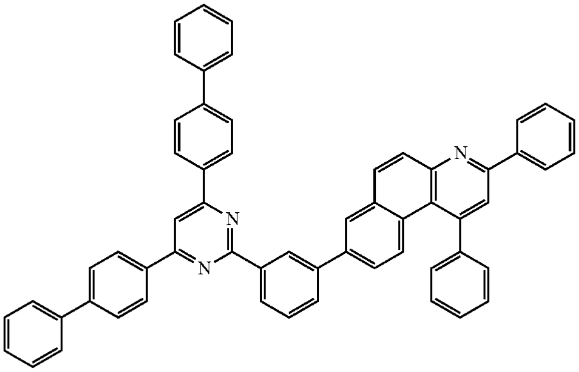
208
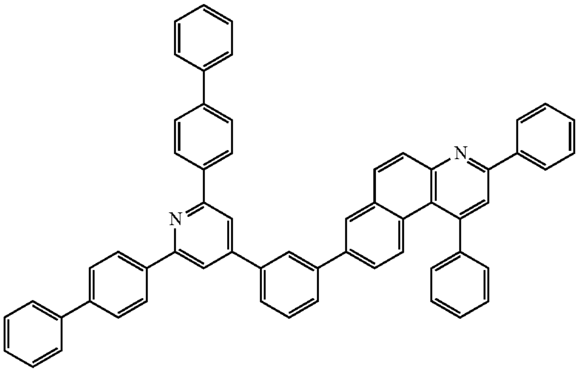

-continued
209
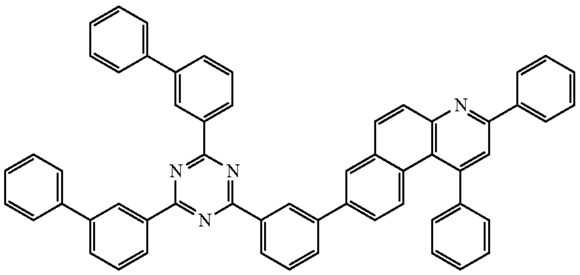
210
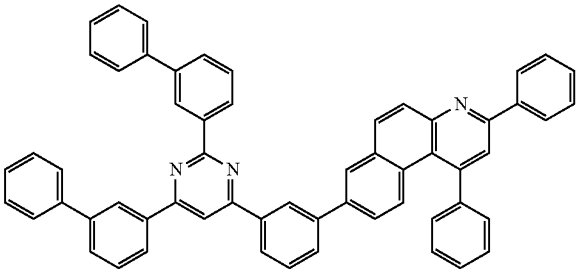
211
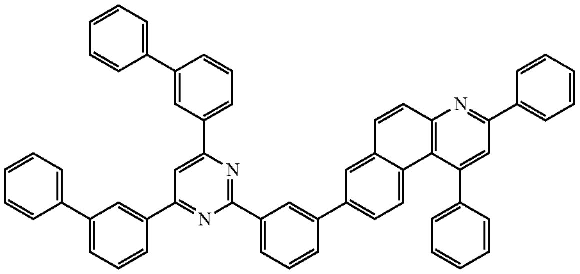
212
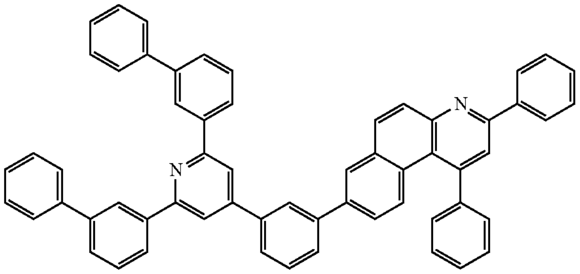
213
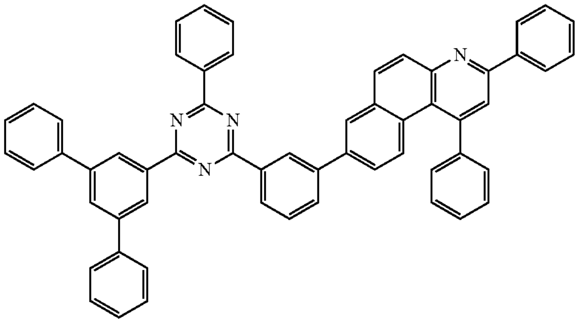
-continued
214
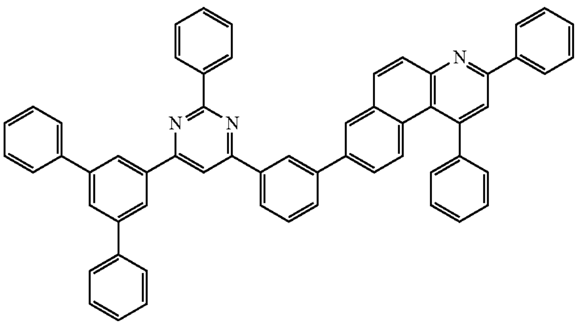
215
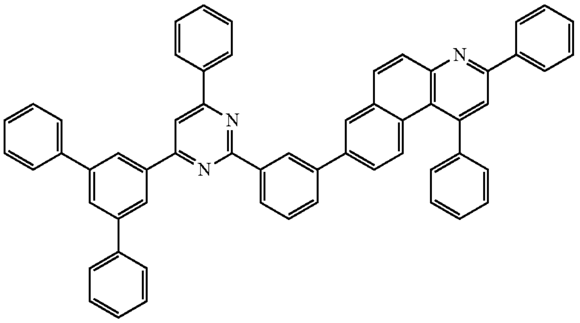
216
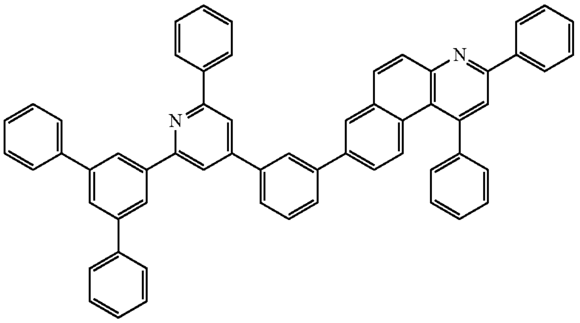
217
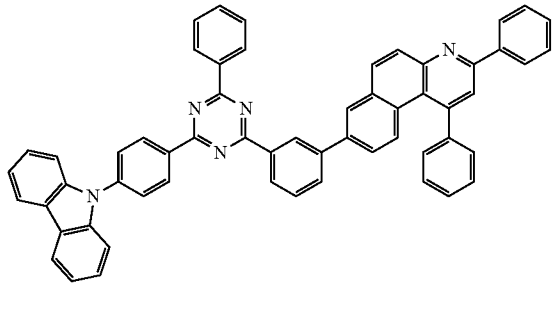

-continued
218
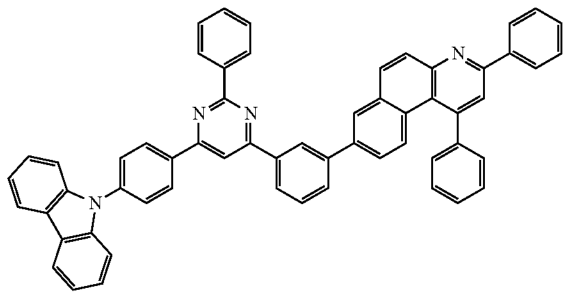
219
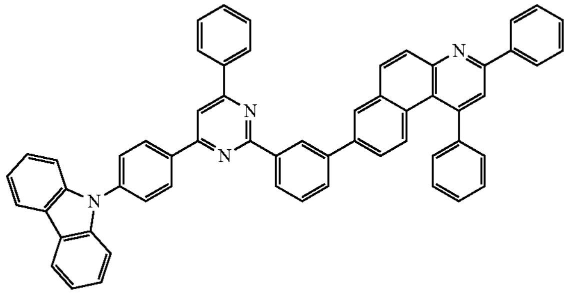
220
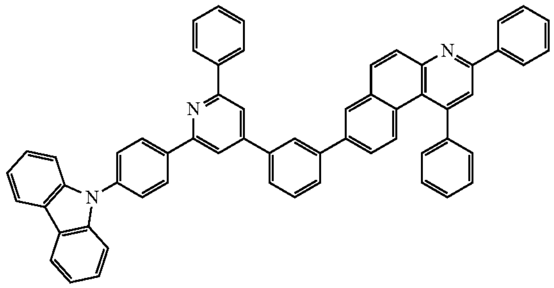
221
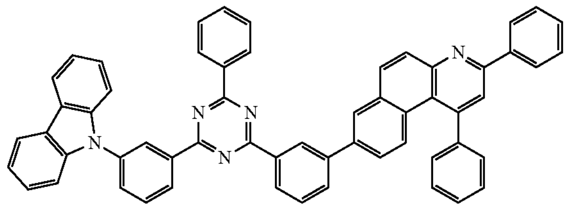
222
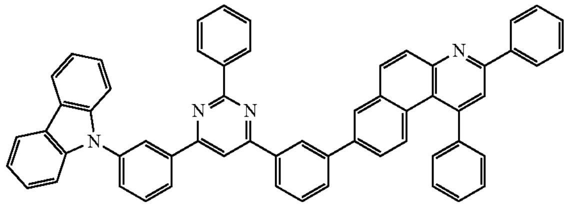
-continued
223
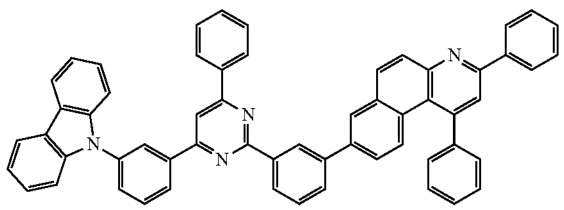
224
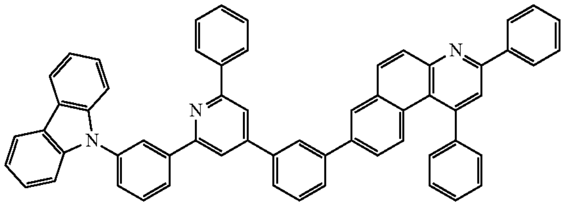
225
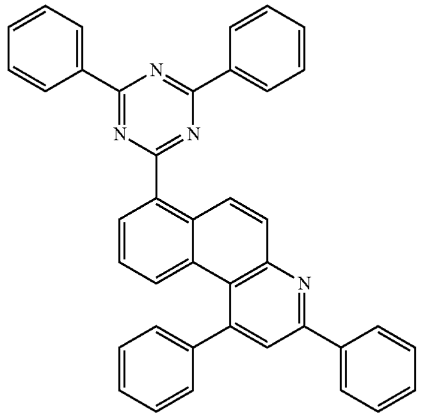
226
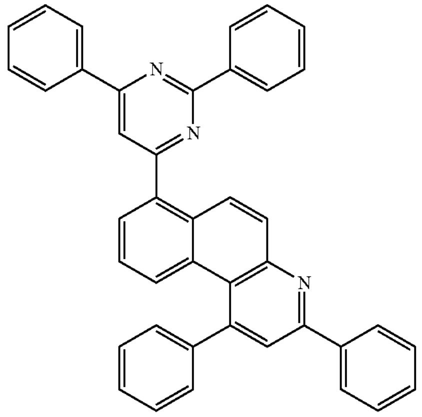

-continued
227
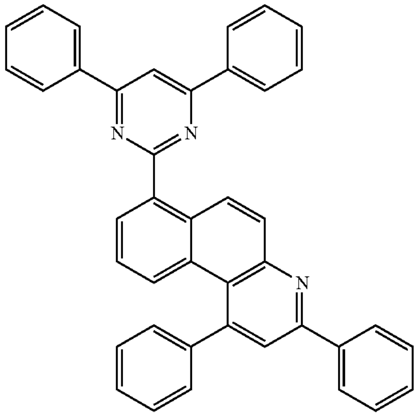
228
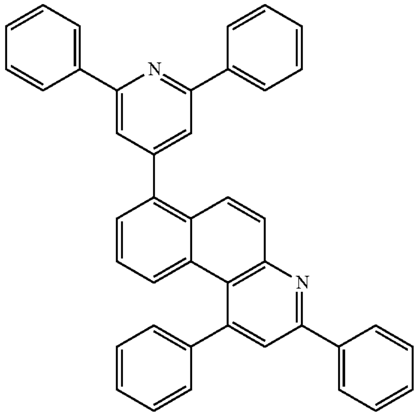
229
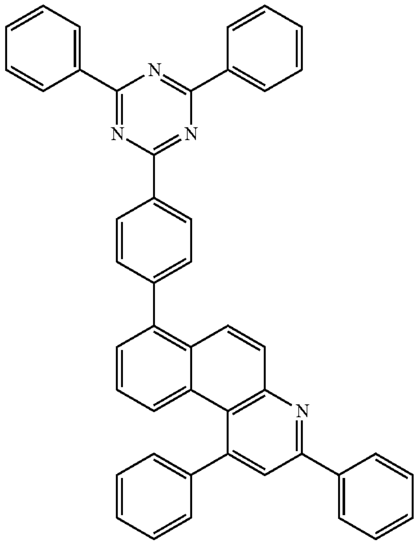
-continued
230
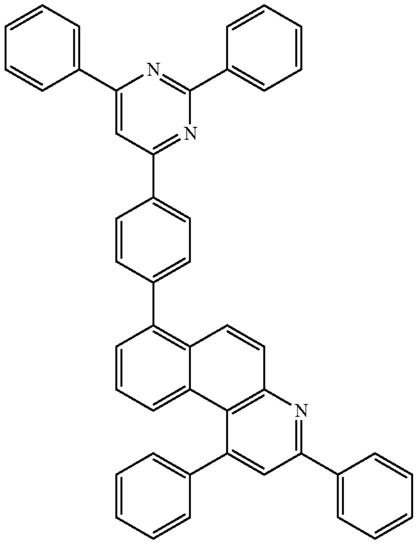
231
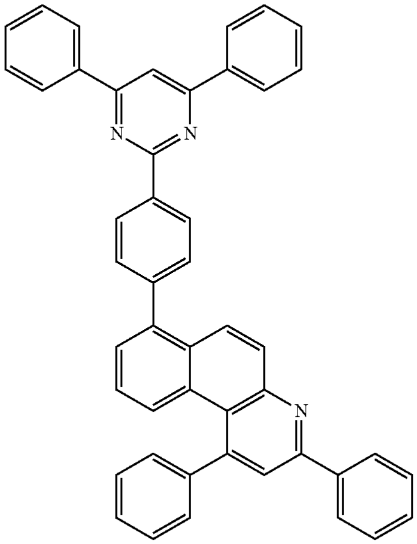
232
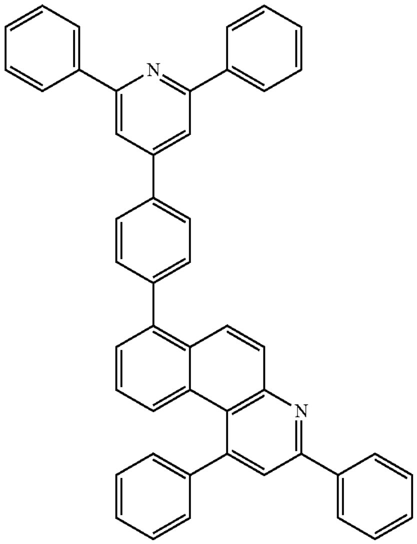

-continued
233
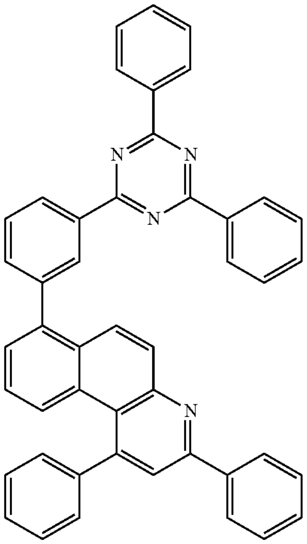
234
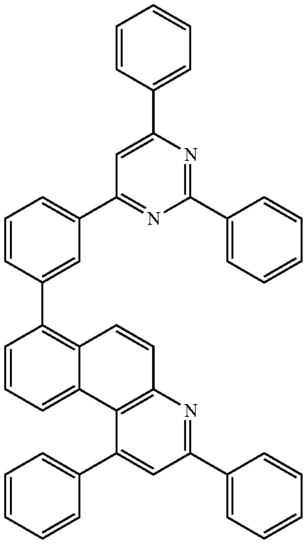
235
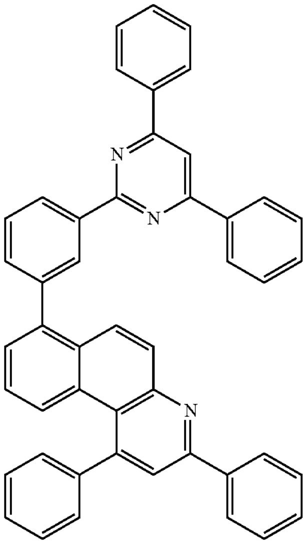
-continued
236
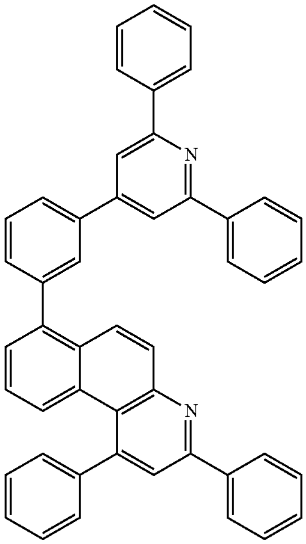
237
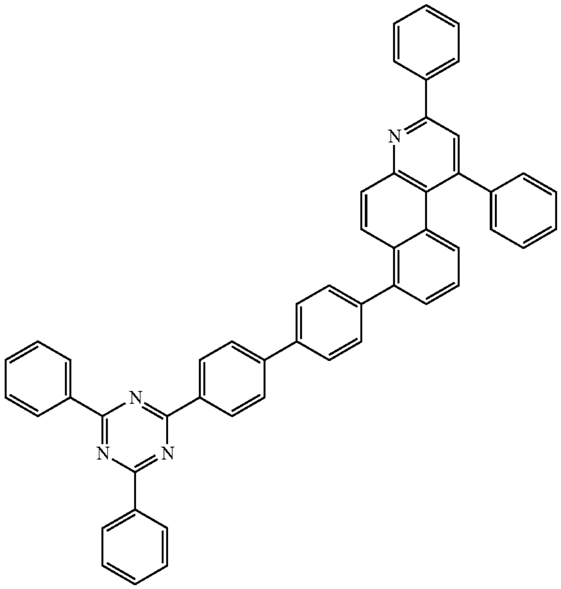

-continued
238
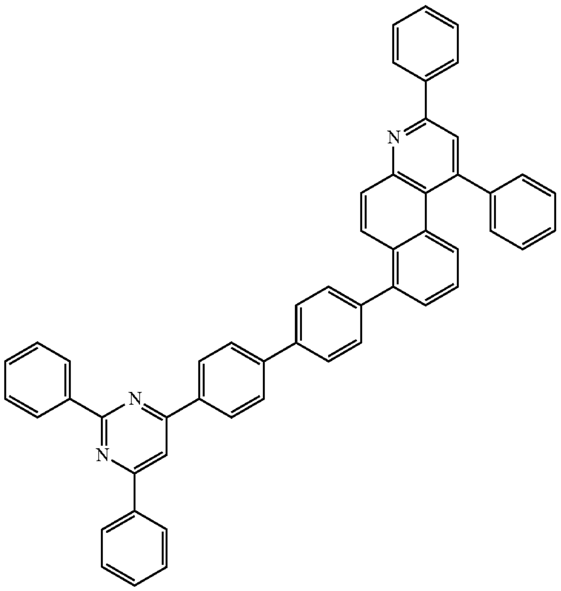
239
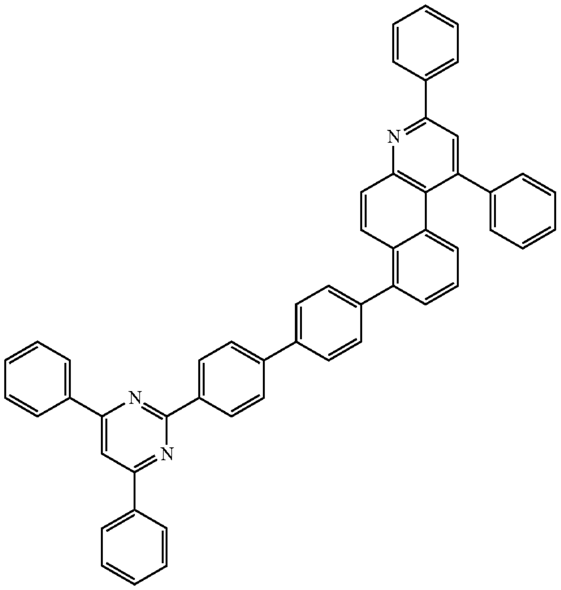
-continued
240
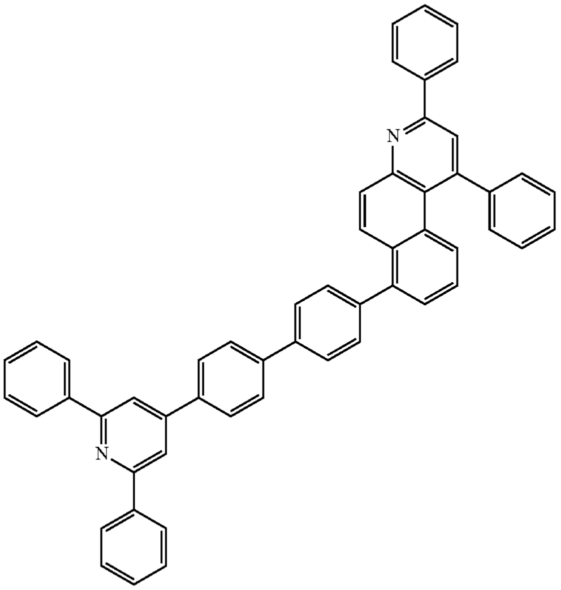
241
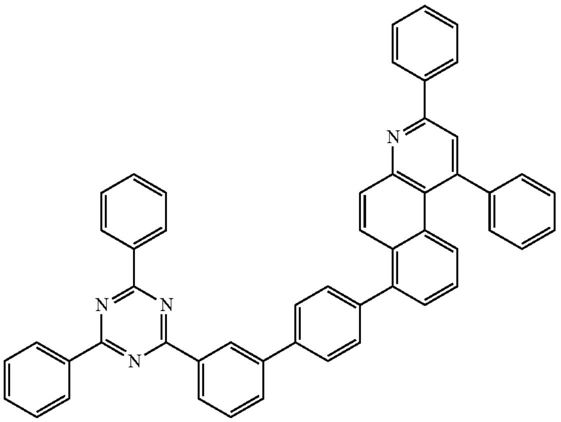
242
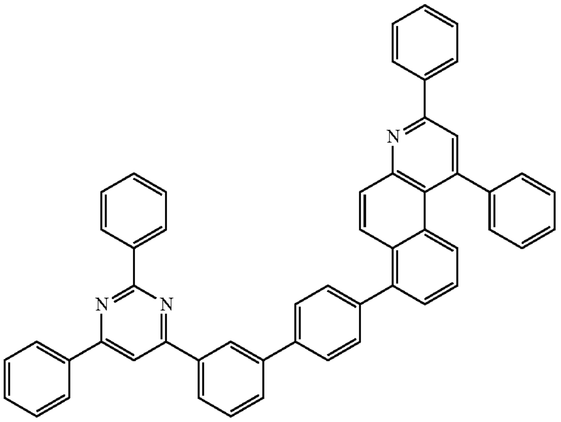

-continued
243
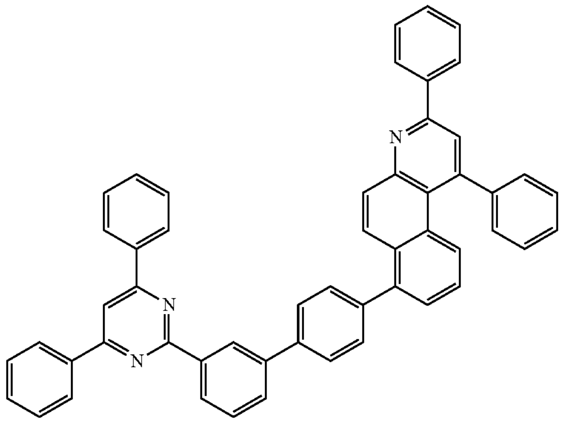
244
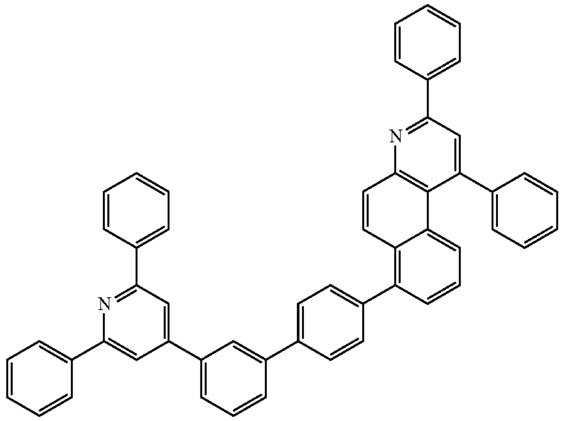
245
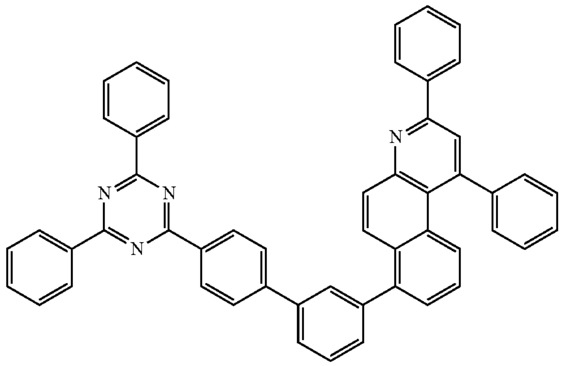
-continued
246
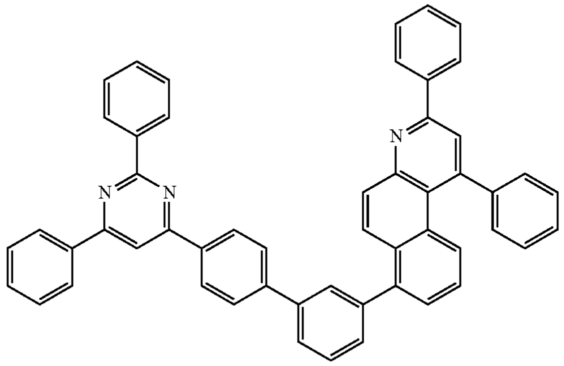
247
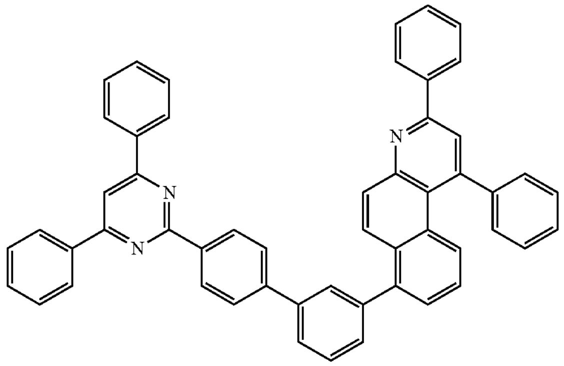
248
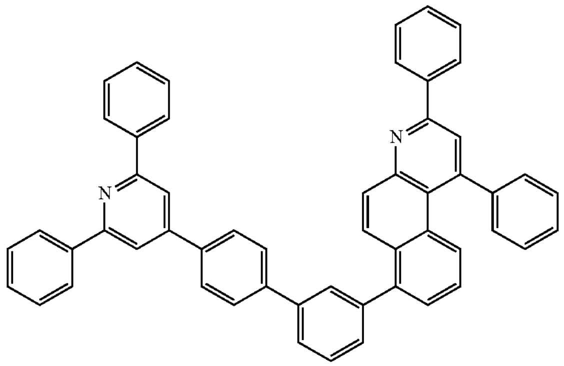

-continued
249
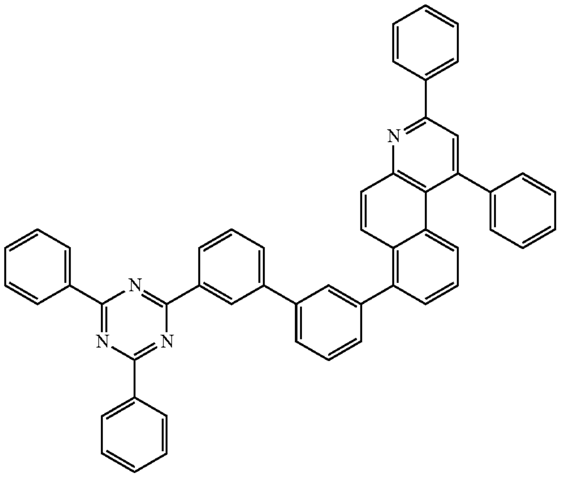
250
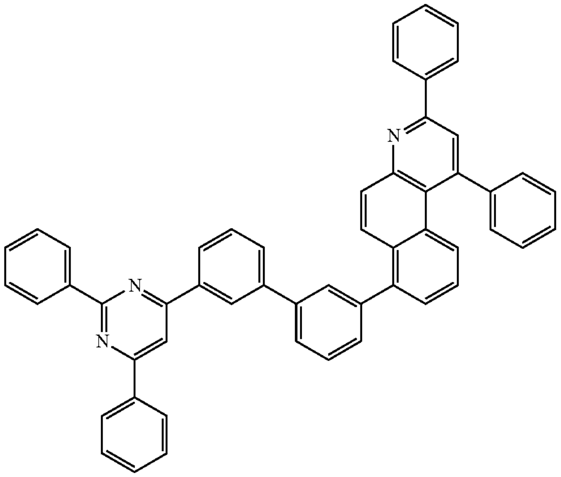
251
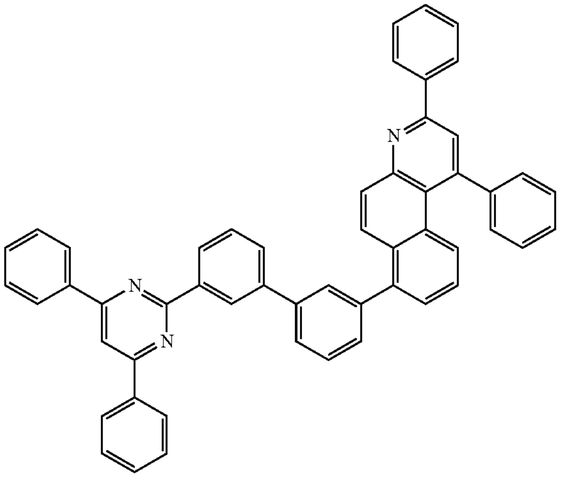
-continued
252
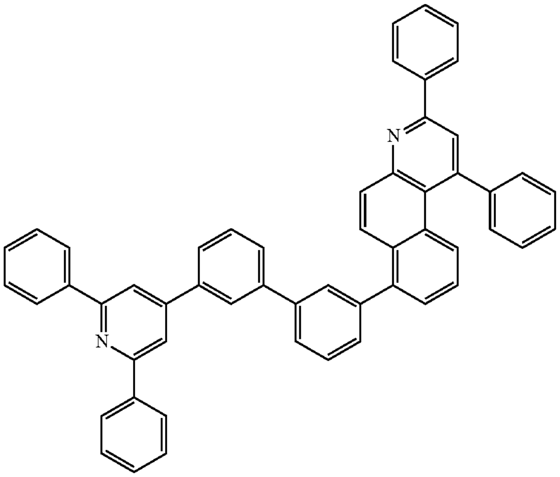
253
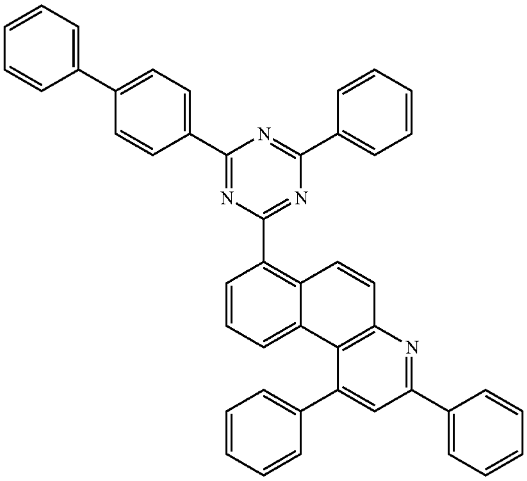
254
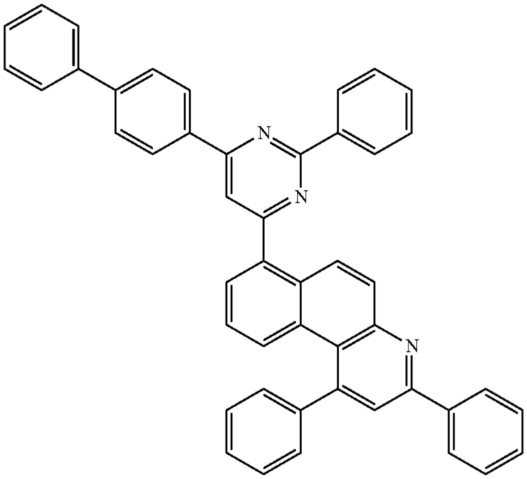

-continued
255
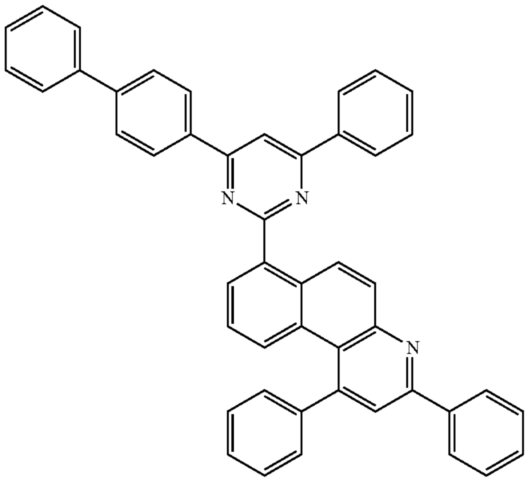
256
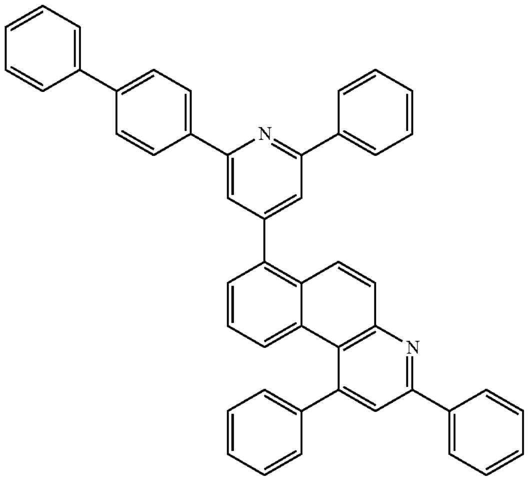
257
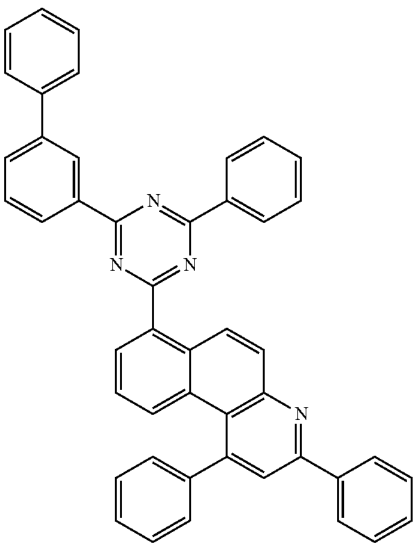
-continued
258
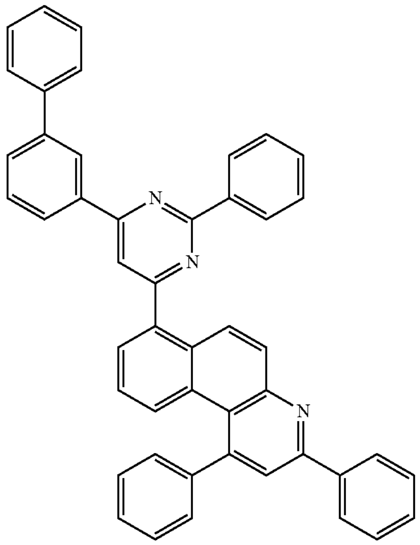
259
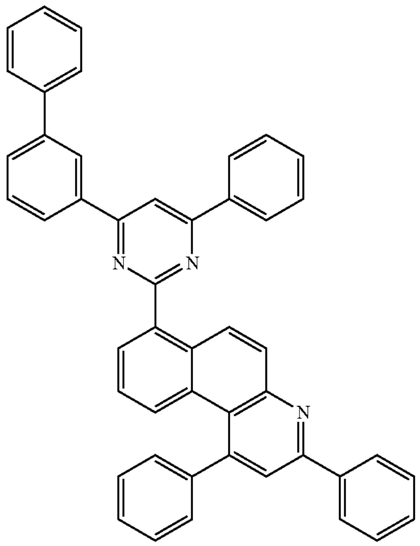
260
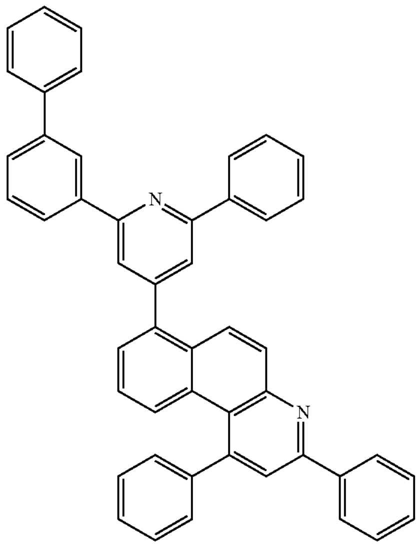

-continued
261
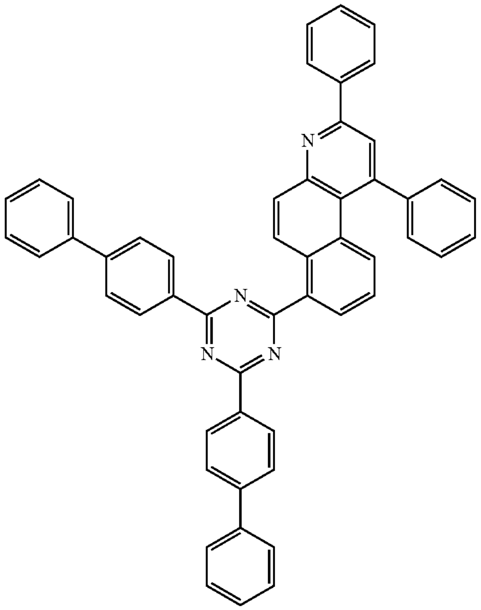
263
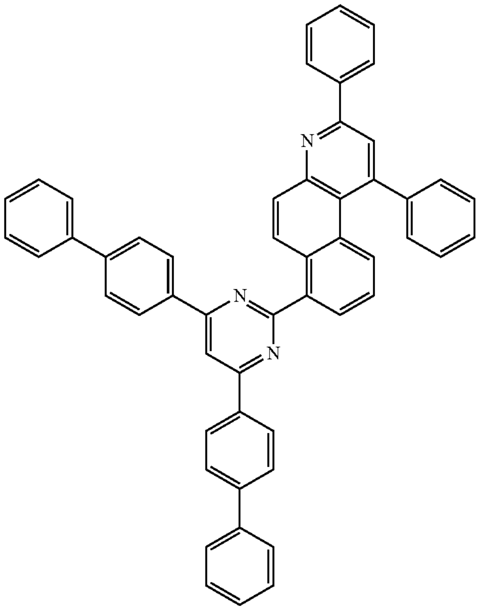
262
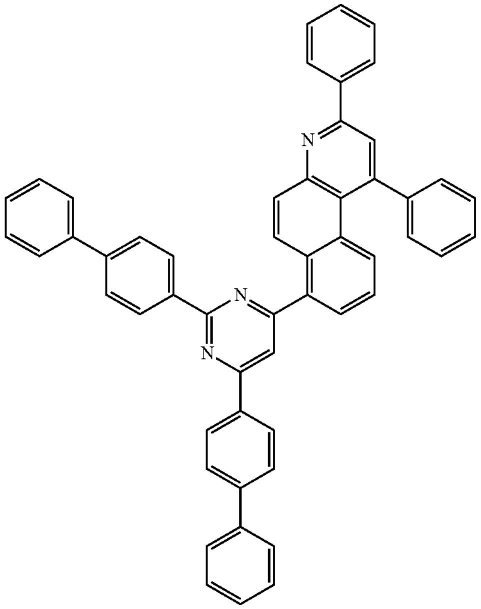
264
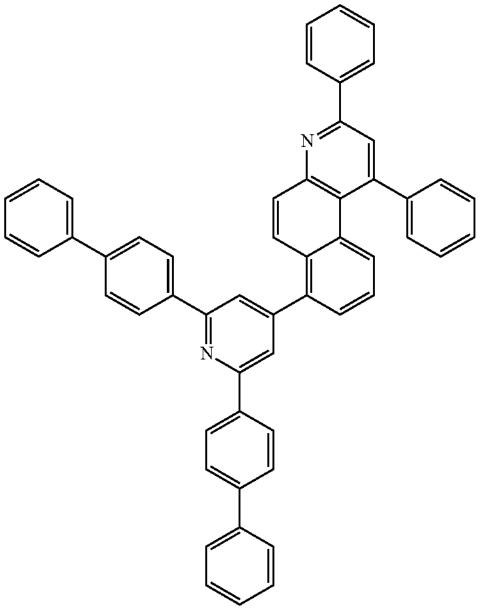

-continued
265
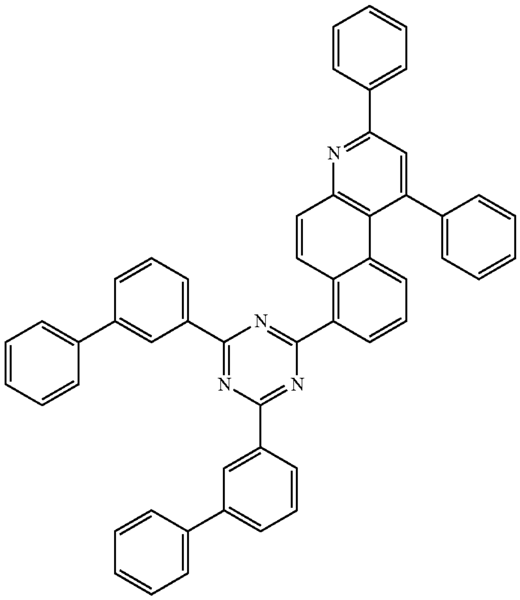
266
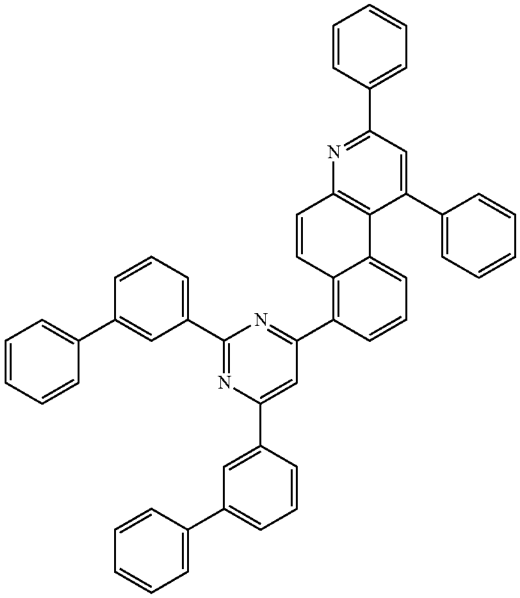
-continued
267
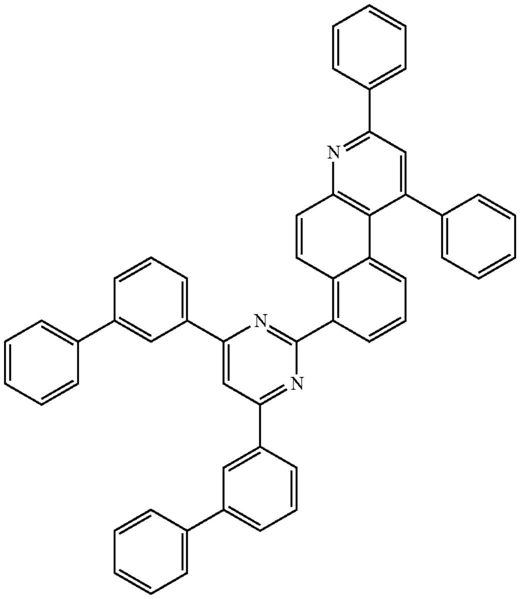
268
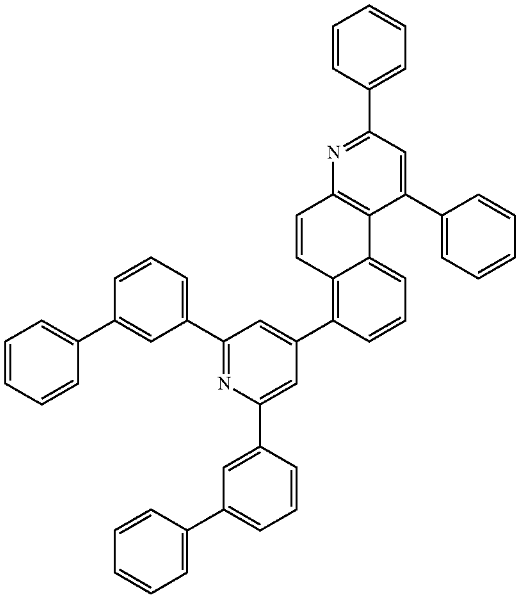

269
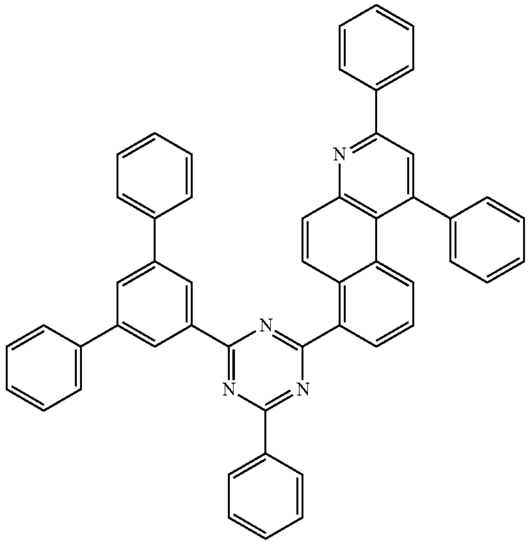
270
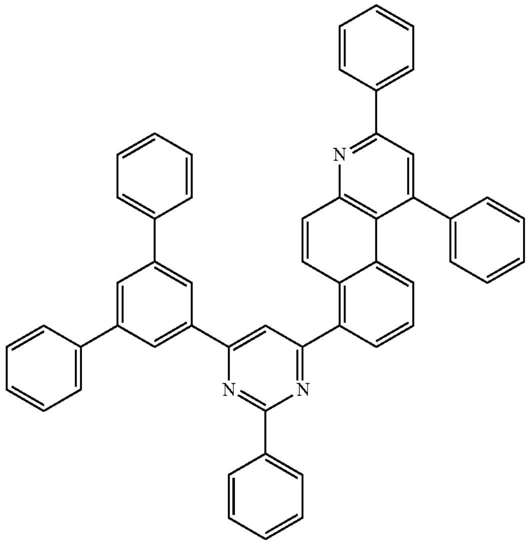
271
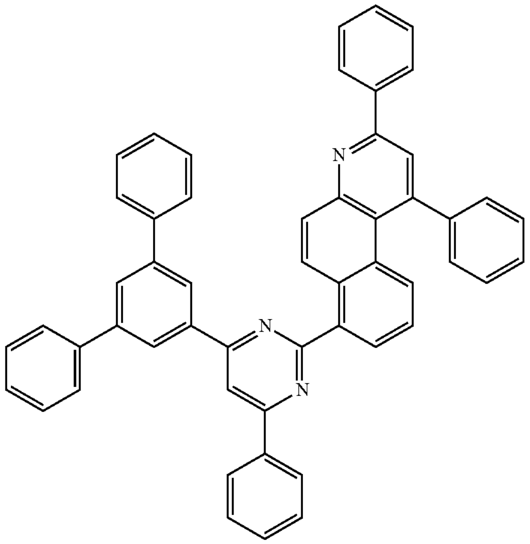
272
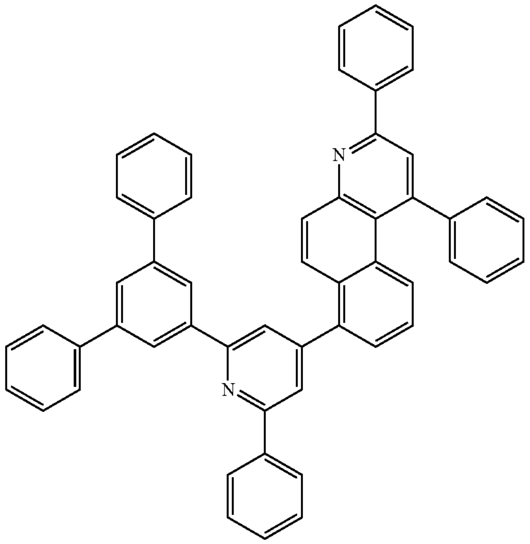

-continued
273
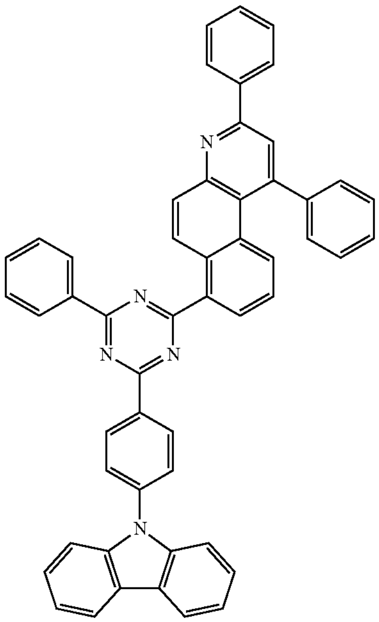
274
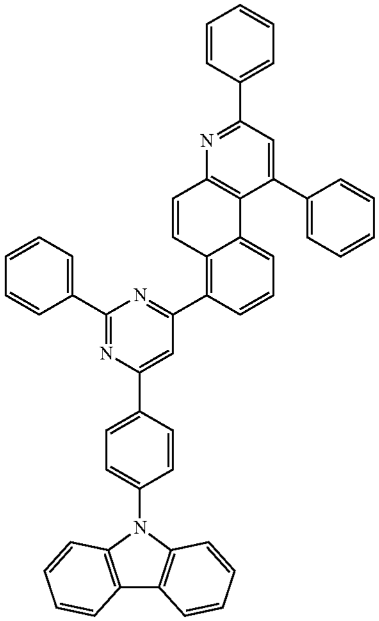
-continued
275
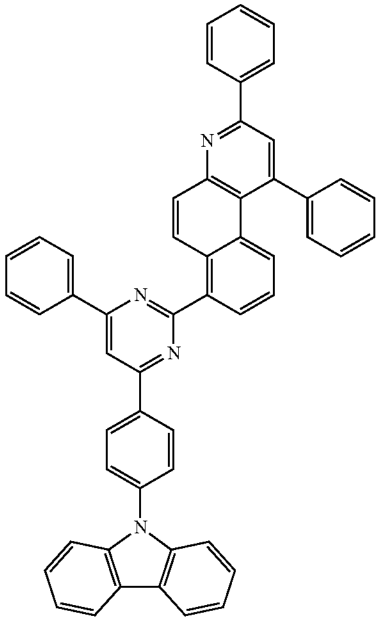
276
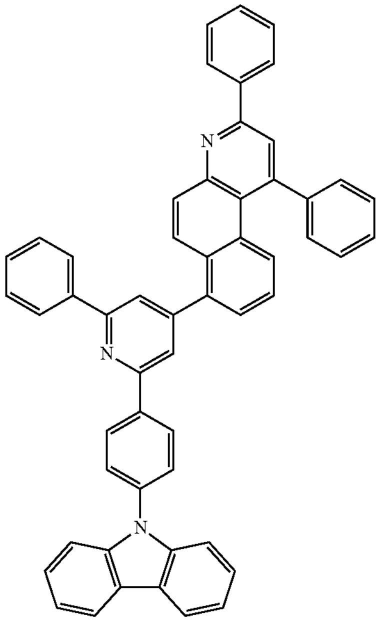

-continued
277
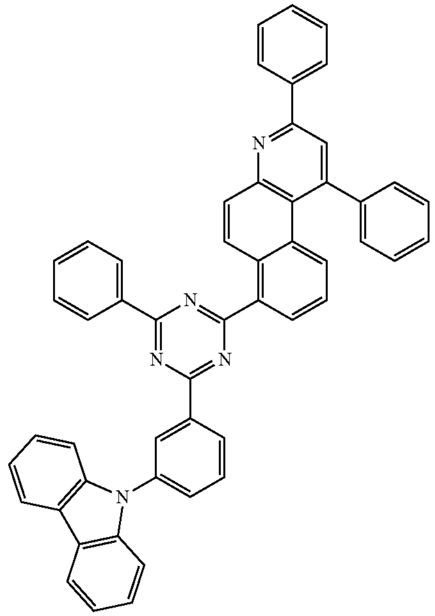
278
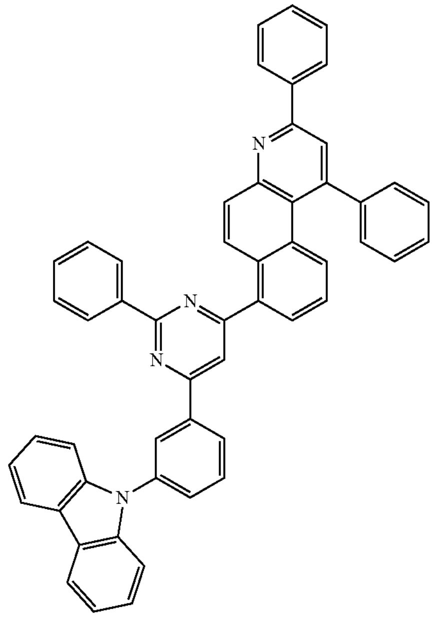
-continued
279
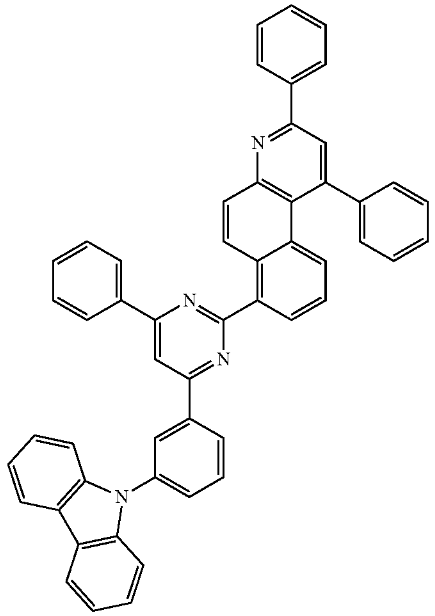
280
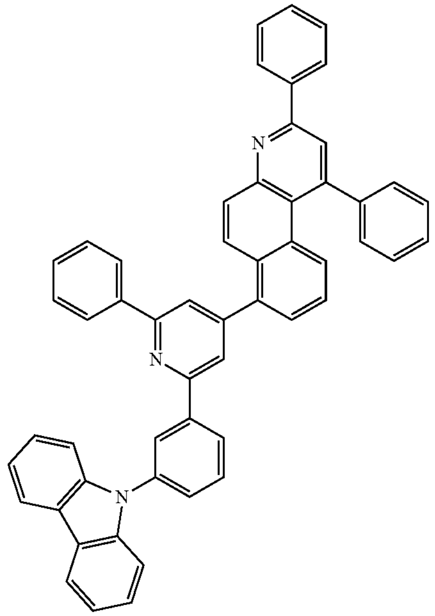

281
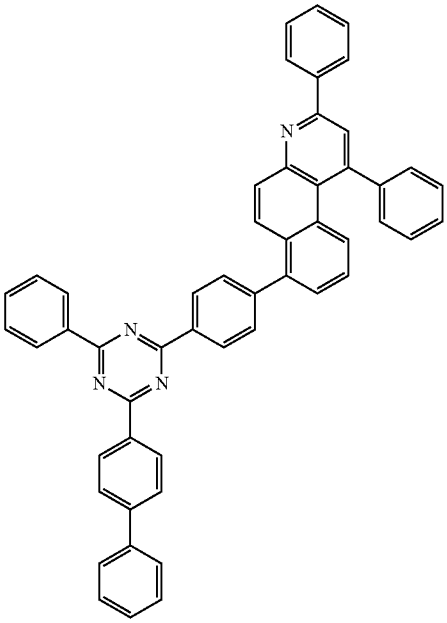
282
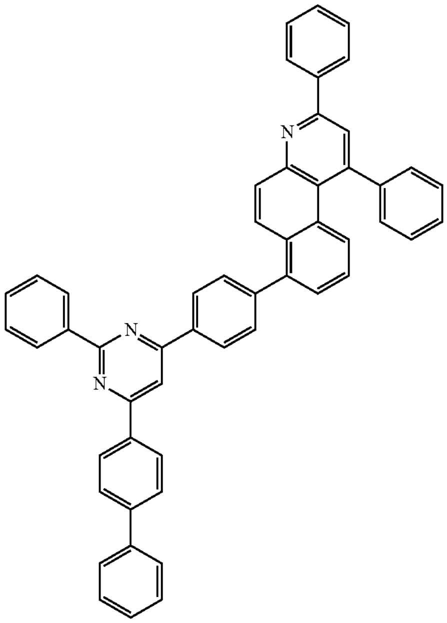
283
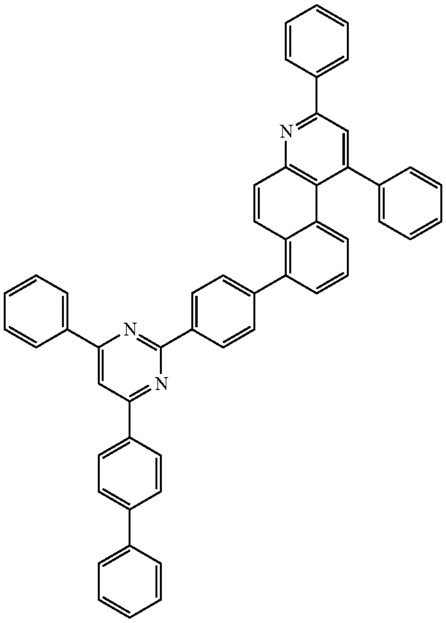
284
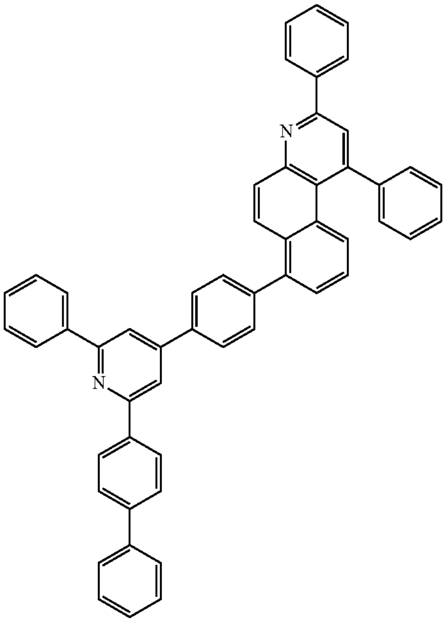

-continued
285
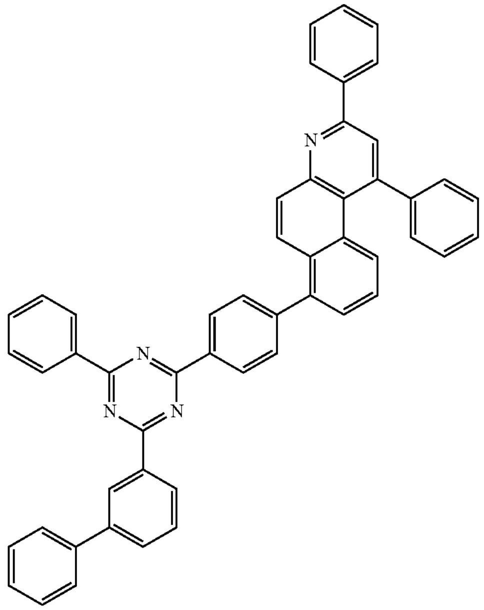
286
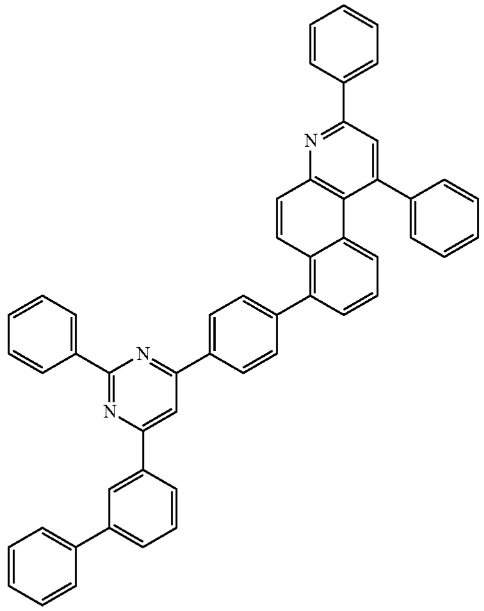
-continued
287
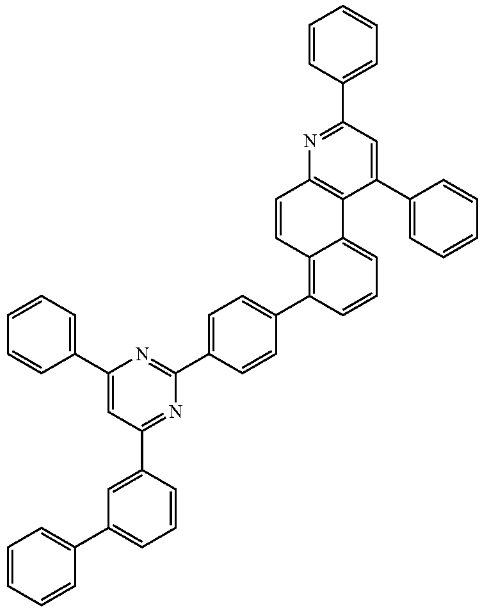
288
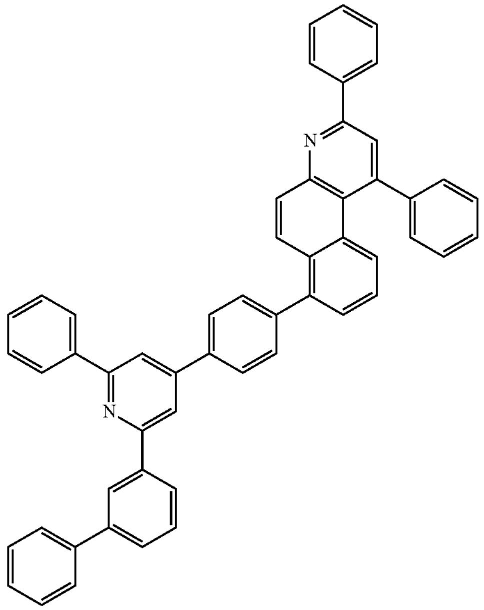

289
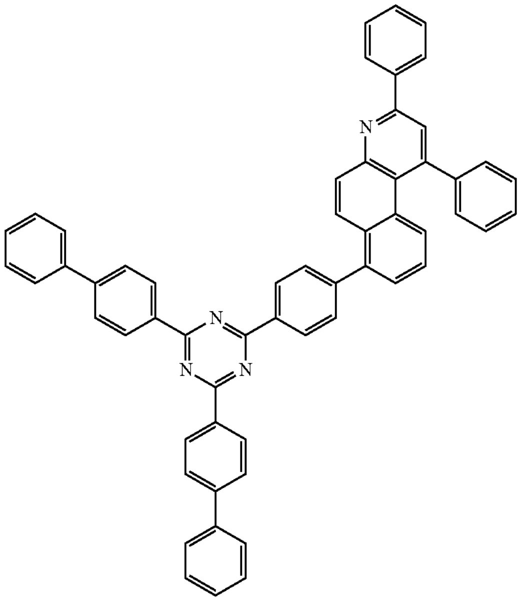
290
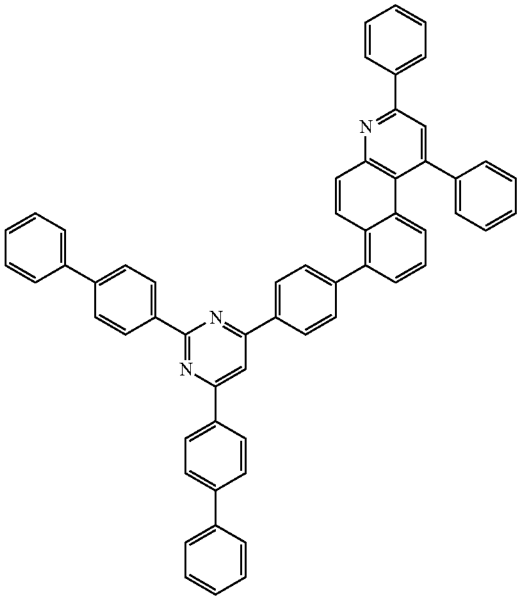
291
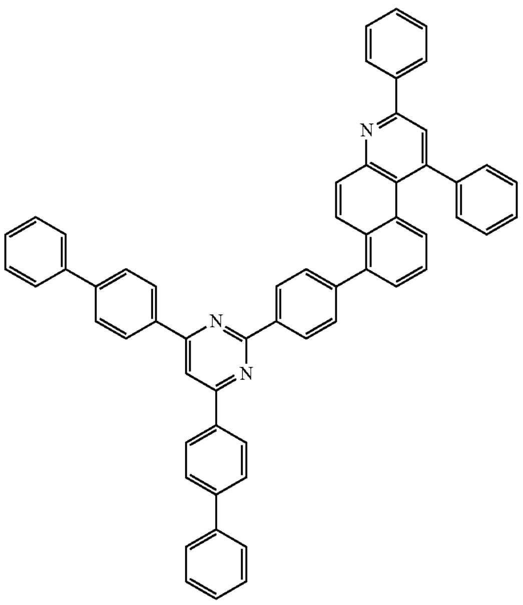
292
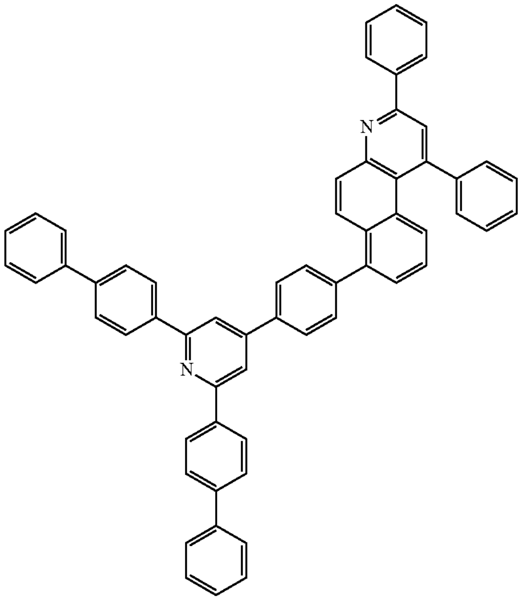

-continued
293
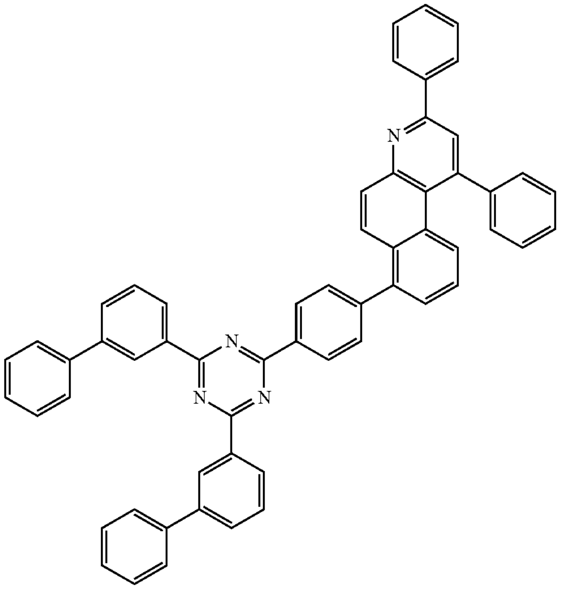
294
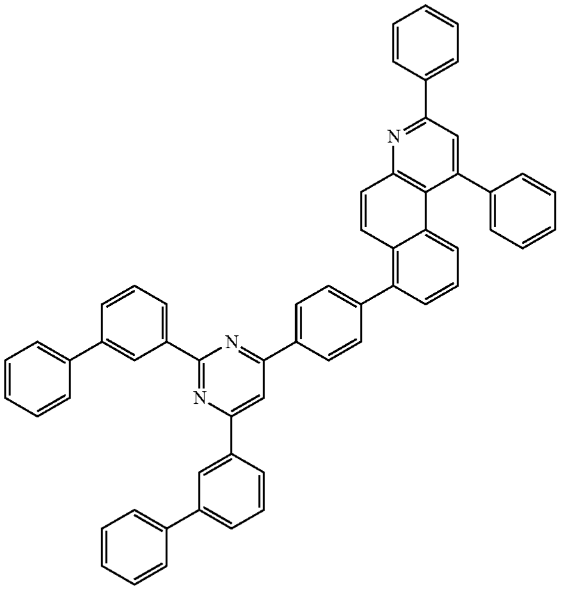
-continued
295
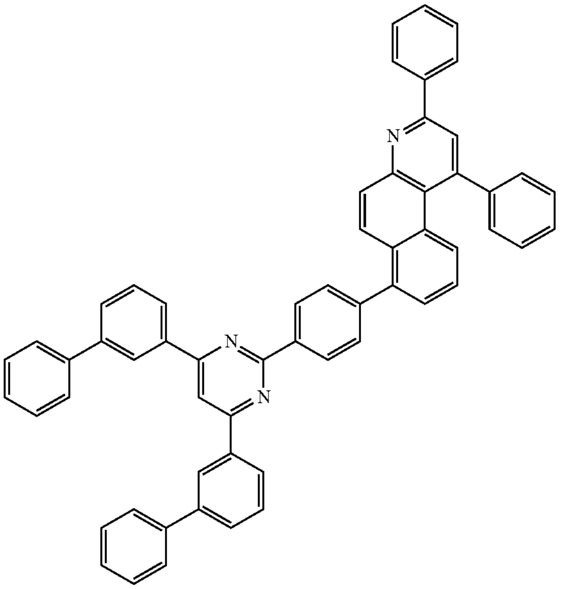
296
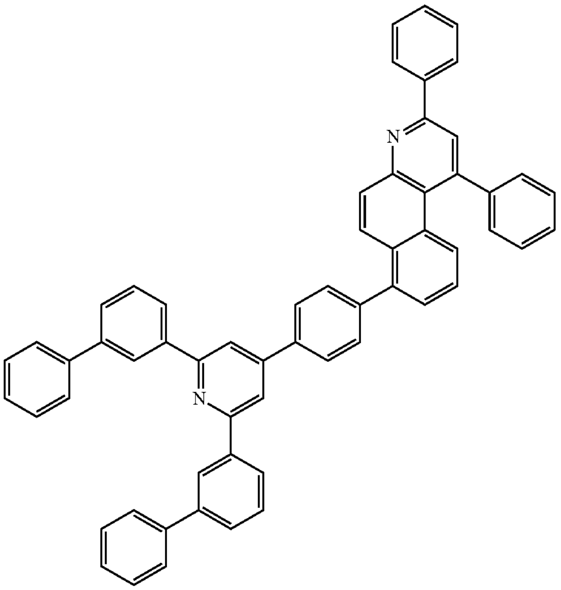

-continued
297
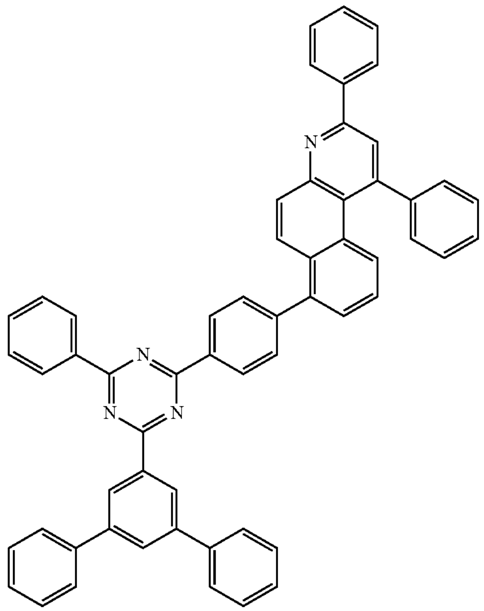
298
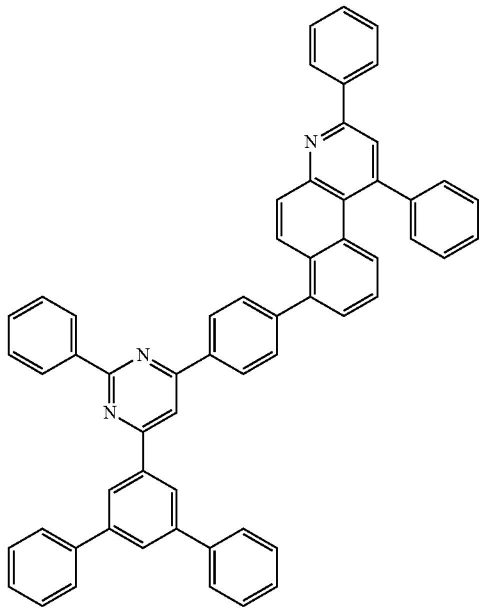
-continued
299
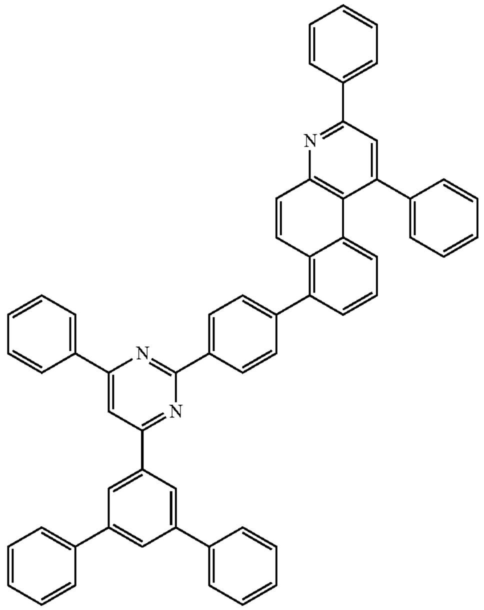
300
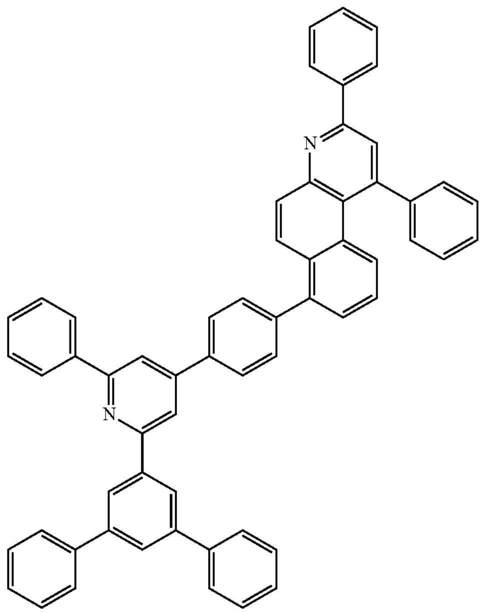

-continued
301
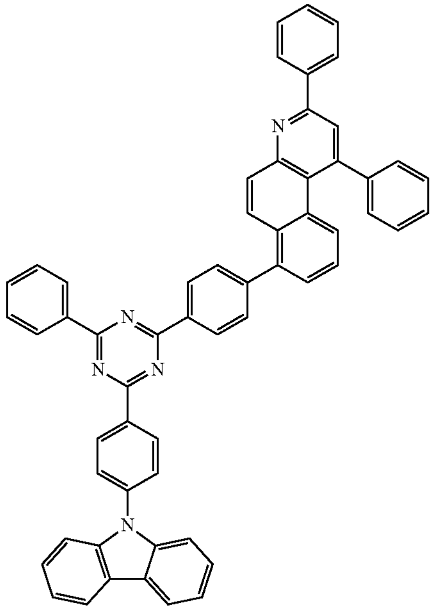
302
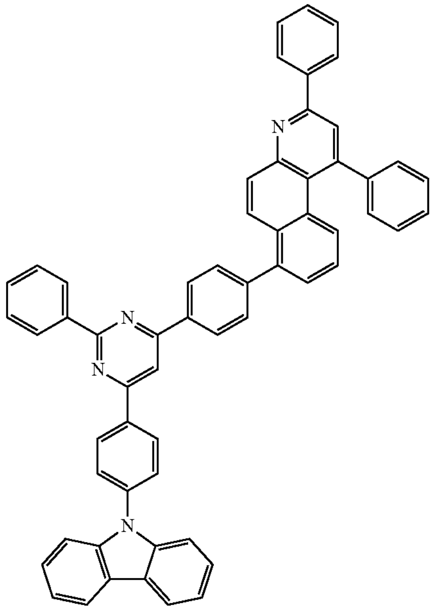
-continued
303
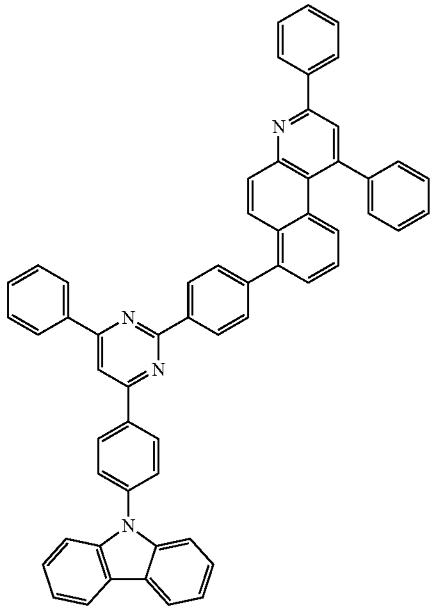
304
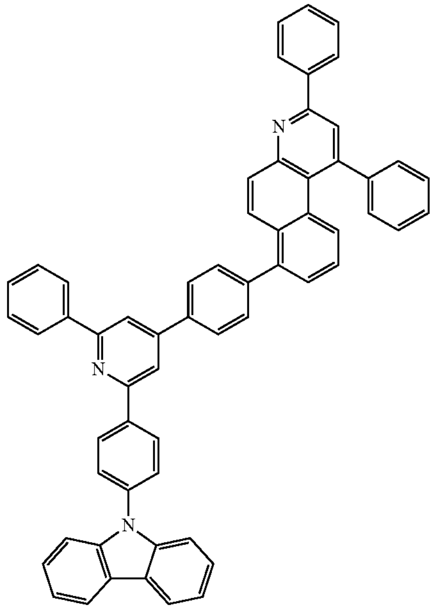

305
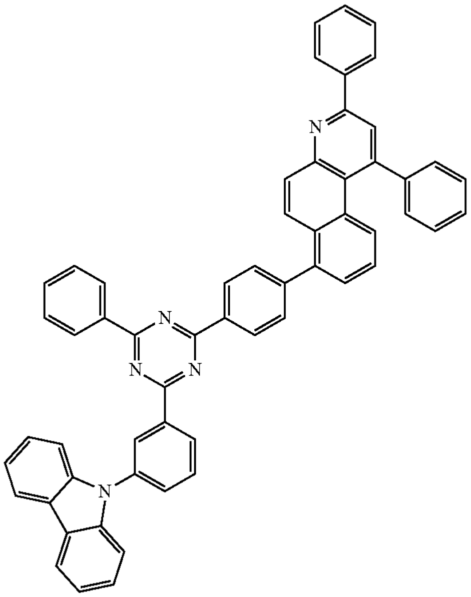
306
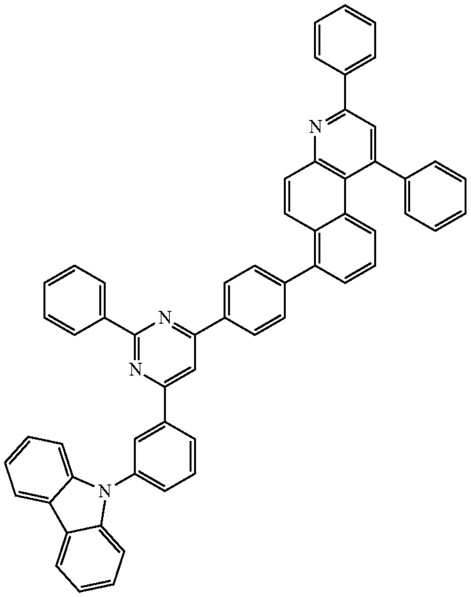
307
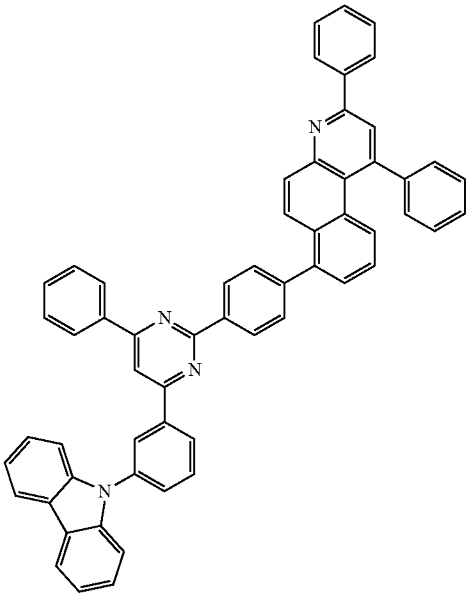
308
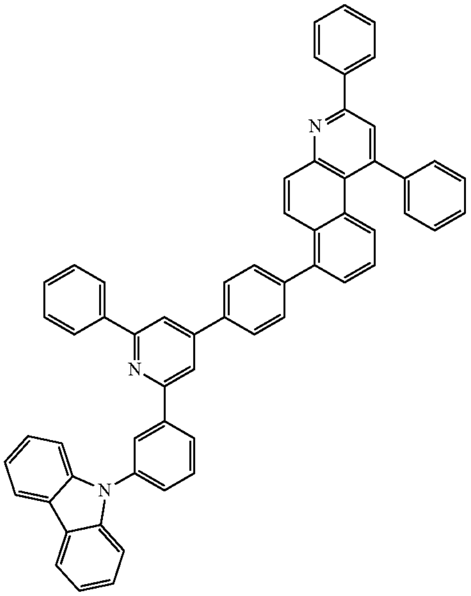
309
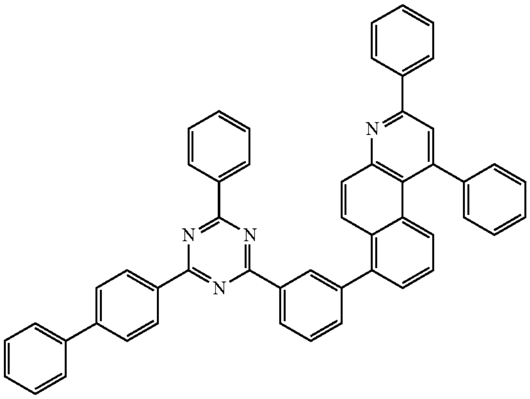

-continued
310
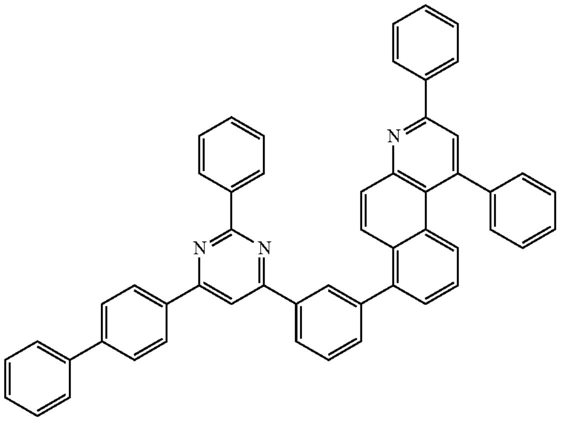
311
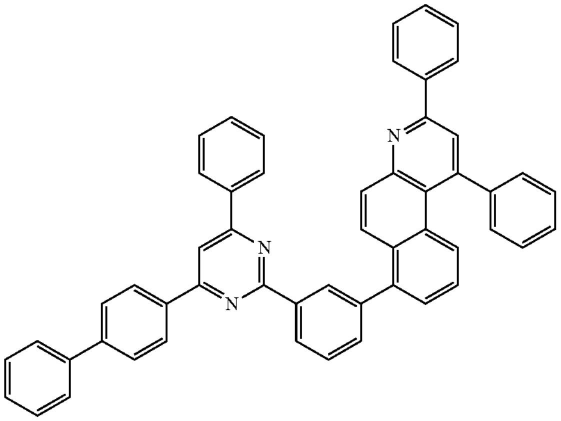
312
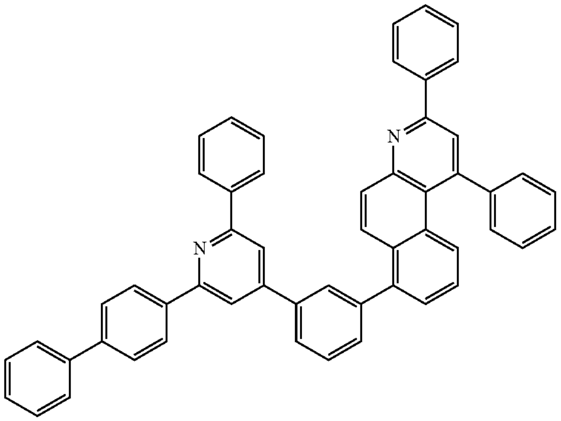
-continued
313
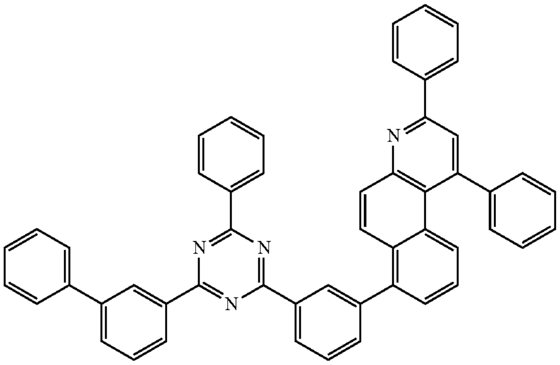
314
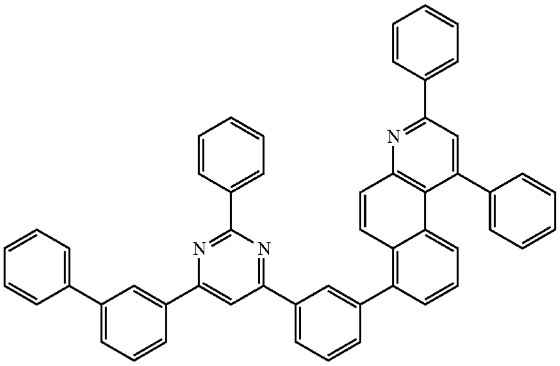
315
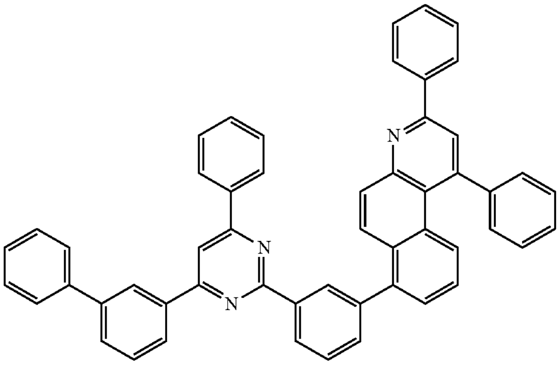
316
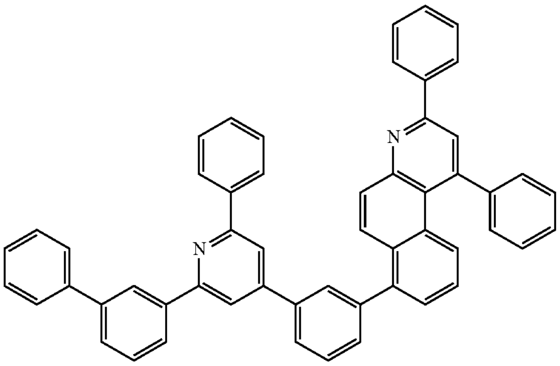

-continued
317
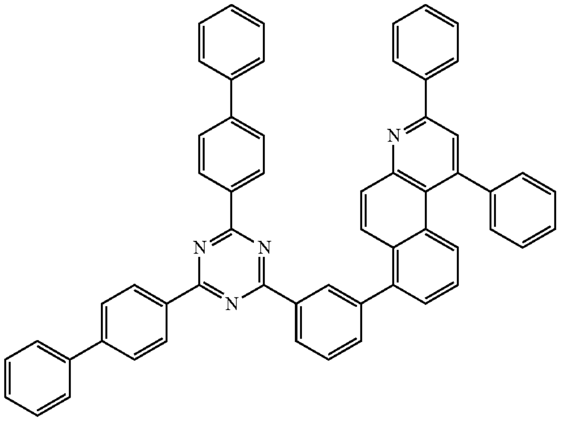
318
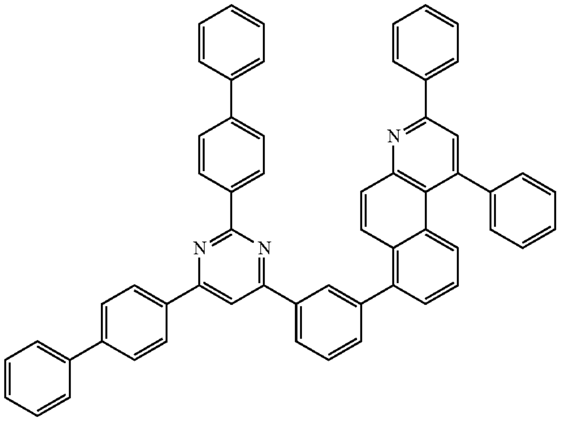
319
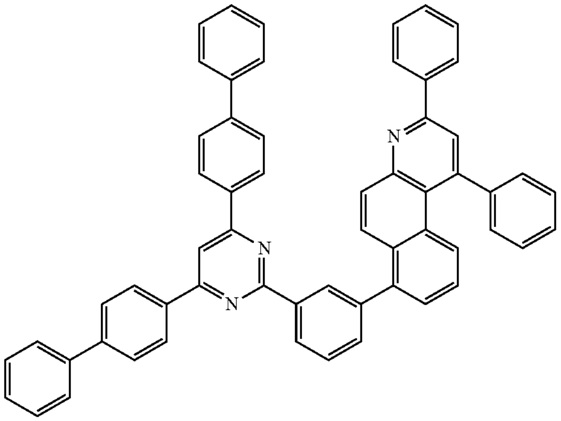
-continued
320
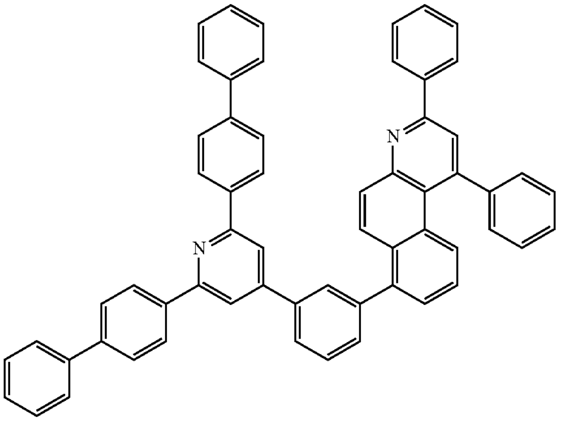
321
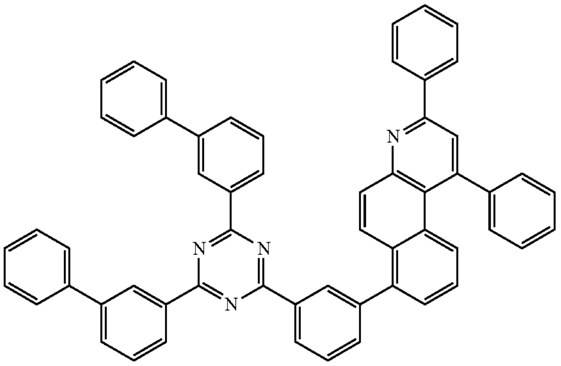
322
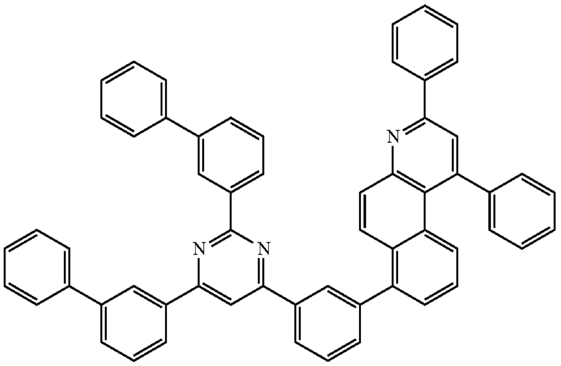
323
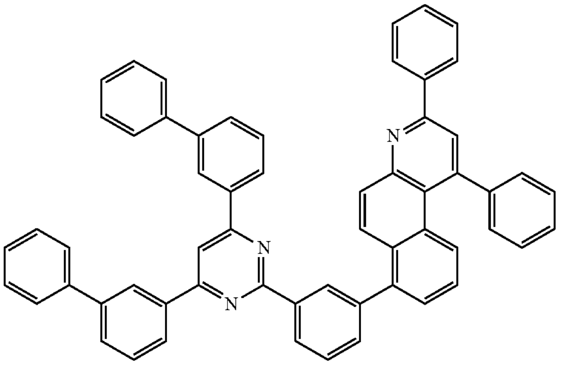

-continued
324
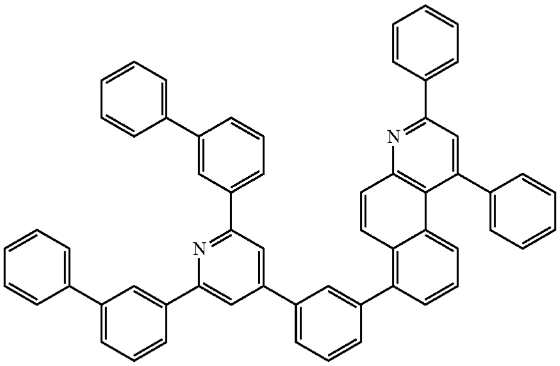
325
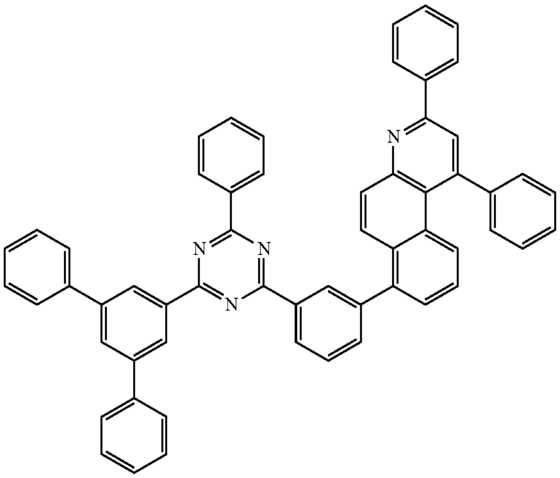
326
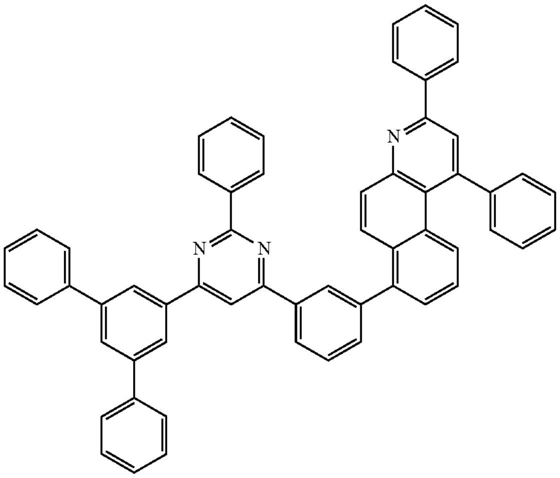
-continued
327
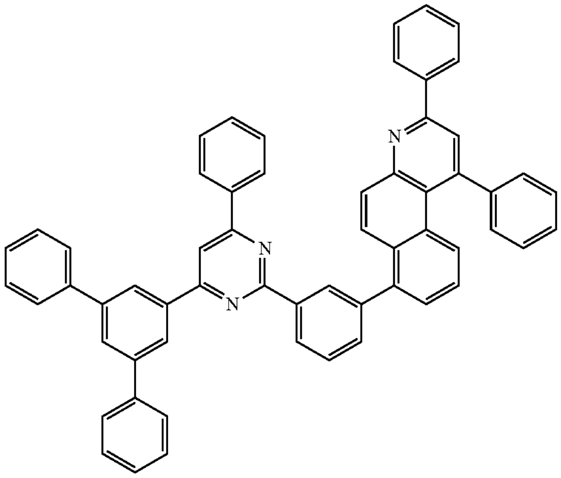
328
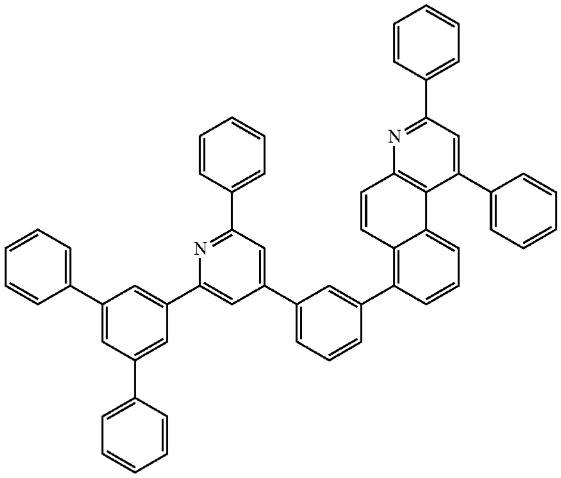
329
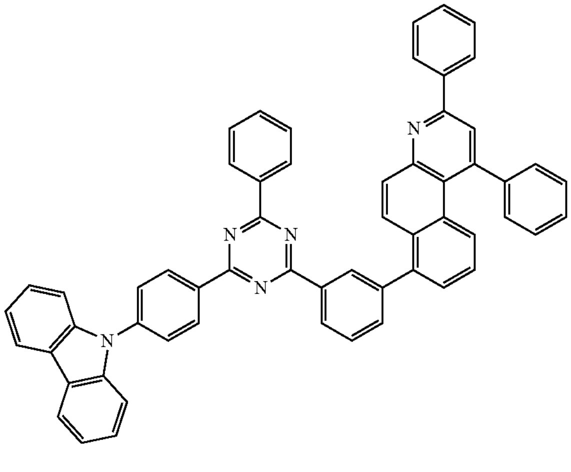

-continued
330
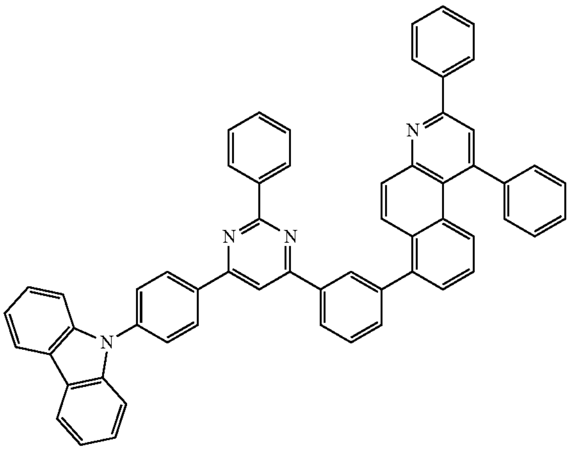
331
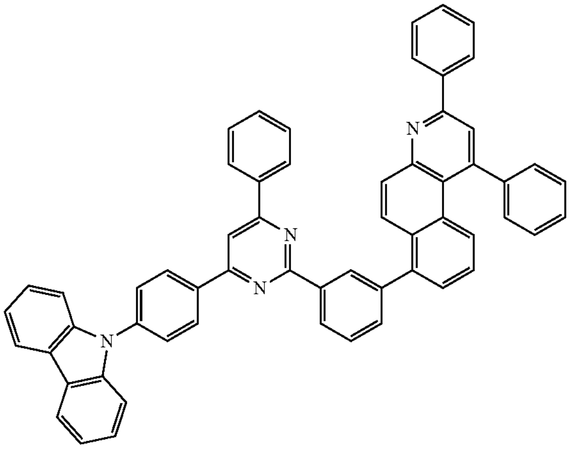
332
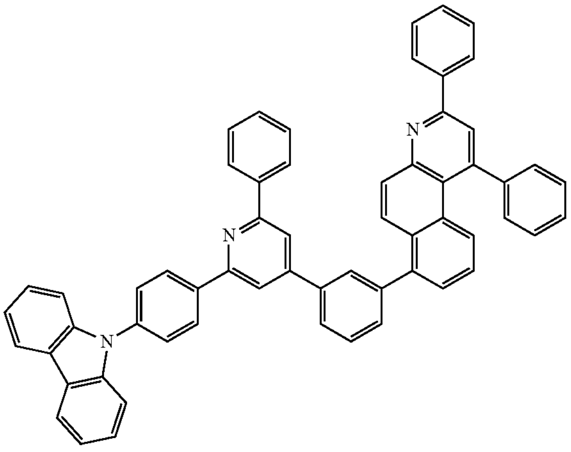
-continued
333
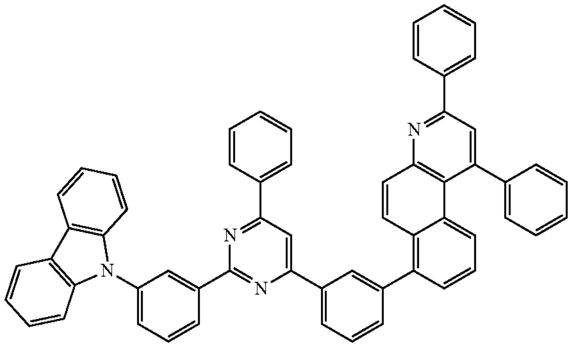
334
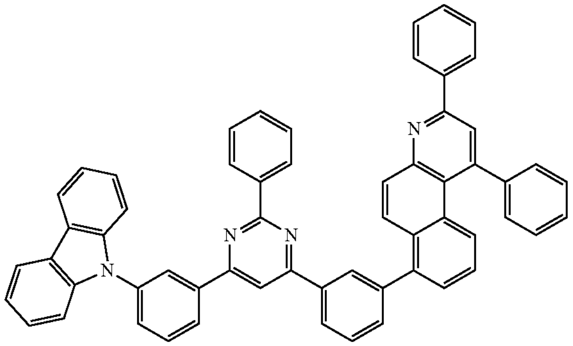
335
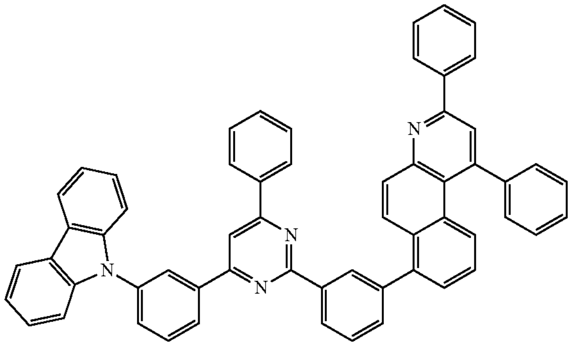
336
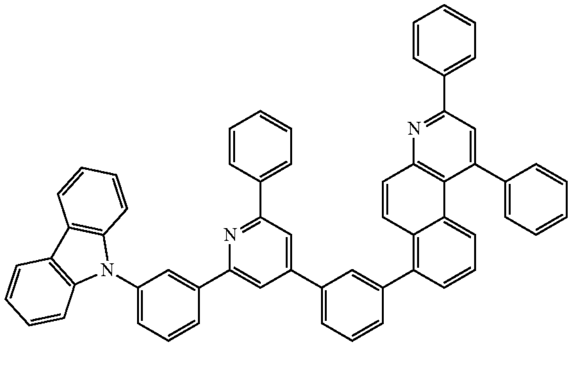

337
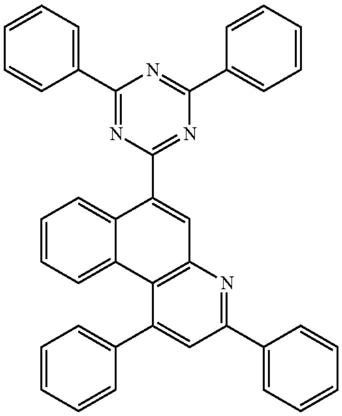
338
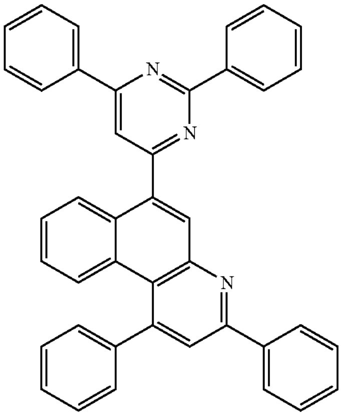
339
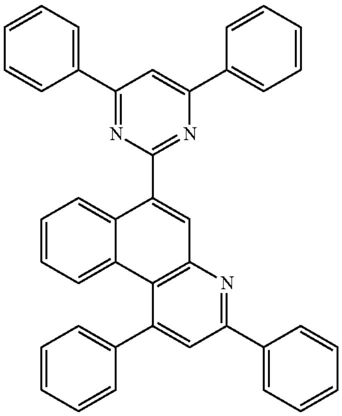
-continued
340
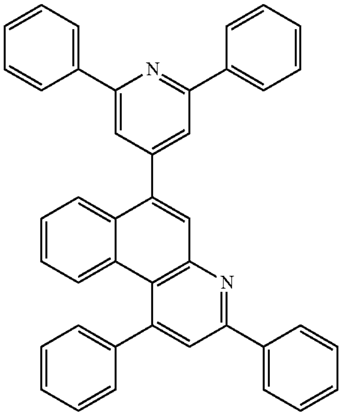
341
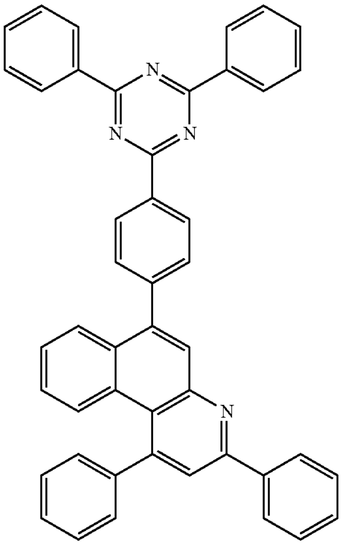
342
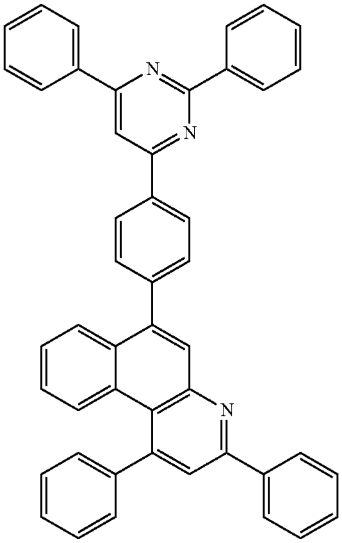

-continued
343
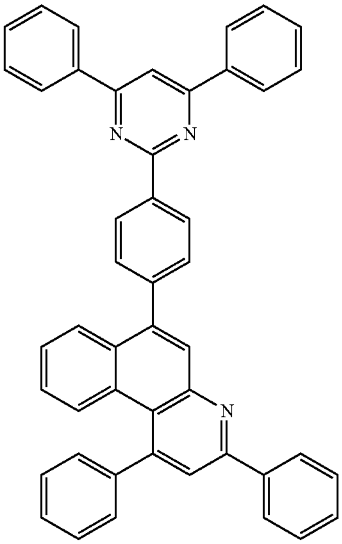
344
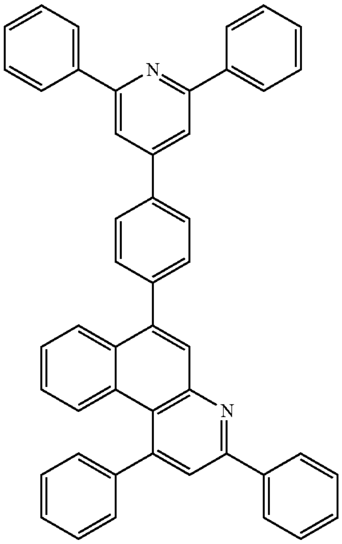
345
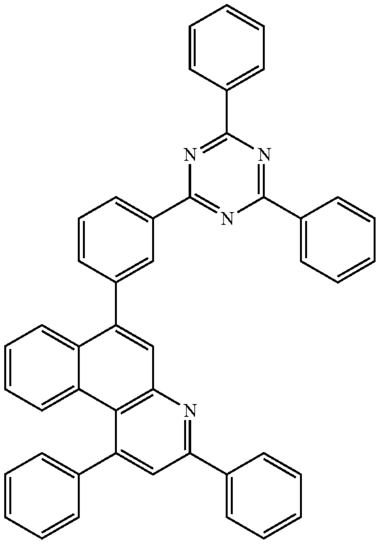
-continued
346
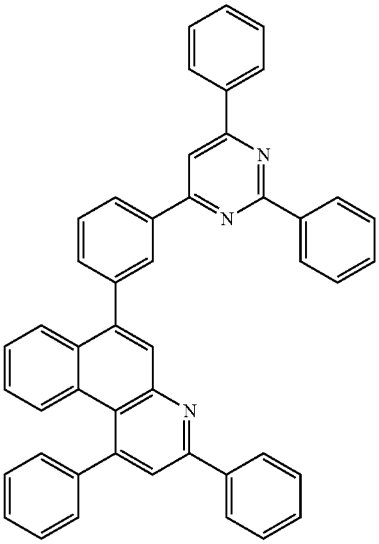
347
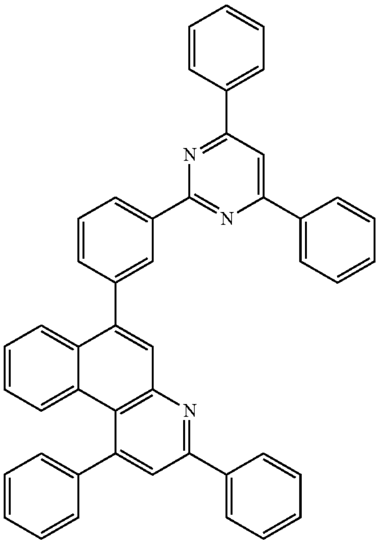
348
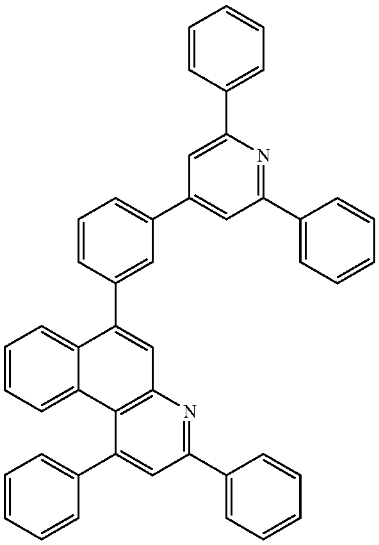

-continued
349
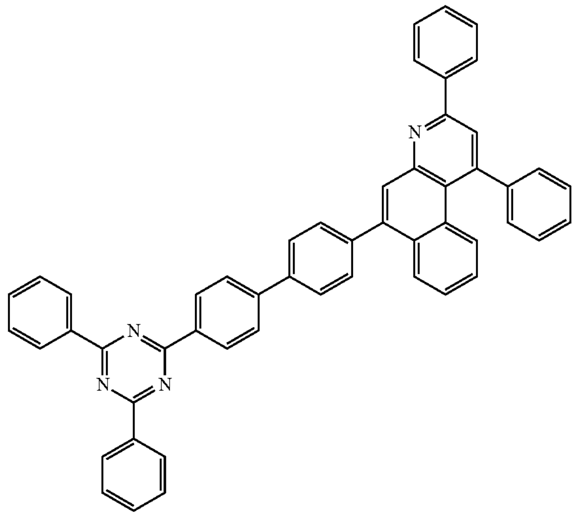
350
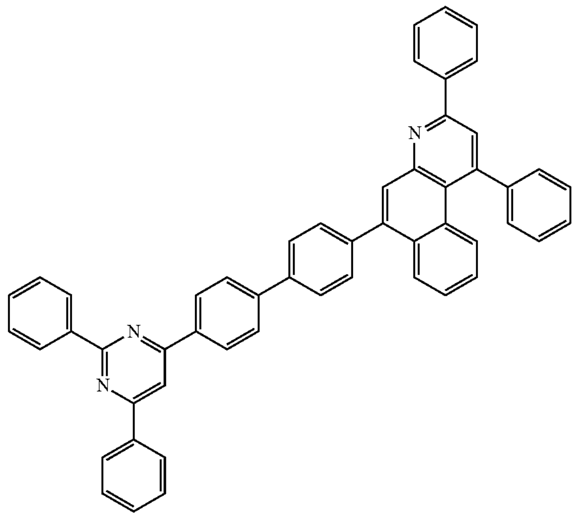
351
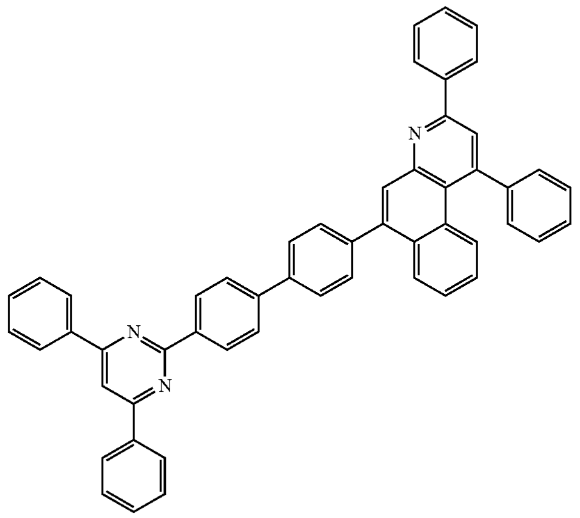
-continued
352
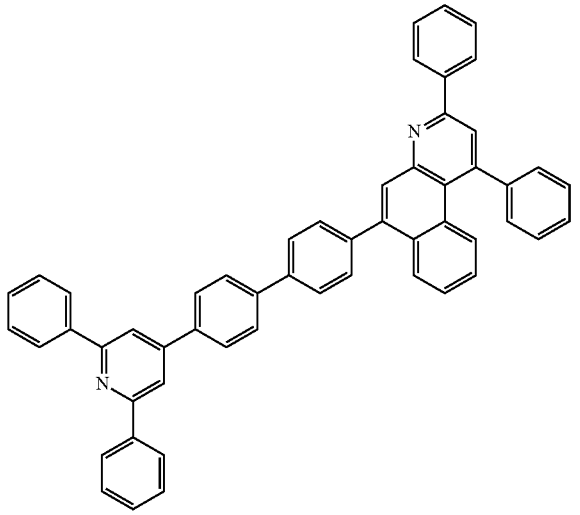
353
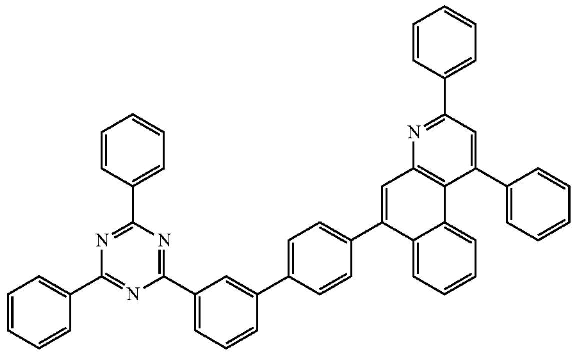
354
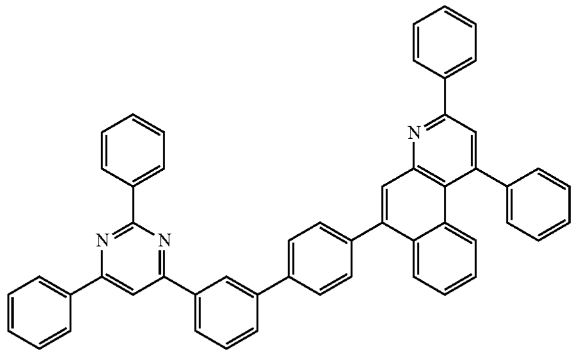

-continued
355
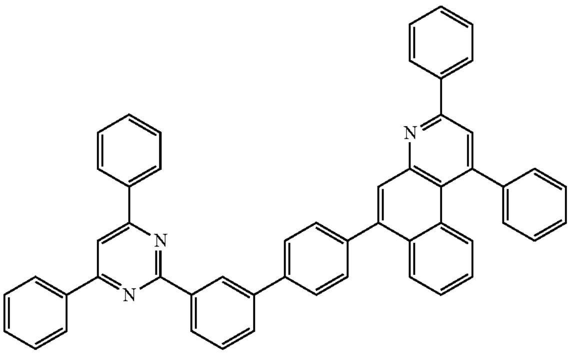
356
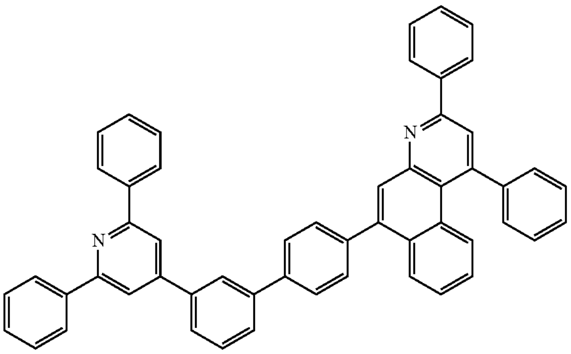
357
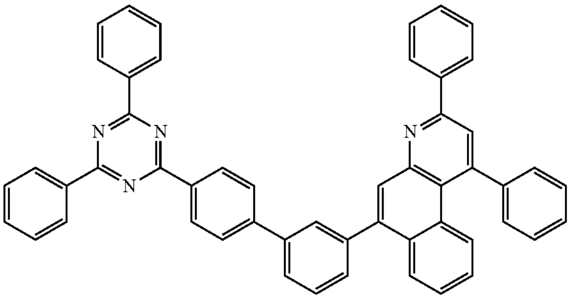
358
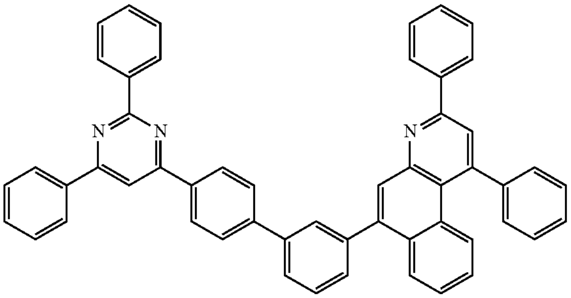
-continued
359
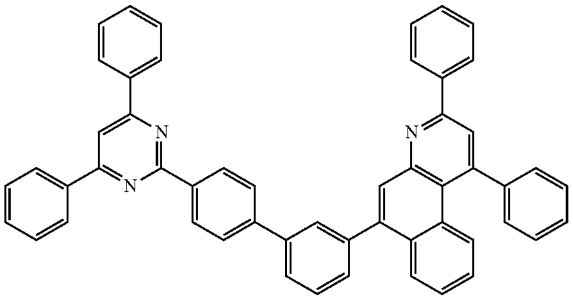
360
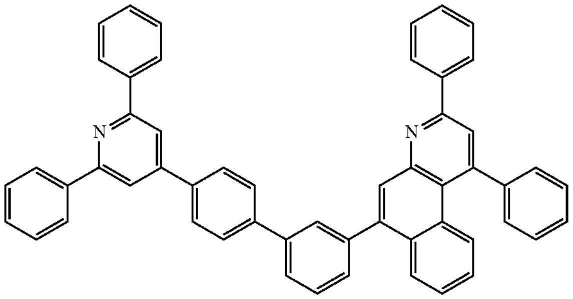
361
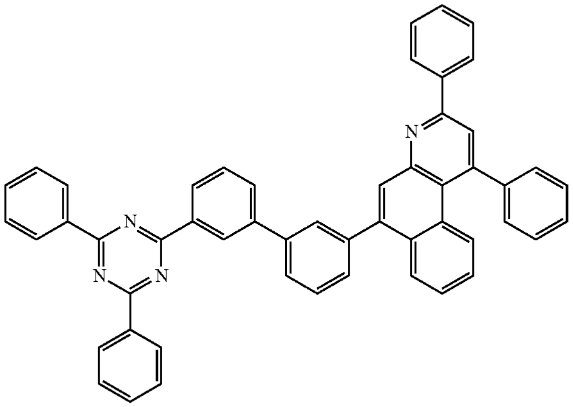
362
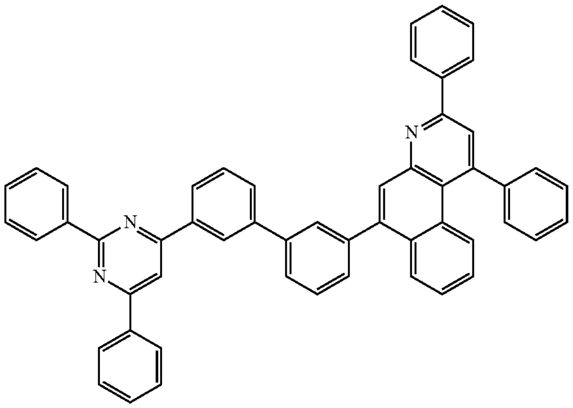

-continued
363
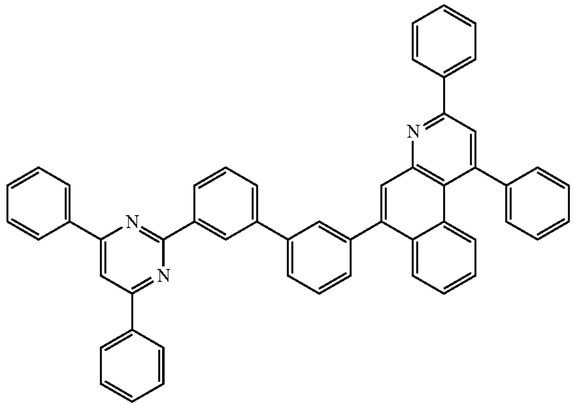
364
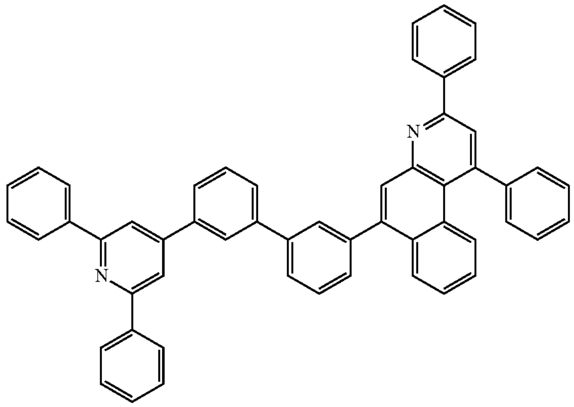
365
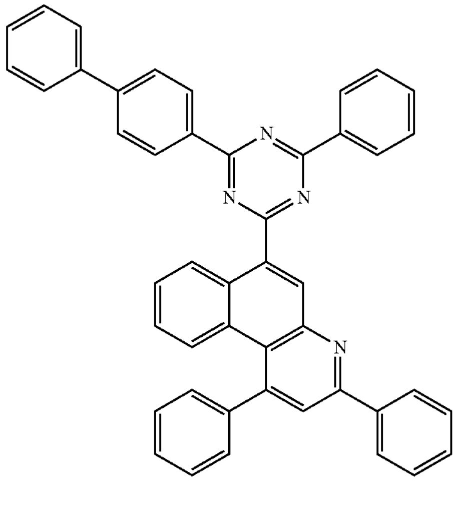
-continued
366
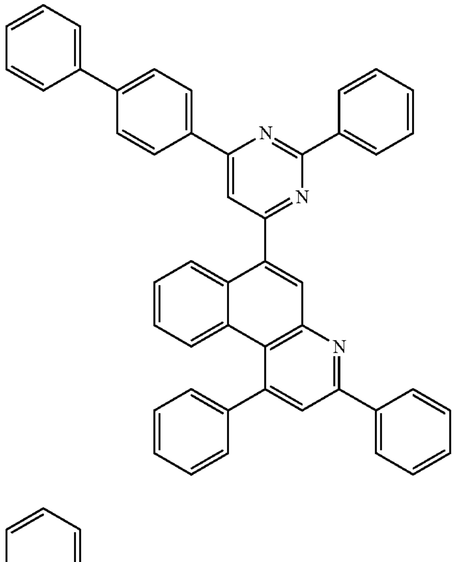
367
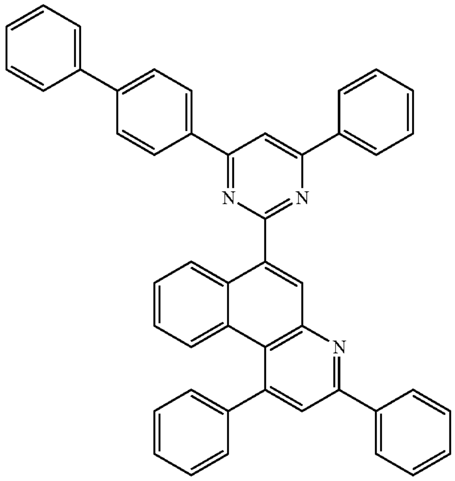
368
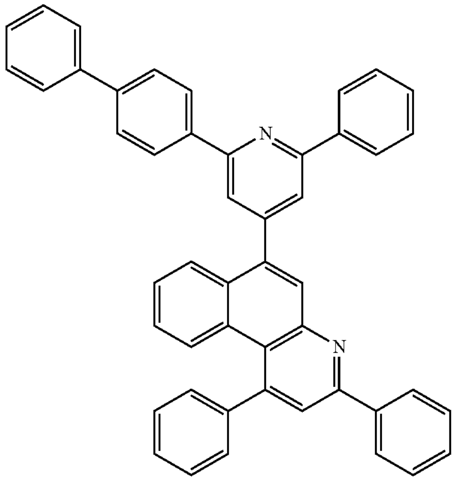

-continued
369
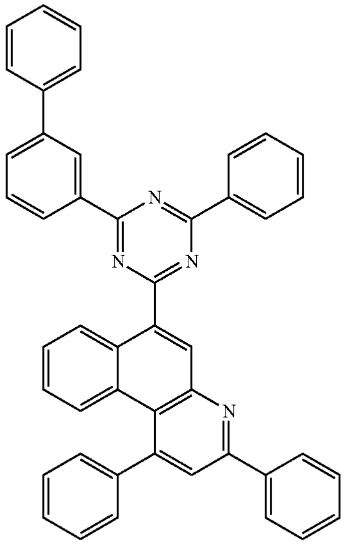
370
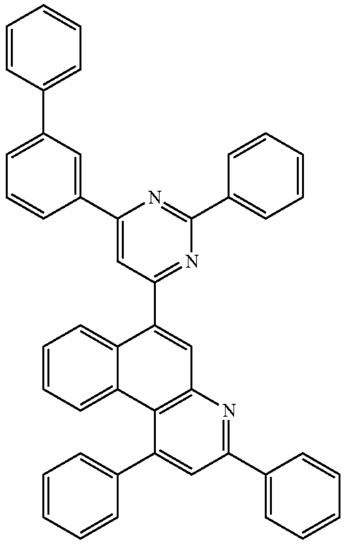
371
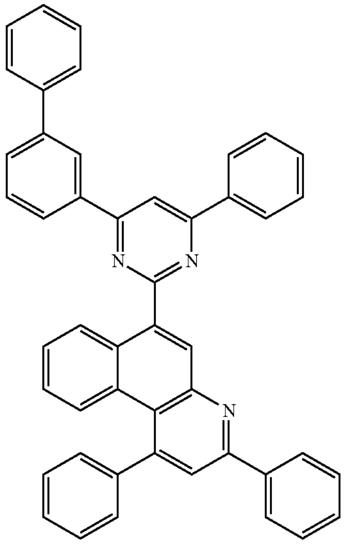
-continued
372
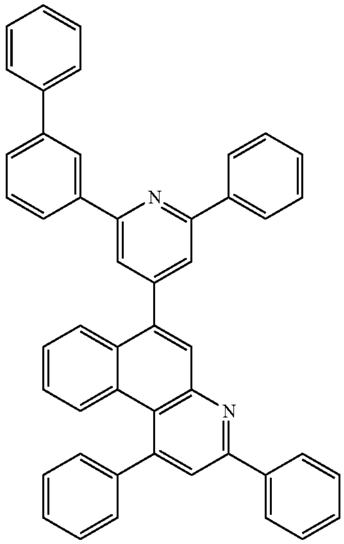
373
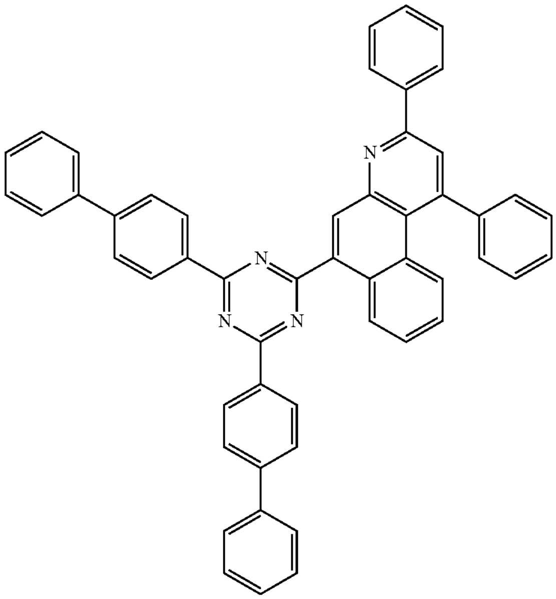

-continued
374
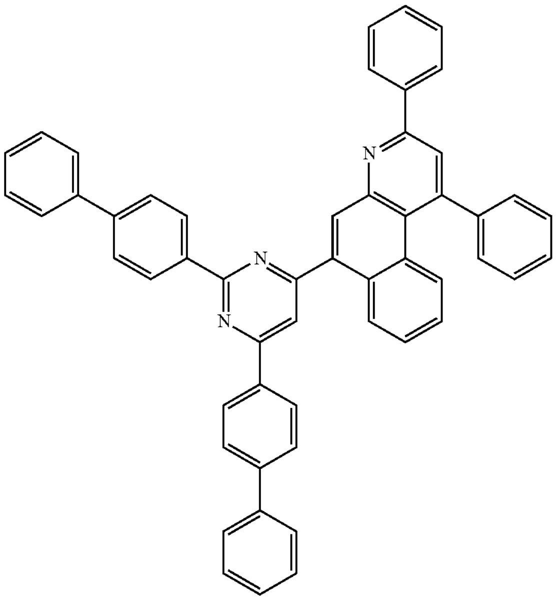
375
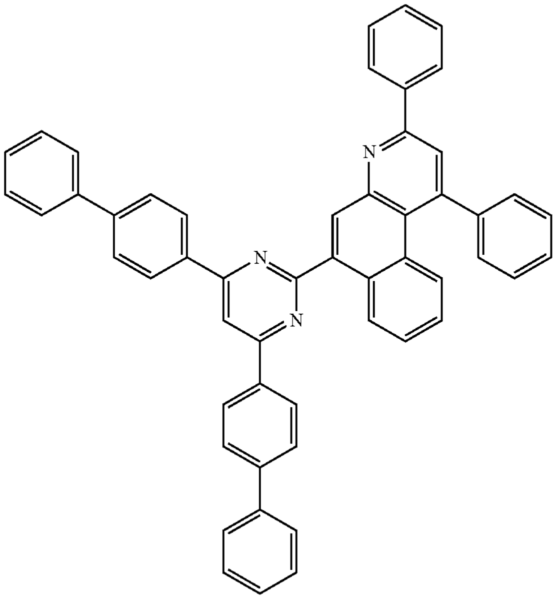
-continued
376
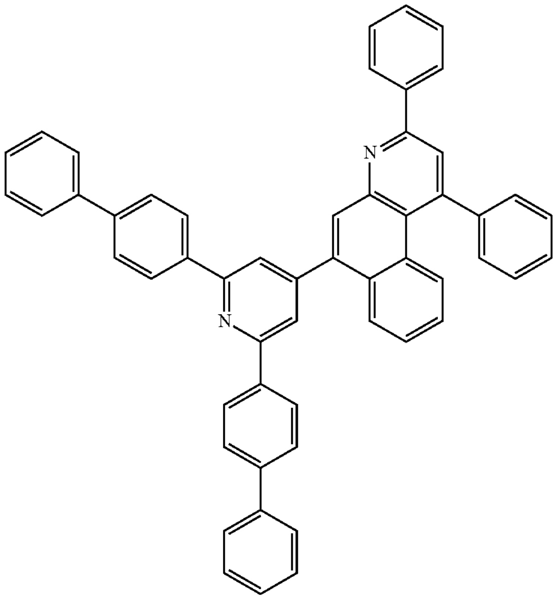
377
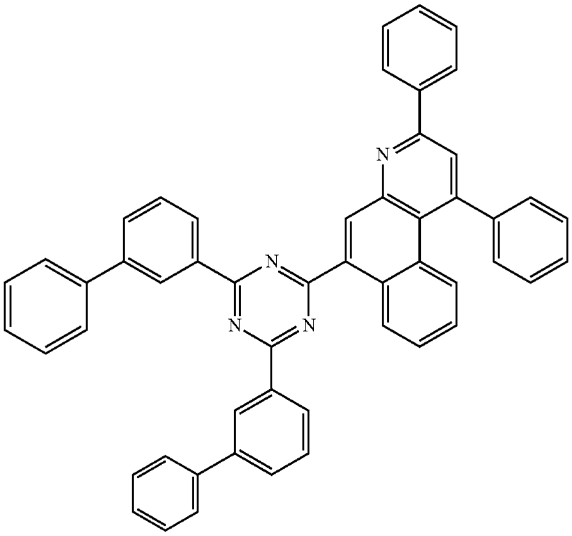

-continued
378
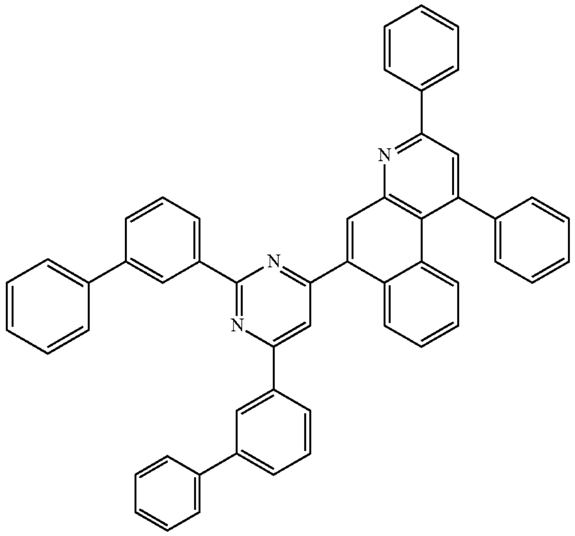
379
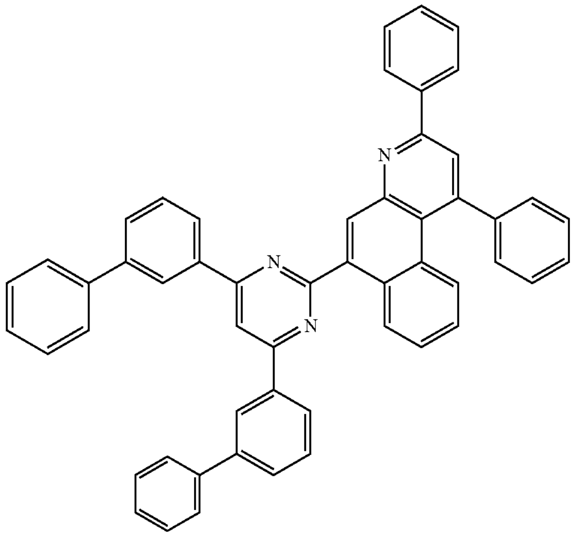
-continued
380
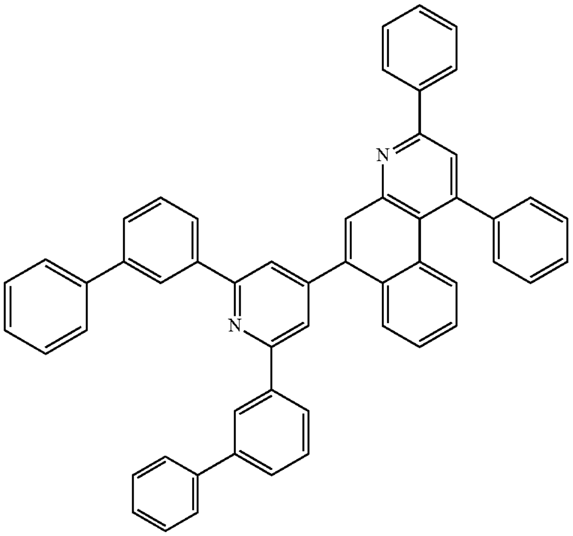
381
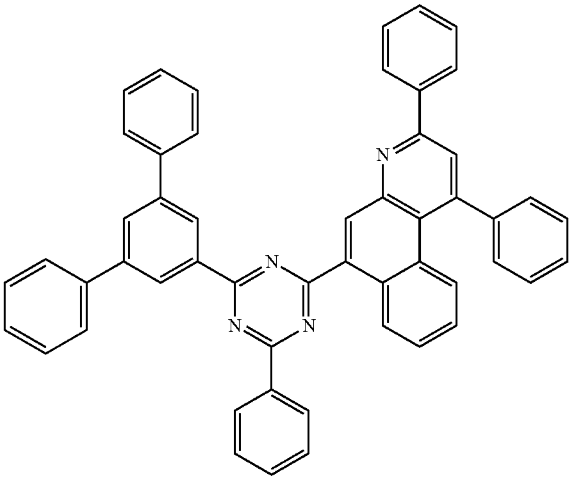
382
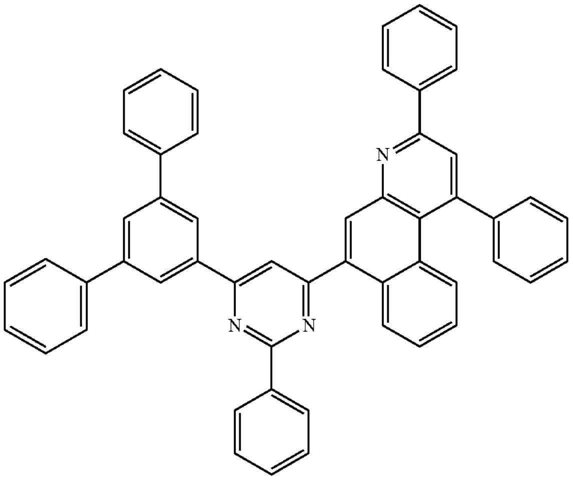

-continued
383
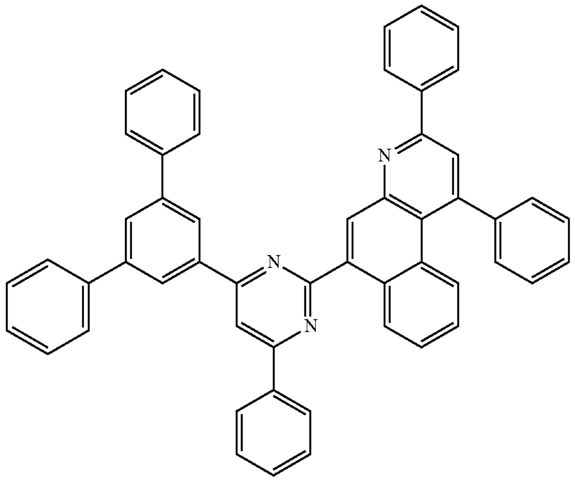
384
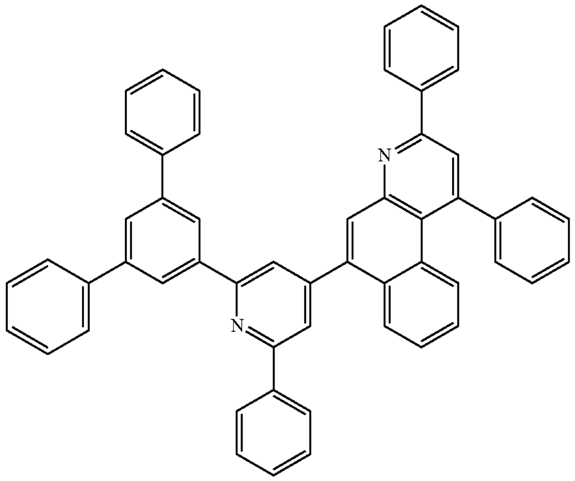
385
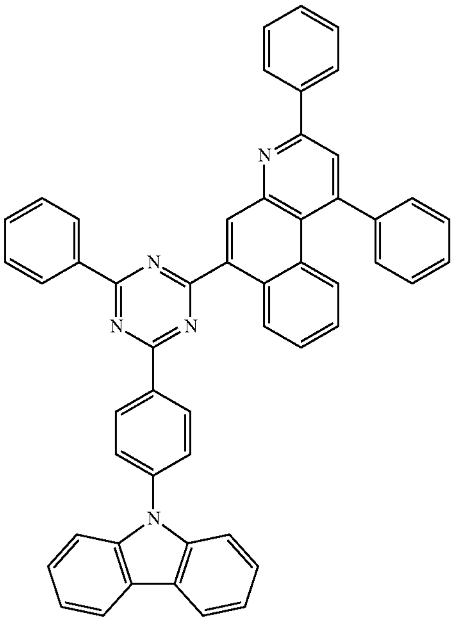
-continued
386
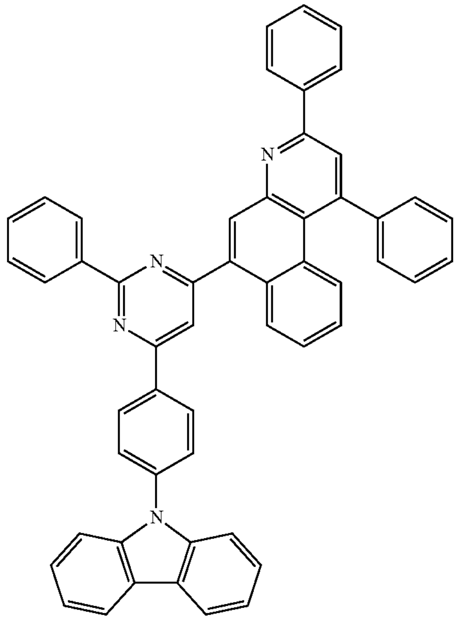
387
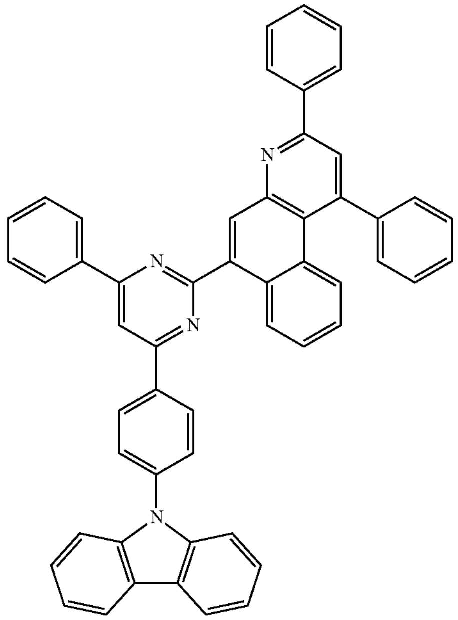

-continued
388
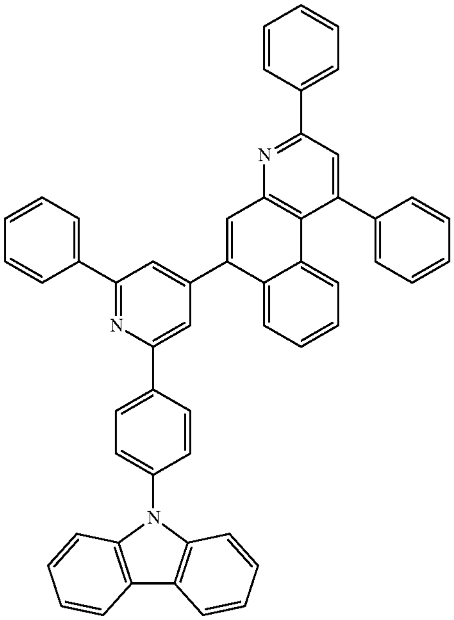
389
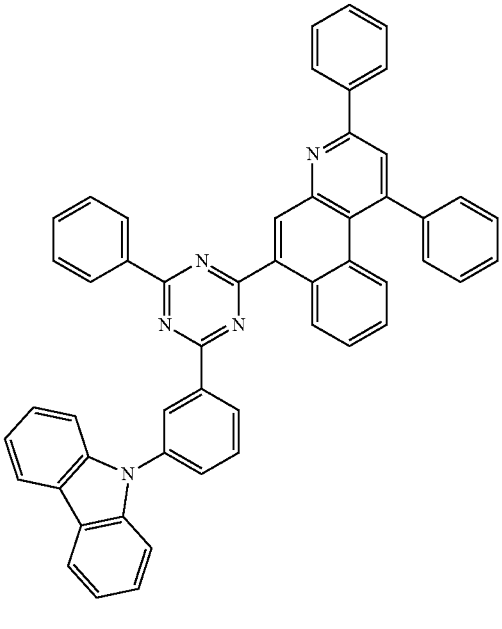
-continued
390
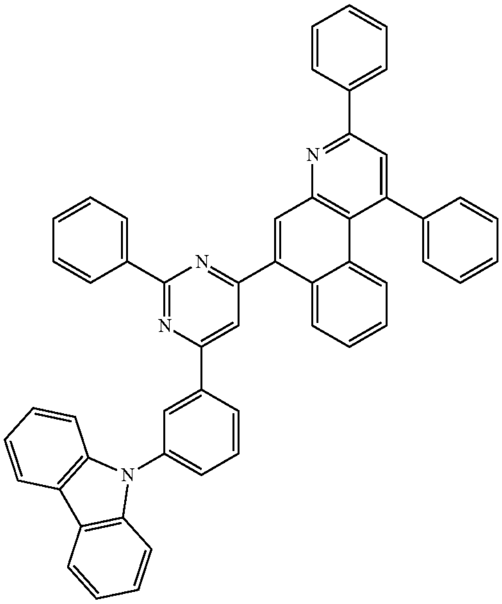
391
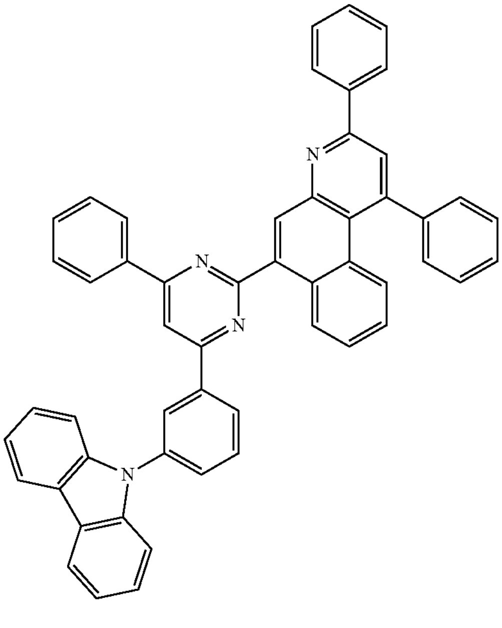

-continued
392
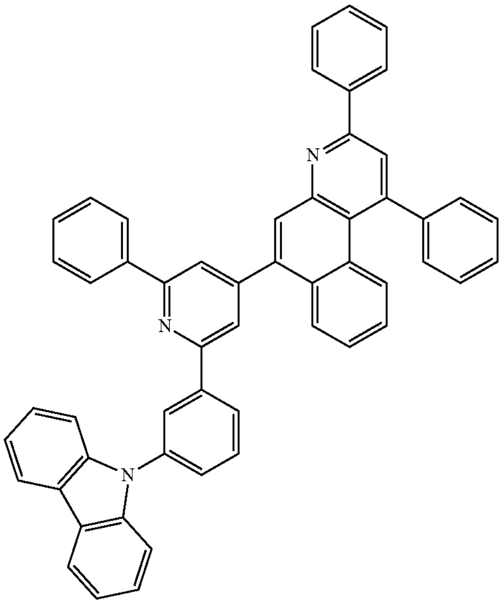
393
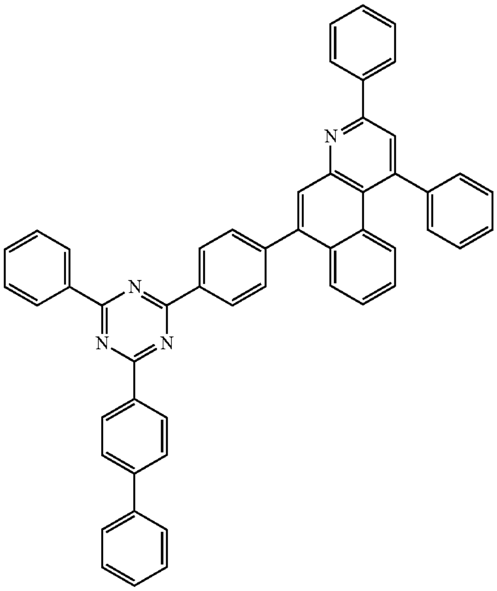
-continued
394
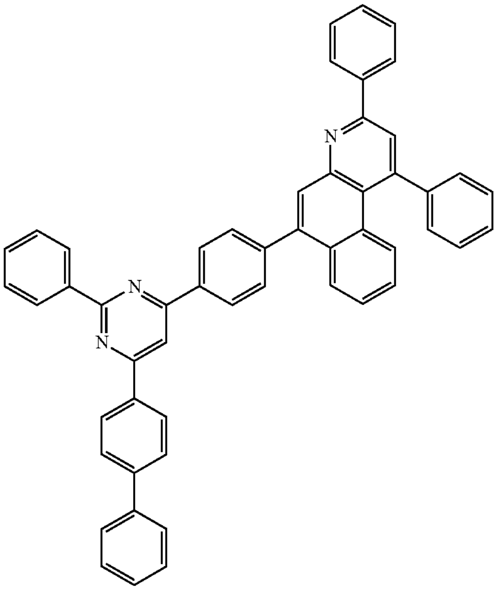
395
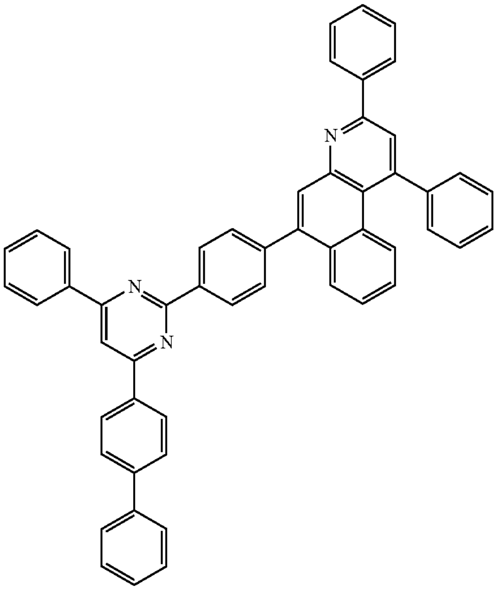

-continued
396
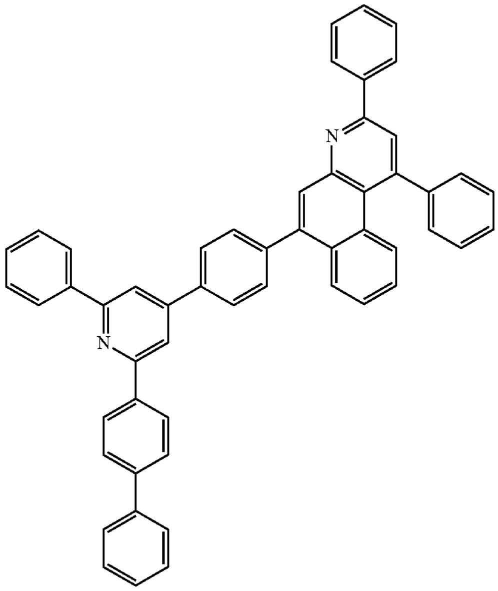
397
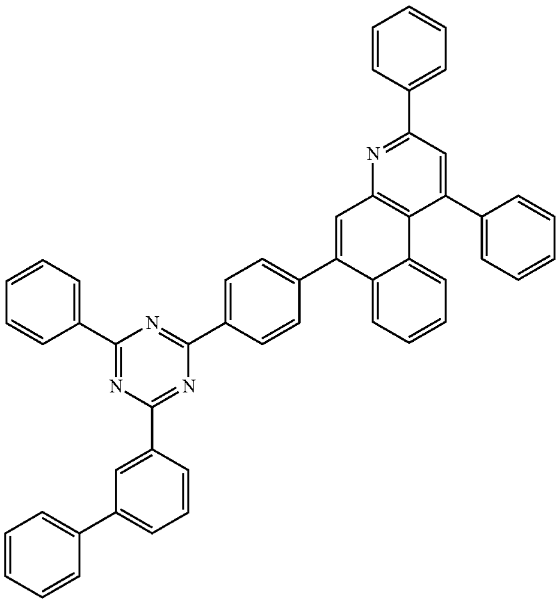
-continued
398
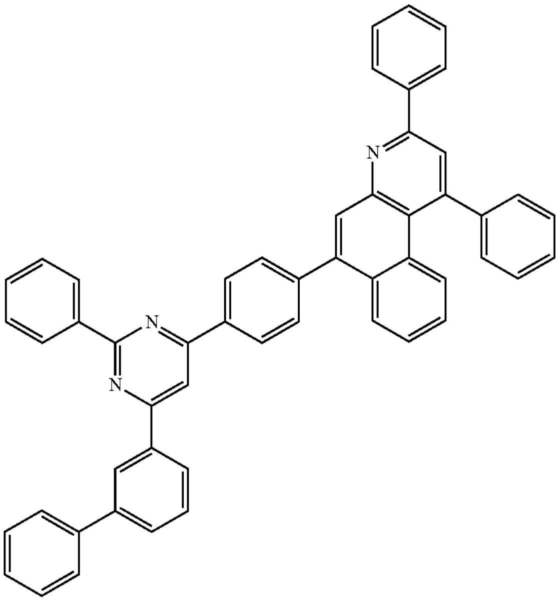
399
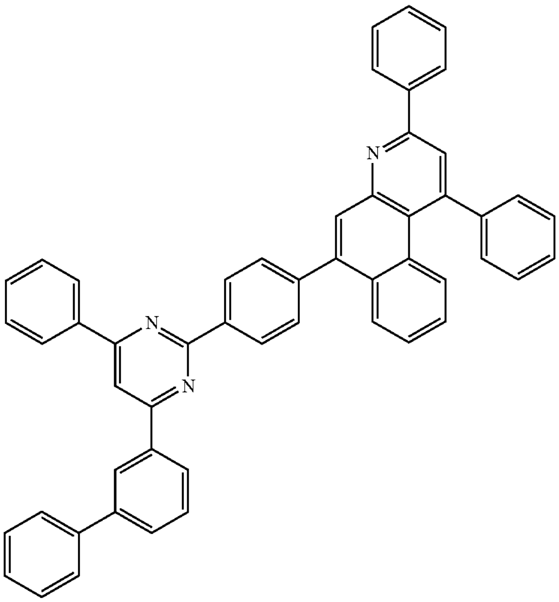

-continued
400
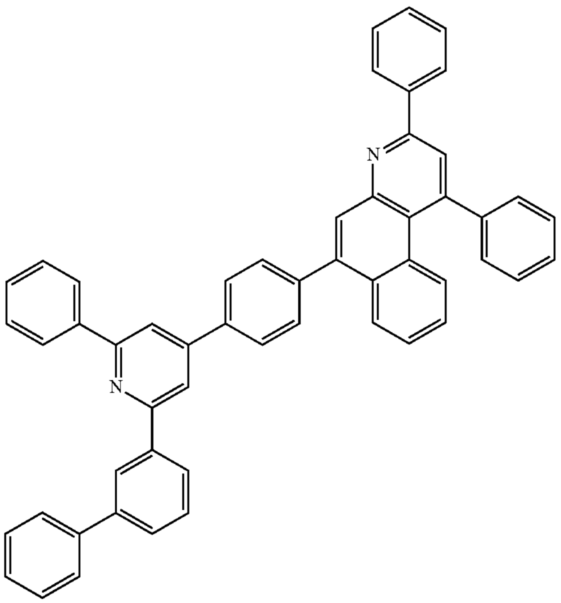
401
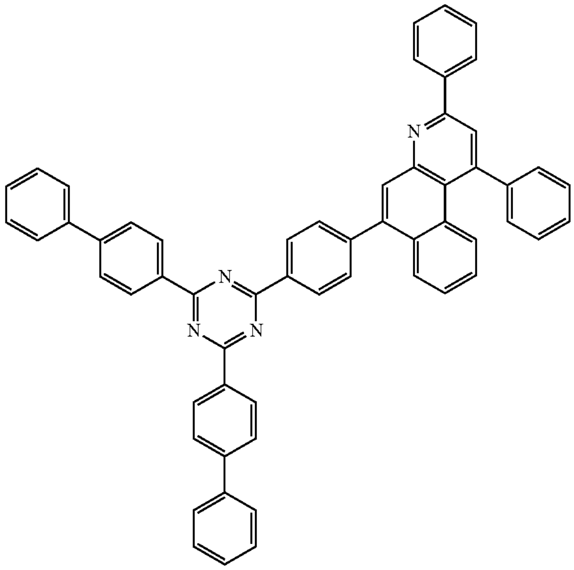
-continued
402
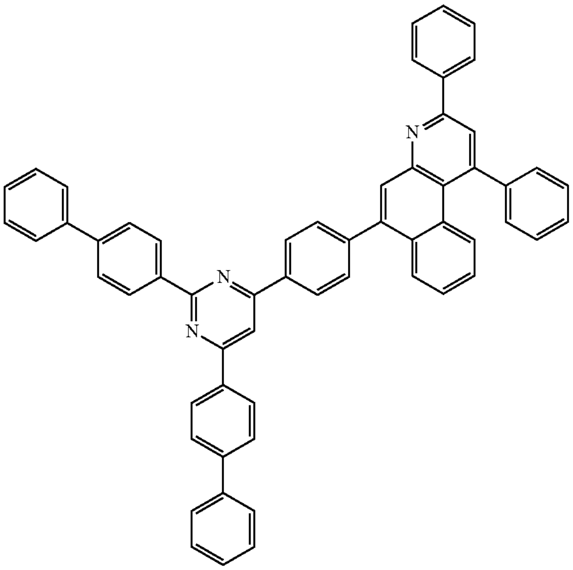
403
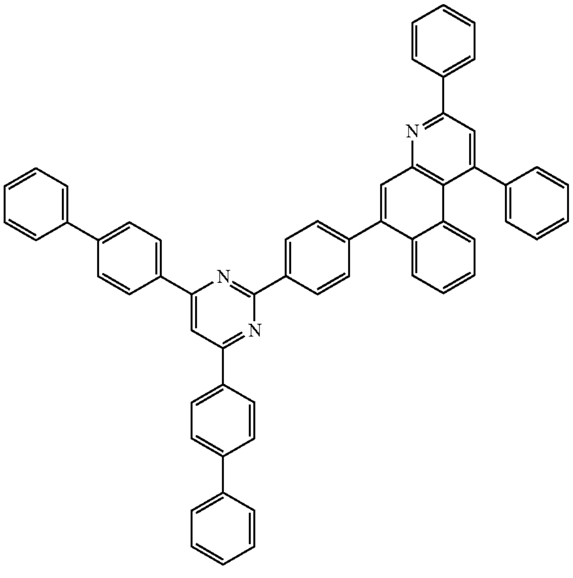

-continued
404
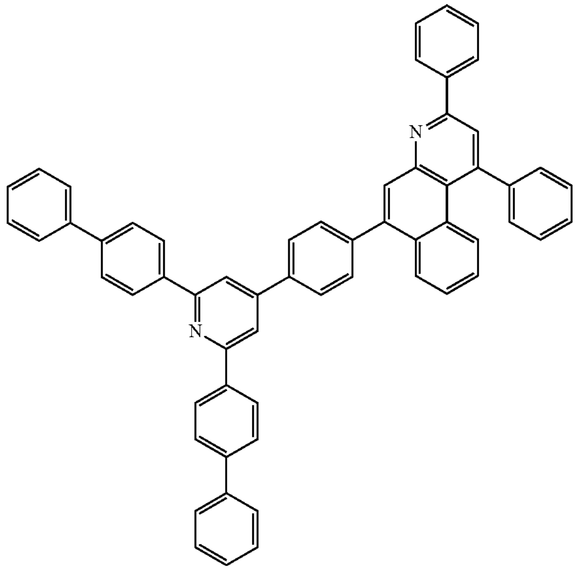
405
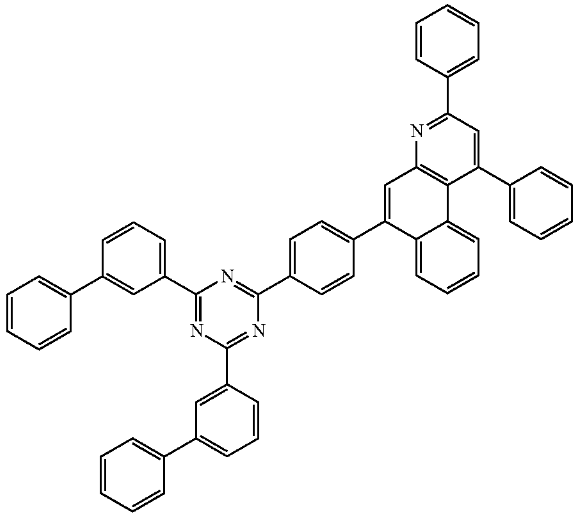
406
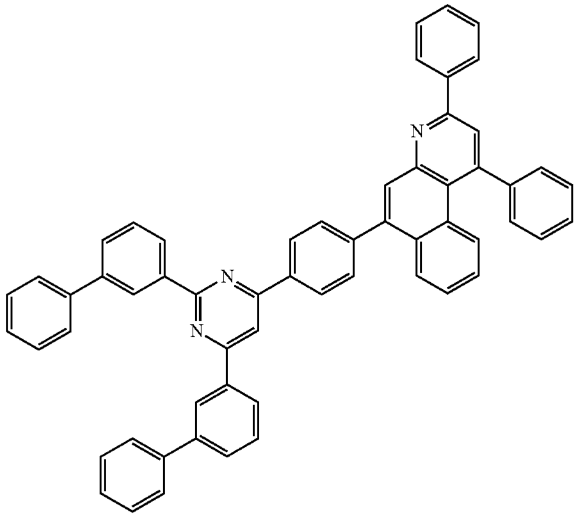
-continued
407
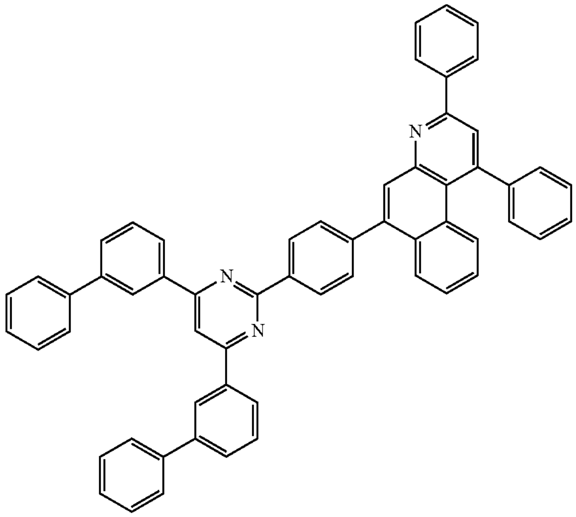
408
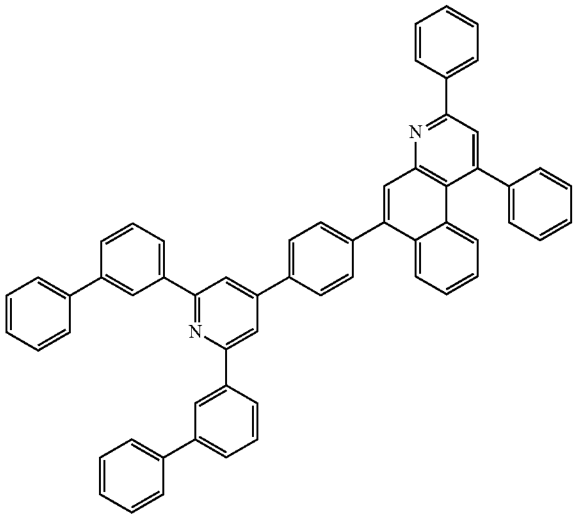

-continued
409
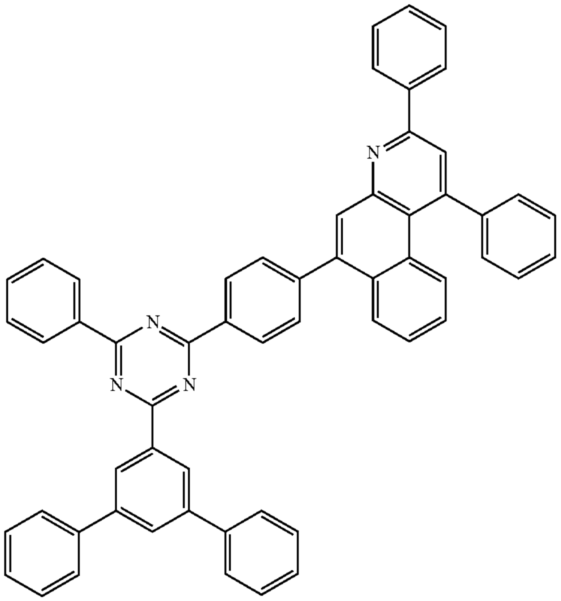
410
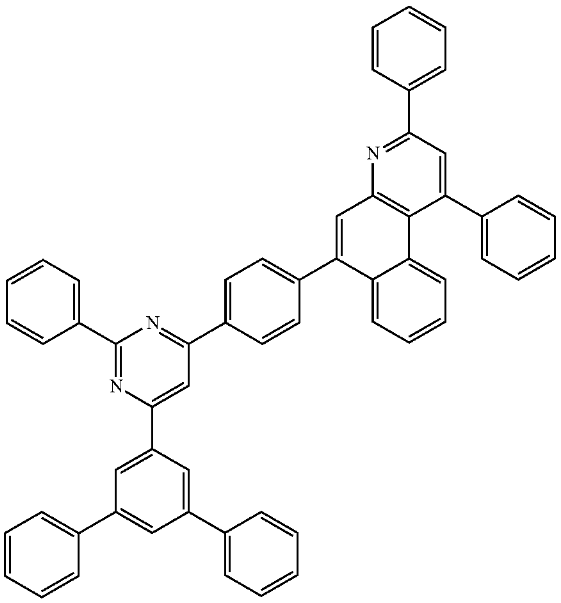
-continued
411
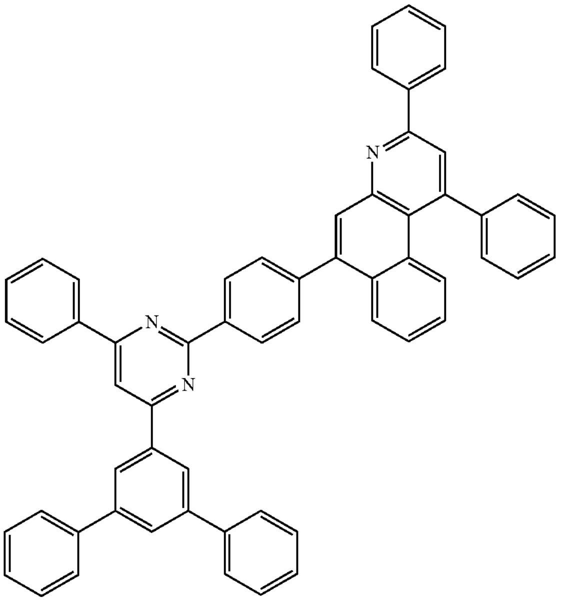
412
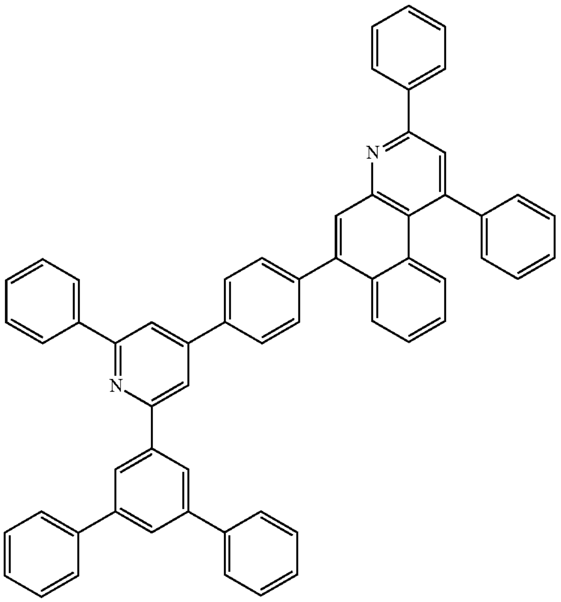

-continued
413
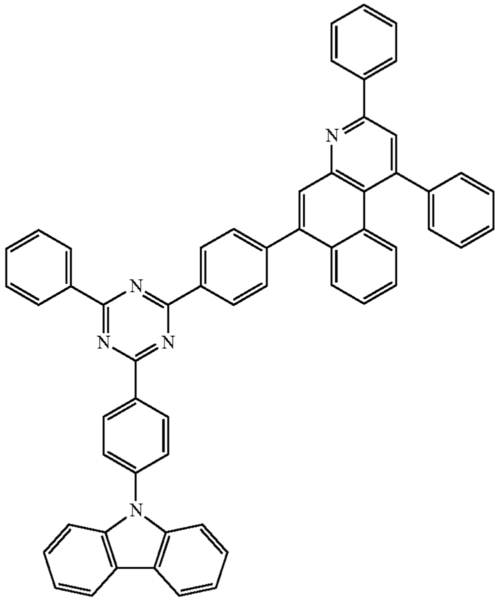
414
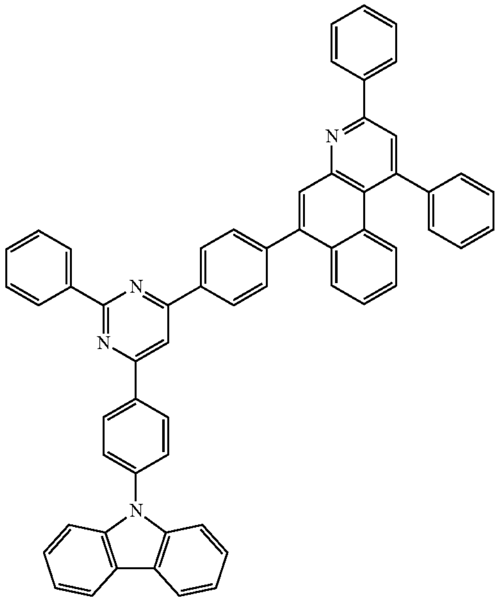
-continued
415
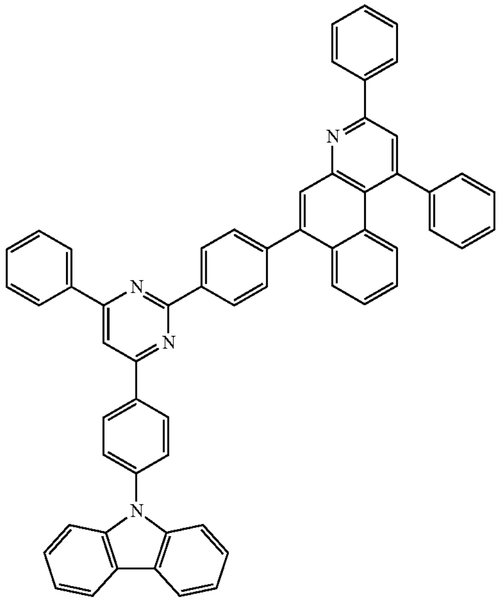
416
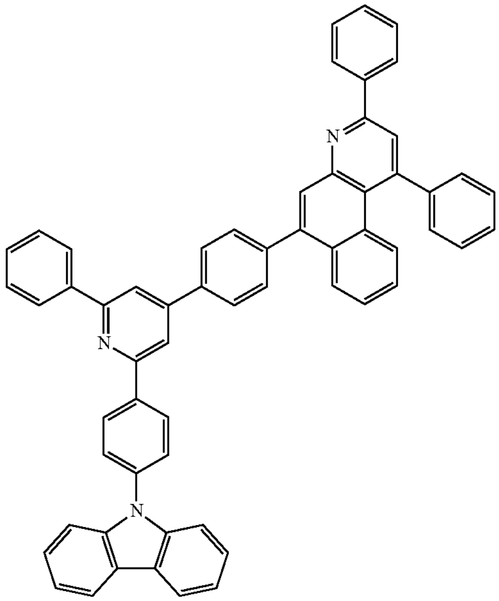

-continued
417
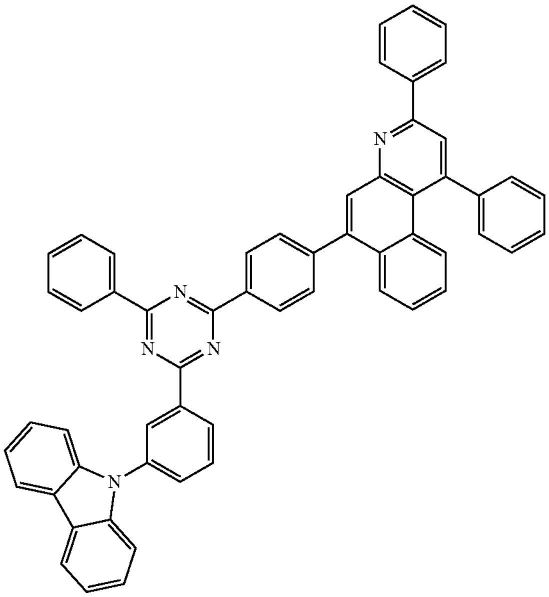
418
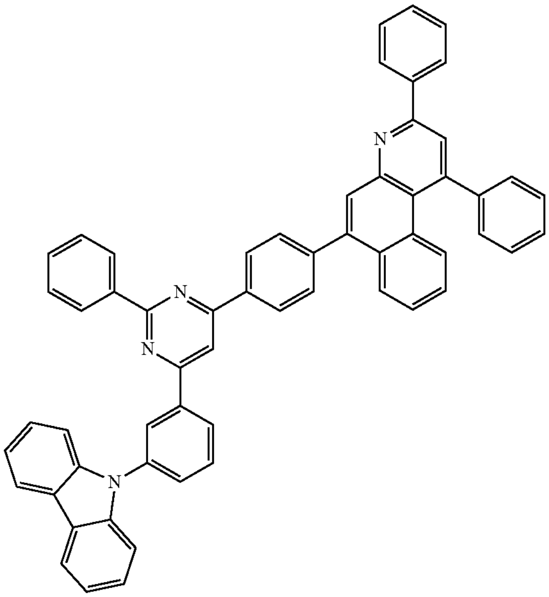
-continued
419
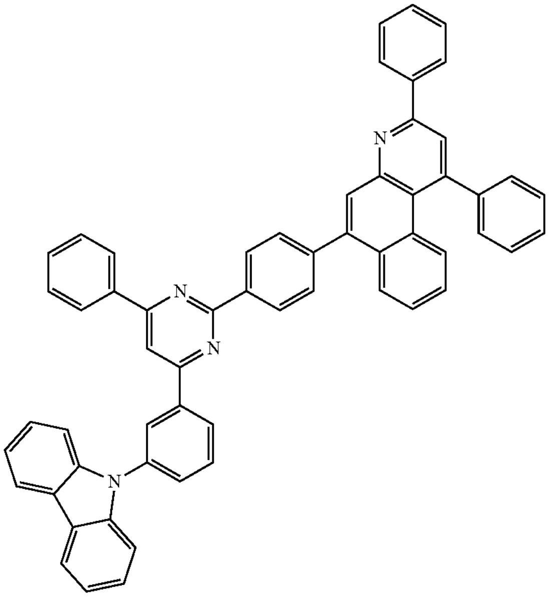
420
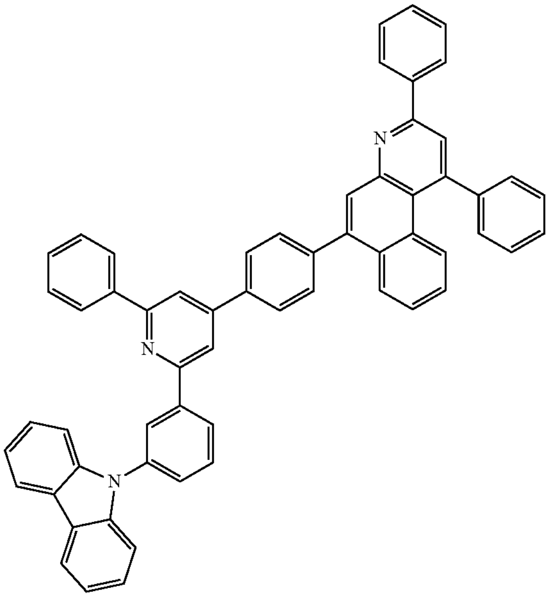
421
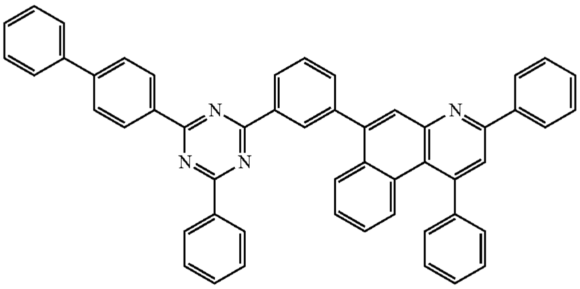

-continued
422
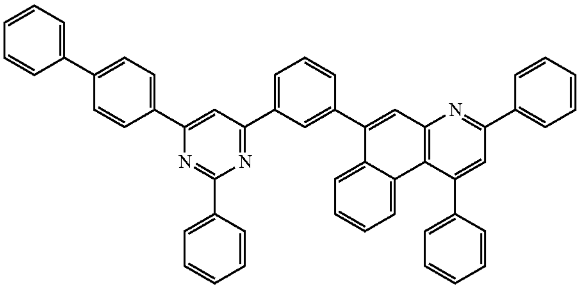
423
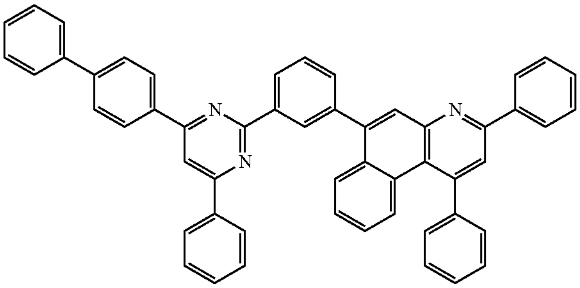
424
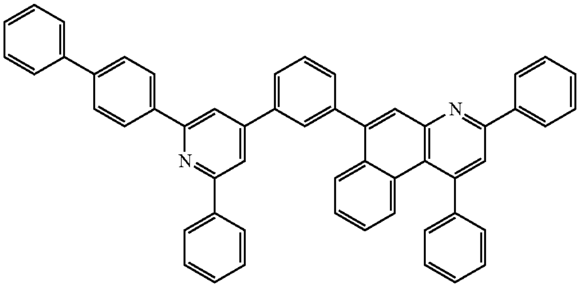
425
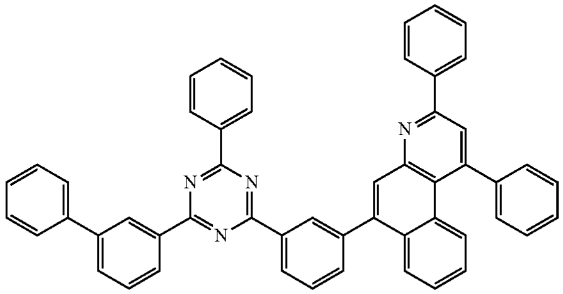
426
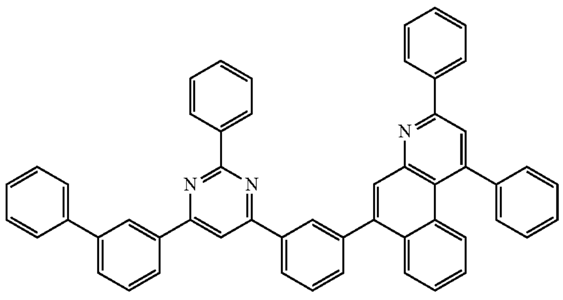
-continued
427
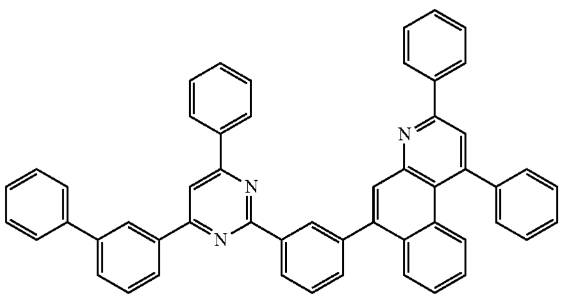
428
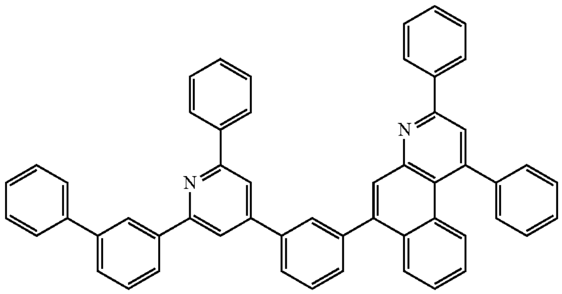
429
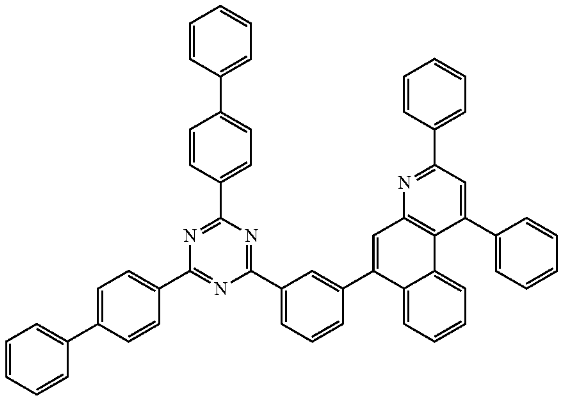
430
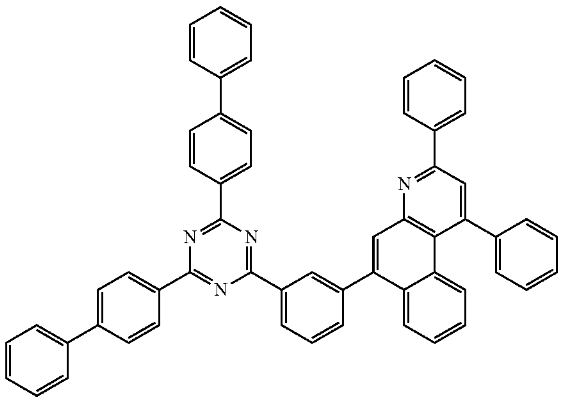

-continued
431
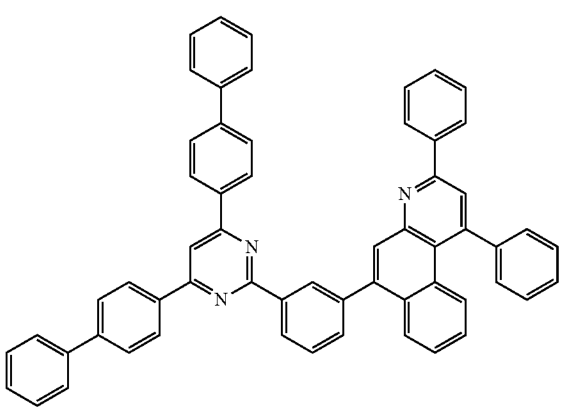
432
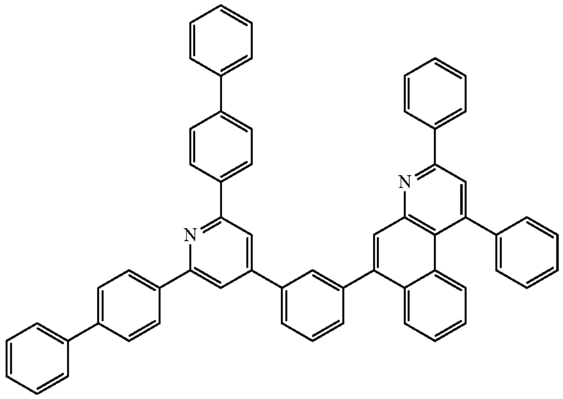
433
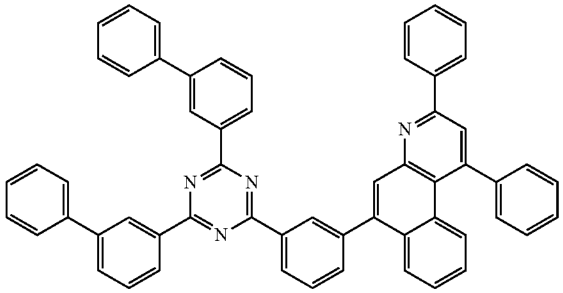
434
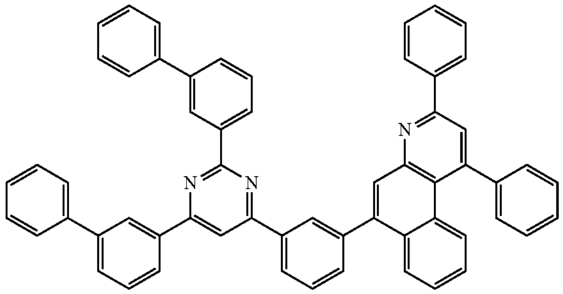
-continued
435
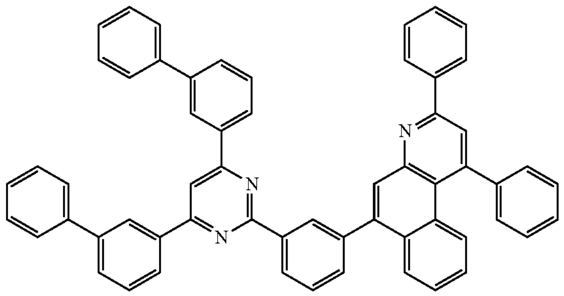
436
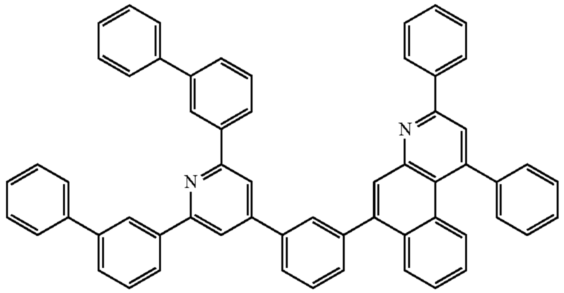
437
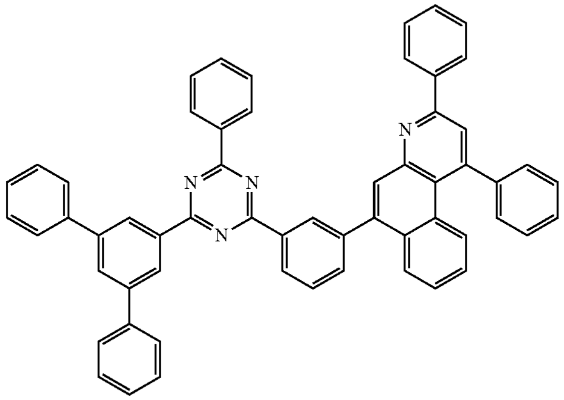
438
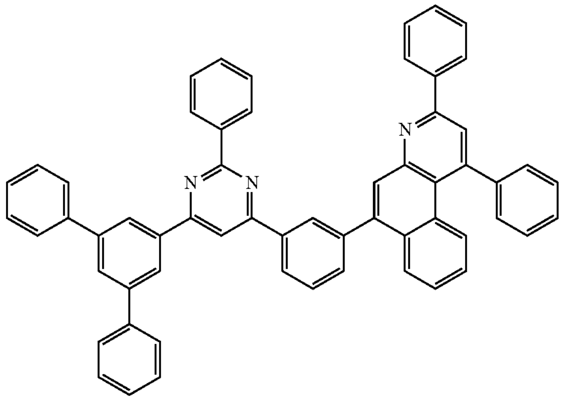

-continued
439
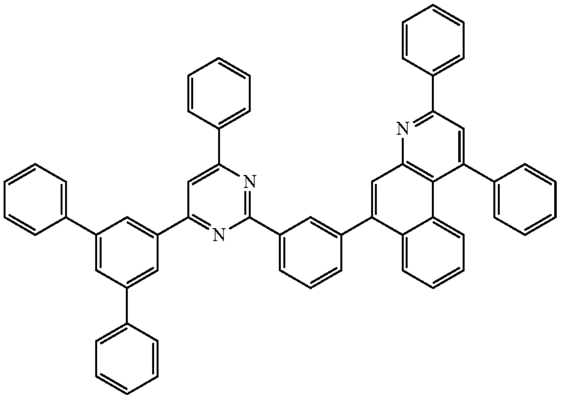
440
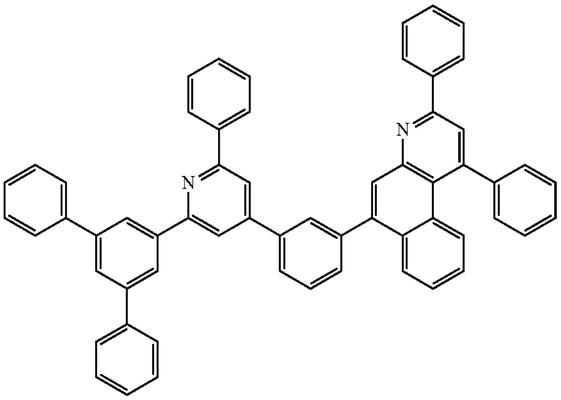
441
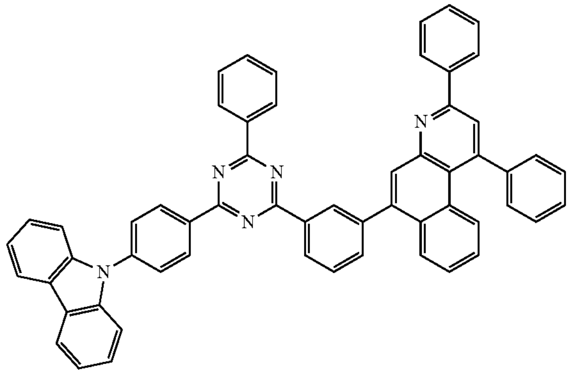
442
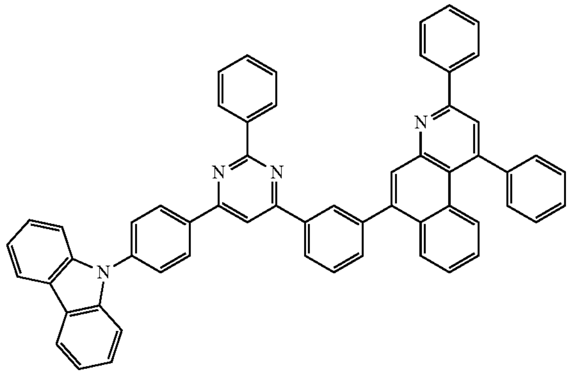
-continued
443
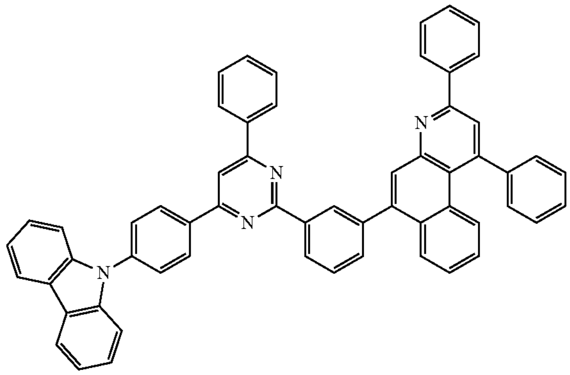
444
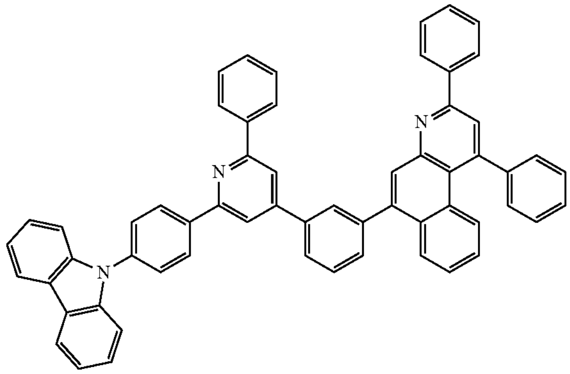
445
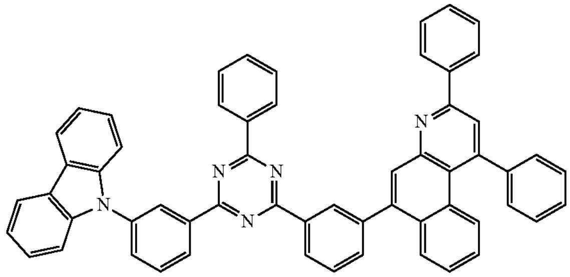
446
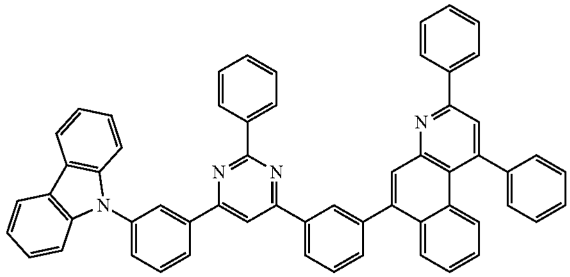

-continued
447
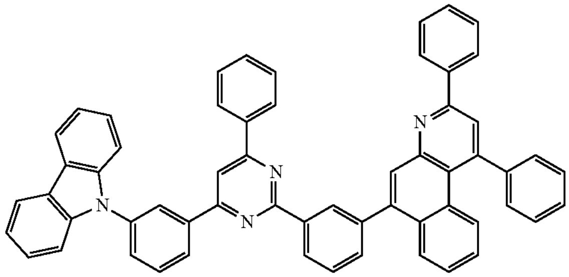
448
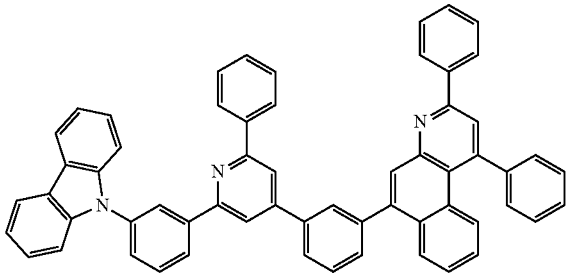
449
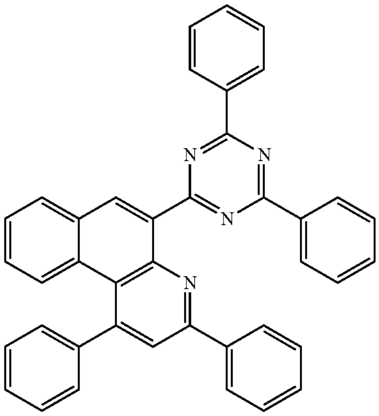
450
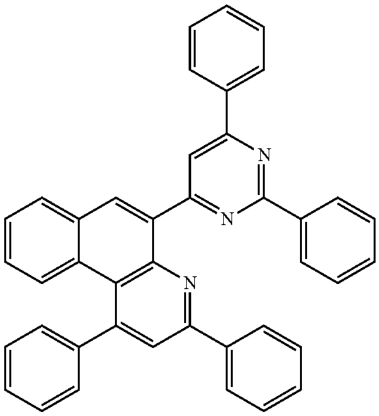
-continued
451
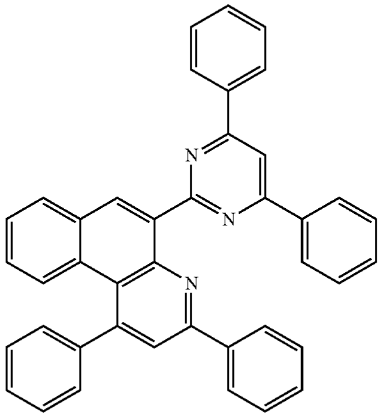
452
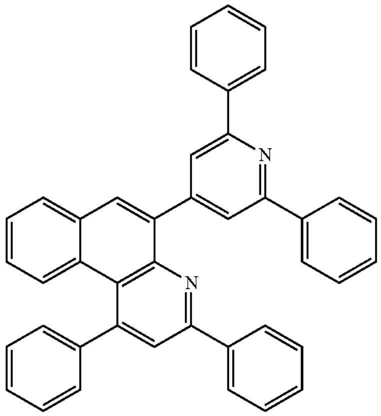
453
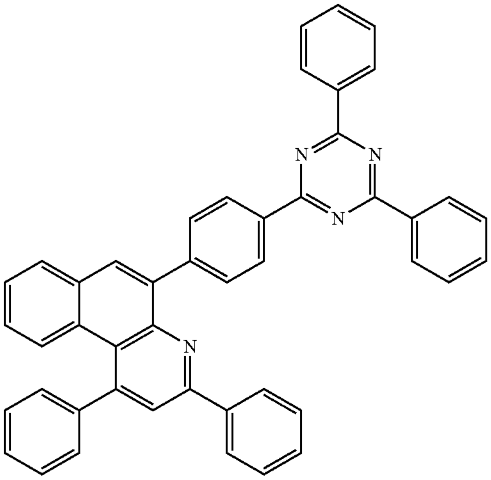

-continued
454
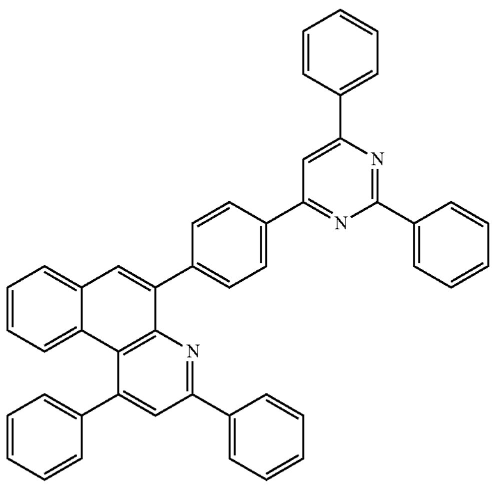
455
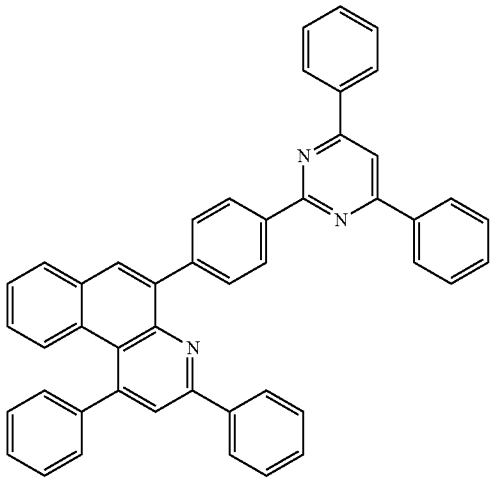
456
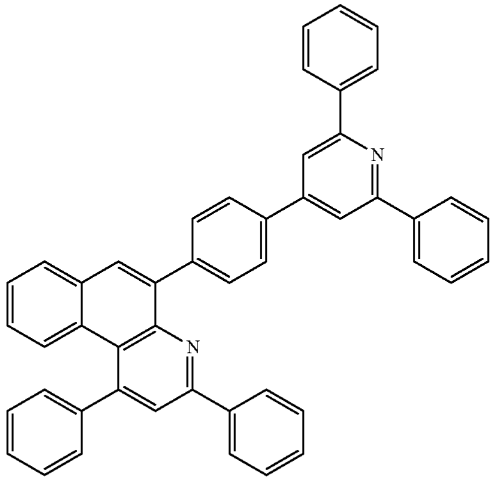
-continued
457
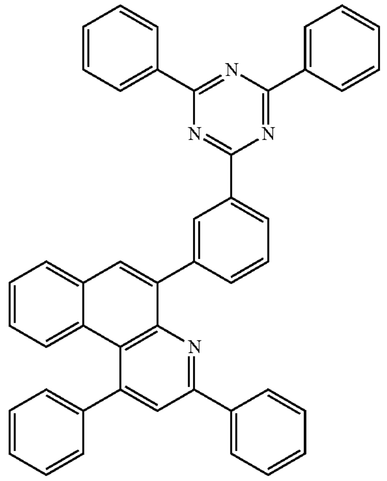
458
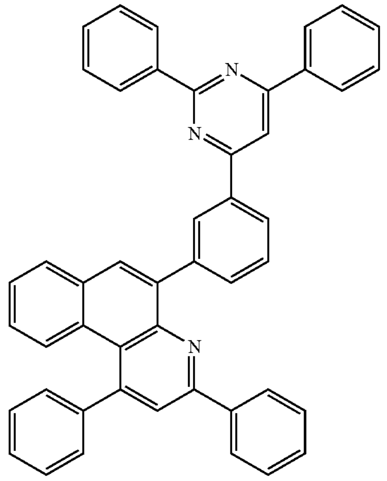
459
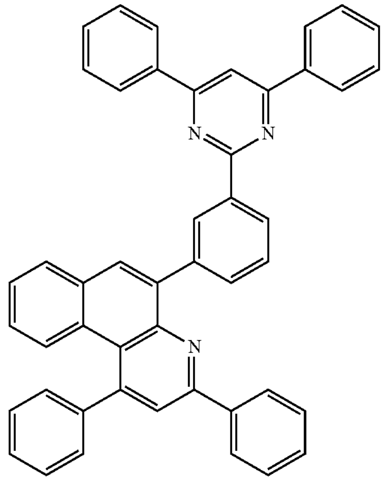

460
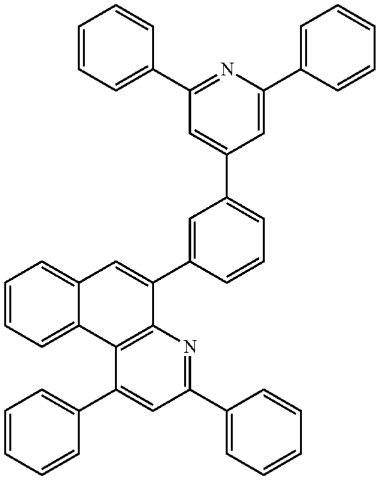
461
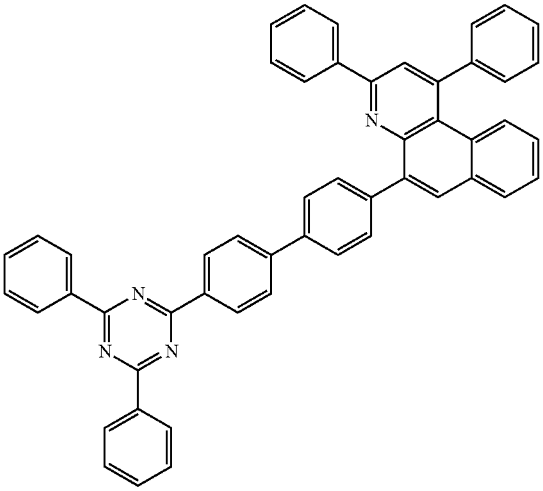
462
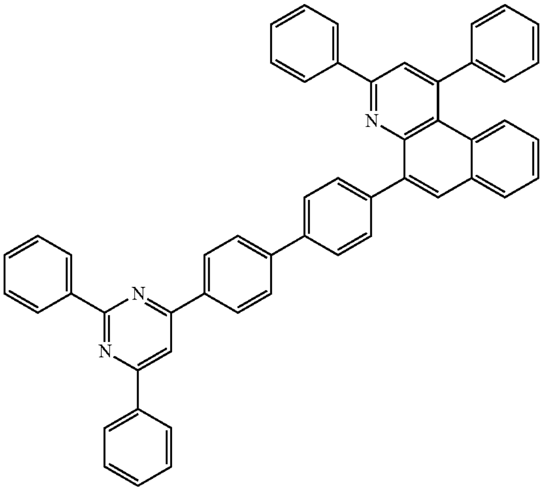
463
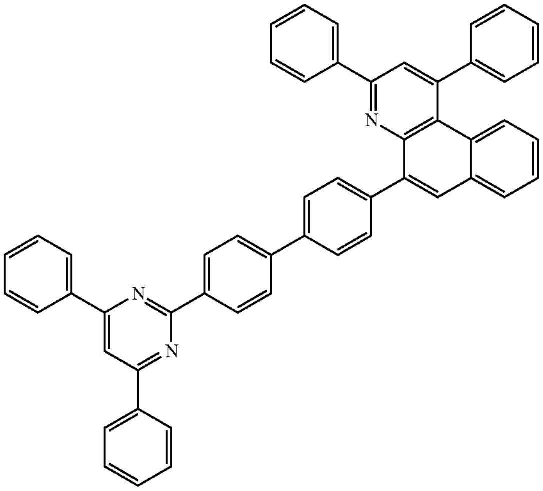
464
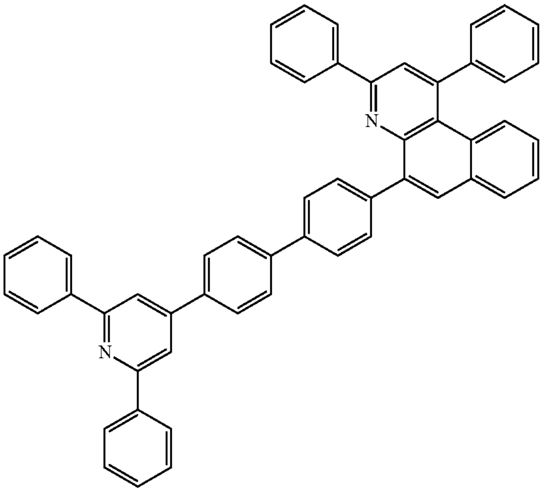
465
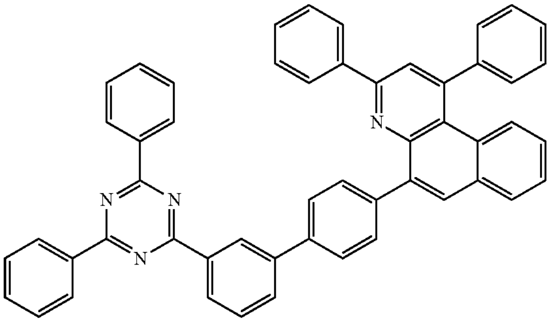

-continued
466
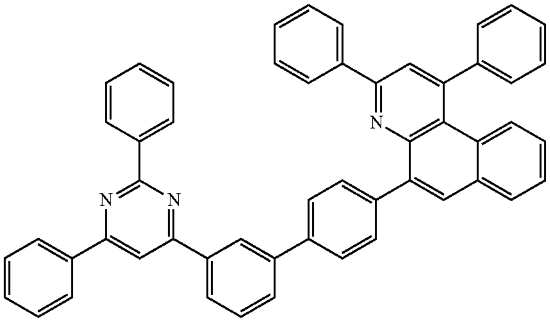
467
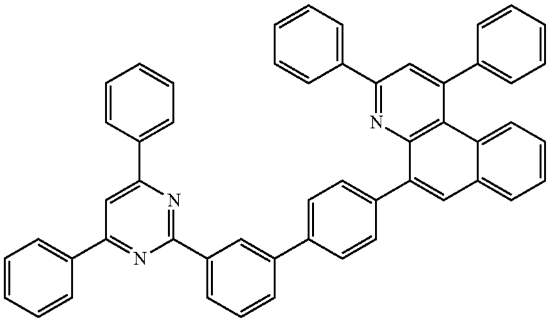
468
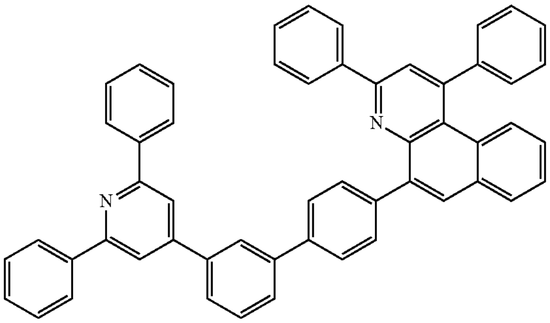
469
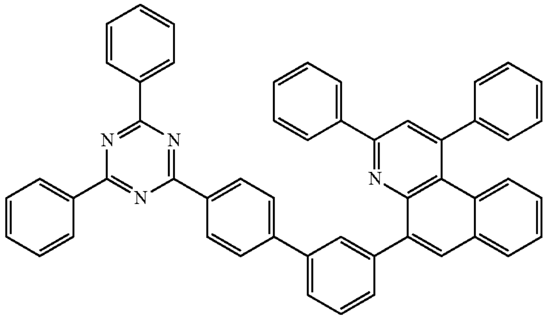
-continued
470
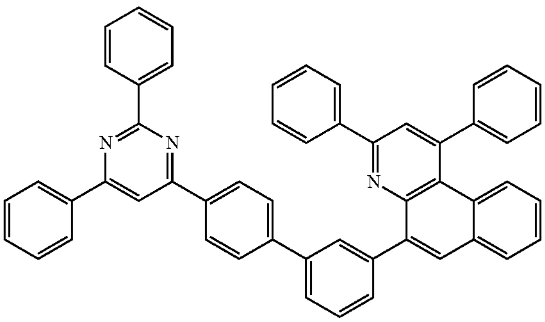
471
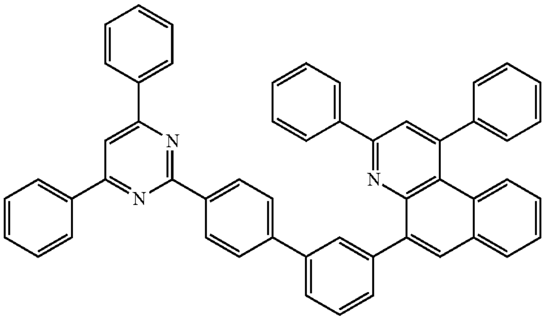
472
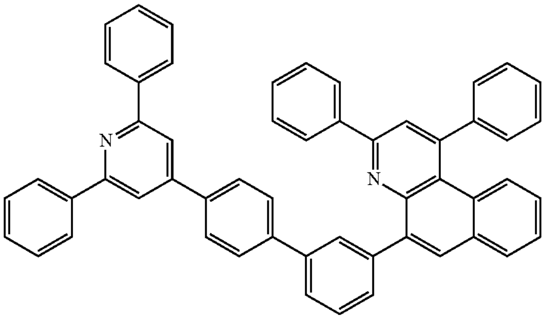
473
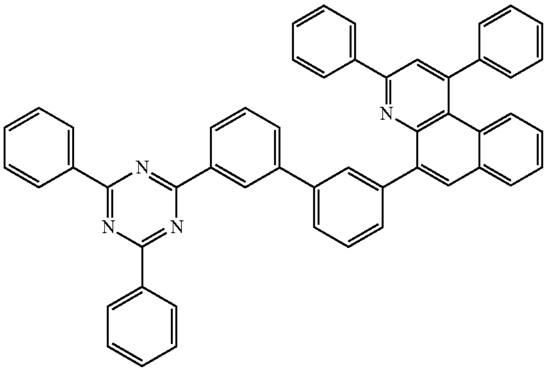

-continued
474
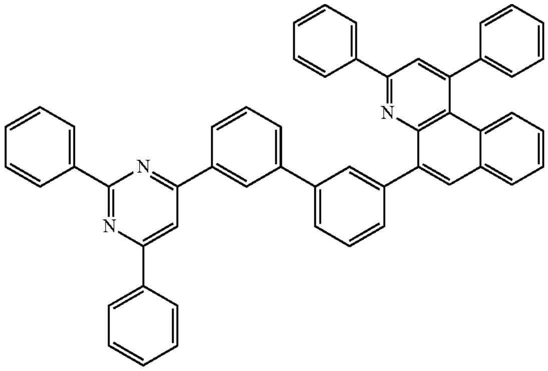
475
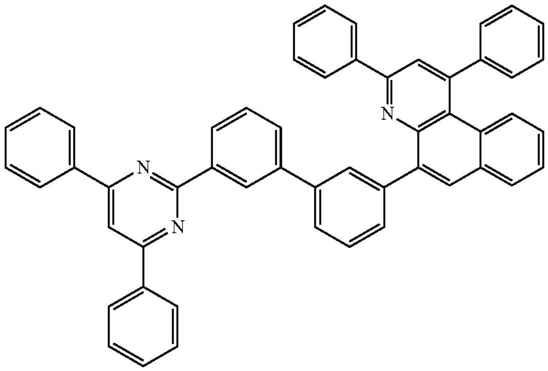
476
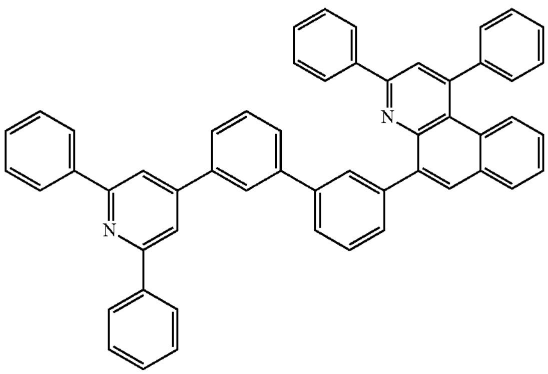
-continued
477
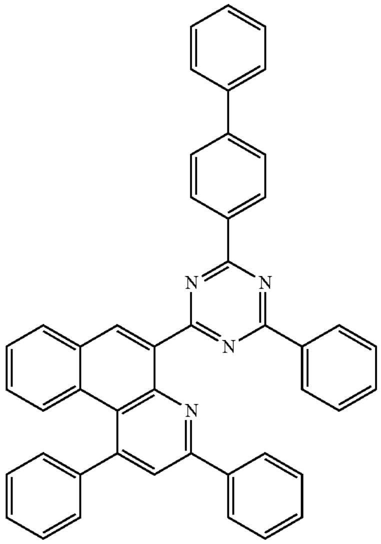
478
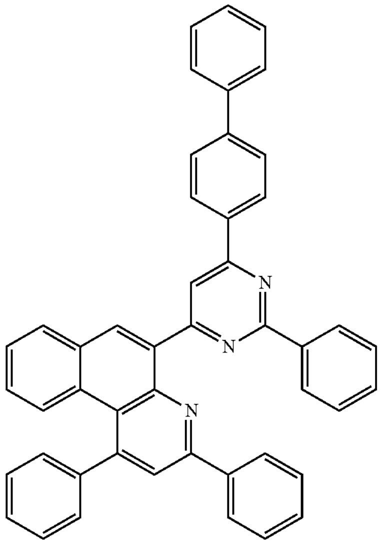
479
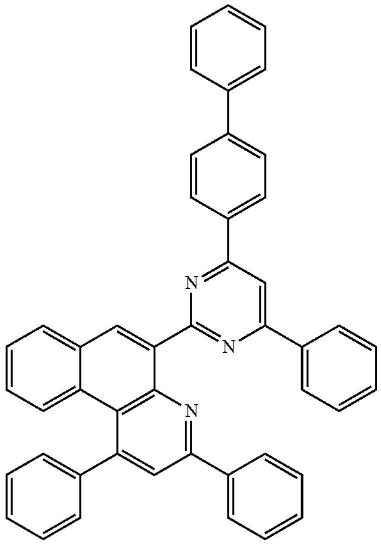

-continued
480
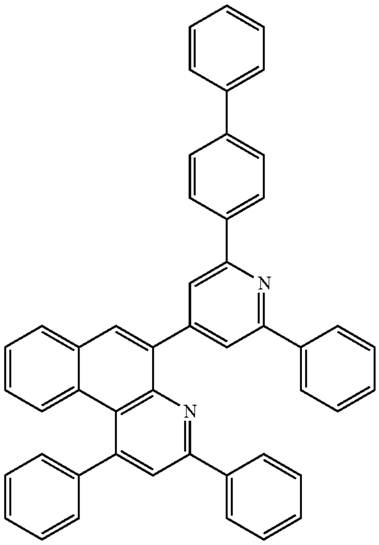
481
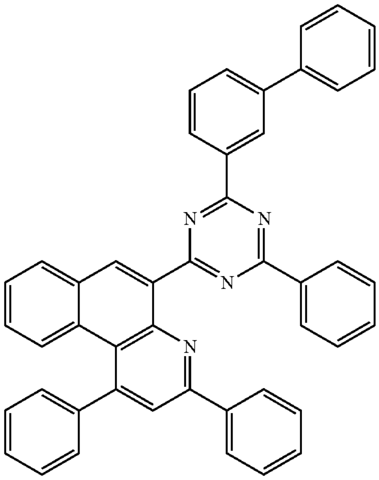
482
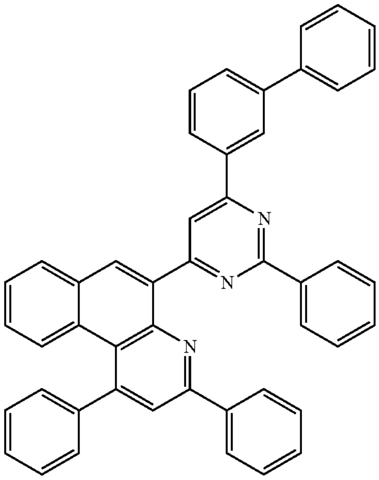
-continued
483
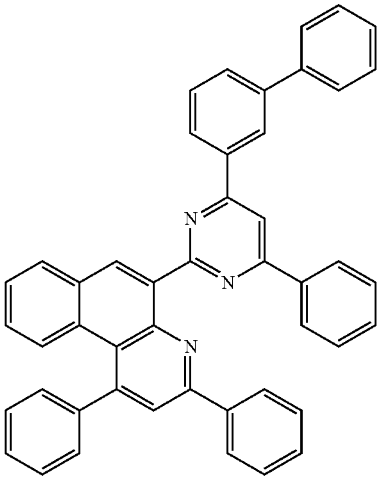
484
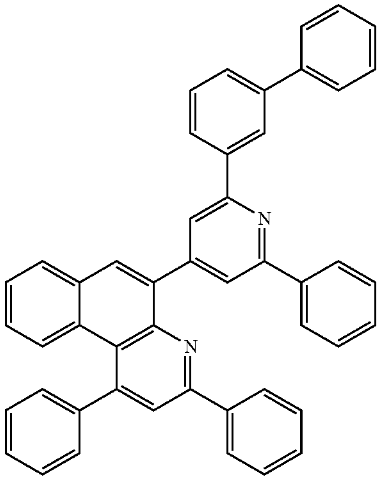
485
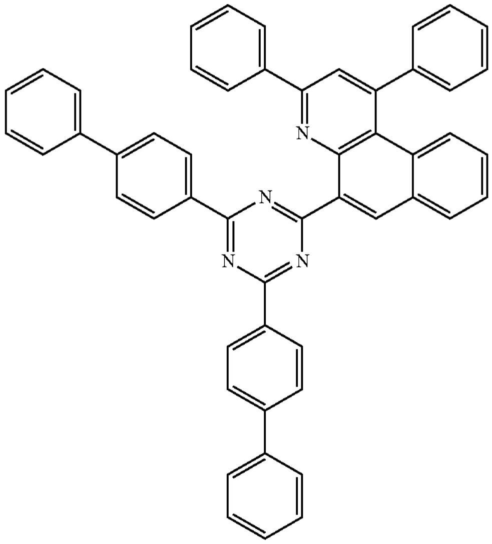

-continued
486
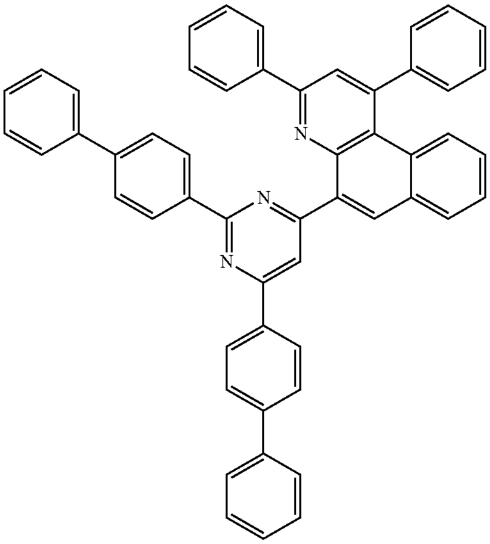
487
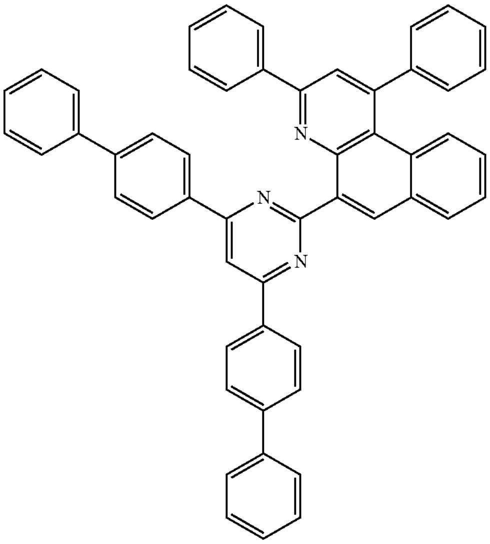
488
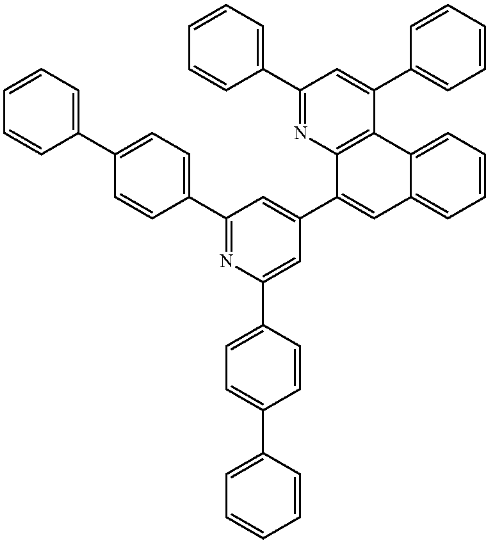
-continued
489
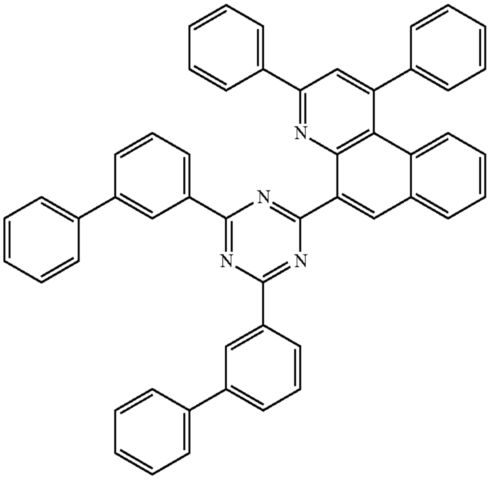
490
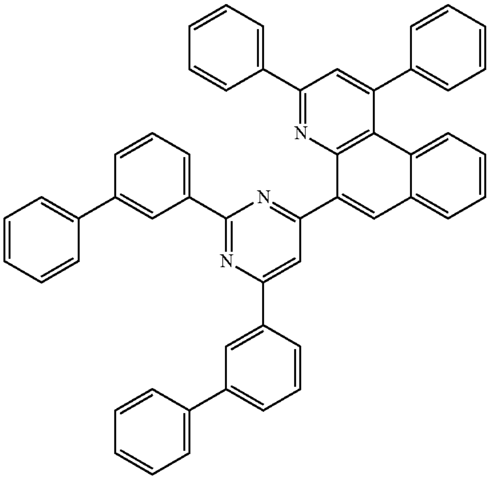
491
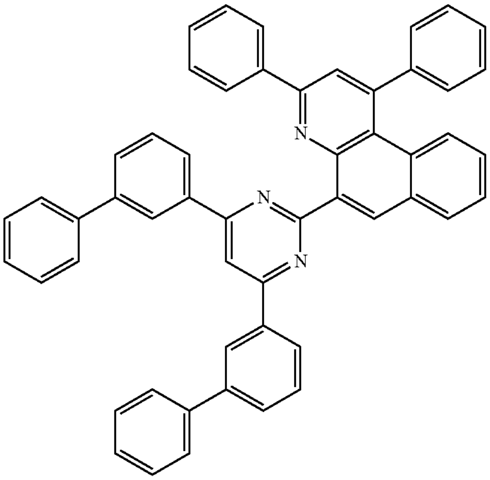

-continued
492
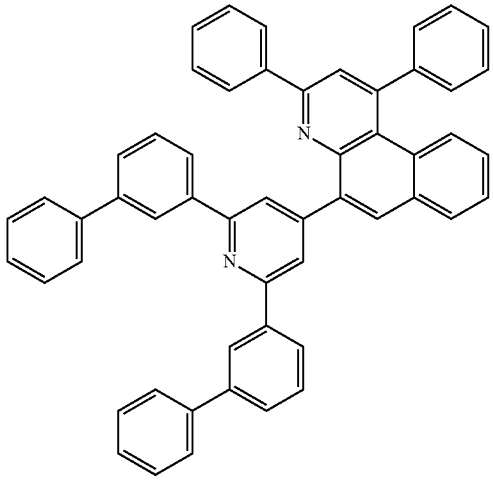
493
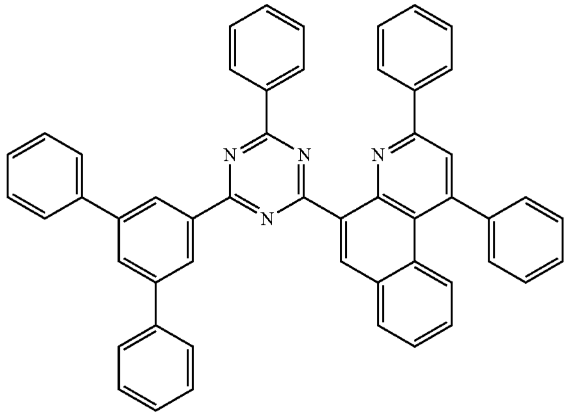
494
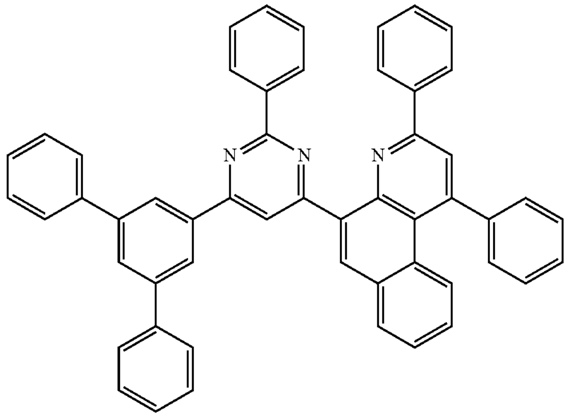
-continued
495
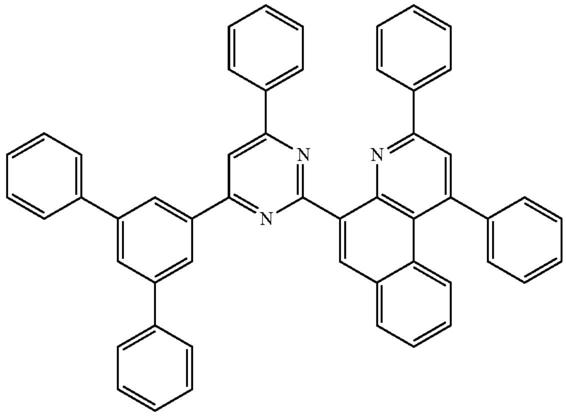
496
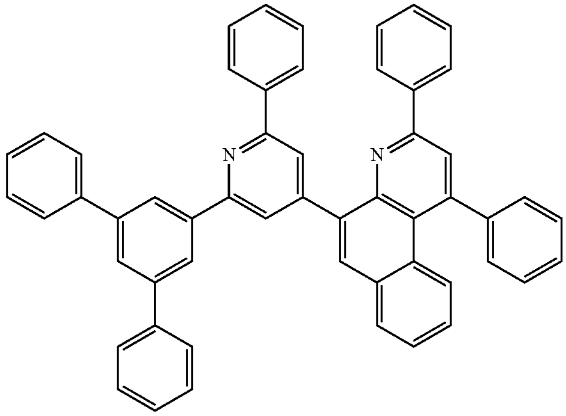
497
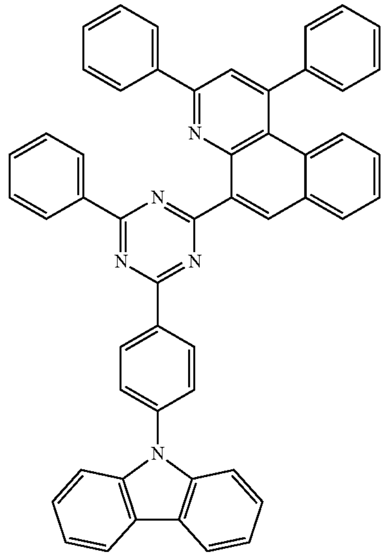

-continued
498
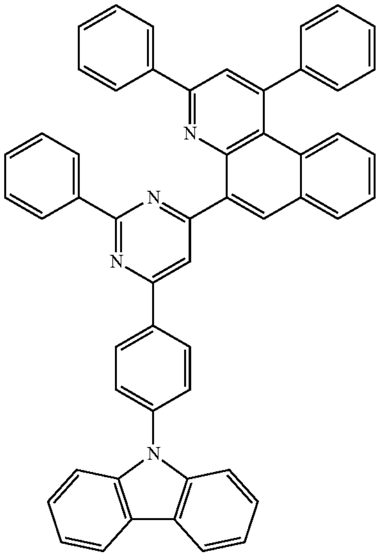
499
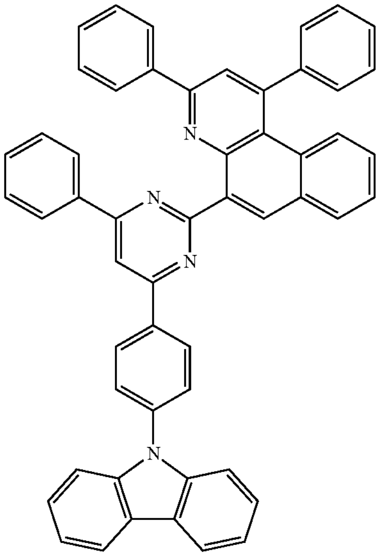
500
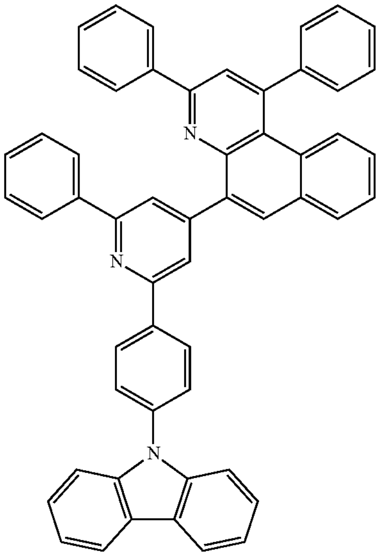
-continued
501
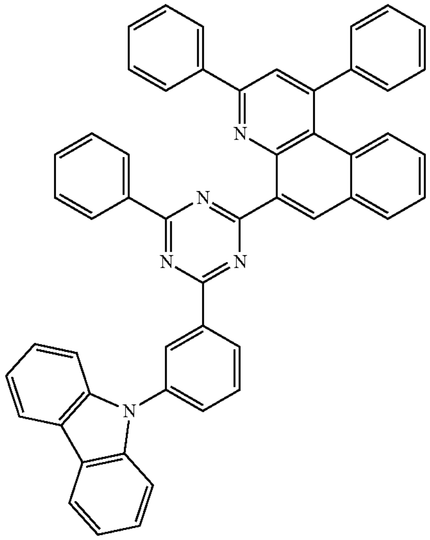
502
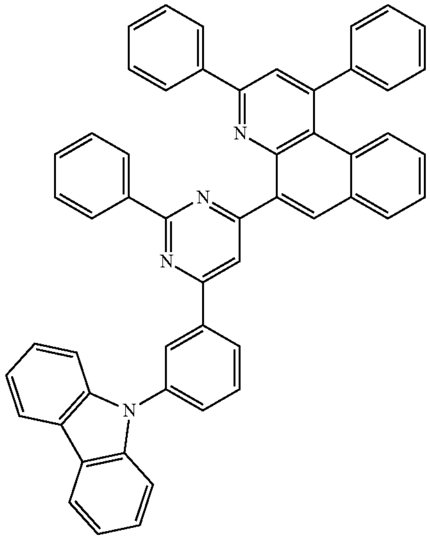
503
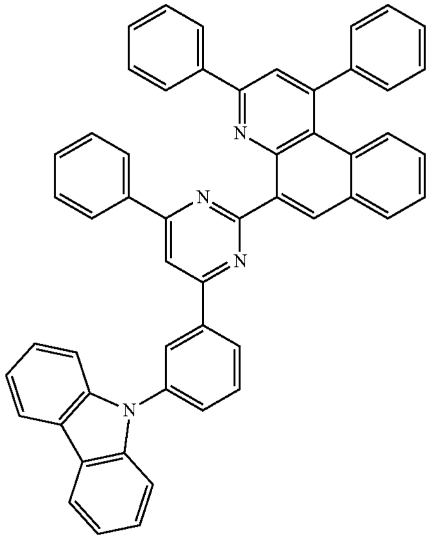

-continued
504
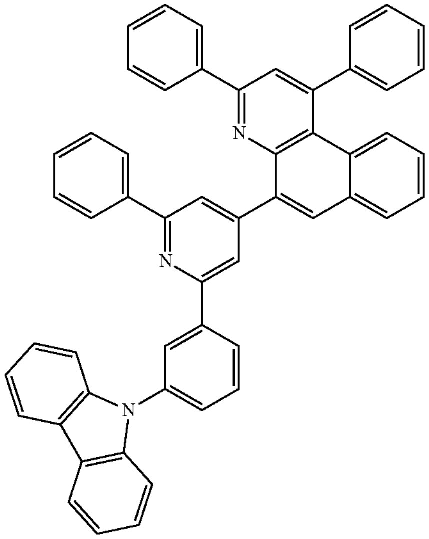
505
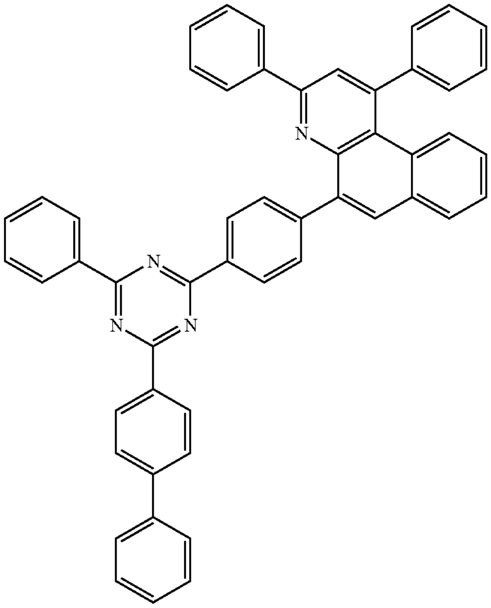
-continued
506
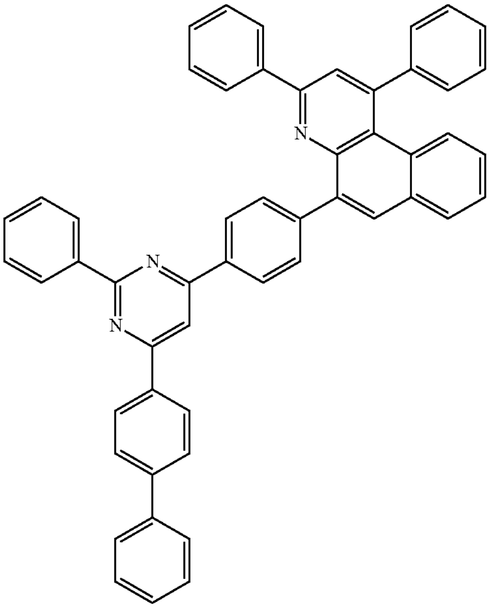
507
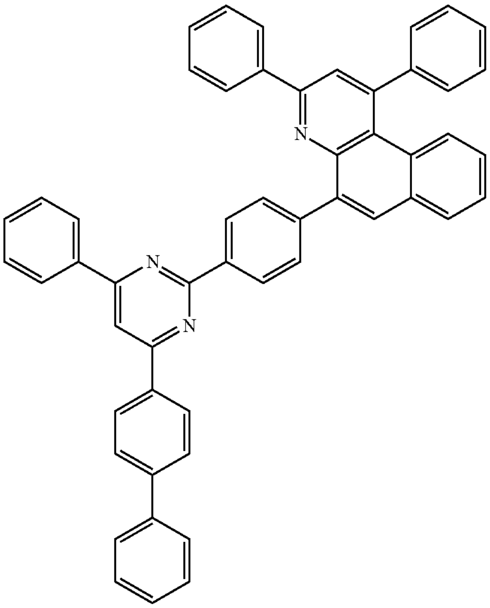

-continued
508
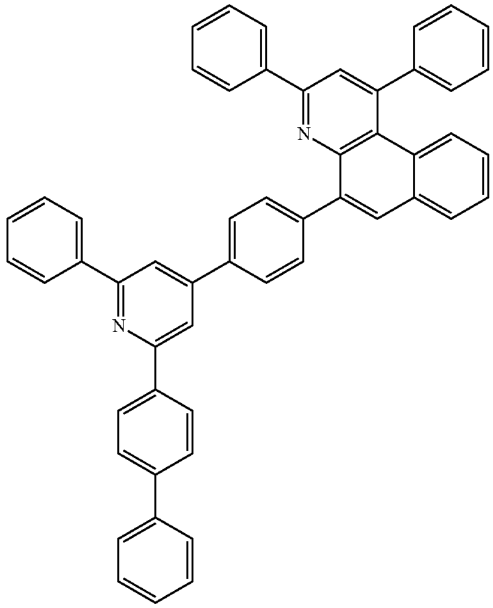
509
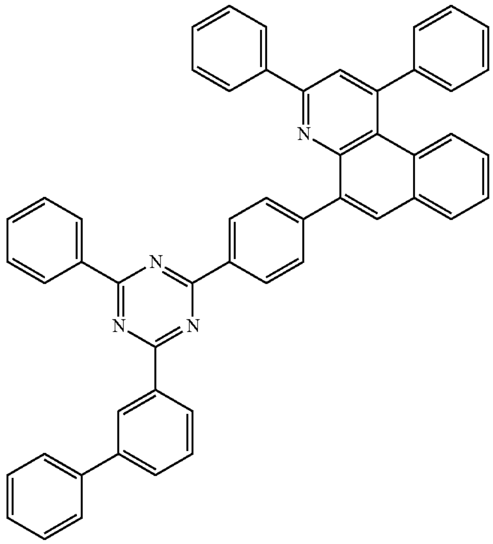
-continued
510
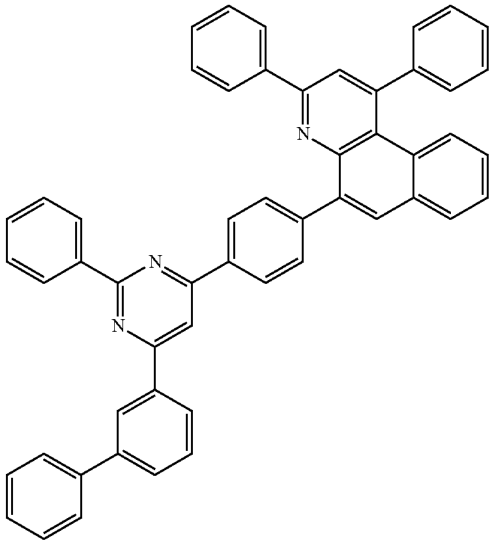
511
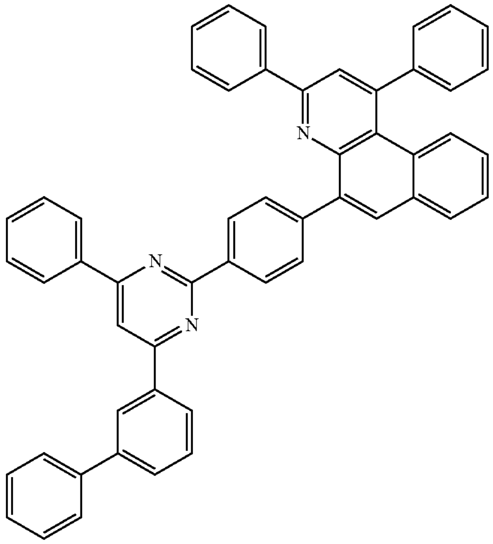
512
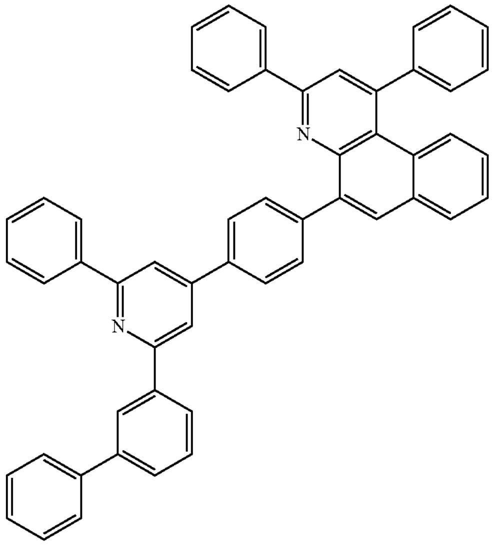

513
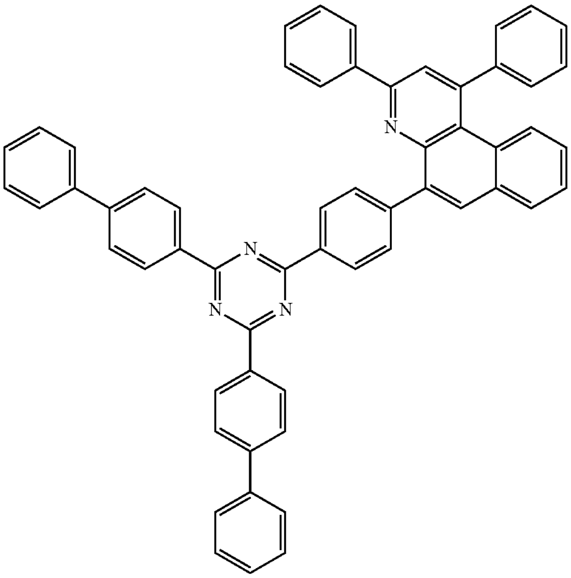
514
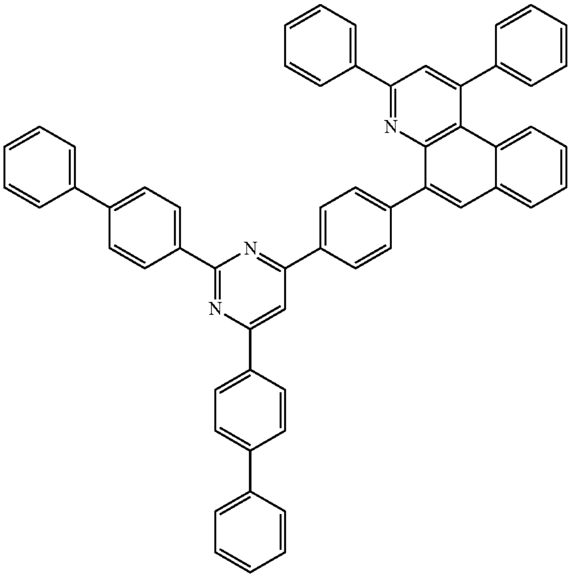
515
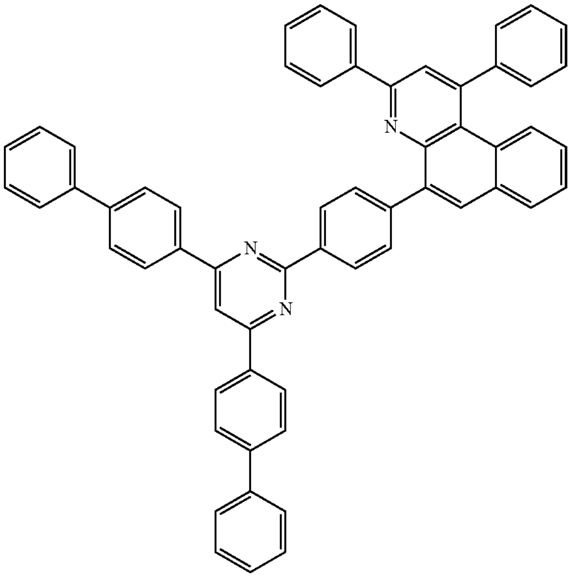
516
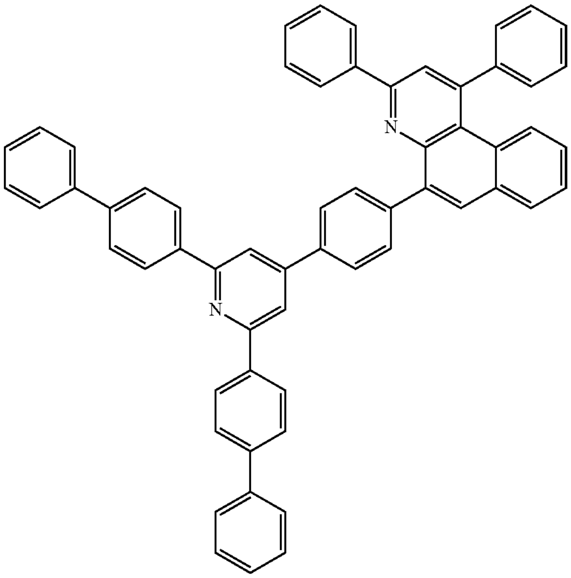

-continued
517
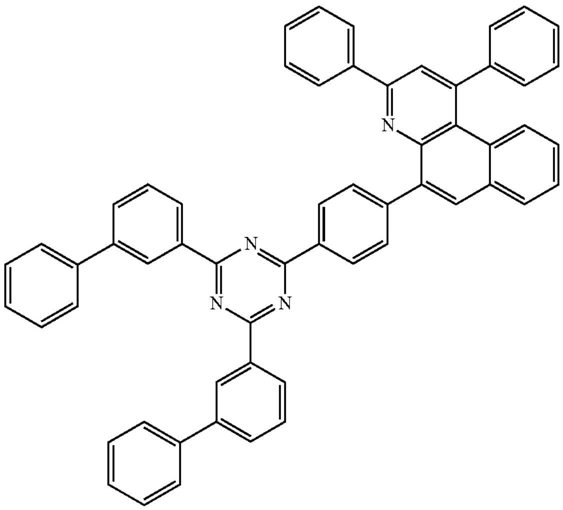
518
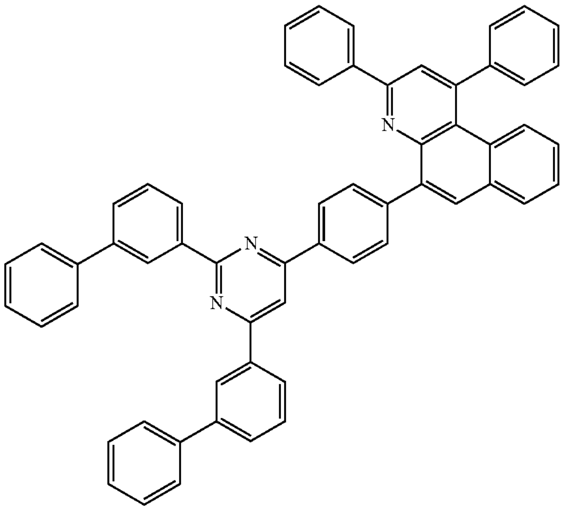
519
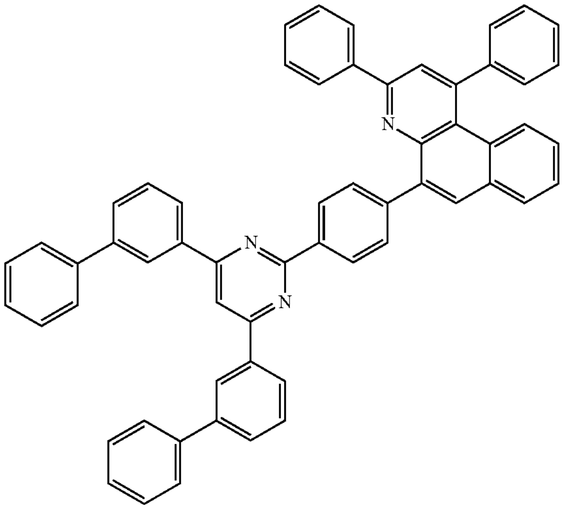
-continued
520
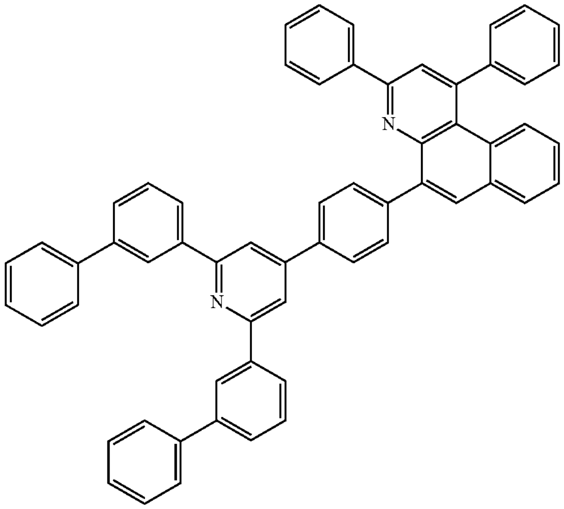
521
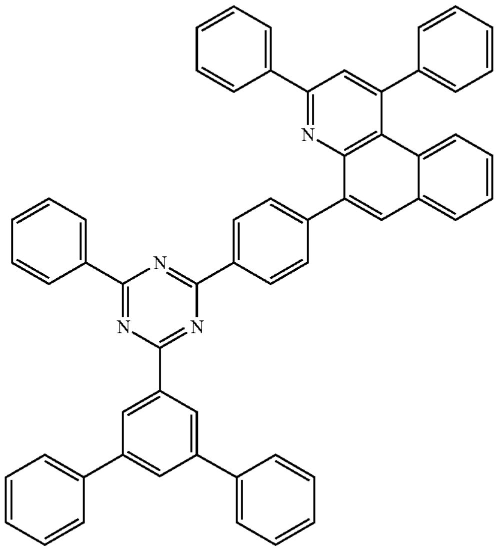
522
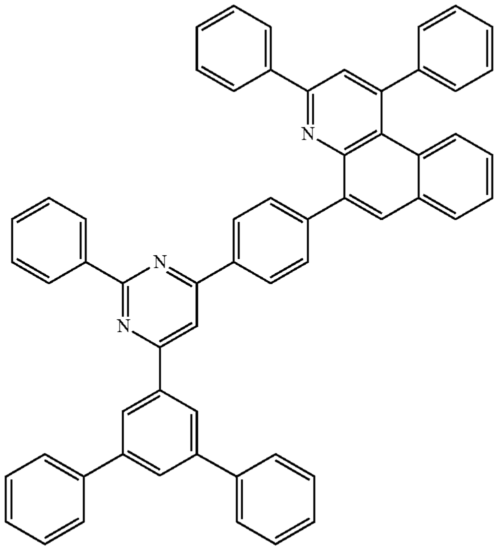

-continued
523
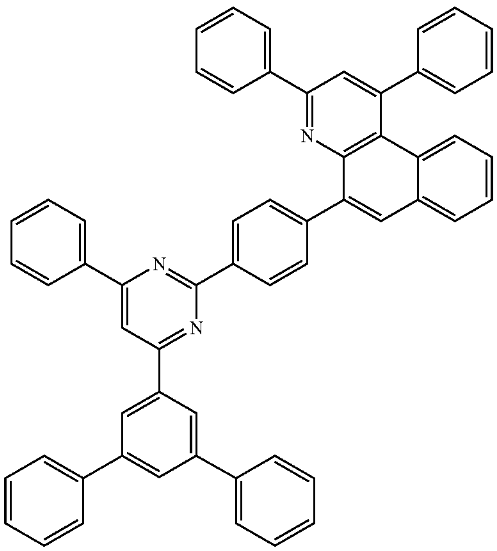
-continued
525
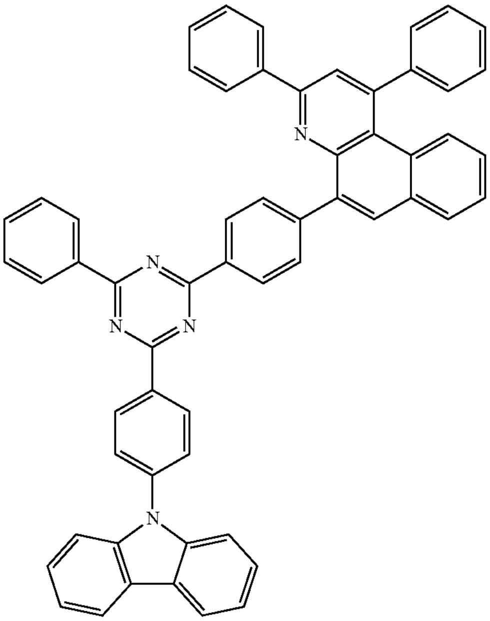
524
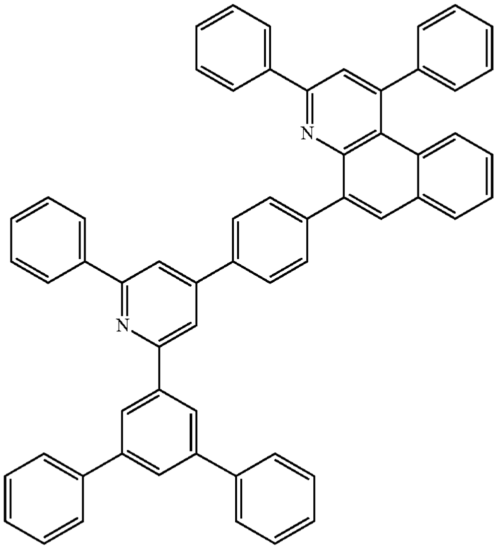
526
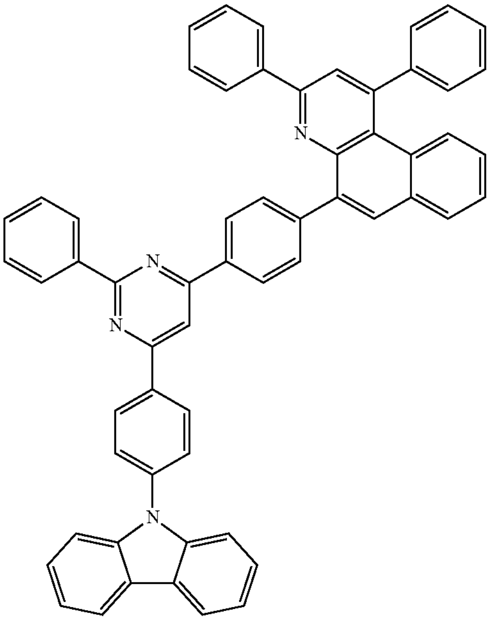

-continued
527
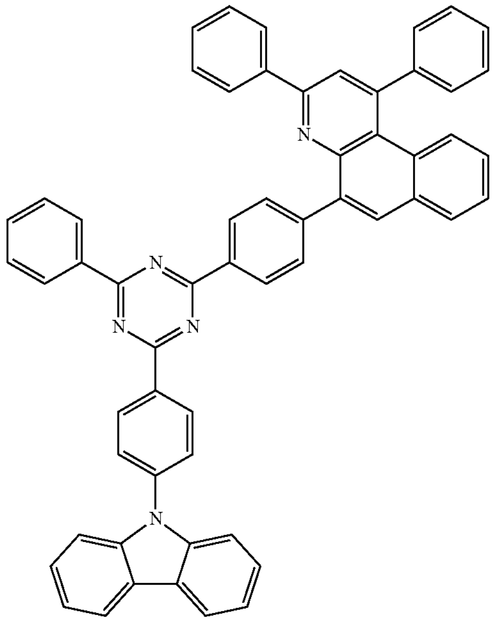
528
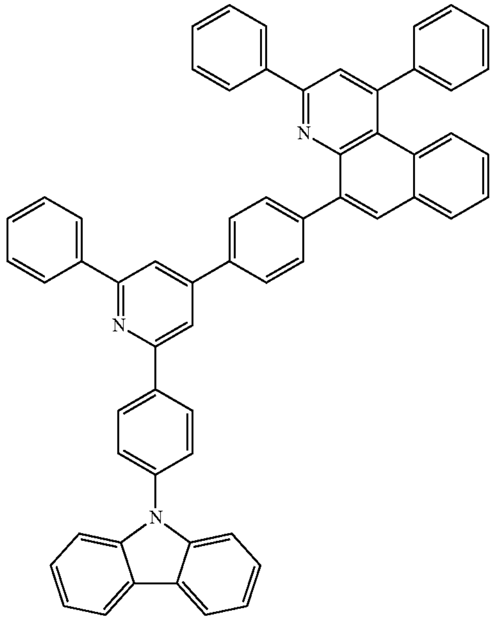
-continued
529
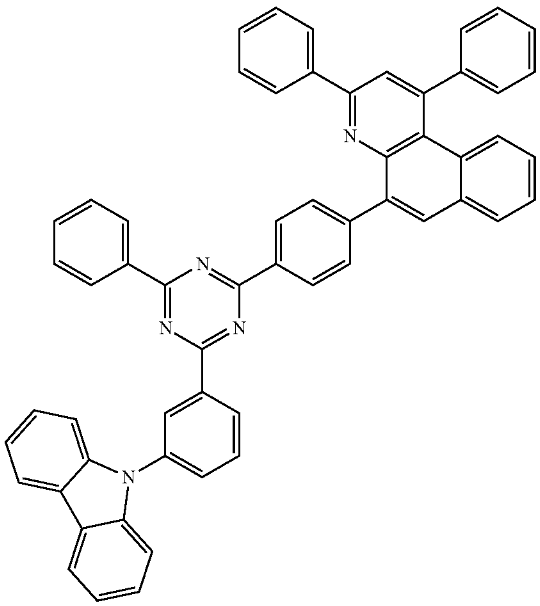
530
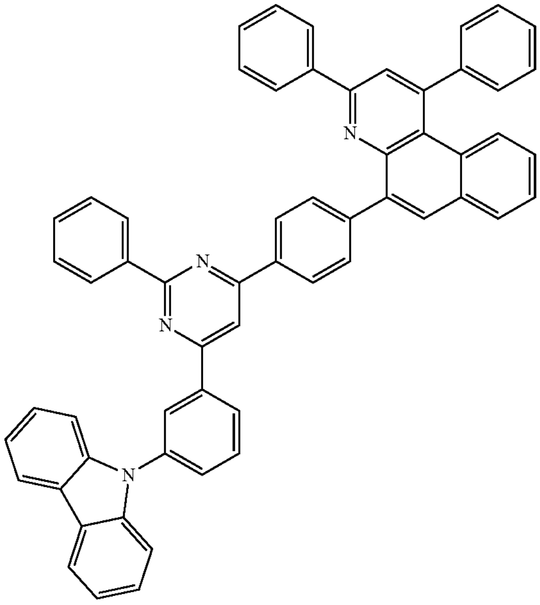

-continued
531
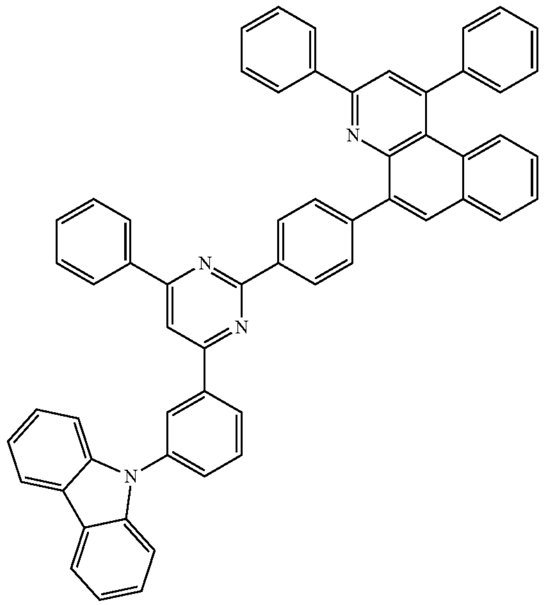
532
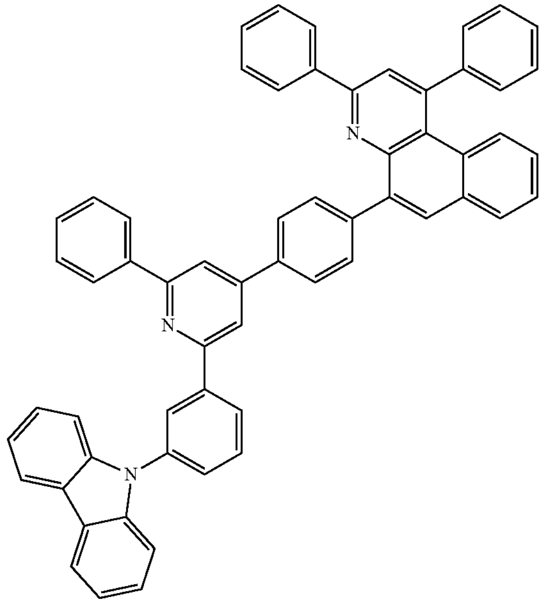
533
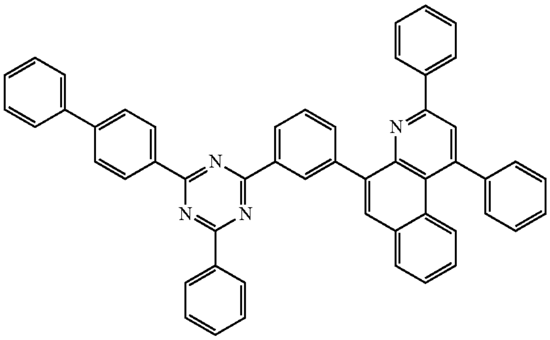
-continued
534
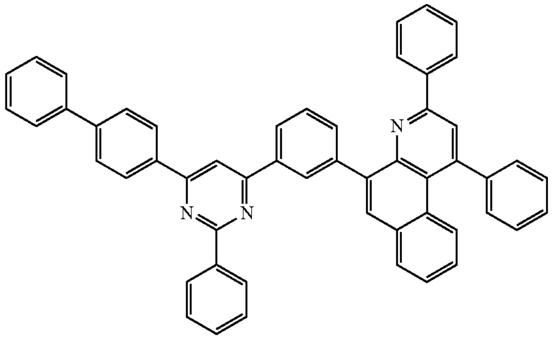
535
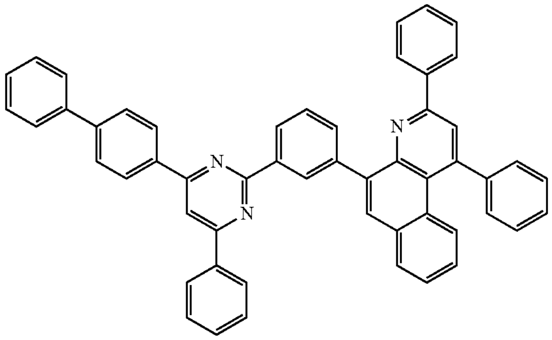
536
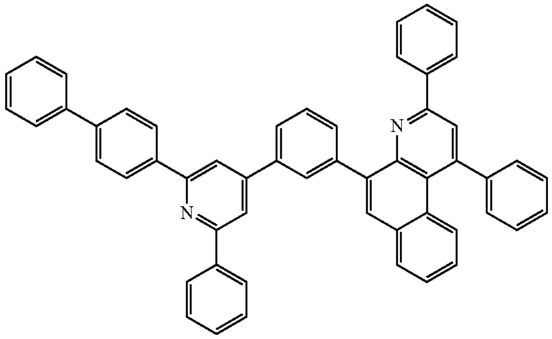
537
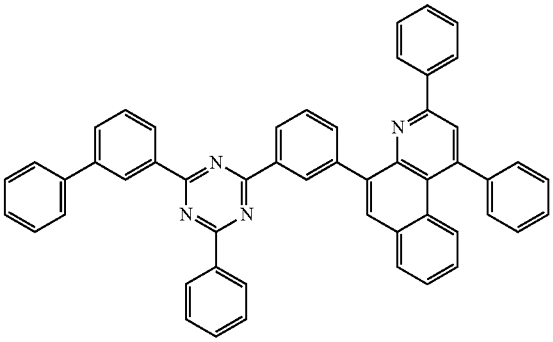

-continued
538
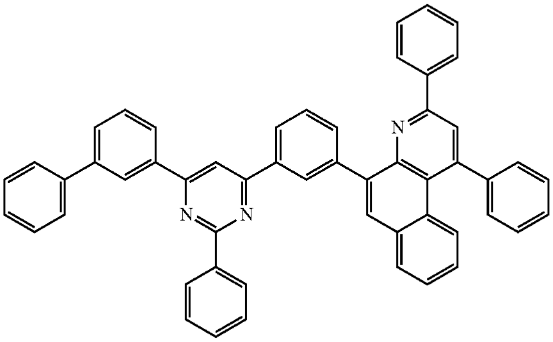
539
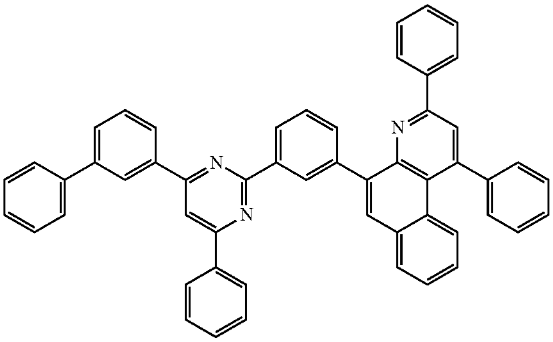
540
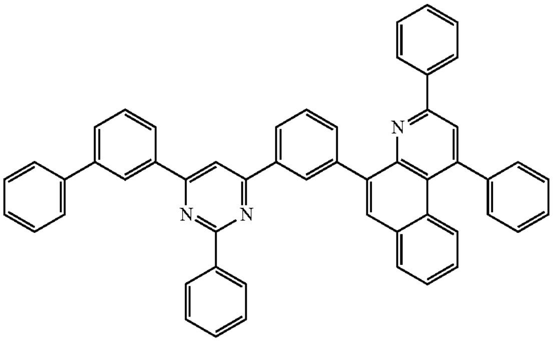
541
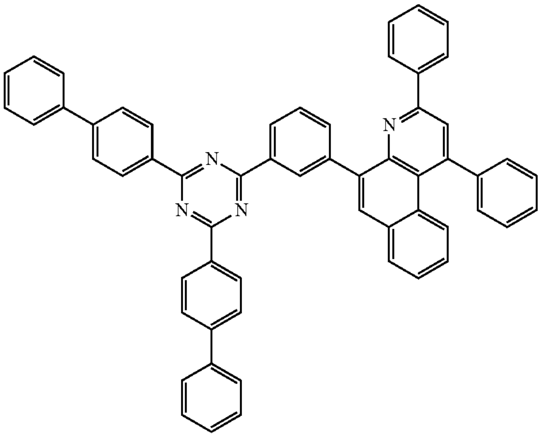
-continued
542
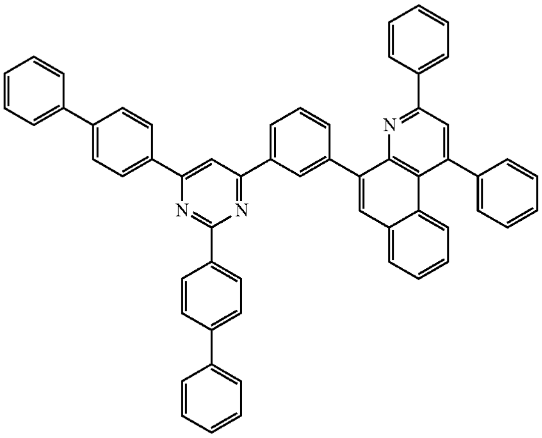
543
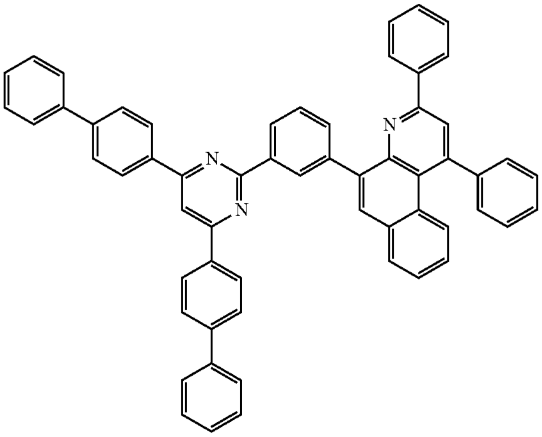
544
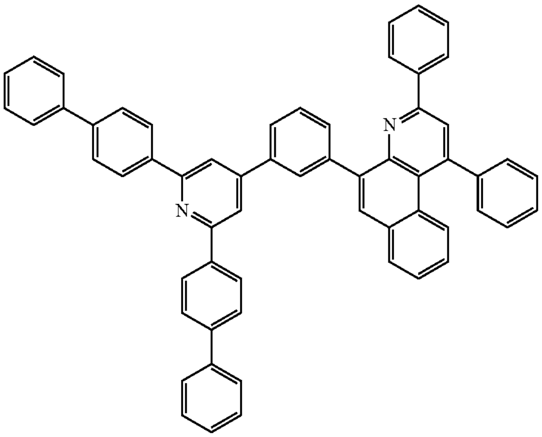

-continued
545
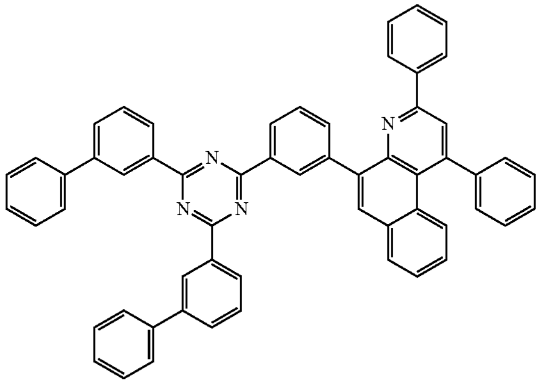
546
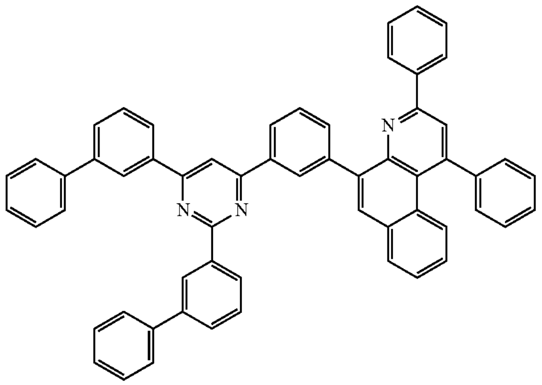
547
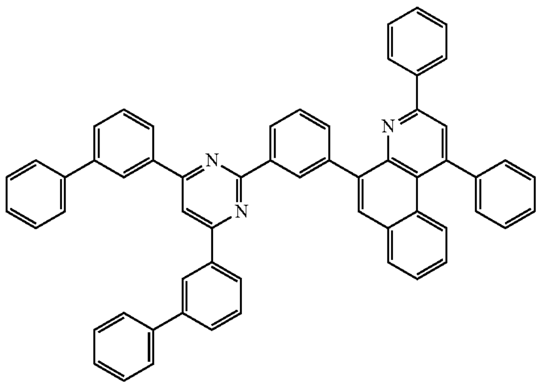
548
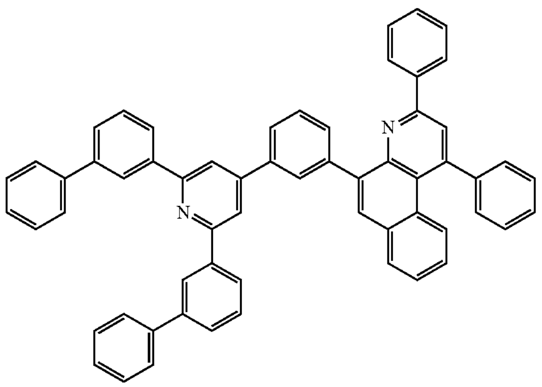
-continued
549
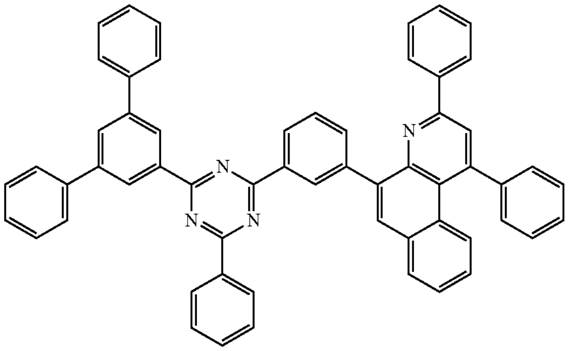
550
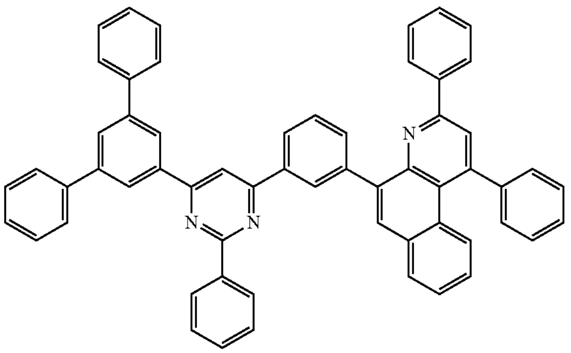
551
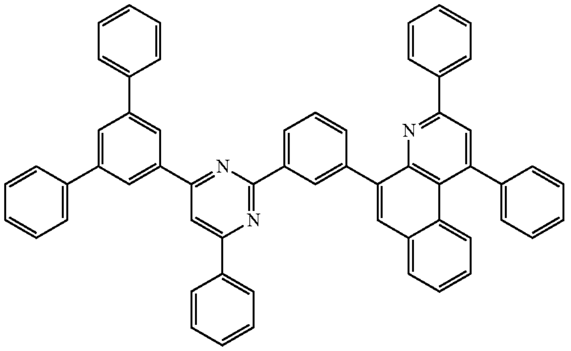
552
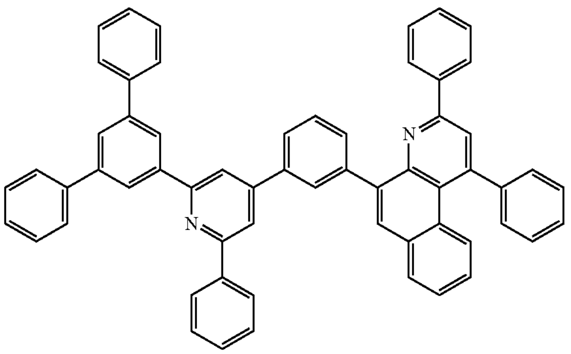

-continued
553
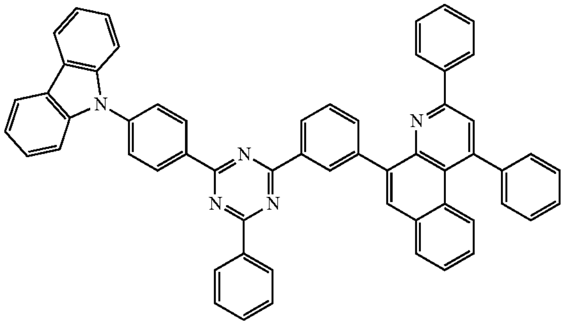
554
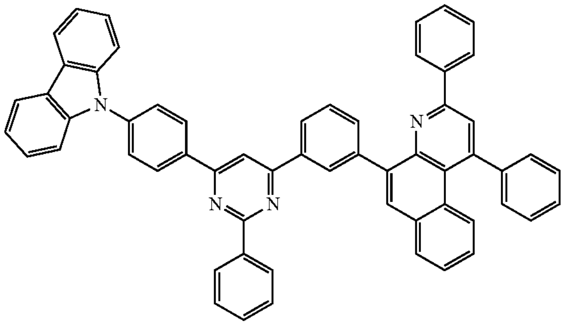
555
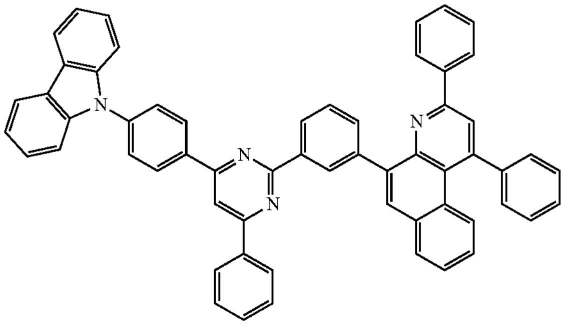
556
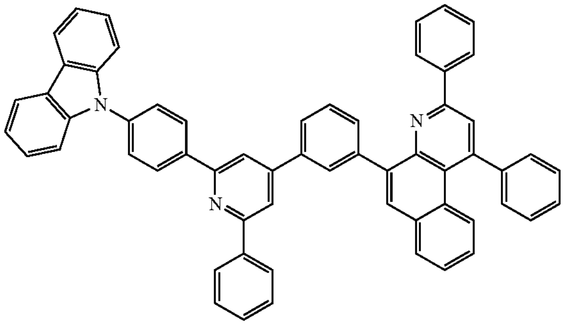
-continued
557
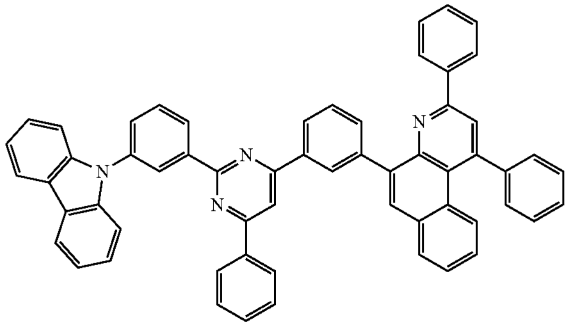
558
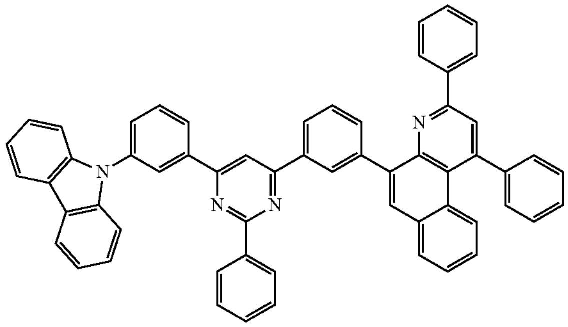
559
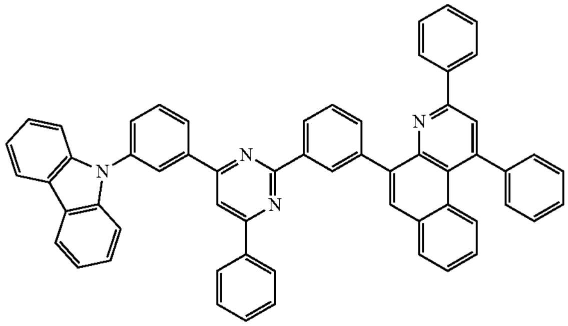
560
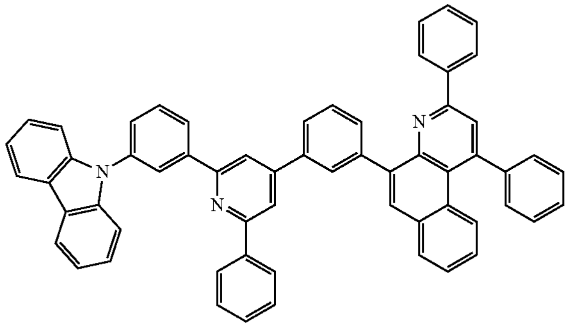

561
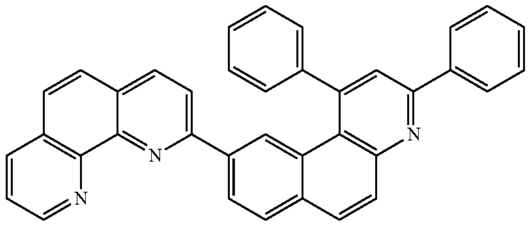
562
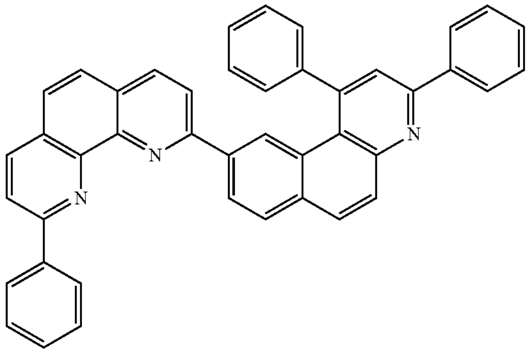
563
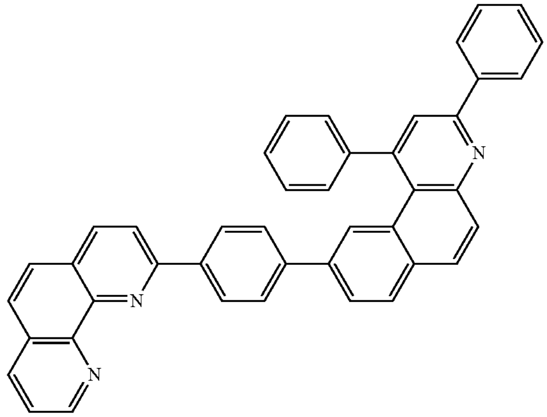
564
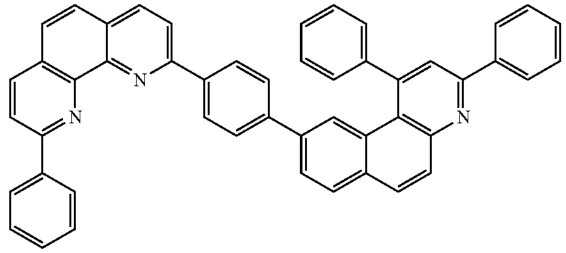
565
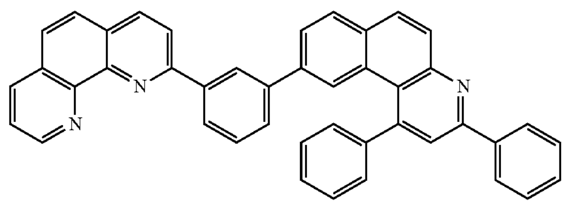
-continued
566
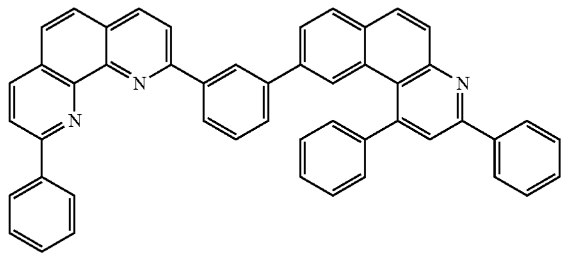
567
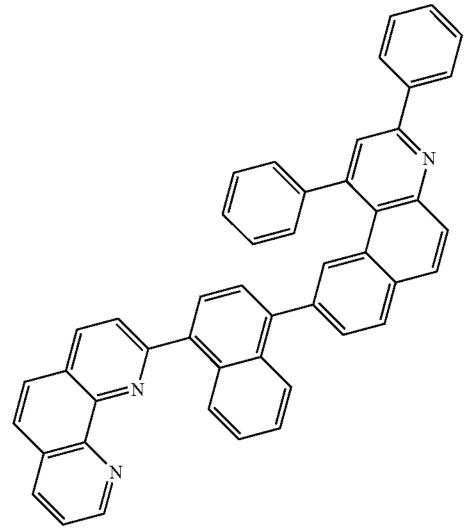
568
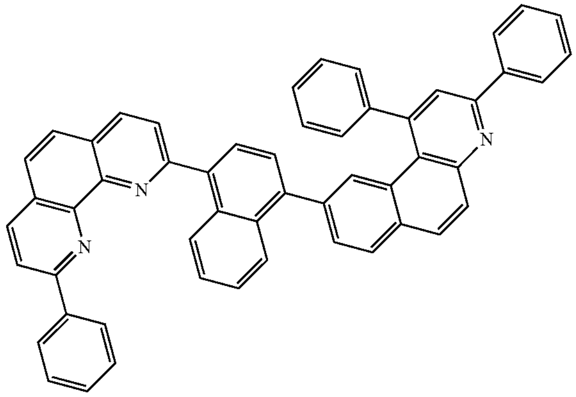
569
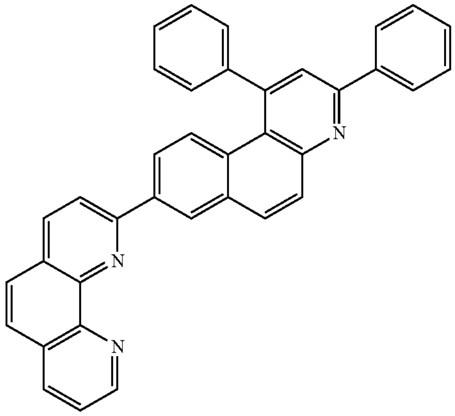

-continued
570
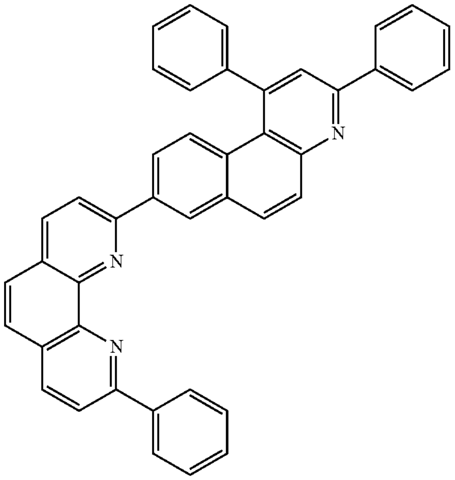
571
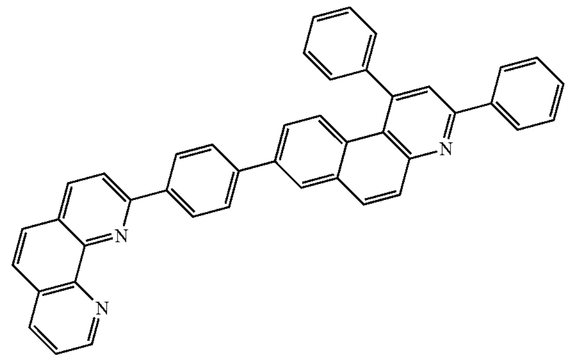
572
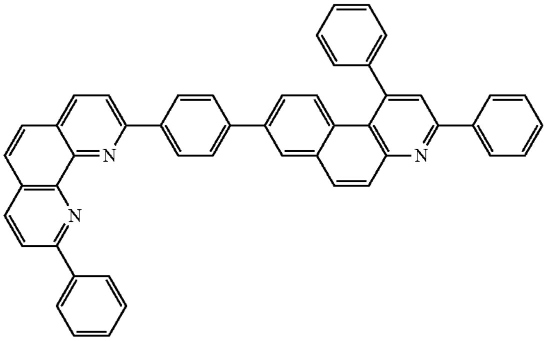
573
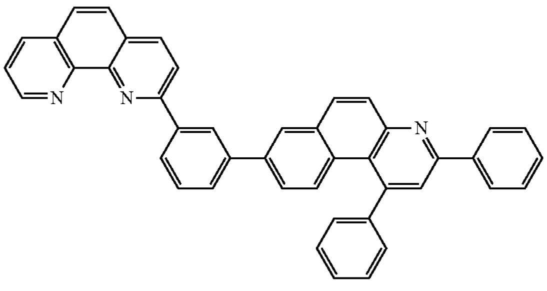
-continued
574
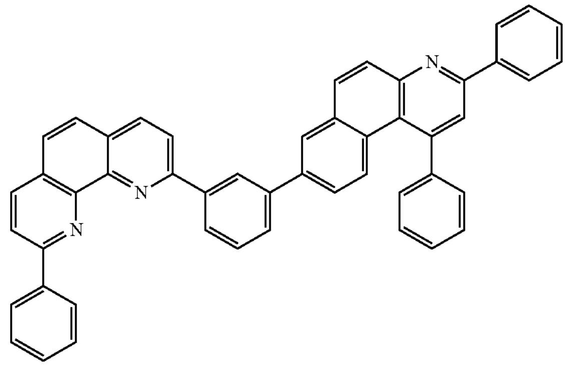
575
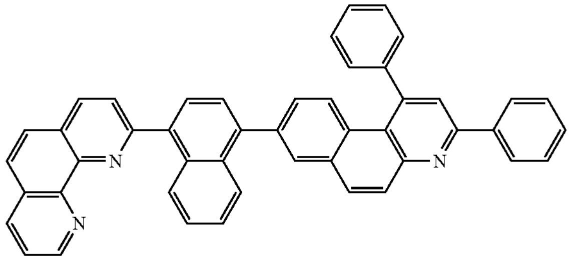
576
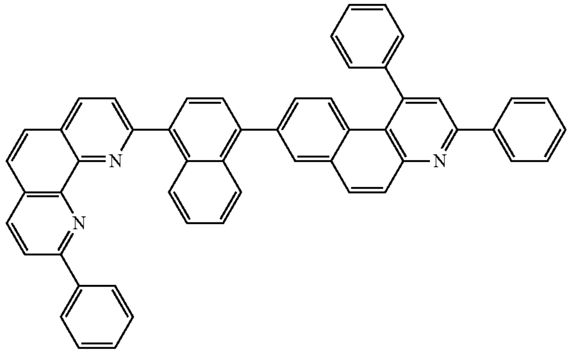
577
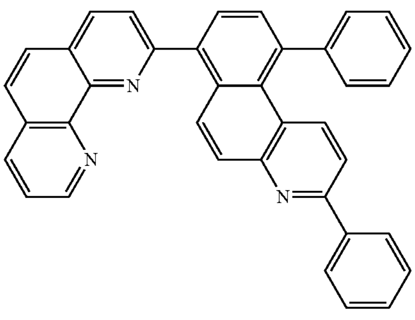

-continued
578
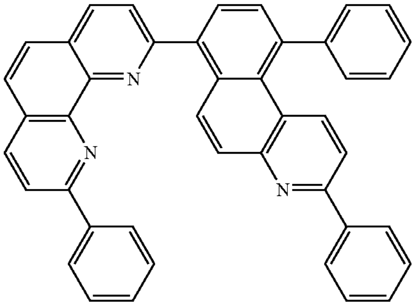
579
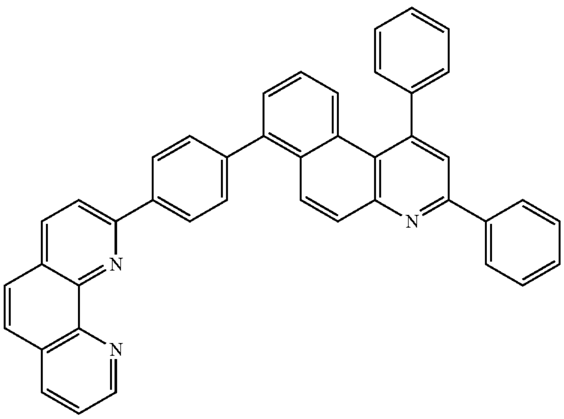
580
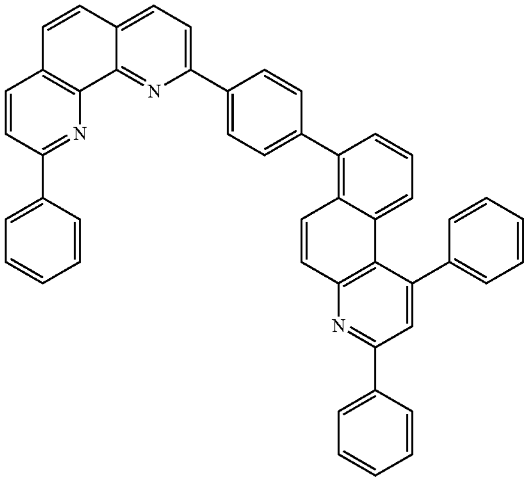
581
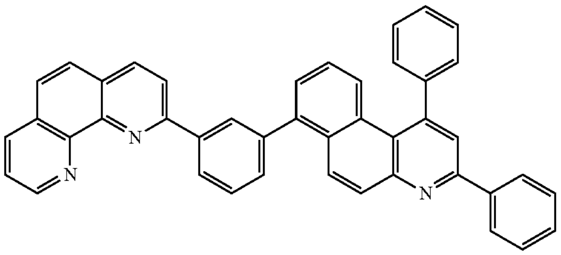
-continued
582
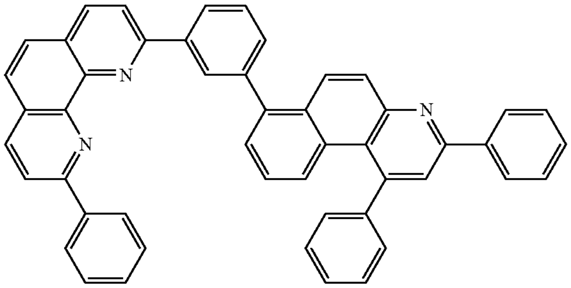
583
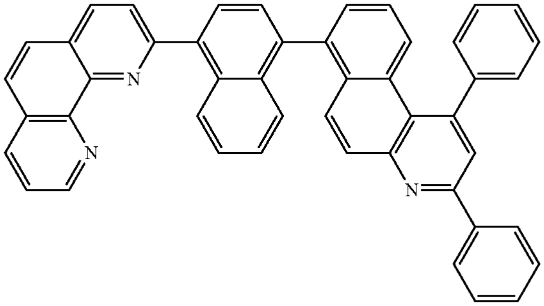
584
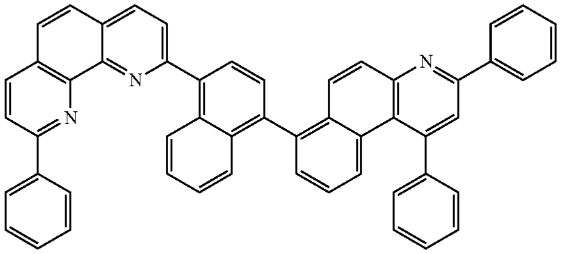
585
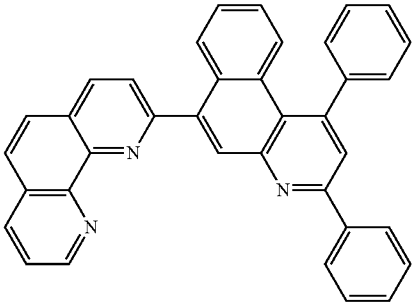
586
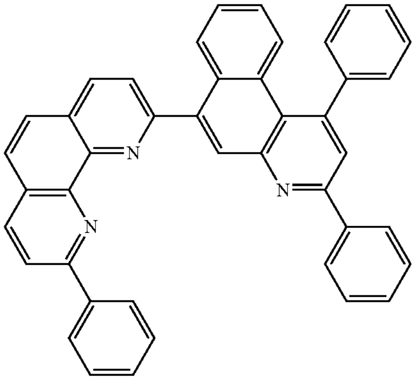

-continued
587
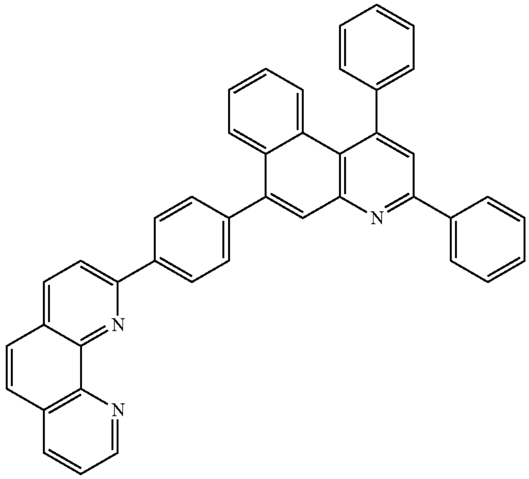
588
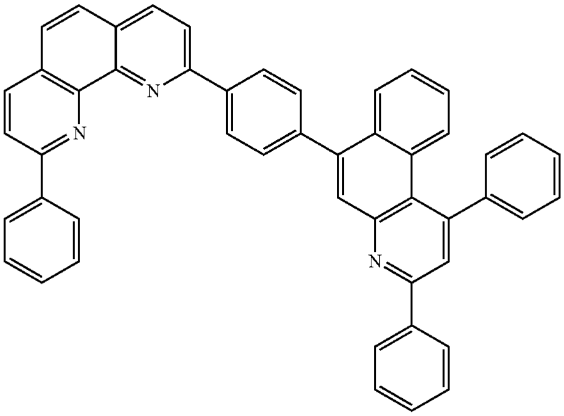
589
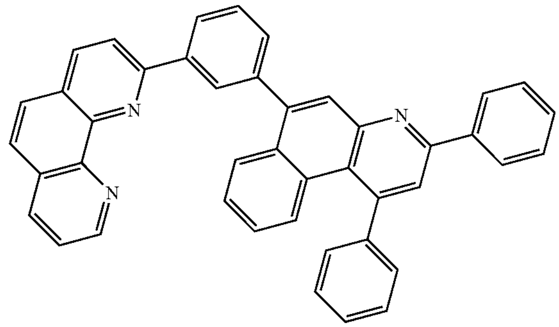
590
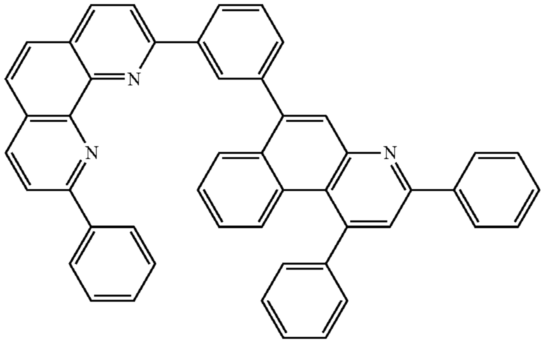
-continued
591
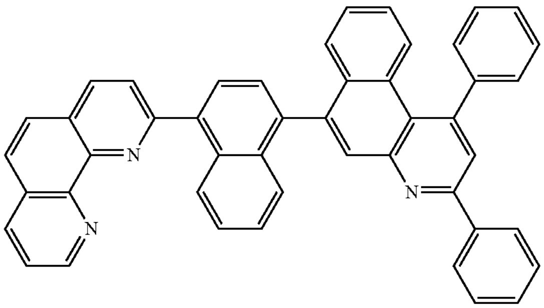
592
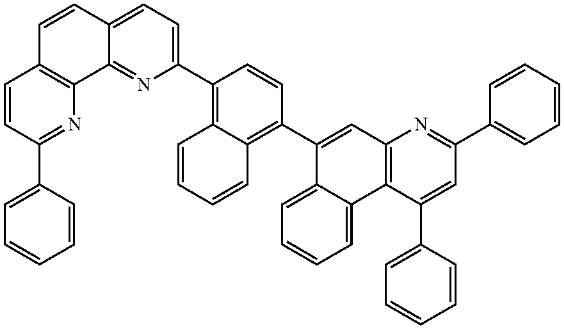
593
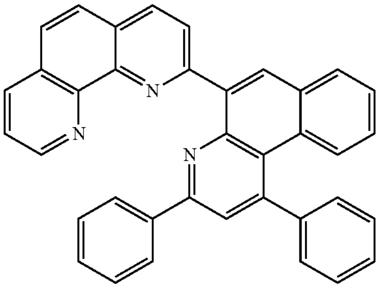
594
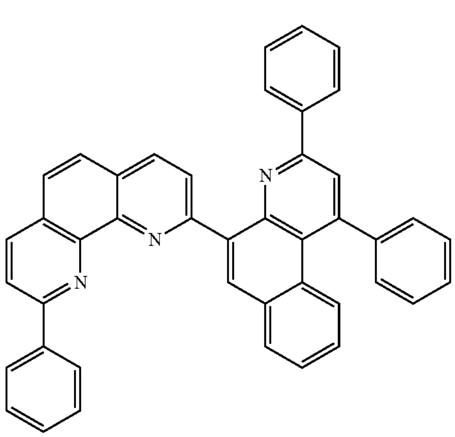

-continued
595
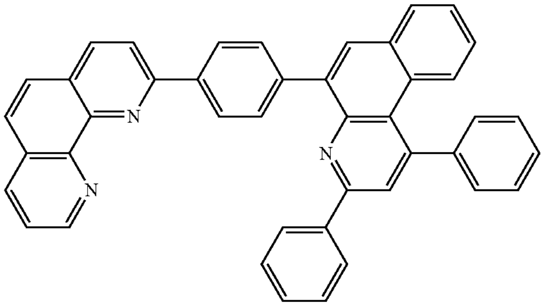
596
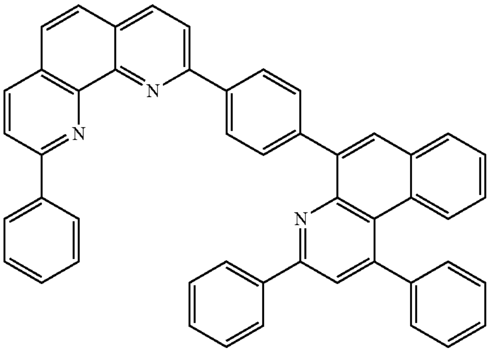
597
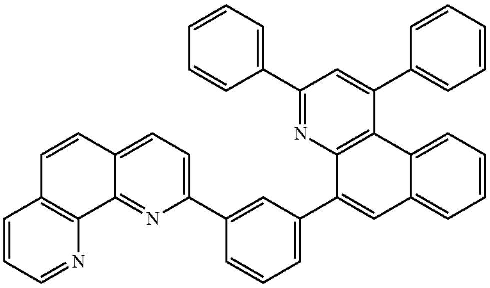
598
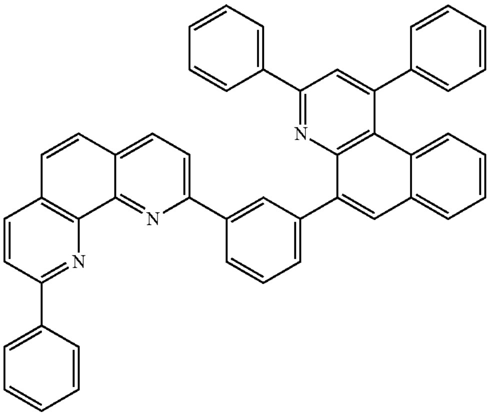
-continued
599
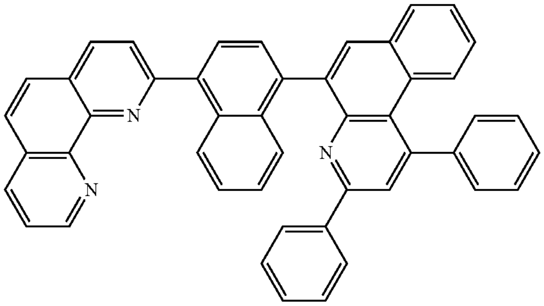
600
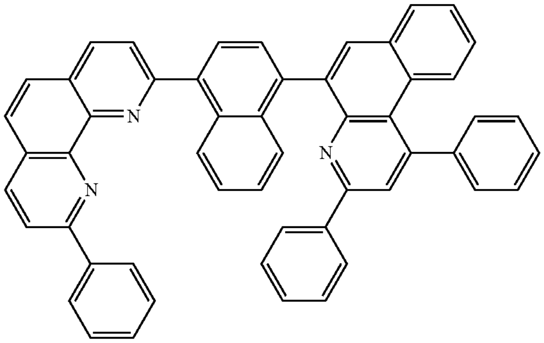
601
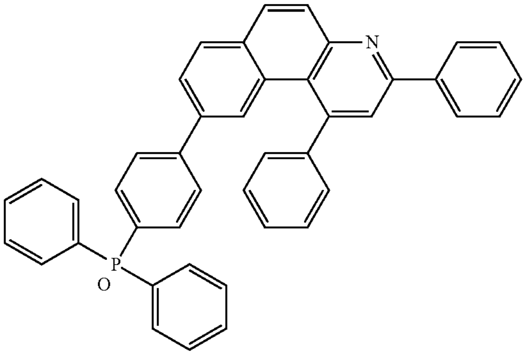
602
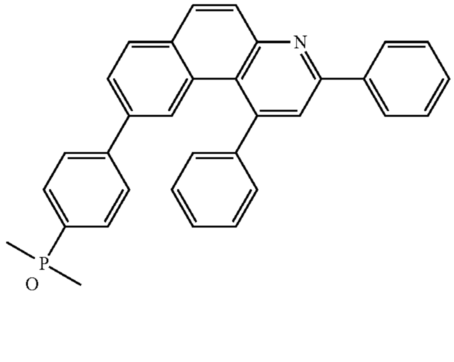

-continued
603
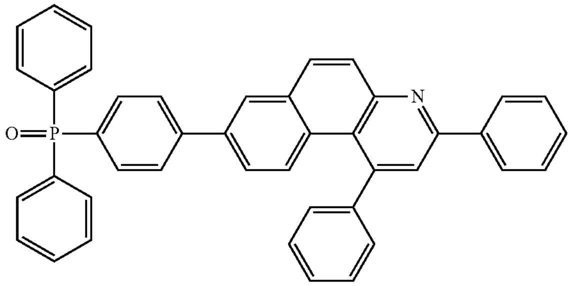
604
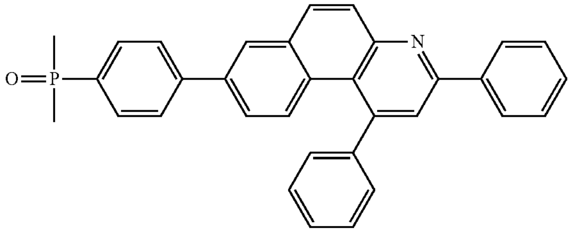
605
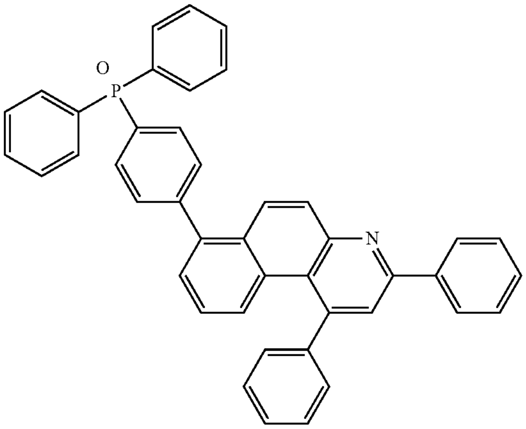
606
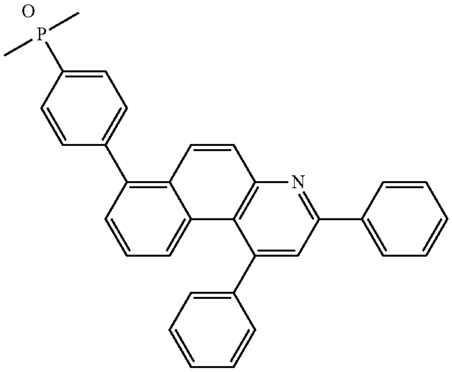
-continued
607
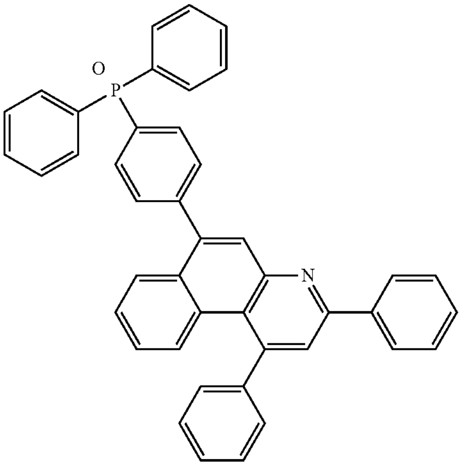
608
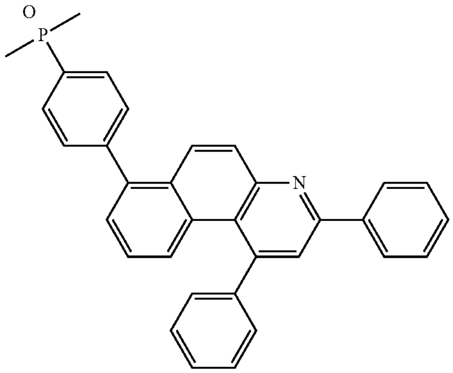
609
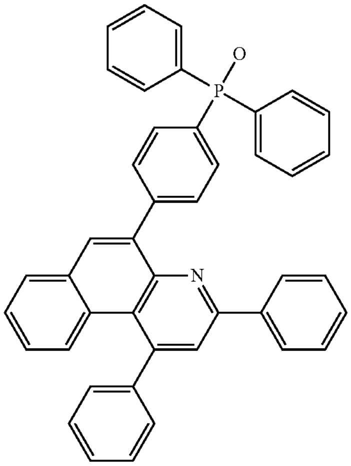

610
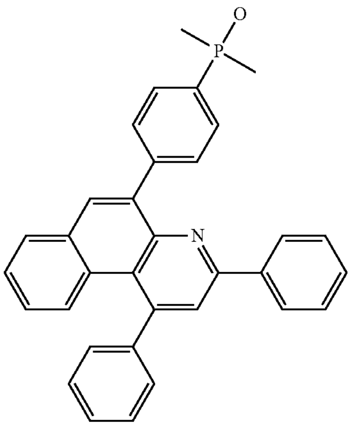
611
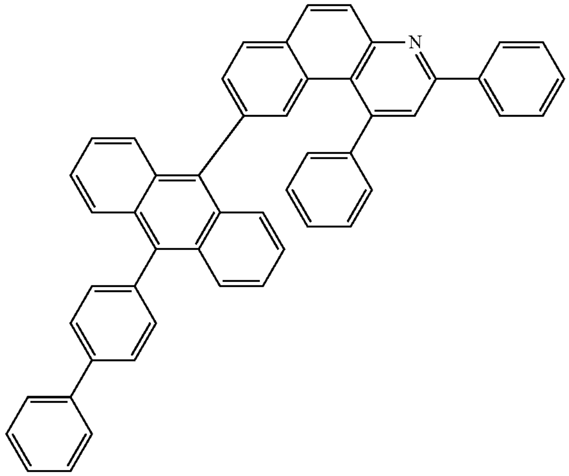
612
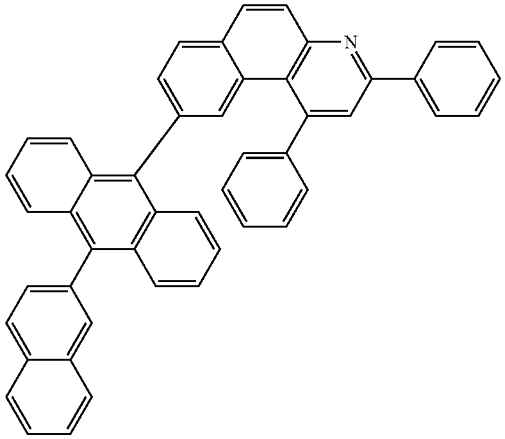
613
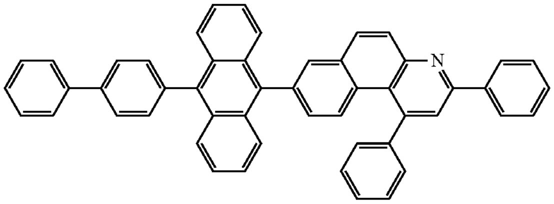
614
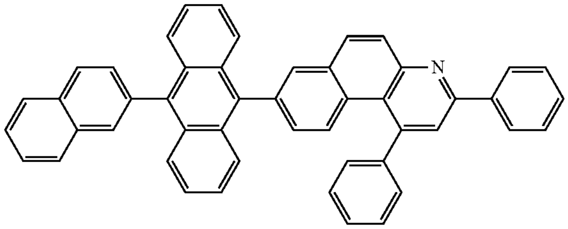
615
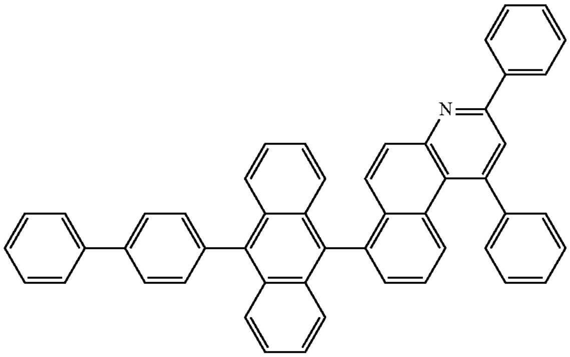
616
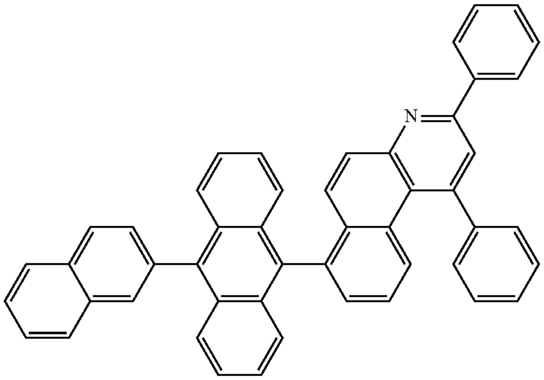
617
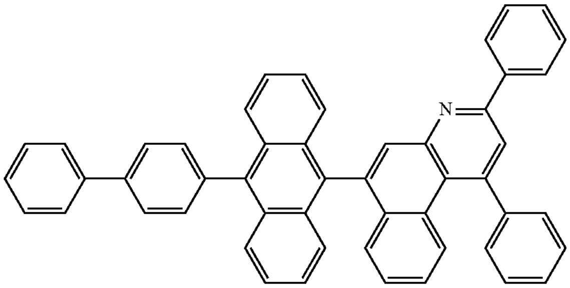

-continued
618
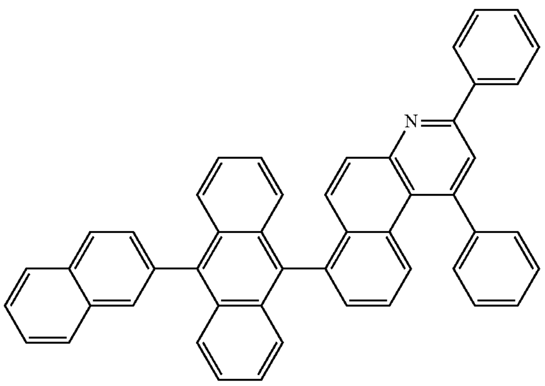
619
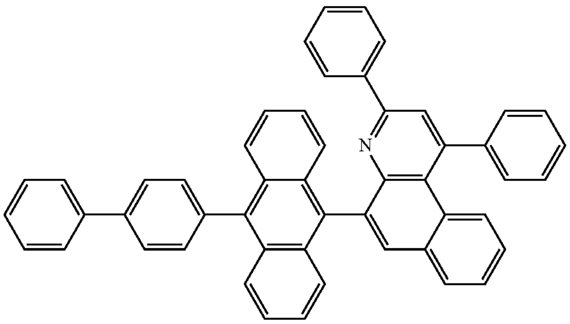
620
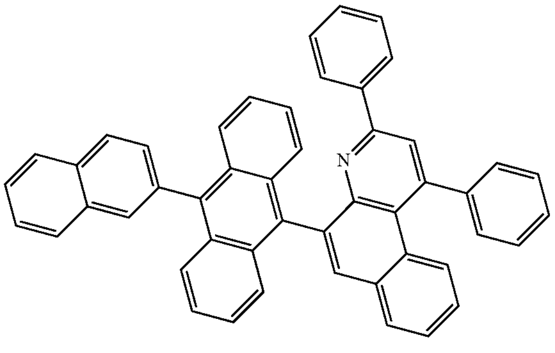
621
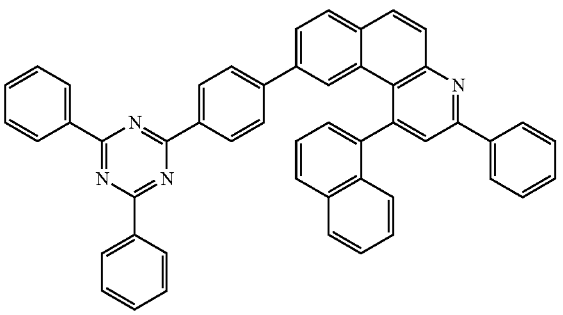
-continued
622
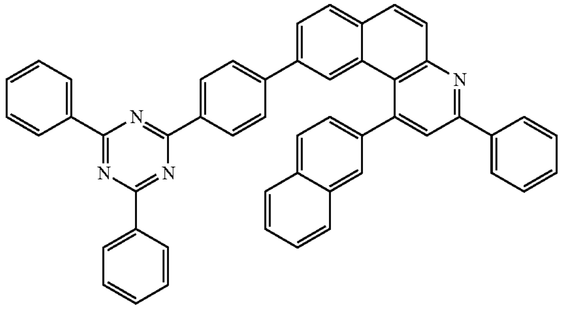
623
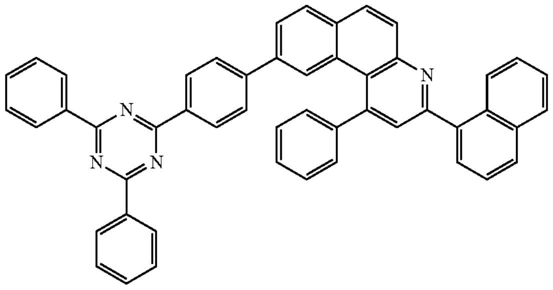
624
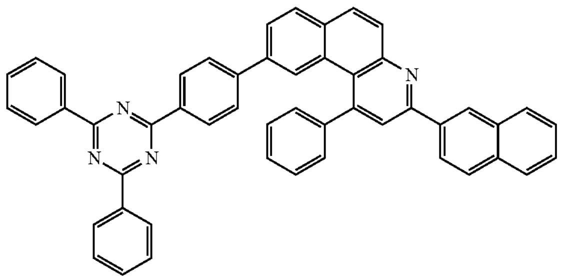
625
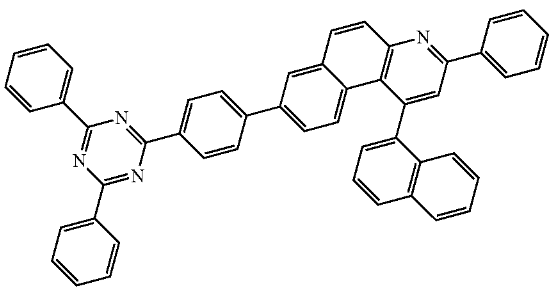
626
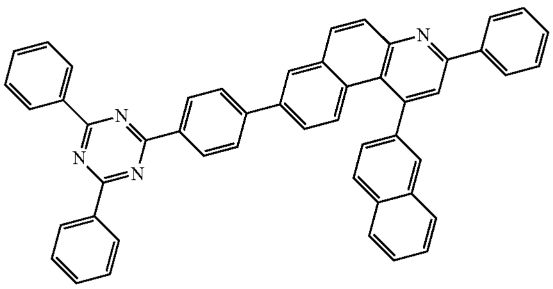

-continued
627
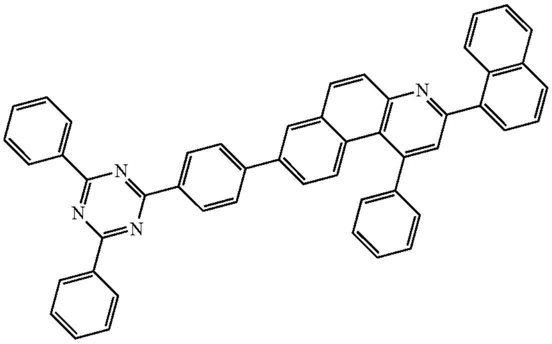
628
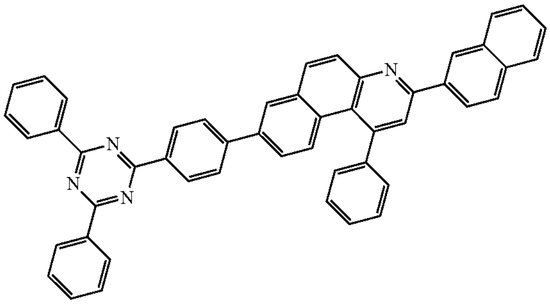
629
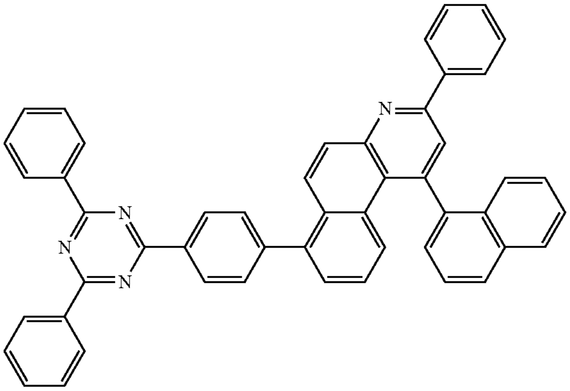
630
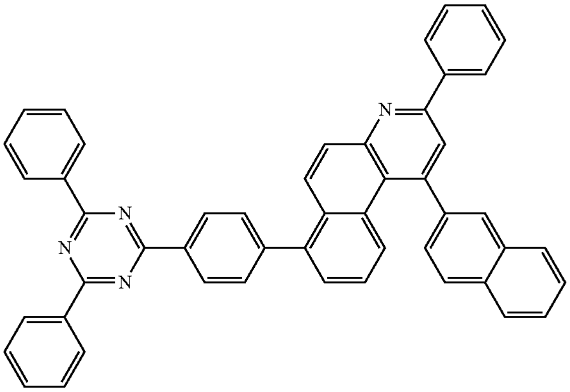
-continued
631
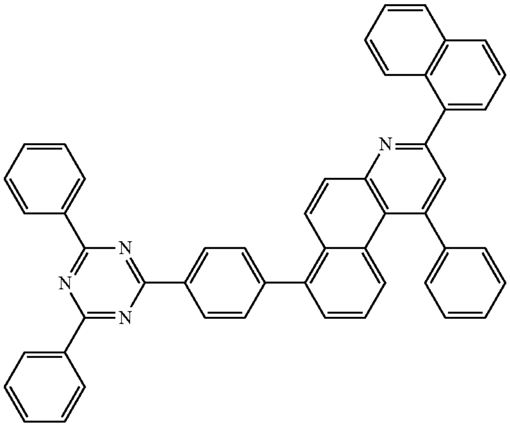
632
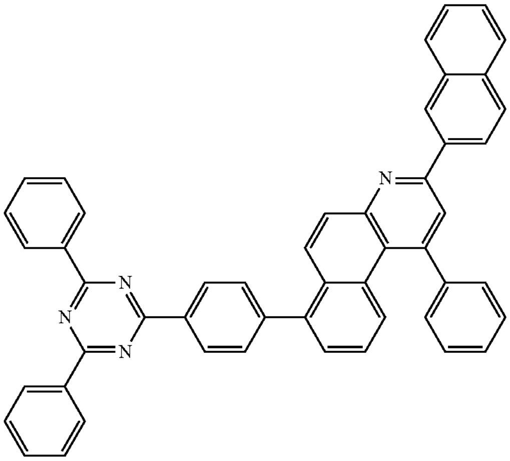
633
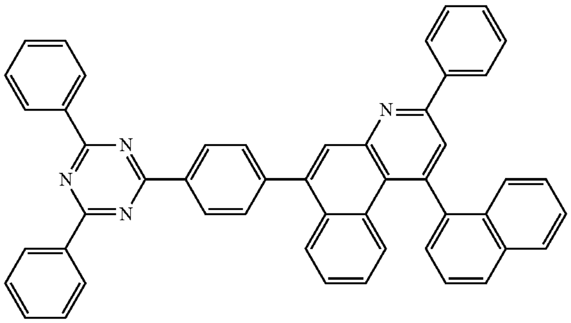
634
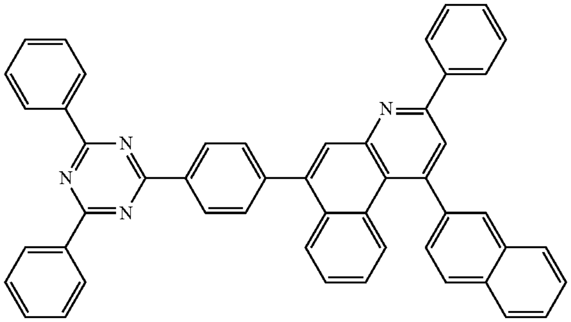

-continued
635
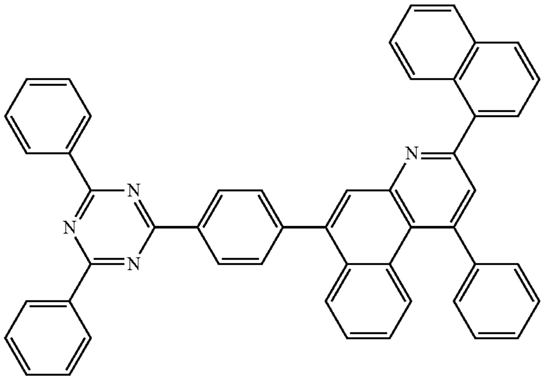
636
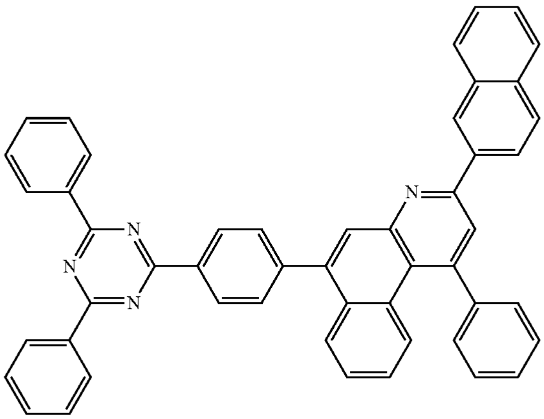
637
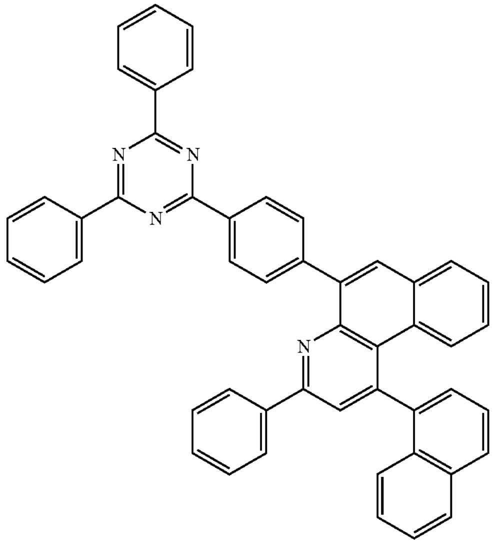
-continued
638
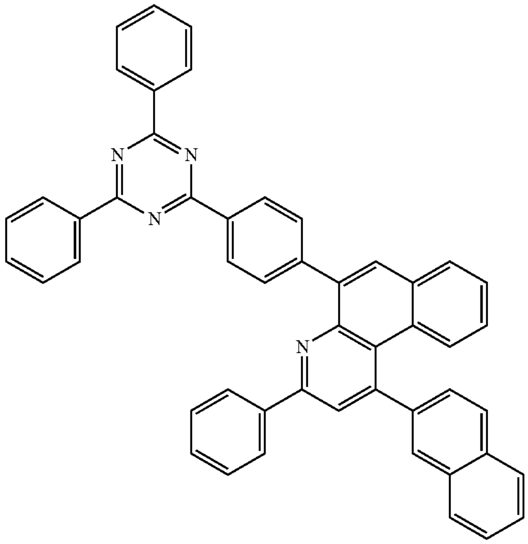
639
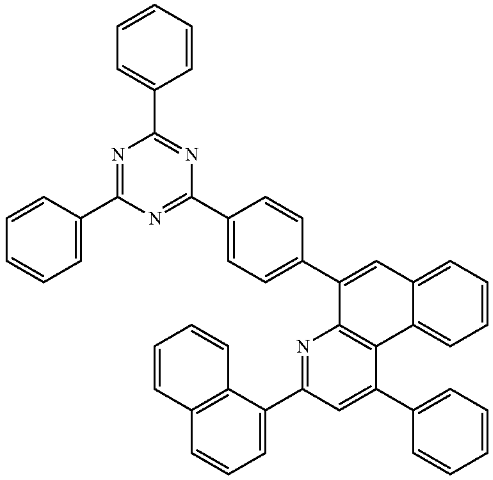
640
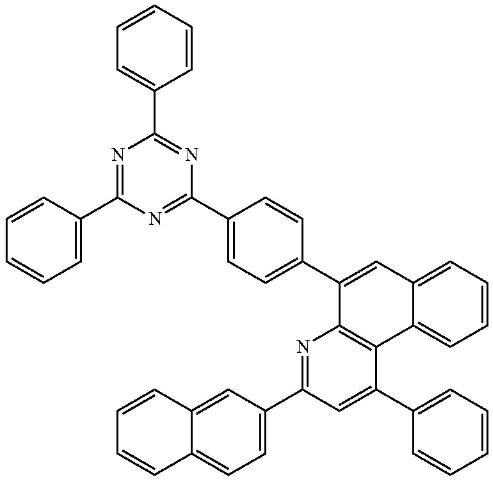

-continued
641
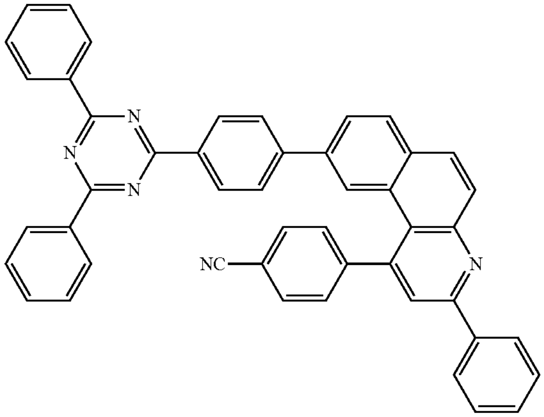
642
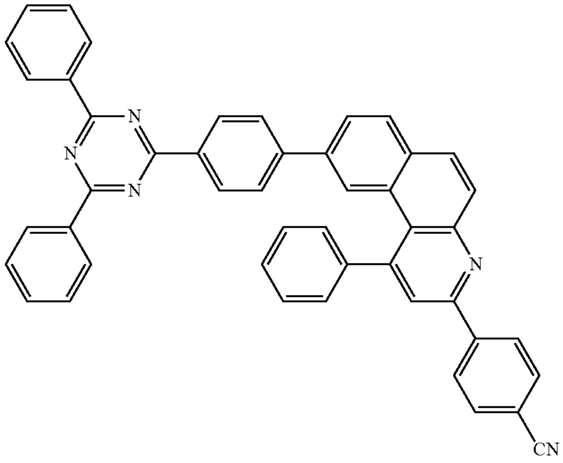
643
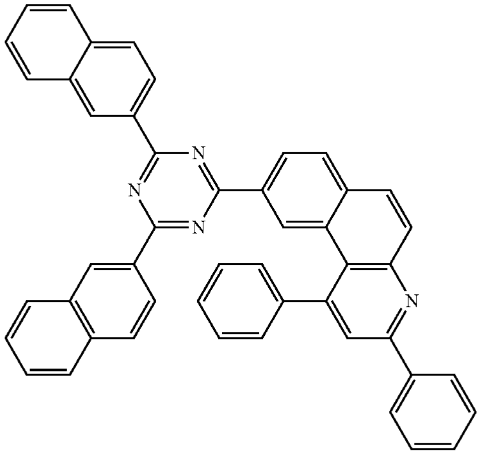
-continued
644
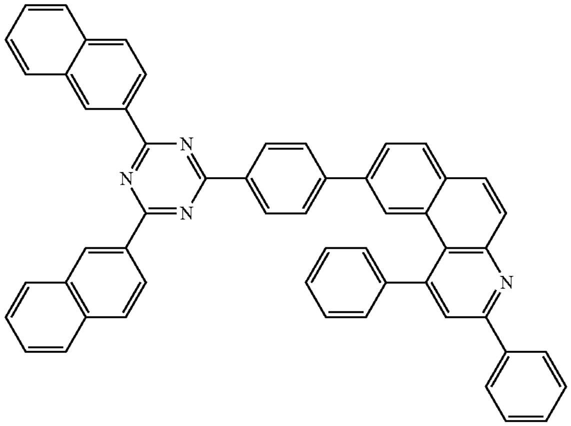
645
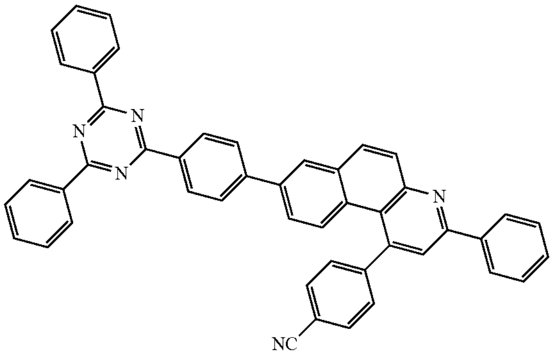
646
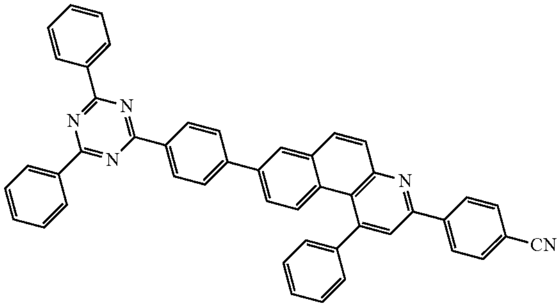
647
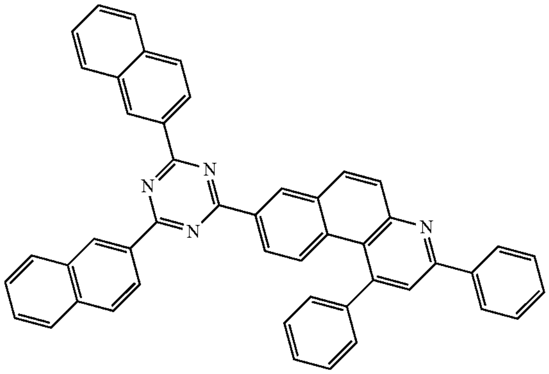

-continued
648
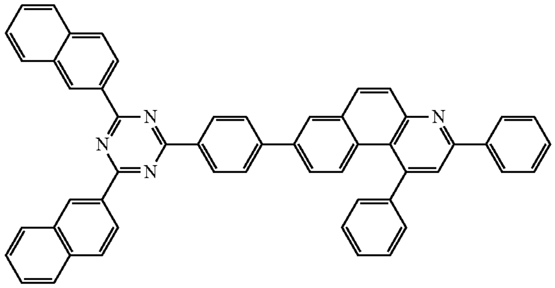
649
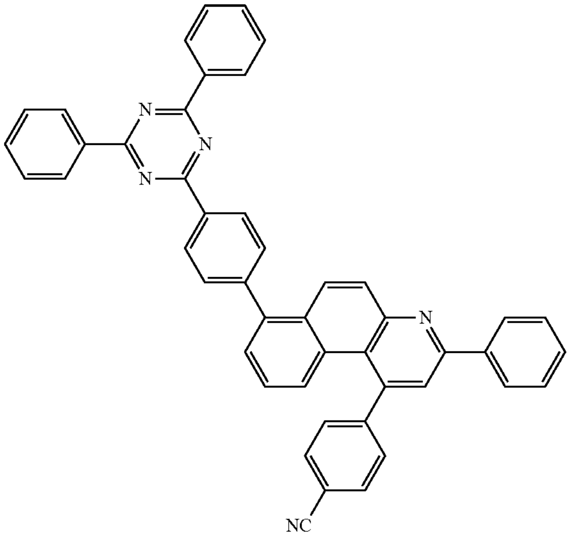
650
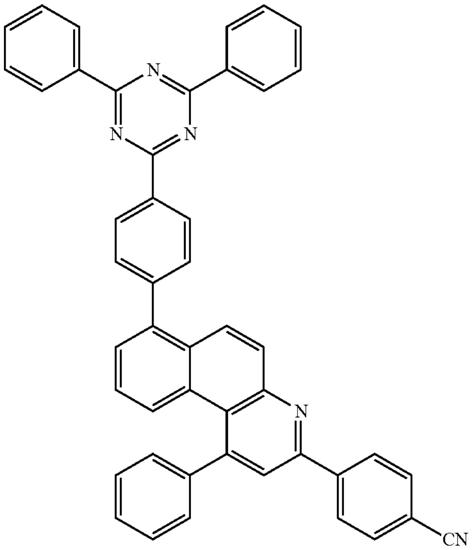
-continued
651
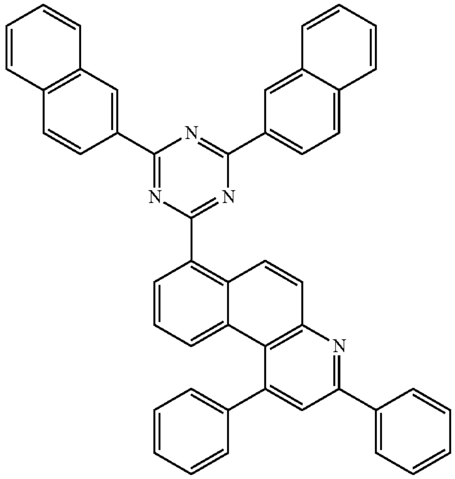
652
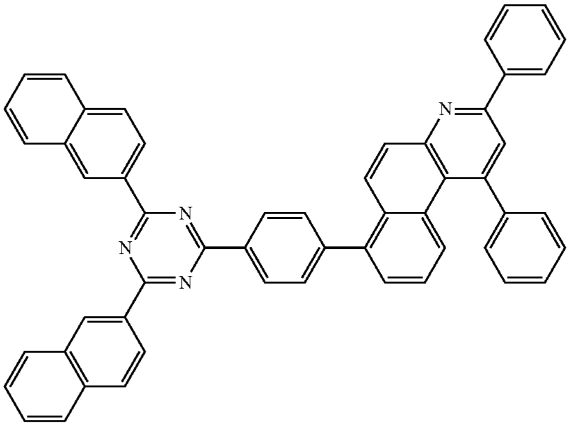
653
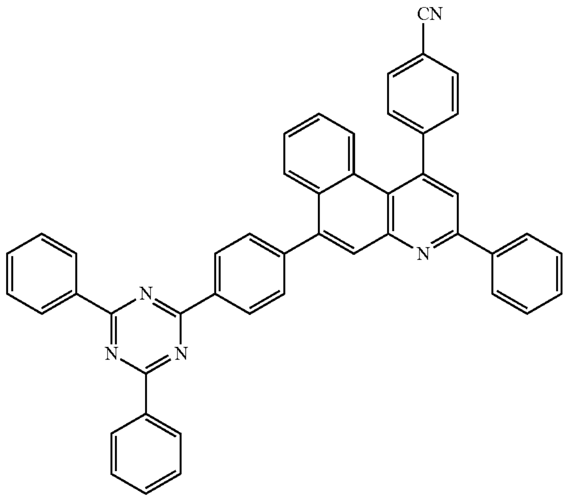

-continued

654

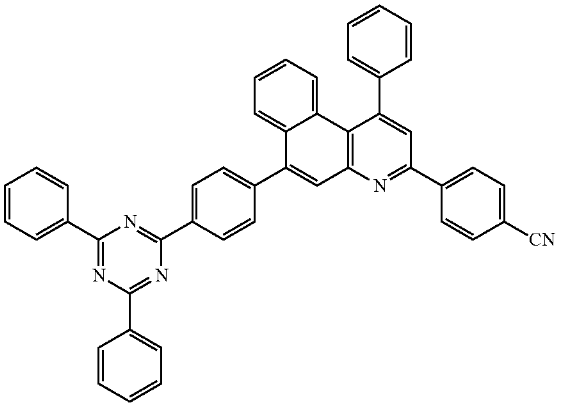

655

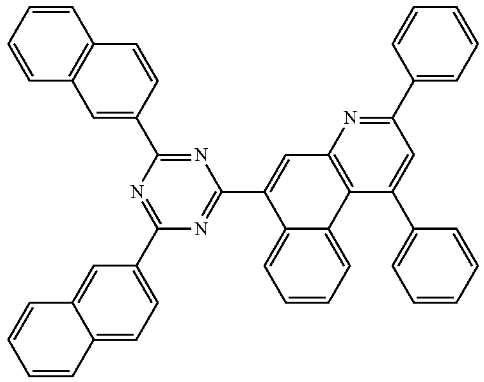

656

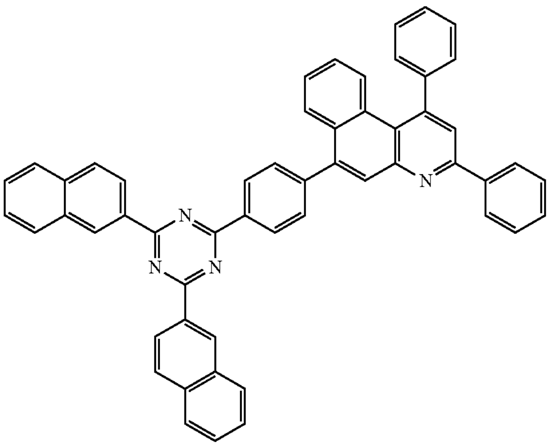

657

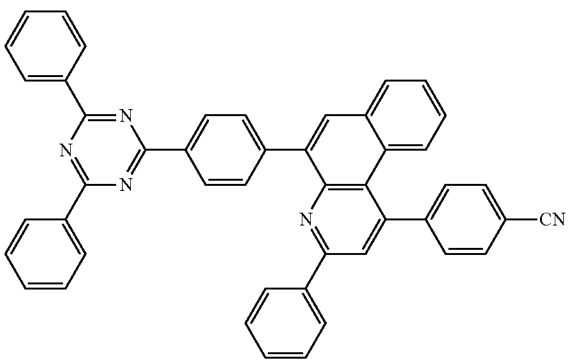

-continued

658

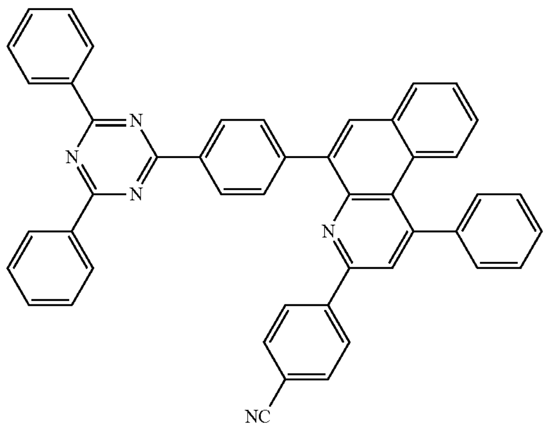

659

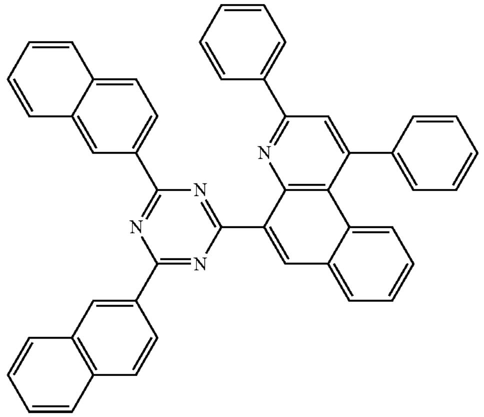

660

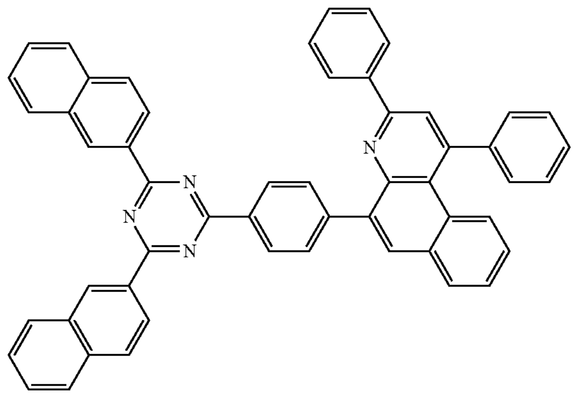

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the heterocyclic compound has a high glass transition temperature (Tg) and thereby has superior thermal stability. Such an increase in the thermal stability becomes an important factor in providing driving stability to a device.

The heterocyclic compound according to one embodiment of the present application may be prepared using a multi-step chemical reaction. Some intermediate compounds are prepared first, and from the intermediate compounds, the heterocyclic compound of Chemical Formula 1 may be prepared. More specifically, the heterocyclic compound according to one embodiment of the present application may be prepared based on preparation examples to describe later.

Another embodiment of the present application provides an organic light emitting device comprising the heterocyclic compound represented by Chemical Formula 1. The "organic light emitting device" may be expressed in terms such as an "organic light emitting diode", an "OLED", an "OLED device" and an "organic electroluminescent device".

One embodiment of the present application provides an organic light emitting device comprising a first electrode; a second electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment of the present application, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In another embodiment of the present application, the organic light emitting device may be a green organic light emitting device, and the heterocyclic compound according to Chemical Formula 1 may be used as a material of the green organic light emitting device.

In another embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present application may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present application may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present application, the organic material layer comprises an electron transfer layer, and the electron transfer layer may comprise the heterocyclic compound. When using the heterocyclic compound in an electron transfer layer, electrons are efficiently transferred without decomposing or destroying the compound, and the organic light emitting device may have superior driving, efficiency and lifetime.

In another organic light emitting device, the organic material layer comprises a hole blocking layer, and the hole blocking layer may comprise the heterocyclic compound. When using the heterocyclic compound in a hole blocking layer, the organic light emitting device may have superior driving, efficiency and lifetime.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer comprising the heterocyclic compound represented by Chemical Formula 1 may further comprise other materials as necessary.

In addition, the organic light emitting device according to one embodiment of the present application comprises a first electrode; a first stack provided on the first electrode and comprising a first light emitting layer; a charge generation layer provided on the first stack; a second stack provided on the charge generation layer and comprising a second light emitting layer; and a second electrode provided on the second stack.

Herein, the charge generation layer may comprise the heterocyclic compound represented by Chemical Formula 1. When using the heterocyclic compound in a charge generation layer, the organic light emitting device may have superior driving, efficiency and lifetime.

In addition, the first stack and the second stack may each independently further comprise one or more types of the hole injection layer, the hole transfer layer, the hole blocking layer, the electron transfer layer, the electron injection layer and the like described above.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is illustrated in FIG. 4.

Herein, the first electron blocking layer, the first hole blocking layer, the second hole blocking layer and the like described in FIG. 4 may not be included in some cases.

In the organic light emitting device according to one embodiment of the present application, materials other than the heterocyclic compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrenesulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed.

For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

EXAMPLE

<Preparation Example 1> Preparation of Compound 1

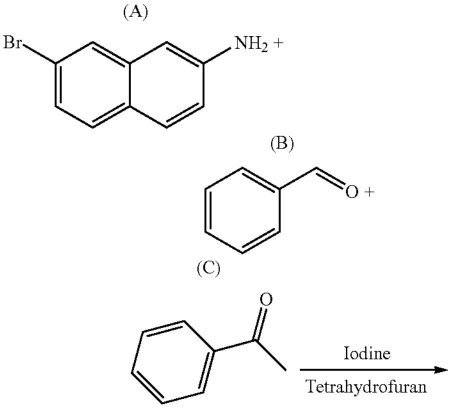

-continued

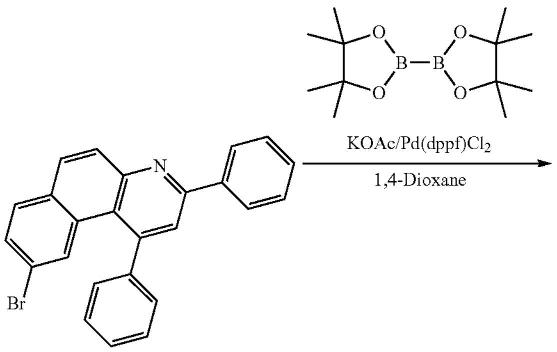

1-1

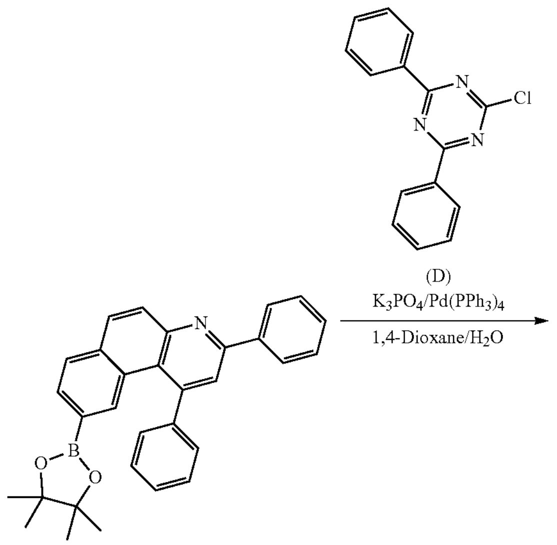

1-2

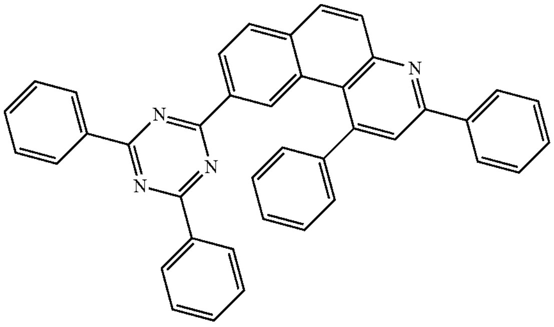

1

1) Preparation of Compound 1-1

After introducing tetrahydrofuran (750 ml) to 7-bromonaphthalen-2-amine (A) (50 g, 0.225 mol, 1 eq.), benzaldehyde (B) (28.6 g, 0.27 mol, 1.2 eq.), acetophenone (C) (32.4 g, 0.27 mol, 1.2 eq.) and iodine (2.85 g, 0.011 mol, 0.05 eq.), the mixture was stirred for 10 hours at 80° C. The reaction was terminated by introducing water thereto, and the result was extracted using methylene chloride (MC) and water. After that, moisture was removed using $MgSO_4$. The result was separated using a silica gel column to obtain Compound 1-1 (42 g) in a 45% yield.

2) Preparation of Compound 1-2

After introducing 1,4-dioxane (420 ml) to Compound 1-1 (42 g, 0.102 mol, 1 eq.), bis(pinacolato)diboron (39 g, 0.15 mol, 1.5 eq.), potassium acetate (KOAc) (30 g, 0.30 mol, 3 eq.) and Pd(dppf)$Cl_2$ (7.5 g, 0.01 mol, 0.1 eq.), the mixture was stirred for 6 hours at 100° C. The reaction was terminated by introducing water thereto, and the result was extracted using methylene chloride (MC) and water. After that, moisture was removed using $MgSO_4$. The result was separated using a silica gel column to obtain Compound 1-2 (34 g) in a 72% yield.

3) Preparation of Compound 1

After introducing 1,4-dioxane (140 ml) and $H_2O$ (35 ml) to Compound 1-2 (7 g, 0.015 mol, 1 eq.), 2-chloro-4,6-diphenyl-1,3,5-triazine (D) (4.3 g, 0.016 mol, 1.05 eq.), $K_3PO_4$ (6.5 g, 0.03 mol, 2 eq.) and Pd($PPh_3$)$_4$ (0.88 g, 0.0007 mol, 0.05 eq.), the mixture was stirred for 6 hours at 100° C. Produced solids were filtered and dried to obtain Compound 1 (6.8 g) in a 79% yield.

Compounds were synthesized in the same manner as in Preparation Example 1 except that Intermediate A of the following Table 1 was used instead of 7-bromonaphthalen-2-amine (A), Intermediate B of the following Table 1 was used instead of benzaldehyde (B), Intermediate C of the following Table 1 was used instead of acetophenone (C), and Intermediate D of the following Table 1 was used instead of 2-chloro-4,6-diphenyl-1,3,5-triazine (D).

TABLE 1
| No. | Intermediate A | Intermediate B | Intermediate C | Intermediate D | Yield |
|---|---|---|---|---|---|
| 9 | 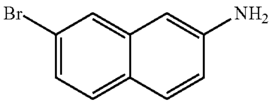 [SMILES: Nc1ccc2ccc(Br)cc2c1] | 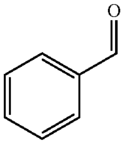 | 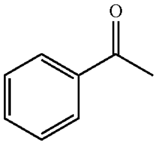 | 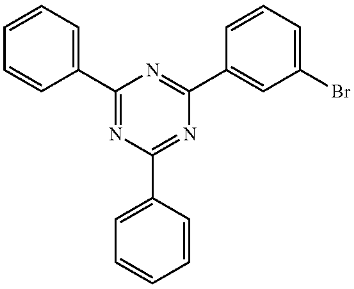 [SMILES: Brc1cccc(-c2nc(-c3ccccc3)nc(-c3ccccc3)n2)c1] | 56% |
| 10 | 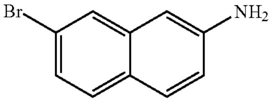 [SMILES: Nc1ccc2ccc(Br)cc2c1] | 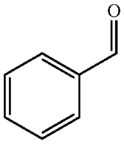 | 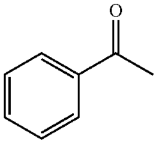 | 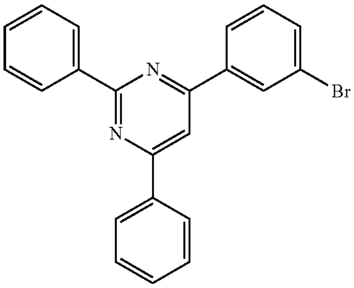 [SMILES: Brc1cccc(-c2cc(-c3ccccc3)nc(-c3ccccc3)n2)c1] | 57% |
| 25 | 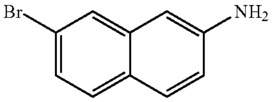 [SMILES: Nc1ccc2ccc(Br)cc2c1] | 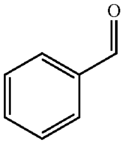 | 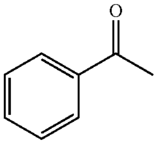 | 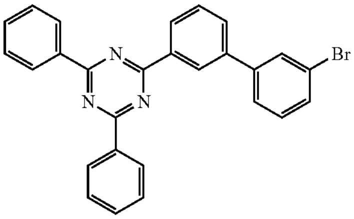 [SMILES: Brc1cccc(-c2cccc(-c3nc(-c4ccccc4)nc(-c4ccccc4)n3)c2)c1] | 49% |
| 26 | 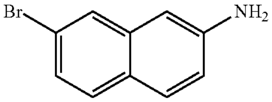 [SMILES: Nc1ccc2ccc(Br)cc2c1] | 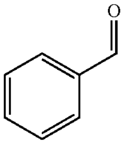 | 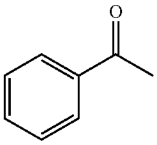 | 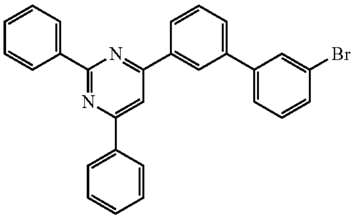 [SMILES: Brc1cccc(-c2cccc(-c3cc(-c4ccccc4)nc(-c4ccccc4)n3)c2)c1] | 41% |
| 33 | 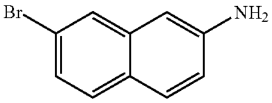 | 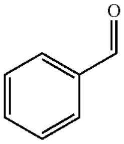 | 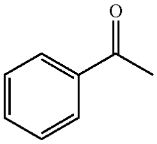 | 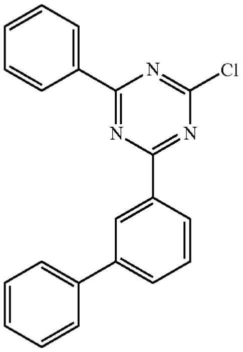 [SMILES: Clc1nc(-c2ccccc2)nc(-c2cccc(-c3ccccc3)c2)n1] | 58% |

TABLE 1-continued
| No. | Intermediate A | Intermediate B | Intermediate C | Intermediate D | Yield |
|---|---|---|---|---|---|
| 42 | 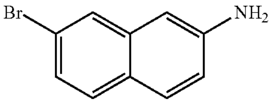 [SMILES: Nc1ccc2ccc(Br)cc2c1] | 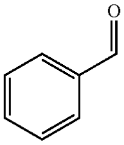 | 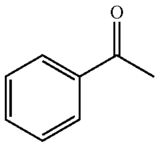 | 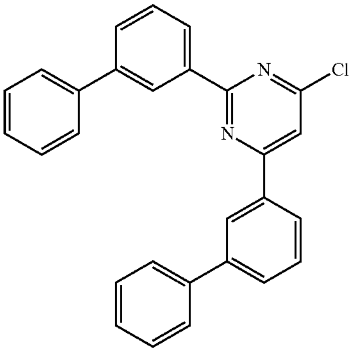 [SMILES: Clc1cc(-c2cccc(-c3ccccc3)c2)nc(-c2cccc(-c3ccccc3)c2)n1] | 40% |
| 81 | 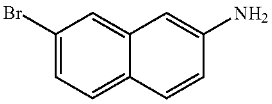 [SMILES: Nc1ccc2ccc(Br)cc2c1] | 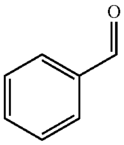 | 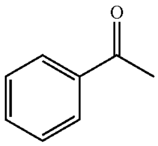 | 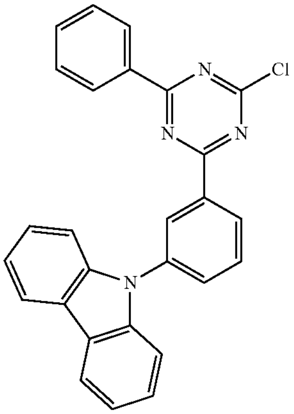 [SMILES: Clc1nc(-c2ccccc2)nc(-c2cccc(-n3c4ccccc4c4ccccc43)c2)n1] | 48% |
| 89 | 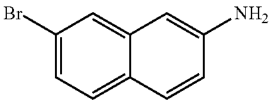 [SMILES: Nc1ccc2ccc(Br)cc2c1] | 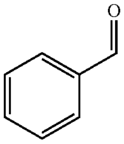 | 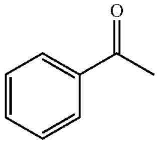 | 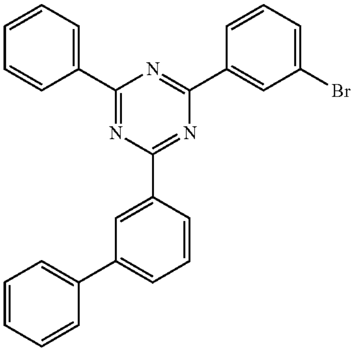 [SMILES: Brc1cccc(-c2nc(-c3ccccc3)nc(-c3cccc(-c4ccccc4)c3)n2)c1] | 52% |
| 110 | 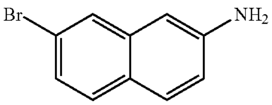 [SMILES: Nc1ccc2ccc(Br)cc2c1] | 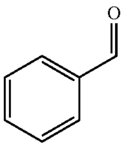 | 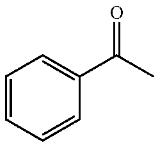 | 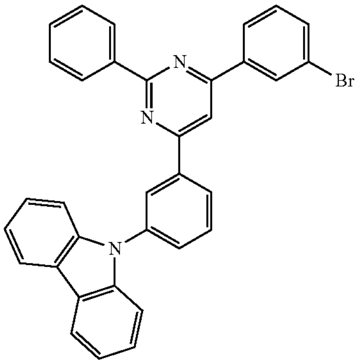 [SMILES: Brc1cccc(-c2cc(-c3cccc(-n4c5ccccc5c5ccccc54)c3)nc(-c3ccccc3)n2)c1] | 58% |

TABLE 1-continued
| No. | Intermediate A | Intermediate B | Intermediate C | Intermediate D | Yield |
|---|---|---|---|---|---|
| 113 | 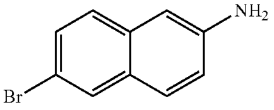 [SMILES: Nc1ccc2cc(Br)ccc2c1] | 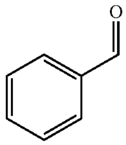 | 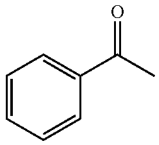 | 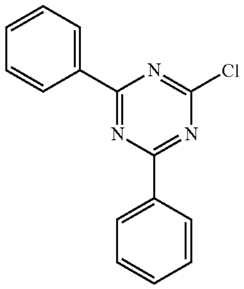 [SMILES: Clc1nc(-c2ccccc2)nc(-c2ccccc2)n1] | 57% |
| 114 | 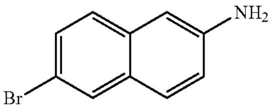 [SMILES: Nc1ccc2cc(Br)ccc2c1] | 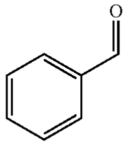 | 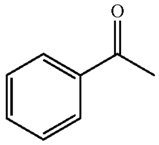 | 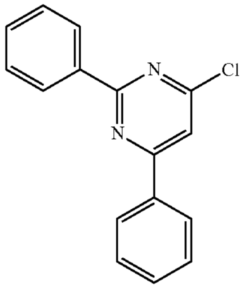 [SMILES: Clc1cc(-c2ccccc2)nc(-c2ccccc2)n1] | 49% |
| 139 | 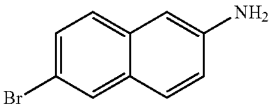 [SMILES: Nc1ccc2cc(Br)ccc2c1] | 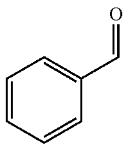 | 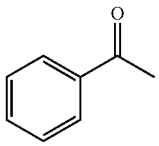 | 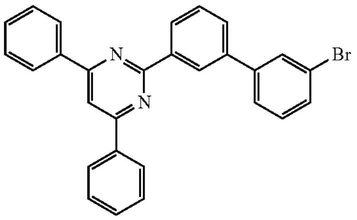 | 51% |
| 140 | 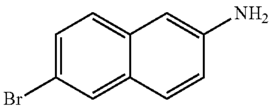 [SMILES: Nc1ccc2cc(Br)ccc2c1] | 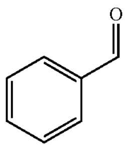 | 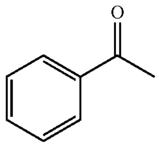 | 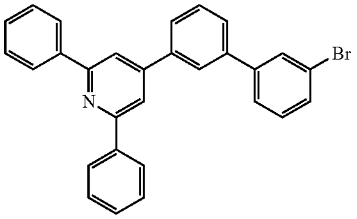 | 60% |
| 153 | 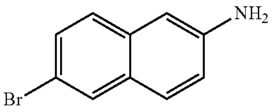 [SMILES: Nc1ccc2cc(Br)ccc2c1] | 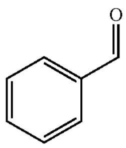 | 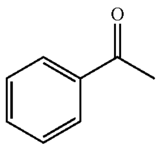 | 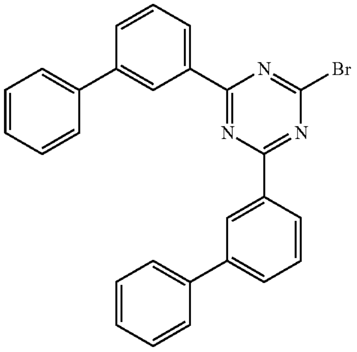 [SMILES: Brc1nc(-c2cccc(-c3ccccc3)c2)nc(-c2cccc(-c3ccccc3)c2)n1] | 55% |

TABLE 1-continued
| No. | Intermediate A | Intermediate B | Intermediate C | Intermediate D | Yield |
|---|---|---|---|---|---|
| 157 | 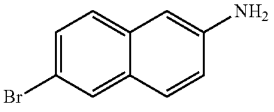 [SMILES: Nc1ccc2cc(Br)ccc2c1] | 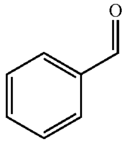 | 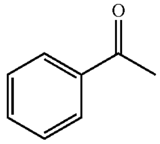 | 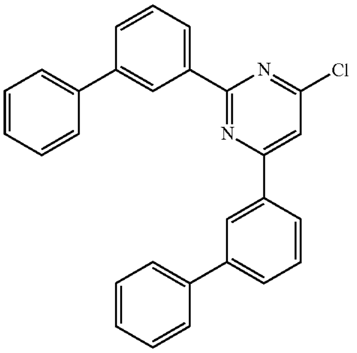 [SMILES: Clc1cc(-c2cccc(-c3ccccc3)c2)nc(-c2cccc(-c3ccccc3)c2)n1] | 62% |
| 222 | 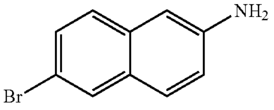 [SMILES: Nc1ccc2cc(Br)ccc2c1] | 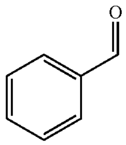 | 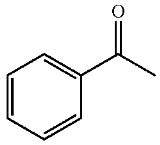 | 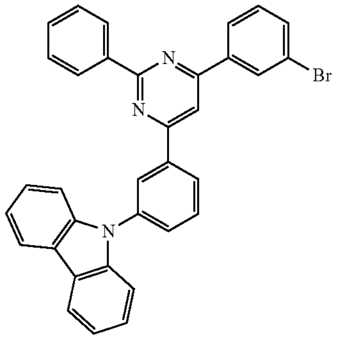 [SMILES: Brc1cccc(-c2cc(-c3cccc(-n4c5ccccc5c5ccccc54)c3)nc(-c3ccccc3)n2)c1] | 47% |
| 250 | 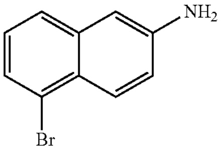 | 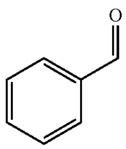 | 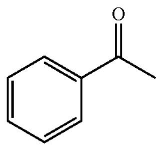 | 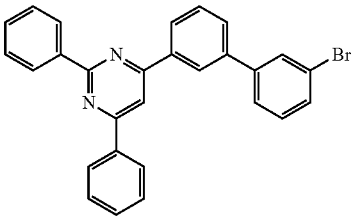 [SMILES: Brc1cccc(-c2cccc(-c3cc(-c4ccccc4)nc(-c4ccccc4)n3)c2)c1] | 50% |
| 258 | 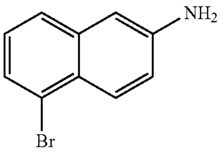 [SMILES: Nc1ccc2c(Br)cccc2c1] | 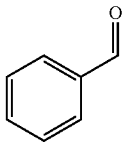 | 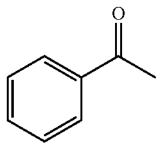 | 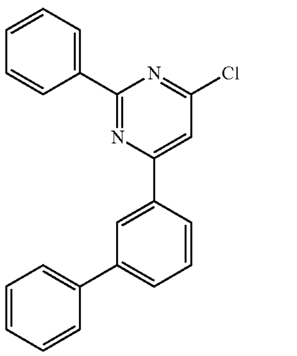 [SMILES: Clc1cc(-c2cccc(-c3ccccc3)c2)nc(-c2ccccc2)n1] | 53% |
| 341 | 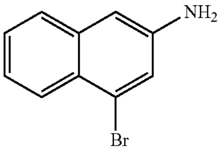 [SMILES: Nc1cc(Br)c2ccccc2c1] | 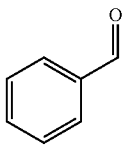 | 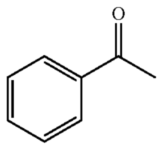 | 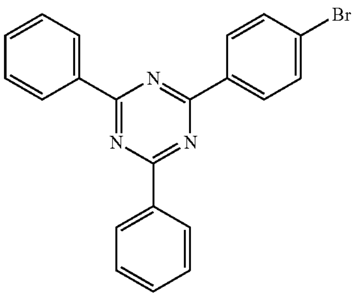 [SMILES: Brc1ccc(-c2nc(-c3ccccc3)nc(-c3ccccc3)n2)cc1] | 60% |

TABLE 1-continued
| No. | Intermediate A | Intermediate B | Intermediate C | Intermediate D | Yield |
|---|---|---|---|---|---|
| 342 | 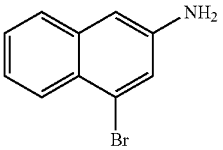 [SMILES: Nc1cc(Br)c2ccccc2c1] | 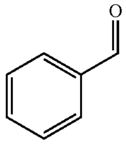 | 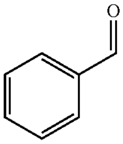 | 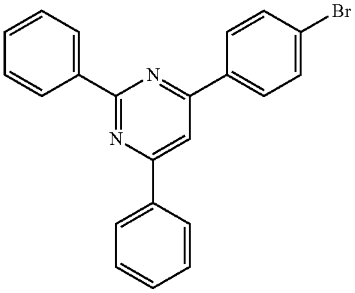 [SMILES: Brc1ccc(-c2cc(-c3ccccc3)nc(-c3ccccc3)n2)cc1] | 58% |
| 361 | 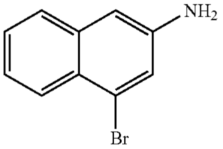 [SMILES: Nc1cc(Br)c2ccccc2c1] | 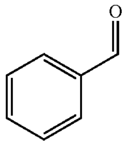 | 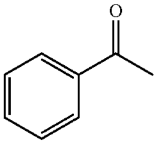 | 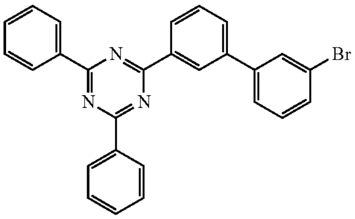 [SMILES: Brc1cccc(-c2cccc(-c3nc(-c4ccccc4)nc(-c4ccccc4)n3)c2)c1] | 55% |
| 362 | 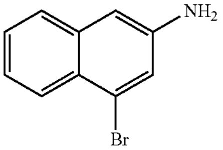 [SMILES: Nc1cc(Br)c2ccccc2c1] | 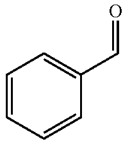 | 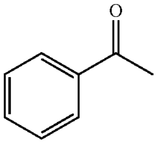 | 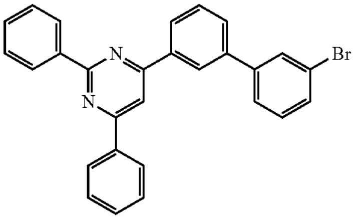 [SMILES: Brc1cccc(-c2cccc(-c3cc(-c4ccccc4)nc(-c4ccccc4)n3)c2)c1] | 50% |
| 453 | 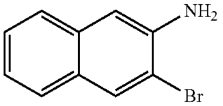 [SMILES: Nc1cc2ccccc2cc1Br] | 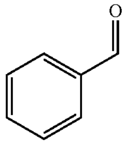 | 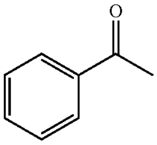 | 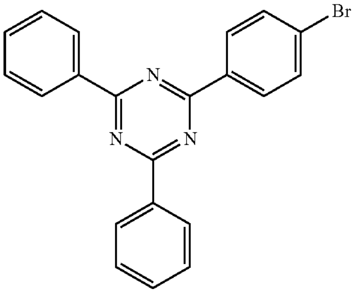 [SMILES: Brc1ccc(-c2nc(-c3ccccc3)nc(-c3ccccc3)n2)cc1] | 53% |
| 454 | 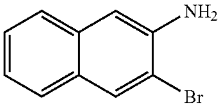 [SMILES: Nc1cc2ccccc2cc1Br] | 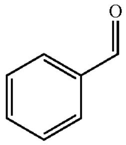 | 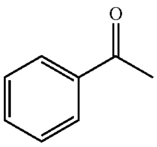 | 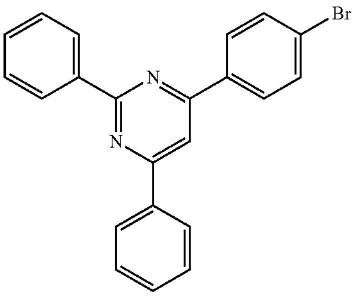 [SMILES: Brc1ccc(-c2cc(-c3ccccc3)nc(-c3ccccc3)n2)cc1] | 48% |

TABLE 1-continued
| No. | Intermediate A | Intermediate B | Intermediate C | Intermediate D | Yield |
|---|---|---|---|---|---|
| 607 | 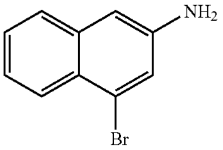 [SMILES: Nc1cc(Br)c2ccccc2c1] | 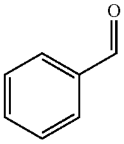 | 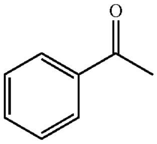 | 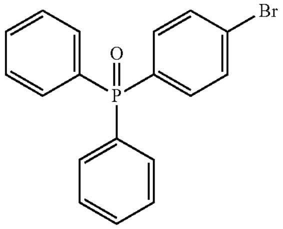 [SMILES: O=P(c1ccccc1)(c1ccccc1)c1ccc(Br)cc1] | 45% |
| 634 | 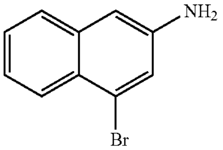 [SMILES: Nc1cc(Br)c2ccccc2c1] | 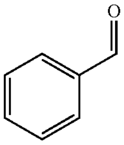 | 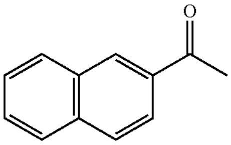 | 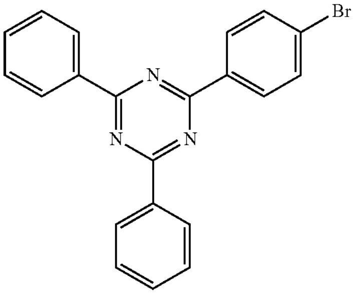 [SMILES: Brc1ccc(-c2nc(-c3ccccc3)nc(-c3ccccc3)n2)cc1] | 40% |
| 635 | 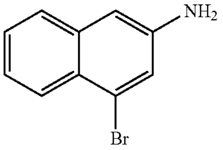 [SMILES: Nc1cc(Br)c2ccccc2c1] | 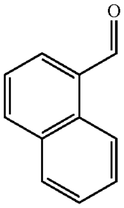 | 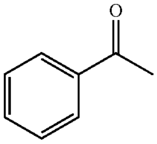 | 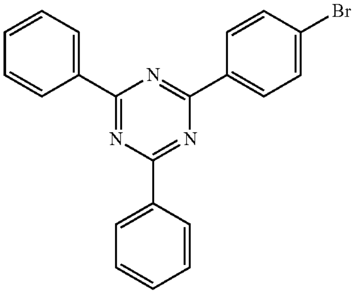 [SMILES: Brc1ccc(-c2nc(-c3ccccc3)nc(-c3ccccc3)n2)cc1] | 41% |
| 659 | 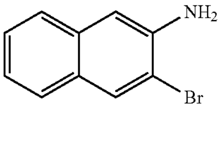 [SMILES: Nc1cc2ccccc2cc1Br] | 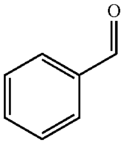 | 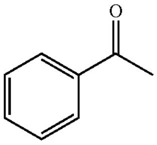 | 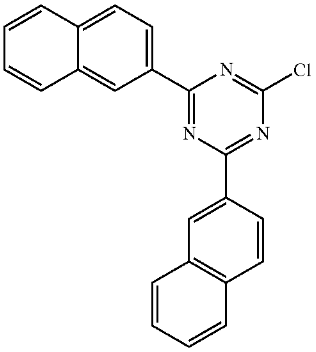 [SMILES: Clc1nc(-c2ccc3ccccc3c2)nc(-c2ccc3ccccc3c2)n1] | 53% |
| 660 | 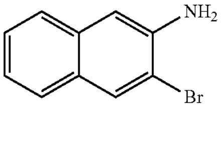 [SMILES: Nc1cc2ccccc2cc1Br] | 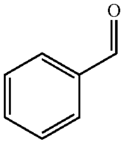 | 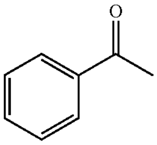 | 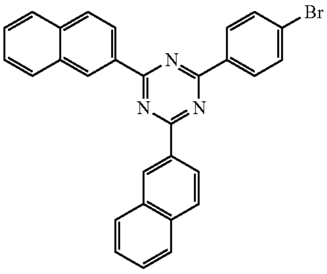 [SMILES: Brc1ccc(-c2nc(-c3ccc4ccccc4c3)nc(-c3ccc4ccccc4c3)n2)cc1] | 45% |

Compounds were prepared in the same manner as in the preparation examples, and the synthesis identification results are shown in the following Table 2 and Table 3. The following Table 2 shows measurement values of $^1$H NMR ($CDCl_3$, 200 Mz), and the following Table 3 shows measurement values of FD-mass spectrometry (FD-MS: field desorption mass spectrometry).

TABLE 2

| Compound | $^1$H NMR ($CDCl_3$, 200 Mz) |
|---|---|
| 1 | δ = 8.49(1H, d), 8.28 (7H, m), 7.92(3H, m), 7.79(2H, m), 7.64(1H, s), 7.51~7.41 (12H, m) |
| 9 | δ = 8.28(8H, m), 7.92(3H, m), 7.73(4H, m), 7.64(1H, s), 7.57~7.41(14H, m) |
| 10 | δ = 8.30(6H, m), 7.92(3H, m), 7.73(7H, m), 7.64(1H, s), 7.57~7.41(14H, m) |
| 25 | δ = 8.28(8H, m), 7.92(3H, m), 7.70(5H, m), 7.64(1H, s), 7.57~7.41(17H, m) |
| 26 | δ = 8.30(6H, m), 7.92(3H, m), 7.70(8H, m), 7.64(1H, s), 7.57~7.41(17H, m) |
| 33 | δ = 8.49(1H, d), 8.28 (6H, m), 7.92(3H, m), 7.79(2H, m), 7.70(1H, s) 7.64(1H, s), 7.51~7.41 (16H, m) |
| 42 | δ = 8.30(5H, m), 7.87(4H, m), 7.70(5H, m), 7.64(1H, s), 7.54~7.41 (20H, m) |
| 81 | δ = 8.55(1H, d), 8.28(6H, m), 8.09(2H, m), 7.94~7.85(9H, m), 7.64(2H, m), 7.51~7.25(17H, m) |
| 89 | δ = 8.28(7H, m), 7.92(3H, m), 7.73(5H, m), 7.64(1H, s), 7.51~7.41 (18H, m) |
| 110 | δ = 8.55(1H, d), 8.28(6H, m), 8.09(2H, m), 7.94(4H, m), 7.85(9H, m), 7.64(2H, m), 7.51~7.25(17H, m) |
| 113 | δ = 9.09(1H, s), 8.49(1H, d), 8.28(6H, m), 7.99(3H, m), 7.79(2H, d), 7.64(1H, s), 7.54~7.41(12H, m) |
| 114 | δ = 8.30(6H, m), 7.99(3H, m), 7.79(5H, d), 7.64(1H, s), 7.54~7.41(12H, m) |
| 139 | δ = 8.24(4H, m), 7.99(3H, m), 7.79(9H, m) 7.64(1H, s), 7.54~7.41(18H, m) |
| 140 | δ = 8.30(6H, m), 8.20(2H, s), 7.99(3H, m), 7.70(5H, d), 7.64(1H, s), 7.54~7.41 (19H, m) |
| 153 | δ = 9.09(1H, m), 8.49(1H, d), 8.30(4H, m), 7.99(3H, m), 7.79(2H, d), 7.70(2H, s), 7.64(1H, s), 7.54~7.41 (20H, m) |
| 157 | δ = 9.09(1H, m), 8.49(1H, d), 8.30(4H, m), 7.99(3H, m), 7.79(2H, d), 7.64(4H, m), 7.54~7.41(19H, m) |
| 222 | δ = 8.55(1H, d), 8.30(5H, m), 8.09(3H, m), 7.94(3H, m), 7.79(6H, m), 7.64(1H, s), 7.63~7.25(19H, m) |
| 250 | δ = 8.51(1H, d), 8.42(1H, d), 8.30(5H, m), 7.99(2H, m), 7.79(7H, m), 7.64(1H, s), 7.51~7.41(18H, m) |
| 258 | δ = 8.51(1H, d), 8.28(5H, m), 7.99(3H, m), 7.70(4H, m), 7.64(1H, s), 7.63~7.25(17H, m) |
| 341 | δ = 8.55(2H, d), 8.30(7H, m), 7.85(4H, m), 7.64(1H, s), 7.54~7.41(14H, m), 7.25(2H, d) |
| 342 | δ = 8.55(2H, d), 8.30(8H, m), 7.79(4H, m), 7.64(1H, s), 7.54~7.41(14H, m), 7.25(2H, d) |
| 361 | δ = 8.55(2H, d), 8.30(8H, m), 7.79(2H, m), 7.70(2H, s), 7.64(1H, s), 7.54~7.41(19H, m), |
| 362 | δ = 8.55(2H, d), 8.28(6H, m), 7.79(5H, m), 7.70(2H, s), 7.64(1H, s), 7.54~7.41(19H, m), |
| 453 | δ = 8.28(6H, m), 8.00(2H, d), 7.85(5H, m), 7.64(1H, s), 7.54~7.41(14H, m), 7.25(2H, d) |
| 454 | δ = 8.28(7H, m), 8.00(2H, d), 7.85(5H, m), 7.64(1H, s), 7.54~7.41(14H, m), 7.25(2H, d) |
| 607 | δ = 8.55(2H, d), 8.30(3H, m), 7.77(10H, m), 7.64(1H, s), 7.54~7.41(14H, m), |
| 634 | δ = 8.55(2H, d), 8.28(7H, m), 7.86(5H, m), 7.75(1H, s), 7.64(1H, s), 7.59~7.41 (14H, m), 7.25(2H, d) |
| 635 | δ = 8.55(3H, m), 8.46(1H, d), 8.27(5H, m), 8.10(2H, m), 7.79(4H, d), 7.64~7.41(15H, m), 7.25(2H, d) |

TABLE 2-continued

| Compound | $^1$H NMR ($CDCl_3$, 200 Mz) |
|---|---|
| 659 | δ = 9.09(2H, s), 8.49(2H, d), 8.30(2H, d), 8.00(8H, m), 7.83(3H, m), 7.64~7.41(13H, m) |
| 660 | δ = 9.09(2H, s), 8.49(2H, d), 8.30(2H, d), 8.00~7.79(13H, m), 7.64~7.41(13H, m), 7.25(2H, d), |

TABLE 3

| Compound | FD-MS | Compound | FD-MS |
|---|---|---|---|
| 1 | m/z = 562.66 (C40H26N4 = 562.22) | 9 | m/z = 638.76 (C46H30N4 = 638.25) |
| 10 | m/z = 637.77 (C47H31N3 = 637.25) | 25 | m/z = 714.85 (C52H34N4 = 714.28) |
| 26 | m/z = 713.87 (C53H35N3 = 713.28) | 33 | m/z = 638.76 (C46H30N4 = 638.25) |
| 42 | m/z = 713.87 (C53H35N3 = 713.28) | 81 | m/z = 803.95 (C58H37N5 = 803.30) |
| 89 | m/z = 714.85 (C52H34N4 = 714.28) | 110 | m/z = 802.96 (C59H38N4 = 802.31) |
| 113 | m/z = 562.66 (C40H26N4 = 562.22) | 114 | m/z = 561.67 (C41H27N3 = 561.22) |
| 139 | m/z = 713.87 (C53H35N3 = 713.28) | 140 | m/z = 712.88 (C54H36N2 = 712.29) |
| 153 | m/z = 714.85 (C52H34N4 = 714.28) | 157 | m/z = 714.85 (C52H34N4 = 714.28) |
| 222 | m/z = 802.96 (C59H38N4 = 802.31) | 250 | m/z = 713.87 (C53H35N3 = 713.28) |
| 258 | m/z = 637.77 (C47H31N3 = 637.25) | 341 | m/z = 638.76 (C46H30N4 = 638.25) |
| 342 | m/z = 637.77 (C47H31N3 = 637.25) | 361 | m/z = 714.85 (C52H34N4 = 714.28) |
| 362 | m/z = 713.87 (C53H35N3 = 713.28) | 453 | m/z = 638.76 (C46H30N4 = 638.25) |
| 454 | m/z = 637.77 (C47H31N3 = 637.25) | 607 | m/z = 607.68 (C43H30NOP = 607.21) |
| 634 | m/z = 688.82 (C50H32N4 = 688.26) | 635 | m/z = 688.82 (C50H32N4 = 688.26) |
| 659 | m/z = 662.78 (C48H30N4 = 662.25) | 660 | m/z = 738.87 (C54H34N4 = 738.28) |

EXPERIMENTAL EXAMPLE

Experimental Example 1

(1) Manufacture of Organic Light Emitting Device

A transparent indium tin oxide (ITO) electrode thin film obtained from glass for an organic light emitting device (manufactured by Samsung-Corning Co., Ltd.) was ultrasonic cleaned using trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N,N-(2-naphthyl)-phenylamino) triphenylamine (2-TNATA) was introduced to a cell in the vacuum deposition apparatus.

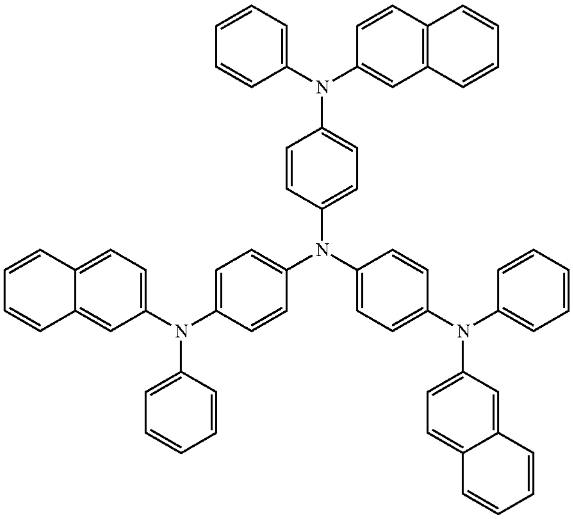

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

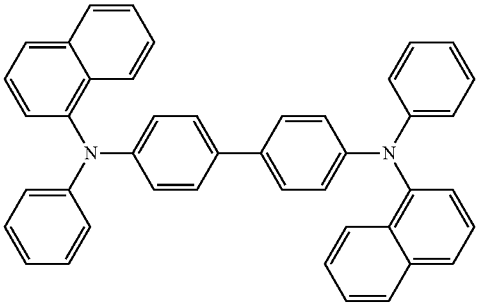

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5 wt % with respect to the host material.

H1

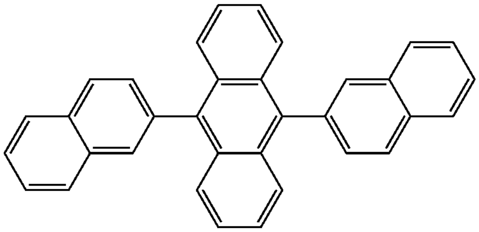

D1

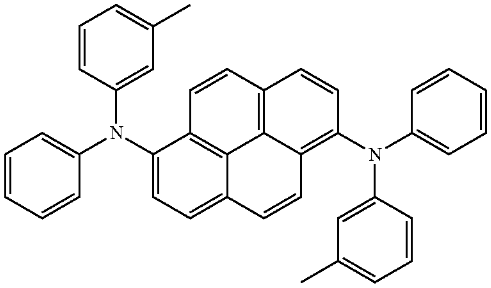

Subsequently, a compound of the following Structural Formula E1 was deposited to a thickness of 300 Å as an electron transfer layer.

E1

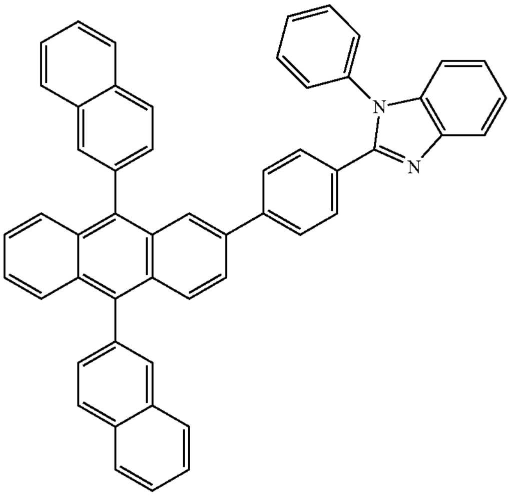

As an electron injection layer, lithium fluoride (LiF) was deposited to a thickness of 10 Å, and an Al cathode was employed to a thickness of 1,000 Å, and as a result, an organic light emitting device was manufactured. Meanwhile, all the organic compounds required to manufacture the organic light emitting device were vacuum sublimation purified under $10^{-8}$ torr to $10^{-6}$ torr by each material to manufacture the organic light emitting device of Comparative Example 1.

In addition, organic light emitting devices of Examples 1 to 30 and Comparative Examples 2 to 5 were manufactured in the same manner as in the method for manufacturing the organic light emitting device of Comparative Example 1, except that compounds, E2 to E5 shown in the following Table 4 were used instead of E1 used when forming the electron transfer layer.

E2

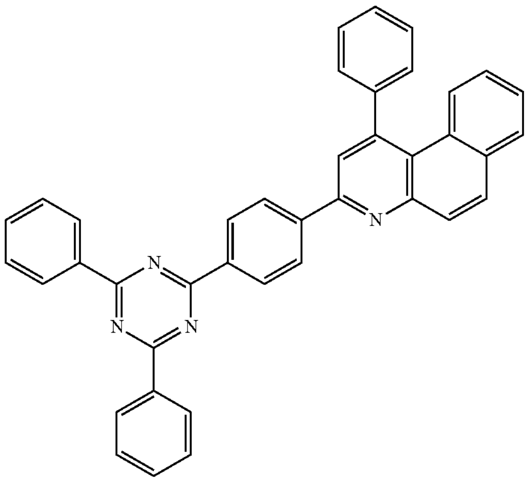

E3

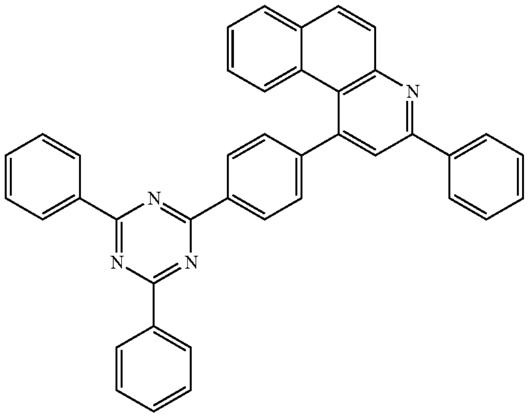

E4

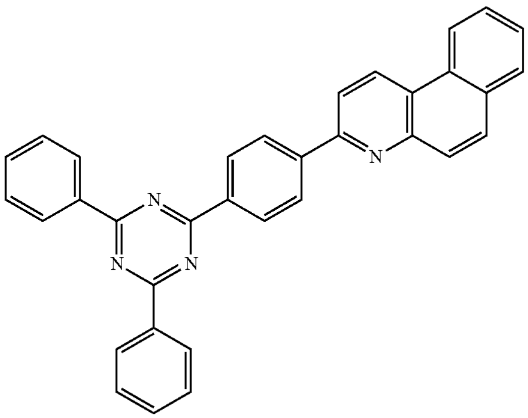

-continued

E5

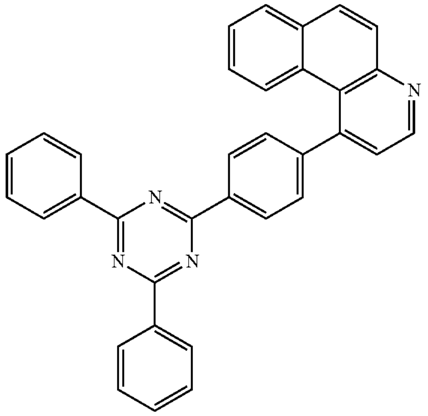

(2) Driving Voltage, Light Emission Efficiency and Color Coordinate (CIE) of Organic Light Emitting Device The organic light emitting device manufactured according to the present disclosure is a blue organic light emitting device, and results of measuring driving voltage, light emission efficiency, color coordinate (CIE) and lifetime of each of the organic light emitting devices of Examples 1 to 30 and Comparative Examples 1 to 5 are as shown in Table 4.

Specifically, for each of the organic light emitting devices of Examples 1 to 30 and Comparative Examples 1 to 5, electroluminescent (EL) properties were measured using M7000 manufactured by McScience Inc., and with the measurement results, a lifetime T95, (unit: h, time) a time taken to become 95% with respect to initial luminance, was measured when standard luminance was 6,000 cd/$m^2$ through a lifetime measurement system (M6000) manufactured by McScience Inc.

TABLE 4

| | Compound | Driving Voltage (V) | Light Emission Efficiency (cd/A) | CIE (x, y) | Lifetime (T95) |
|---|---|---|---|---|---|
| Example 1 | 1 | 4.88 | 6.77 | (0.134, 0.102) | 40 |
| Example 2 | 9 | 4.89 | 6.80 | (0.134, 0.102) | 39 |
| Example 3 | 10 | 4.86 | 6.80 | (0.134, 0.100) | 43 |
| Example 4 | 25 | 4.92 | 6.98 | (0.134, 0.100) | 51 |
| Example 5 | 26 | 4.80 | 6.89 | (0.134, 0.102) | 47 |
| Example 6 | 33 | 4.96 | 6.75 | (0.134, 0.102) | 52 |
| Example 7 | 42 | 4.98 | 6.93 | (0.134, 0.100) | 50 |
| Example 8 | 81 | 4.88 | 6.84 | (0.134, 0.102) | 51 |
| Example 9 | 89 | 5.02 | 6.70 | (0.134, 0.102) | 50 |
| Example 10 | 110 | 4.98 | 6.85 | (0.134, 0.101) | 44 |
| Example 11 | 113 | 4.99 | 6.92 | (0.134, 0.102) | 47 |
| Example 12 | 114 | 5.01 | 6.80 | (0.134, 0.100) | 46 |
| Example 13 | 139 | 4.80 | 6.70 | (0.134, 0.101) | 50 |
| Example 14 | 140 | 4.85 | 6.93 | (0.134, 0.101) | 43 |
| Example 15 | 153 | 4.82 | 6.84 | (0.134, 0.101) | 45 |
| Example 16 | 157 | 4.84 | 6.77 | (0.134, 0.102) | 51 |
| Example 17 | 222 | 4.90 | 6.81 | (0.134, 0.101) | 40 |
| Example 18 | 250 | 4.88 | 6.82 | (0.134, 0.102) | 47 |
| Example 19 | 258 | 4.89 | 6.75 | (0.134, 0.101) | 51 |
| Example 20 | 341 | 4.86 | 6.82 | (0.134, 0.102) | 53 |
| Example 21 | 342 | 4.95 | 6.74 | (0.134, 0.102) | 46 |
| Example 22 | 361 | 4.90 | 6.88 | (0.134, 0.101) | 41 |
| Example 23 | 362 | 4.98 | 6.80 | (0.134, 0.101) | 39 |
| Example 24 | 453 | 4.90 | 6.72 | (0.134, 0.102) | 39 |
| Example 25 | 454 | 5.00 | 6.80 | (0.134, 0.103) | 37 |
| Example 26 | 607 | 4.97 | 6.82 | (0.134, 0.102) | 40 |
| Example 27 | 634 | 4.91 | 6.85 | (0.134, 0.101) | 43 |

TABLE 4-continued

| | Compound | Driving Voltage (V) | Light Emission Efficiency (cd/A) | CIE (x, y) | Lifetime (T95) |
|---|---|---|---|---|---|
| Example 28 | 635 | 4.80 | 6.83 | (0.134, 0.100) | 50 |
| Example 29 | 659 | 4.89 | 6.80 | (0.134, 0.100) | 49 |
| Example 30 | 660 | 4.88 | 6.82 | (0.134, 0.100) | 48 |
| Comparative Example 1 | E1 | 5.80 | 6.00 | (0.134, 0.101) | 29 |
| Comparative Example 2 | E2 | 5.78 | 6.02 | (0.134, 0.101) | 26 |
| Comparative Example 3 | E3 | 5.77 | 6.09 | (0.134, 0.101) | 28 |
| Comparative Example 4 | E4 | 5.82 | 5.97 | (0.134, 0.101) | 23 |
| Comparative Example 5 | E5 | 5.84 | 5.94 | (0.134, 0.101) | 25 |

As seen from the results of Table 4, the organic light emitting device using the electron transfer layer material of the blue organic light emitting device of the present disclosure had lower driving voltage and significantly improved light emission efficiency and lifetime compared to Comparative Examples 1 to 5. Such a result is considered to be due to the fact that, when using the compound having proper length and strength, and flatness as an electron transfer layer, a compound in an excited state is made by receiving electrons under a specific condition, and particularly when an excited state is formed in the hetero-skeleton site of the compound, excited energy will move to a stable state before the excited hetero-skeleton site goes through other reactions, and as a result, the relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

Experimental Example 2

(1) Manufacture of Organic Light Emitting Device

A transparent indium tin oxide (ITO) electrode thin film obtained from glass for an organic light emitting device (manufactured by Samsung-Corning Co., Ltd.) was ultrasonic cleaned using trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N,N-(2-naphthyl)-phenylamino) triphenylamine (2-TNATA) was introduced to a cell in the vacuum deposition apparatus.

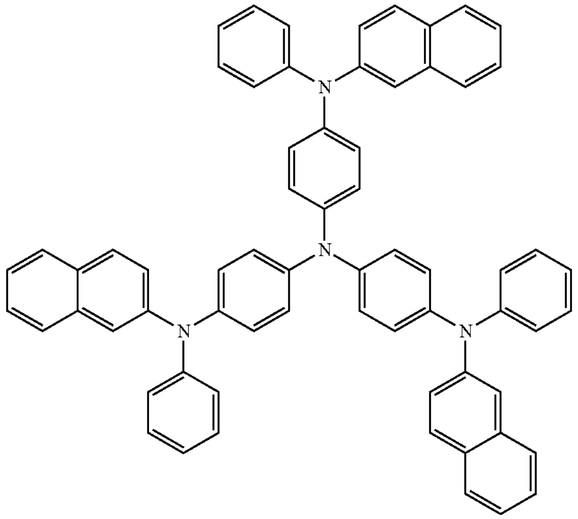

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

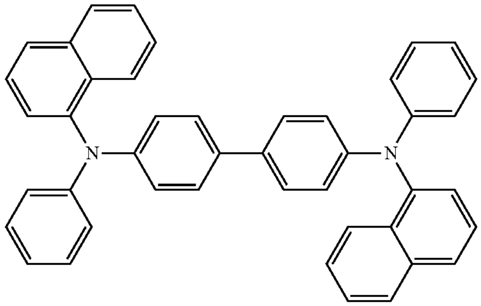

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5 wt % with respect to the host material.

H1

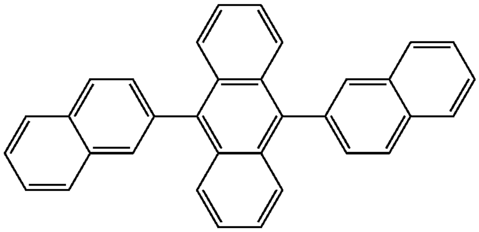

D1

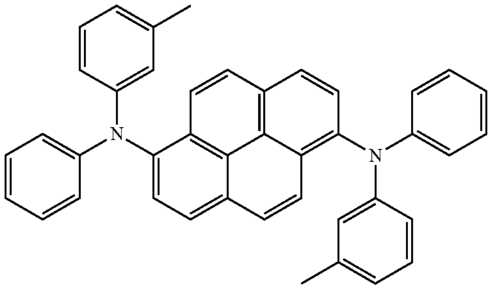

Subsequently, a compound of the following Structural Formula E1 was deposited to a thickness of 300 Å as an electron transfer layer.

E1

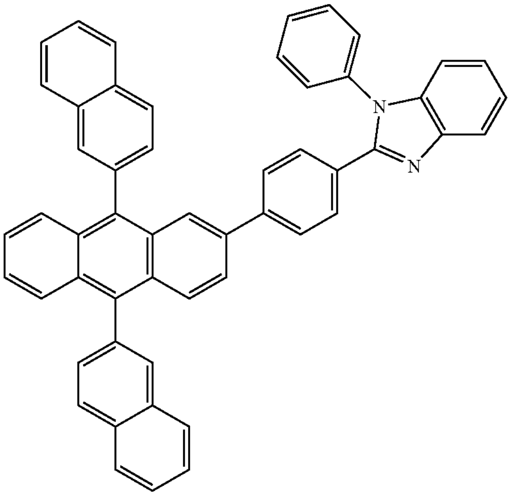

As an electron injection layer, lithium fluoride (LiF) was deposited to a thickness of 10 Å, and an Al cathode was employed to a thickness of 1,000 Å, and as a result, an organic light emitting device of Comparative Example 6 was manufactured. Meanwhile, all the organic compounds required to manufacture the organic light emitting device were vacuum sublimation purified under $10^{-8}$ torr to $10^{-6}$ torr by each material to manufacture the organic light emitting device of Comparative Example 6.

In addition, organic light emitting devices of Examples 31 to 60 and Comparative Examples 7 to 10 were manufactured in the same manner as in the method for manufacturing the organic light emitting device of Comparative Example 6 except that, instead of depositing the compound of E1 to a thickness of 300 Å to form the electron transfer layer, the electron transfer layer E1 was formed to a thickness of 250 Å, and then a hole blocking layer was formed to a thickness of 50 Å on the electron transfer layer using compounds shown in the following Table 5.

E2

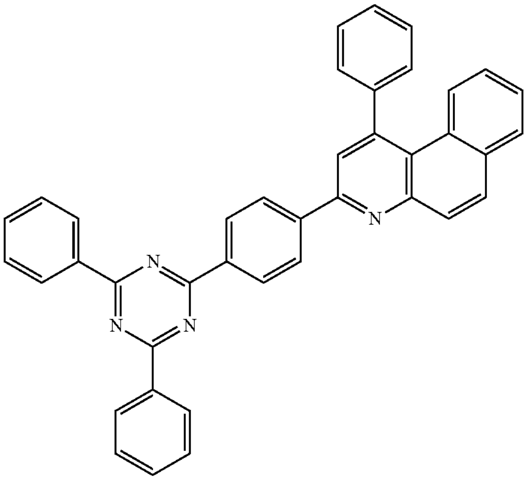

E3

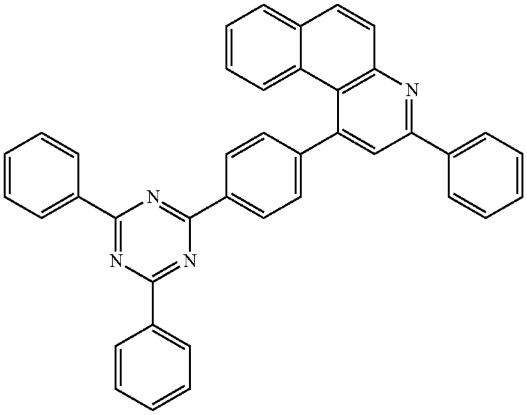

E4

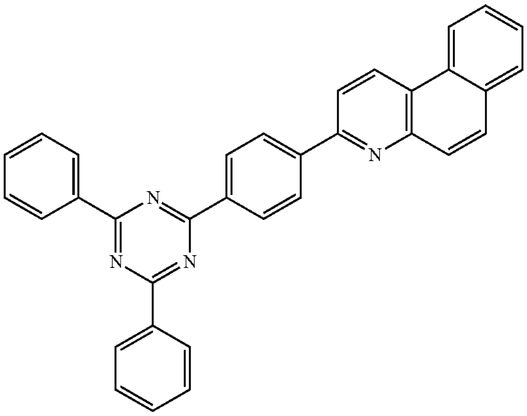

-continued

E5

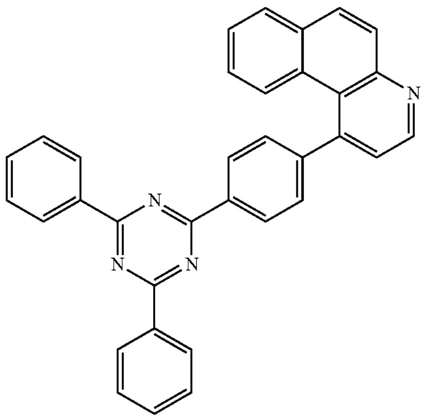

In the following Table 5, E1 of Comparative Example 6 means the electron transfer layer E1 having a thickness of 300 Å (no separate hole blocking layer formed).

(2) Driving Voltage, Light Emission Efficiency and Color Coordinate (CIE) of Organic Light Emitting Device The organic light emitting device manufactured according to the present disclosure is a blue organic light emitting device, and results of measuring driving voltage, light emission efficiency, color coordinate (CIE) and lifetime of each of the organic light emitting devices of Examples 31 to 60 and Comparative Examples 6 to 10 are as shown in the following Table 5.

Specifically, for each of the organic light emitting devices of Examples 31 to 60 and Comparative Examples 6 to 10, electroluminescent (EL) properties were measured using M7000 manufactured by McScience Inc., and with the measurement results, a lifetime T95 (unit: h, time), a time taken to become 95% with respect to initial luminance, was measured when standard luminance was 6,000 cd/$m^2$ through a lifetime measurement system (M6000) manufactured by McScience Inc.

TABLE 5

| | Compound | Driving Voltage (V) | Light Emission Efficiency (cd/A) | CIE (x, y) | Lifetime (T95) |
|---|---|---|---|---|---|
| Example 31 | 1 | 5.09 | 6.42 | (0.134, 0.100) | 51 |
| Example 32 | 9 | 5.05 | 6.47 | (0.134, 0.100) | 54 |
| Example 33 | 10 | 4.84 | 6.18 | (0.134, 0.100) | 55 |
| Example 34 | 25 | 4.93 | 6.48 | (0.134, 0.101) | 61 |
| Example 35 | 26 | 4.60 | 6.31 | (0.134, 0.101) | 57 |
| Example 36 | 33 | 4.71 | 6.75 | (0.134, 0.102) | 60 |
| Example 37 | 42 | 4.86 | 6.71 | (0.134, 0.102) | 51 |
| Example 38 | 81 | 4.61 | 6.59 | (0.134, 0.101) | 60 |
| Example 39 | 89 | 4.77 | 6.79 | (0.134, 0.101) | 55 |
| Example 40 | 110 | 4.63 | 6.58 | (0.134, 0.102) | 62 |
| Example 41 | 113 | 4.77 | 6.66 | (0.134, 0.101) | 51 |
| Example 42 | 114 | 4.70 | 6.68 | (0.134, 0.102) | 53 |
| Example 43 | 139 | 5.12 | 6.34 | (0.134, 0.101) | 51 |
| Example 44 | 140 | 5.03 | 5.99 | (0.134, 0.101) | 52 |
| Example 45 | 153 | 5.17 | 6.09 | (0.134, 0.102) | 51 |
| Example 46 | 157 | 5.12 | 6.01 | (0.134, 0.101) | 55 |
| Example 47 | 222 | 5.04 | 6.36 | (0.134, 0.100) | 59 |
| Example 48 | 250 | 4.64 | 6.58 | (0.134, 0.101) | 55 |
| Example 49 | 258 | 5.02 | 6.58 | (0.134, 0.100) | 52 |
| Example 50 | 341 | 5.13 | 6.40 | (0.134, 0.101) | 48 |
| Example 51 | 342 | 4.73 | 6.37 | (0.134, 0.101) | 56 |
| Example 52 | 361 | 4.61 | 6.69 | (0.134, 0.100) | 50 |
| Example 53 | 362 | 5.03 | 5.96 | (0.134, 0.101) | 55 |
| Example 54 | 453 | 5.01 | 6.19 | (0.134, 0.101) | 54 |
| Example 55 | 454 | 5.03 | 5.85 | (0.134, 0.102) | 54 |
| Example 56 | 607 | 4.93 | 6.25 | (0.134, 0.100) | 51 |
| Example 57 | 634 | 4.91 | 5.90 | (0.134, 0.100) | 49 |
| Example 58 | 635 | 4.84 | 6.12 | (0.134, 0.101) | 50 |
| Example 59 | 659 | 4.91 | 5.93 | (0.134, 0.101) | 51 |
| Example 60 | 660 | 5.03 | 6.30 | (0.134, 0.101) | 56 |
| Comparative Example 6 | E1 | 5.95 | 5.86 | (0.134, 0.101) | 40 |
| Comparative Example 7 | E2 | 5.78 | 5.83 | (0.134, 0.101) | 42 |
| Comparative Example 8 | E3 | 5.79 | 5.89 | (0.134, 0.101) | 41 |
| Comparative Example 9 | E4 | 5.75 | 5.70 | (0.134, 0.101) | 39 |
| Comparative Example 10 | E5 | 5.80 | 5.86 | (0.134, 0.101) | 39 |

As seen from the results of Table 5, the organic light emitting device using the hole blocking layer material of the blue organic light emitting device of the present disclosure had lower driving voltage and significantly improved light emission efficiency and lifetime compared to Comparative Examples 6 to 10. Such results are due to the fact that, when holes pass through an electron transfer layer and reach a cathode without binding in a light emitting layer, efficiency and lifetime decrease in an OLED. When using a compound having a deep HOMO level as a hole blocking layer in order to prevent such a phenomenon, the holes trying to pass through the light emitting layer and reach the cathode are blocked by an energy barrier of the hole blocking layer. As a result, it is considered that probability of the holes and electrons forming excitons increases, and possibility of being emitted as light in the light emitting layer increases, and the compound of the present disclosure brings excellence in all aspects of driving, efficiency and lifetime.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

The invention claimed is:

1. A heterocyclic compound represented by the following Chemical Formula 1:

[Chemical Formula 1]

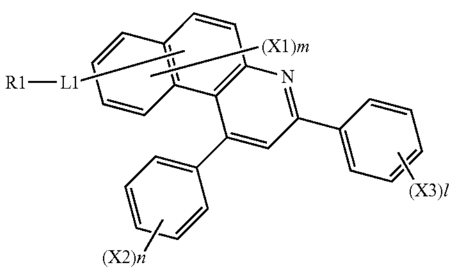

wherein, in Chemical Formula 1,

L1 is a direct bond;

a substituted or unsubstituted phenylene group; a substituted or unsubstituted biphenylene group; a substituted or unsubstituted naphthylene group; or a substituted or unsubstituted anthracene group;

R1 is a substituted or unsubstituted phenyl group; a substituted or unsubstituted biphenyl group; a substituted or unsubstituted naphthyl group; a substituted or unsubstituted anthracene group; a substituted or unsubstituted pyridine group; a substituted or unsubstituted pyrimidine group; a substituted or unsubstituted triazine group; a substituted or unsubstituted phenanthridine group; a substituted or unsubstituted phenanthroline group; or a substituted or unsubstituted phosphine oxide group, X1 is hydrogen; or deuterium, X2 and X3 are each independently hydrogen; deuterium; a cyano group; or groups adjacent to each other bonded to each other to form a benzene ring;

m, n and l are each independently an integer of 1 to 5; and when m, n and l are each 2 or greater, substituents in the parentheses are the same as or different from each other.

2. The heterocyclic compound of claim 1, wherein the "substituted or unsubstituted" means being substituted with one or more substituents selected from the group consisting of a linear or branched alkyl group having 1 to 60 carbon atoms; a linear or branched alkenyl group having 2 to 60 carbon atoms; a linear or branched alkynyl group having 2 to 60 carbon atoms; a monocyclic or polycyclic cycloalkyl group having 3 to 60 carbon atoms; a monocyclic or polycyclic heterocycloalkyl group having 2 to 60 carbon atoms; a monocyclic or polycyclic aryl group having 6 to 60 carbon atoms; a monocyclic or polycyclic heteroaryl group having 2 to 60 carbon atoms; a silyl group; a phosphine oxide group; and an amine group, or being unsubstituted, or being substituted with a substituent linking two or more substituents selected from among the substituents illustrated above, or being unsubstituted.

3. The heterocyclic compound of claim 1, wherein Chemical Formula 1 is represented by any one of the following Chemical Formula 2 to Chemical Formula 6:

[Chemical Formula 2]

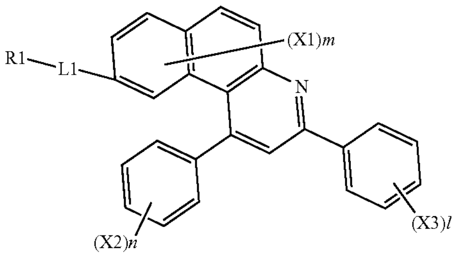

[Chemical Formula 3]

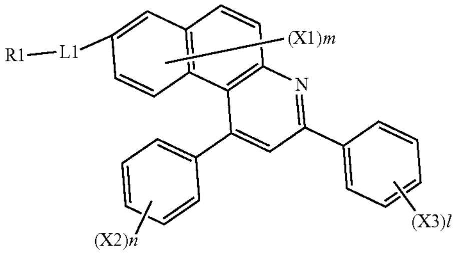

[Chemical Formula 4]

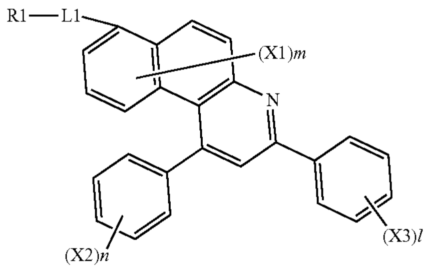

[Chemical Formula 5]

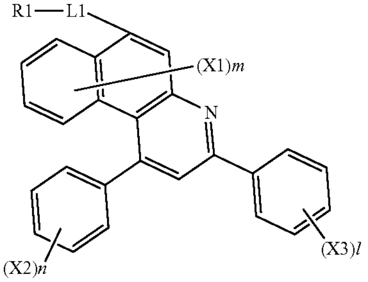

[Chemical Formula 6]

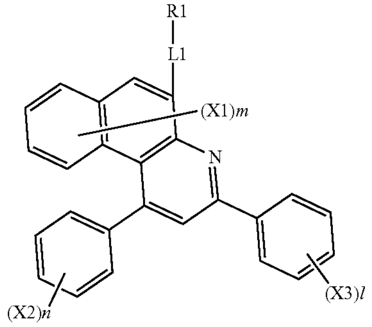

in Chemical Formula 2 to Chemical Formula 6, each substituent has the same definition as in Chemical Formula 1.

4. The heterocyclic compound of claim 1, wherein Chemical Formula 1 is represented by any one of the following compounds:

-continued
1
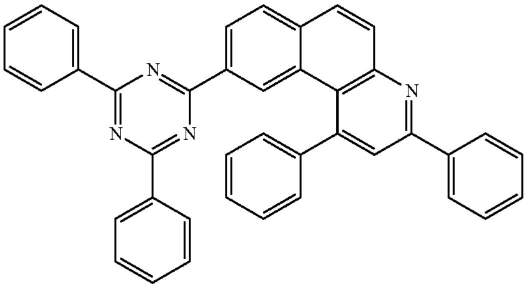
2
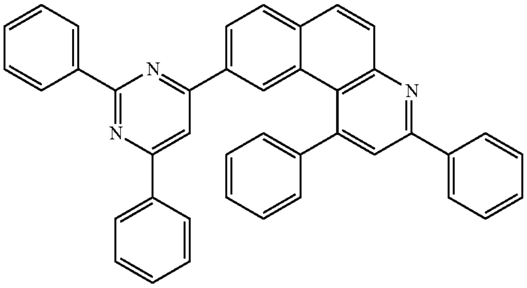
3
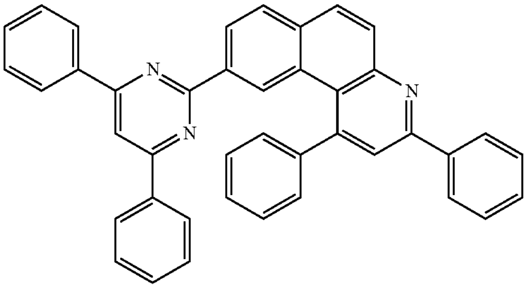
4
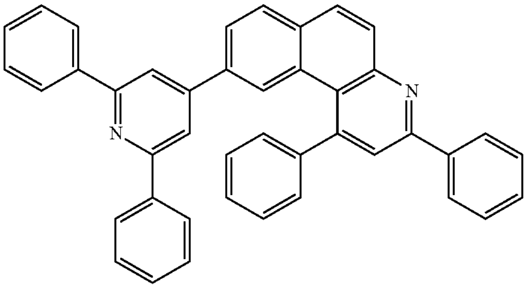
5
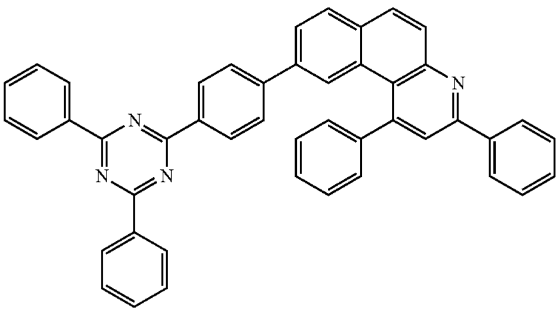
6
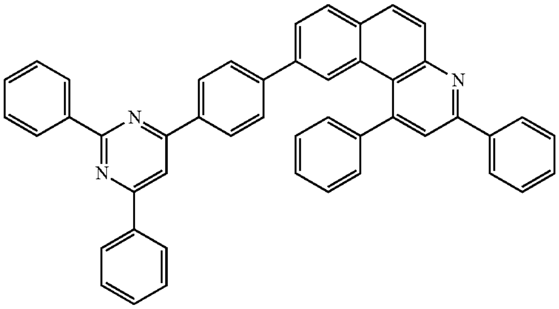
7
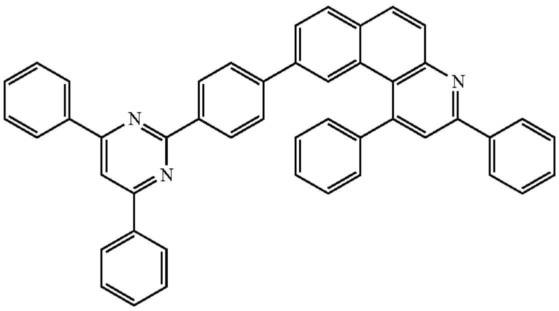
8
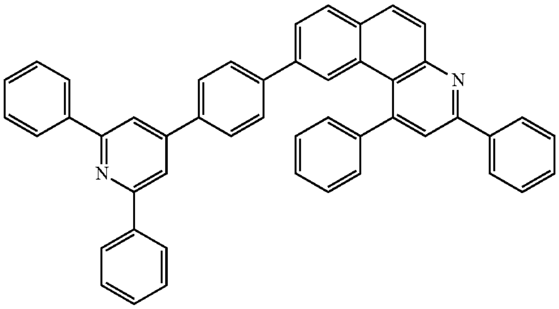
9
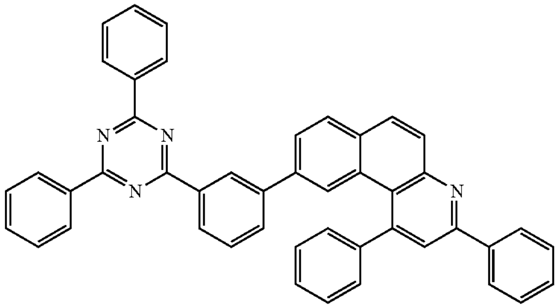

-continued
10
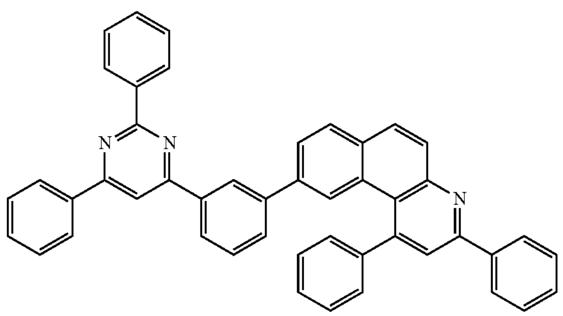
11
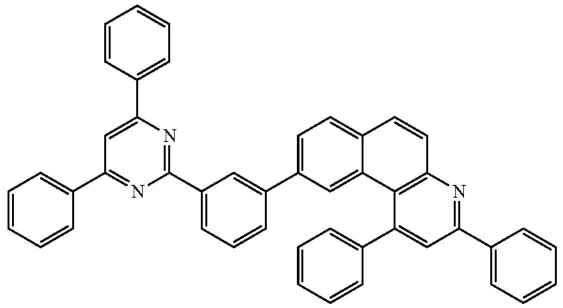
12
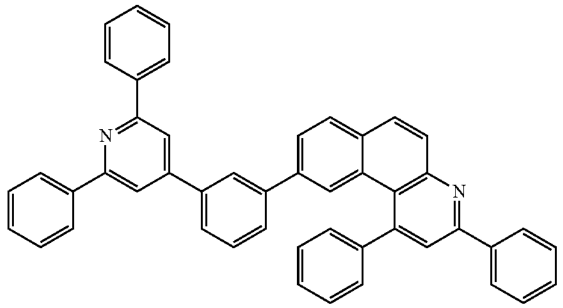
13
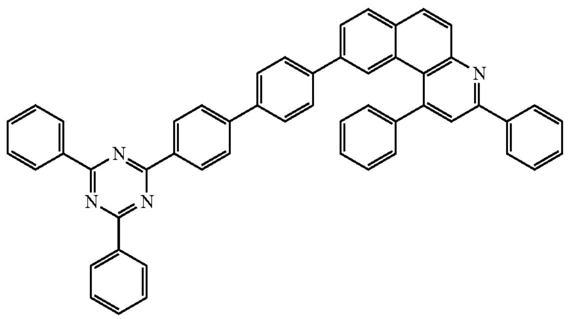
-continued
14
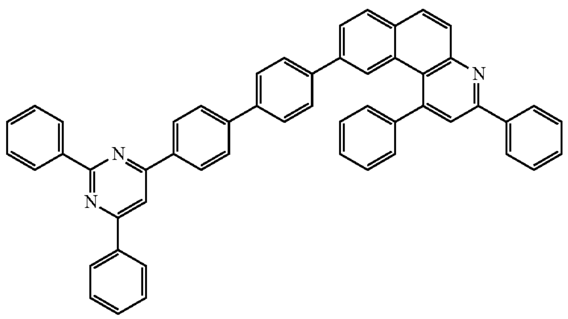
15
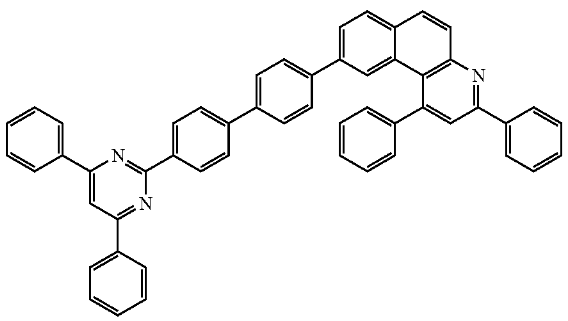
16
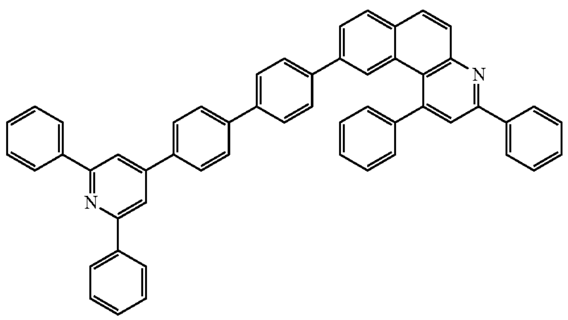
17
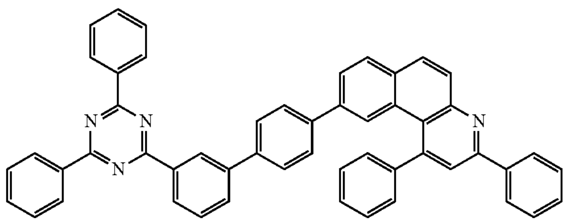
18
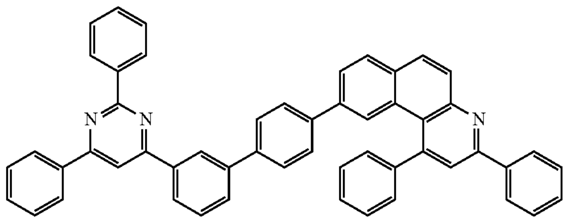

-continued
19
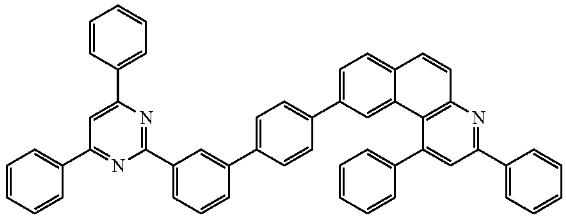
20
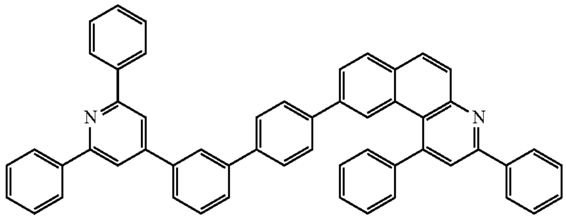
21
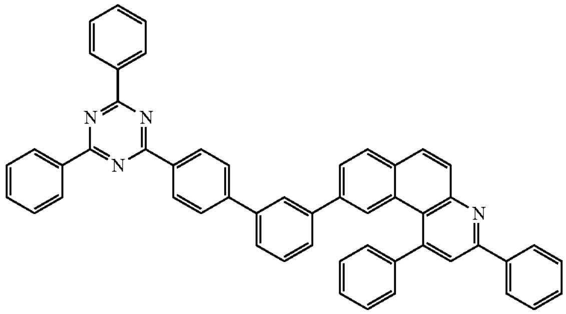
22
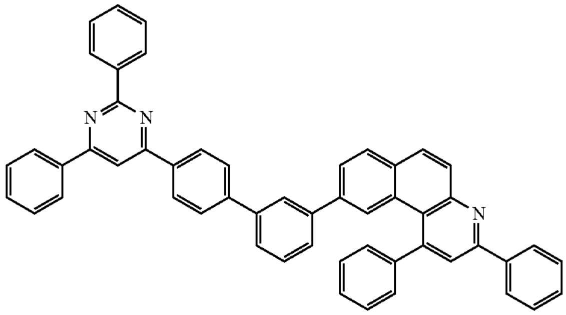
23
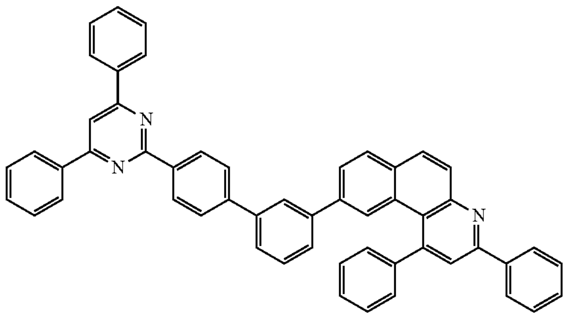
-continued
24
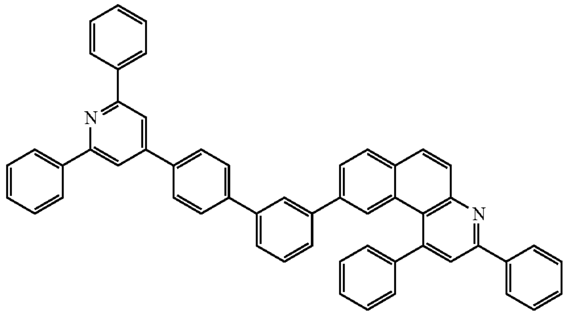
25
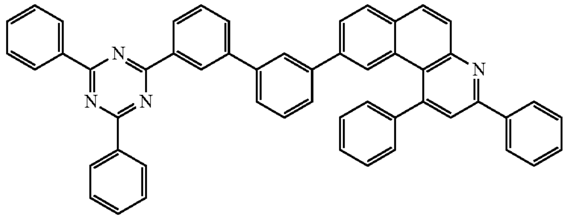
26
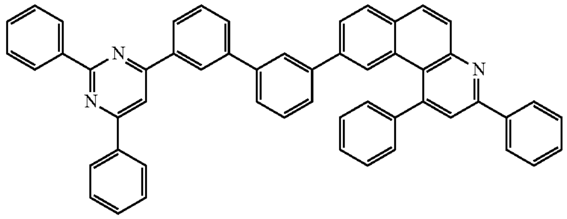
27
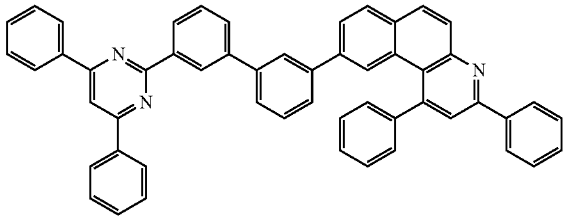
28
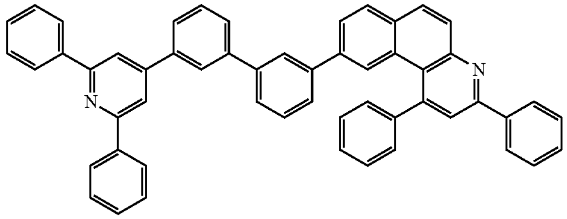

-continued
29
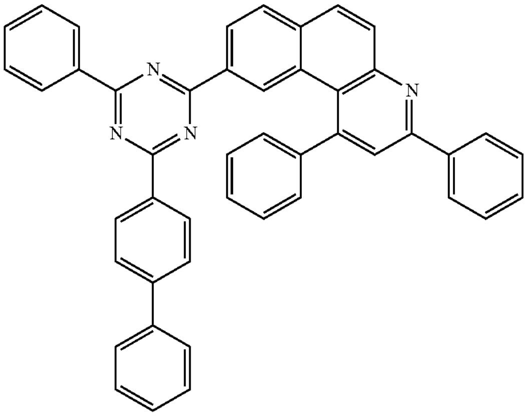
30
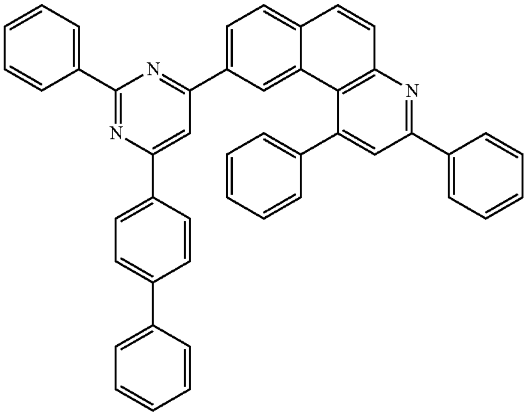
31
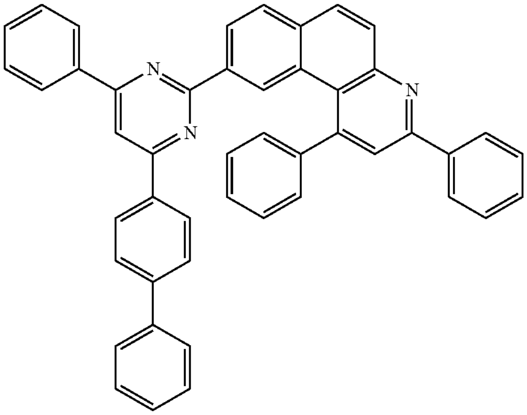
-continued
32
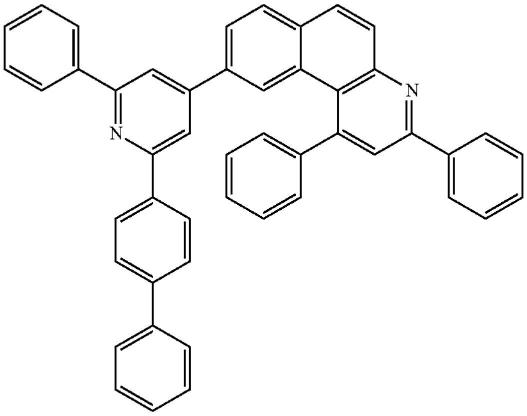
33
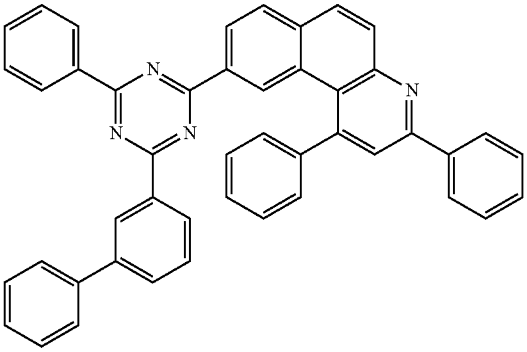
34
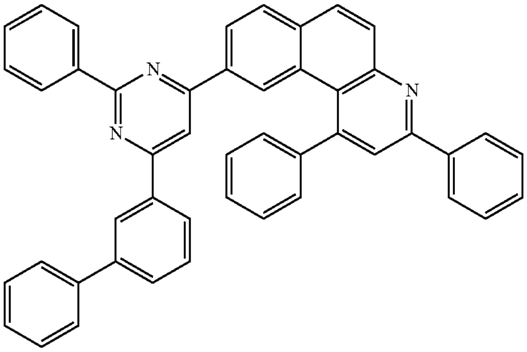
35
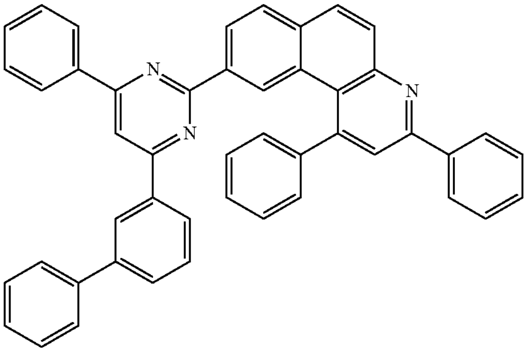

-continued
36
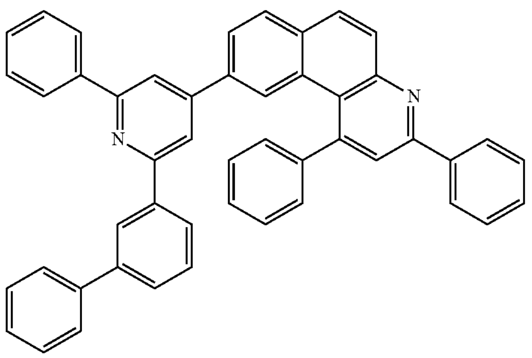
37
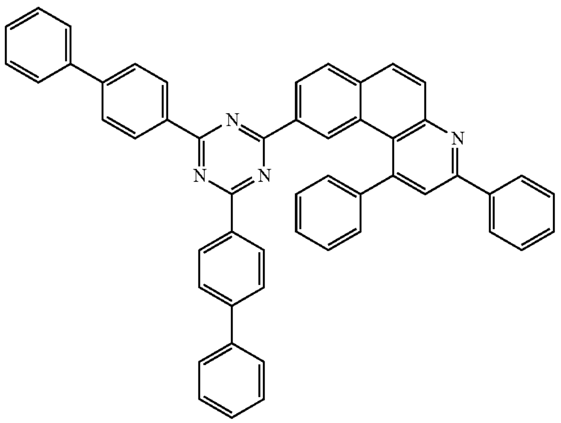
38
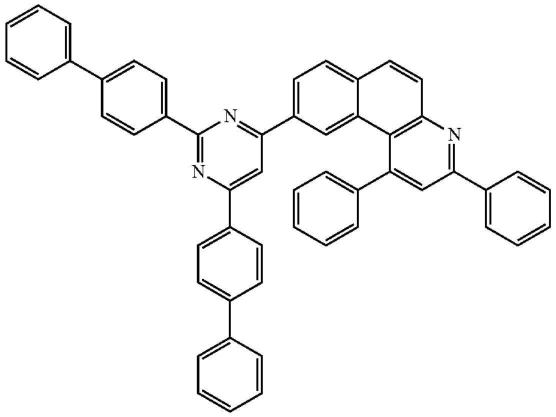
-continued
39
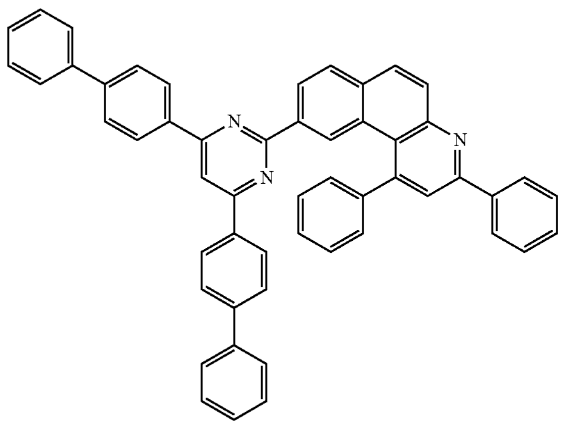
40
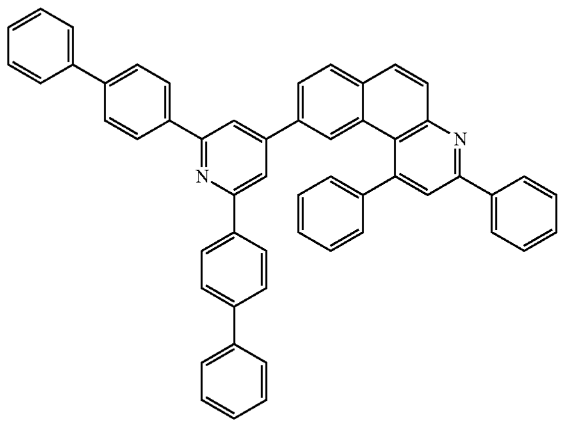
41
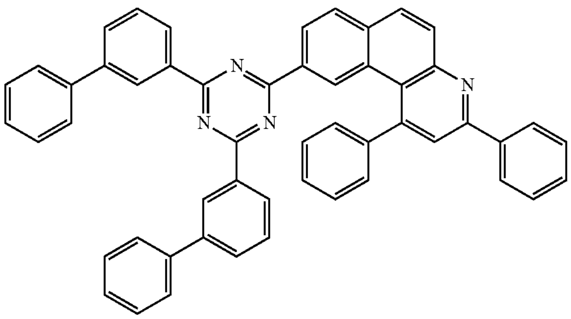
42
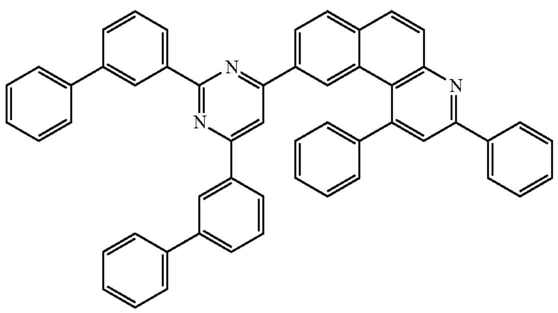

-continued
43
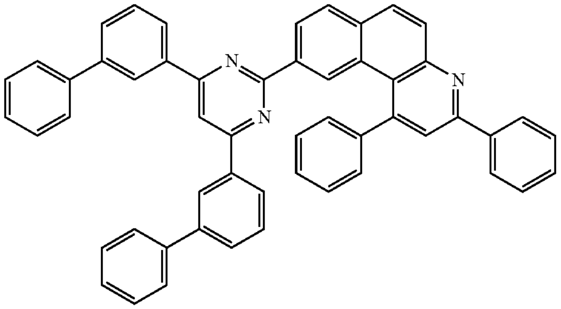
44
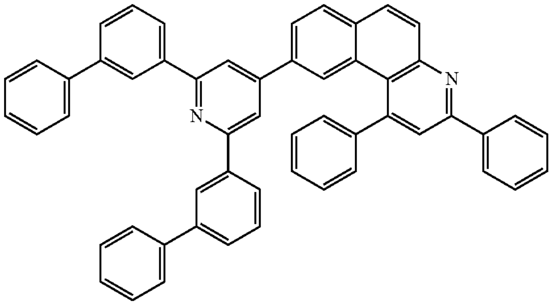
45
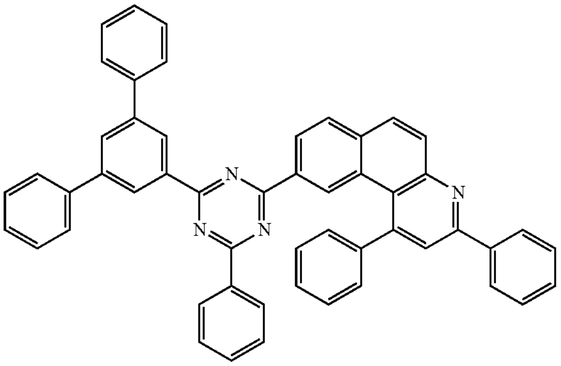
46
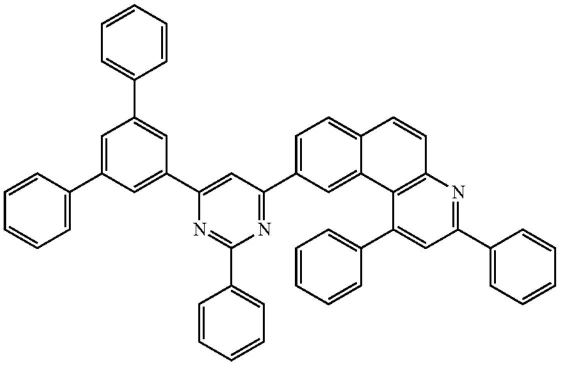
-continued
47
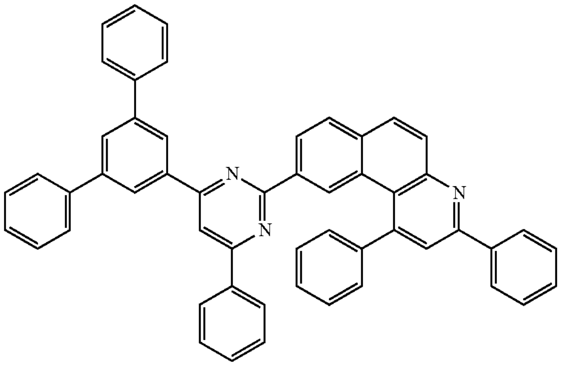
48
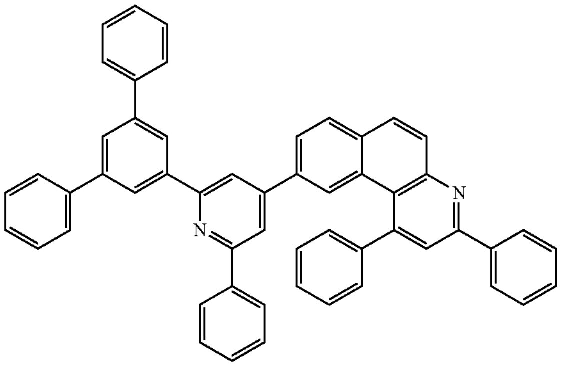
49
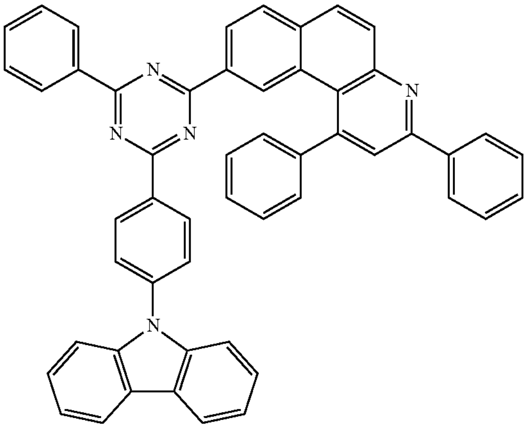

-continued
50
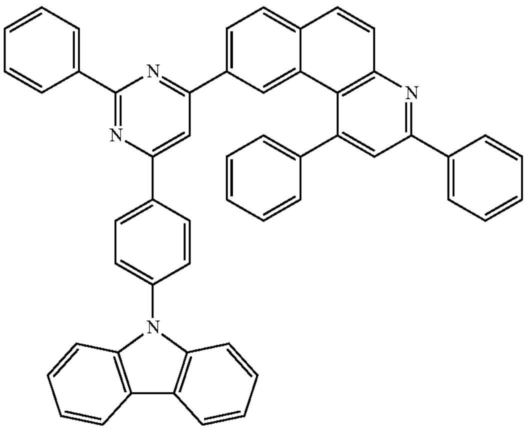
51
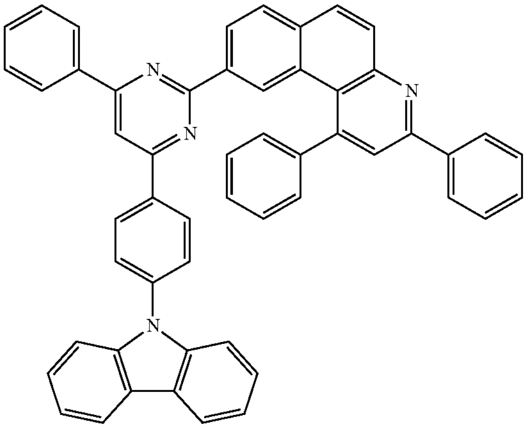
52
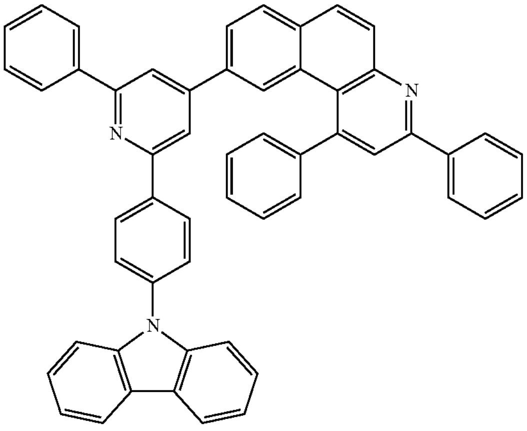
-continued
53
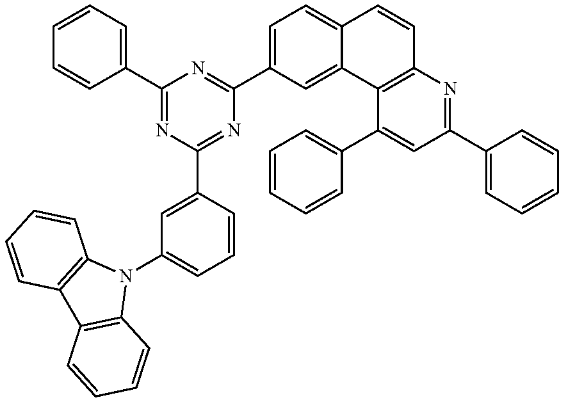
54
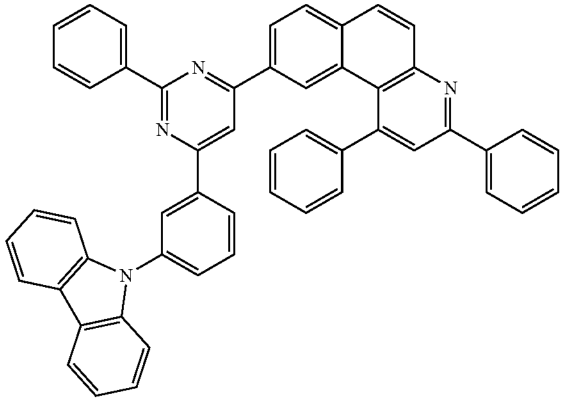
55
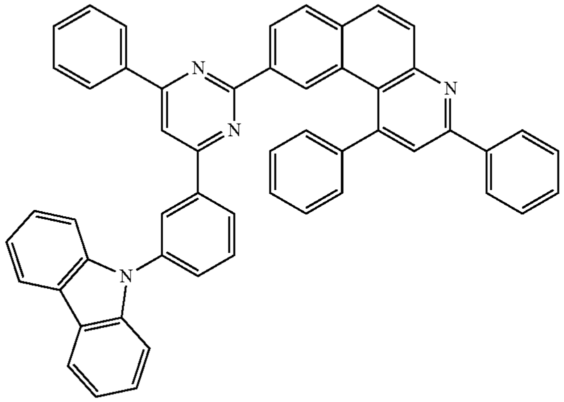

-continued
56
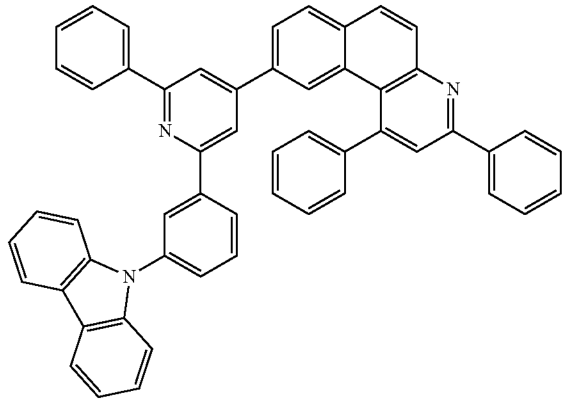
57
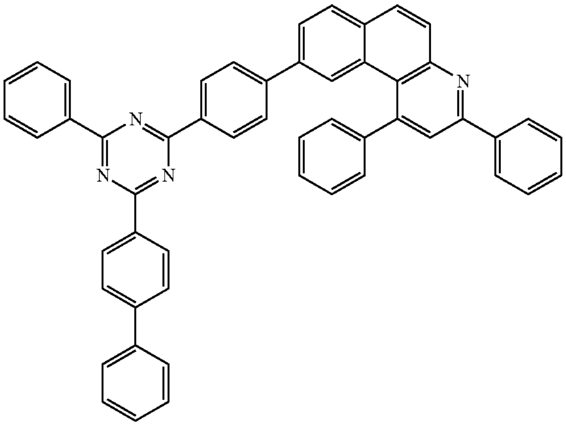
58
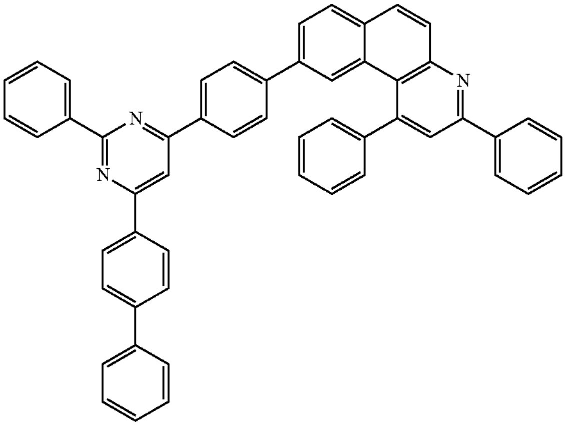
-continued
59
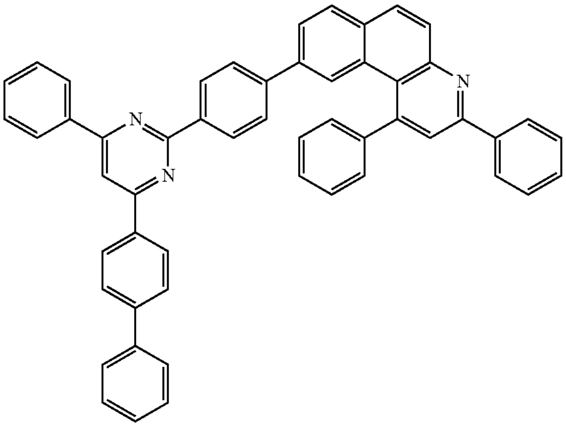
60
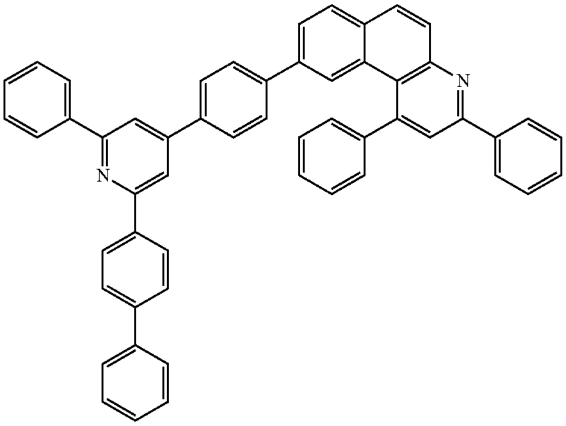
61
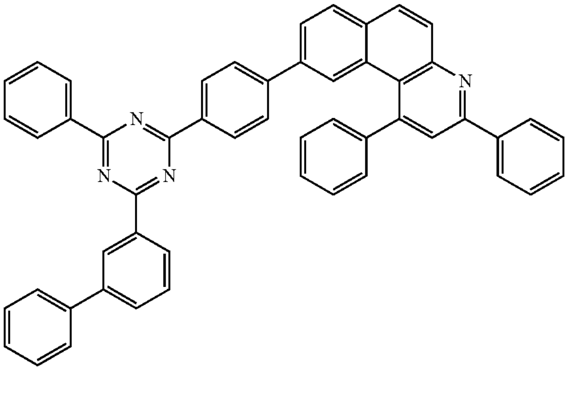

-continued
62
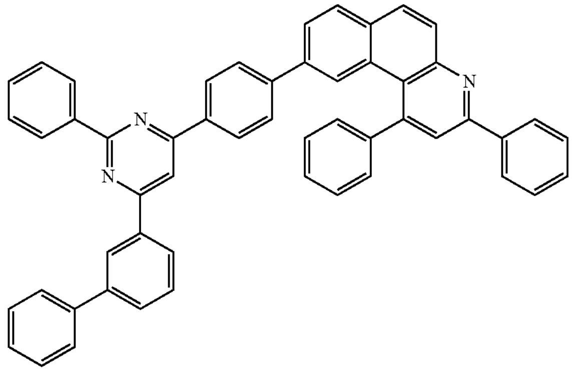
63
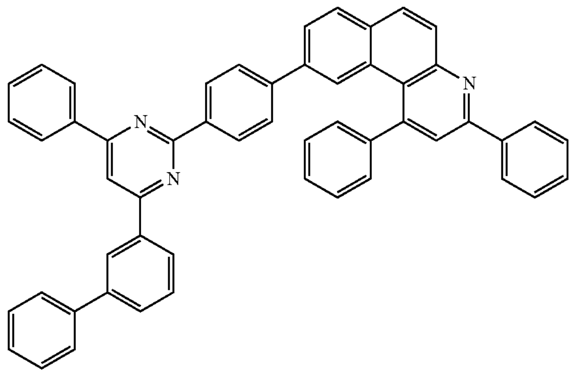
64
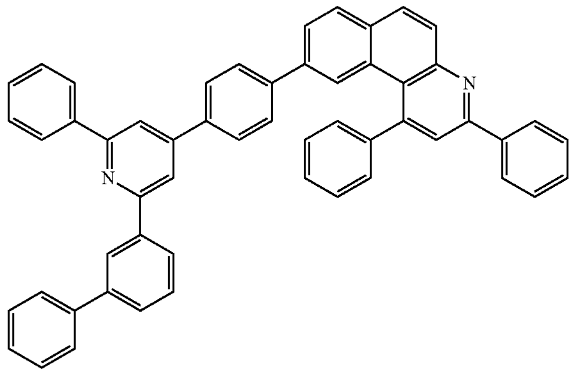
65
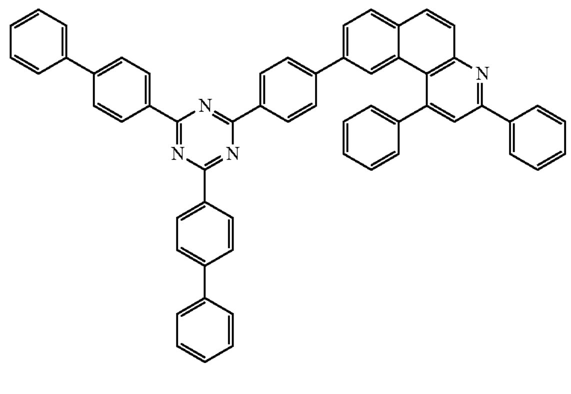
-continued
66
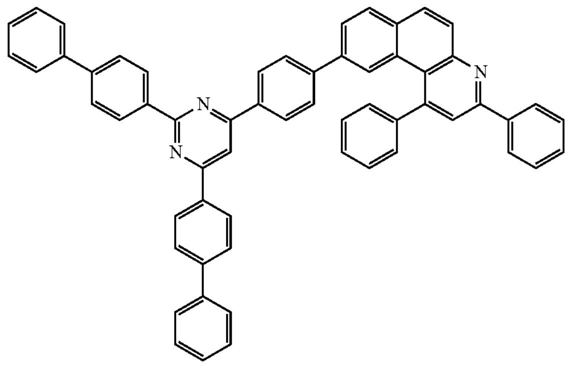
67
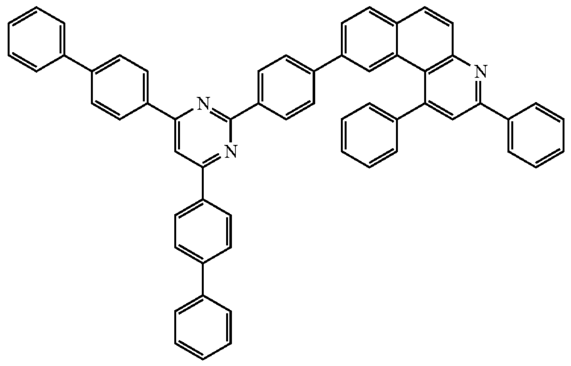
68
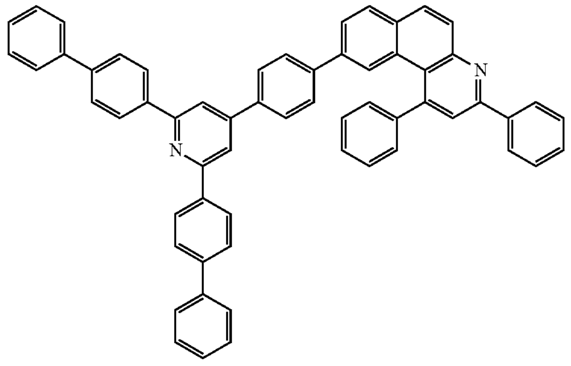
69
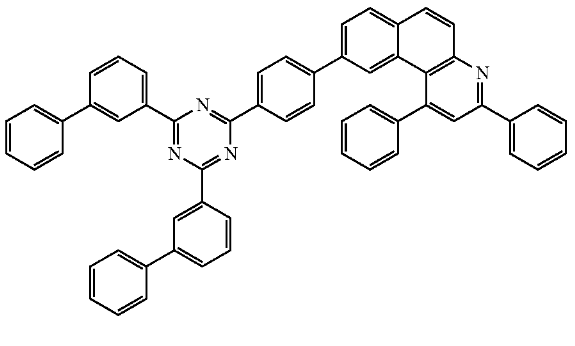

-continued
70
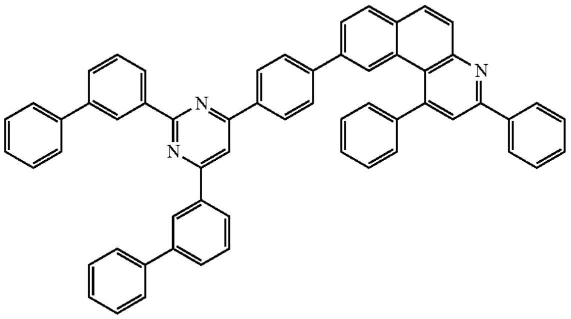
71
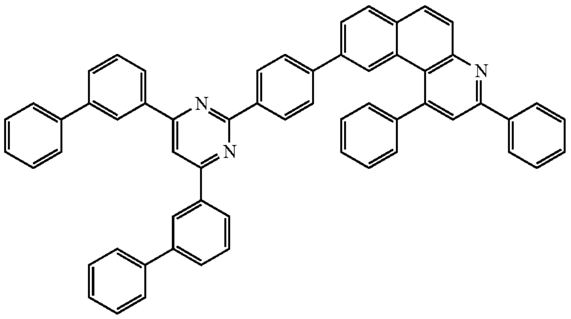
72
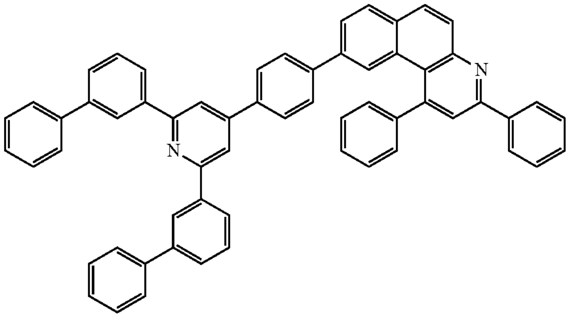
73
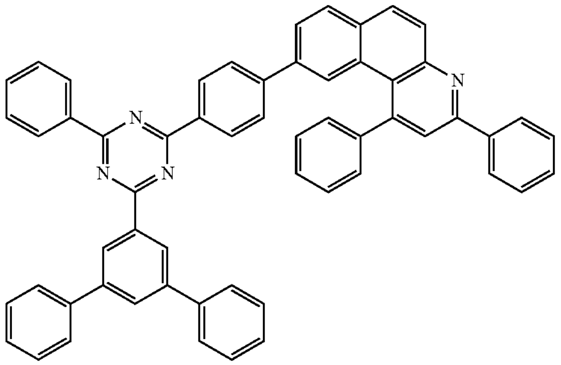
-continued
74
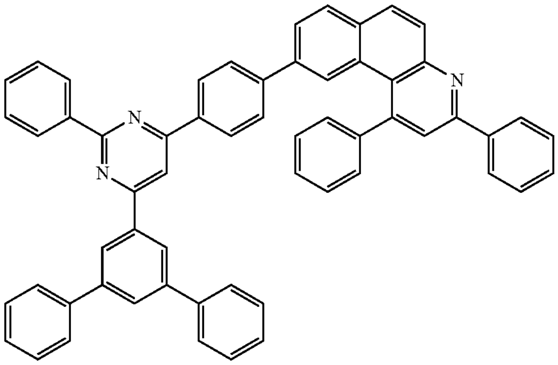
75
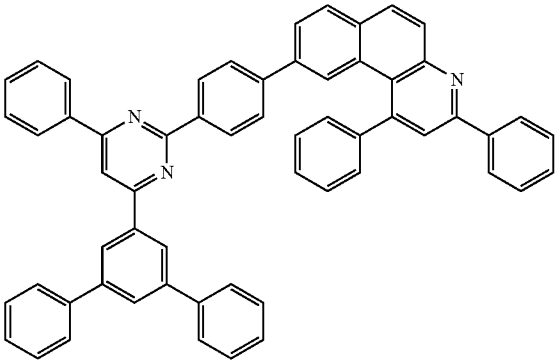
76
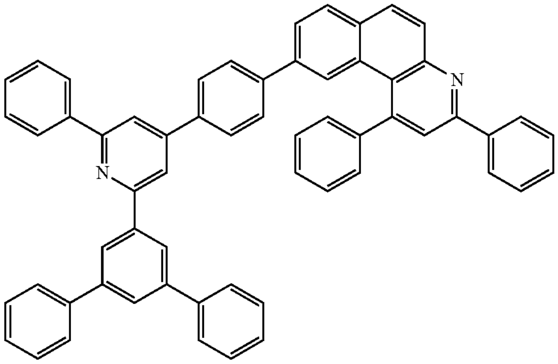
77
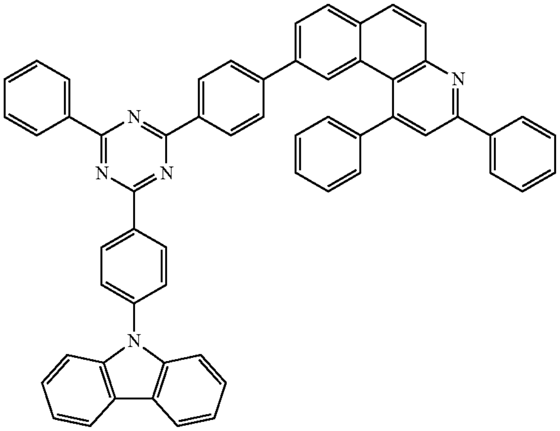

-continued
78
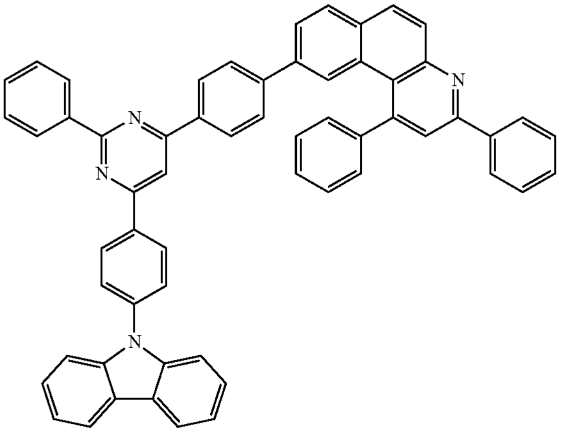
79
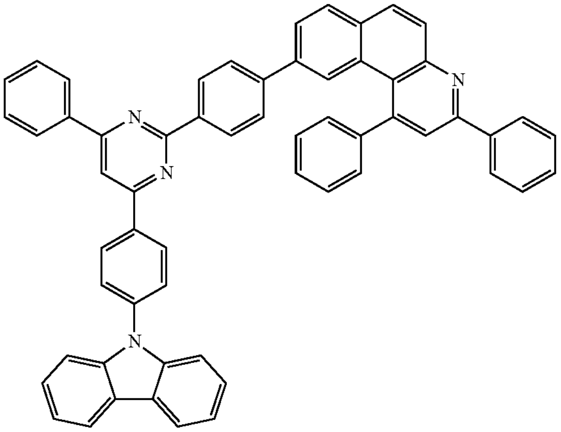
80
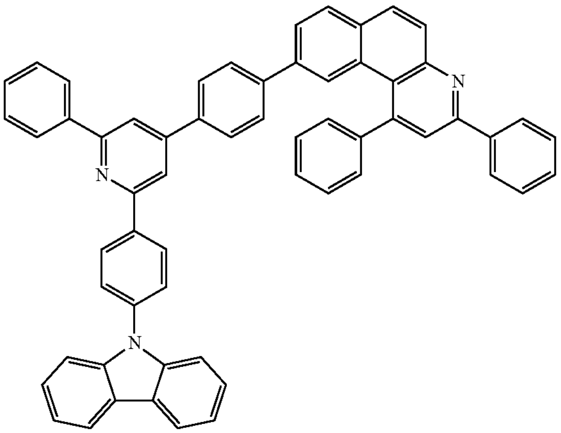
-continued
81
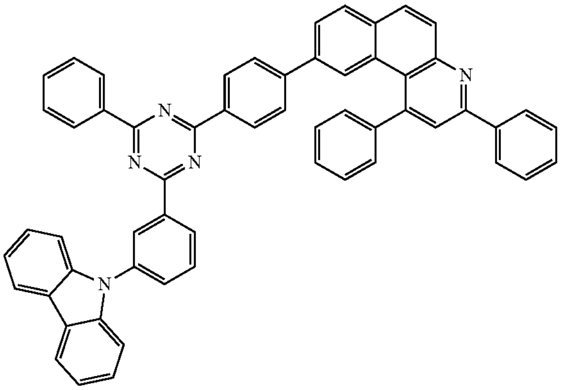
82
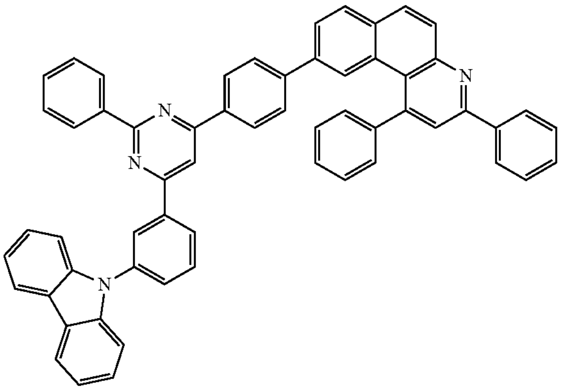
83
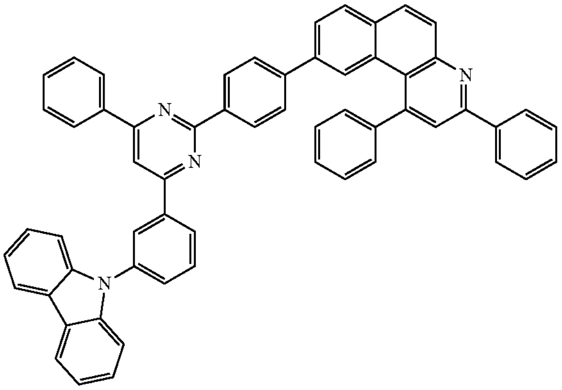
84
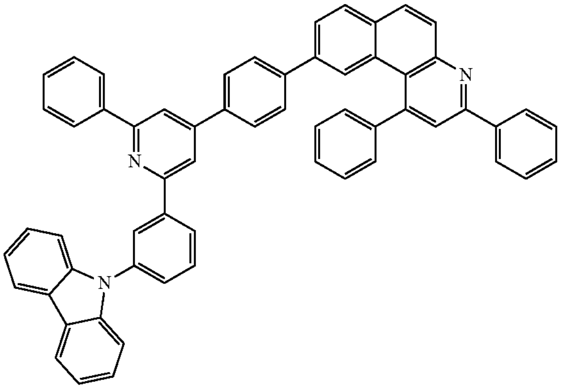

-continued
85
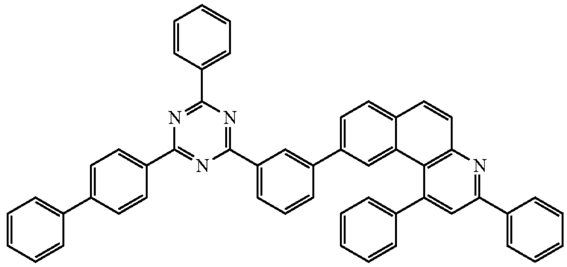
86
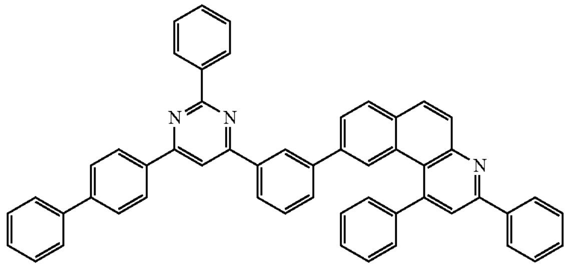
87
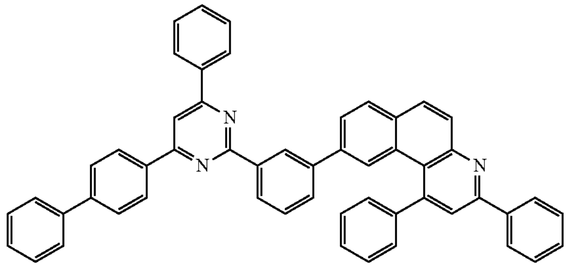
88
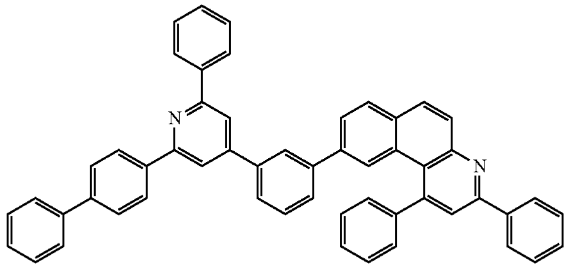
89
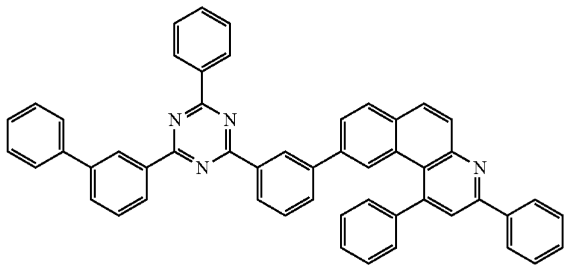
-continued
90
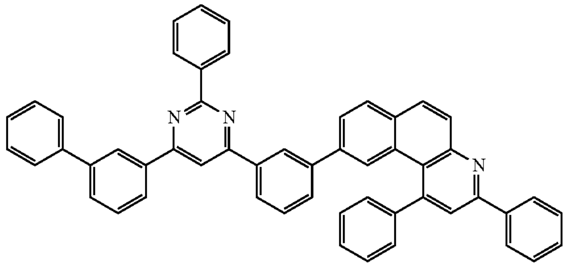
91
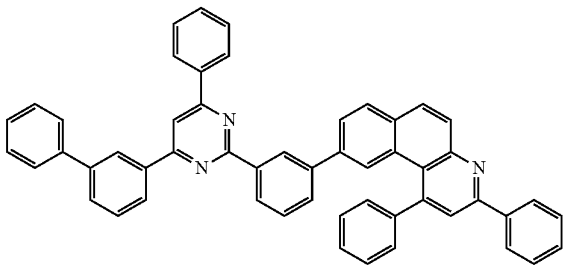
92
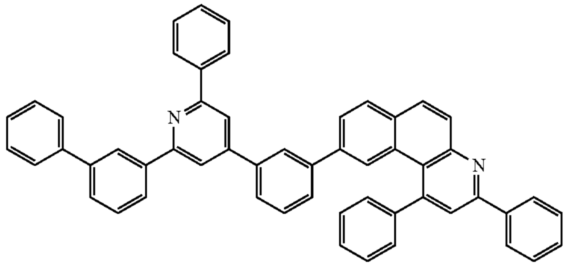
93
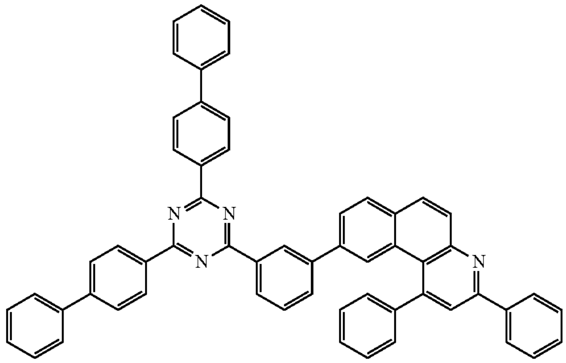
94
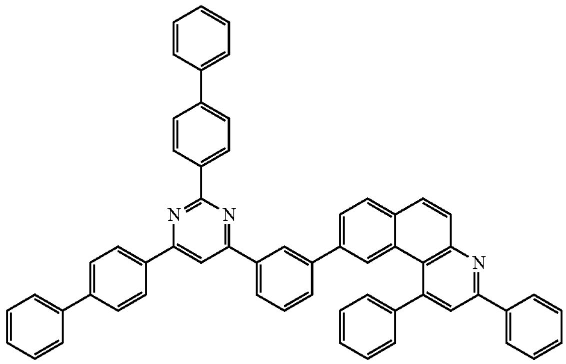

-continued
95
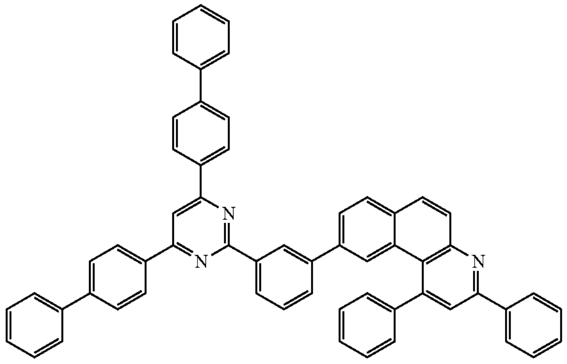
96
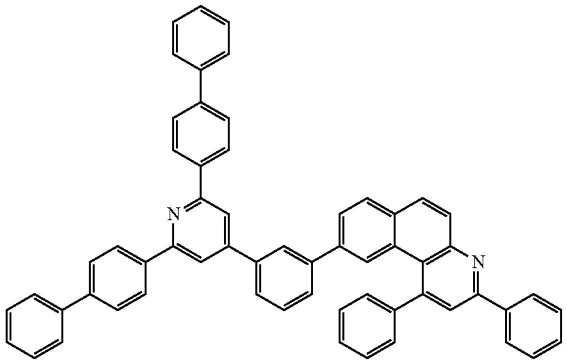
97
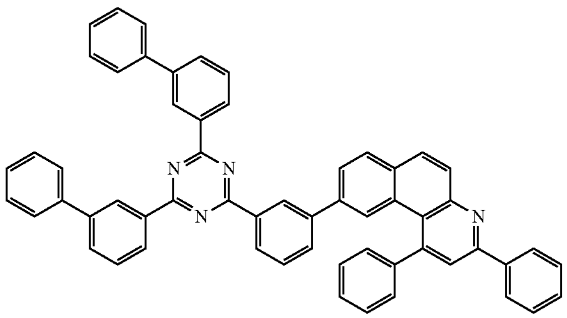
98
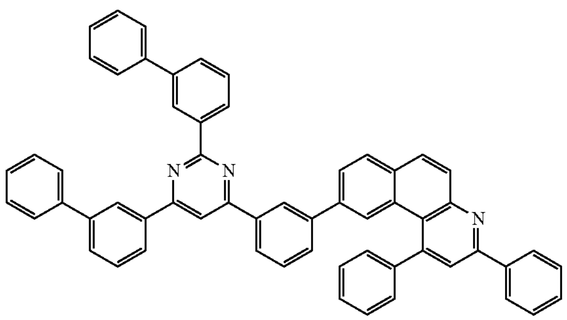
-continued
99
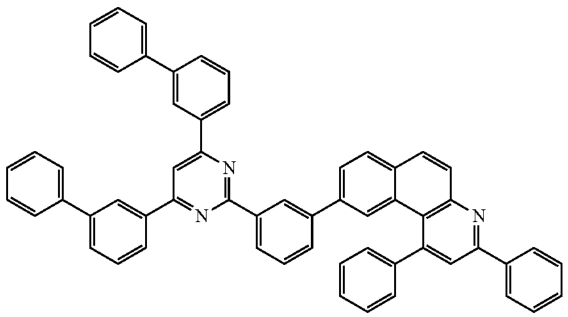
100
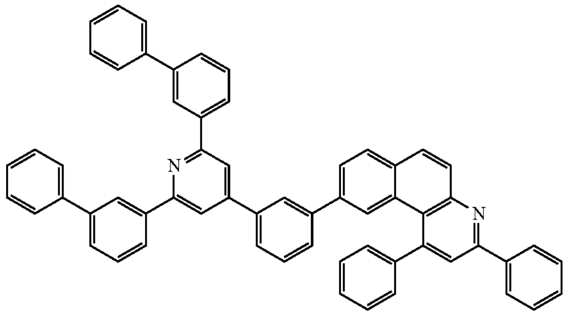
101
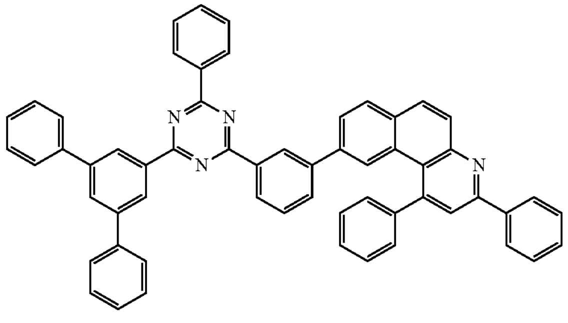
102
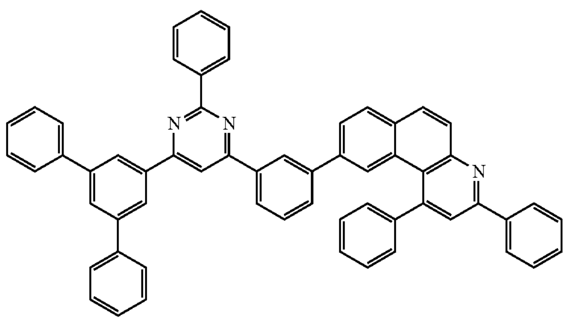

-continued
103
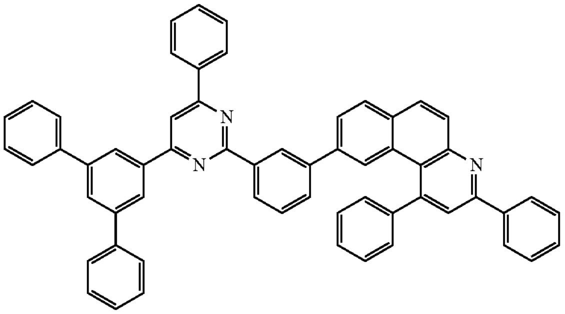
104
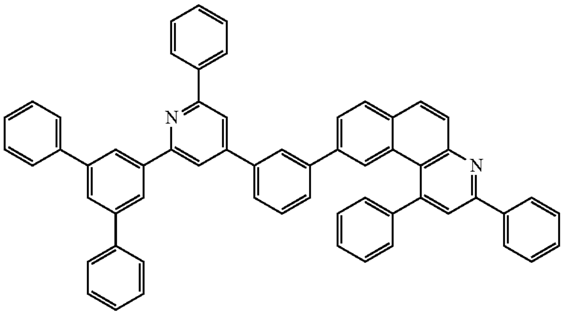
105
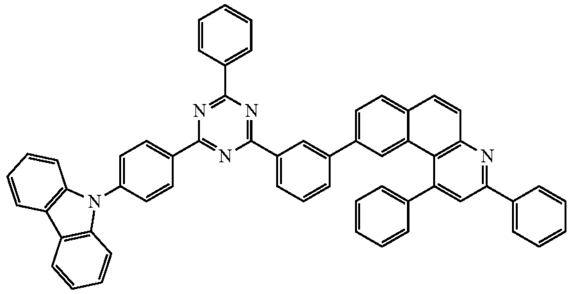
106
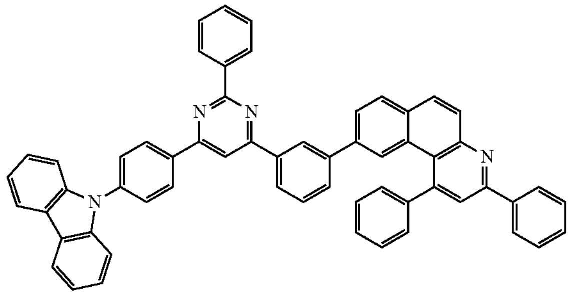
107
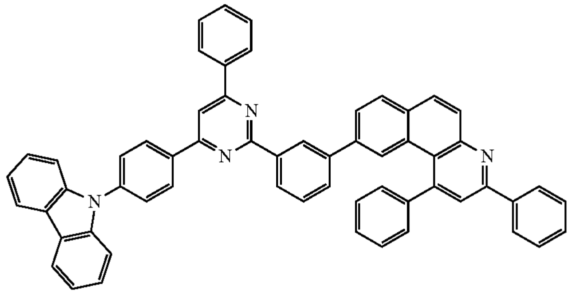
-continued
108
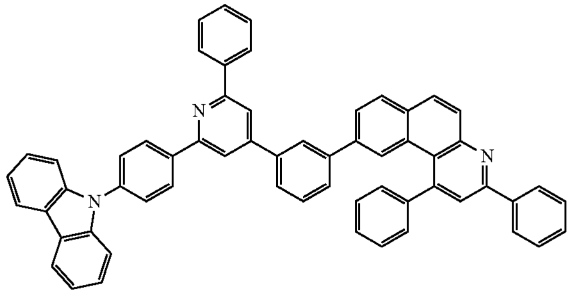
109
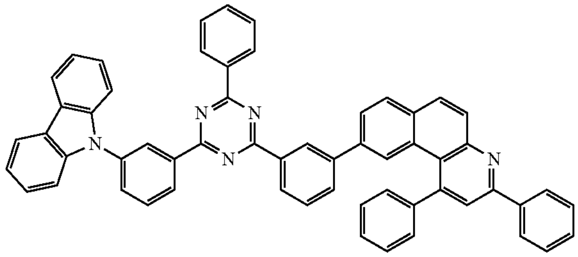
110
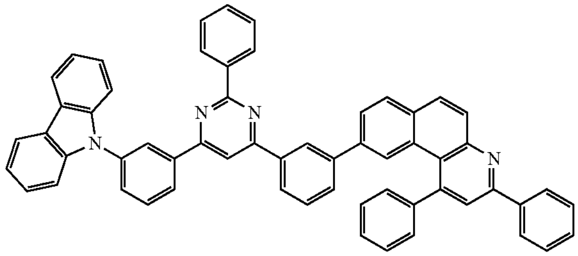
111
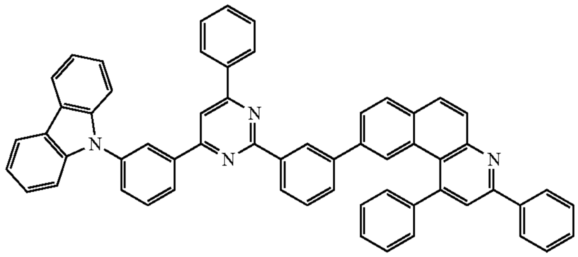
112
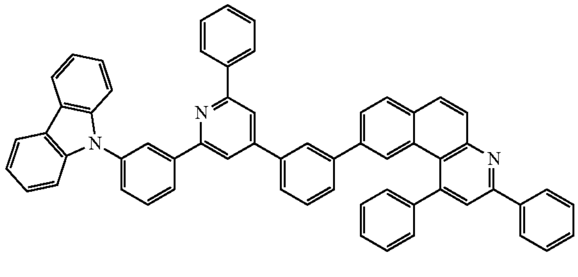

113
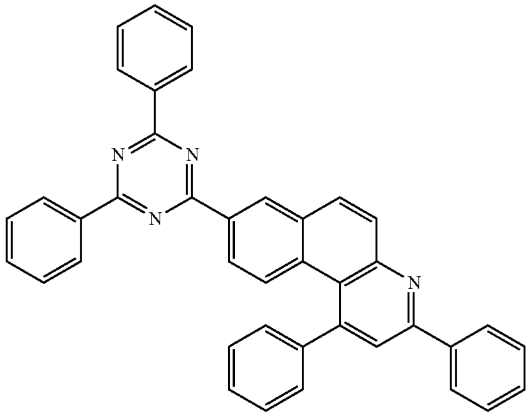
114
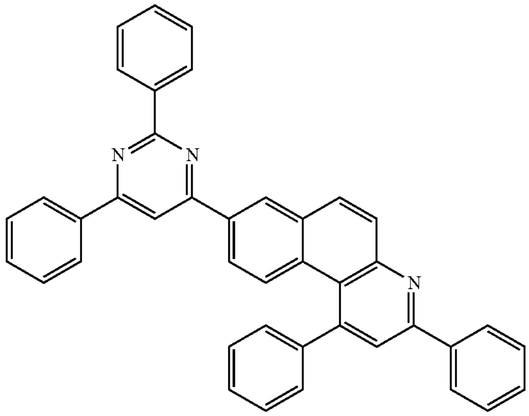
115
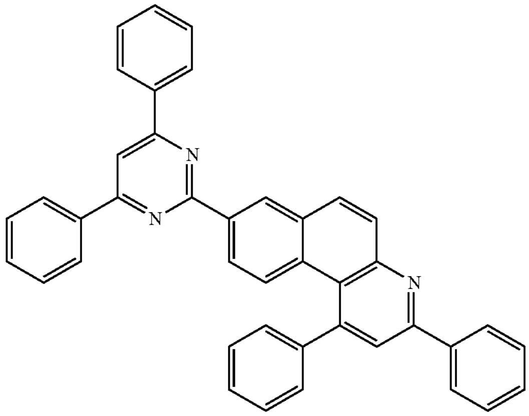
-continued
116
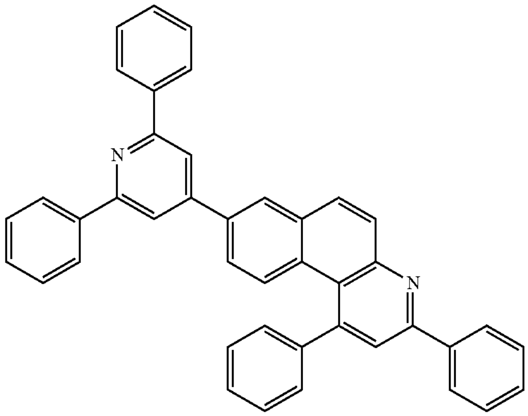
117
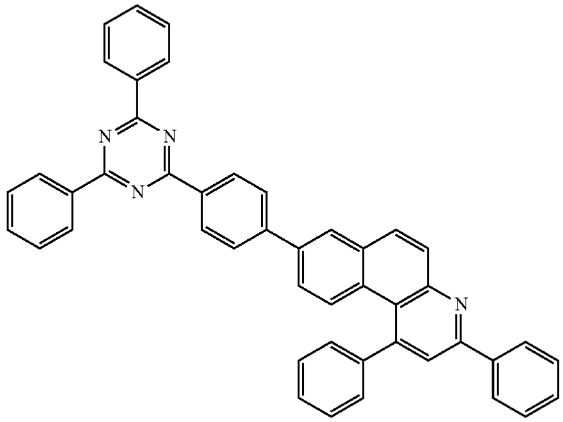
118
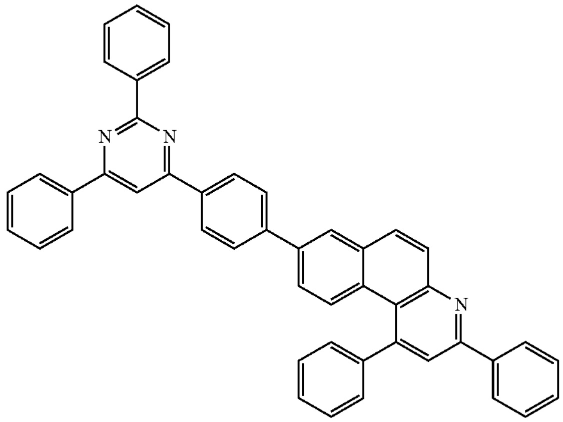

-continued
119
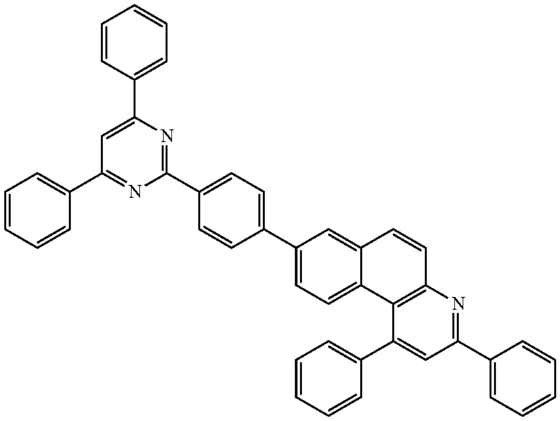
120
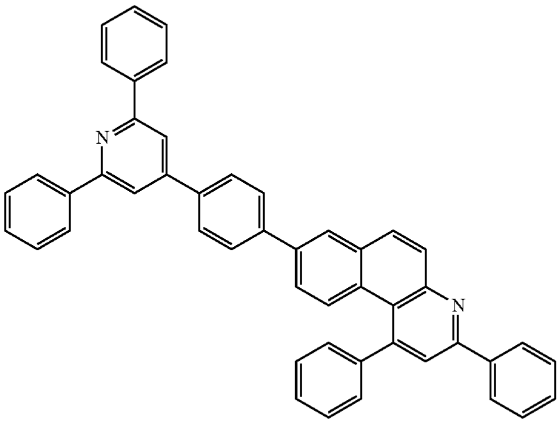
121
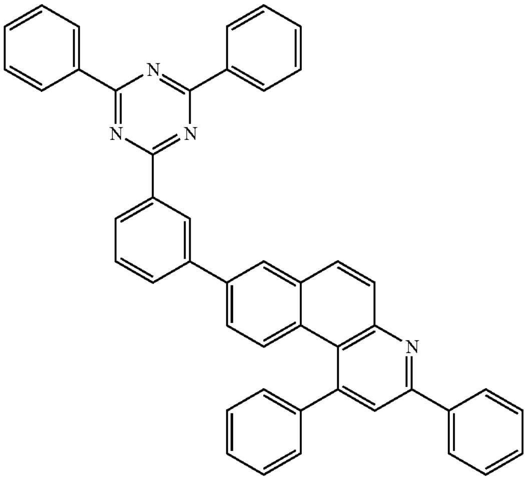
-continued
122
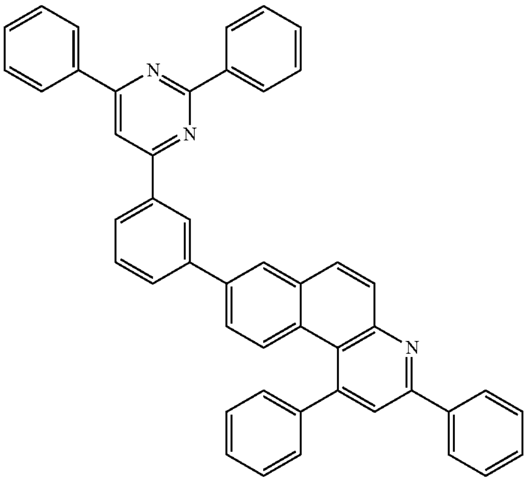
123
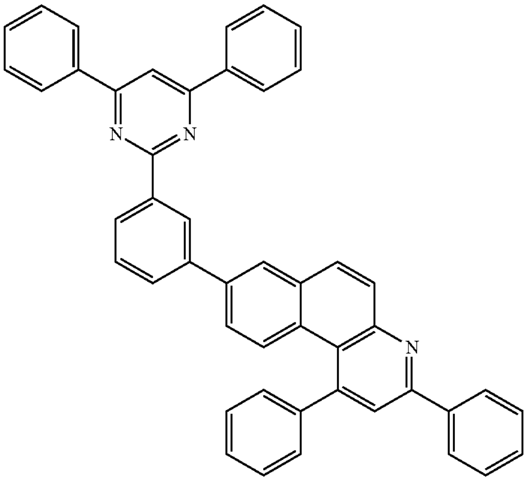
124
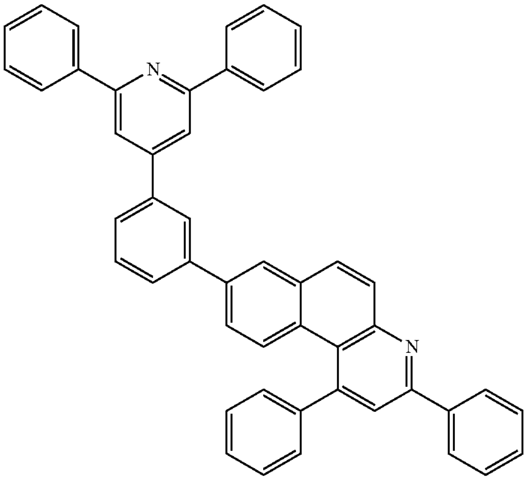

-continued
125
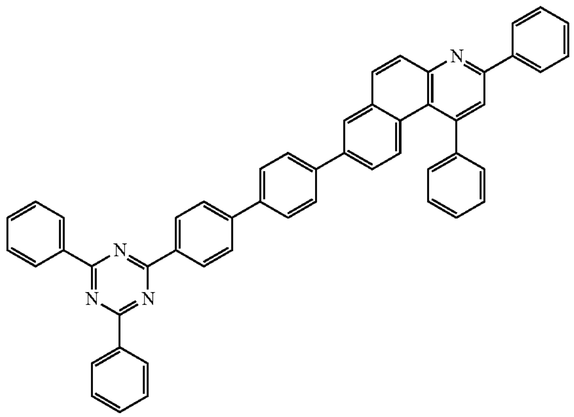
126
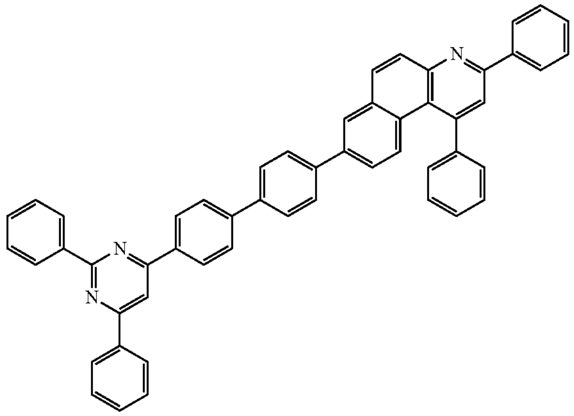
127
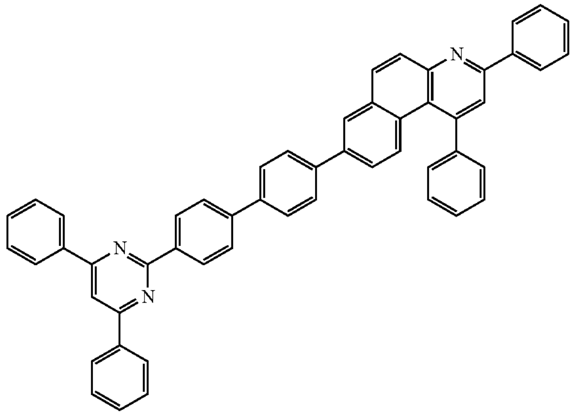
-continued
128
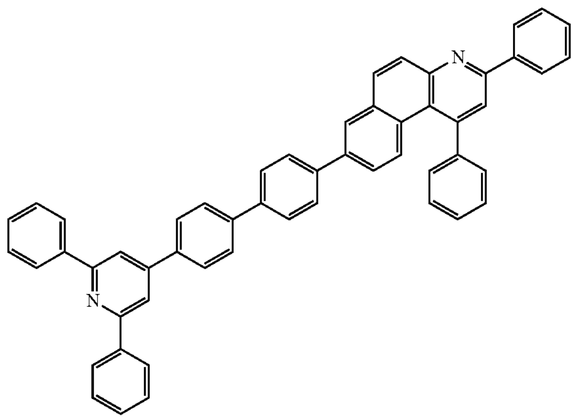
129
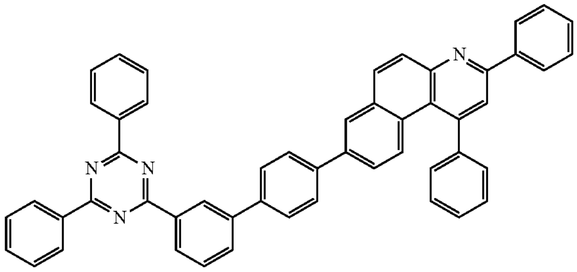
130
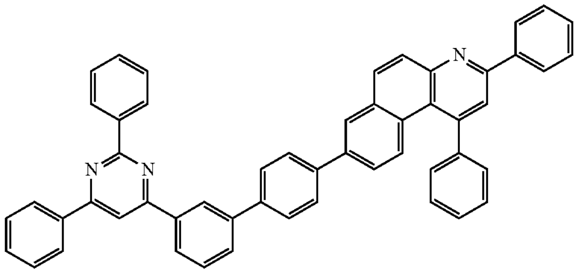
131
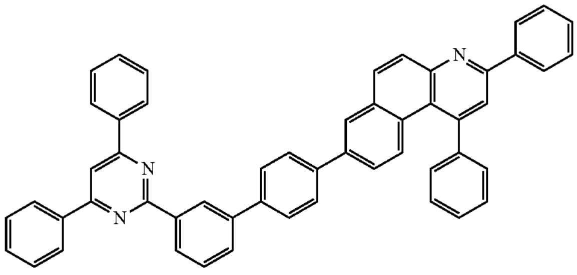
132
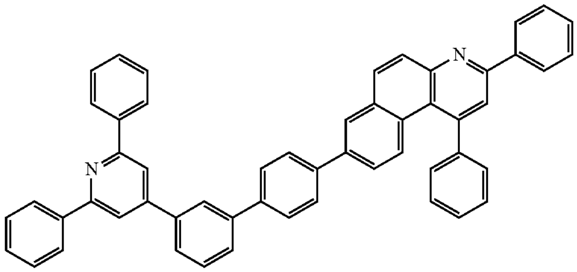

133
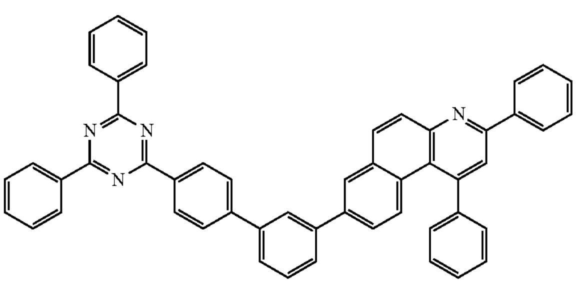
134
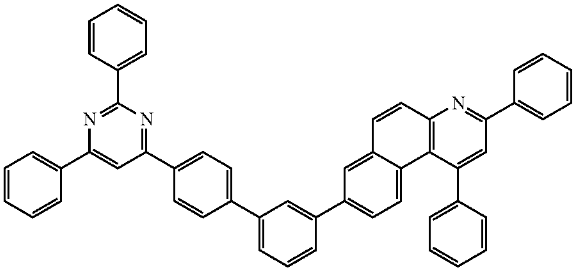
135
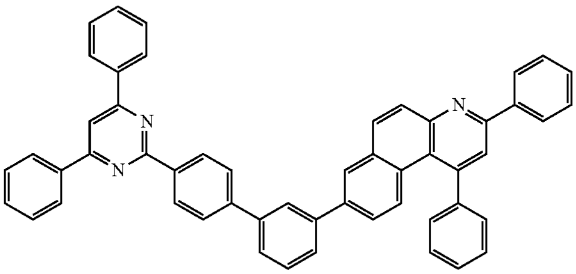
136
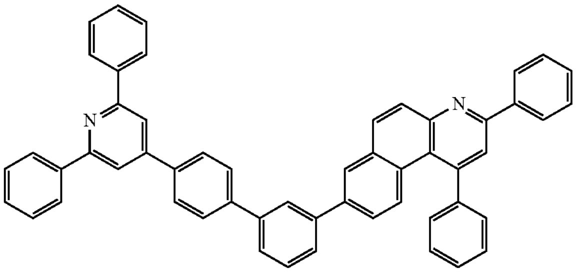
137
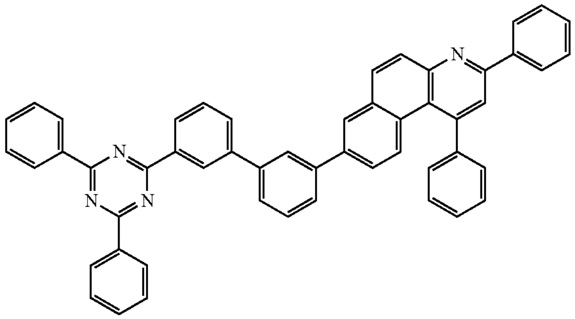
138
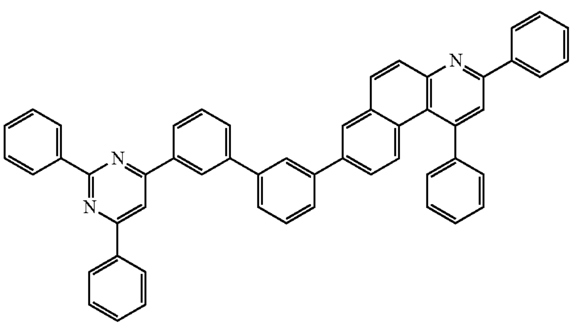
139
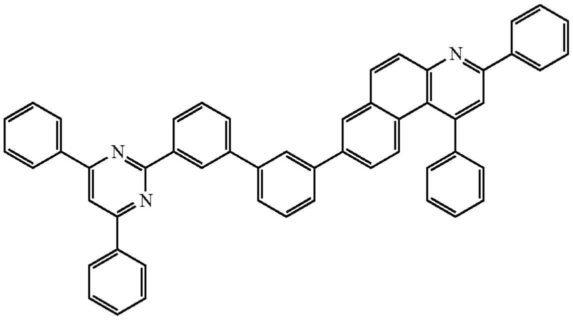
140
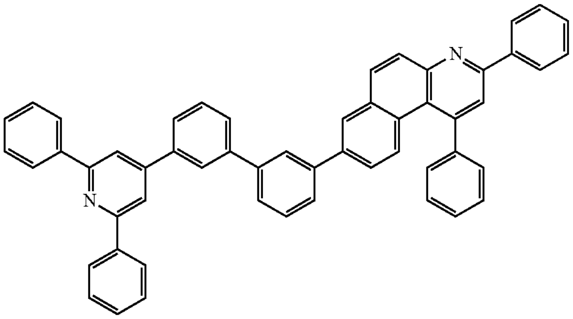
141
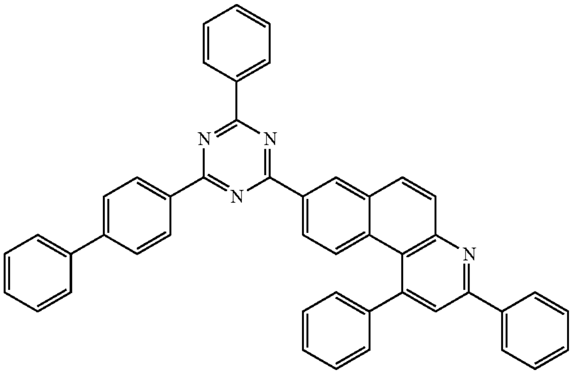

-continued
142
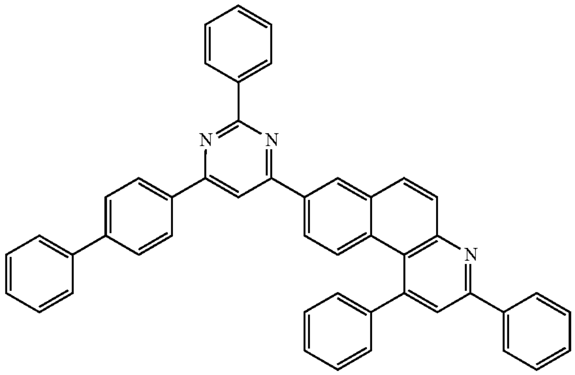
143
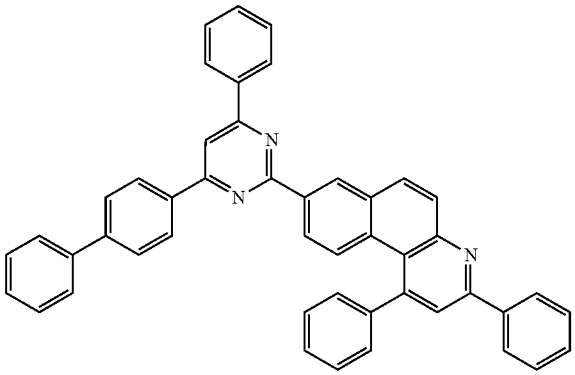
144
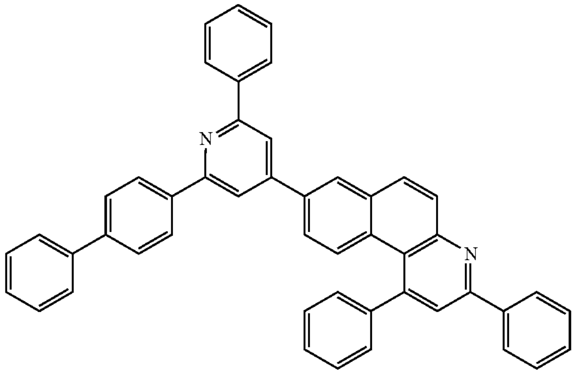
145
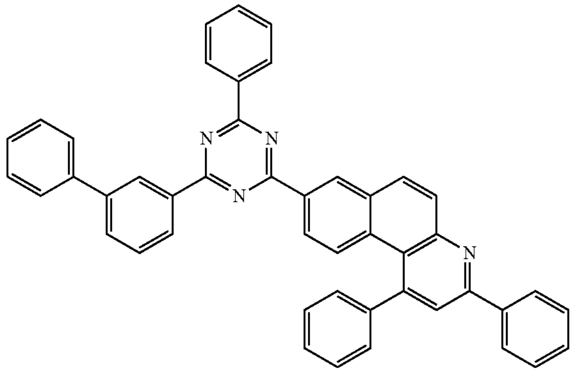
-continued
146
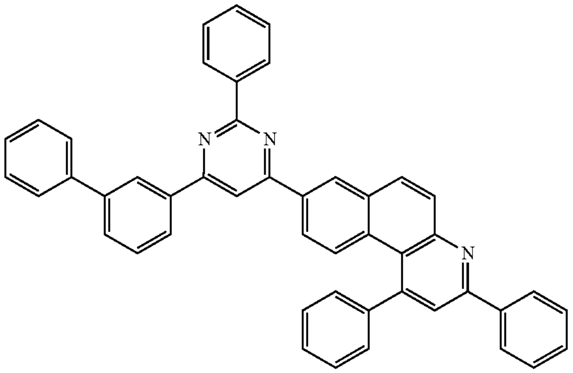
147
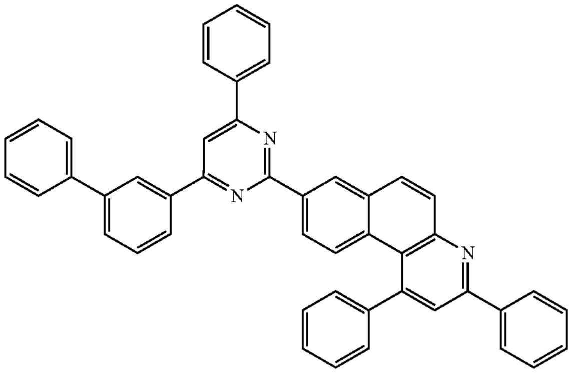
148
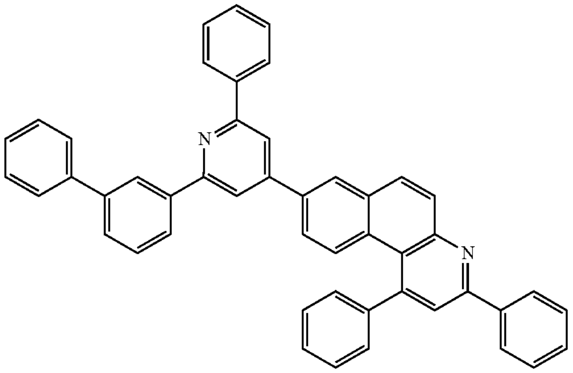

-continued
149
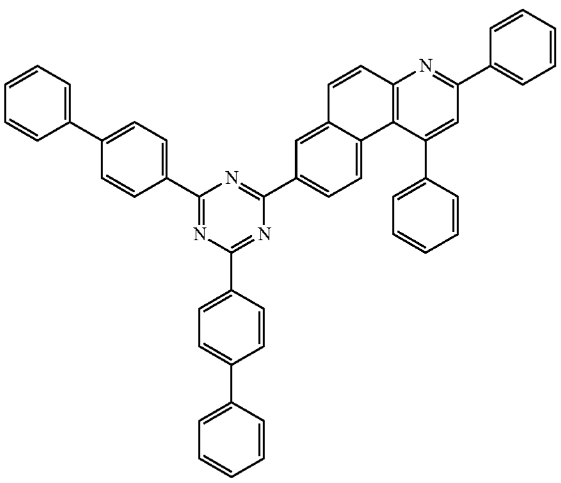
150
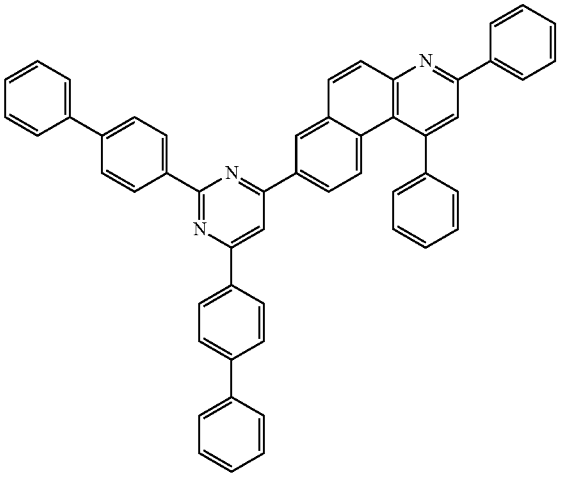
151
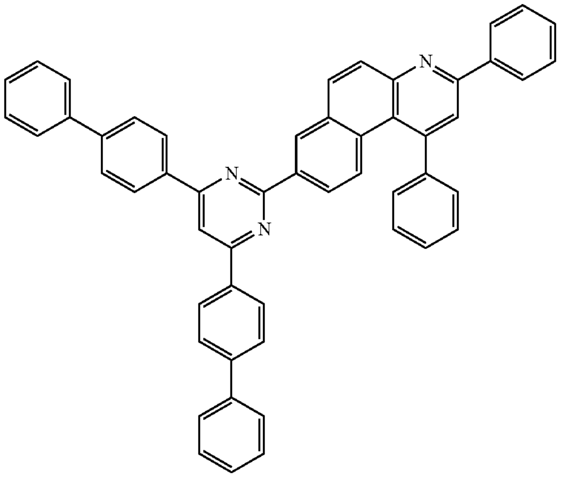
-continued
152
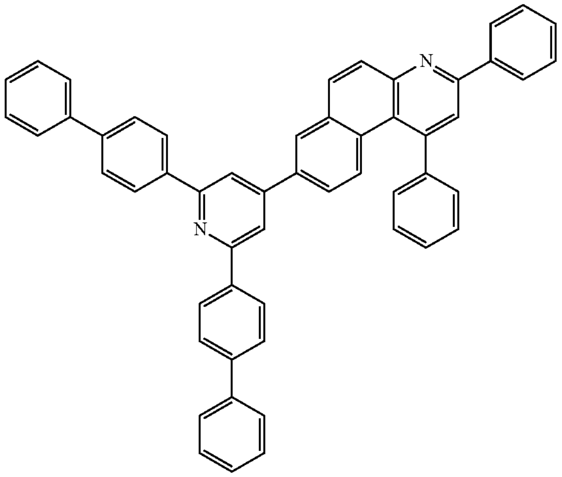
153
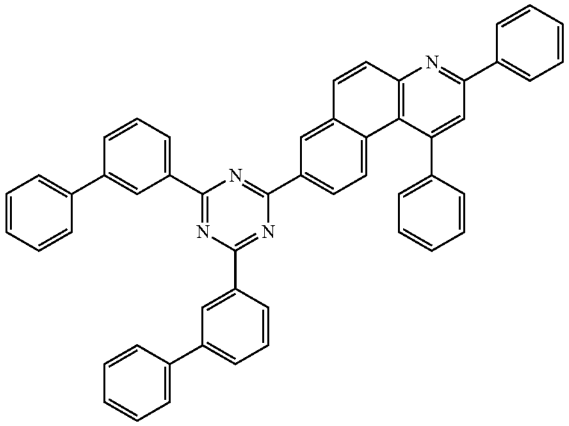
154
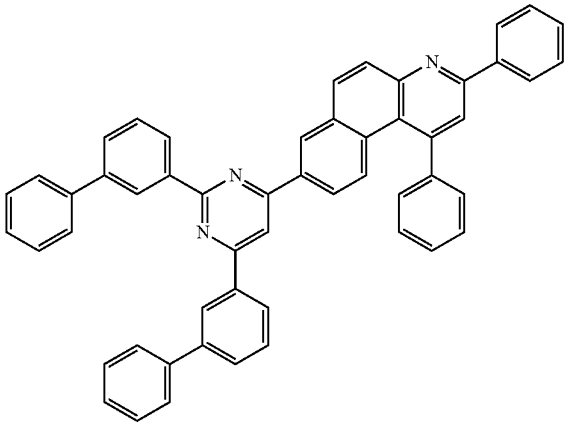

-continued
155
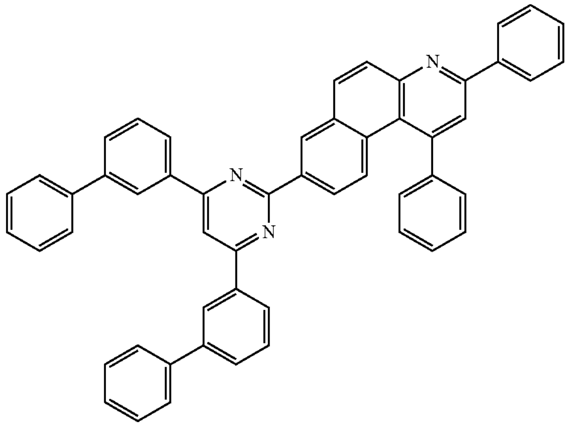
156
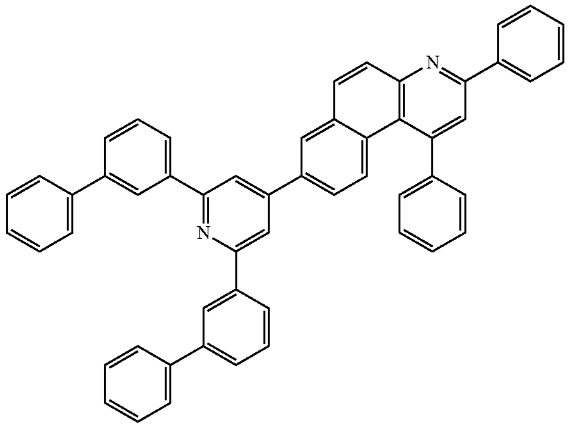
157
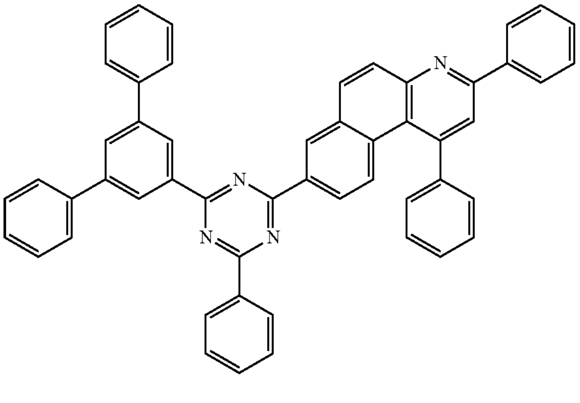
-continued
158
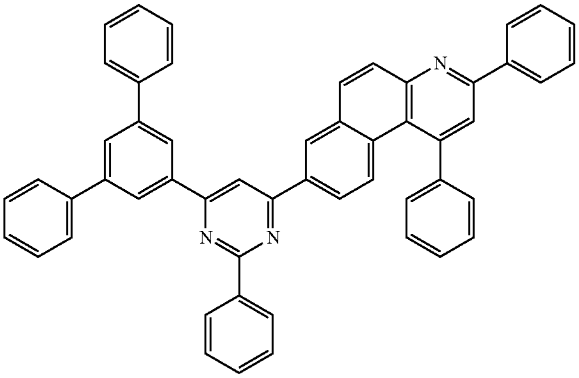
159
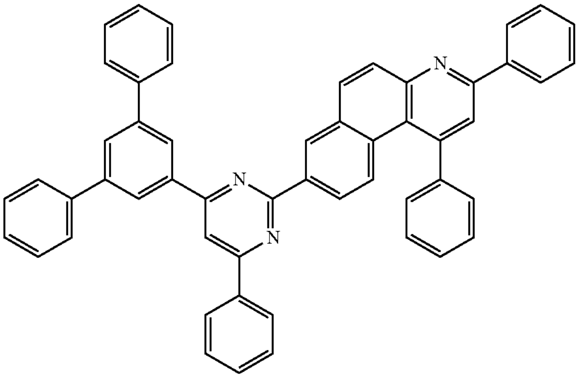
160
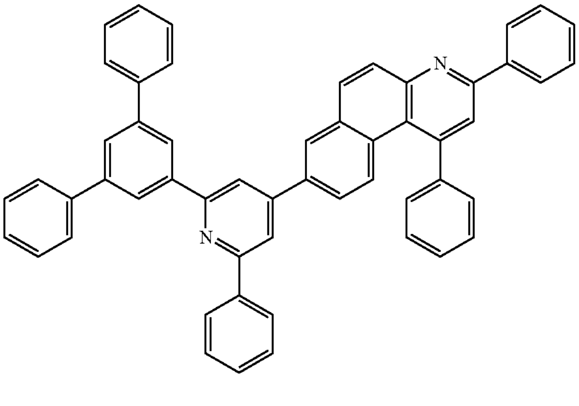

-continued
161
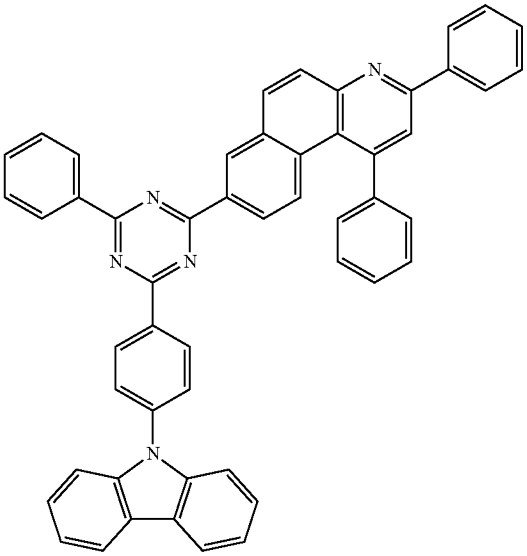
162
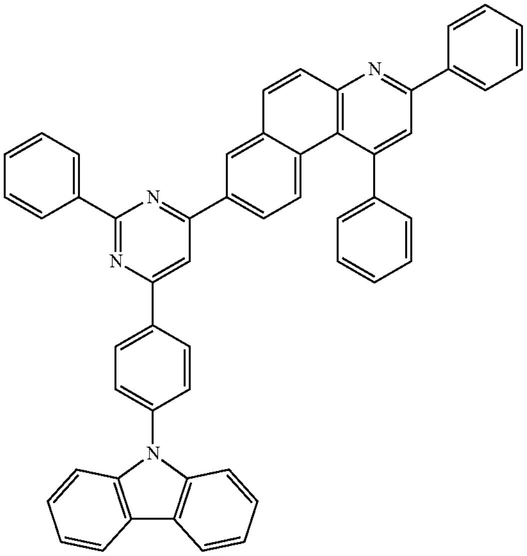
-continued
163
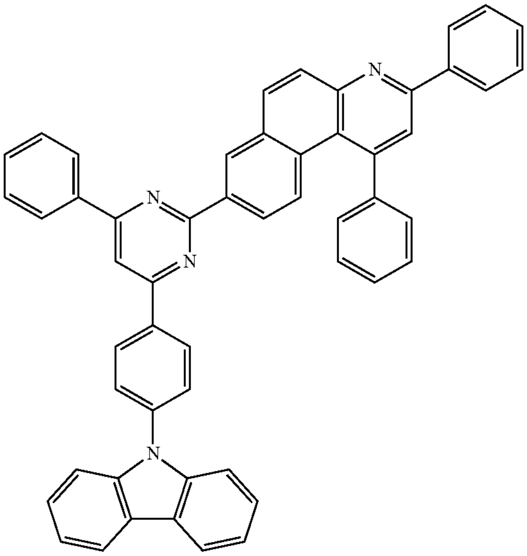
164
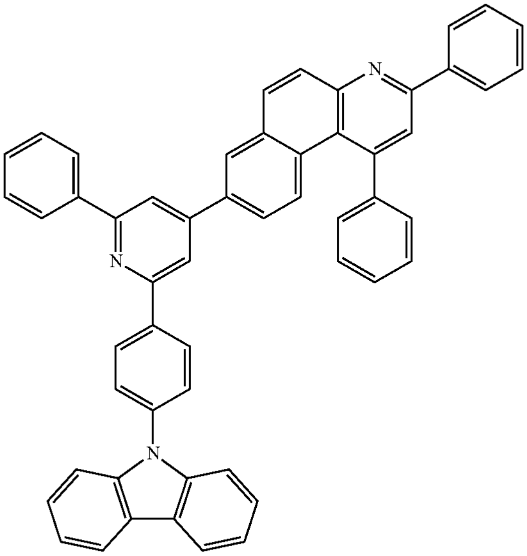

-continued
165
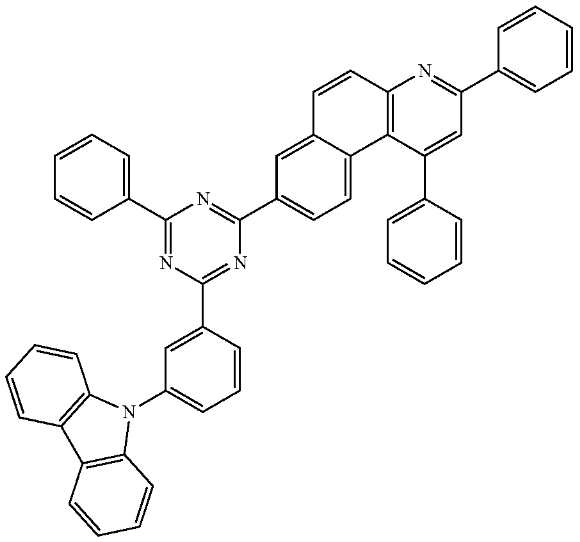
166
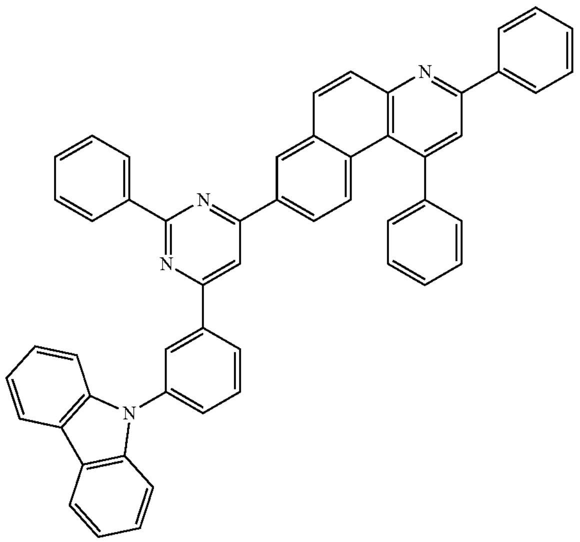
-continued
167
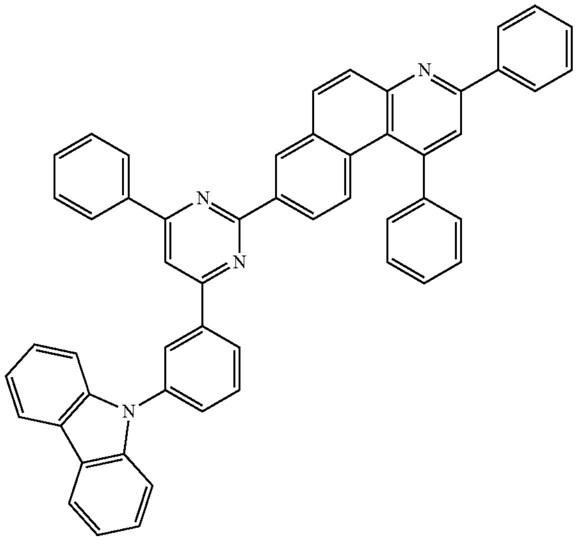
168
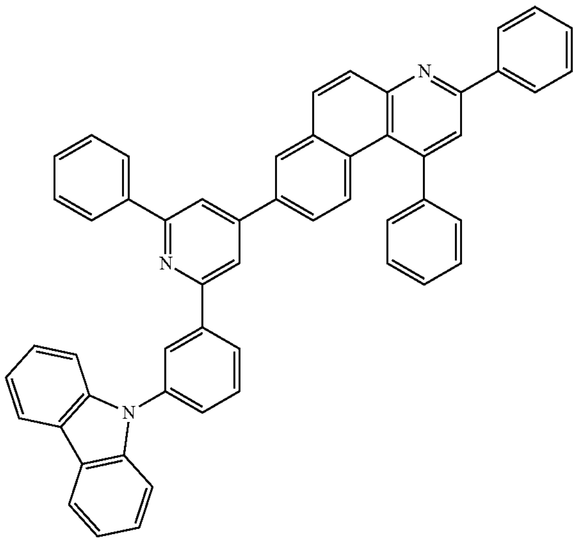

-continued
169
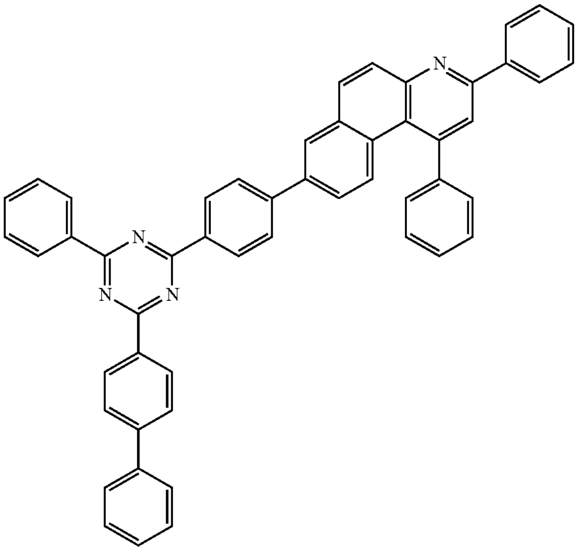
170
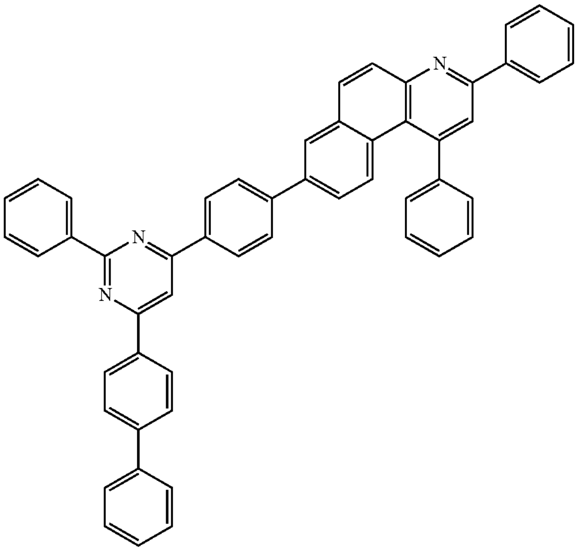
-continued
171
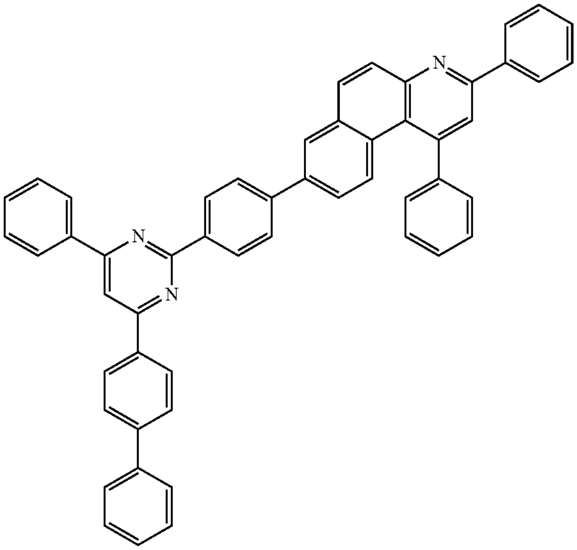
172
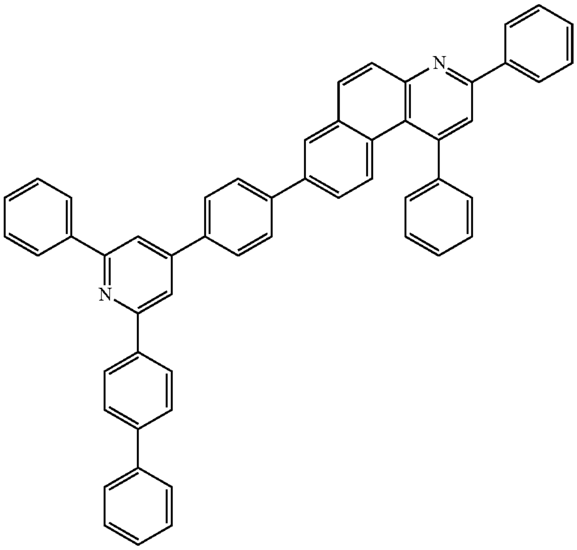
173
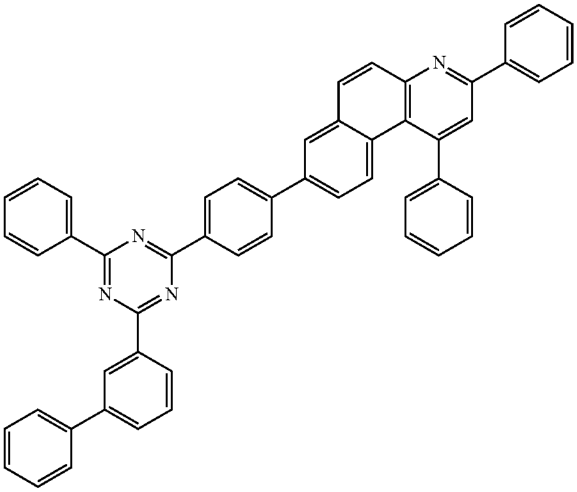

-continued
174
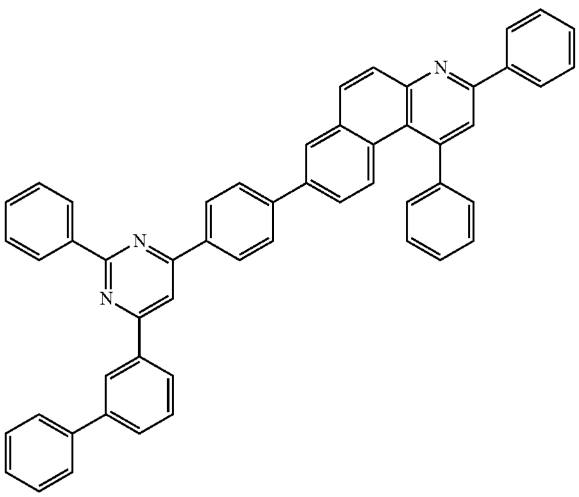
175
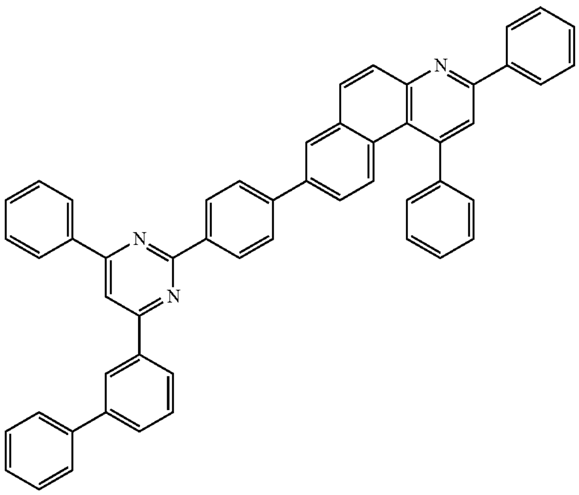
176
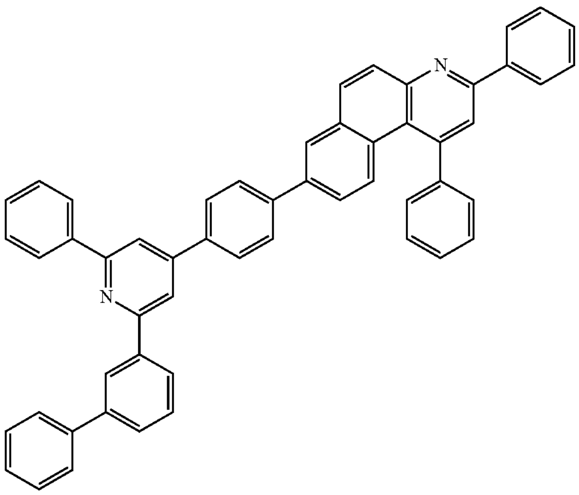
-continued
177
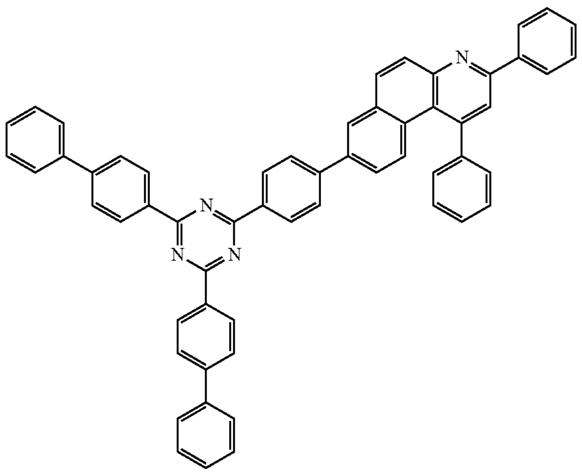
178
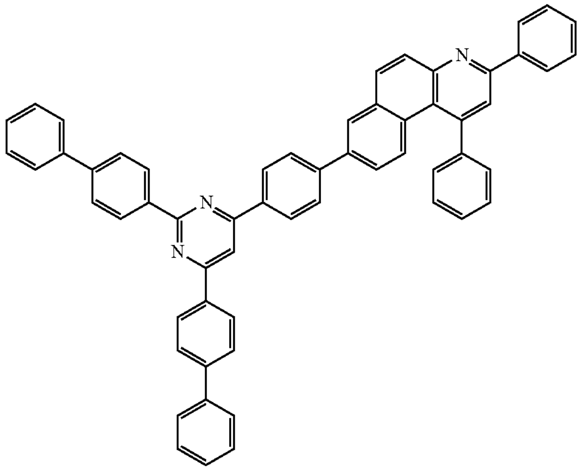
179
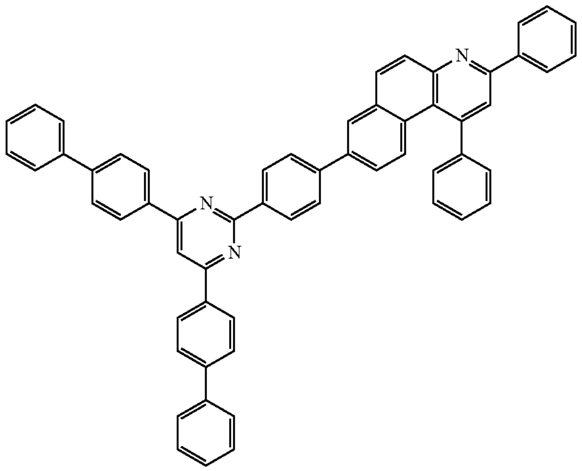

-continued
180
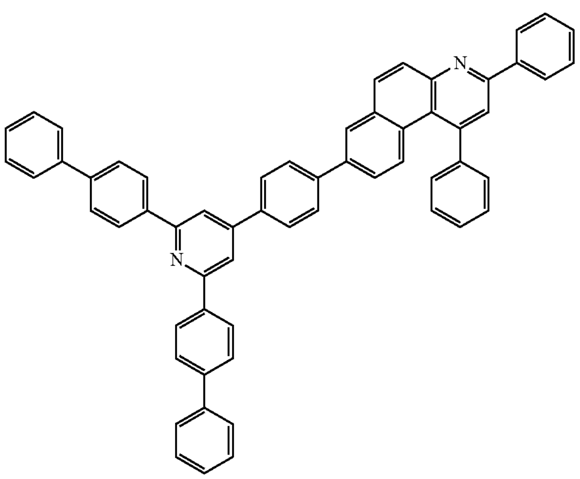
181
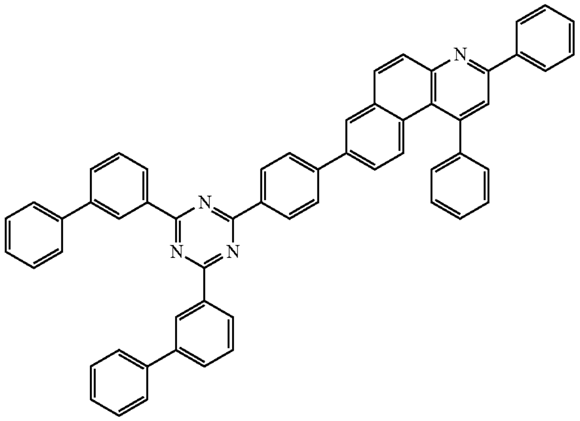
182
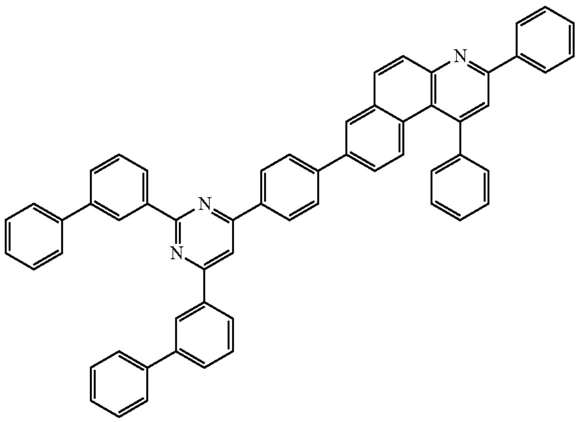
-continued
183
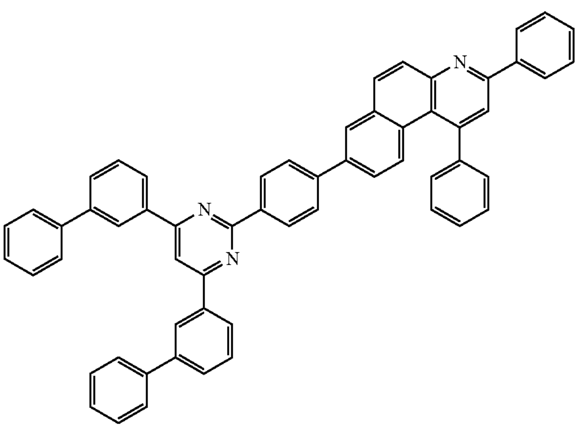
184
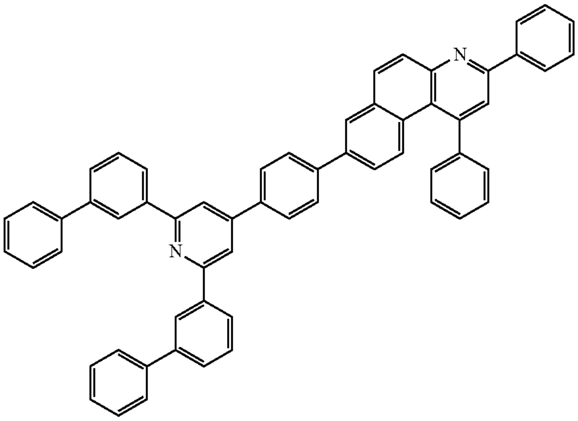
185
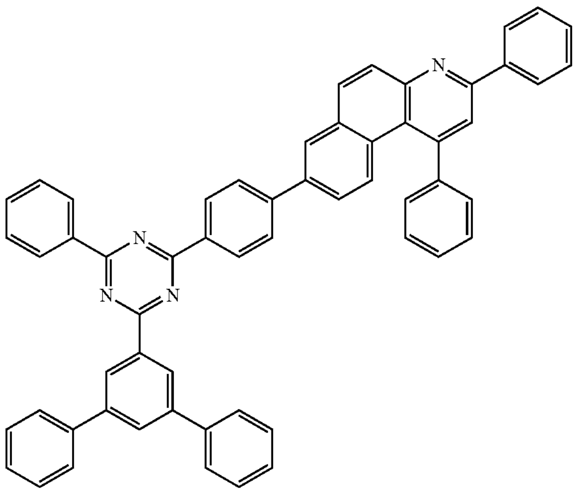

-continued
186
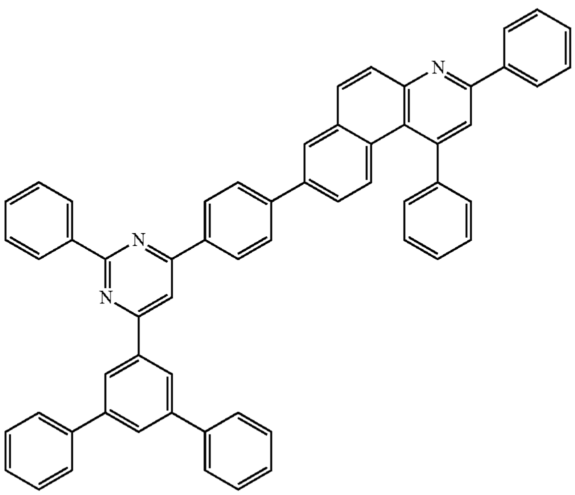
187
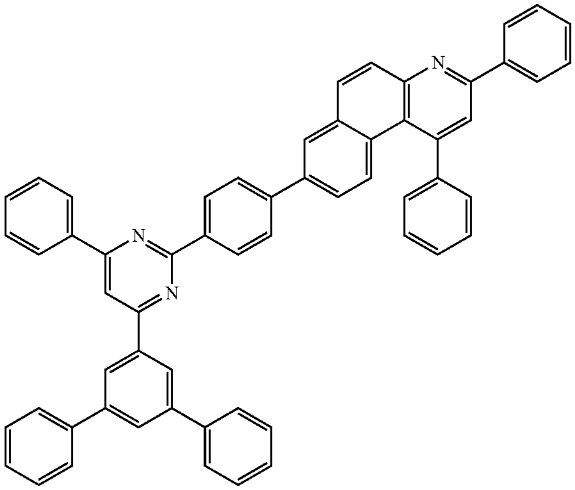
188
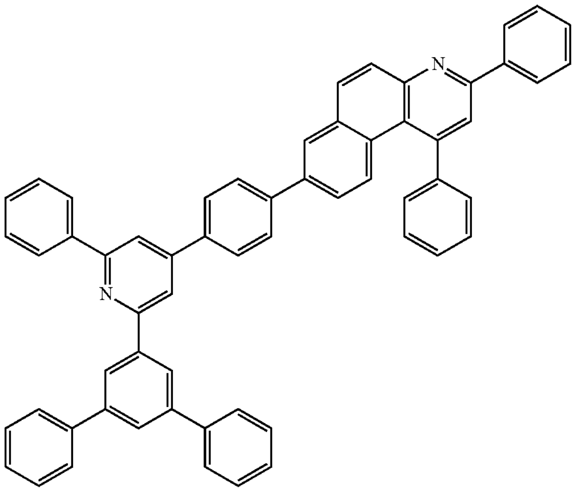
-continued
189
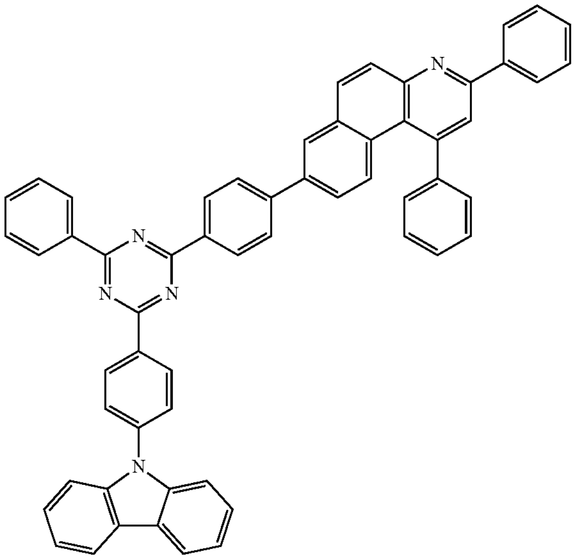
190
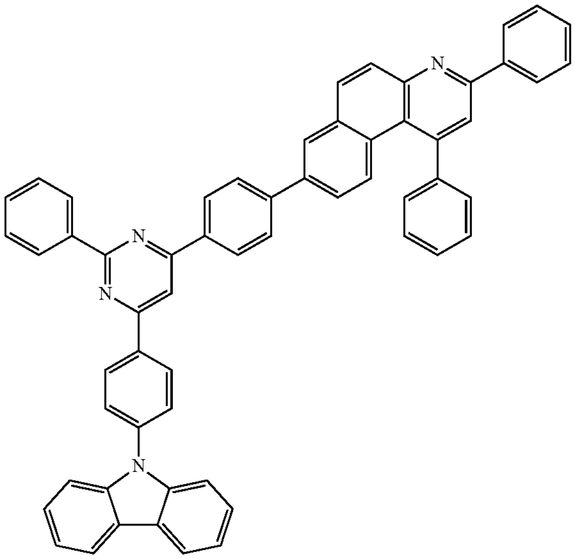

-continued
191
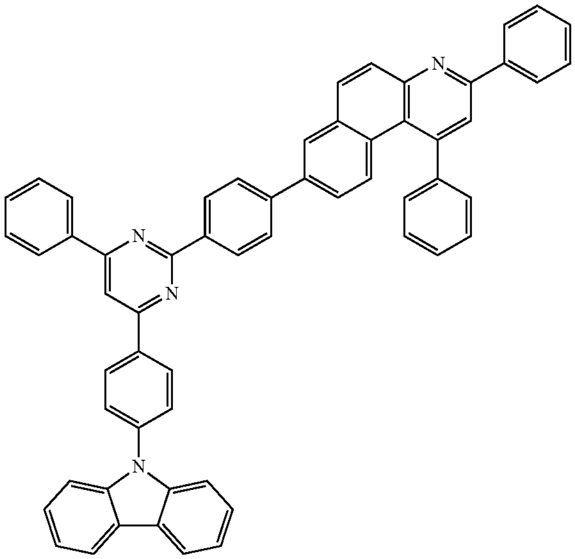
192
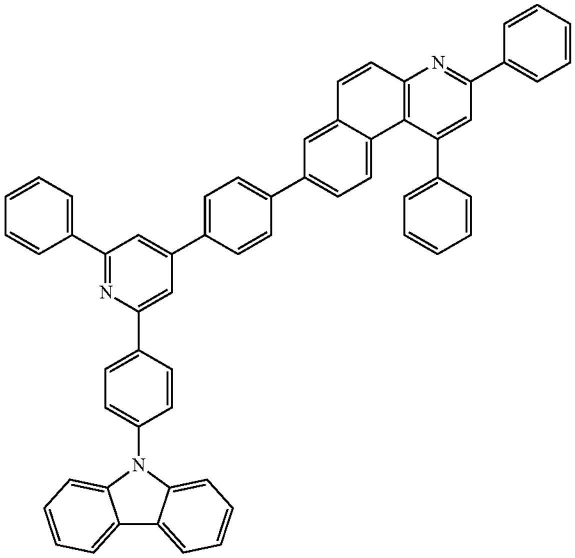
-continued
193
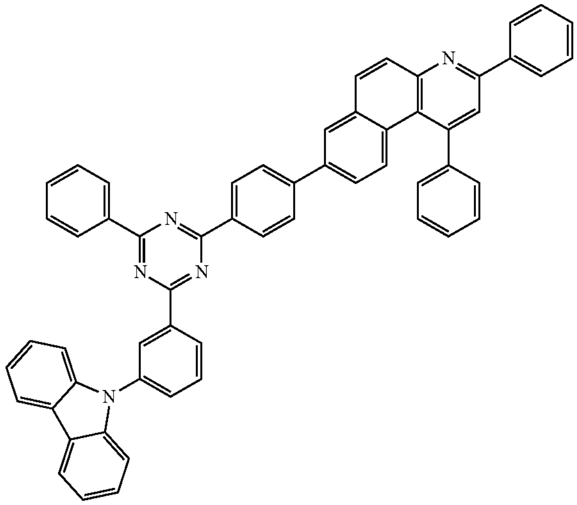
194
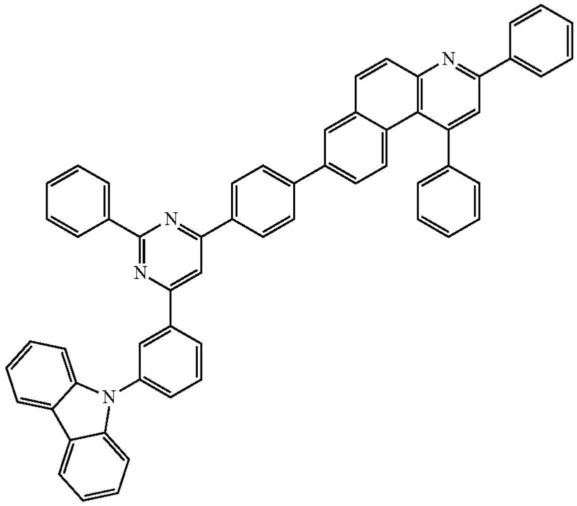
195
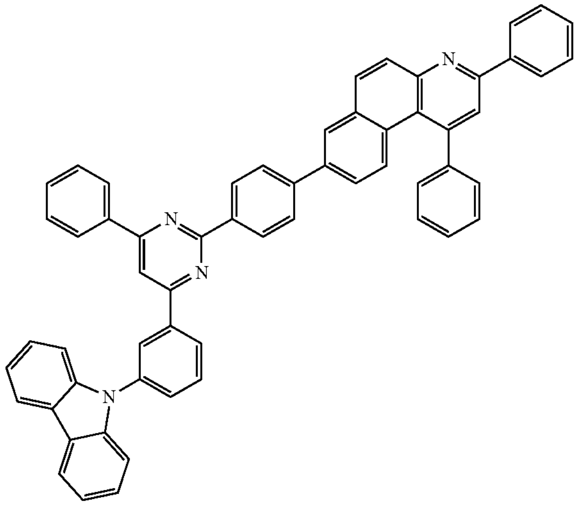

196
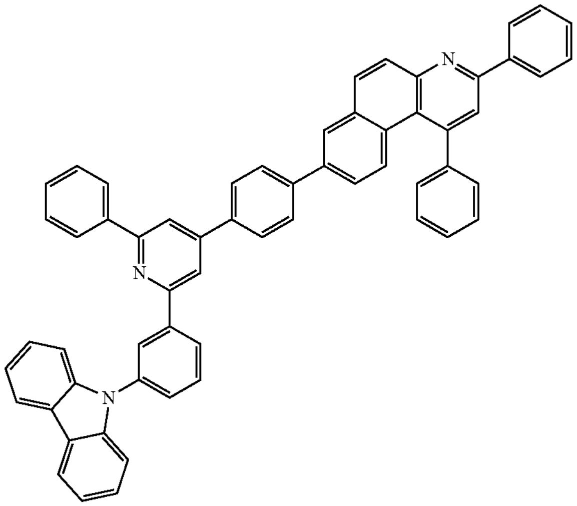
197
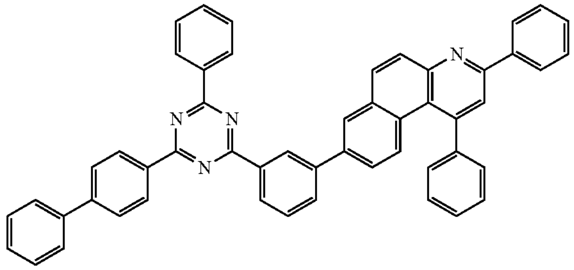
198
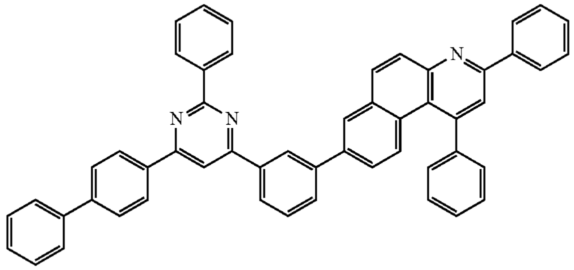
199
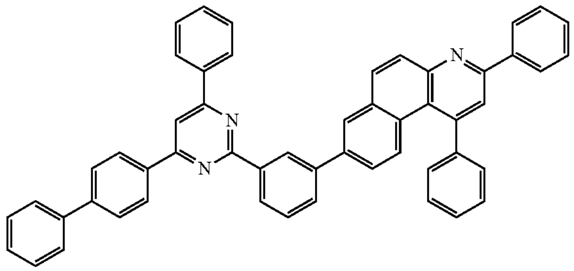
200
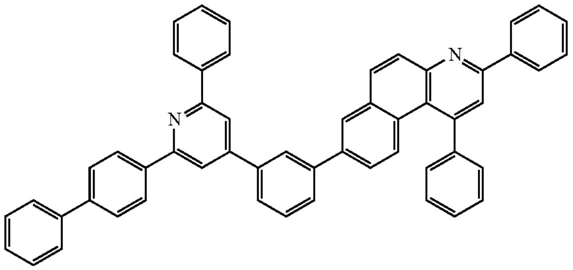
201
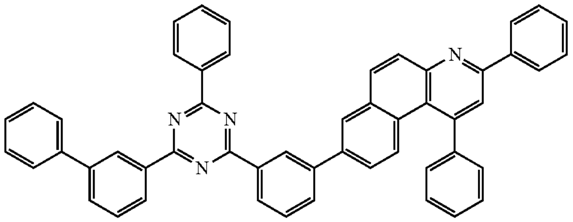
202
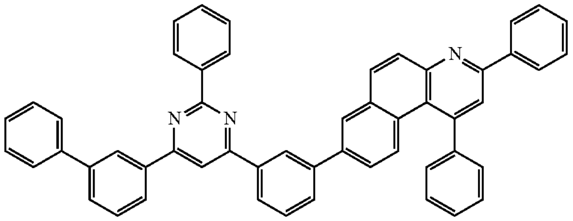
203
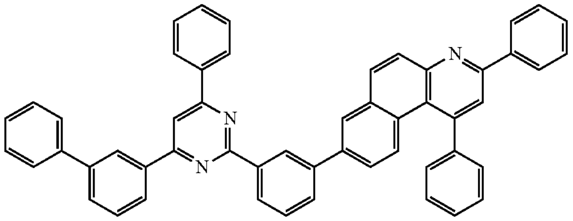
204
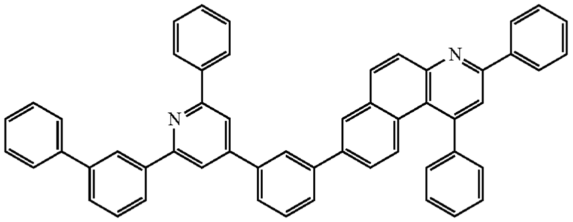

-continued
205
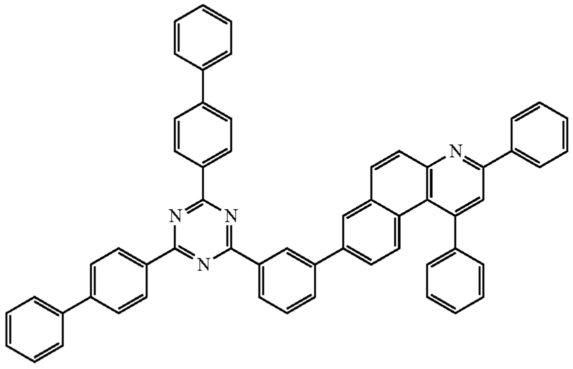
206
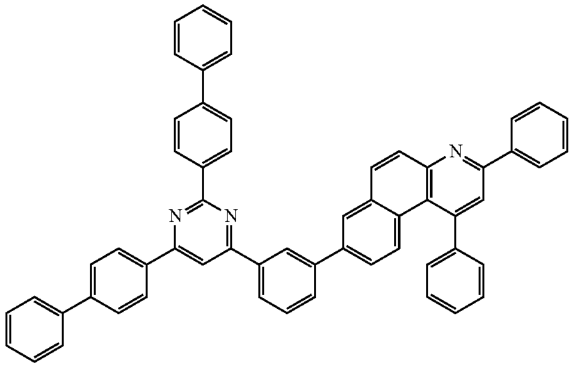
207
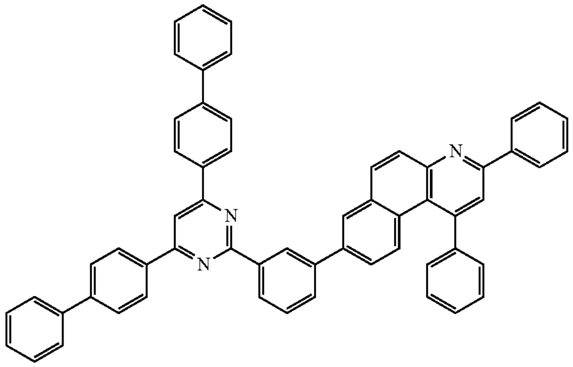
208
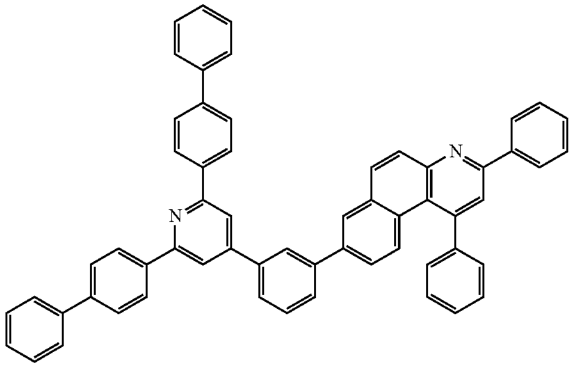
-continued
209
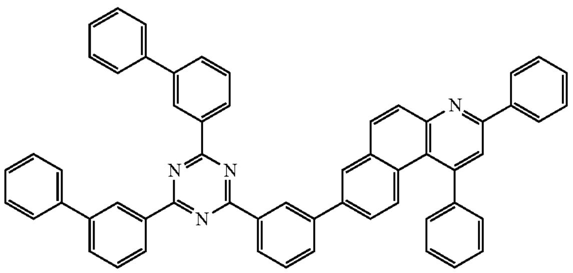
210
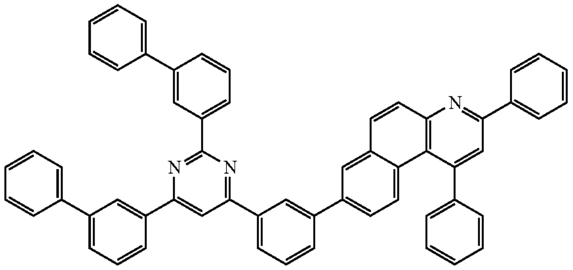
211
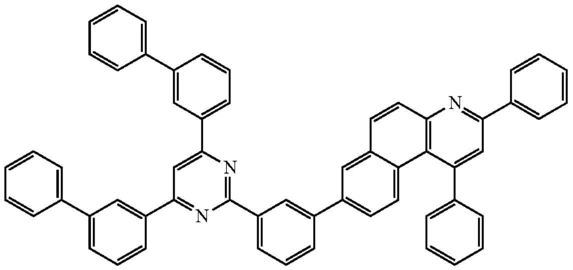
212
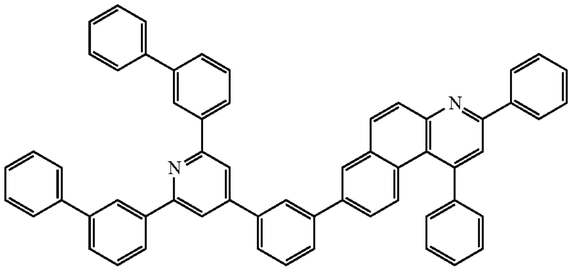
213
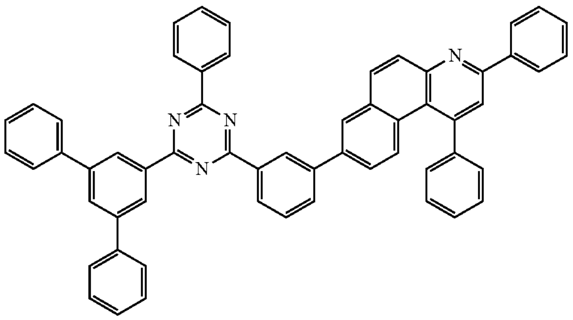

-continued
214
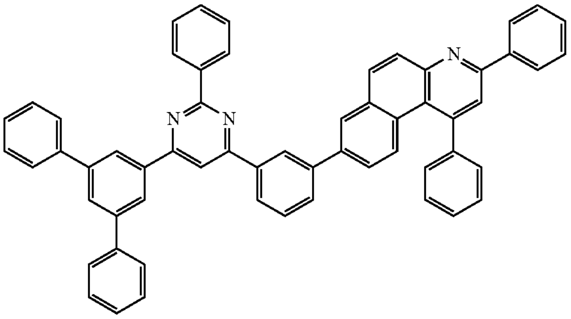
215
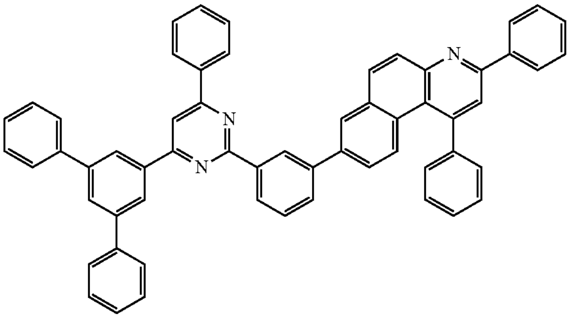
216
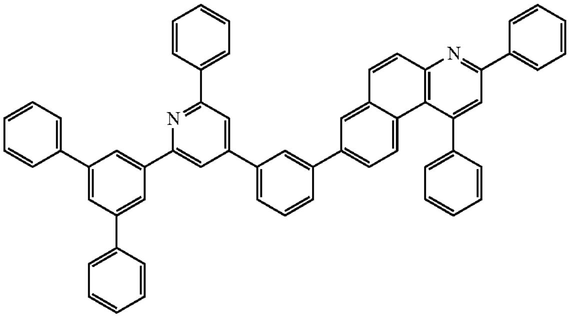
217
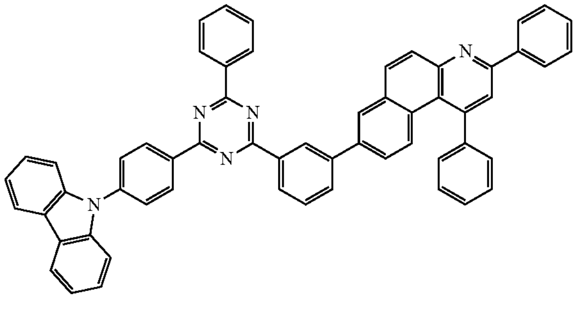
-continued
218
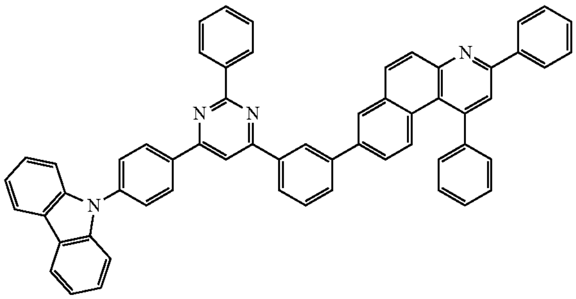
219
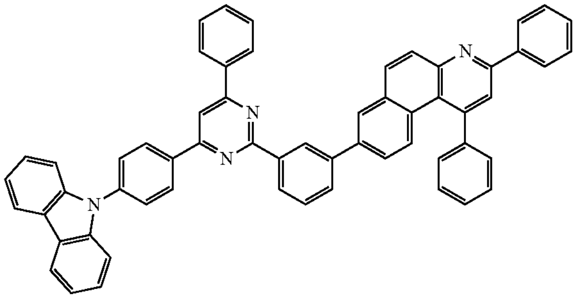
220
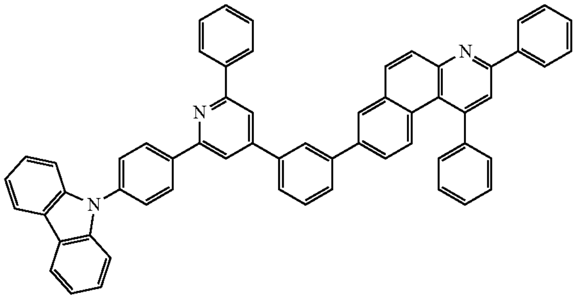
221
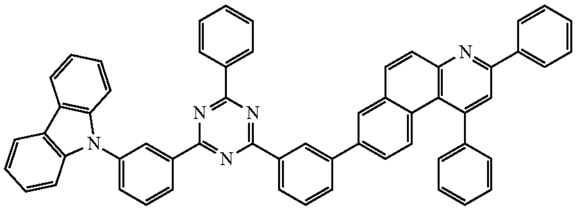
222
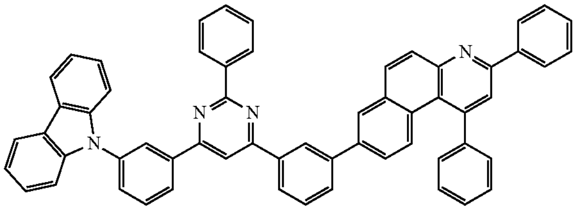

-continued
223
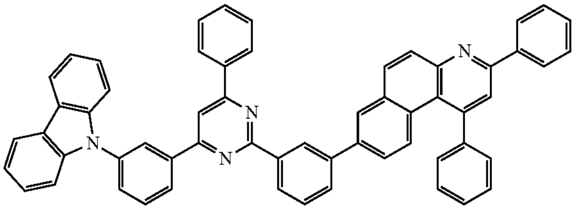
224
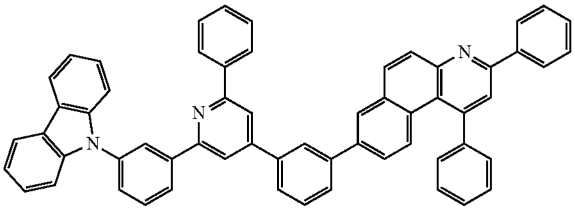
225
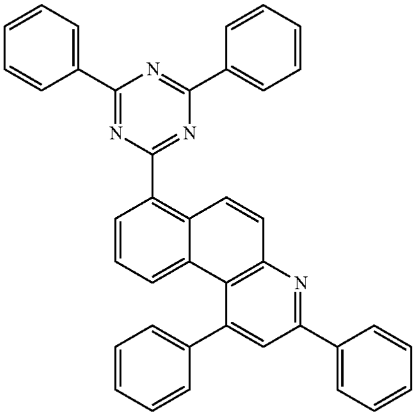
226
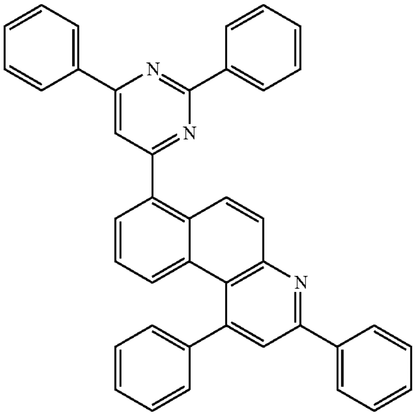
-continued
227
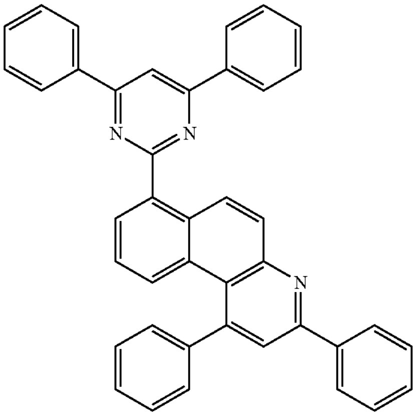
228
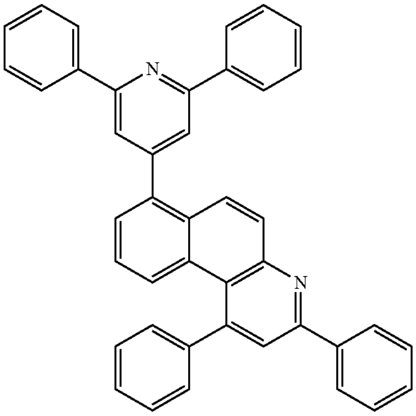
229
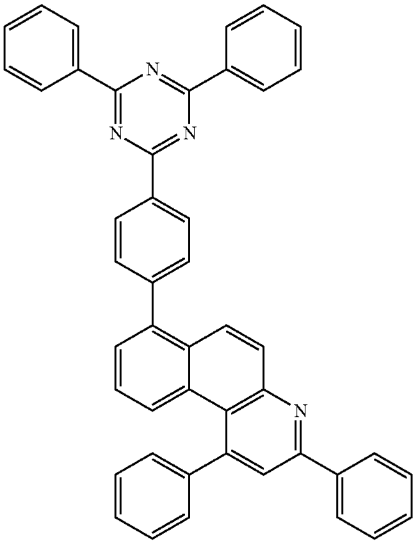

230
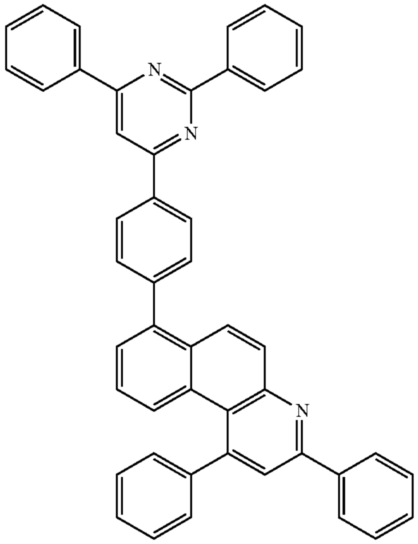
231
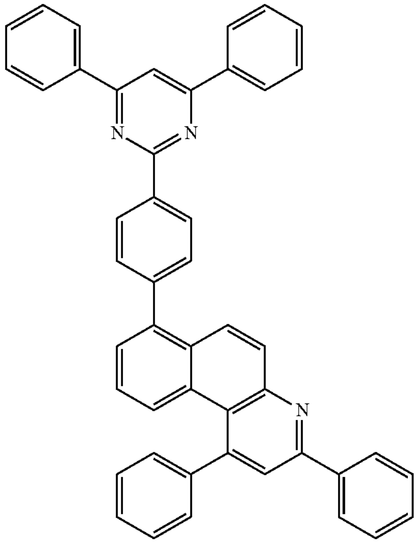
232
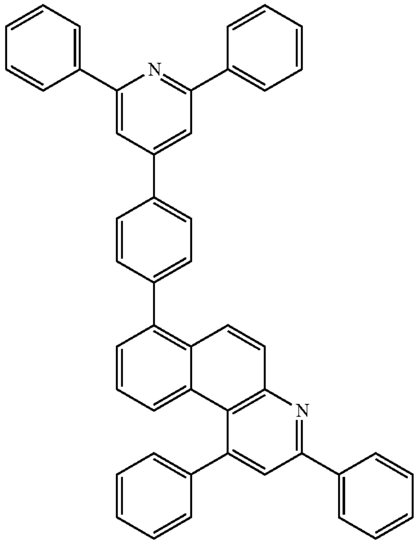
233
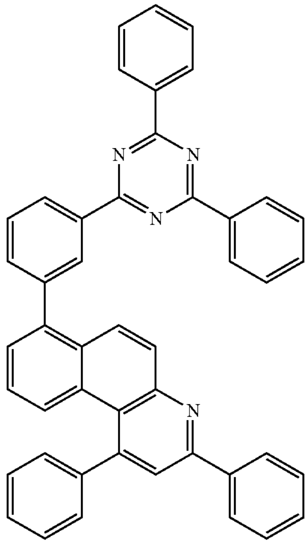
234
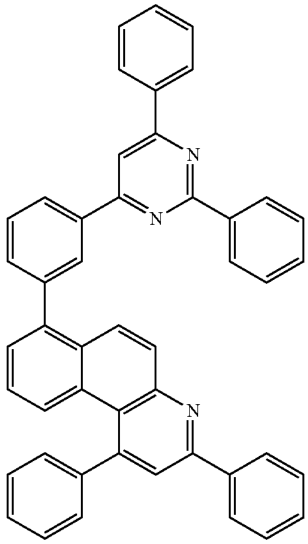
235
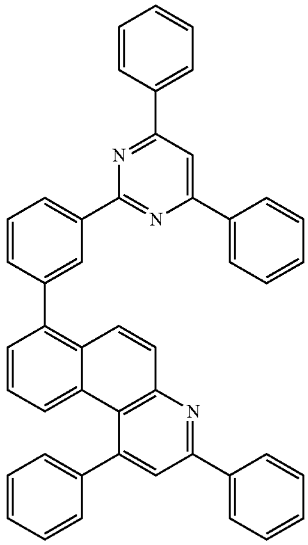

-continued
236
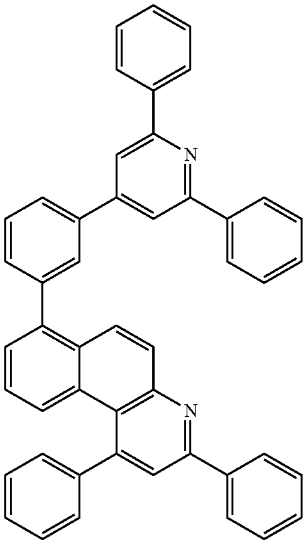
237
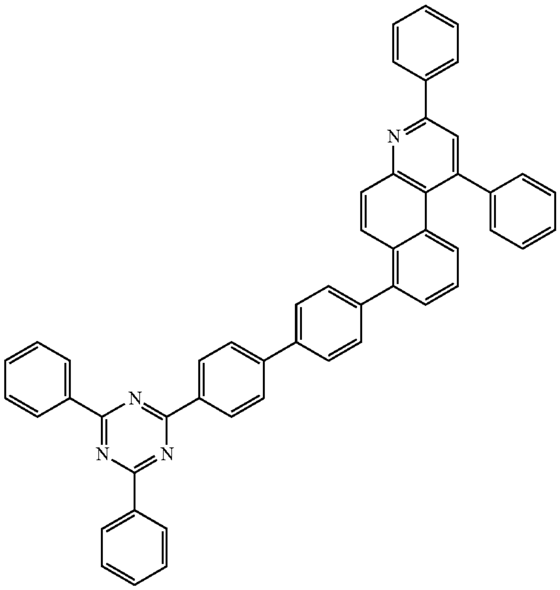
-continued
238
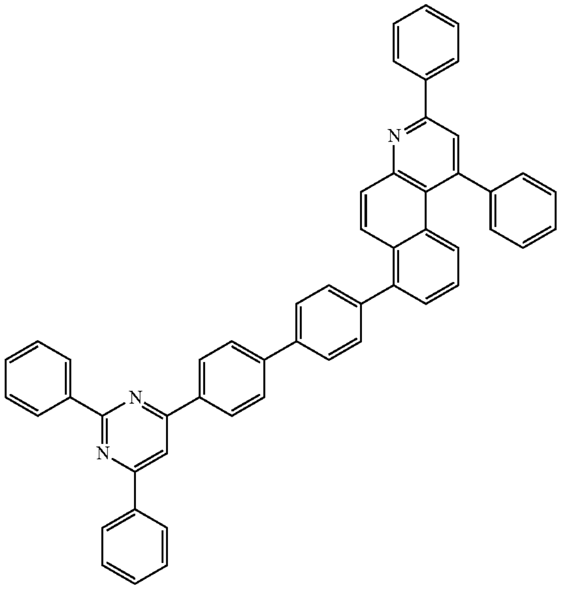
239
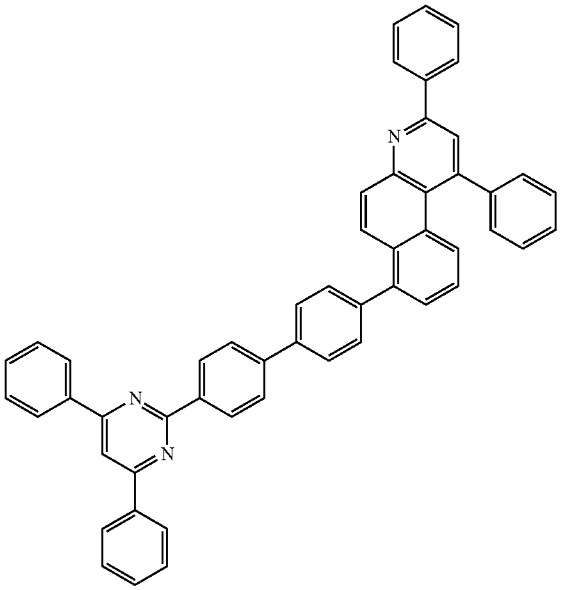

-continued
240
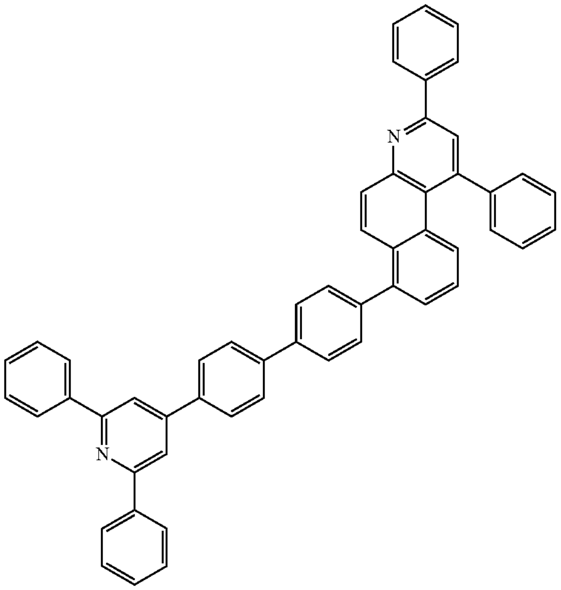
241
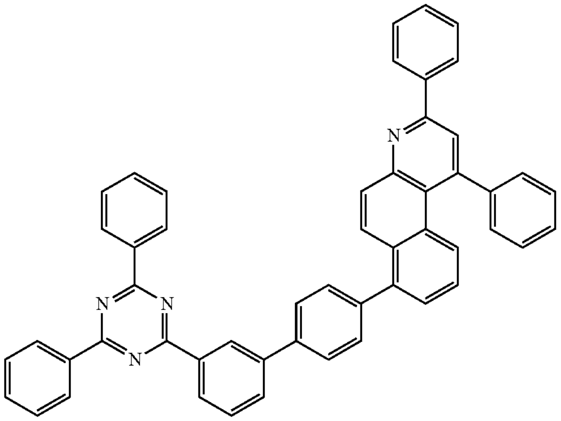
242
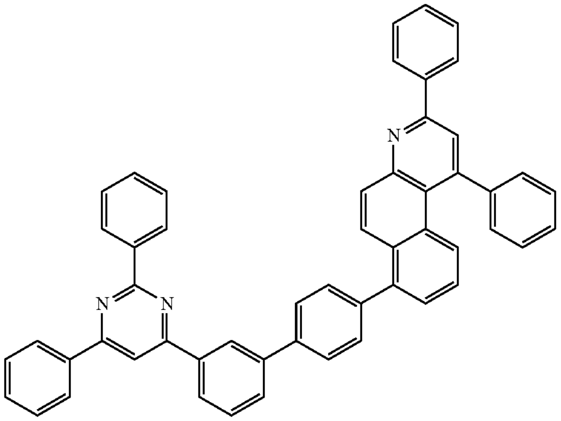
-continued
243
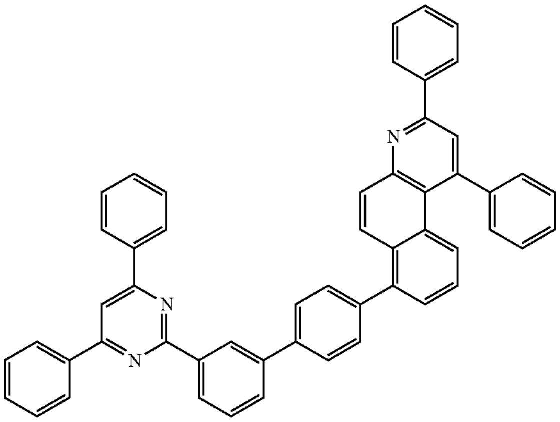
244
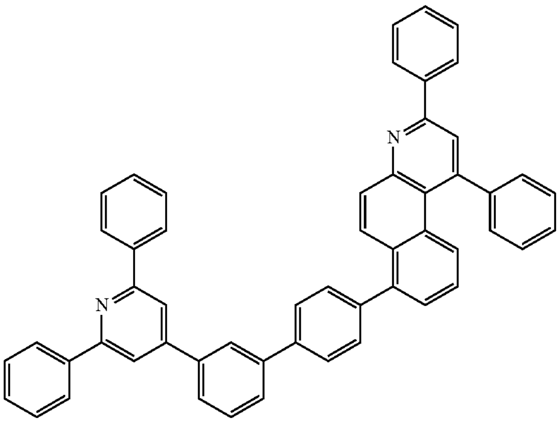
245
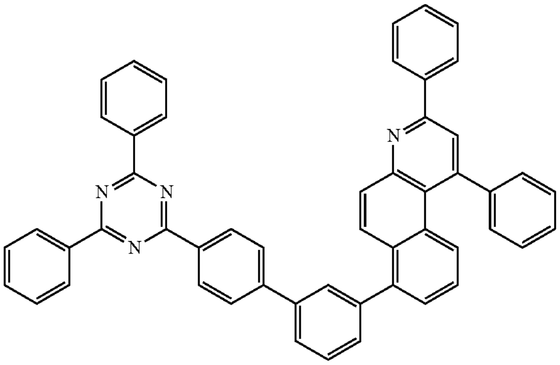

-continued
246
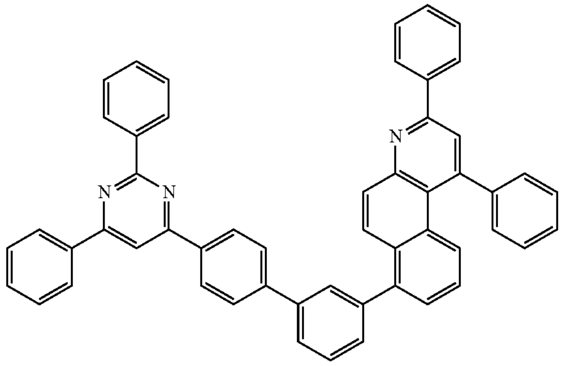
247
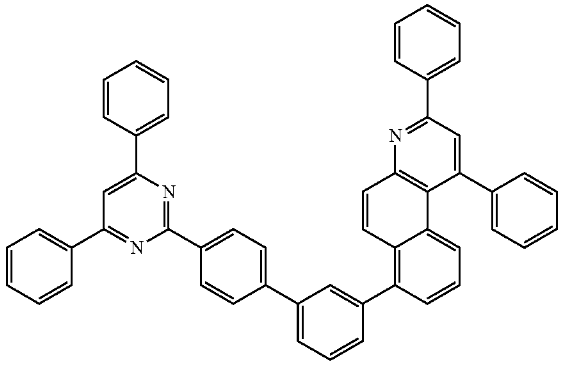
248
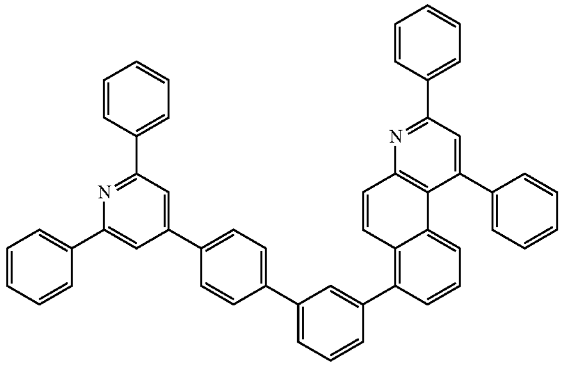
-continued
249
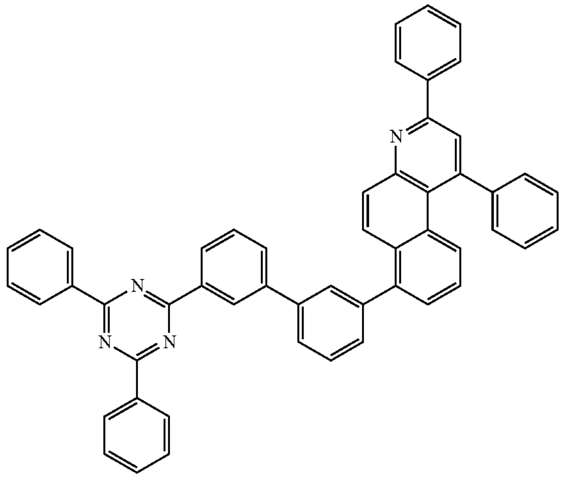
250
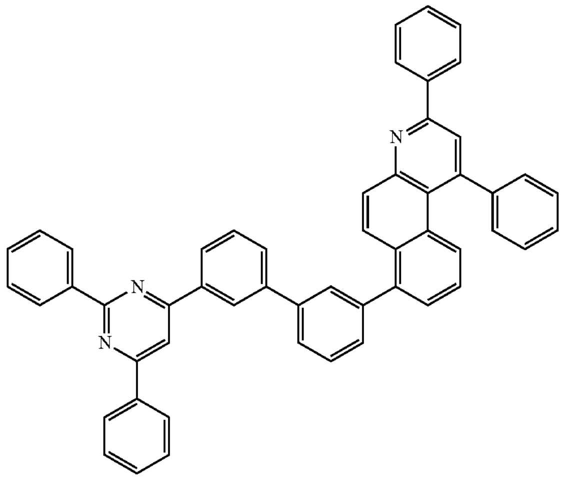
251
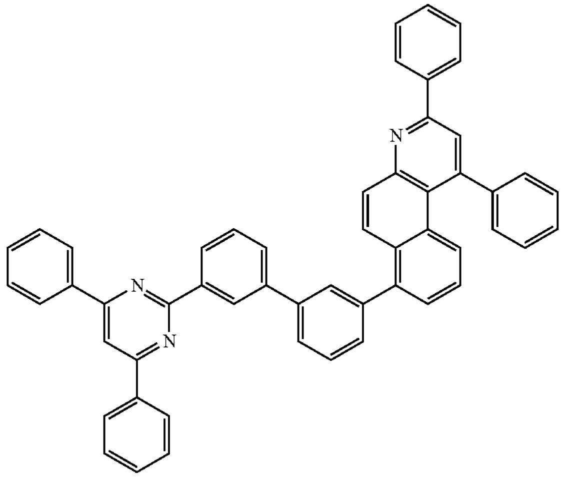

-continued
252
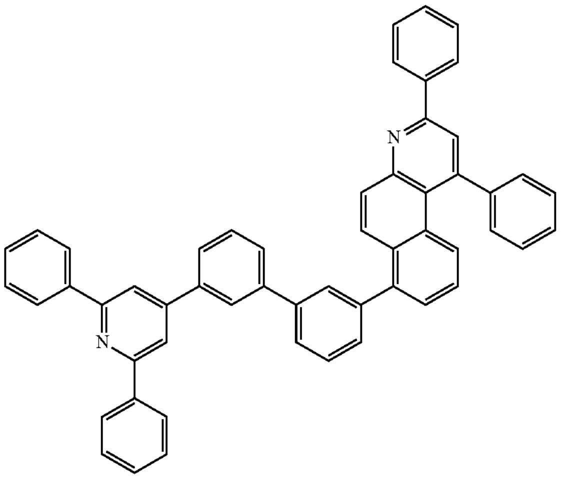
253
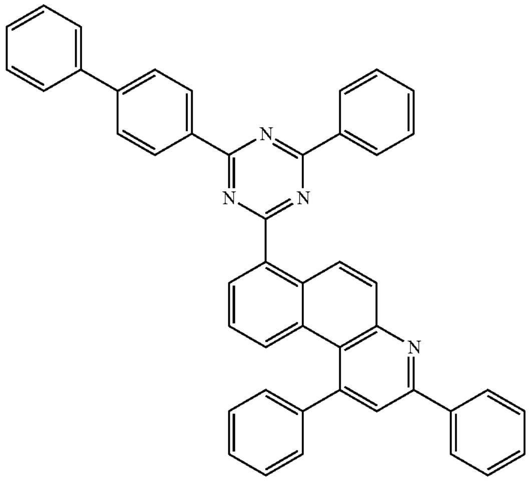
254
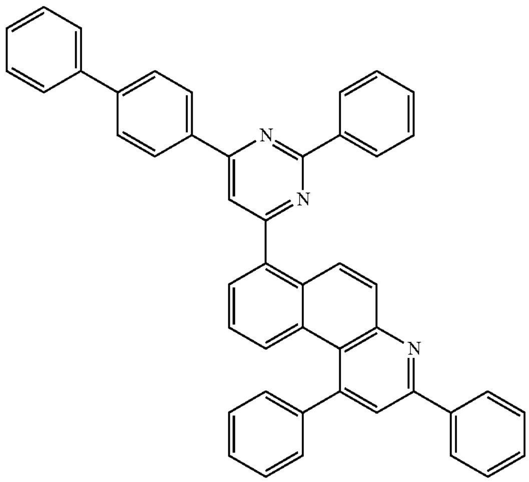
-continued
255
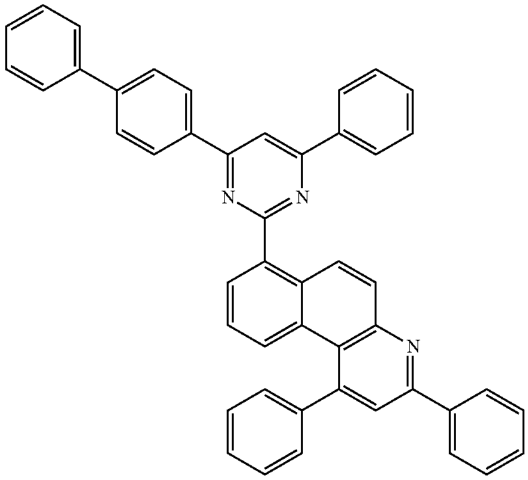
256
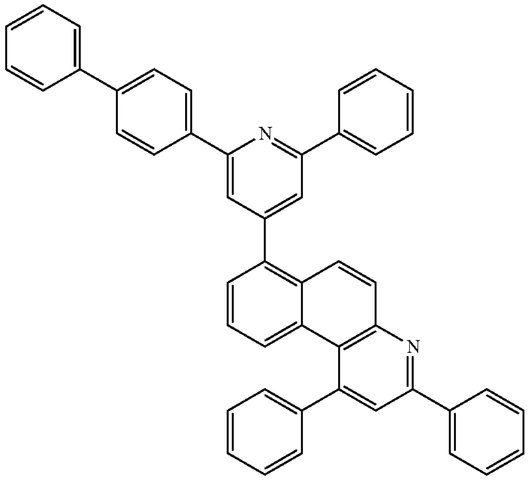
257
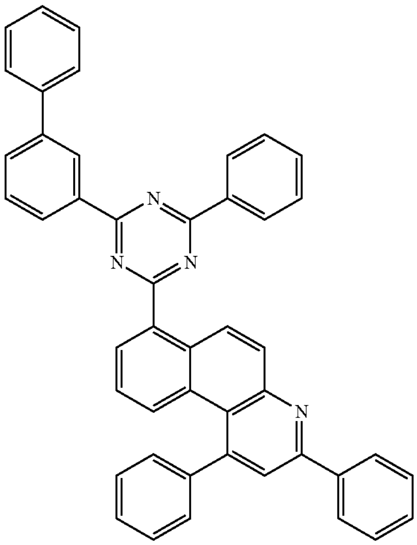

258
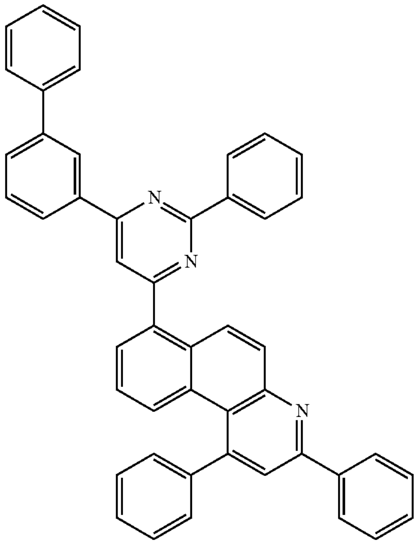
259
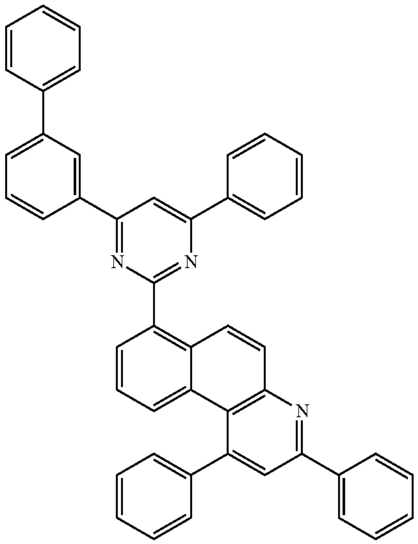
260
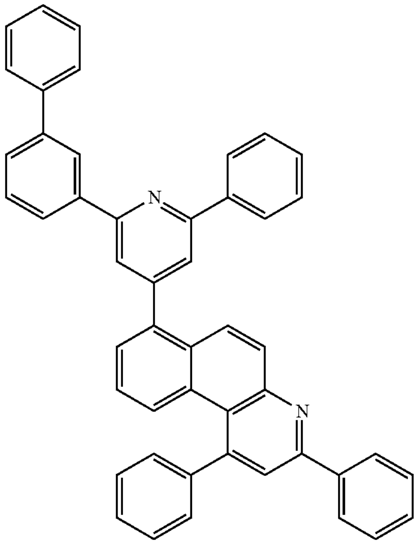
261
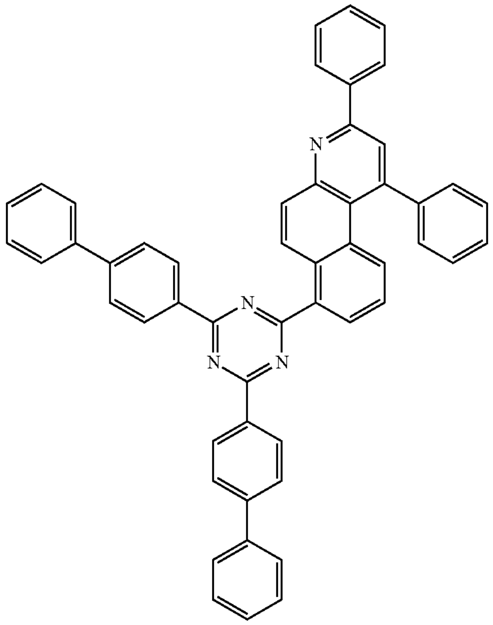
262
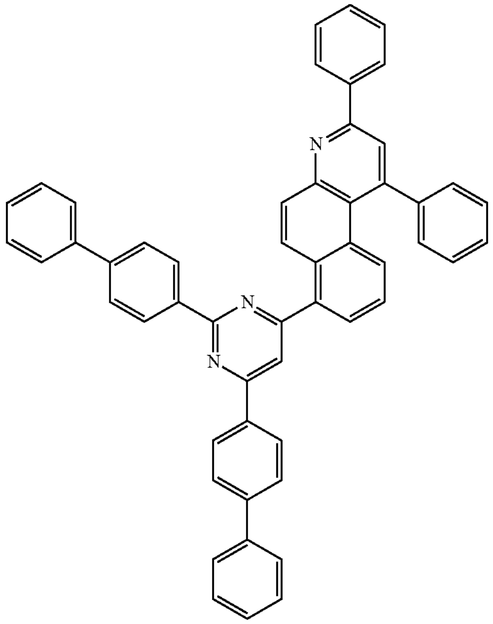

-continued
263
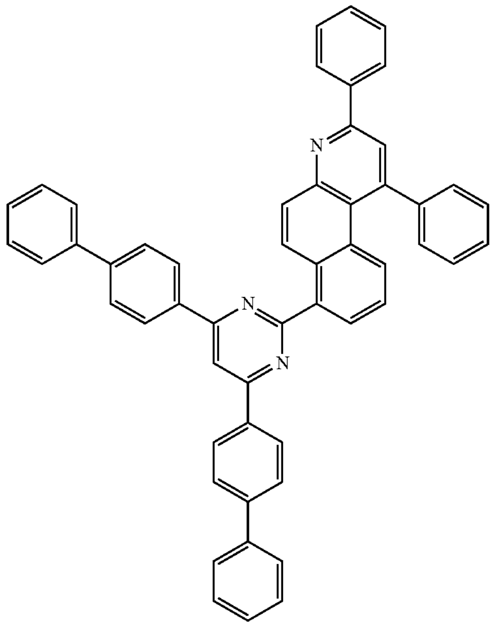
264
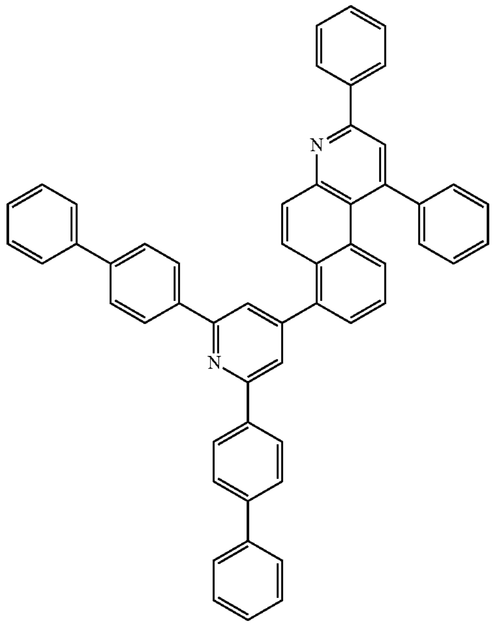
-continued
265
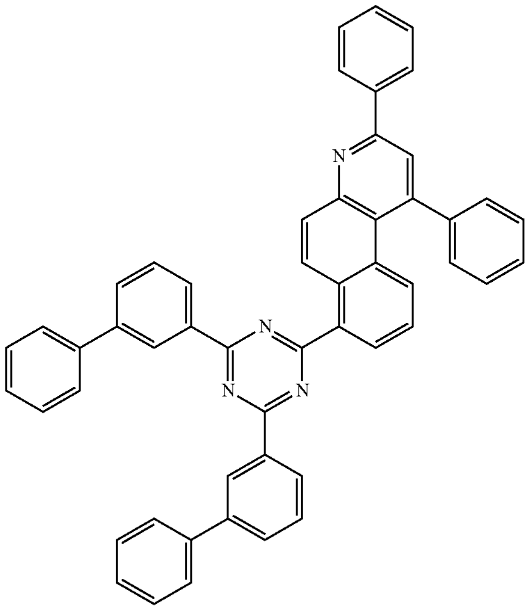
266
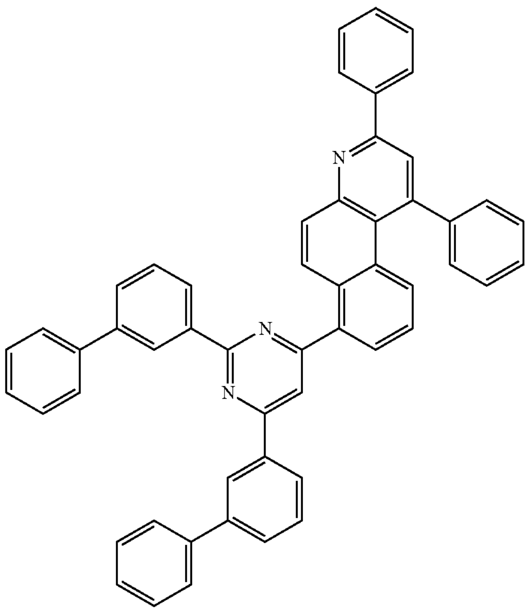

-continued
267
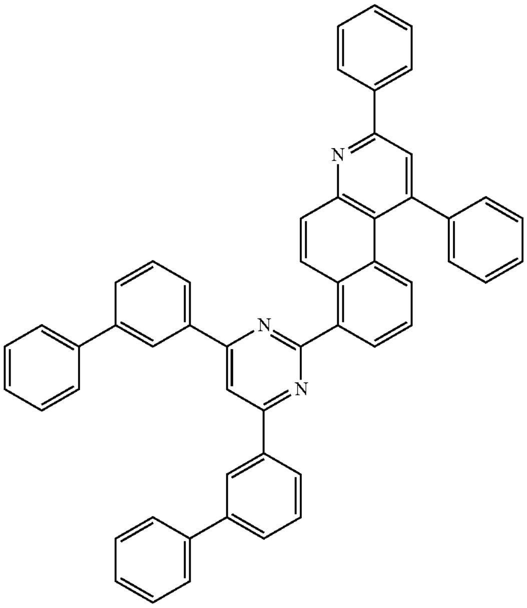
268
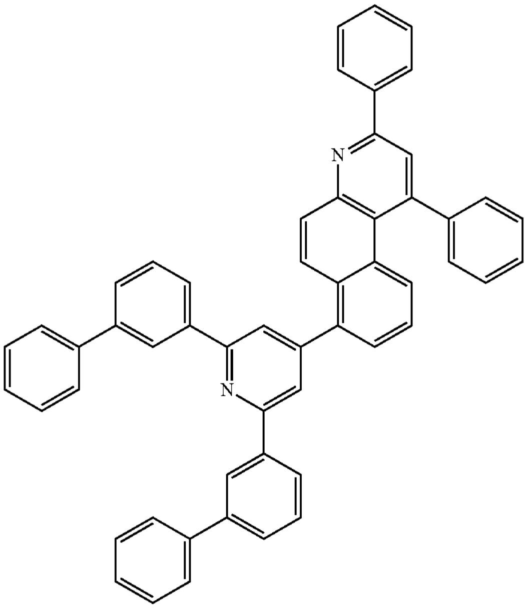
-continued
269
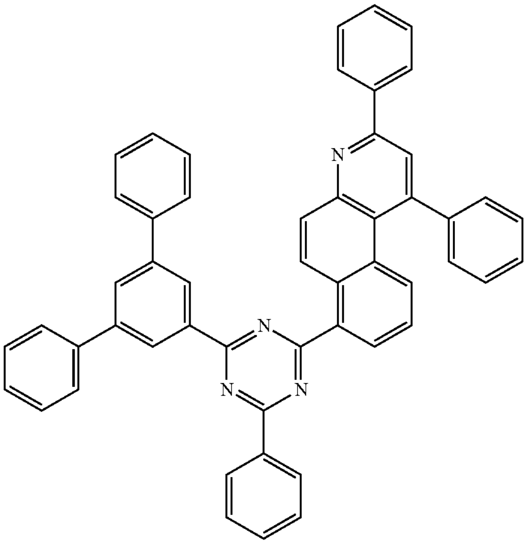
270
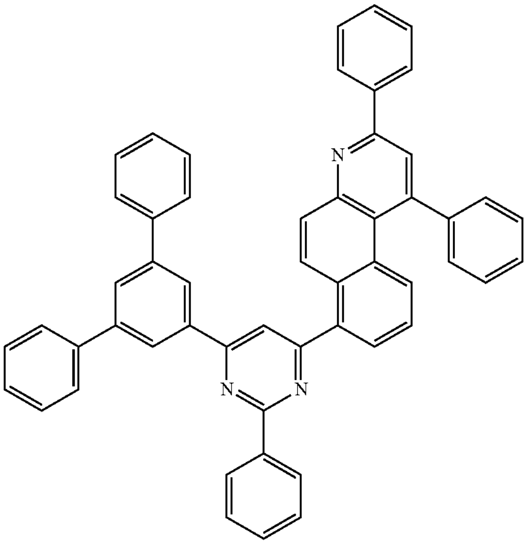

-continued
271
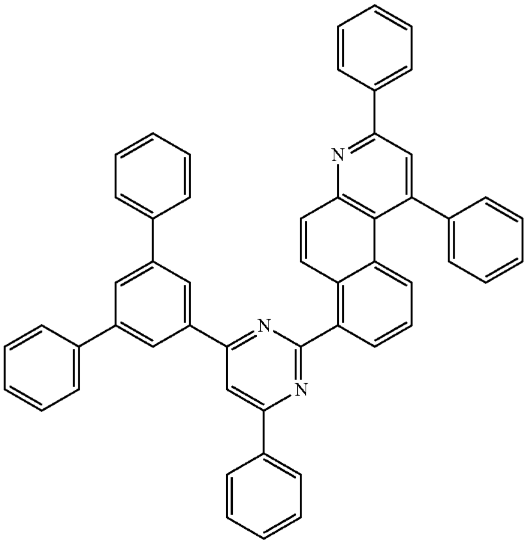
272
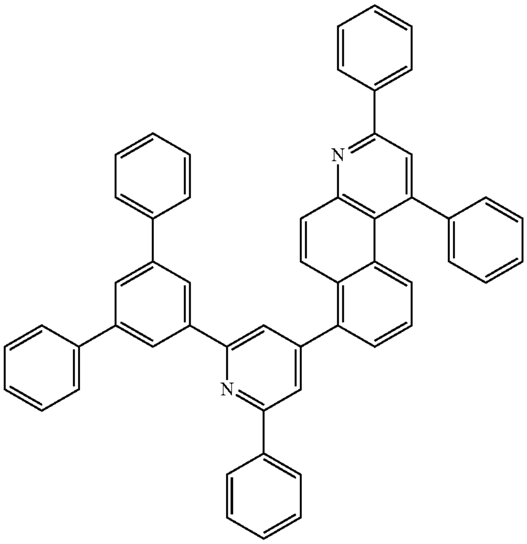
-continued
273
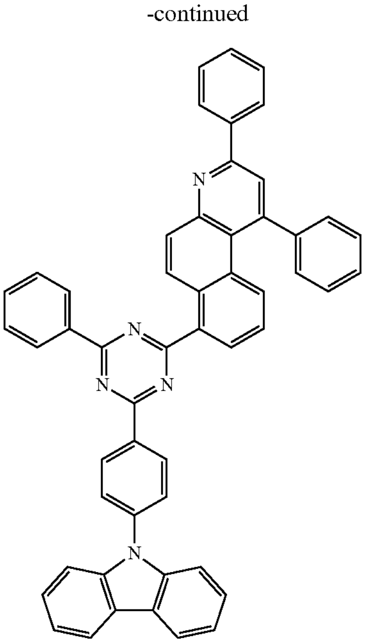
274
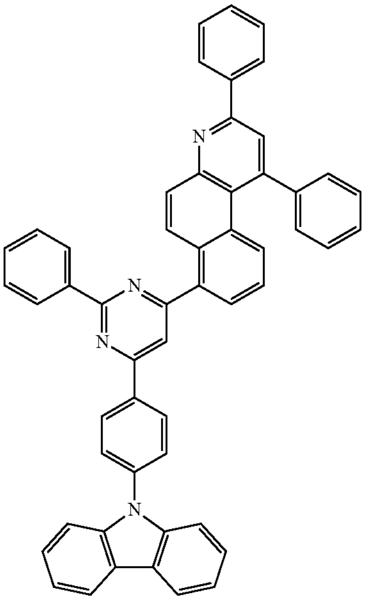

-continued
275
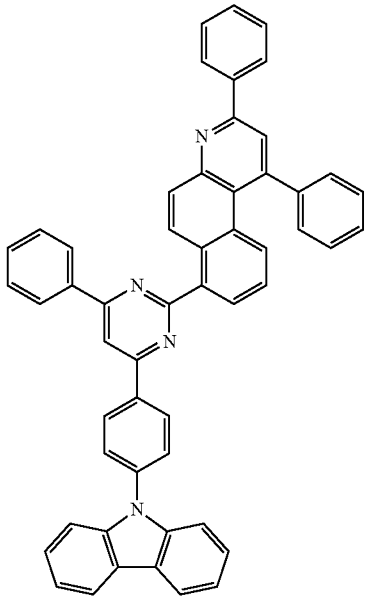
276
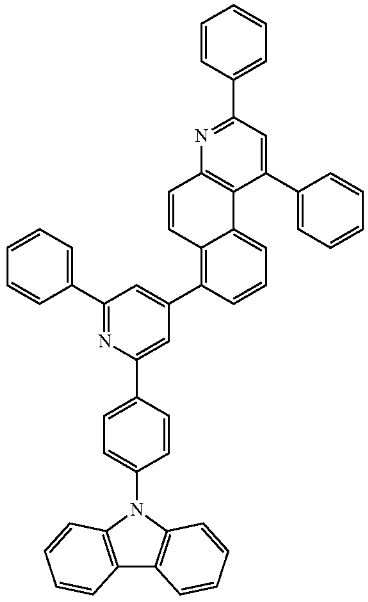
-continued
277
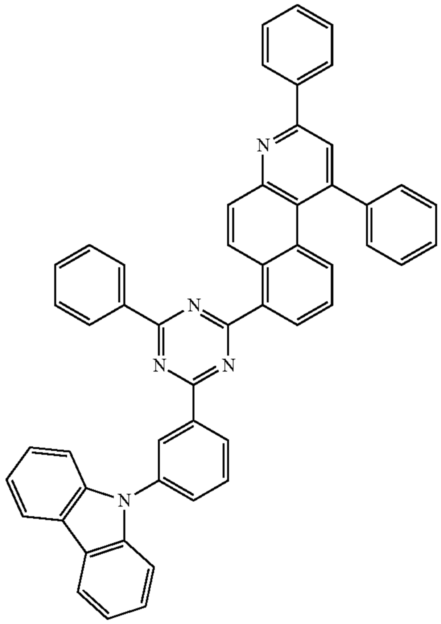
278
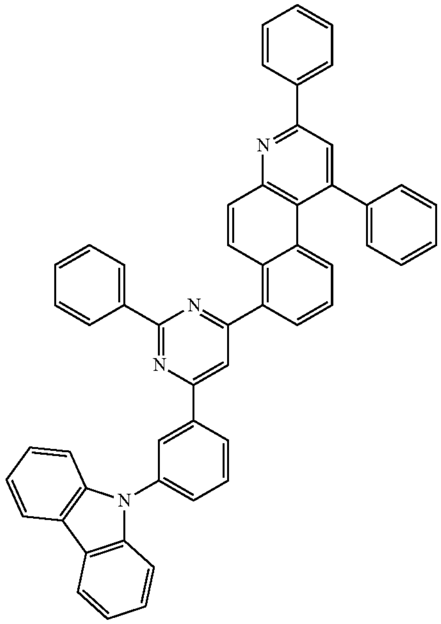

-continued
279
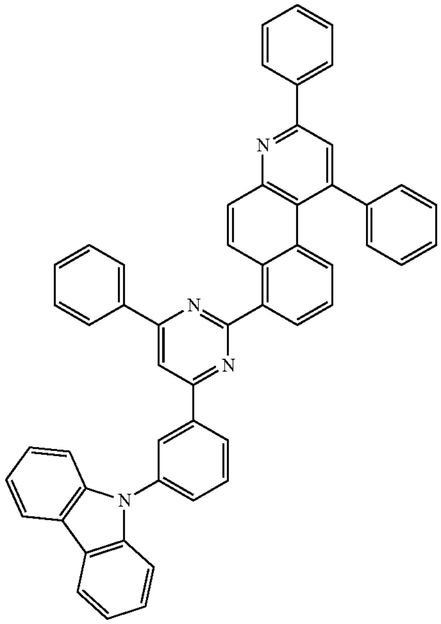
280
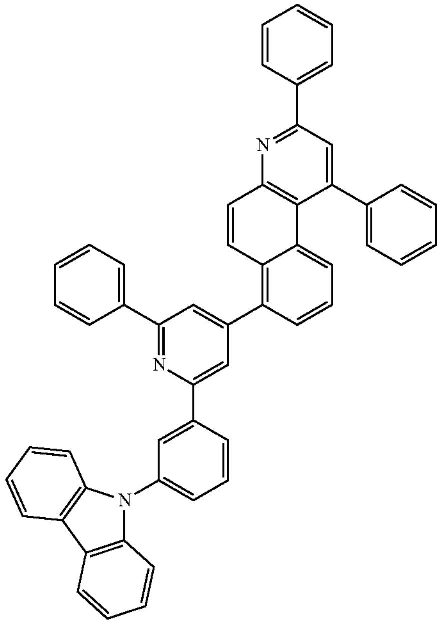
-continued
281
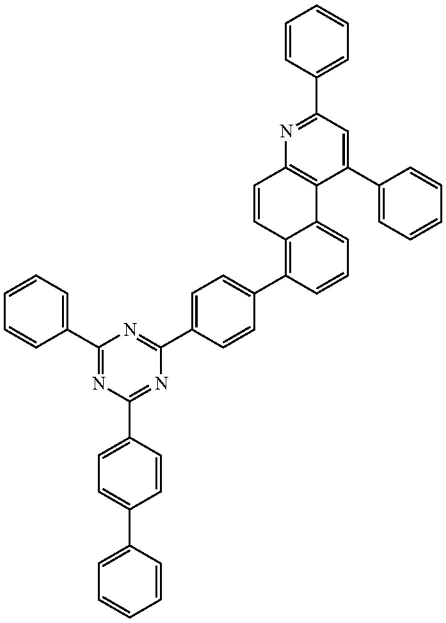
282
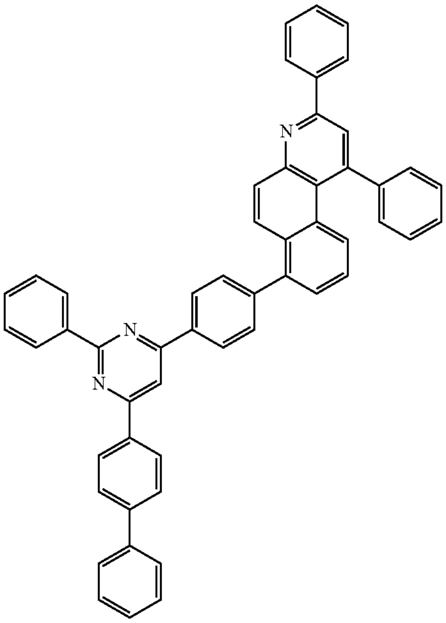

238
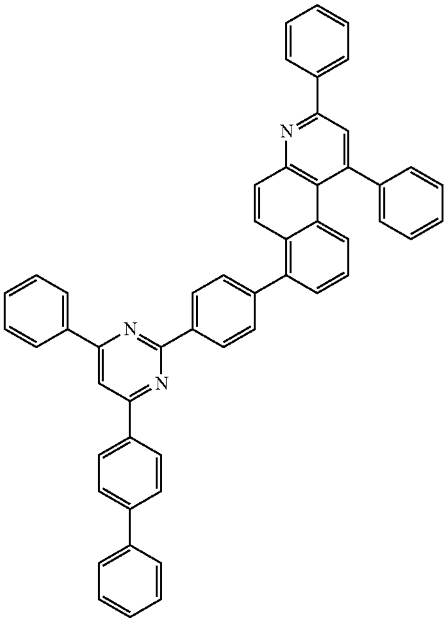
284
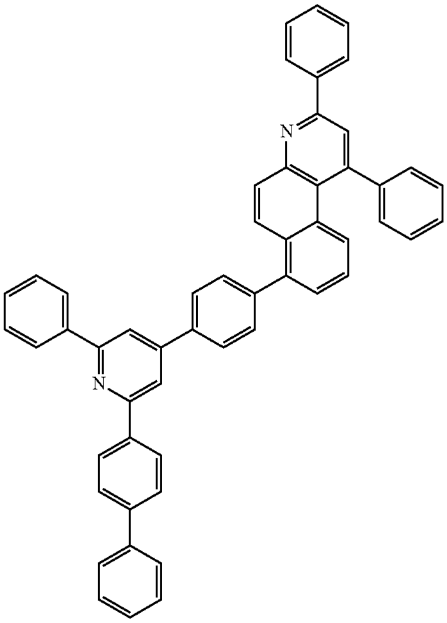
285
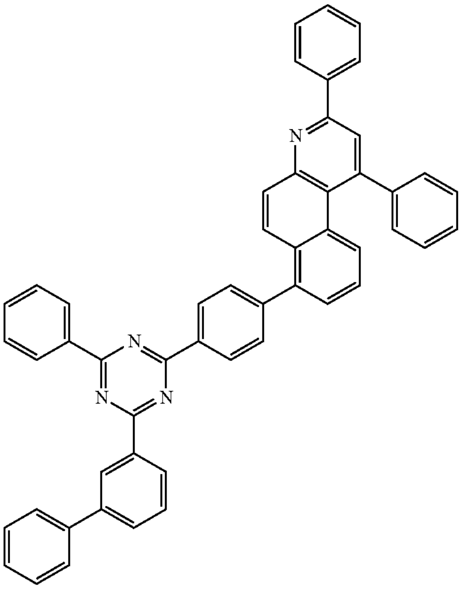
286
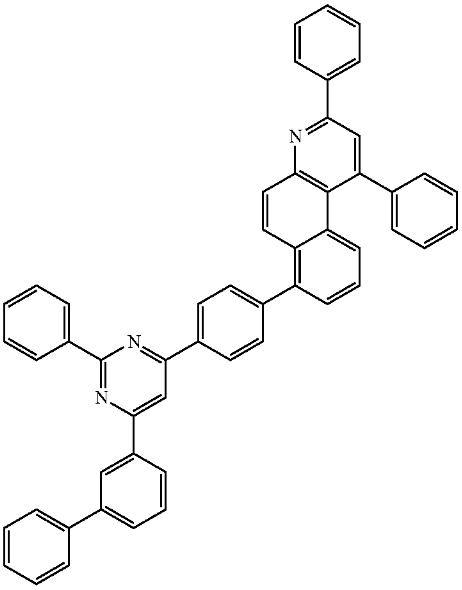

-continued
287
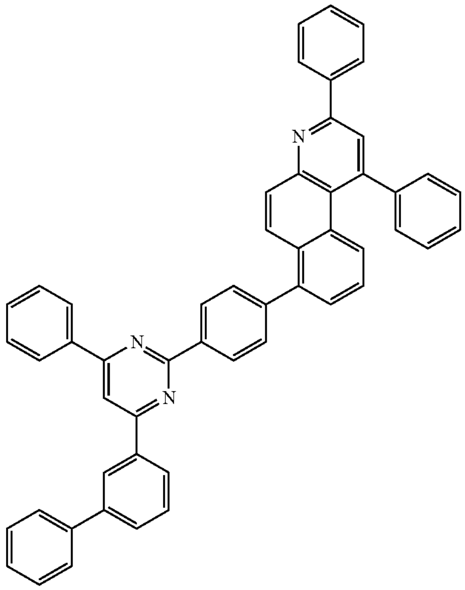
288
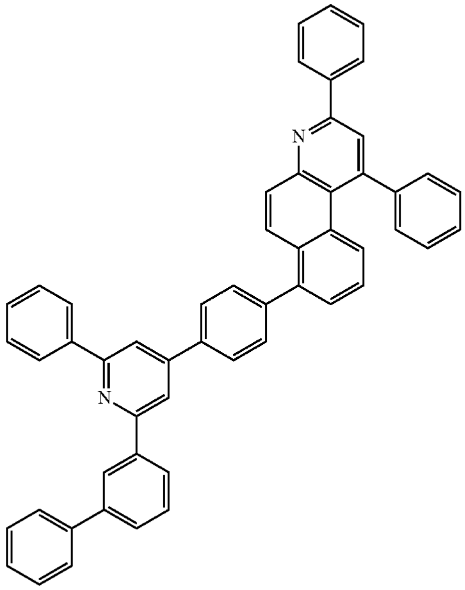
-continued
289
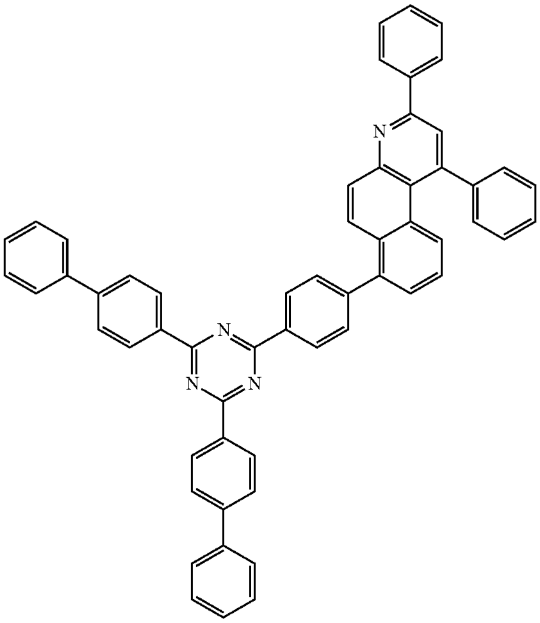
290
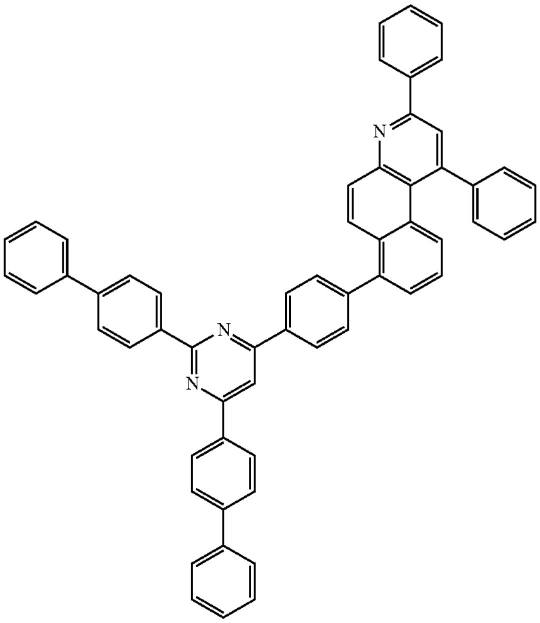

-continued
291
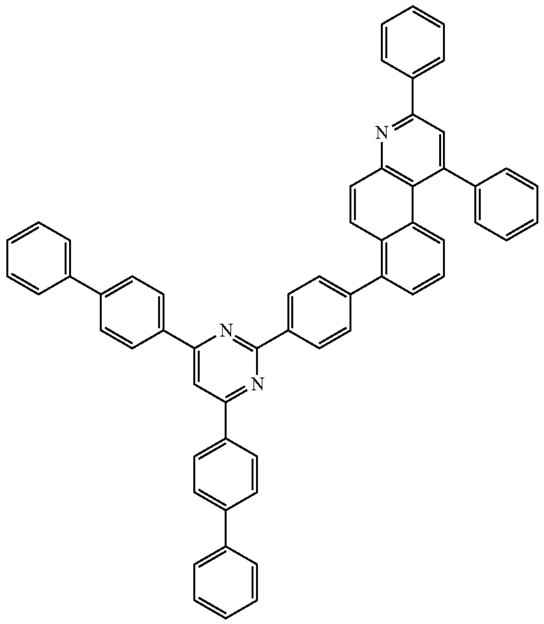
292
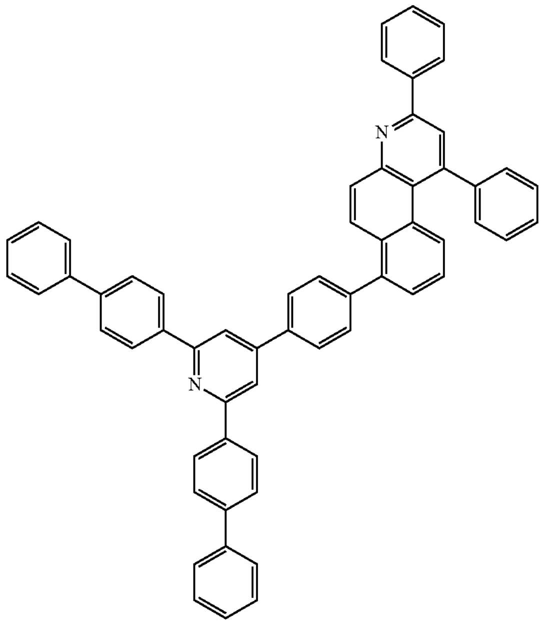
-continued
293
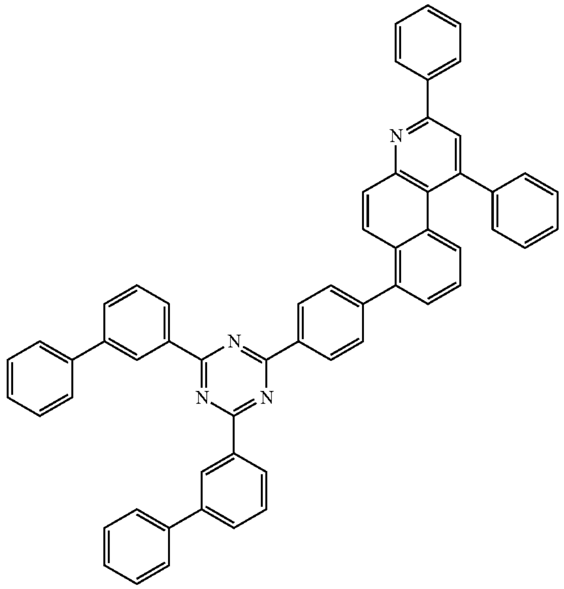
294
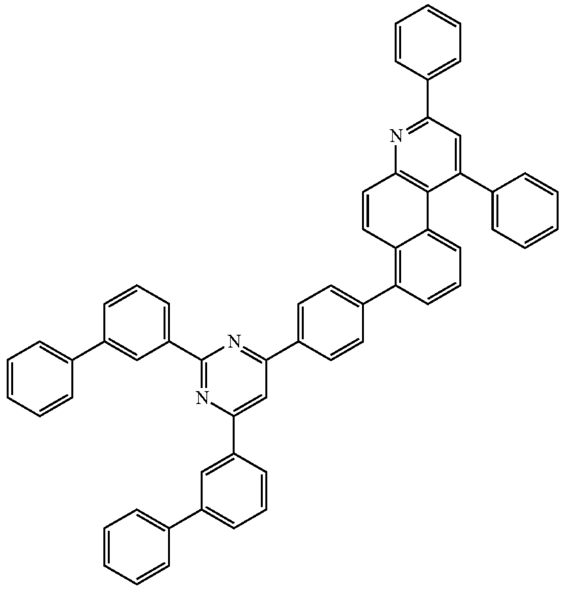

-continued
295
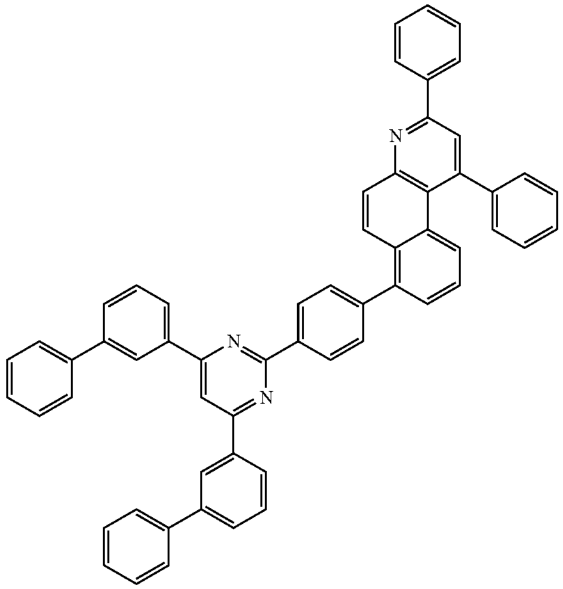
297
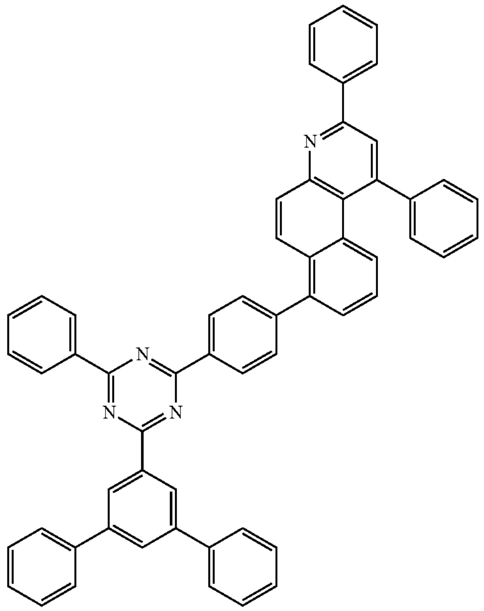
296
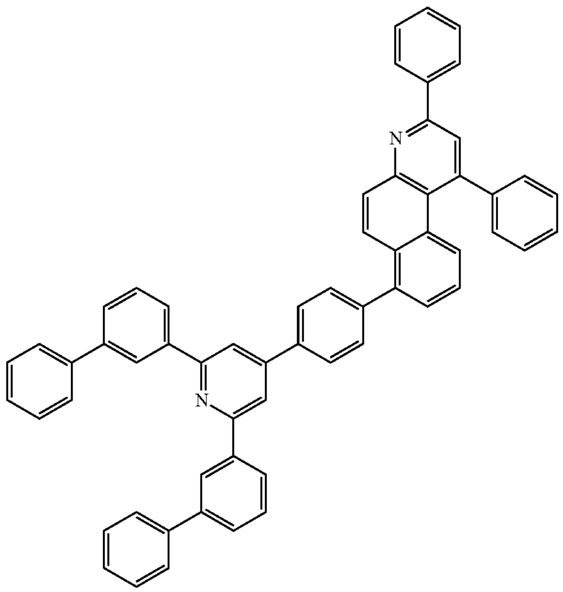
298
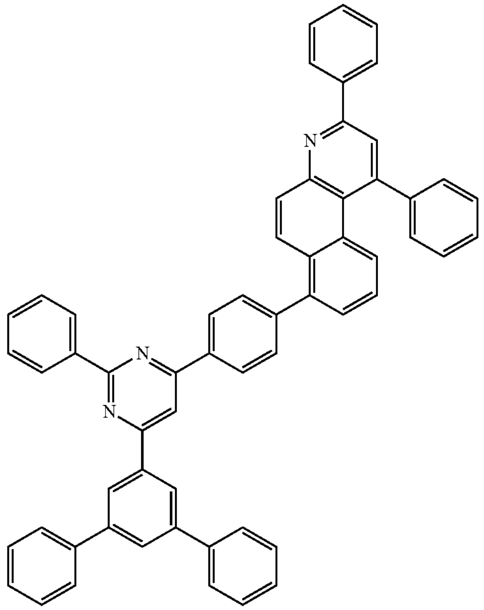

-continued
299
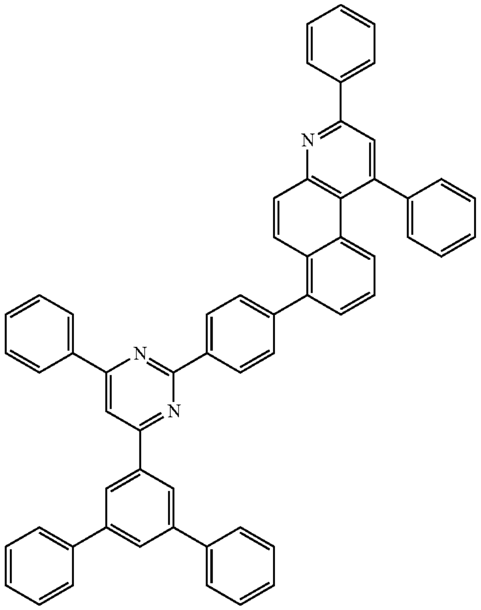
300
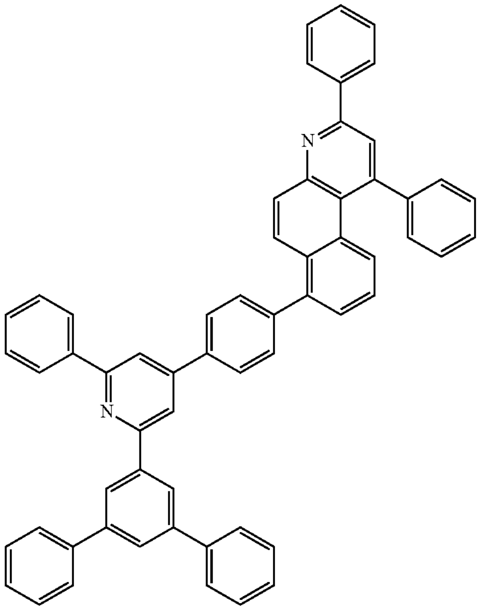
-continued
301
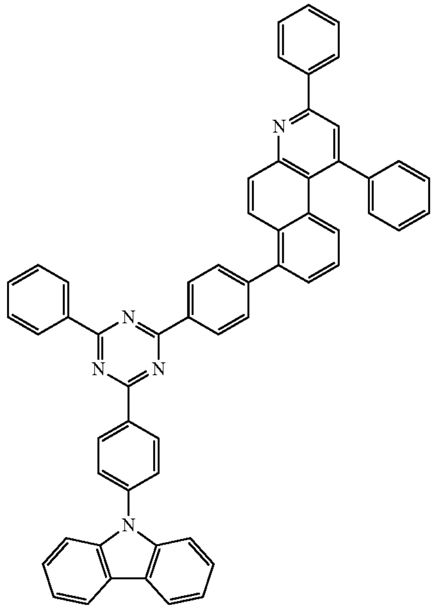
302
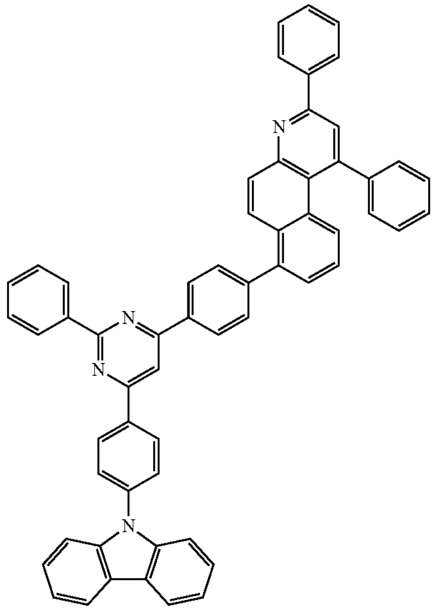

-continued
303
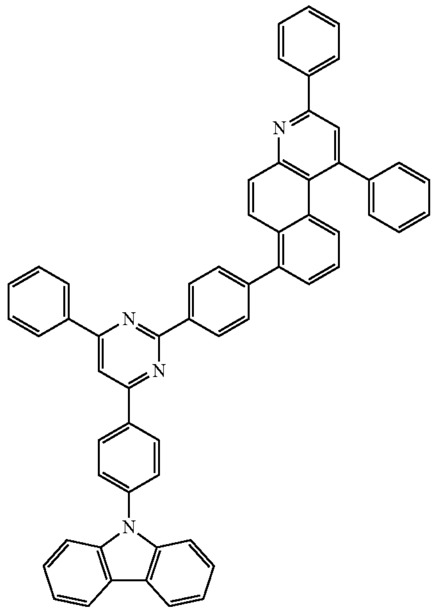
304
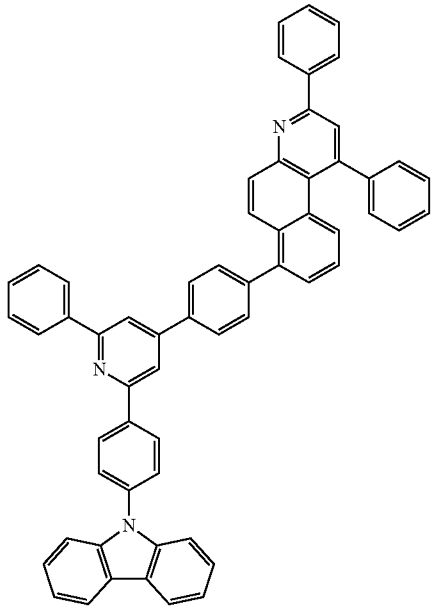
-continued
305
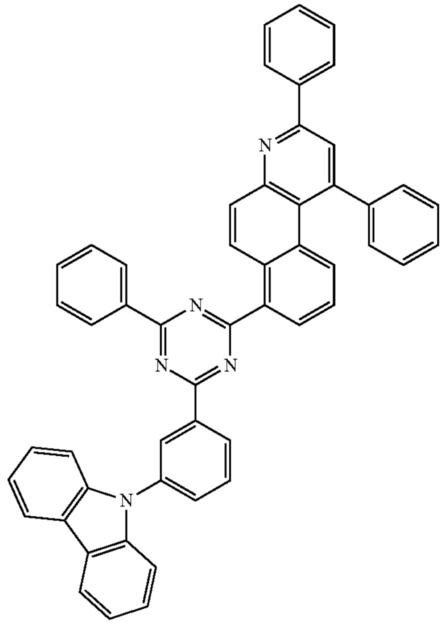
306
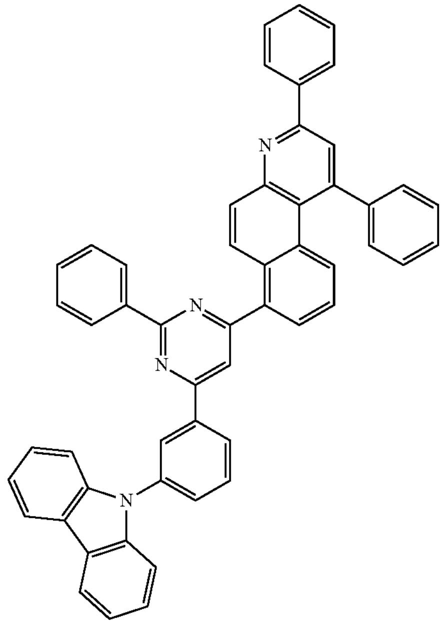

-continued
307
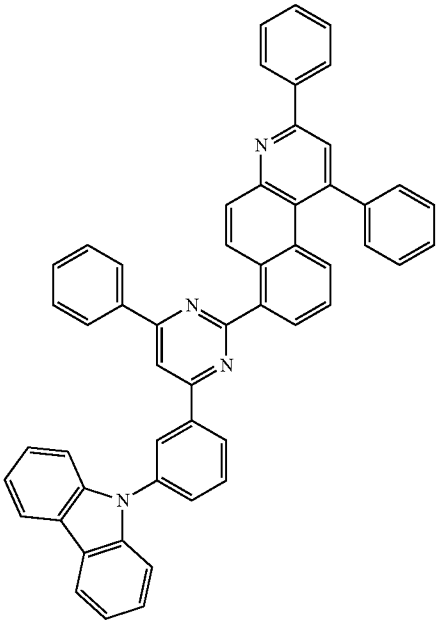
308
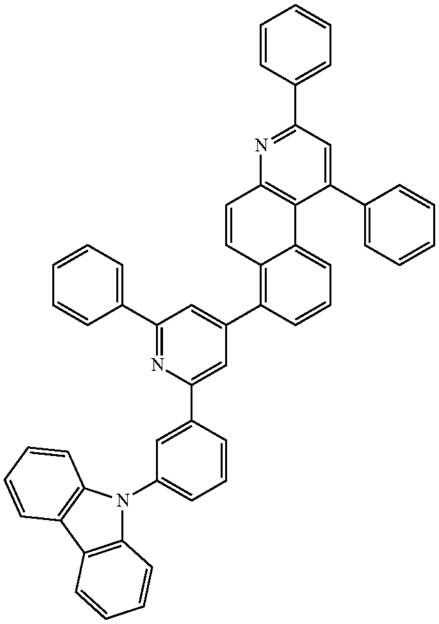
-continued
309
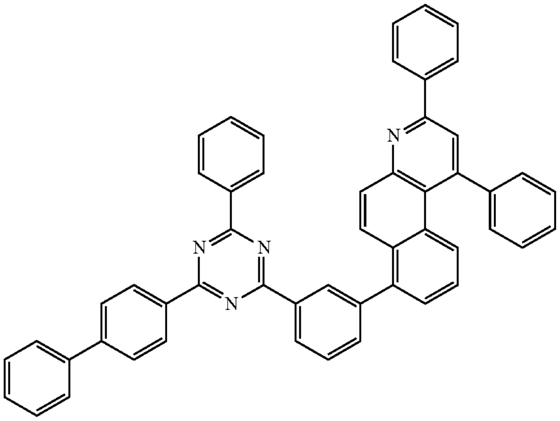
310
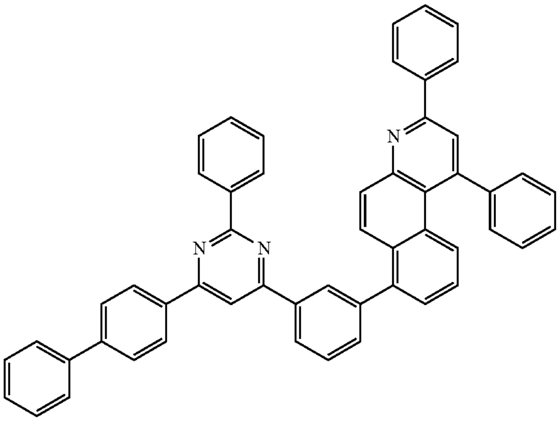
311
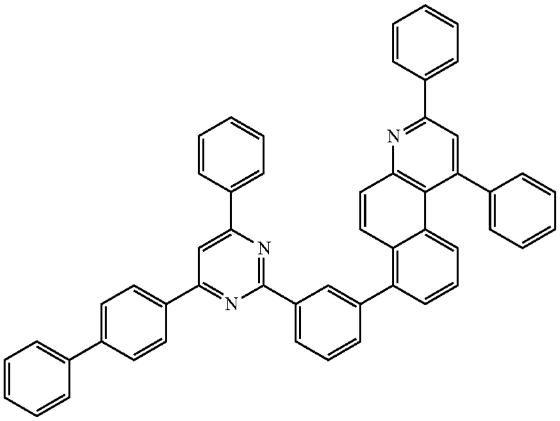

-continued
312
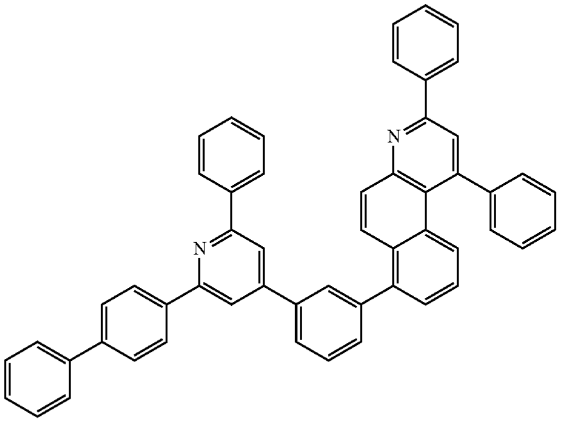
313
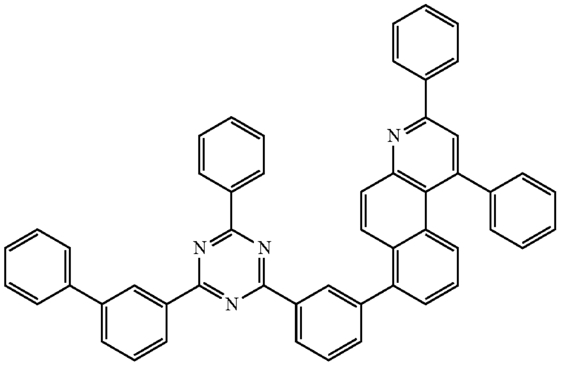
314
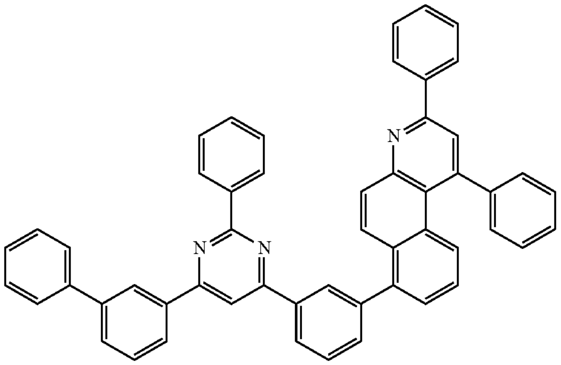
315
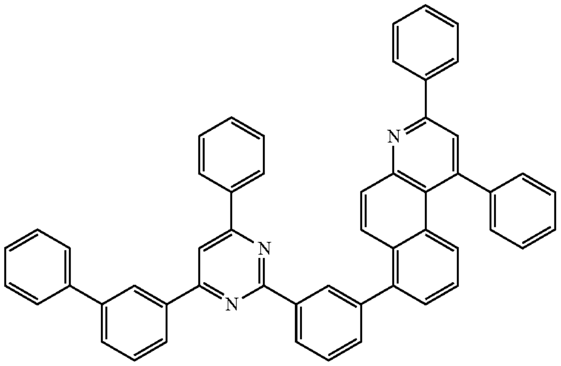
-continued
316
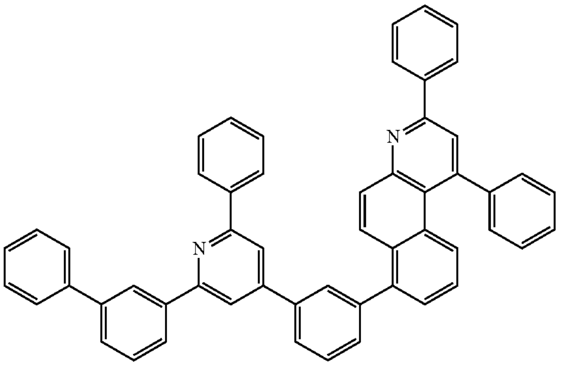
317
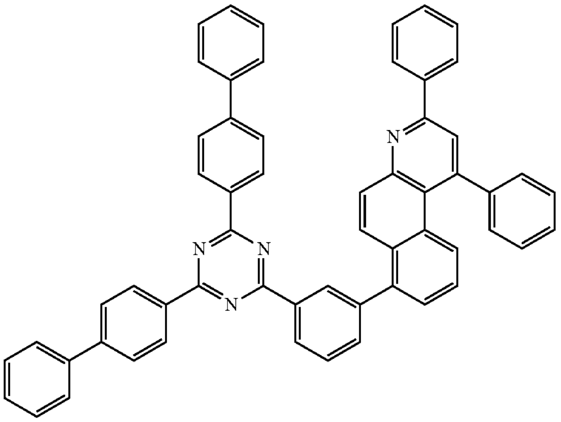
318
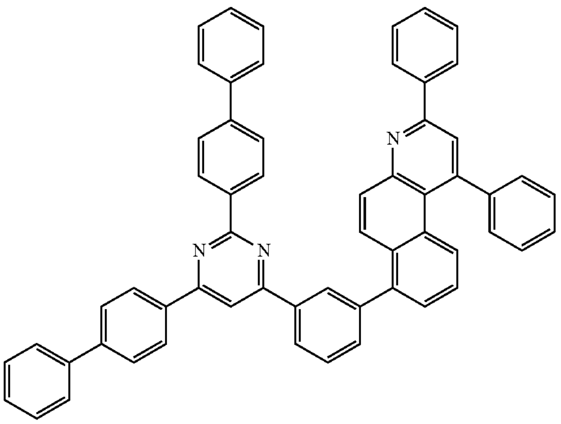

-continued
319
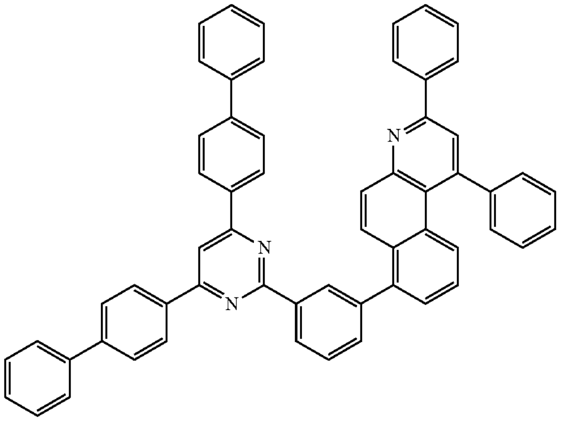
320
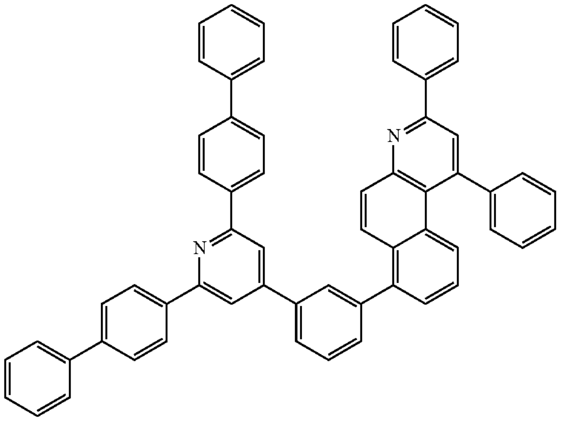
321
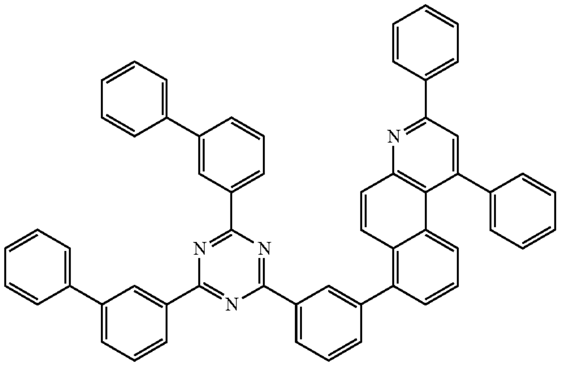
-continued
322
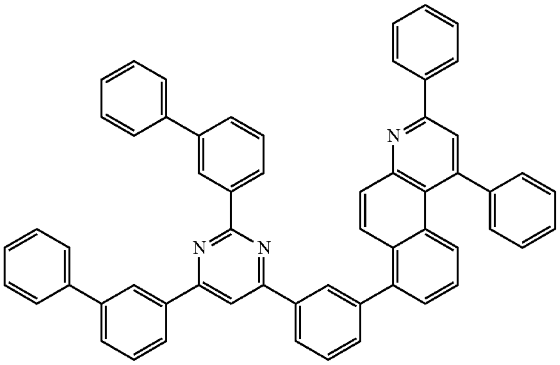
323
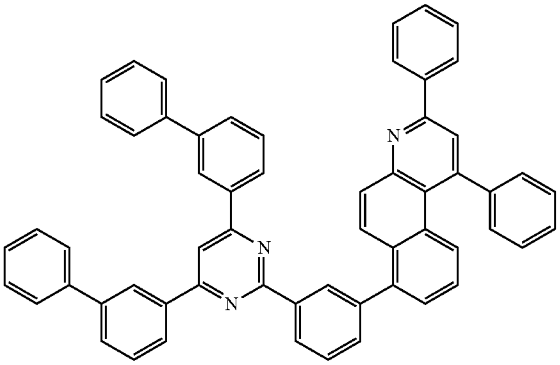
324
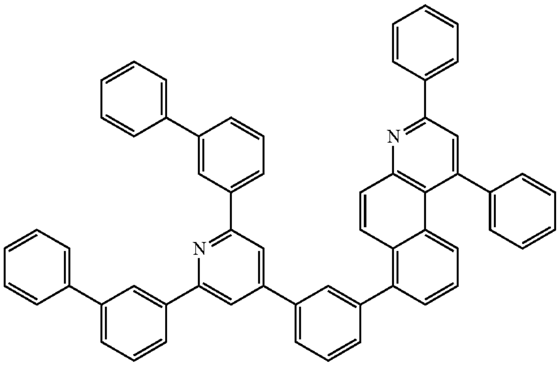

-continued
325
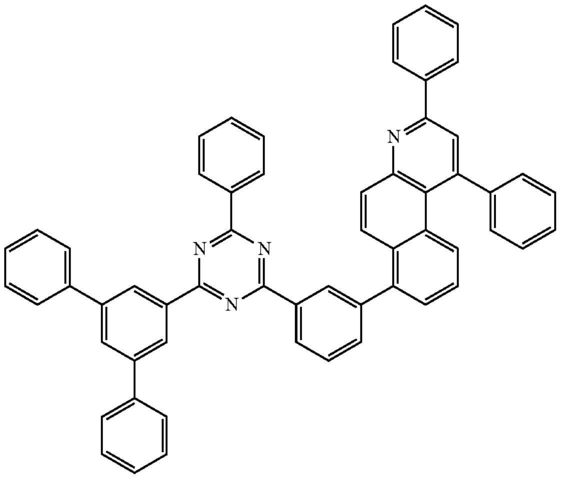
326
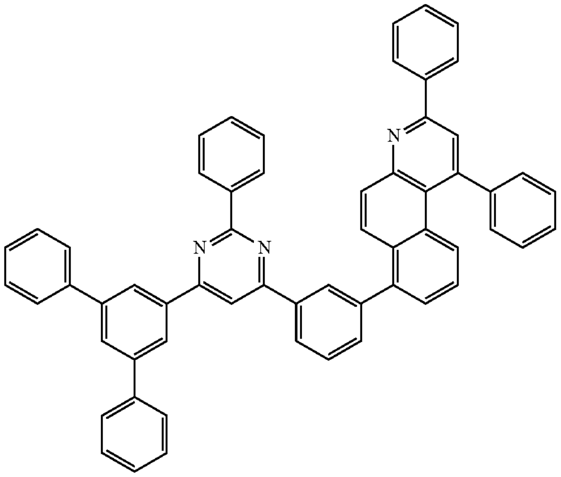
327
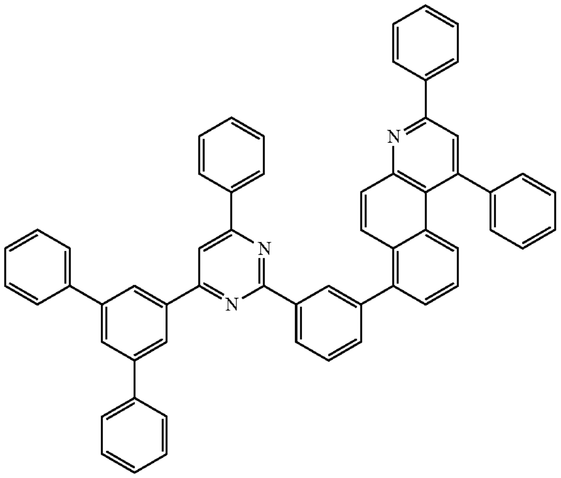
-continued
328
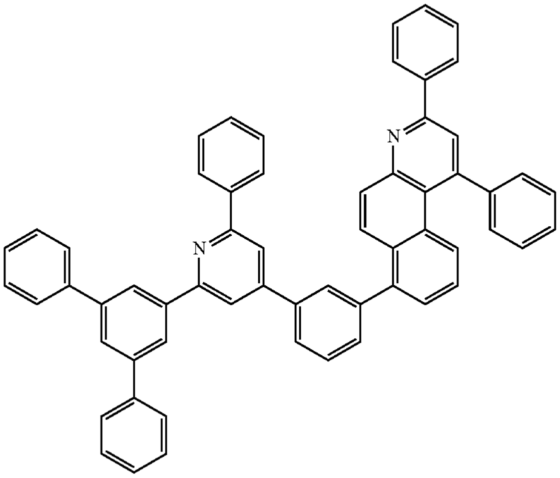
329
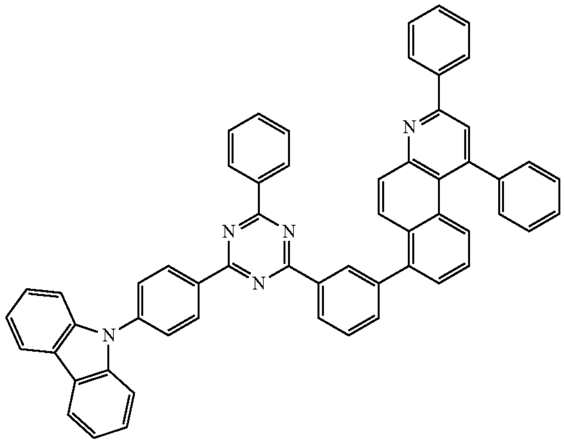
330
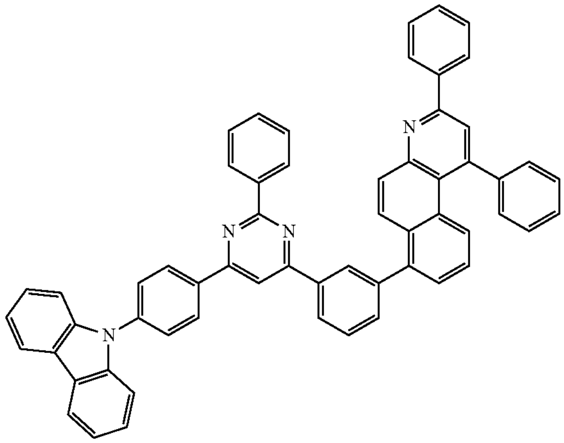

-continued
331
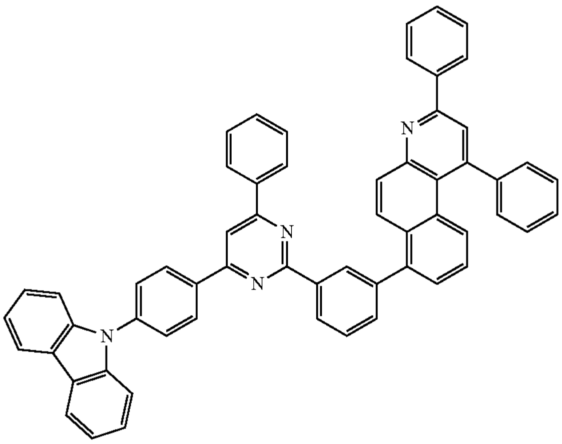
332
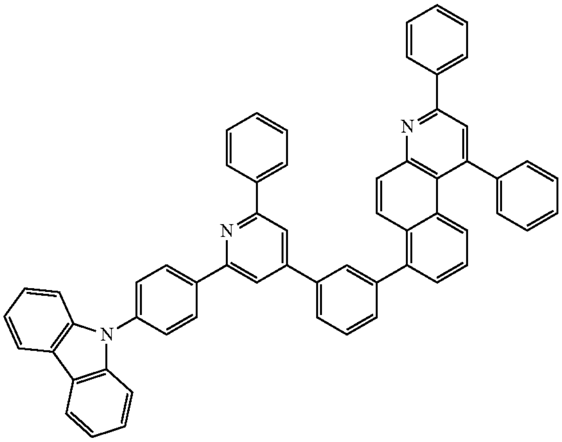
333
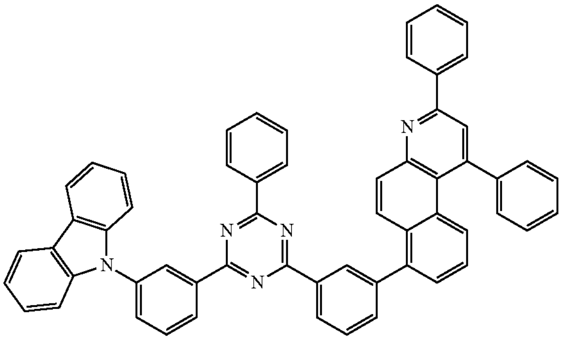
334
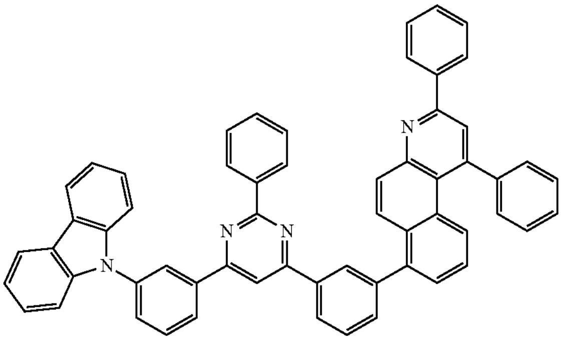
-continued
335
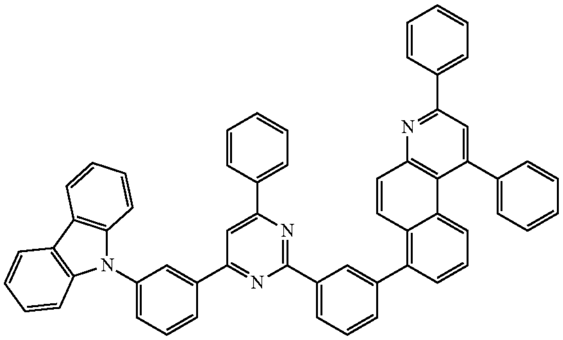
336
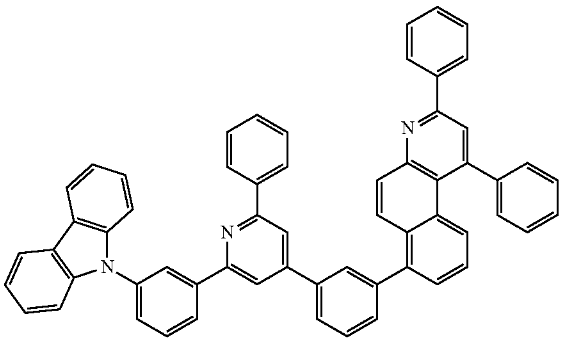
337
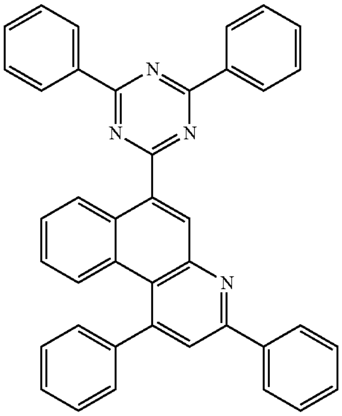
338
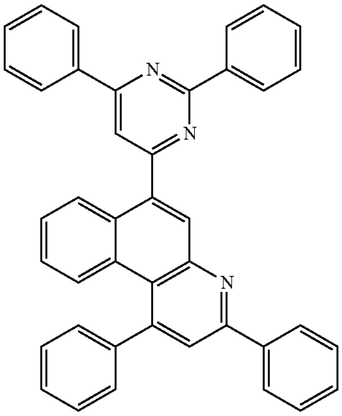

-continued
339
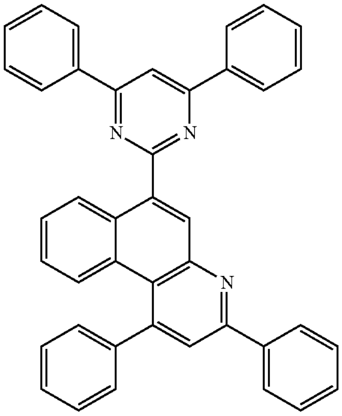
340
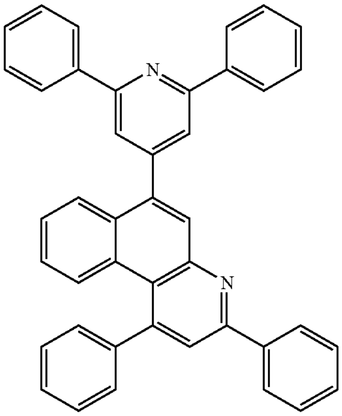
341
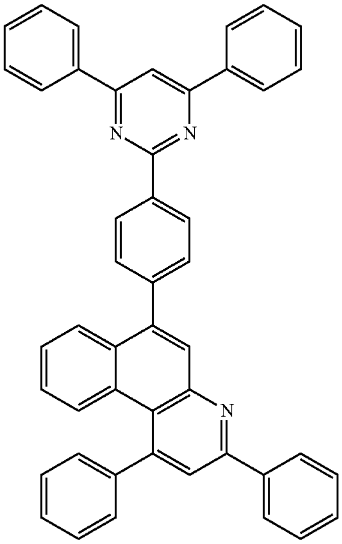
-continued
342
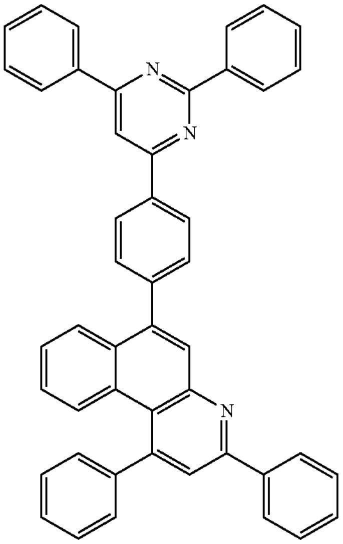
343
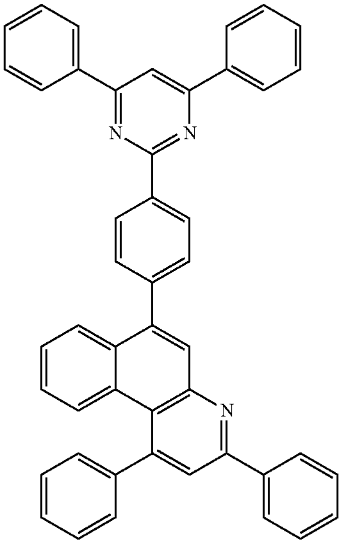
344
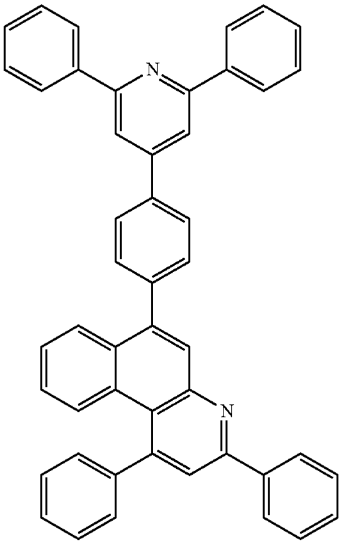

-continued
345
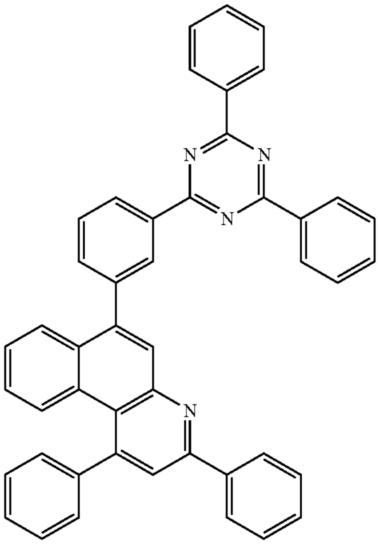
346
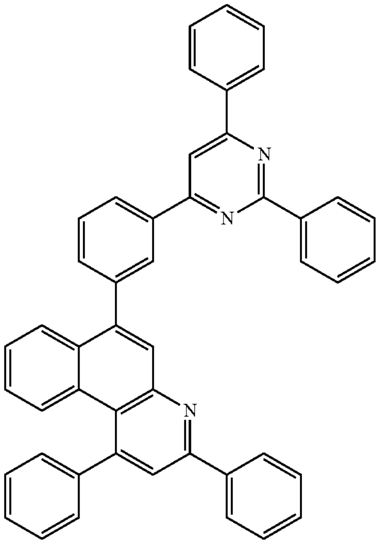
347
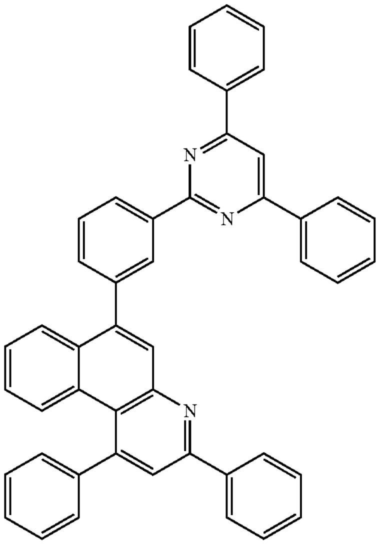
-continued
348
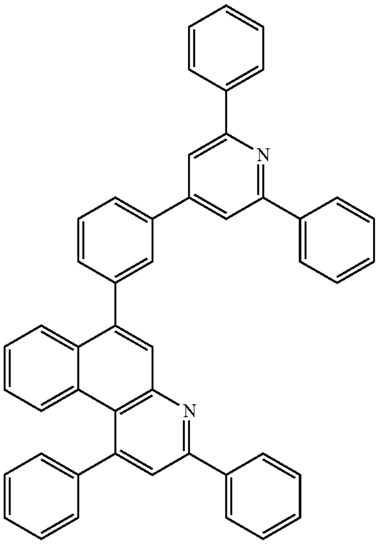
349
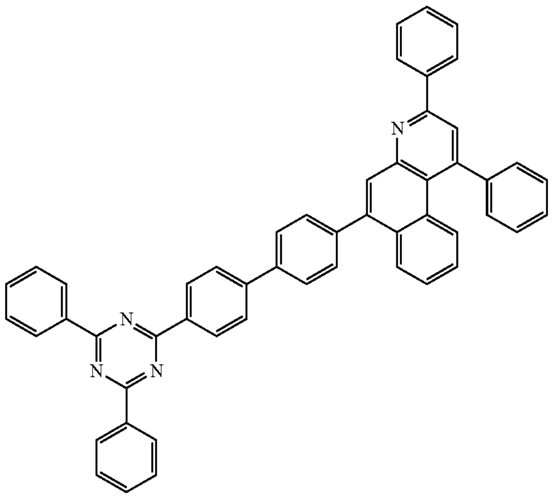
350
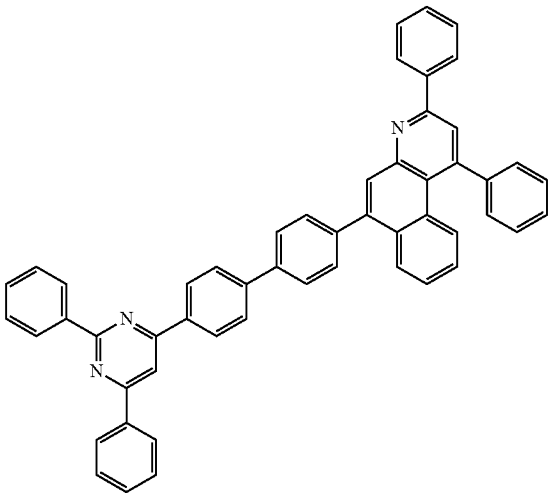

-continued
351
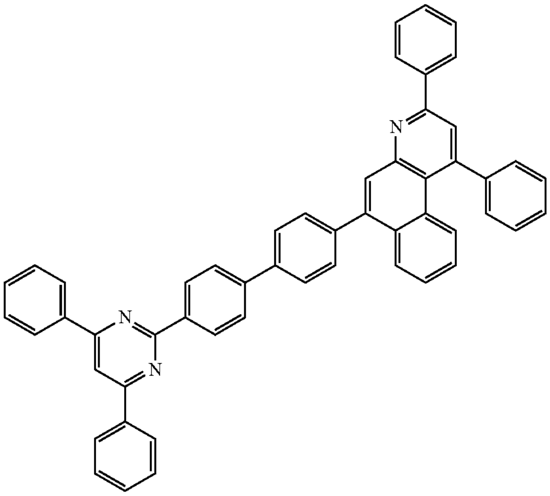
352
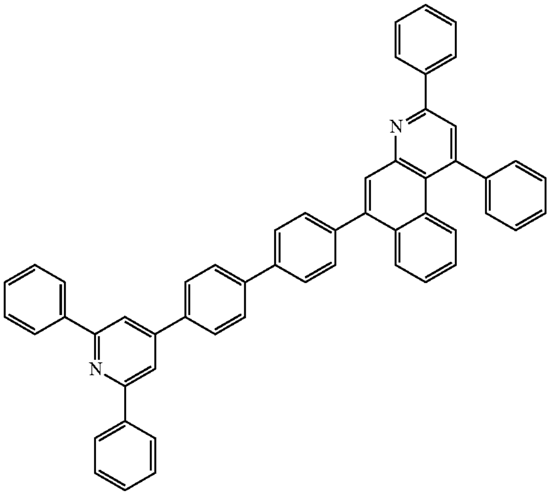
353
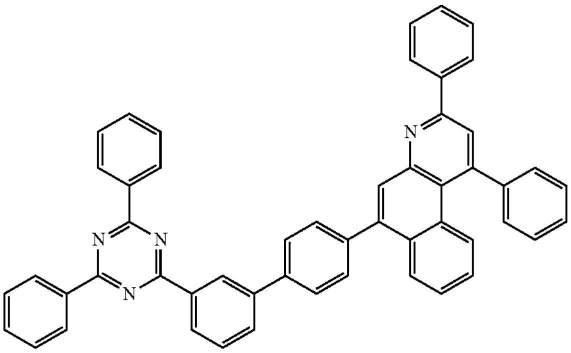
-continued
354
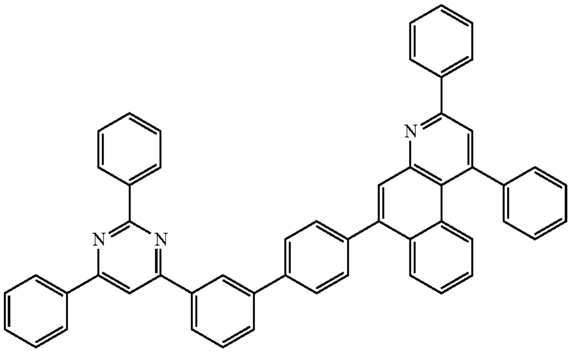
355
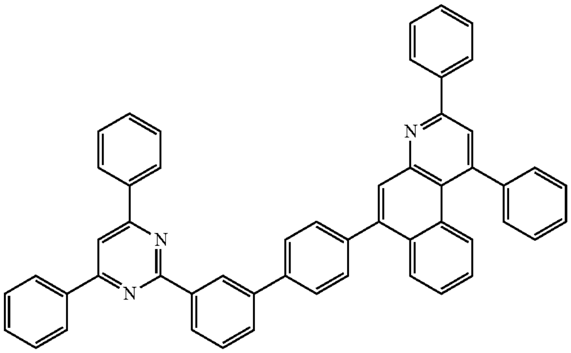
356
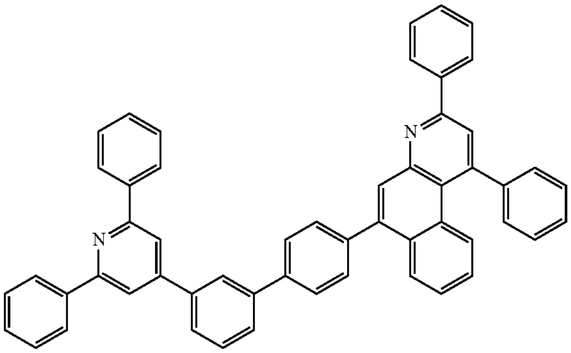
357
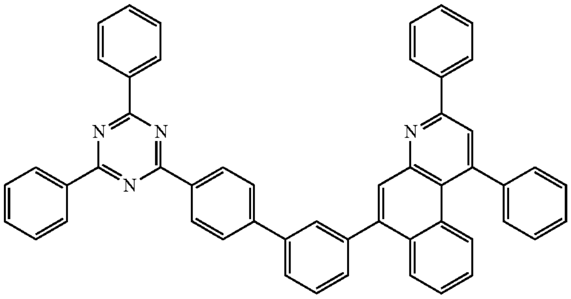

358
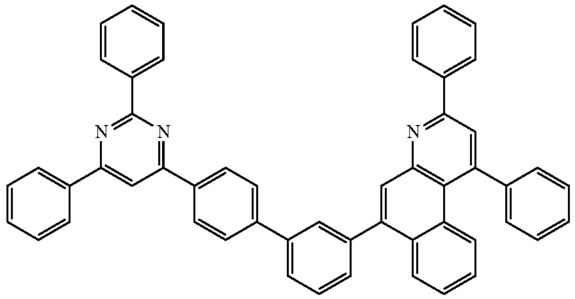
359
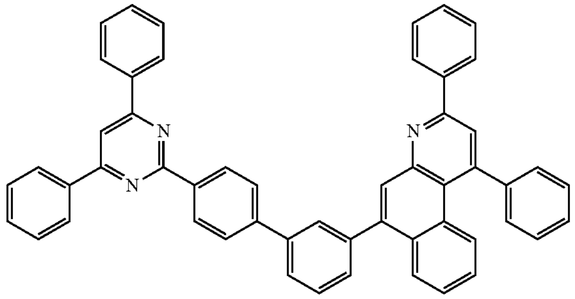
360
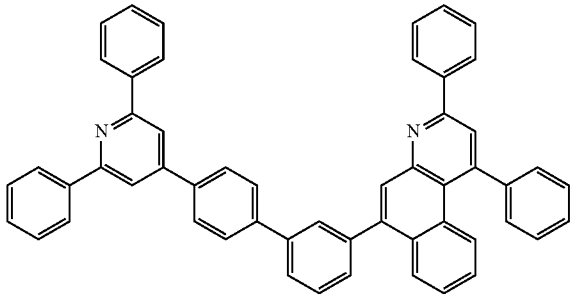
361
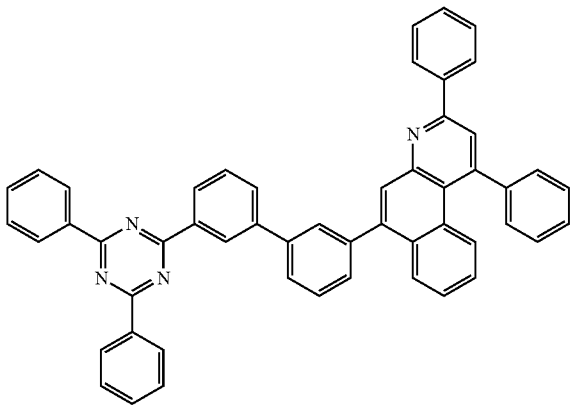
362
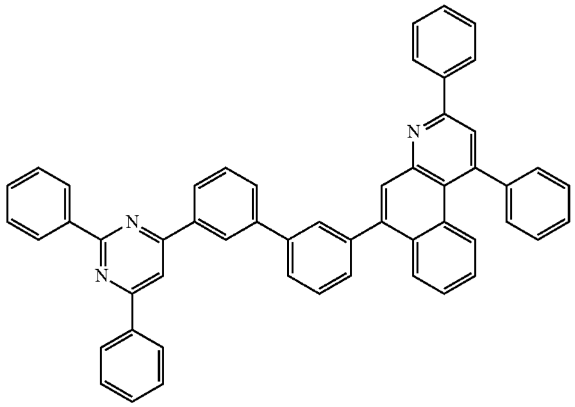
363
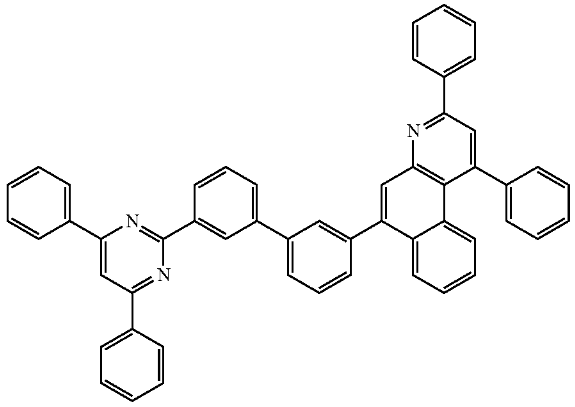
364
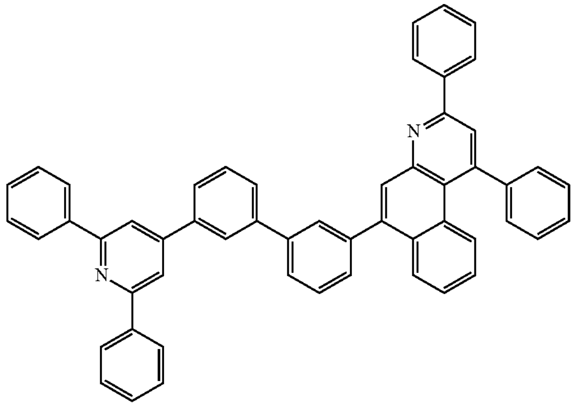

-continued
365
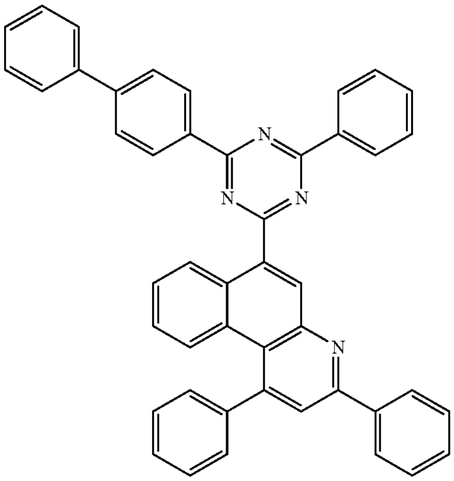
366
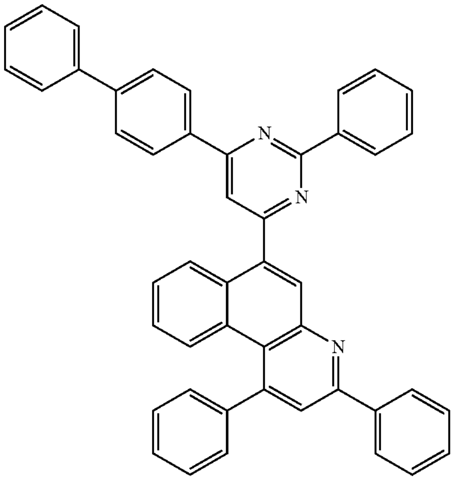
367
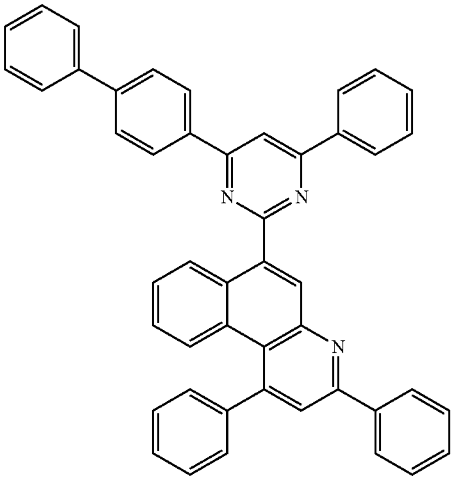
-continued
368
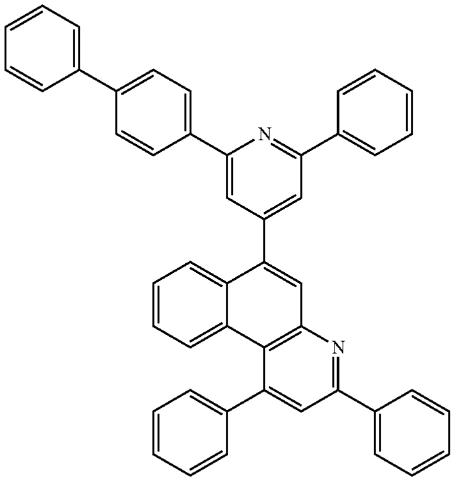
369
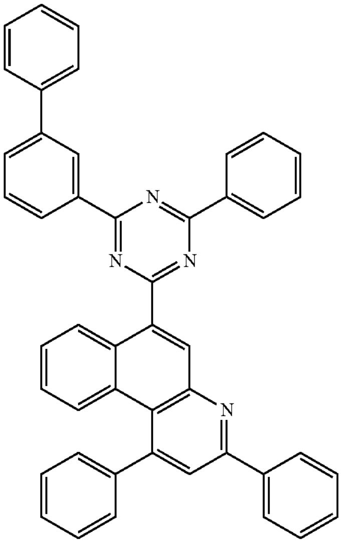
370
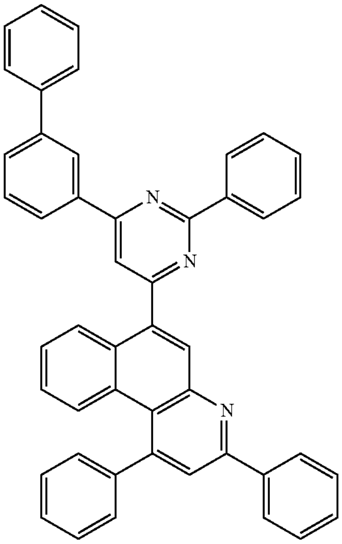

-continued
371
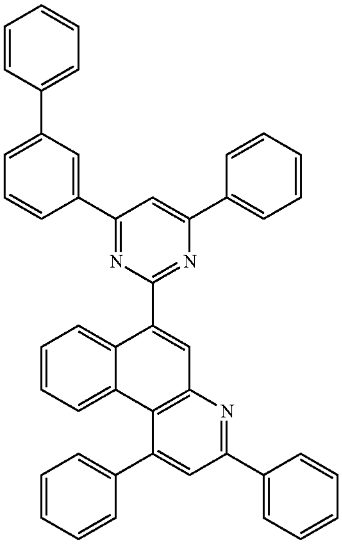
-continued
373
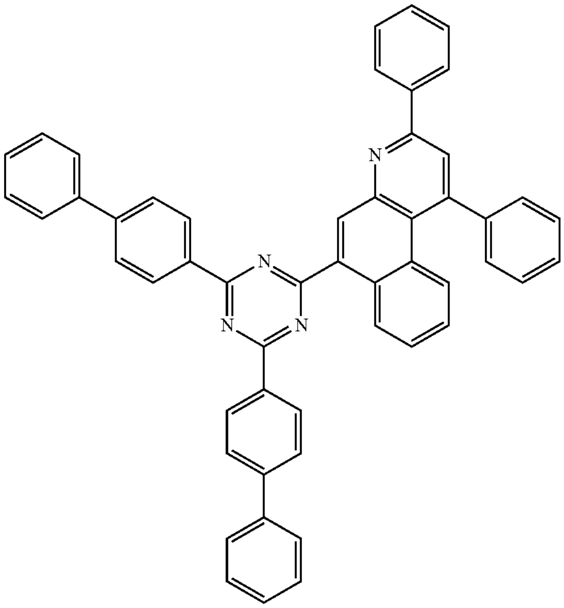
372
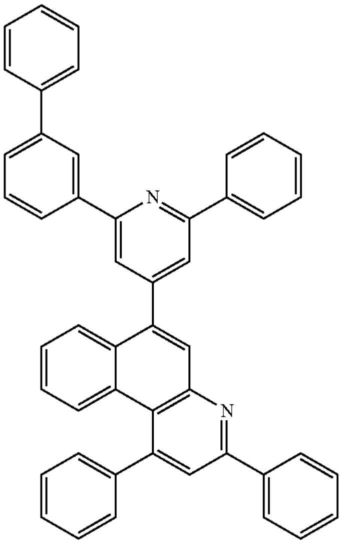
374
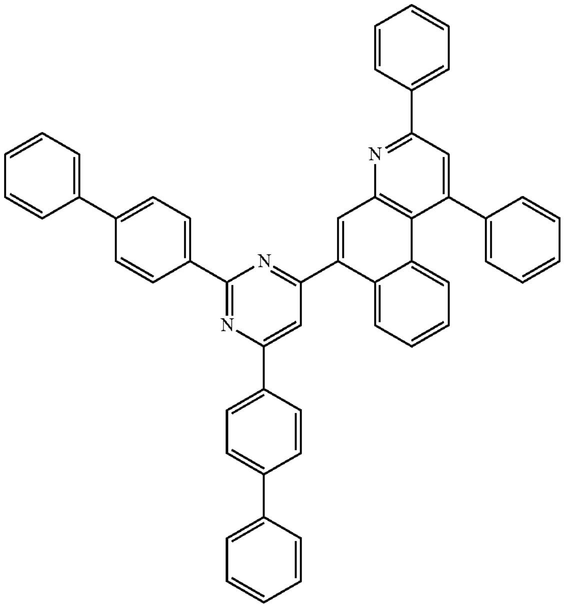

-continued
375
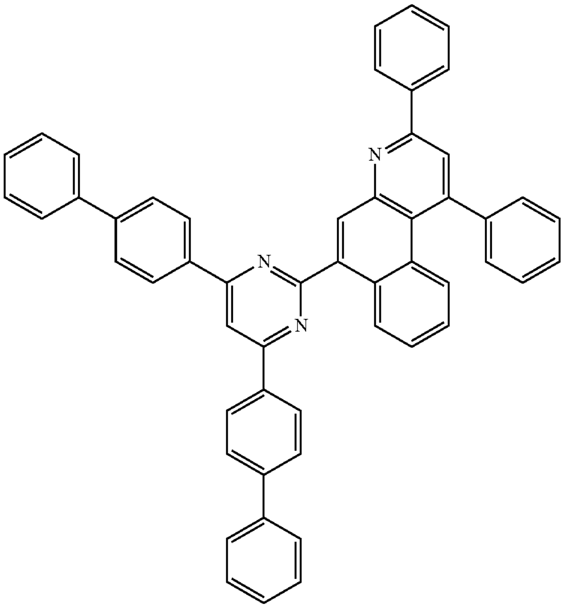
376
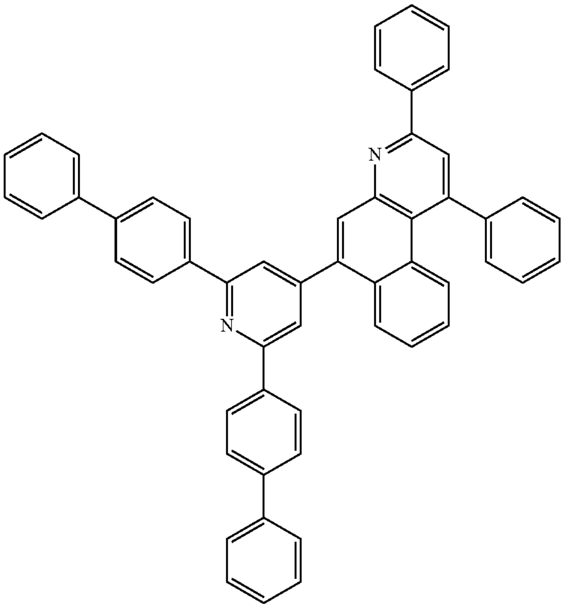
-continued
377
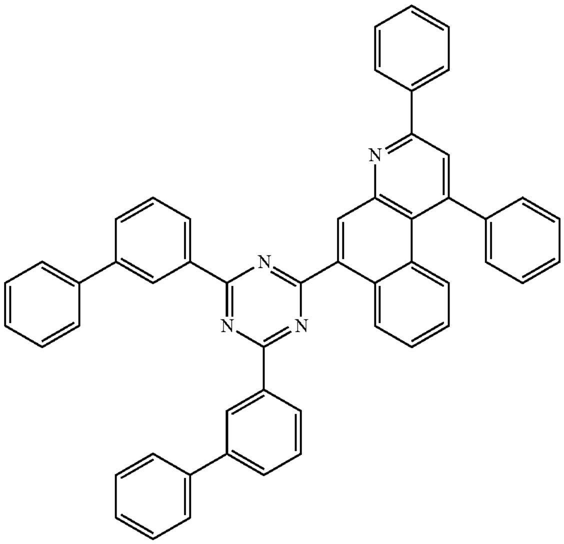
378
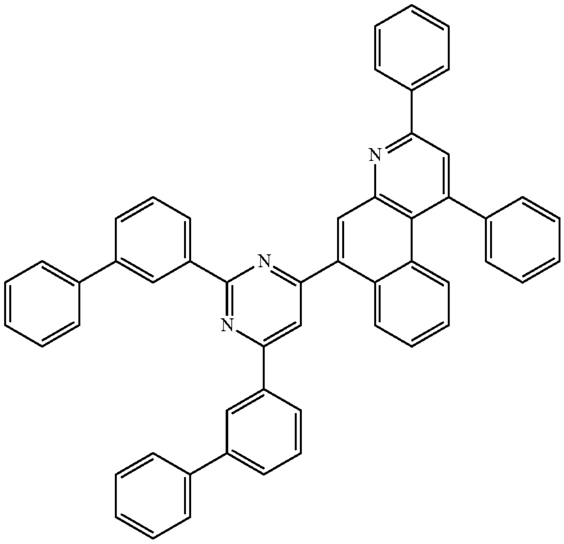

-continued
379
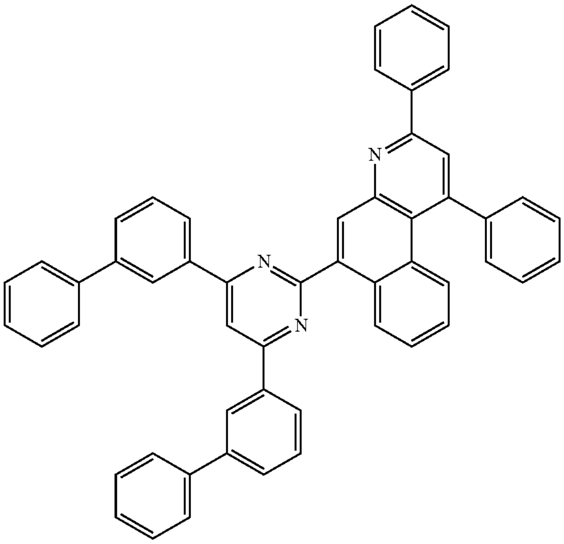
380
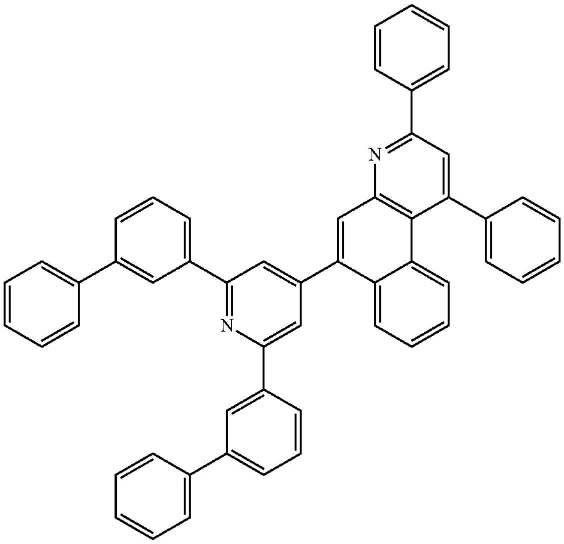
381
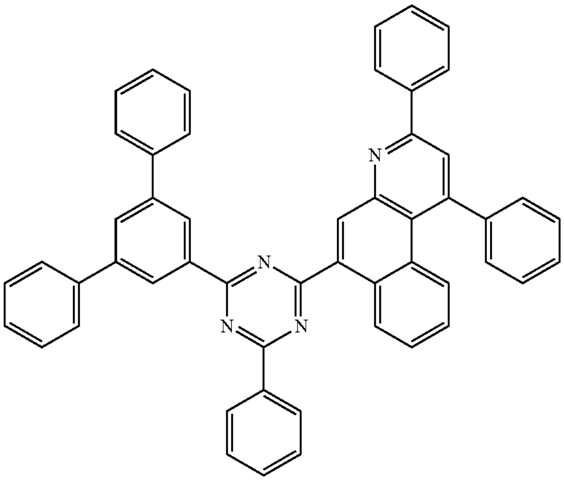
-continued
382
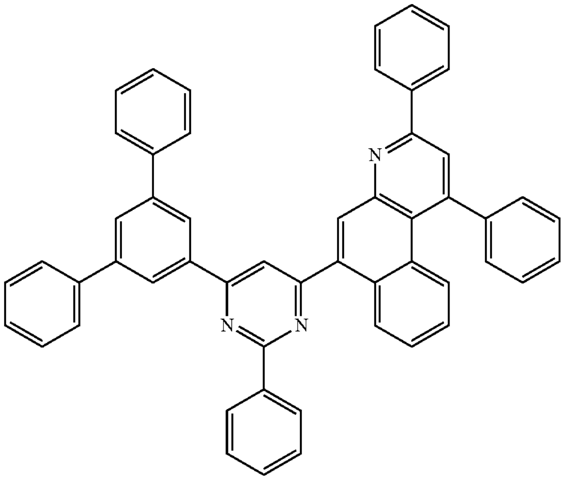
383
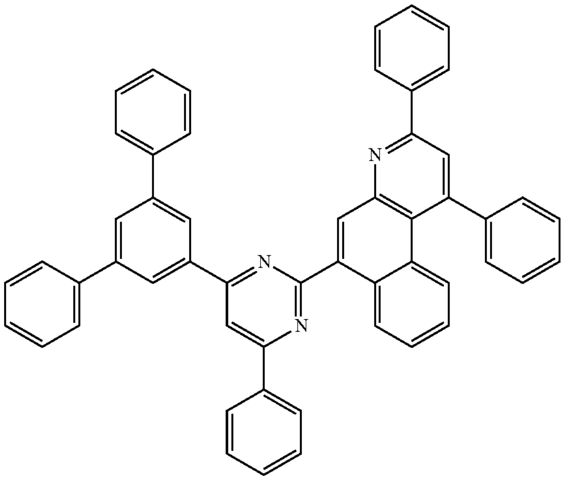
384
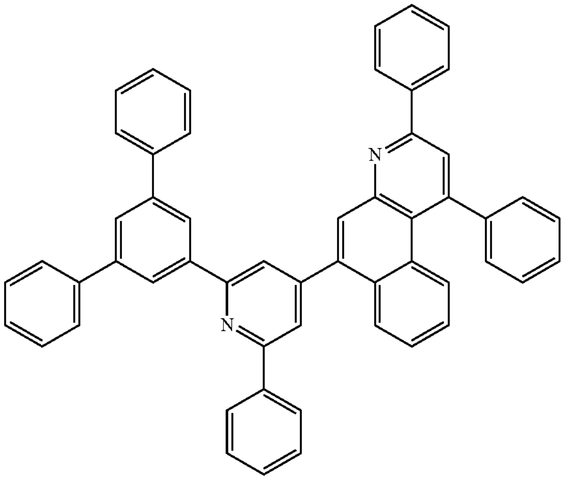

-continued
385
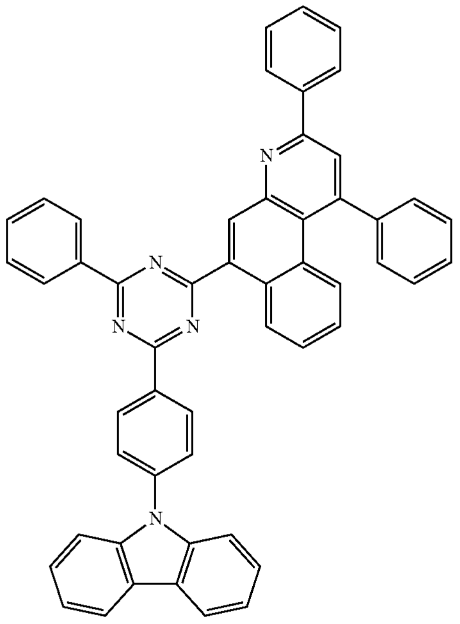
386
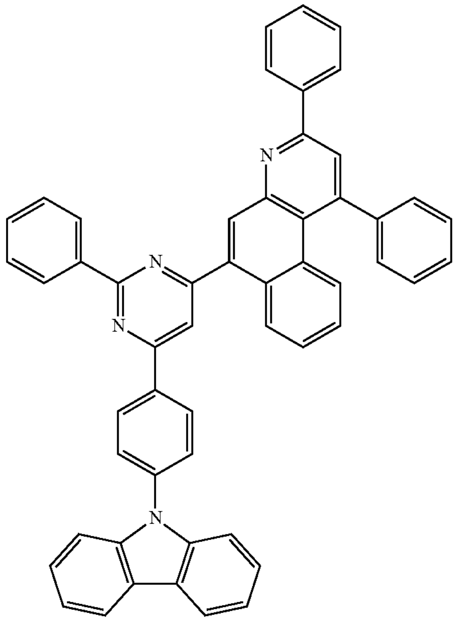
-continued
387
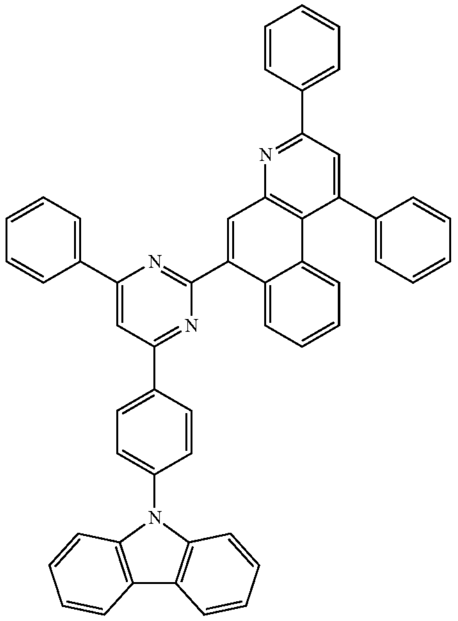
388
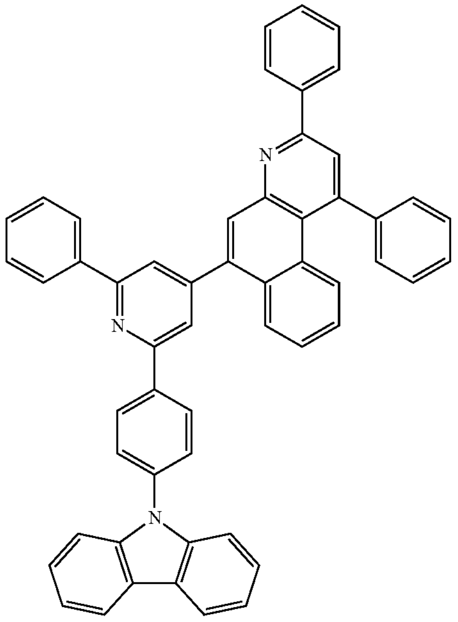

-continued
389
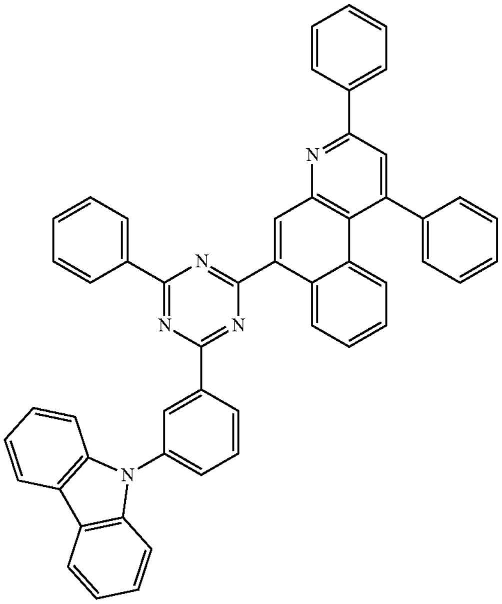
390
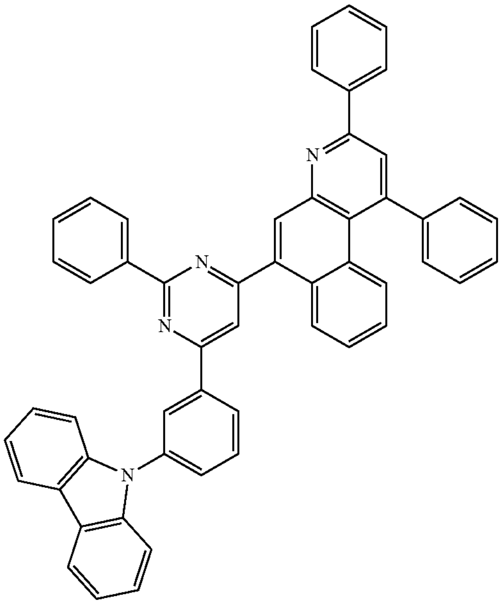
-continued
391
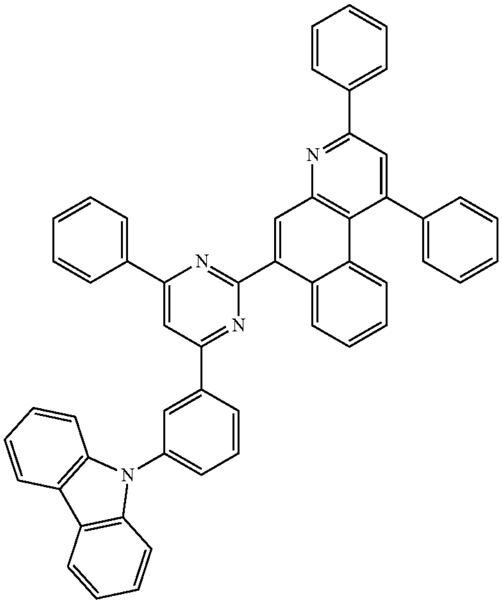
392
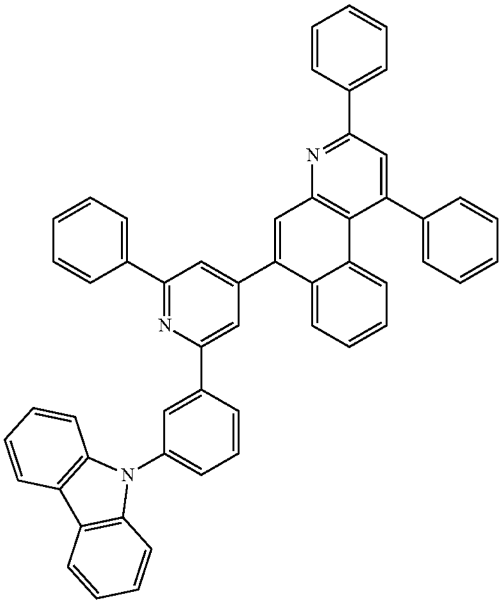

-continued
393
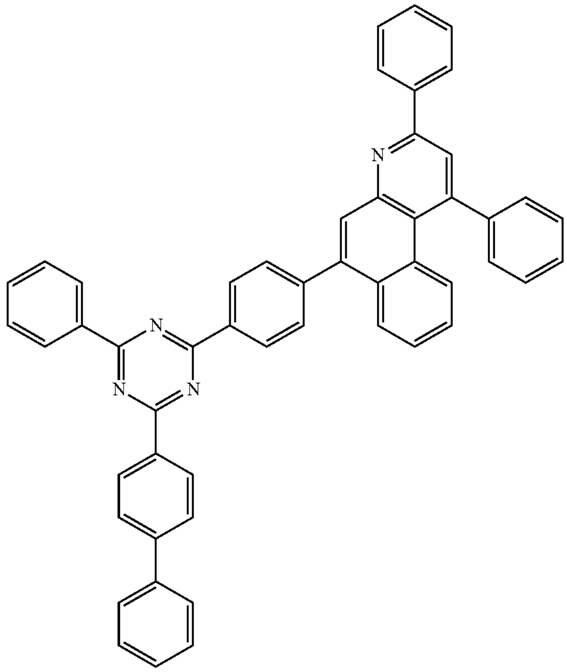
394
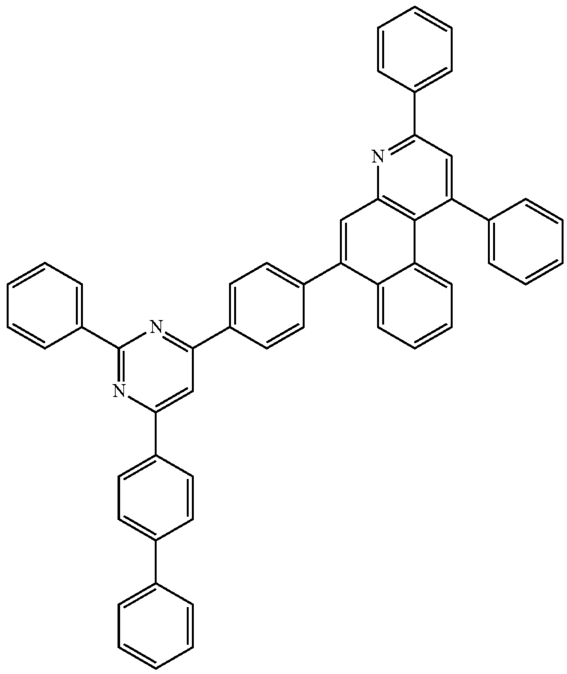
-continued
395
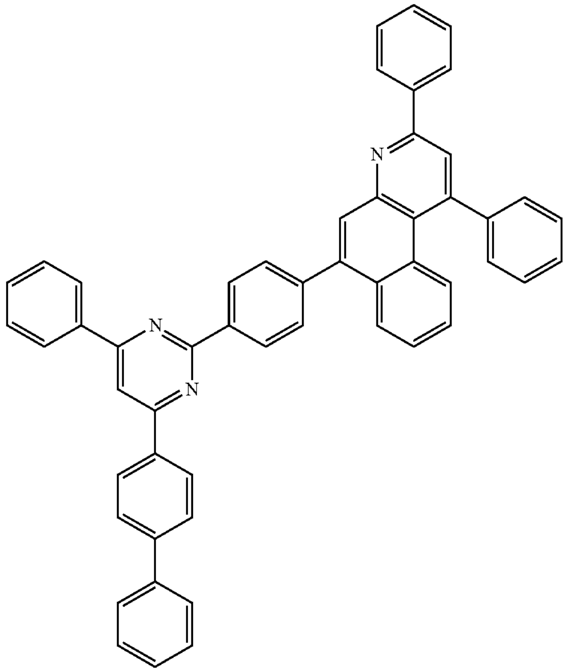
396
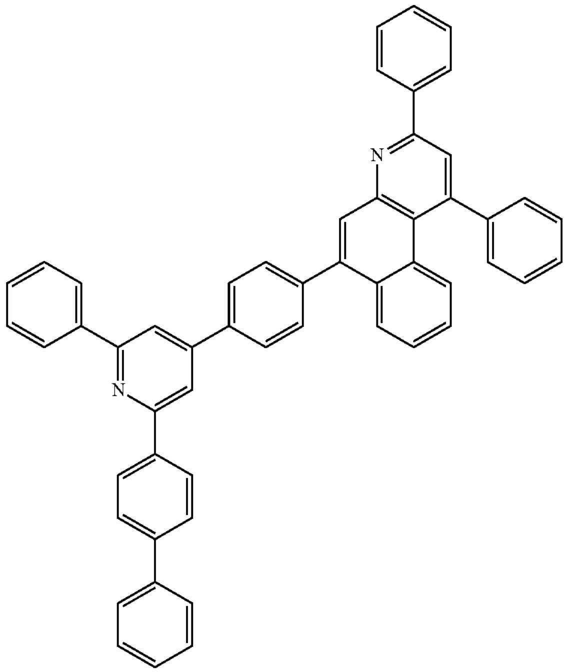

-continued
397
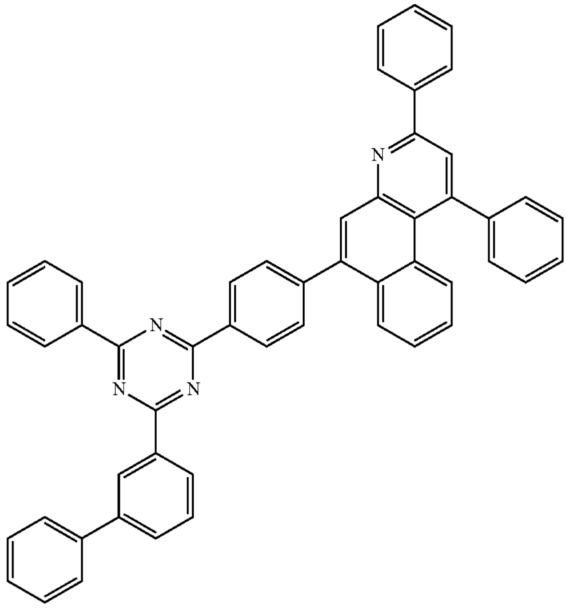
398
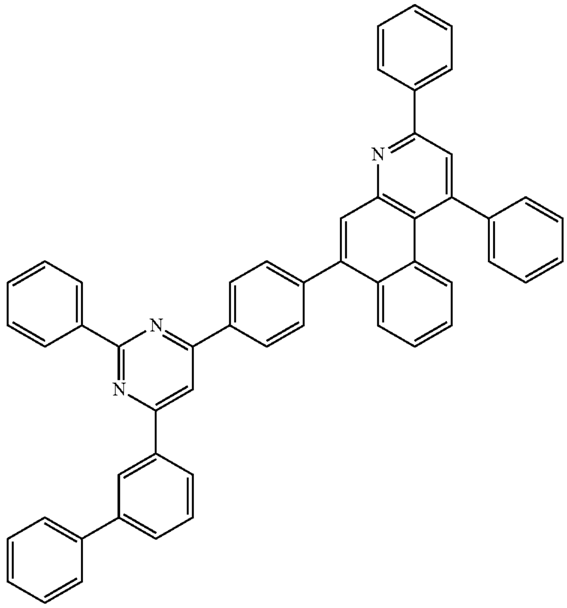
-continued
399
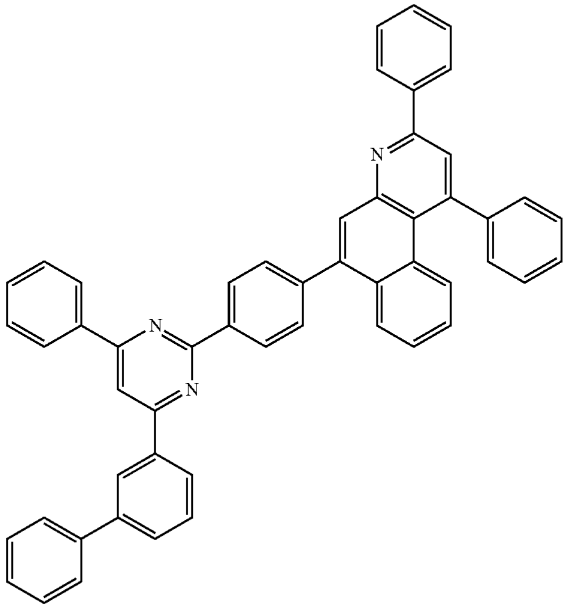
400
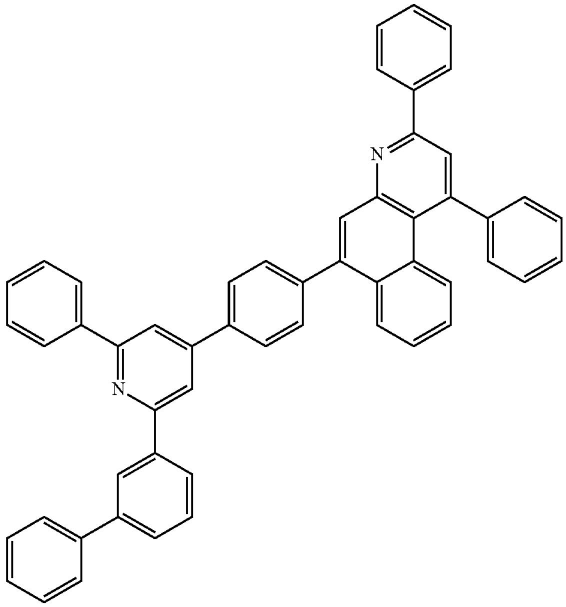

-continued
401
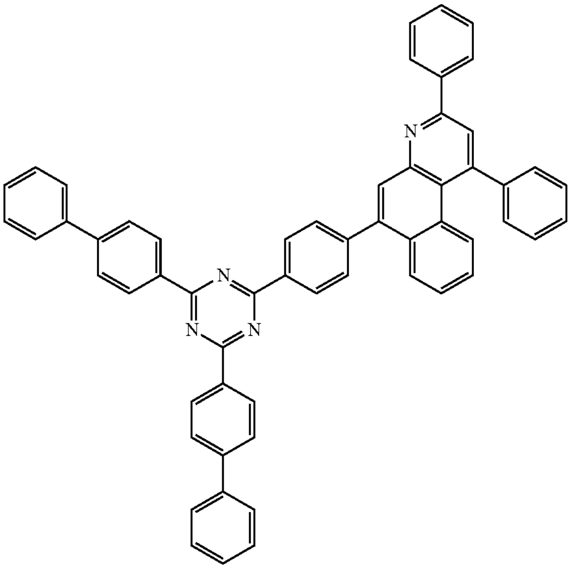
402
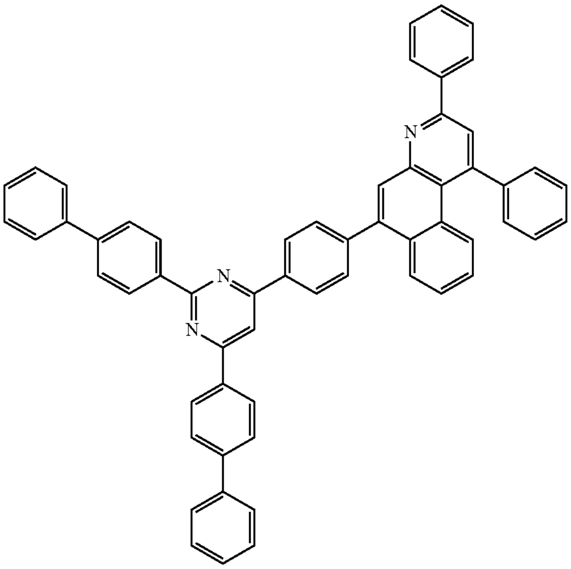
-continued
403
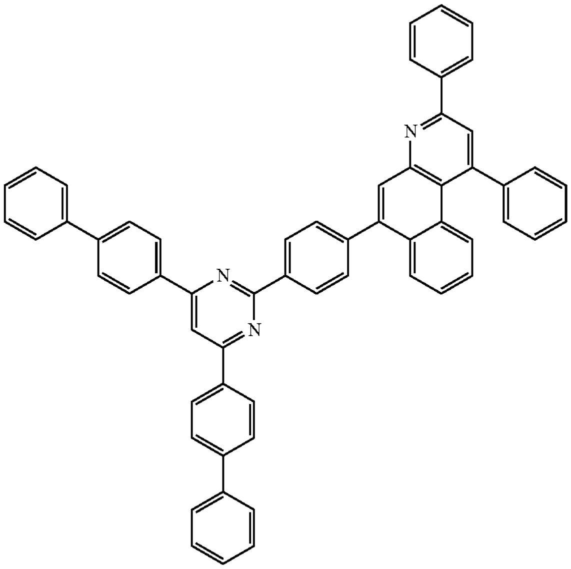
404
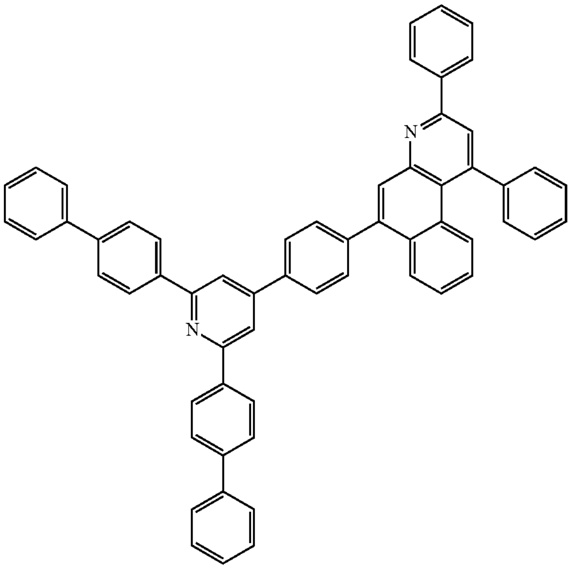

-continued
405
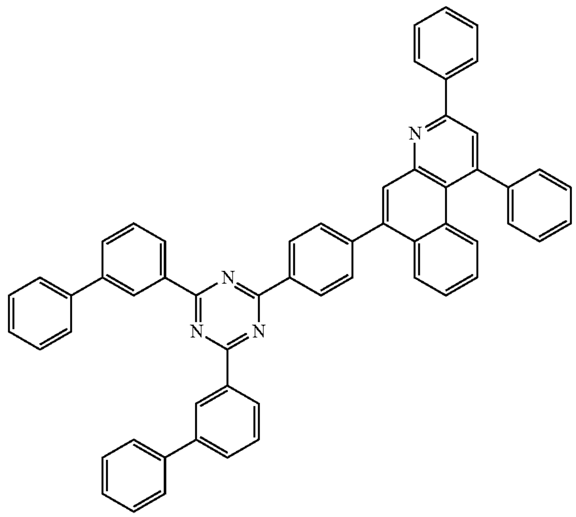
406
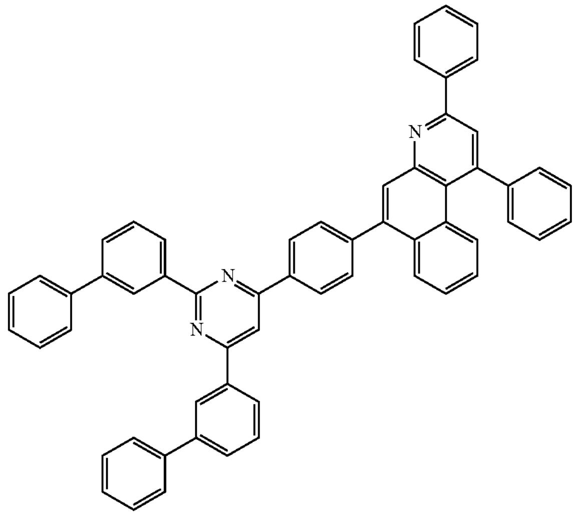
407
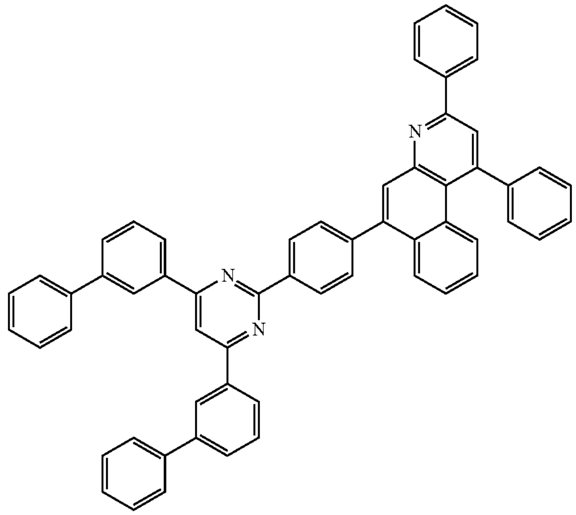
-continued
408
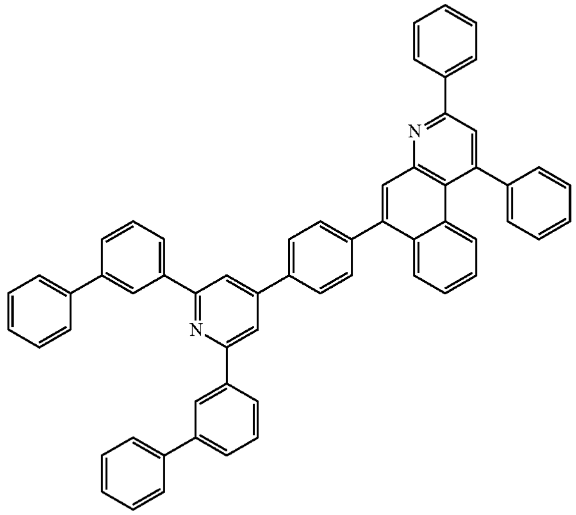
409
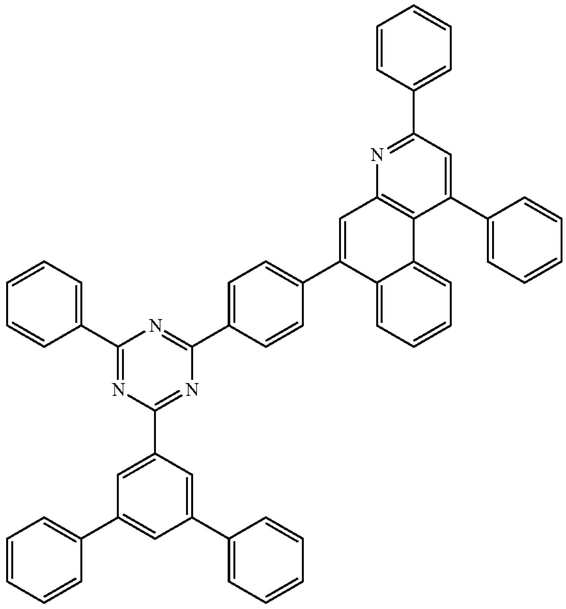

410
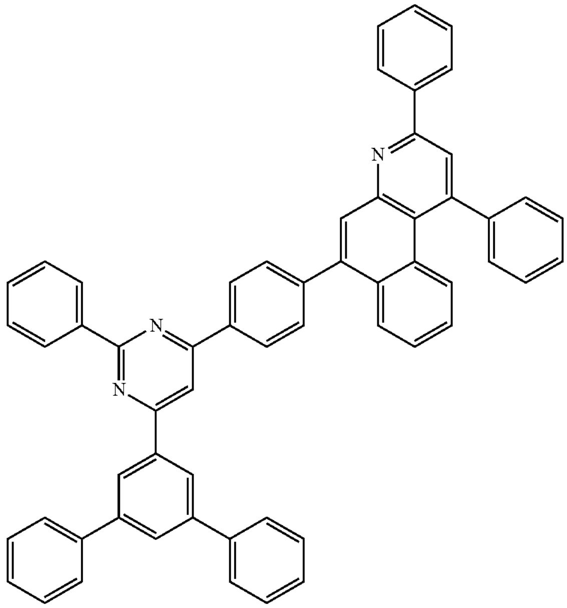
411
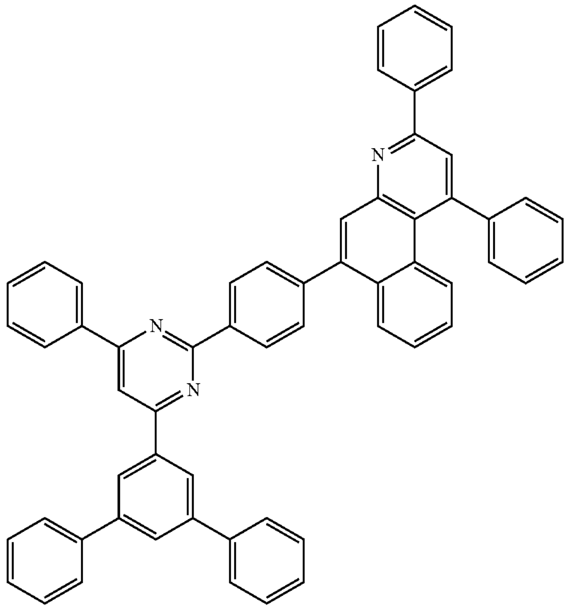
412
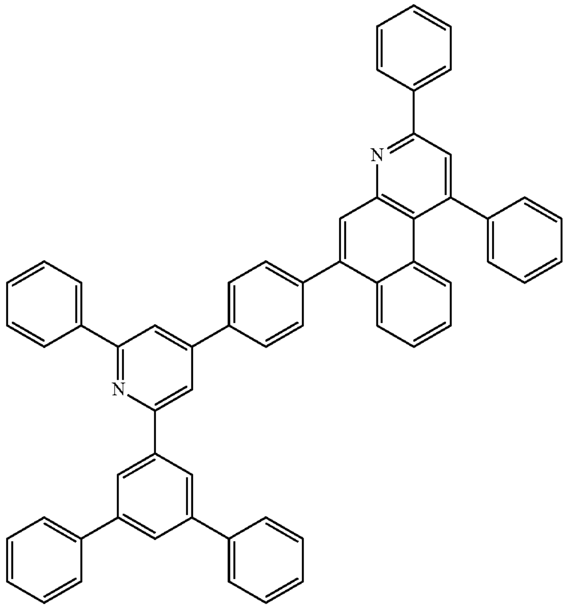
413
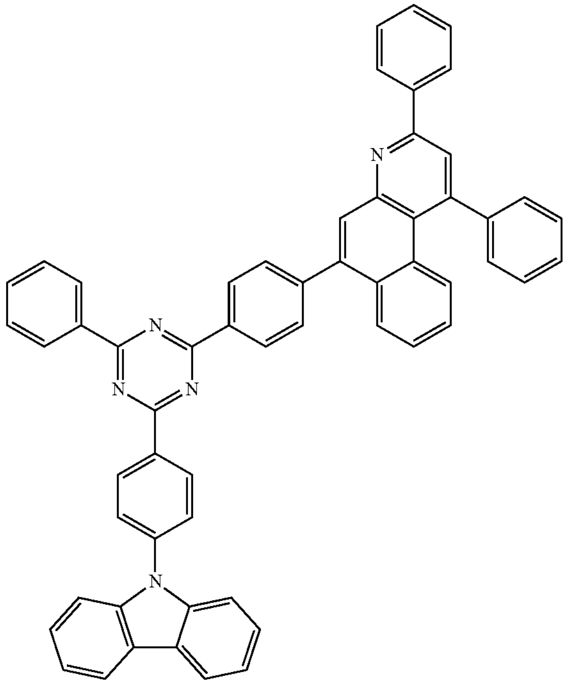

-continued
414
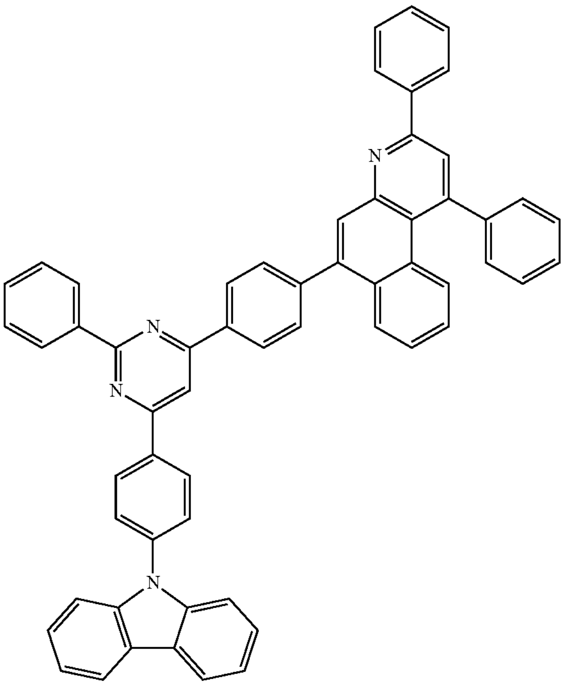
415
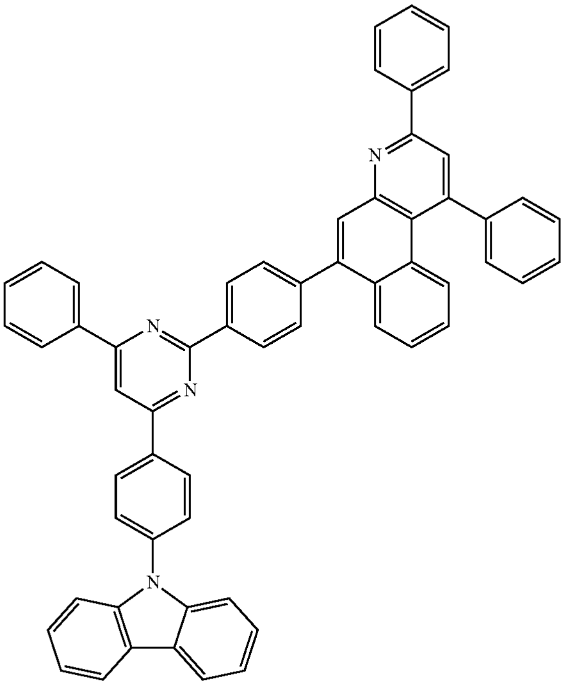
-continued
416
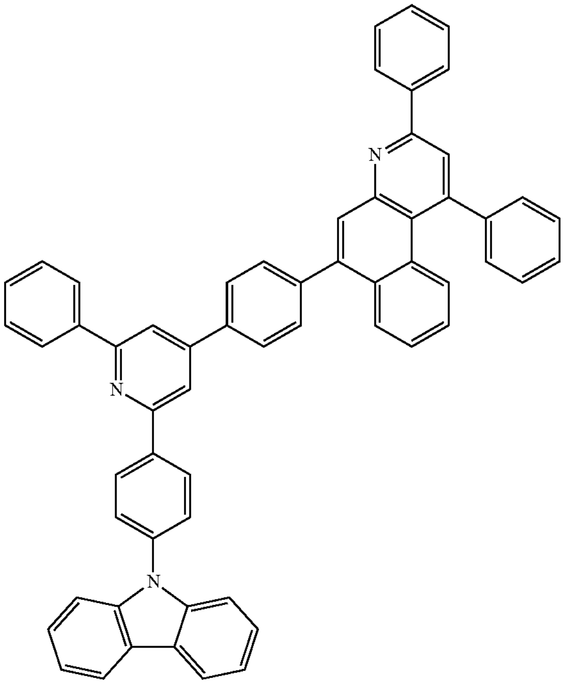
417
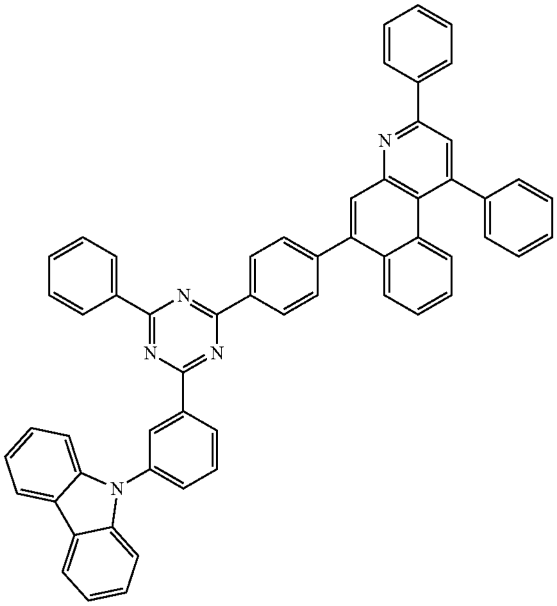

-continued
418
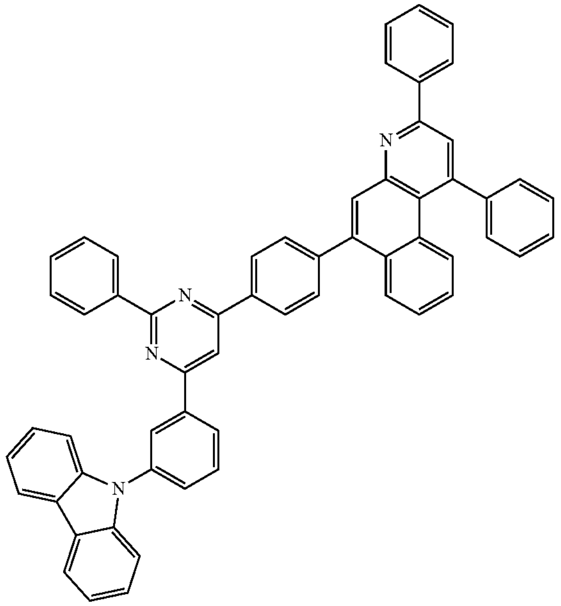
419
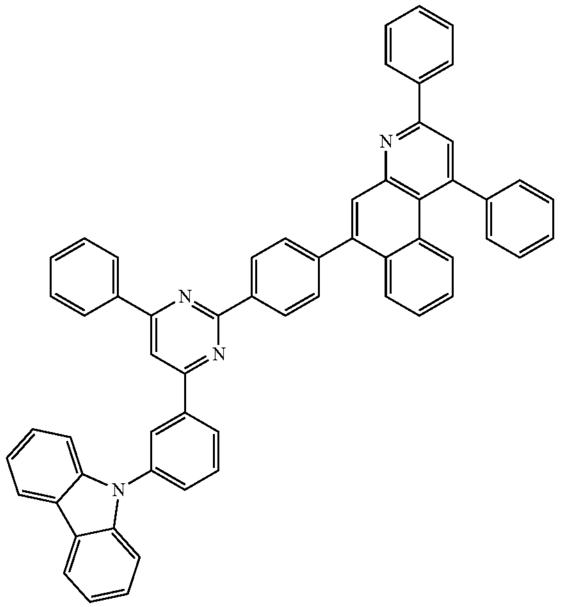
-continued
420
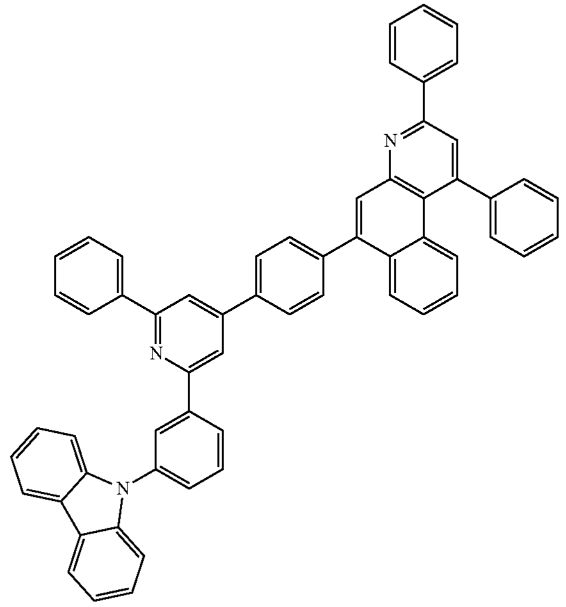
421
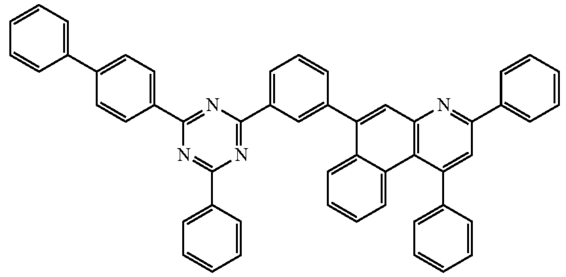
422
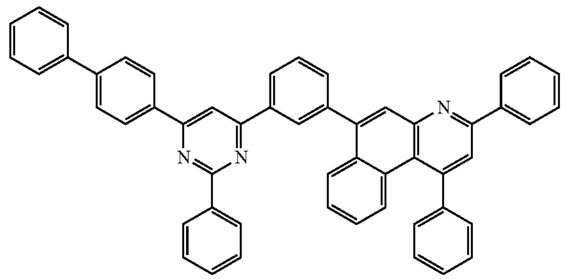
423
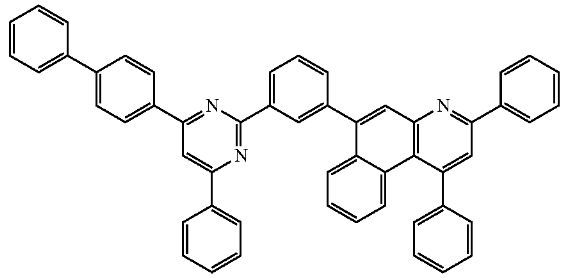

-continued
424
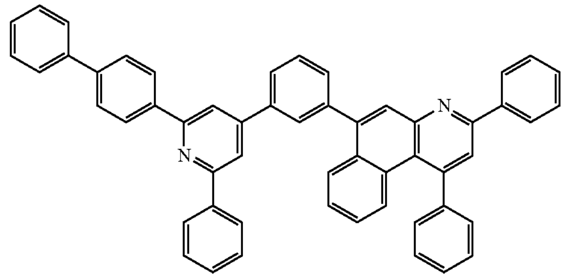
425
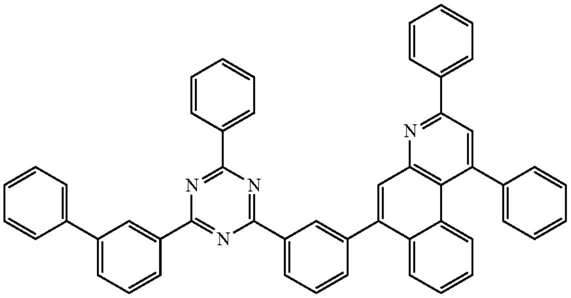
426
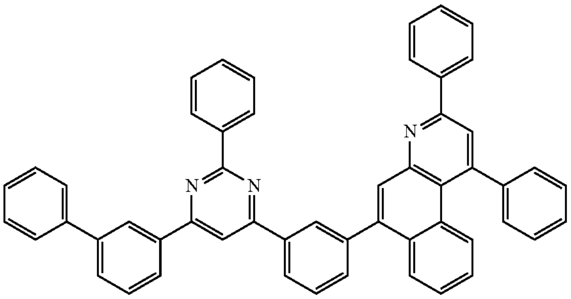
427
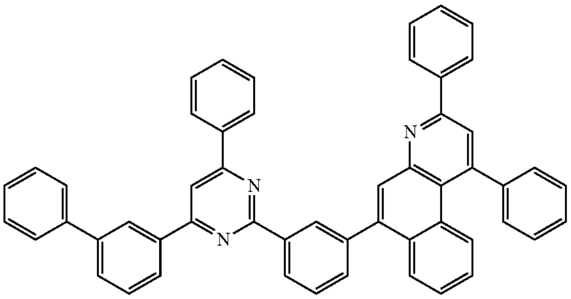
428
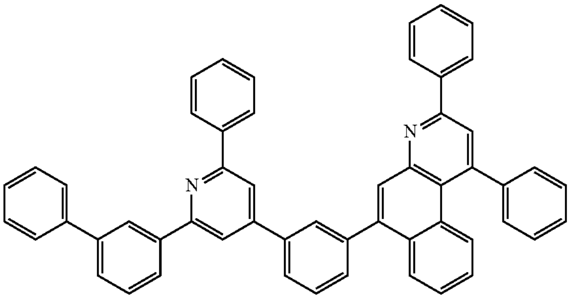
-continued
429
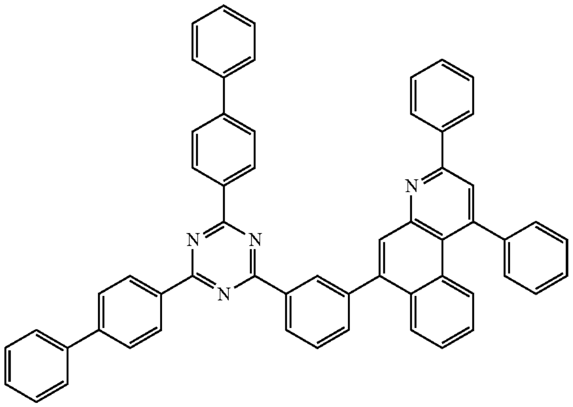
430
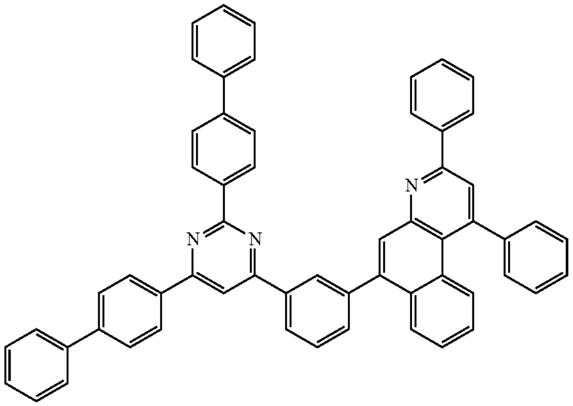
431
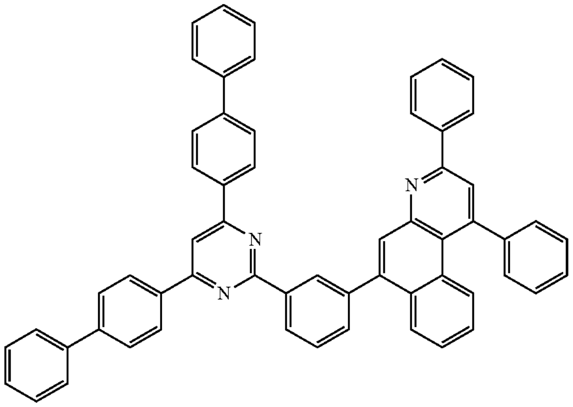

-continued
432
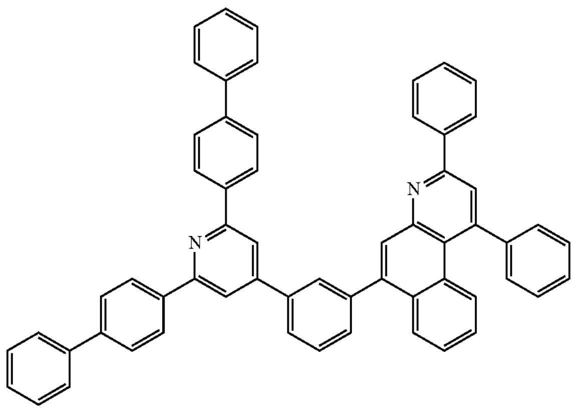
433
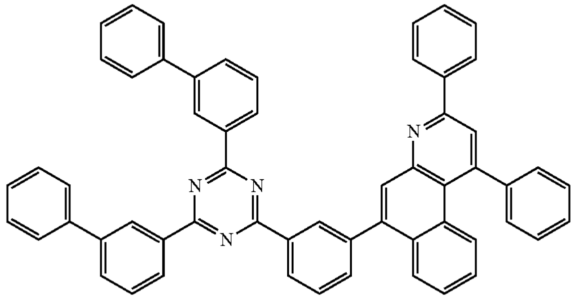
434
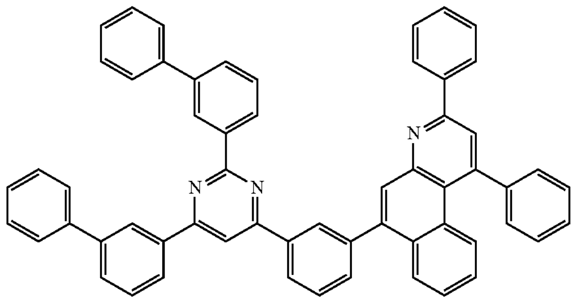
435
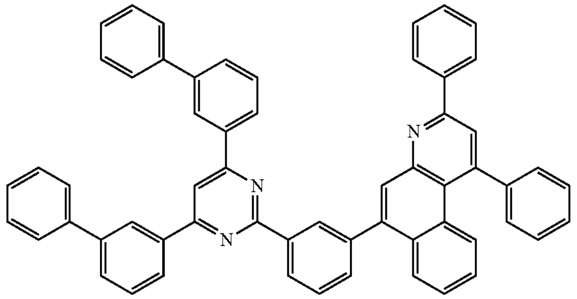
-continued
436
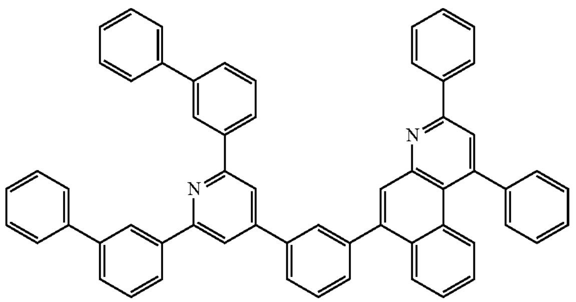
437
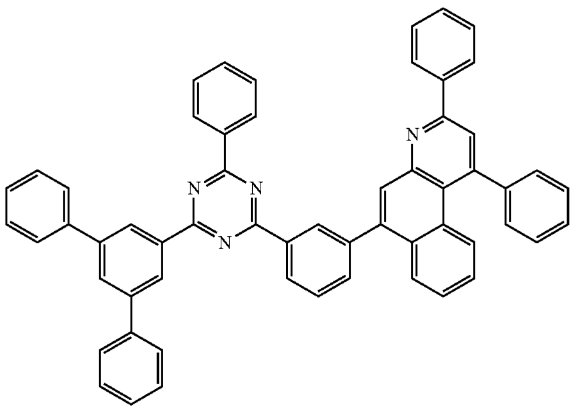
438
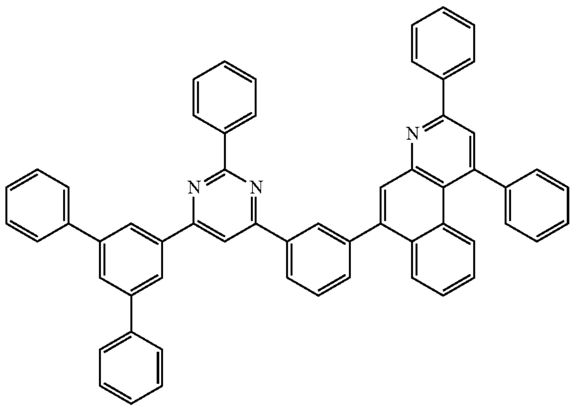
439
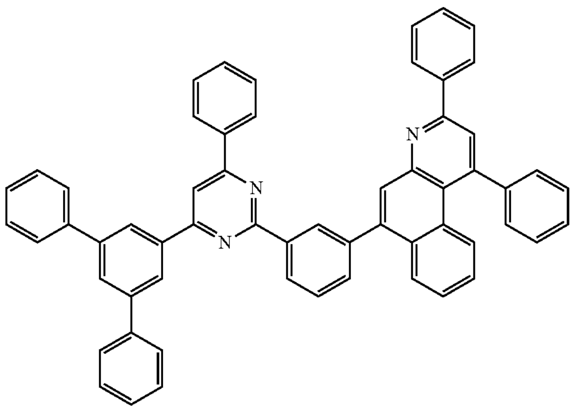

-continued
440
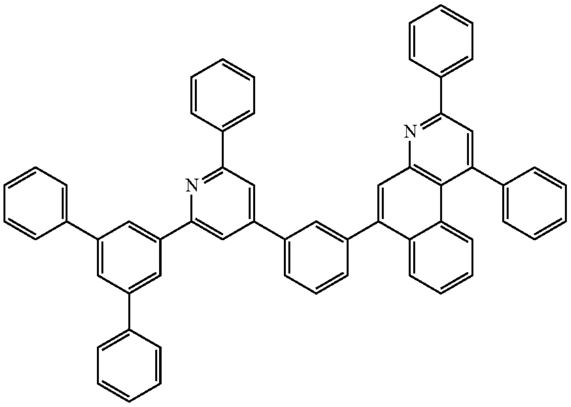
441
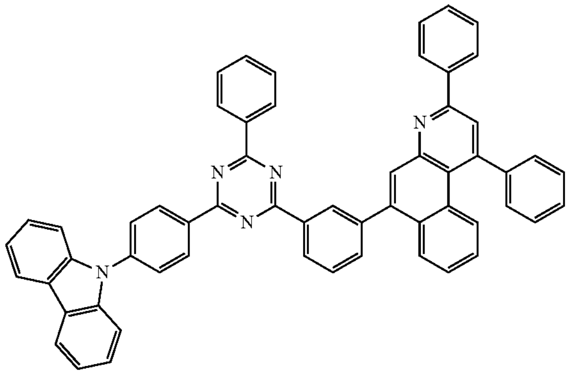
442
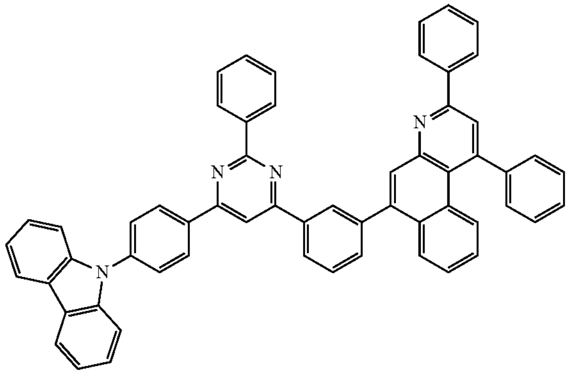
443
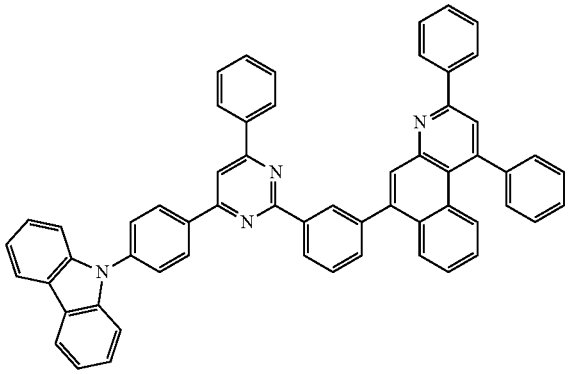
-continued
444
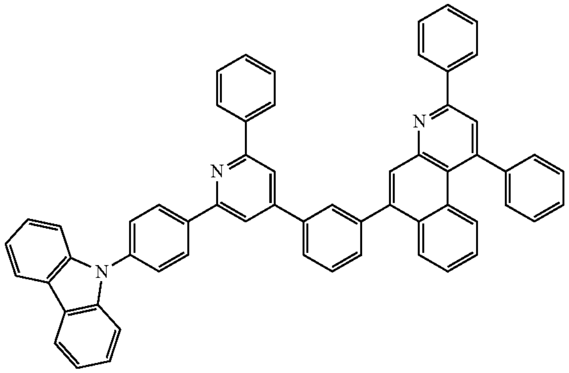
445
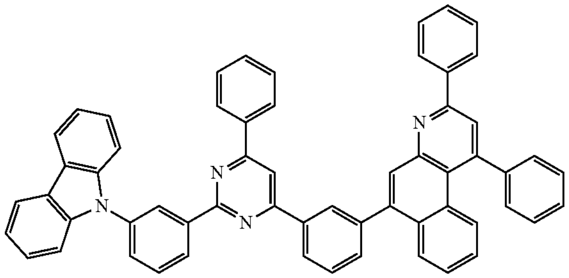
446
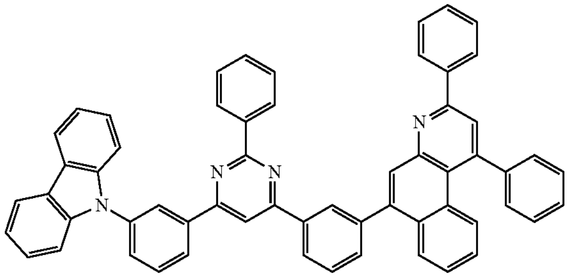
447
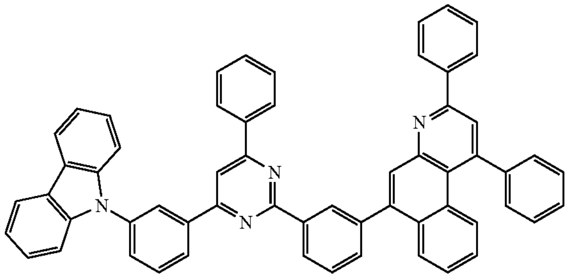
448
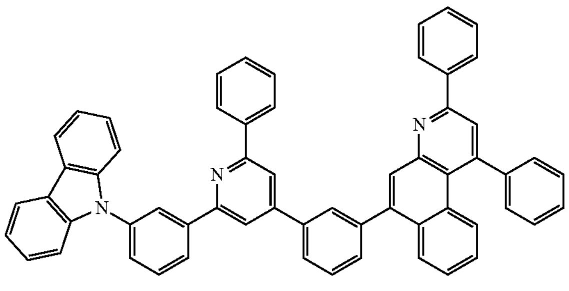

-continued
449
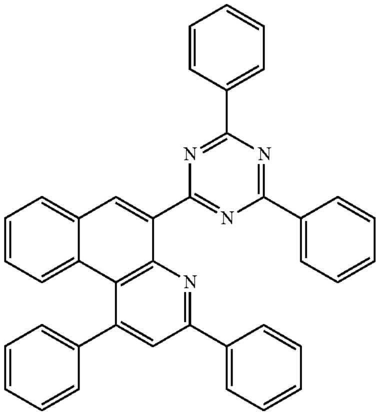
452
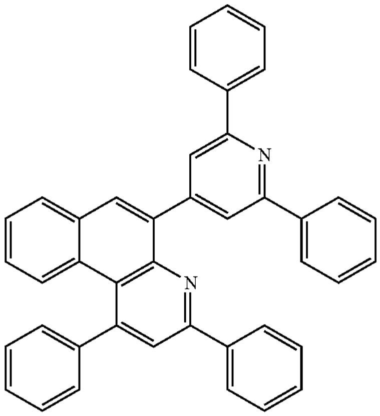
450
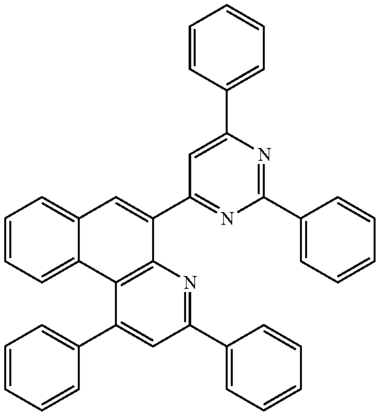
453
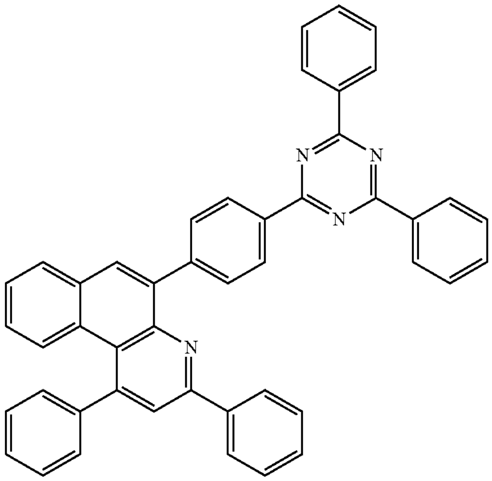
451
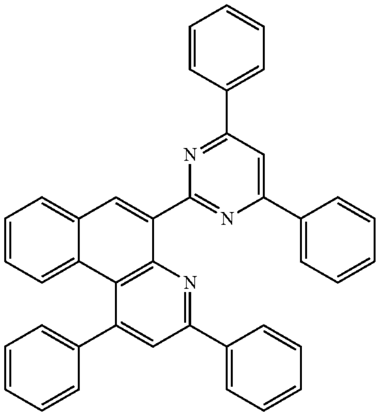
454
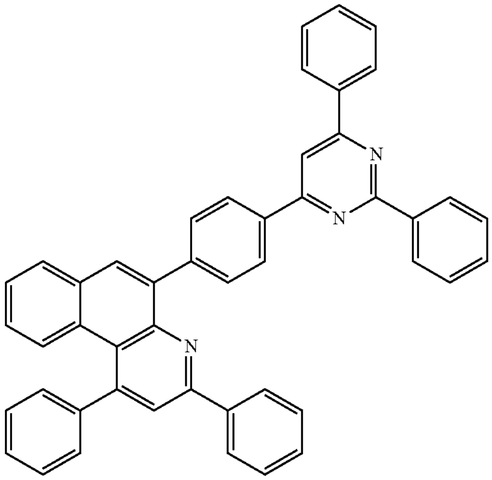

-continued
455
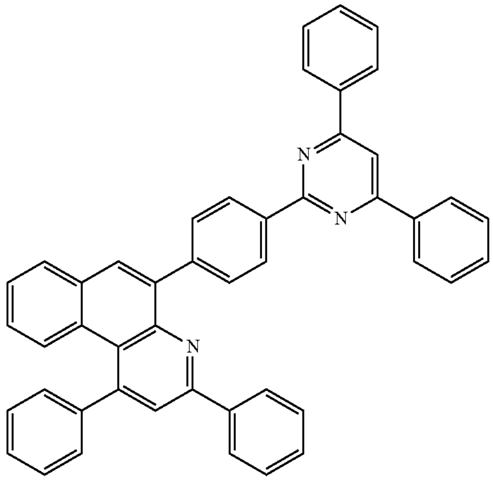
456
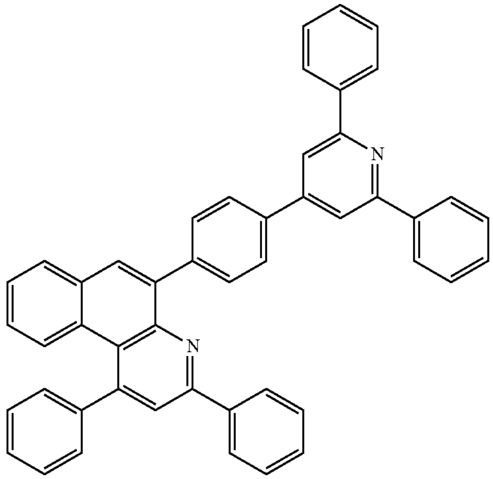
457
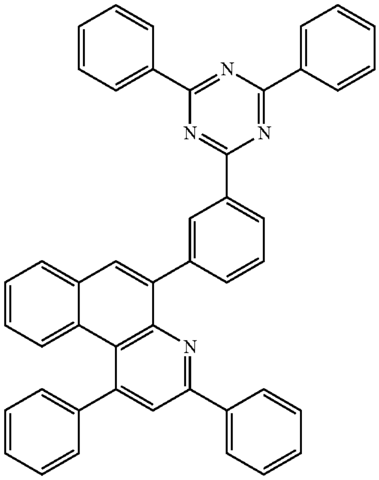
-continued
458
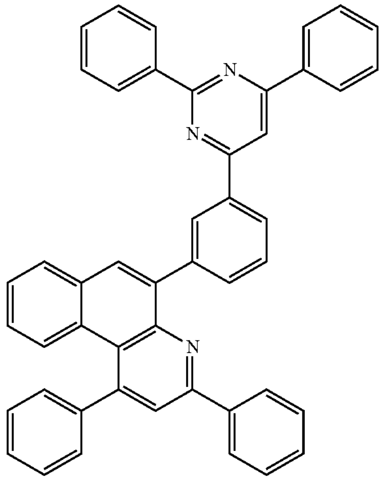
459
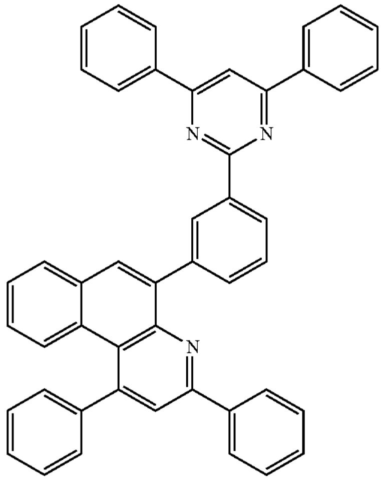
460
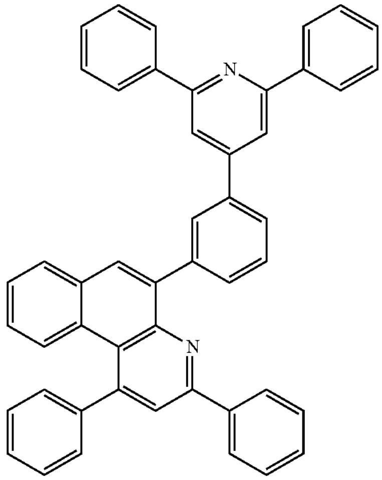

-continued
461
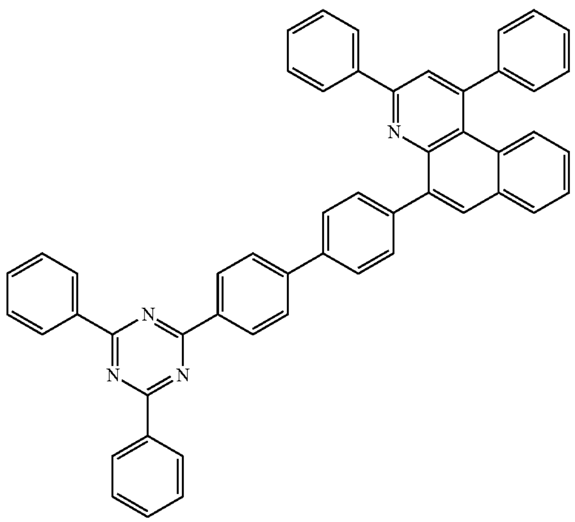
462
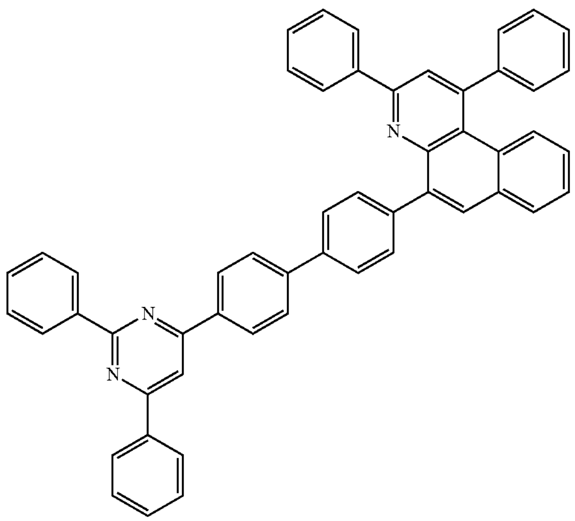
463
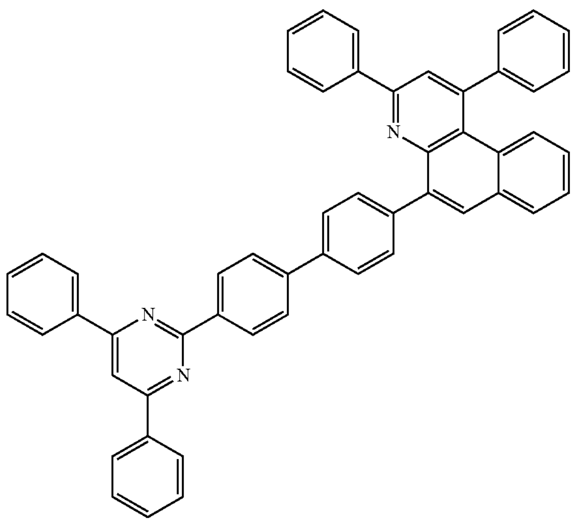
-continued
464
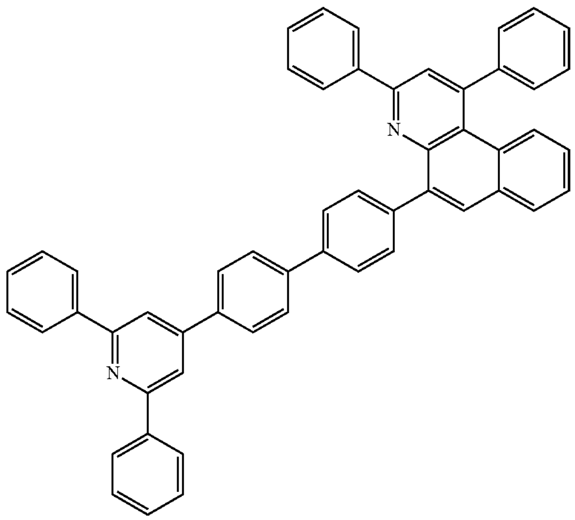
465
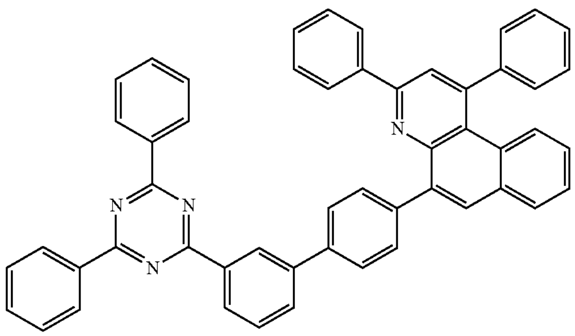
466
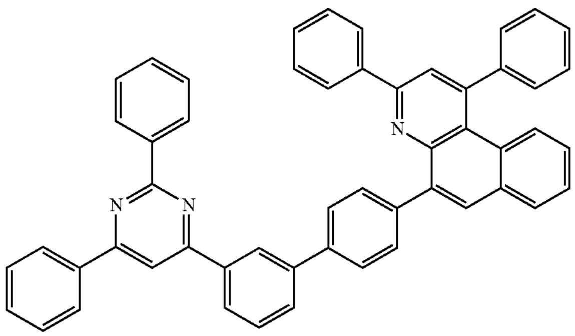
467
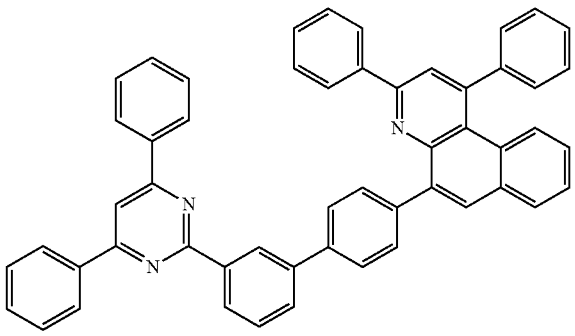

468
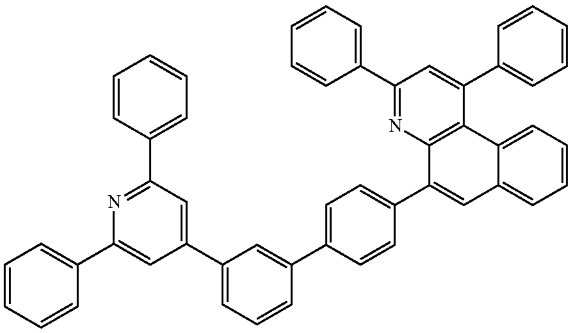
469
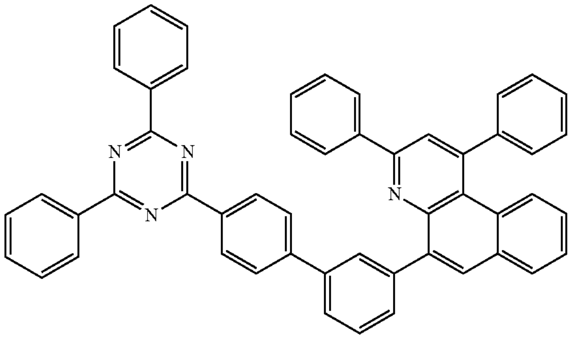
470
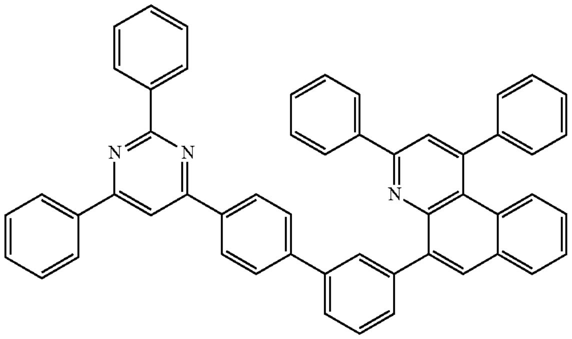
471
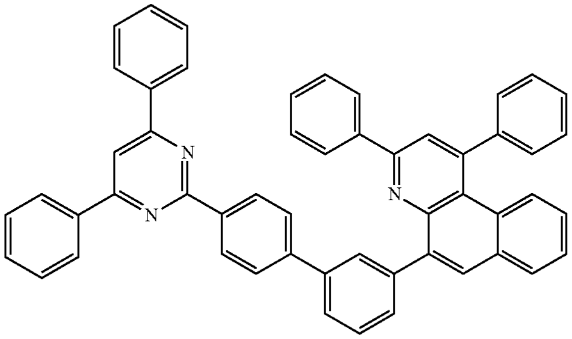
472
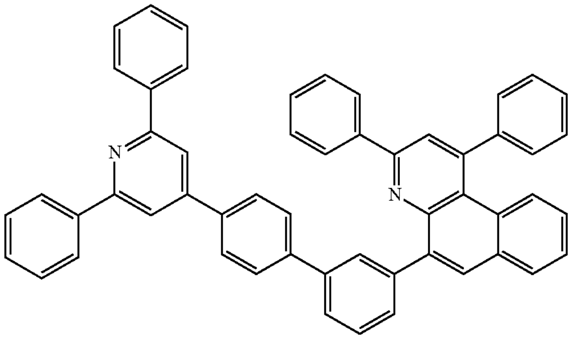
473
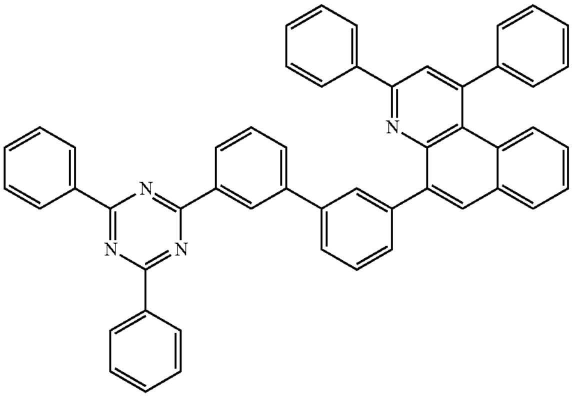
474
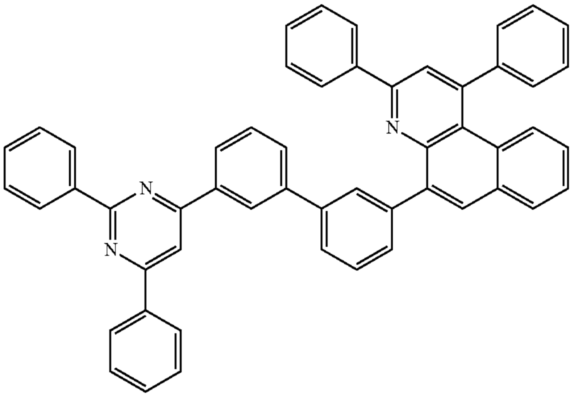
475
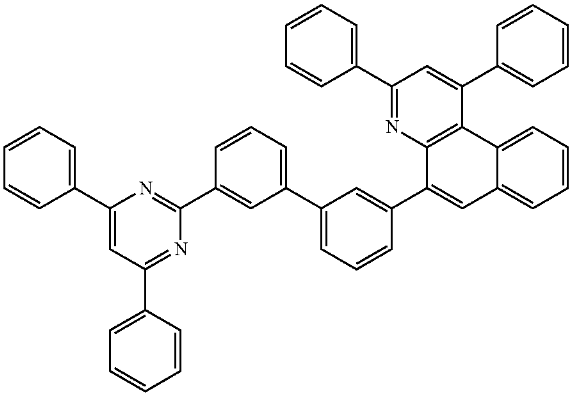

-continued
476
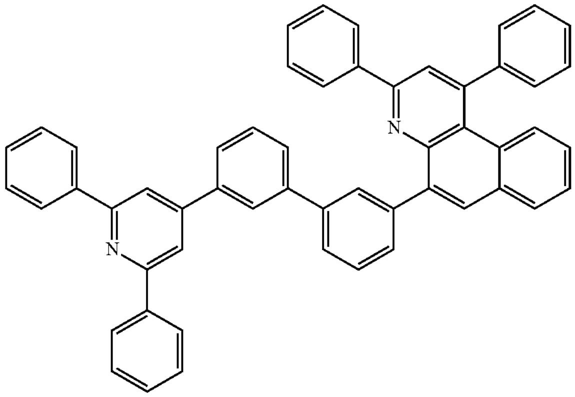
477
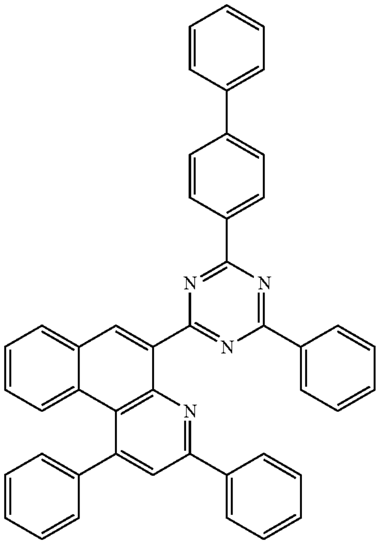
478
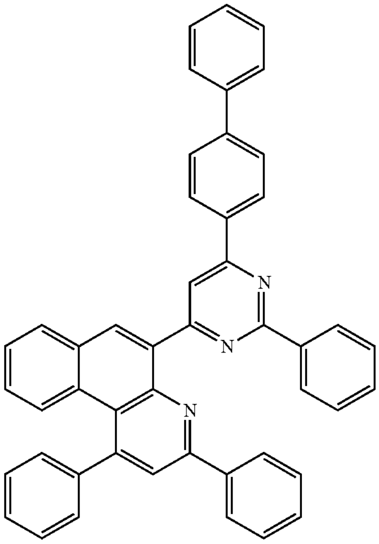
-continued
479
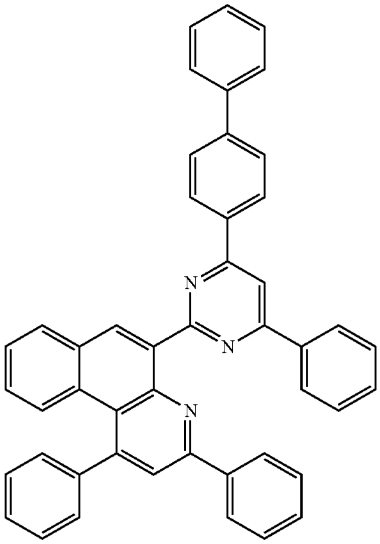
480
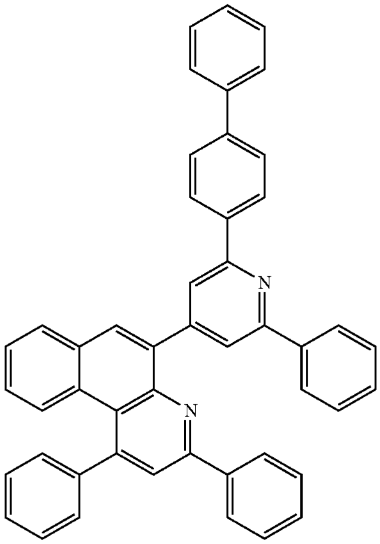
481
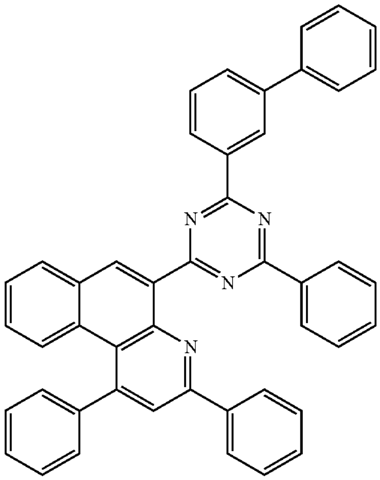

-continued
482
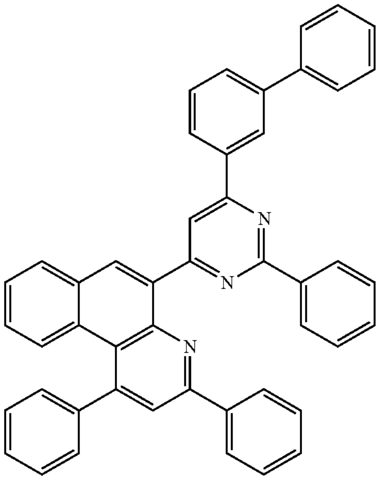
483
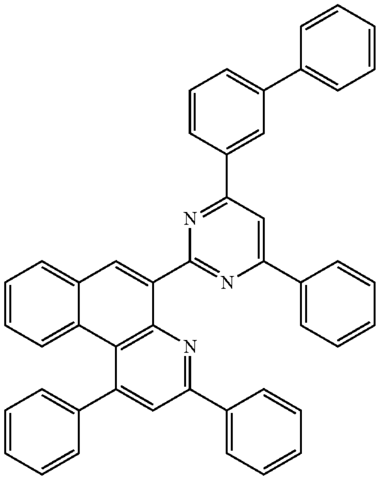
484
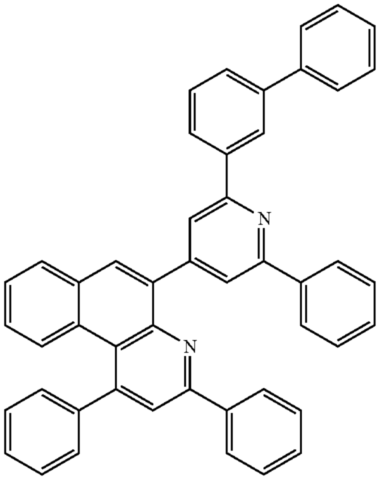
-continued
485
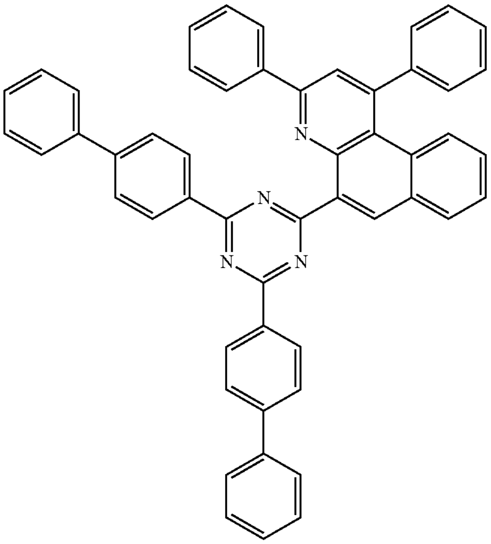
486
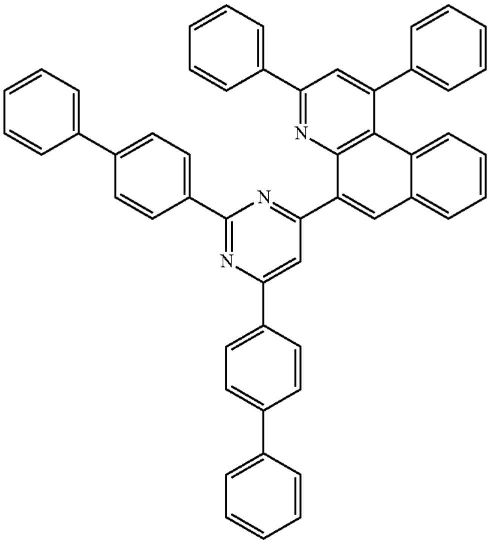

-continued
487
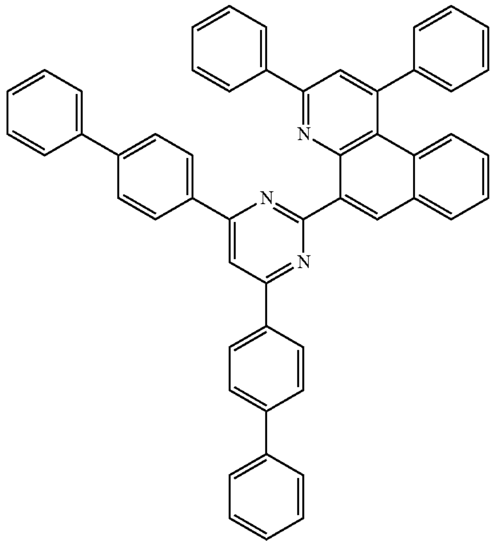
488
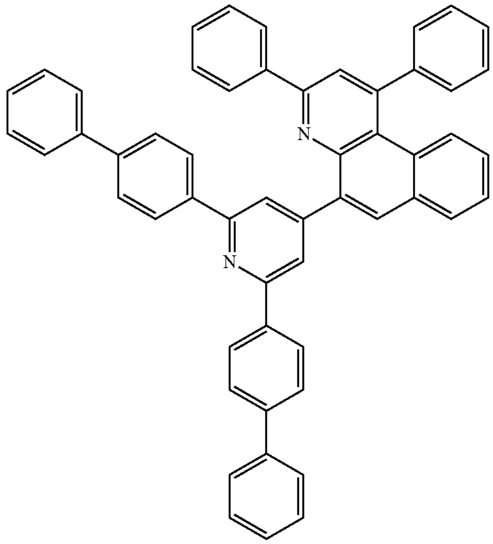
489
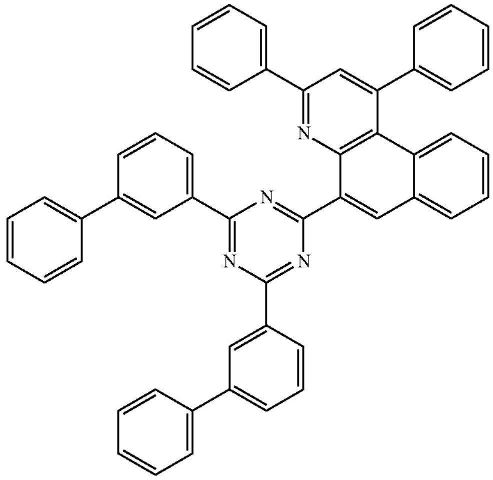
-continued
490
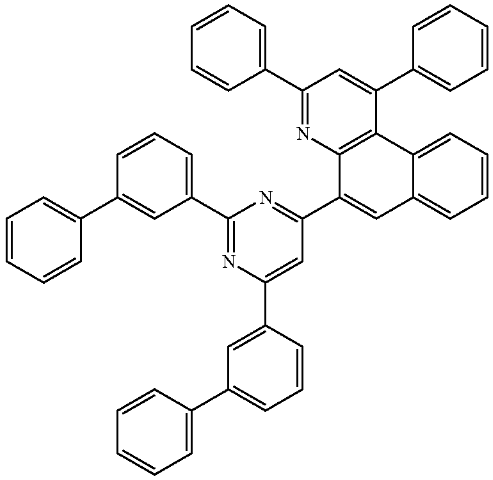
491
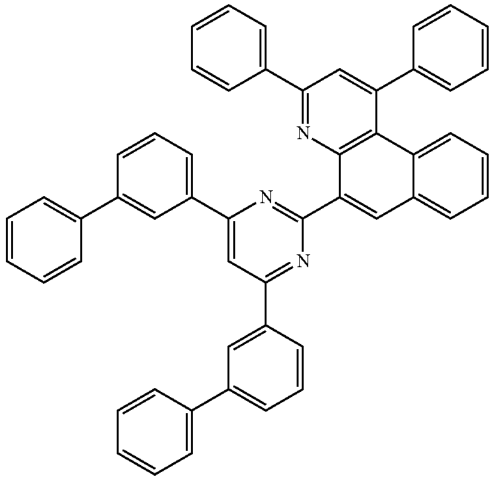
492
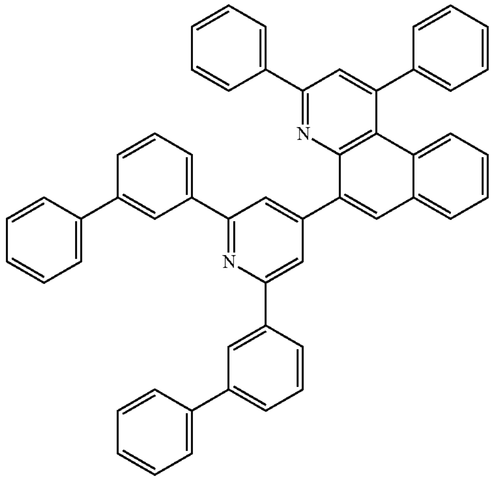

-continued
493
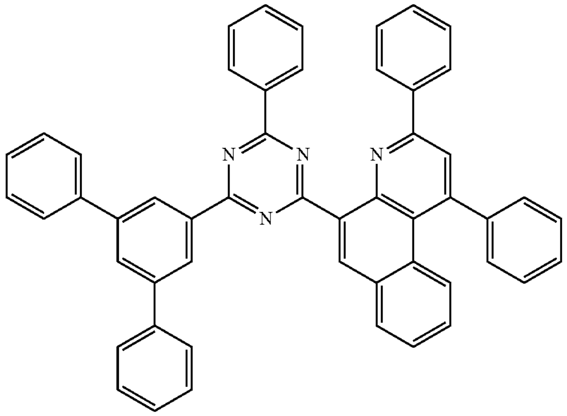
494
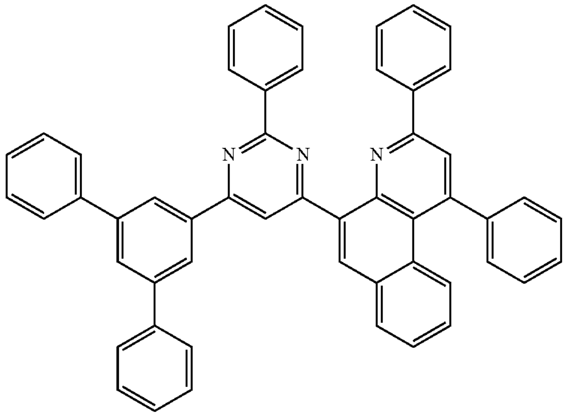
495
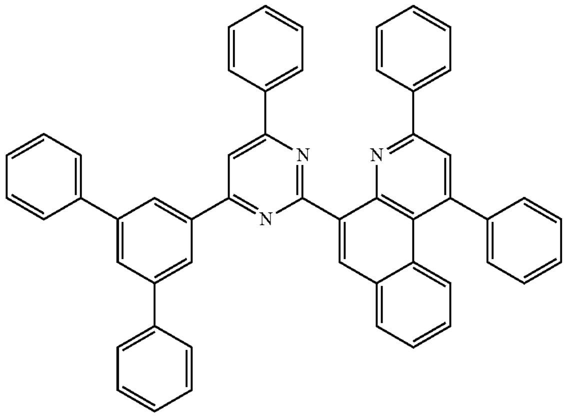
-continued
496
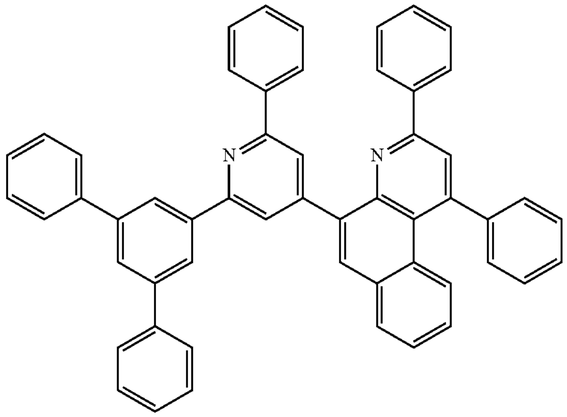
497
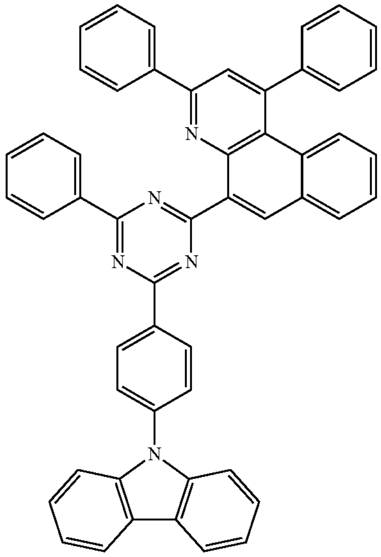
498
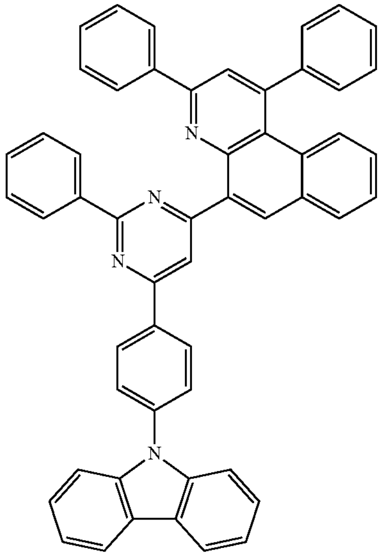

-continued
499
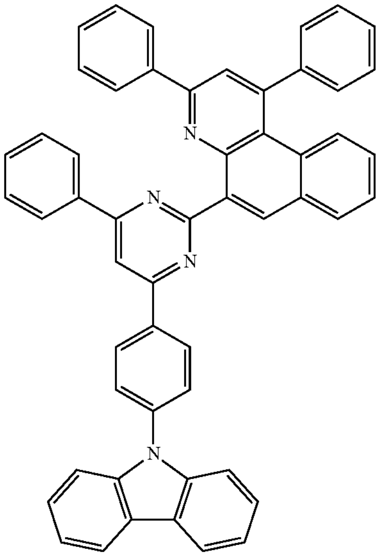
500
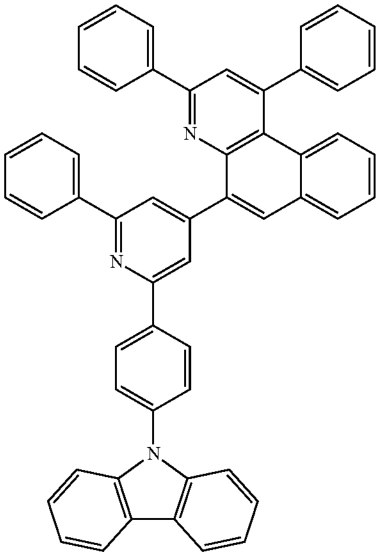
501
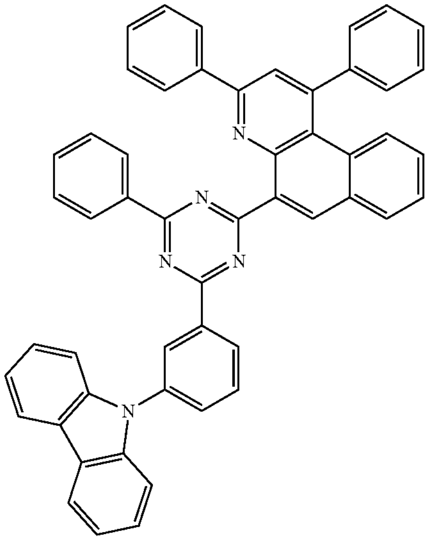
-continued
502
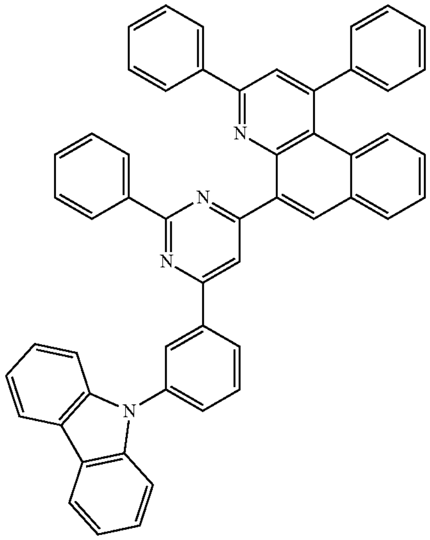
503
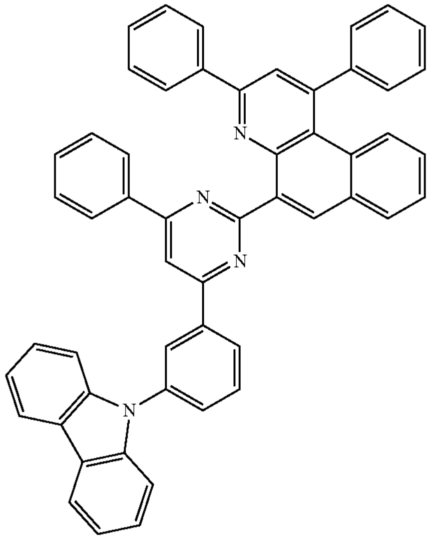
504
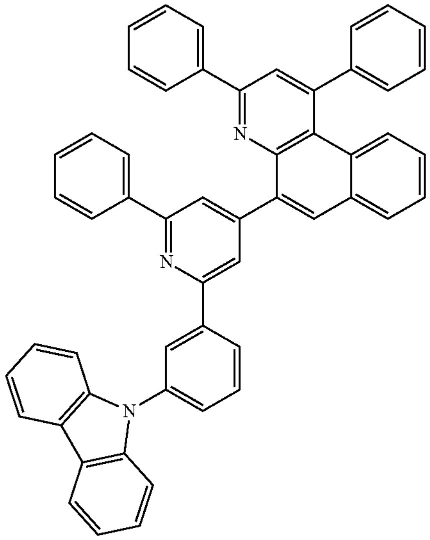

-continued
505
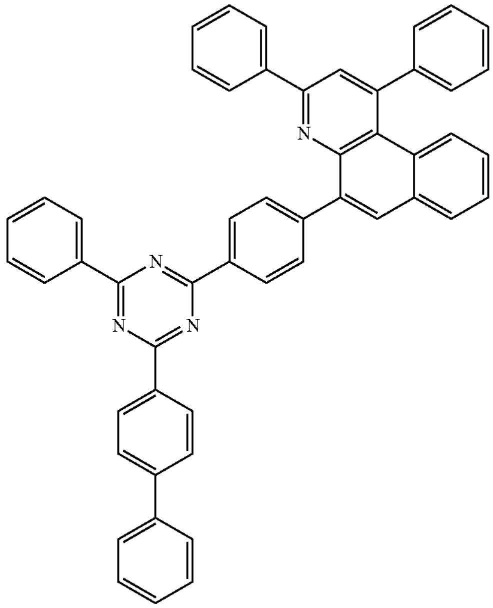
506
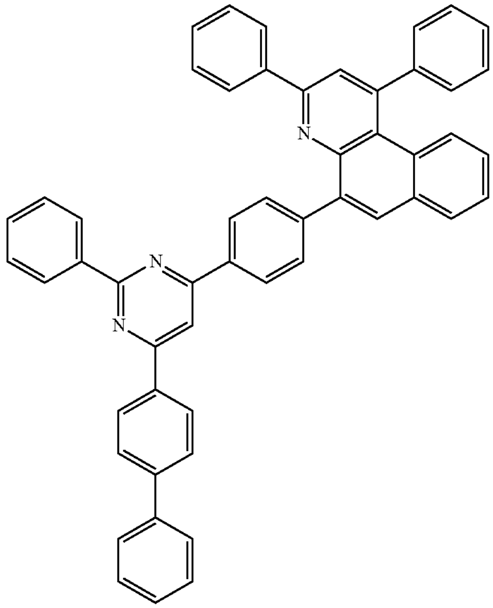
-continued
507
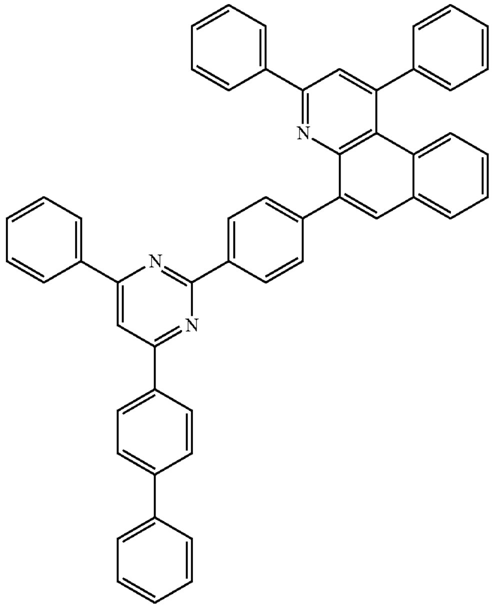
508
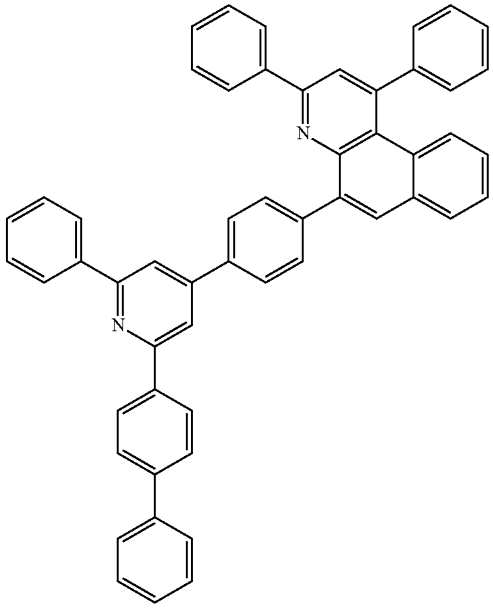

-continued
509
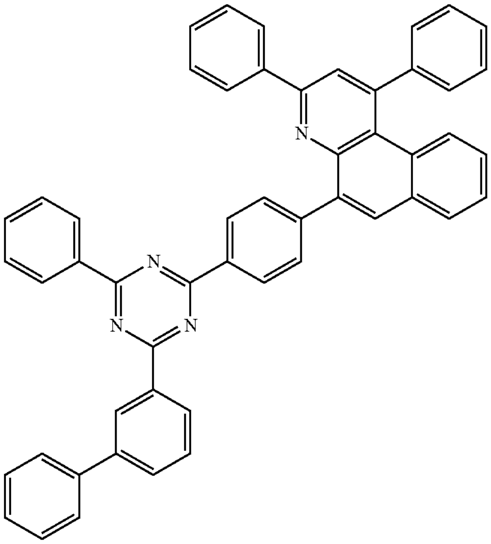
510
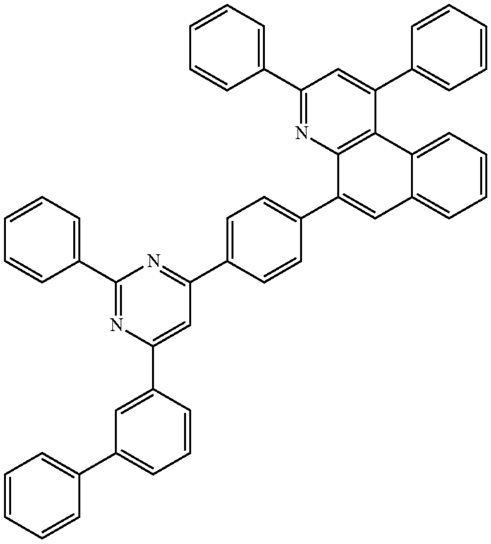
511
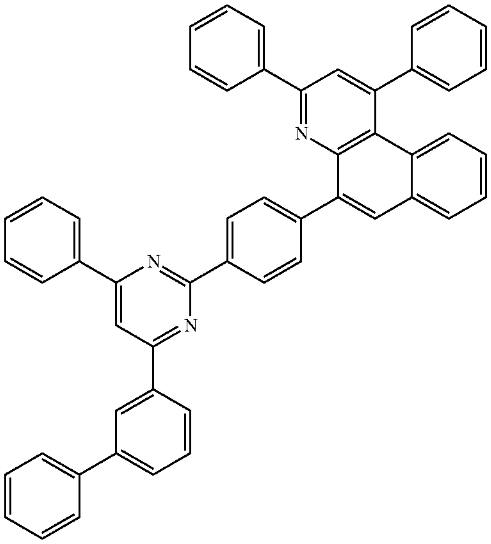
-continued
512
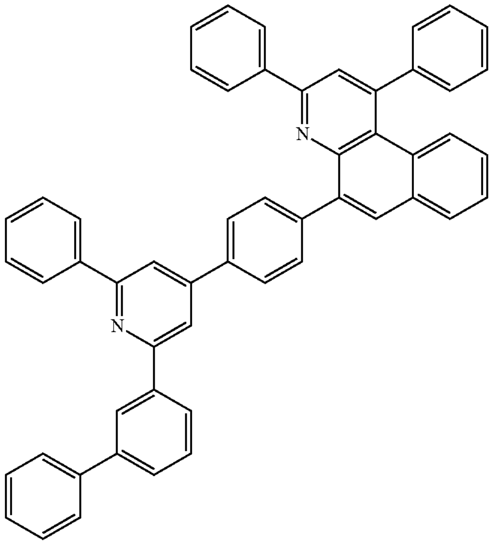
513
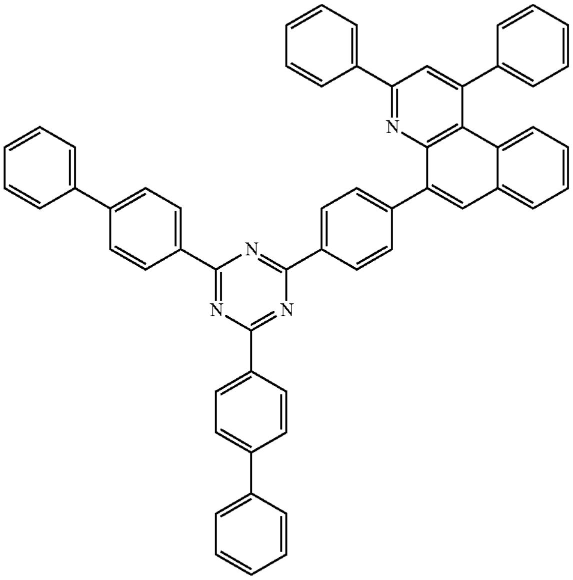

-continued
514
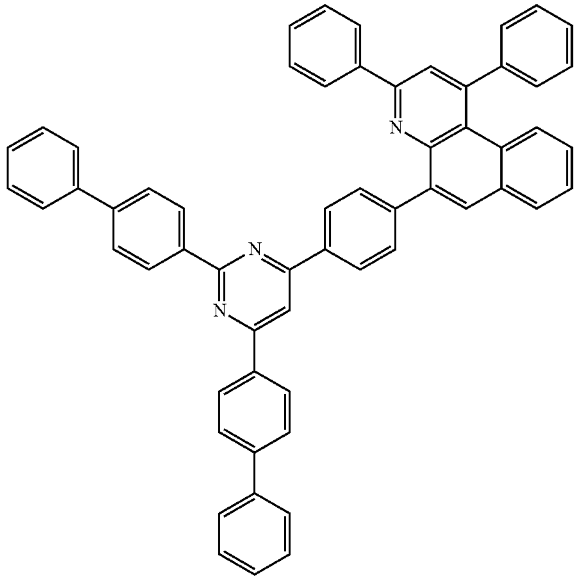
515
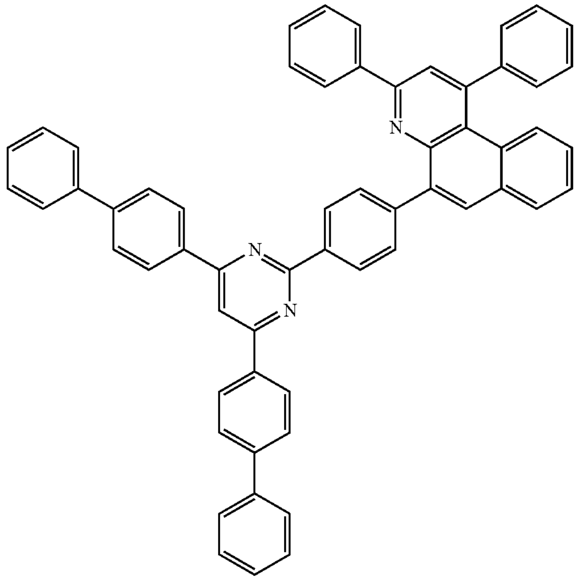
-continued
516
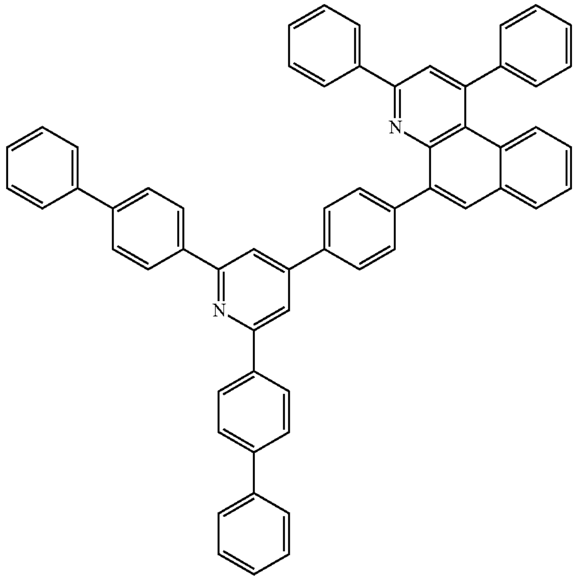
517
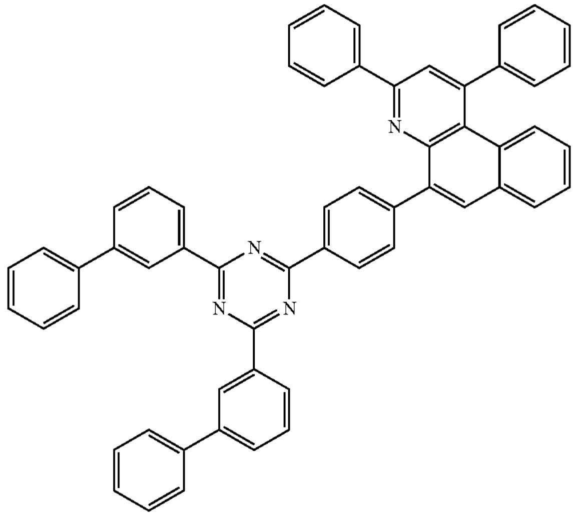

-continued
518
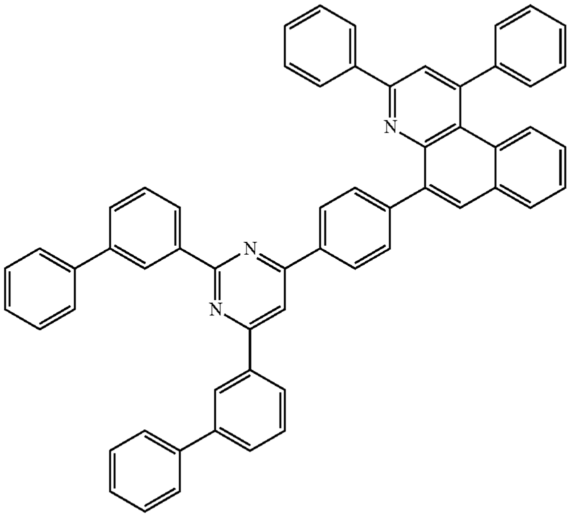
519
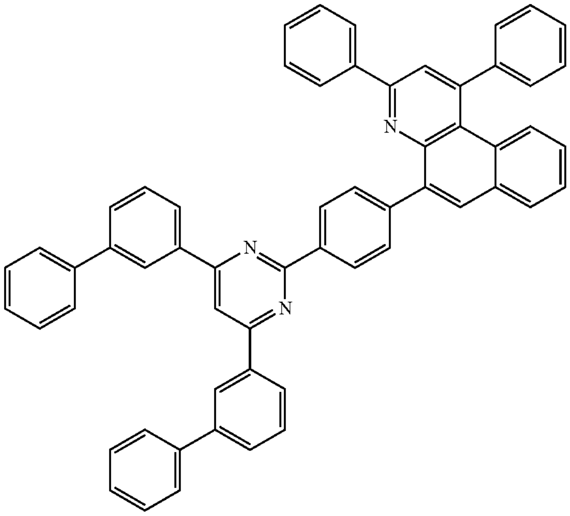
520
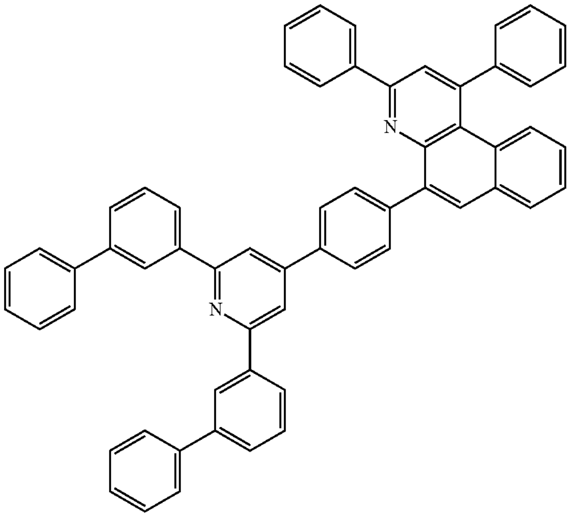
-continued
521
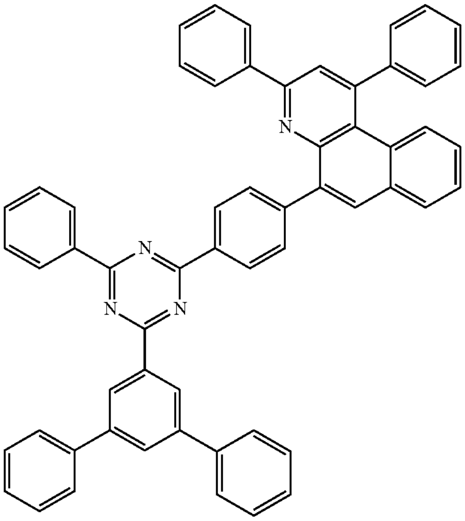
522
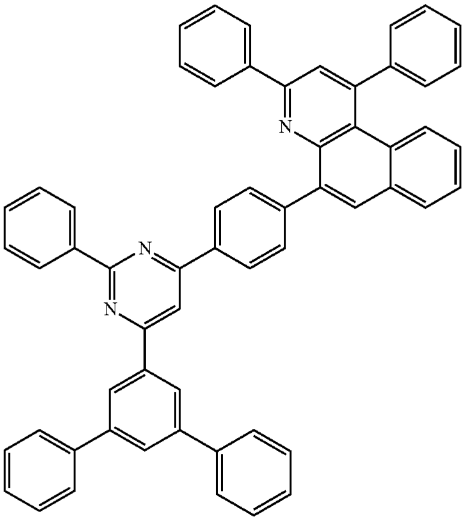
523
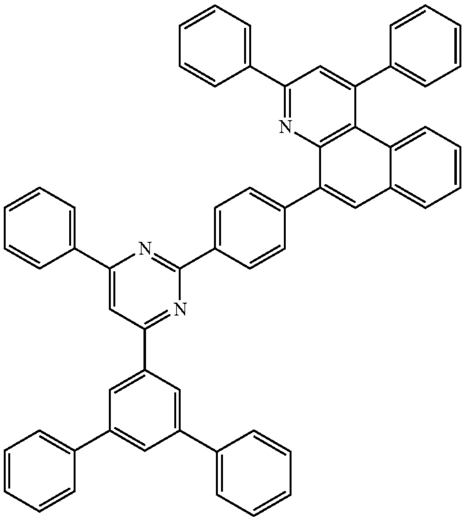

-continued
524
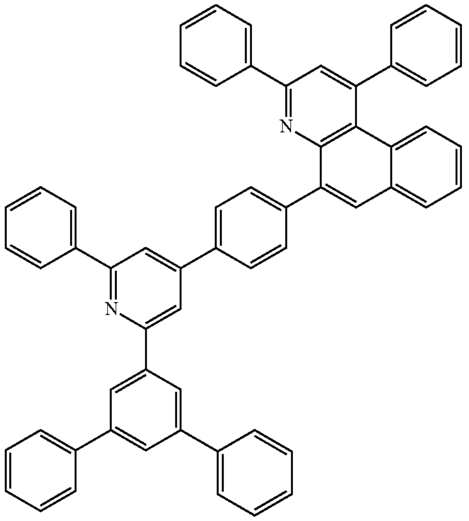
525
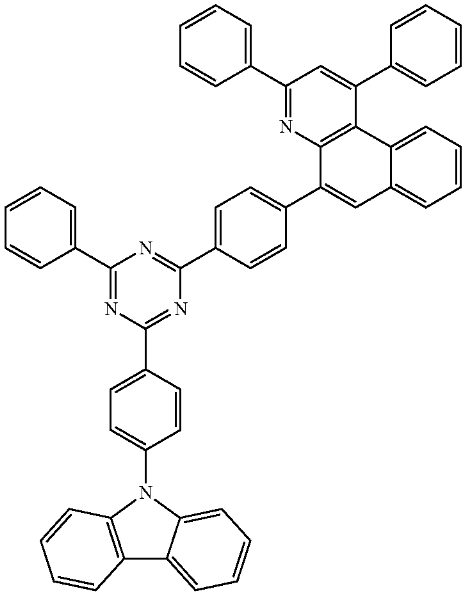
-continued
526
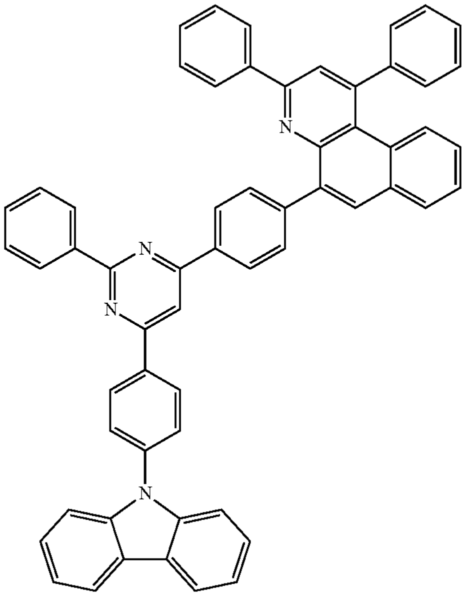
527
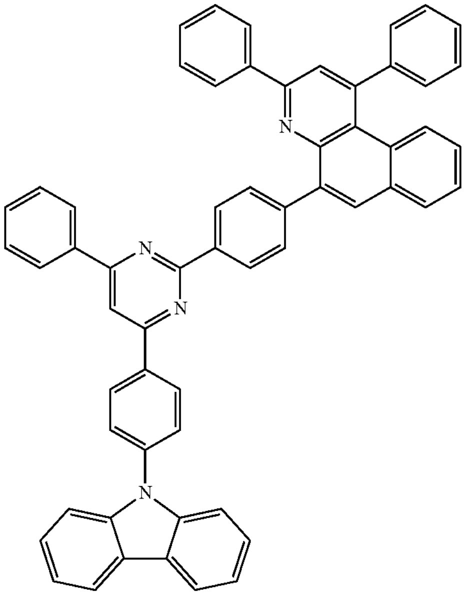

-continued
528
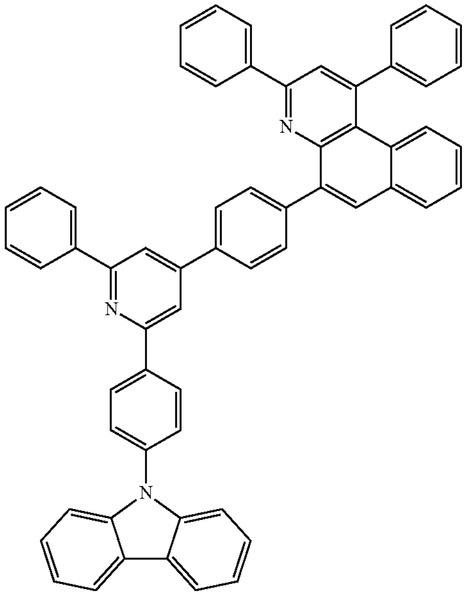
530
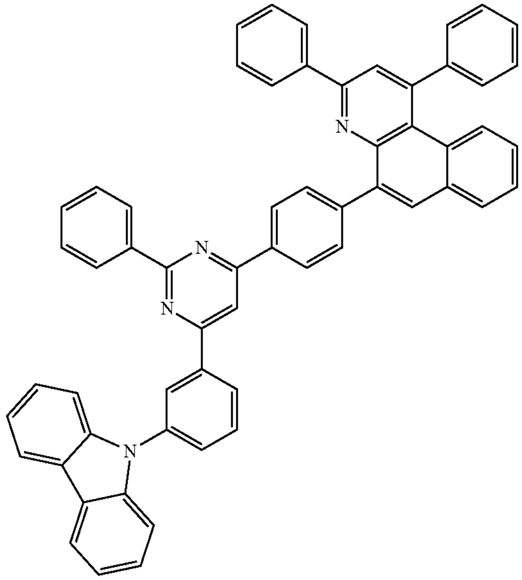
529
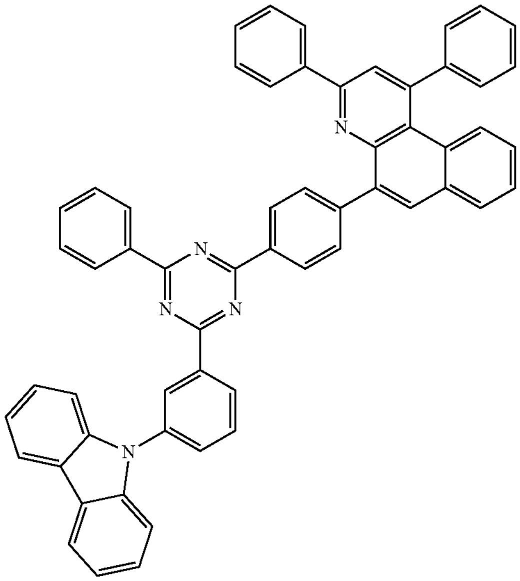
531
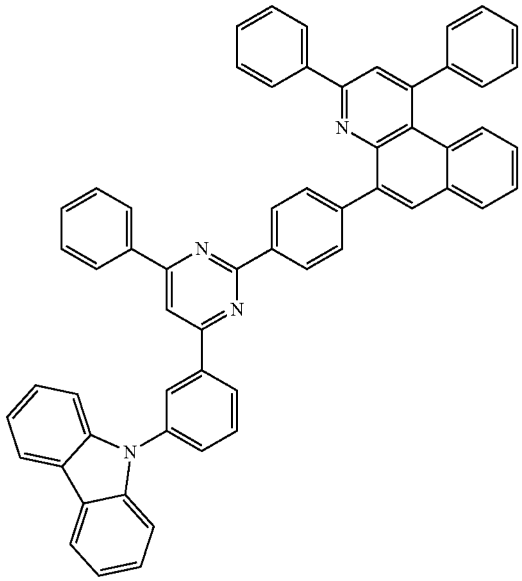

-continued
532
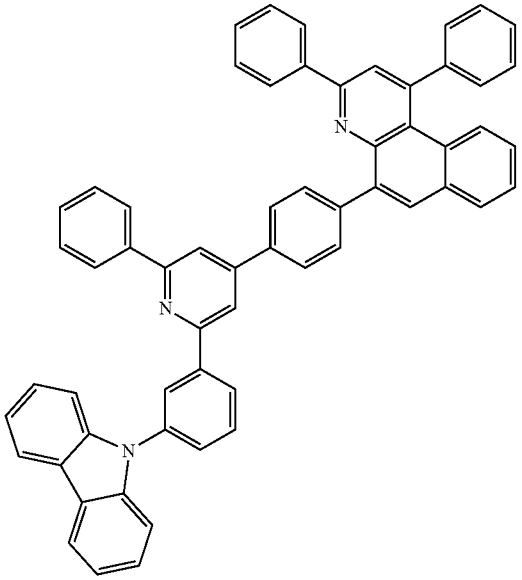
533
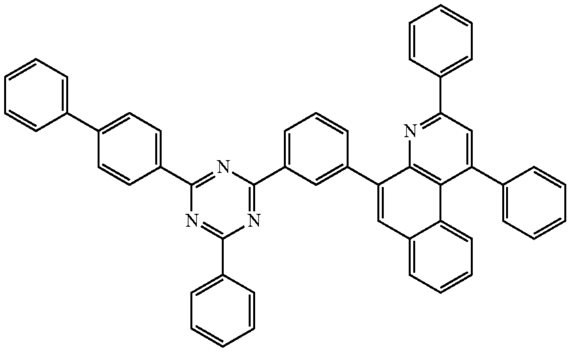
534
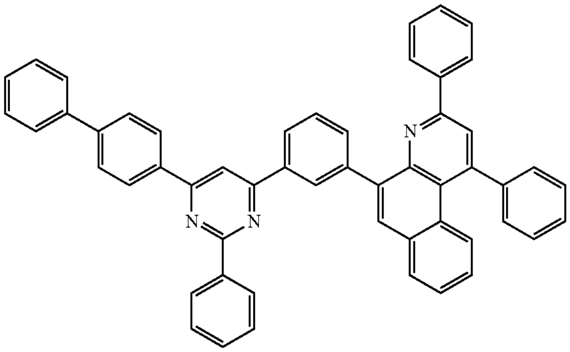
-continued
535
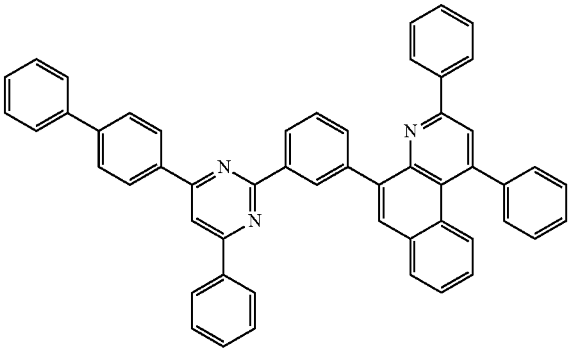
536
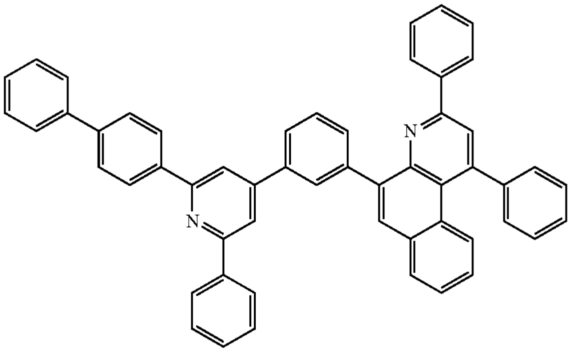
537
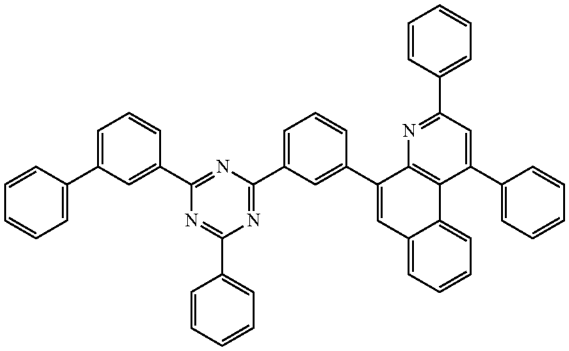
538
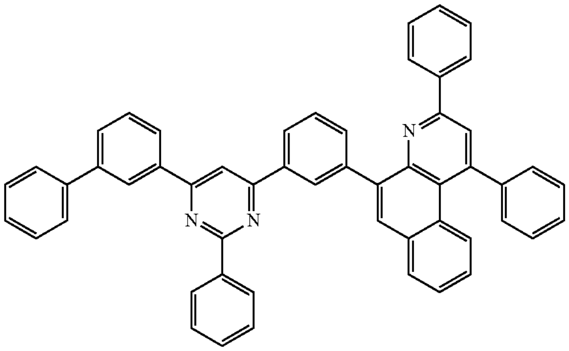

-continued
539
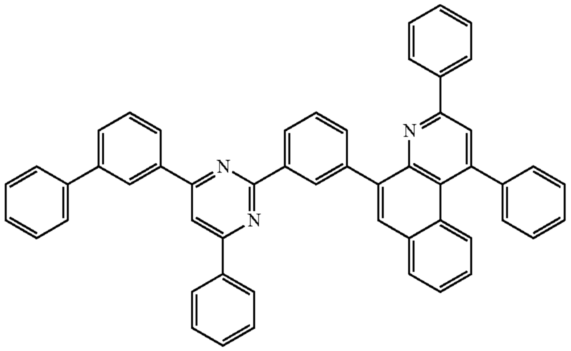
540
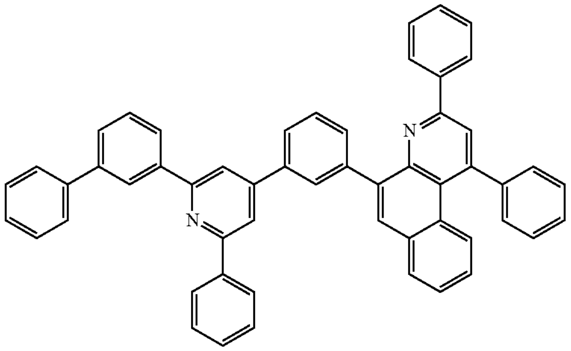
541
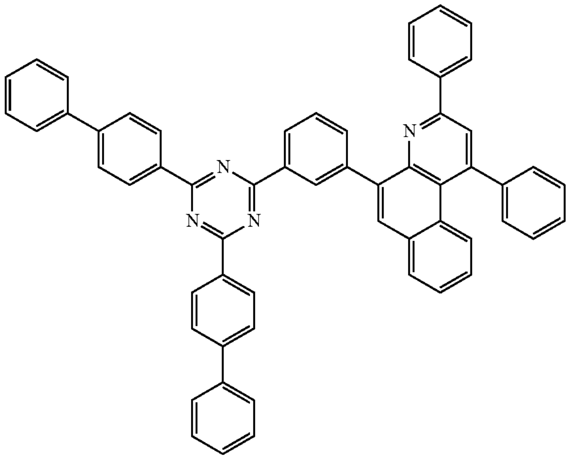
-continued
542
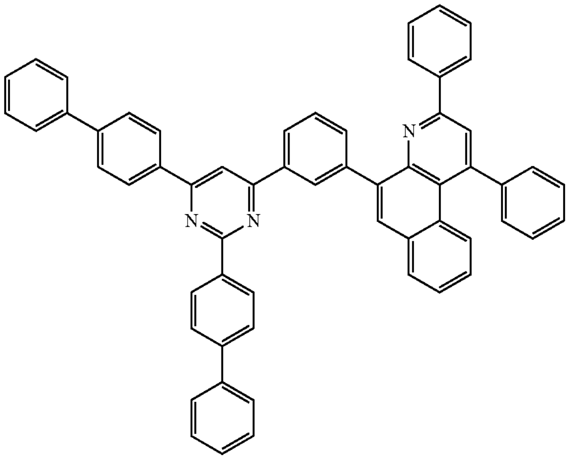
543
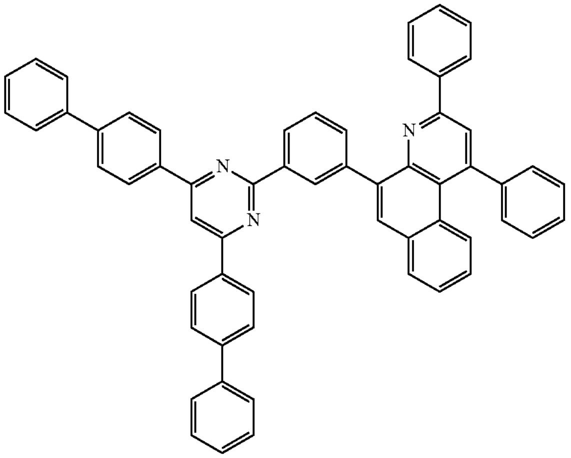
544
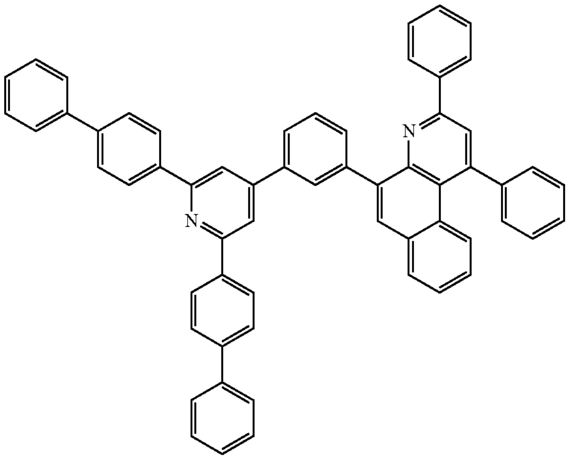

-continued
545
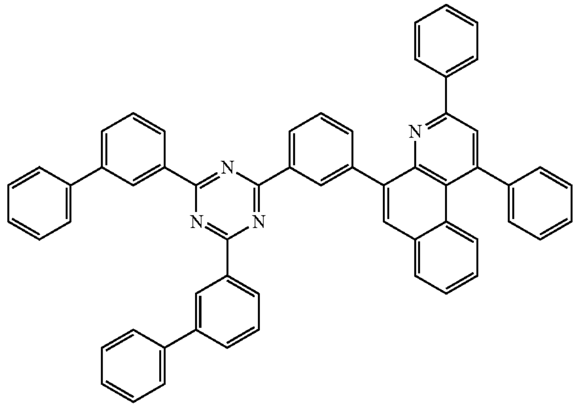
546
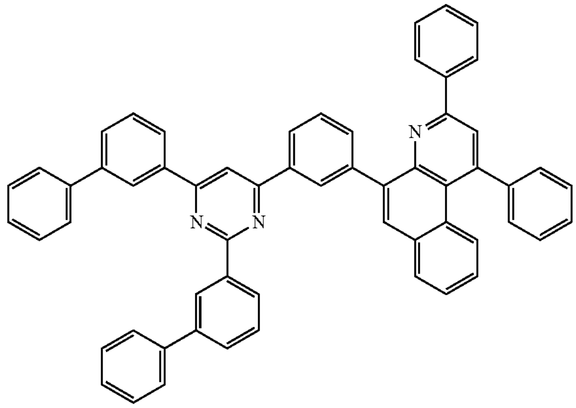
547
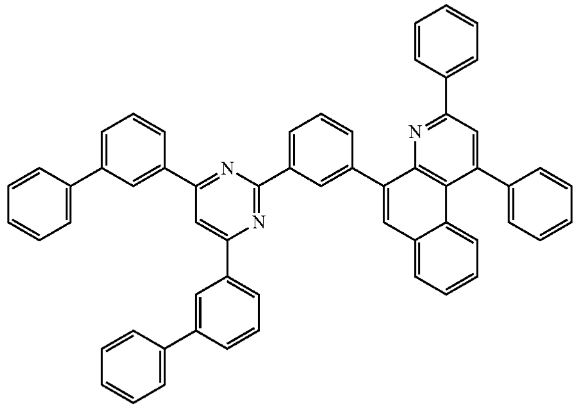
-continued
548
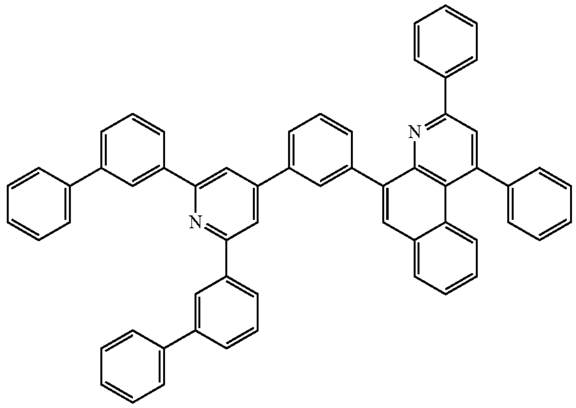
549
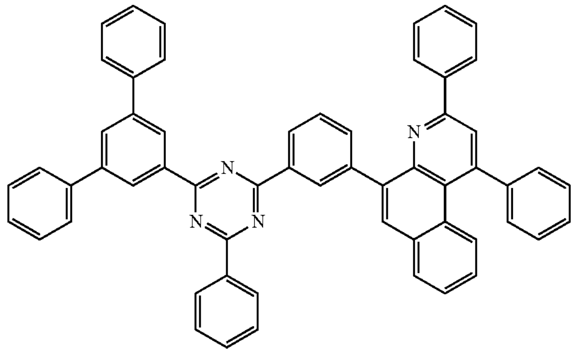
550
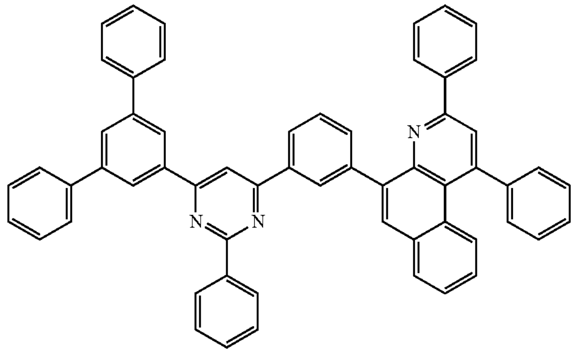
551
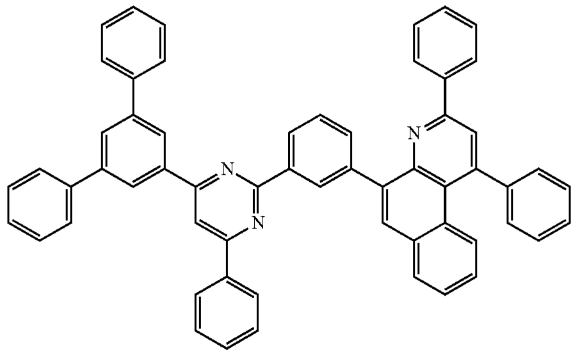

-continued
552
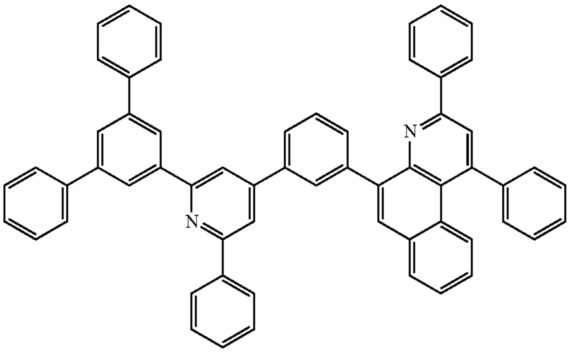
553
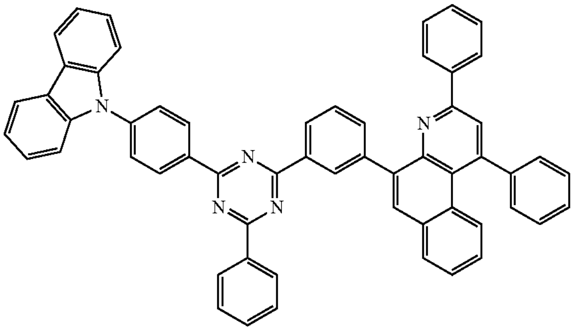
554
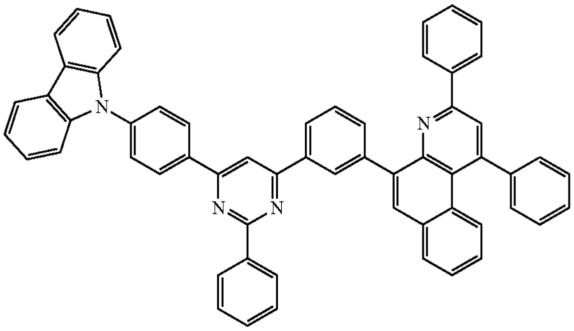
555
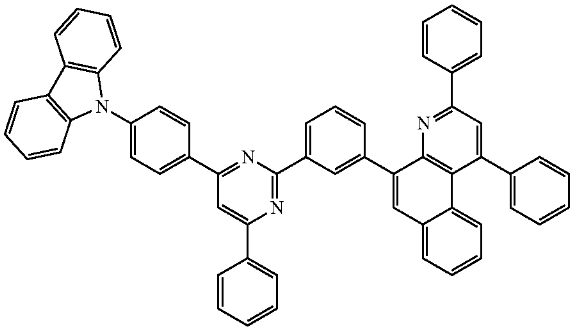
-continued
556
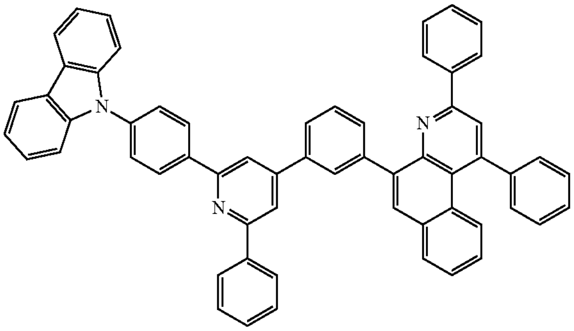
557
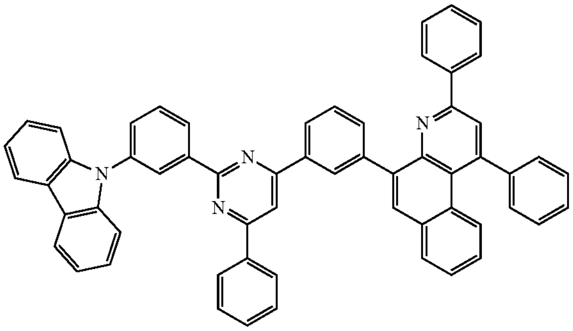
558
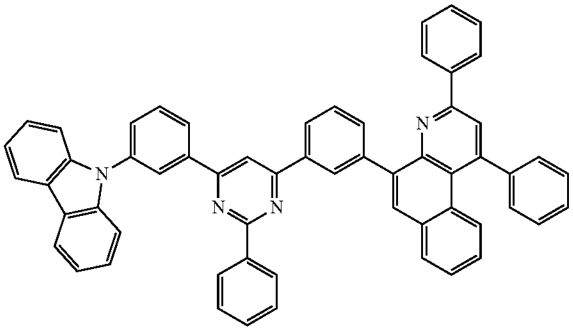
559
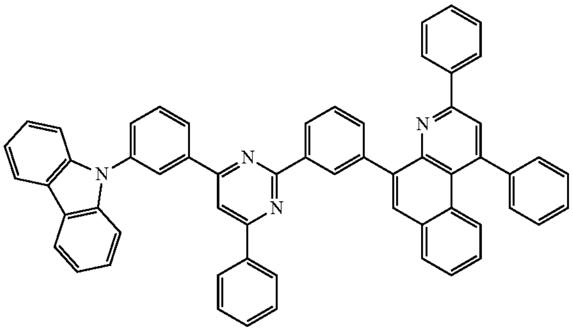

-continued
560
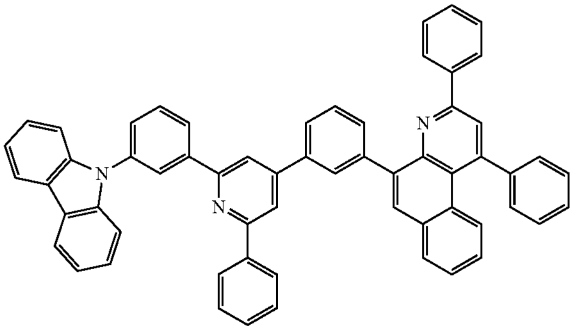
561
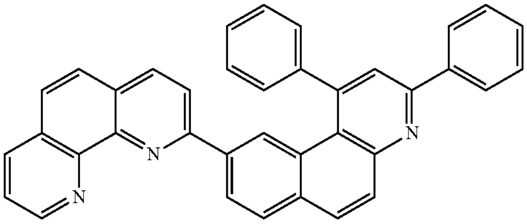
562
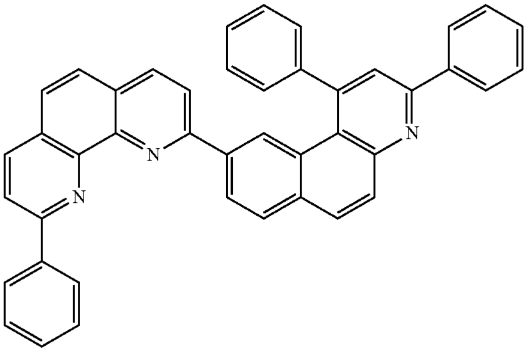
563
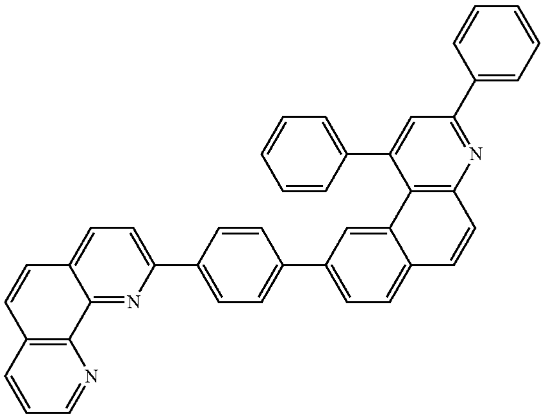
-continued
564
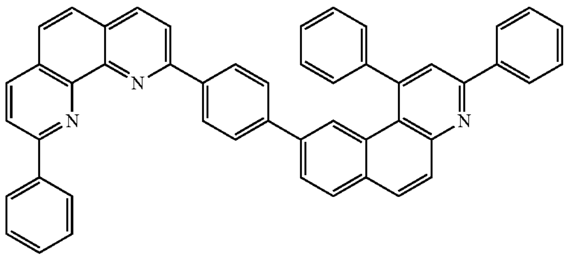
565
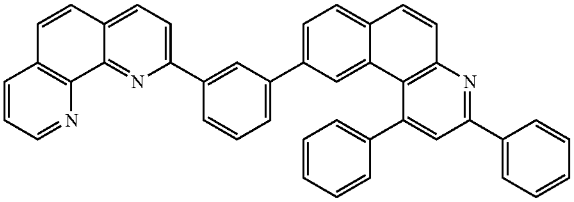
566
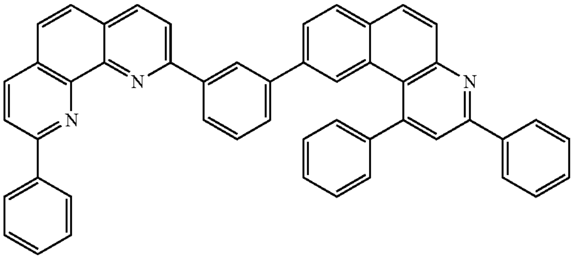
567
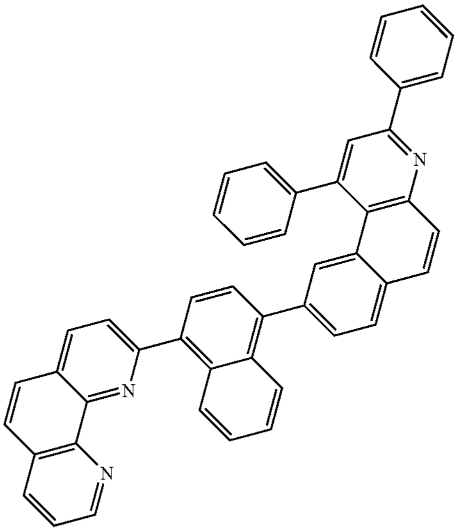

-continued
568
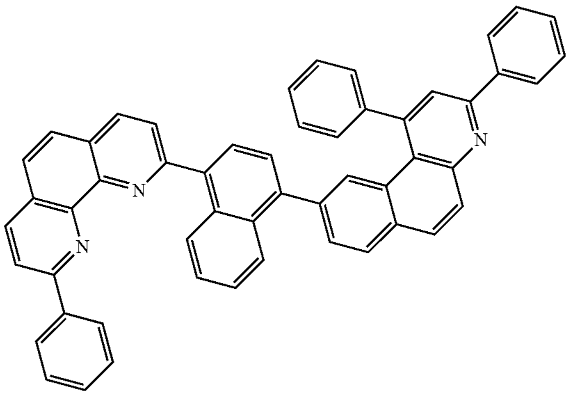
569
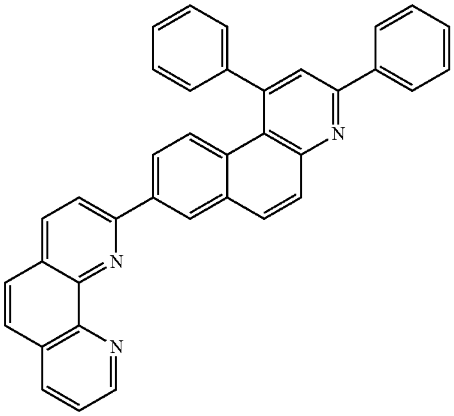
570
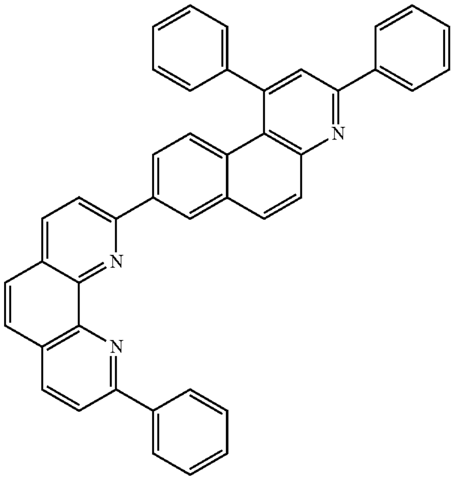
-continued
571
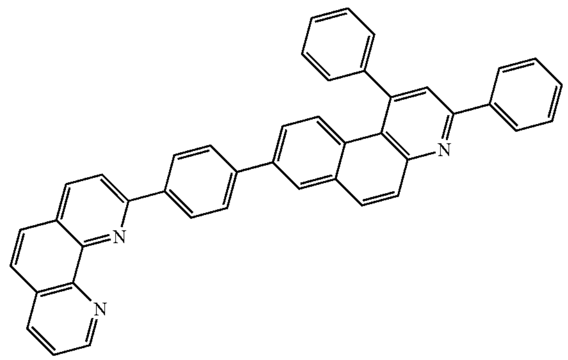
572
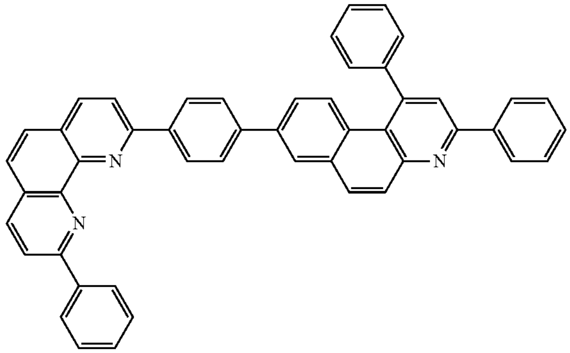
573
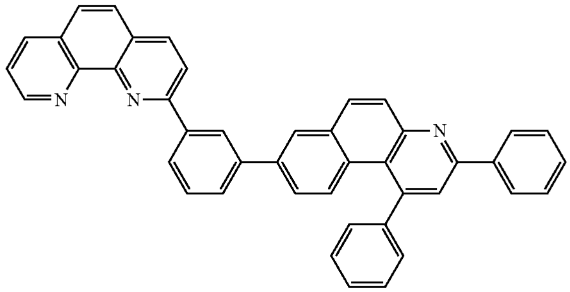
574
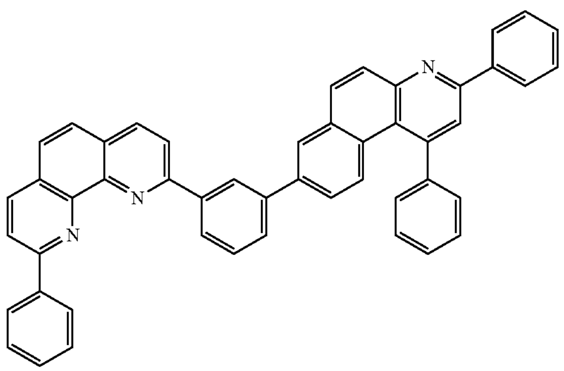

-continued
575
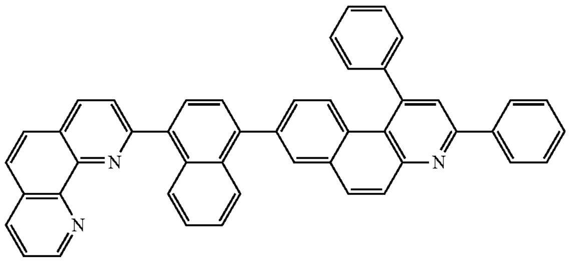
576
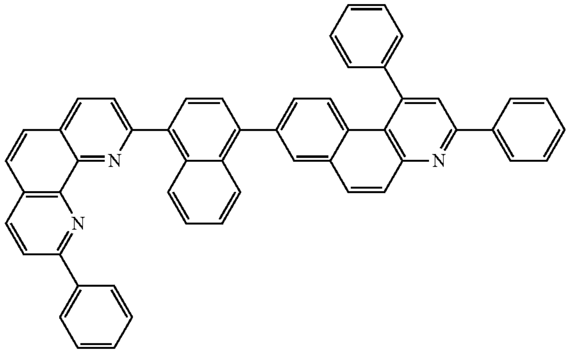
577
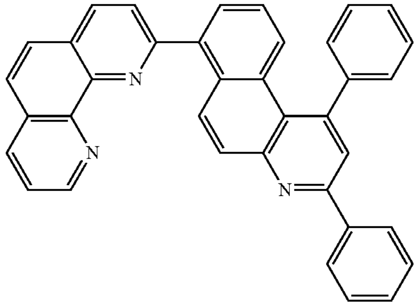
578
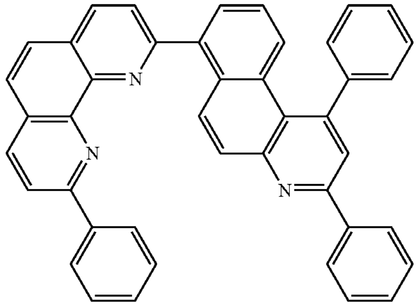
-continued
579
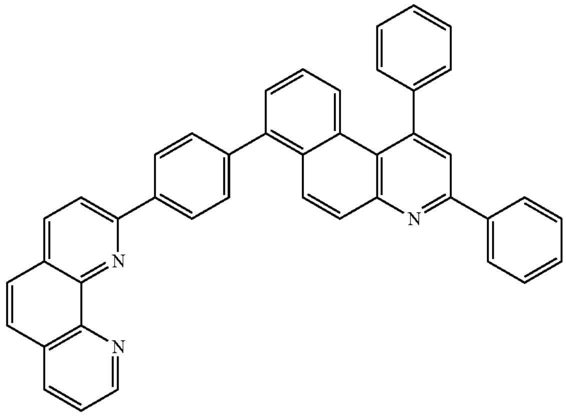
580
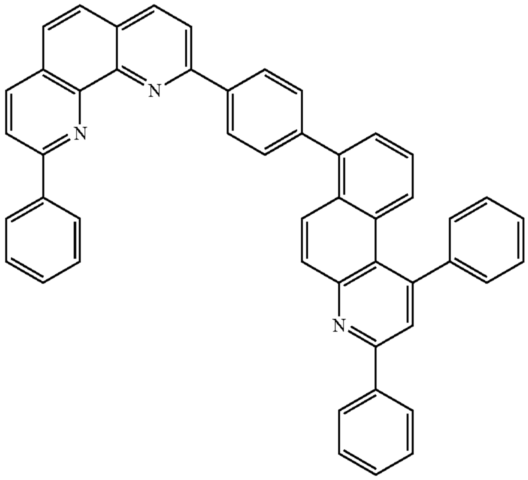
581
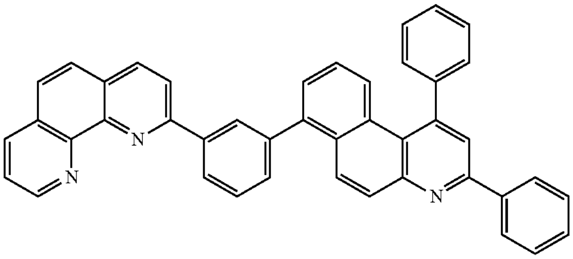
582
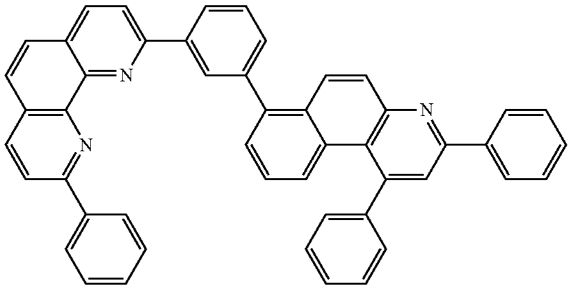

-continued
583
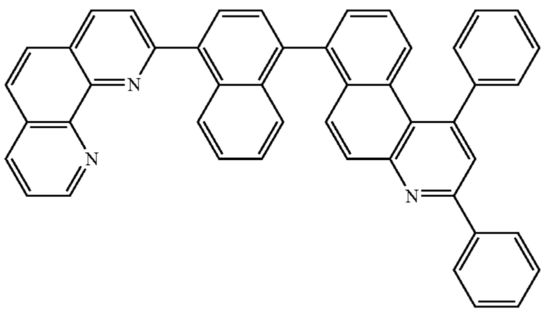
584
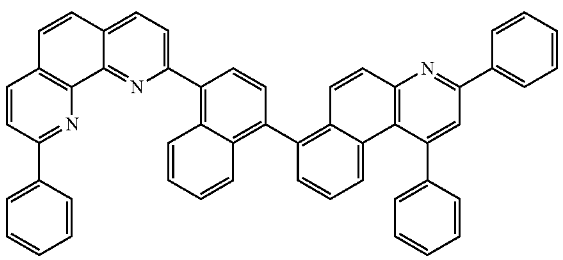
585
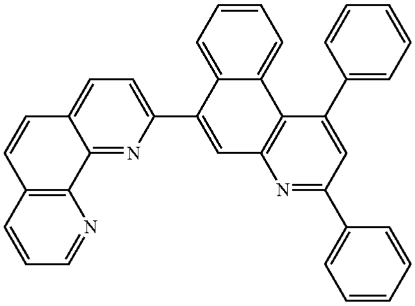
586
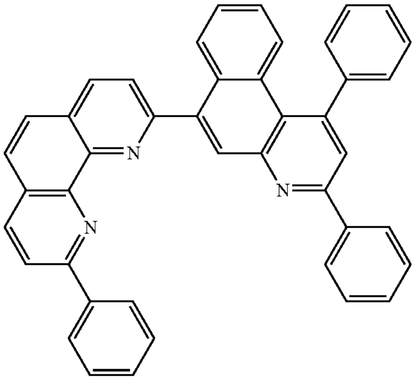
-continued
587
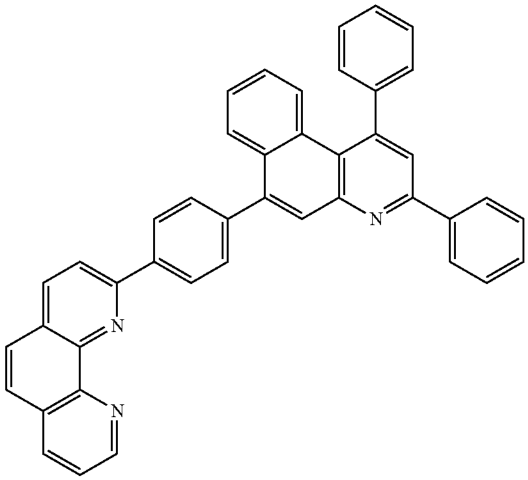
588
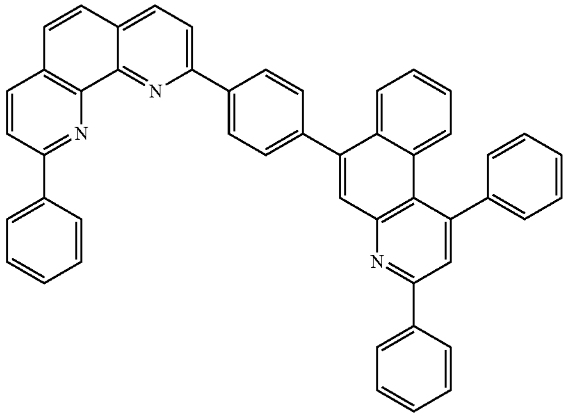
589
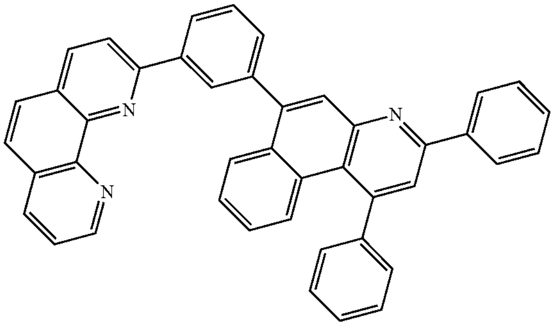
590
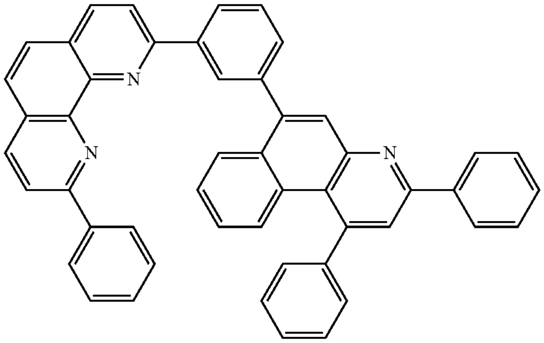

591
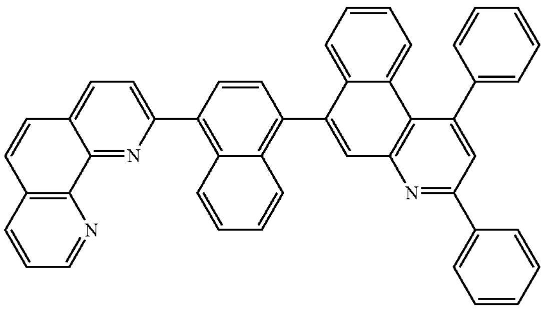
592
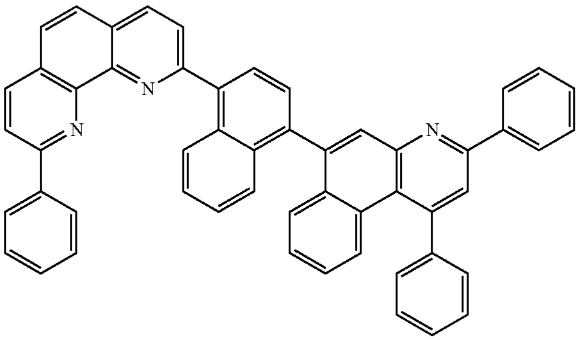
593
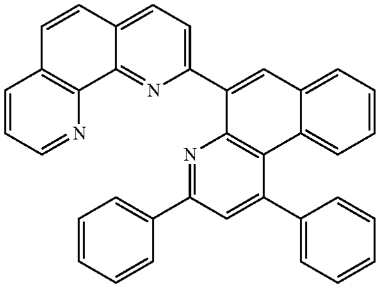
594
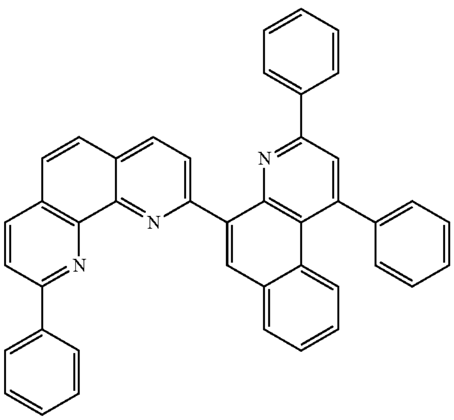
595
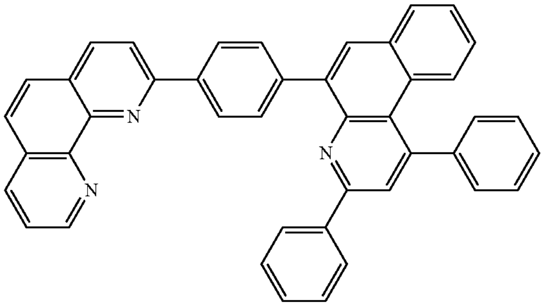
596
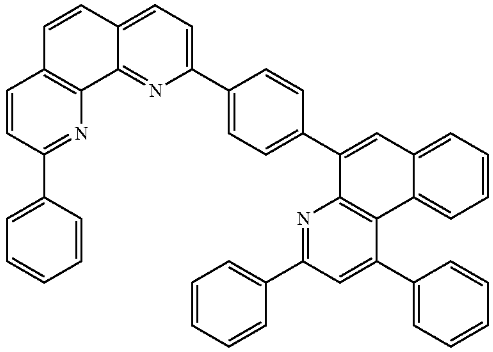
597
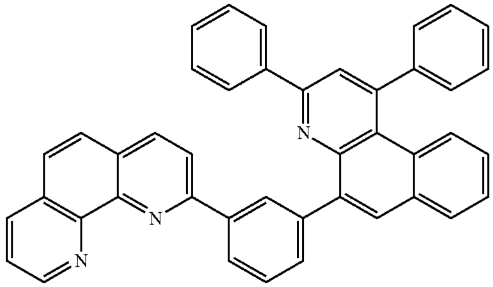
598
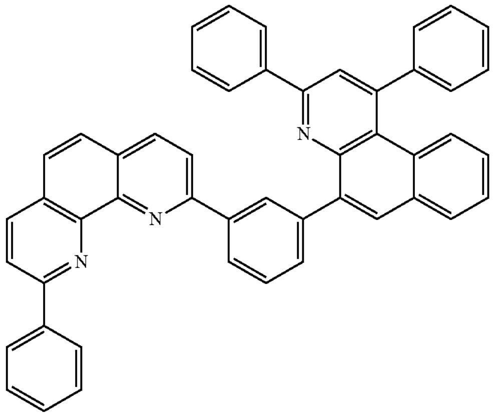

-continued
599
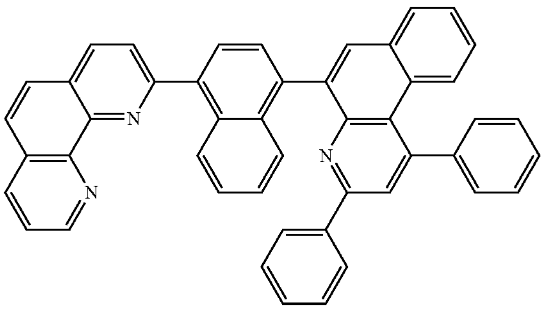
600
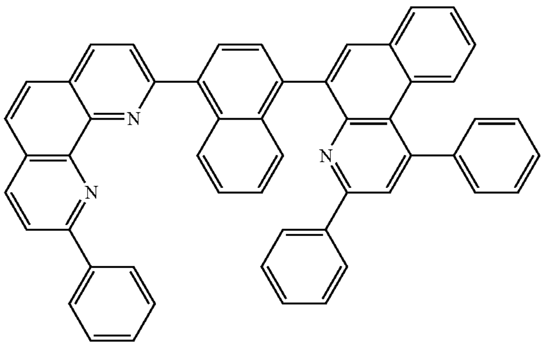
601
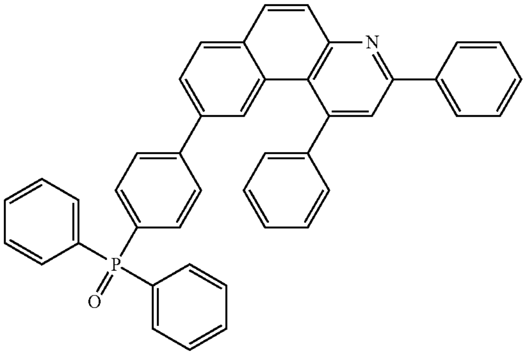
602
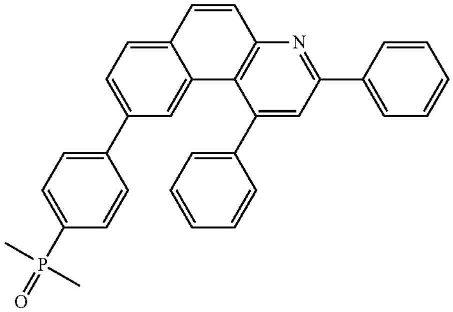
-continued
603
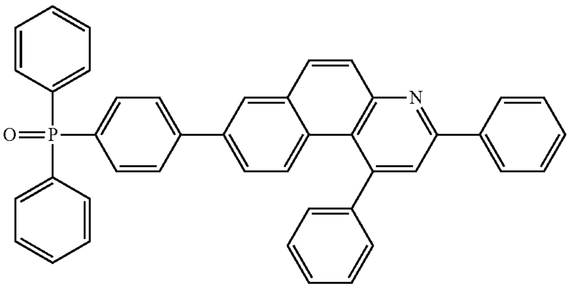
604
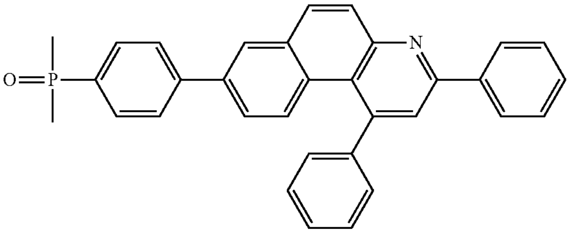
605
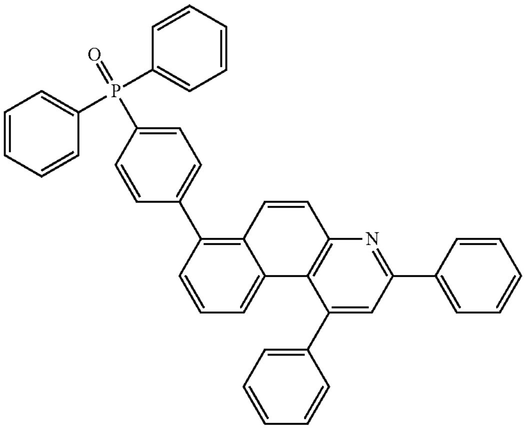
606
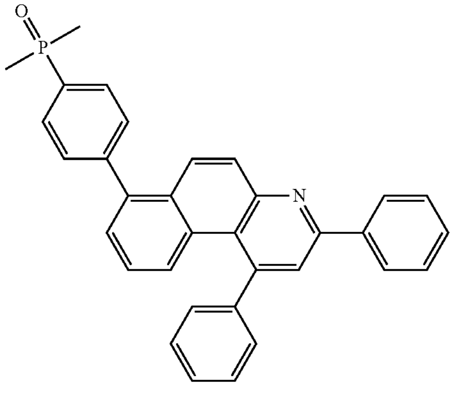

607
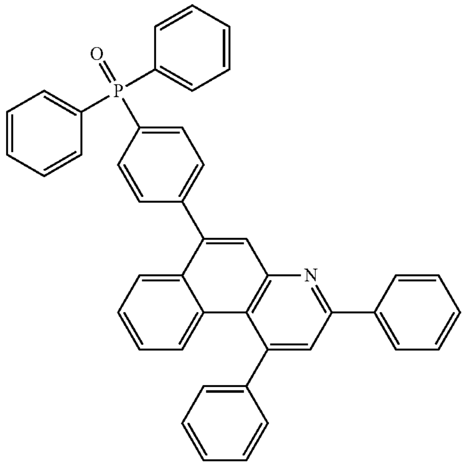
608
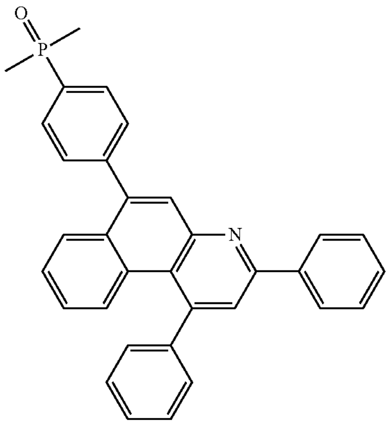
609
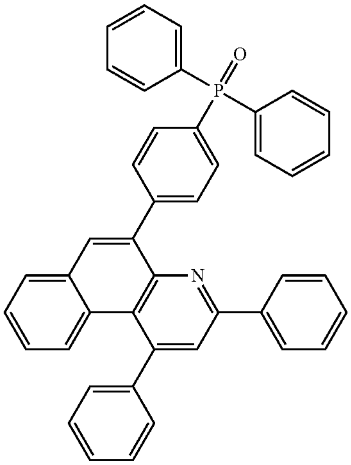
610
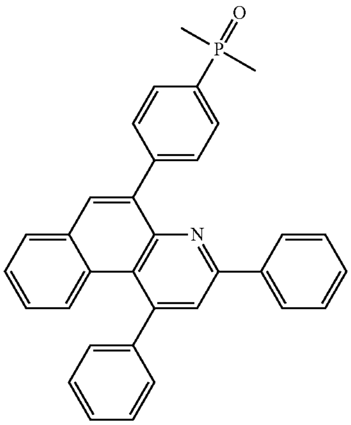
611
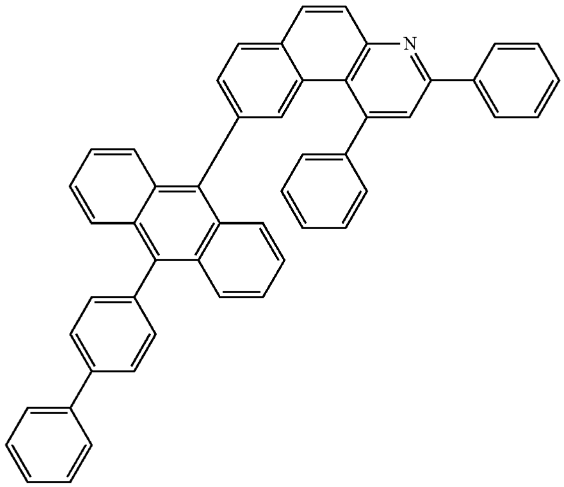
612
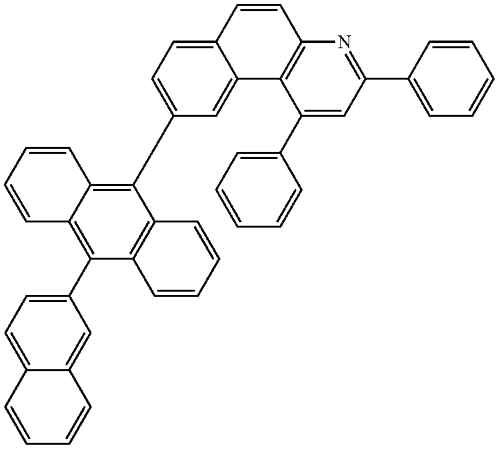
613
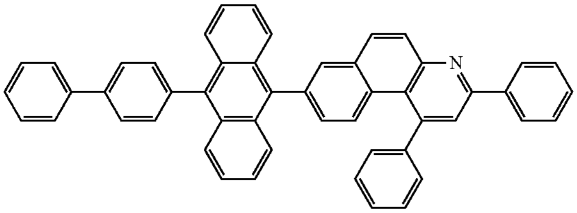

-continued
614
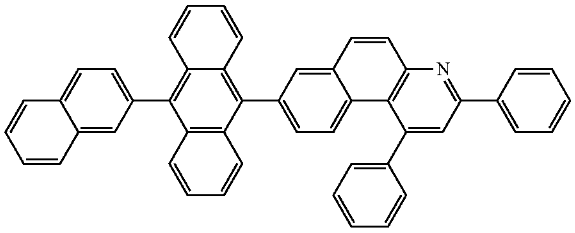
615
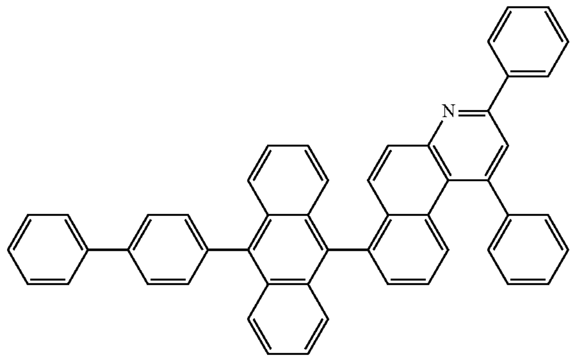
616
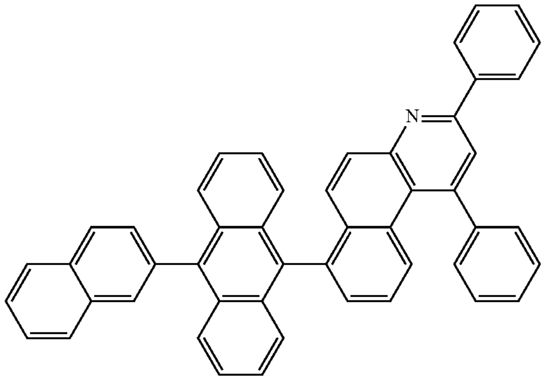
617
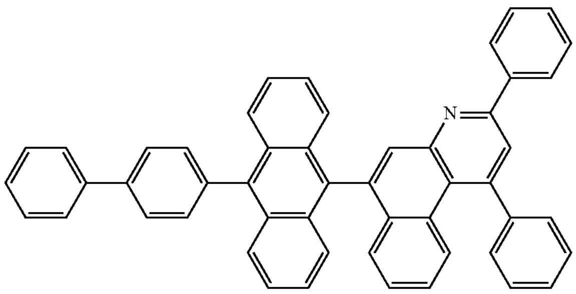
-continued
618
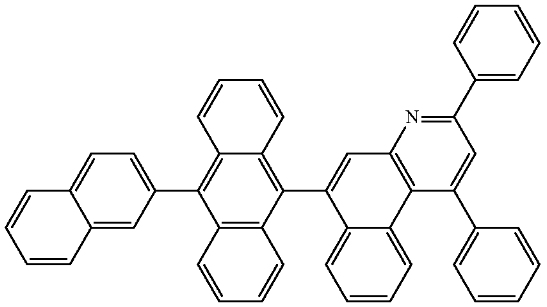
619
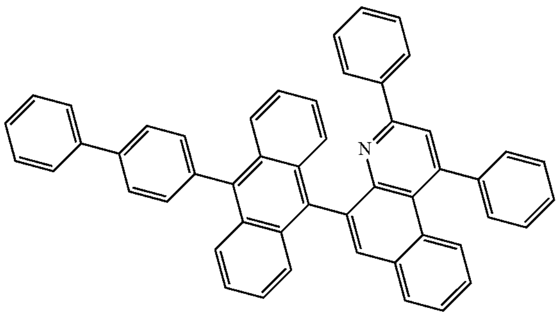
620
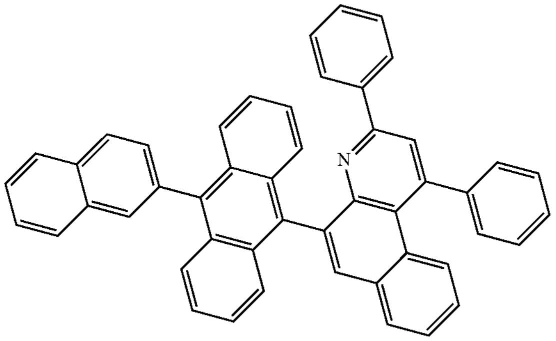
621
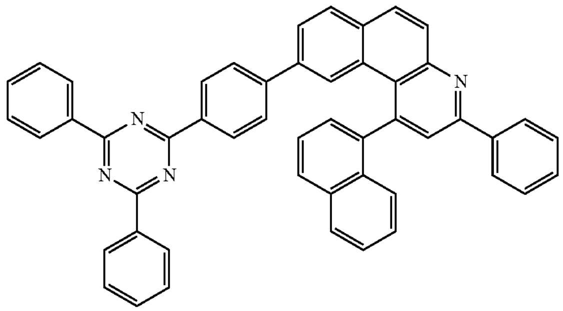

-continued
622
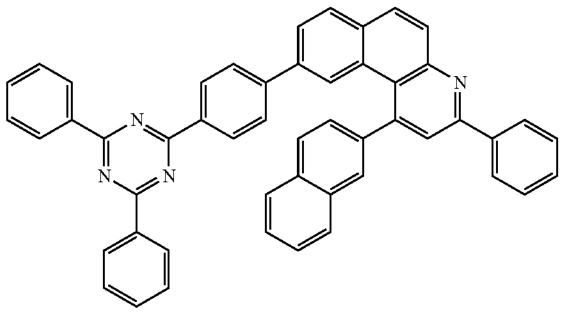
623
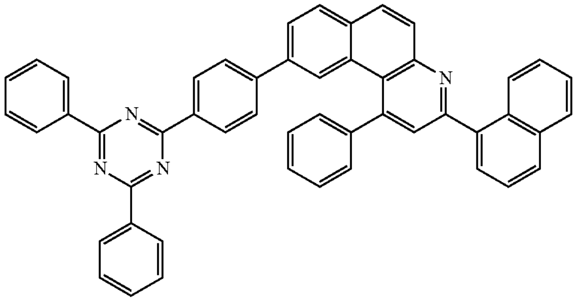
624
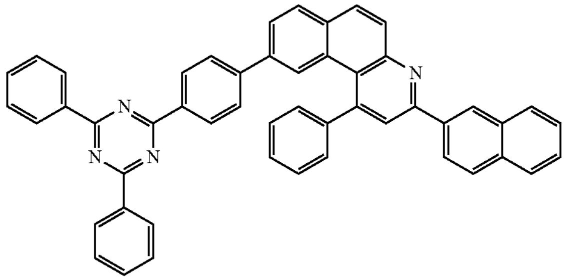
625
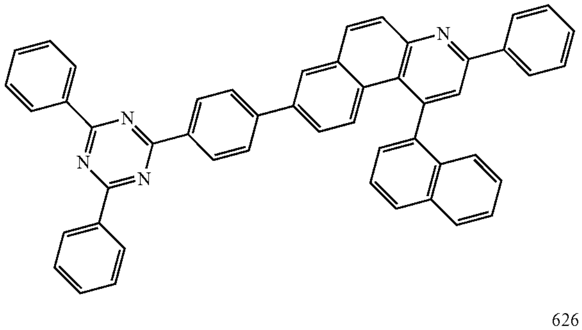
626
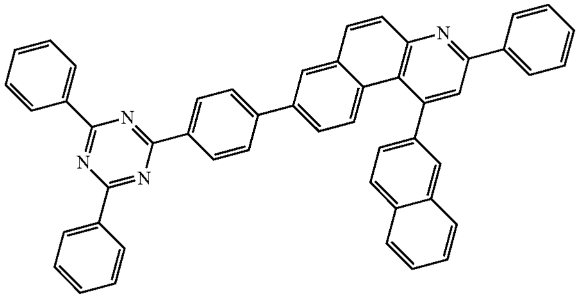
-continued
627
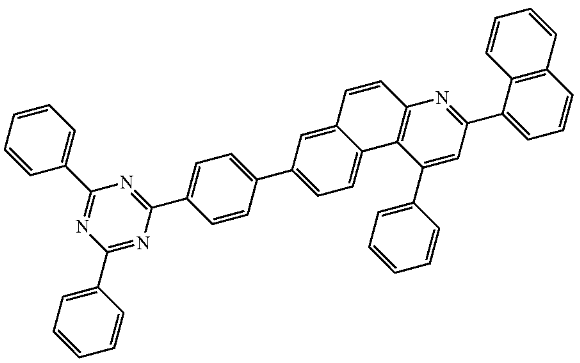
628
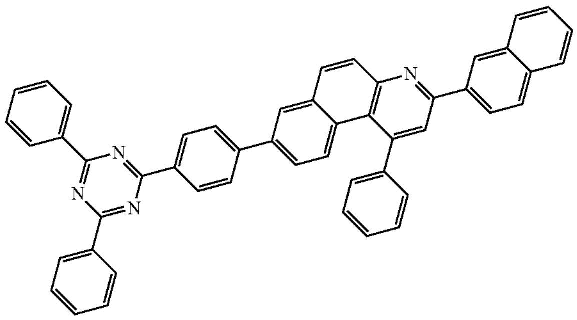
629
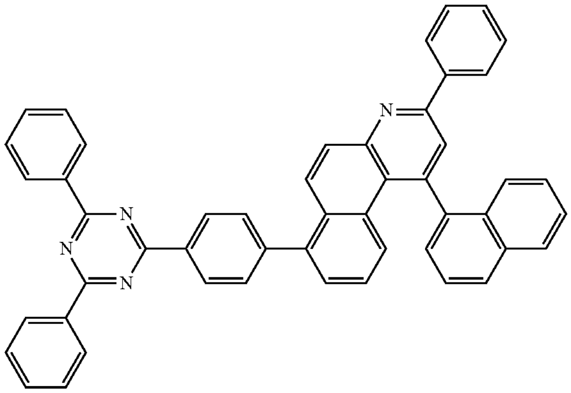
630
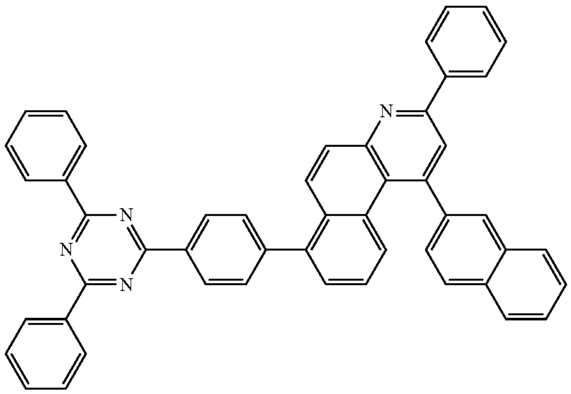

-continued
631
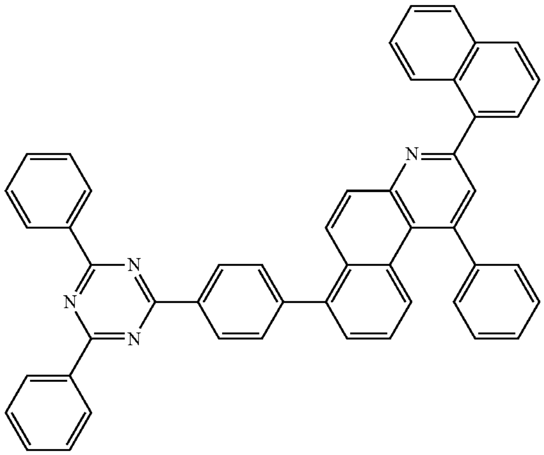
632
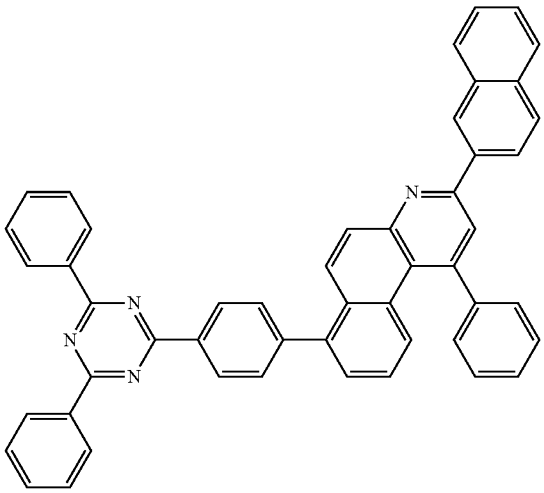
633
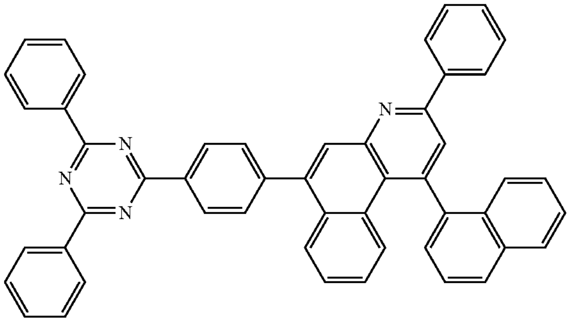
-continued
634
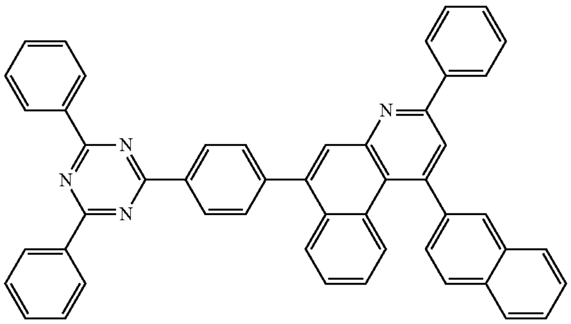
635
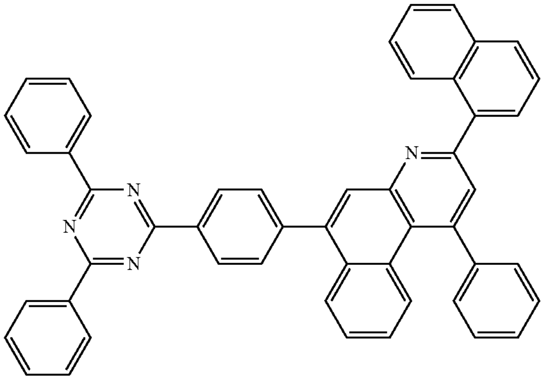
636
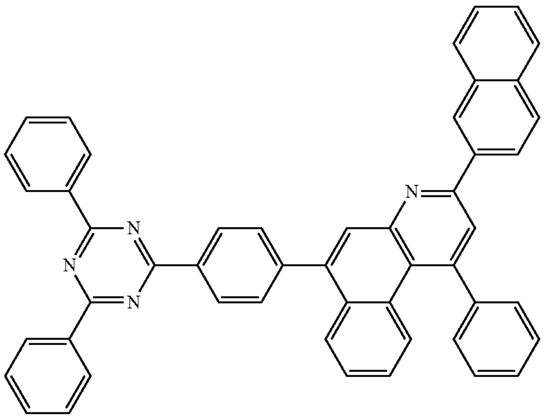

-continued
637
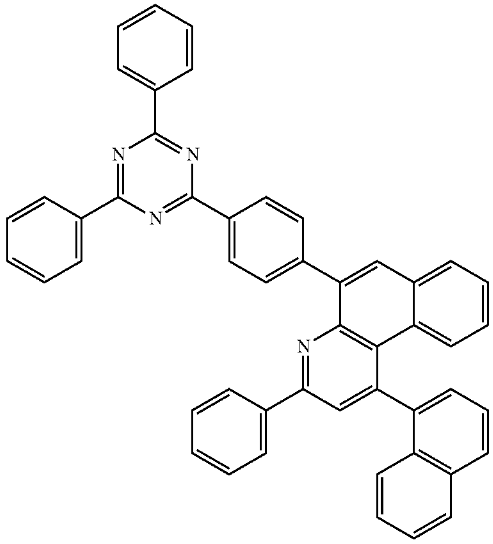
638
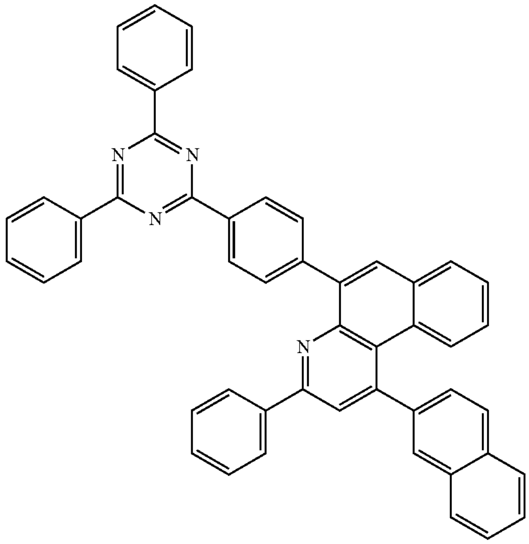
639
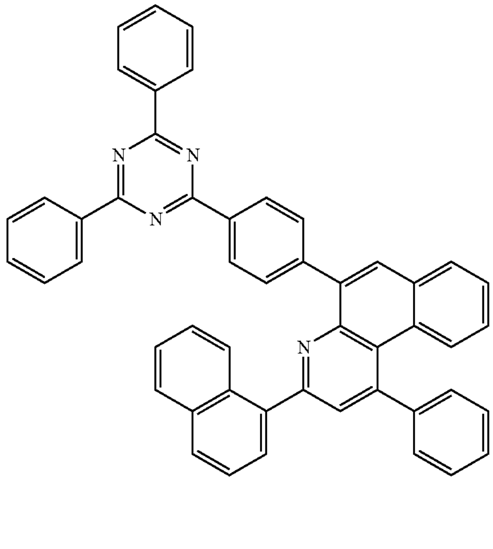
-continued
640
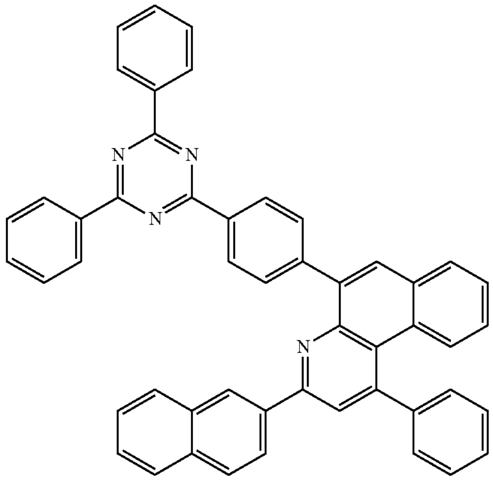
641
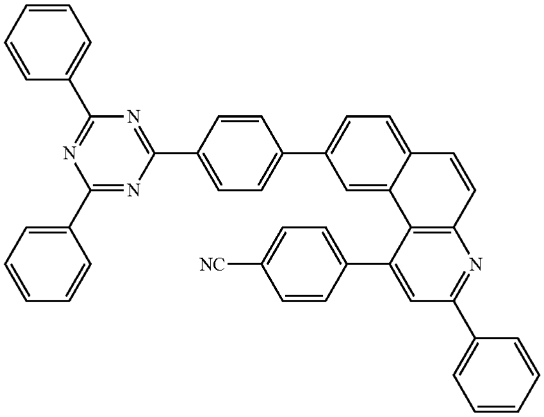
642
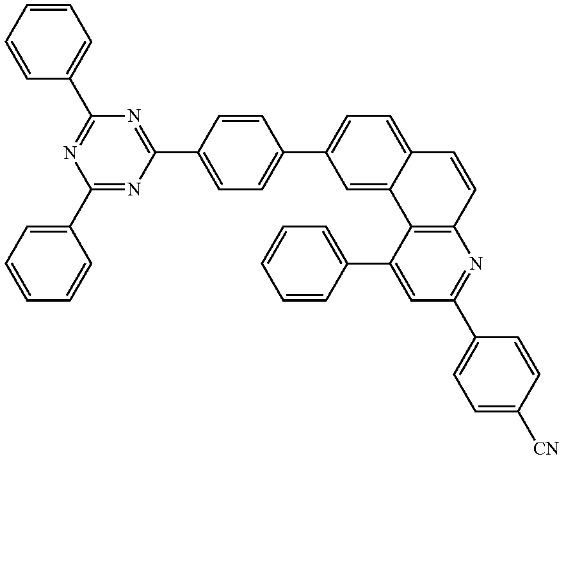

-continued
643
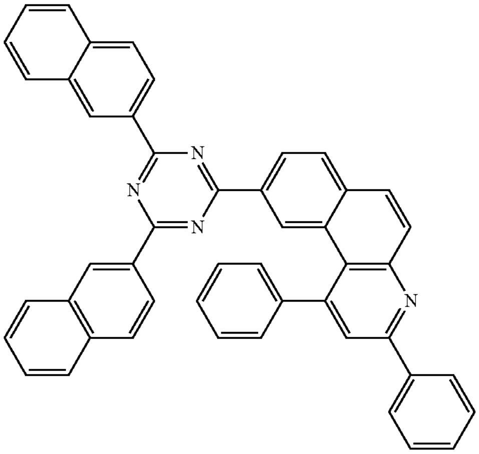
644
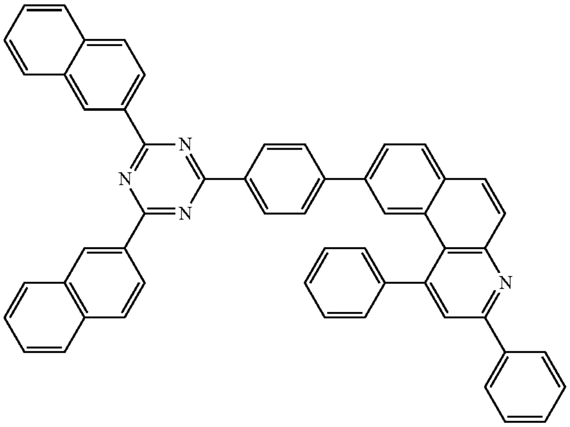
645
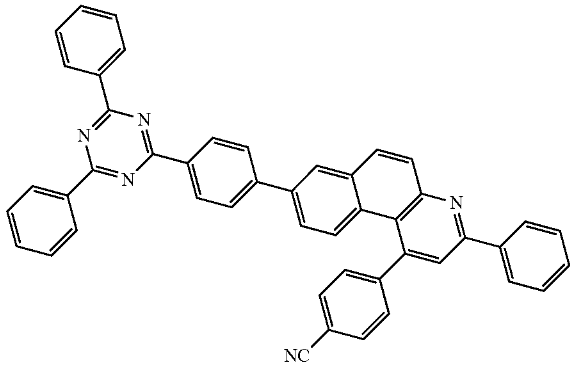
646
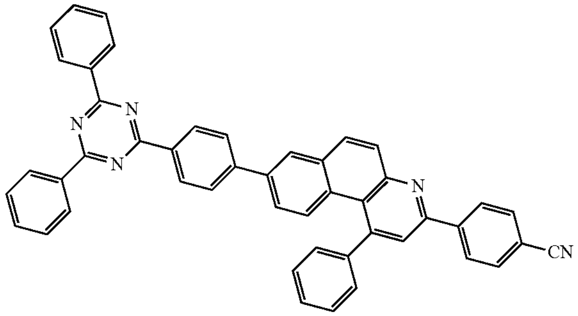
-continued
647
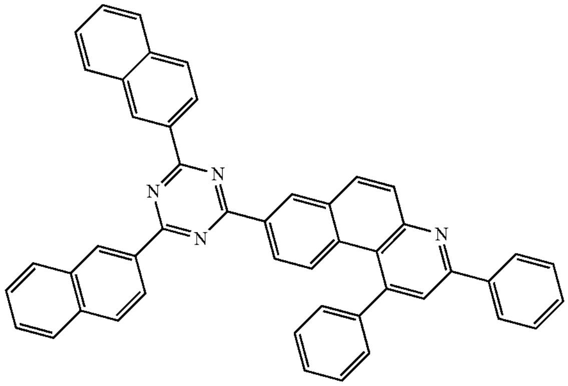
648
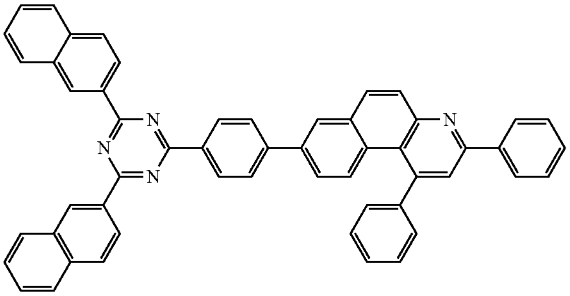
649
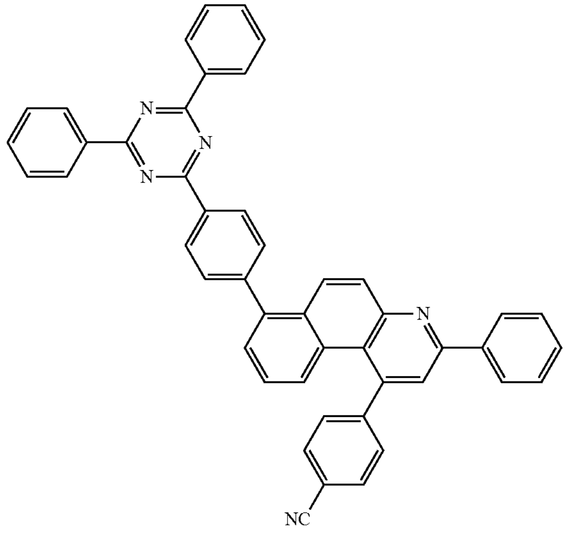

-continued
650
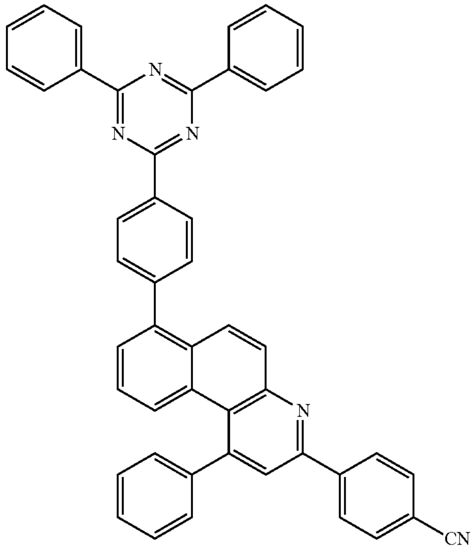
651
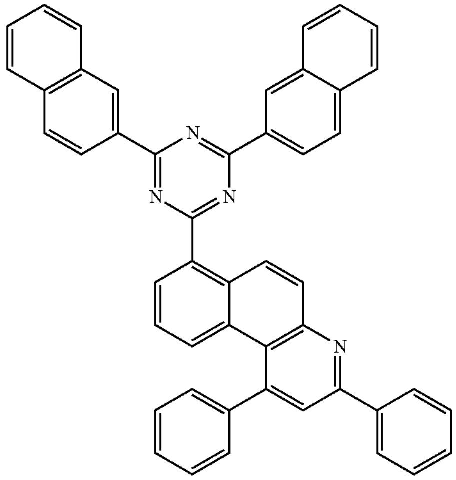
652
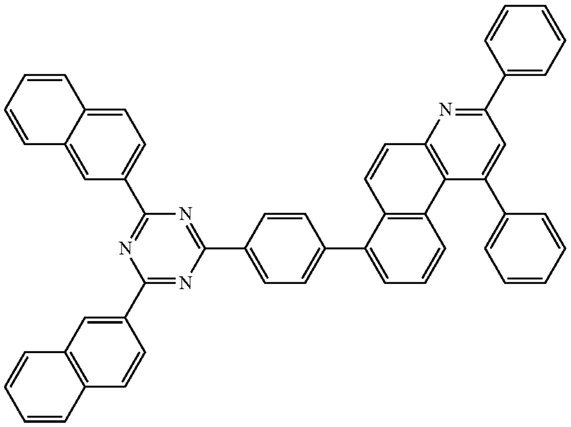
-continued
653
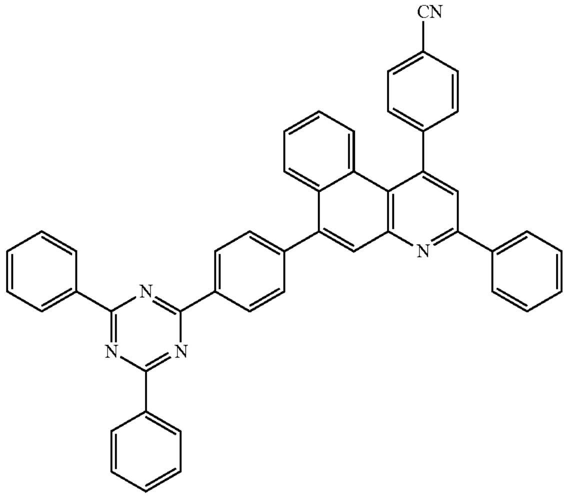
654
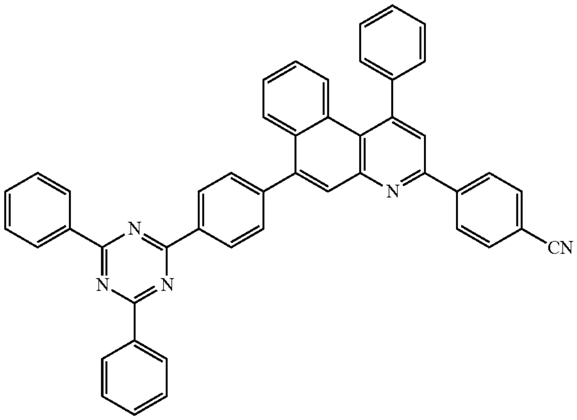
655
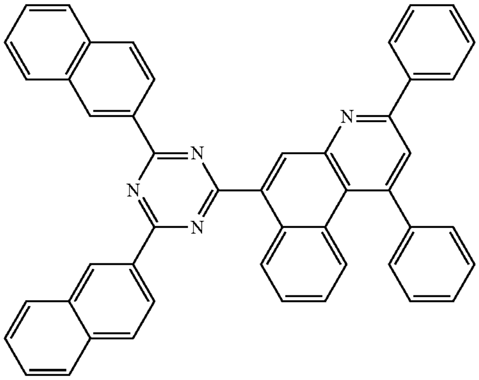

-continued

656

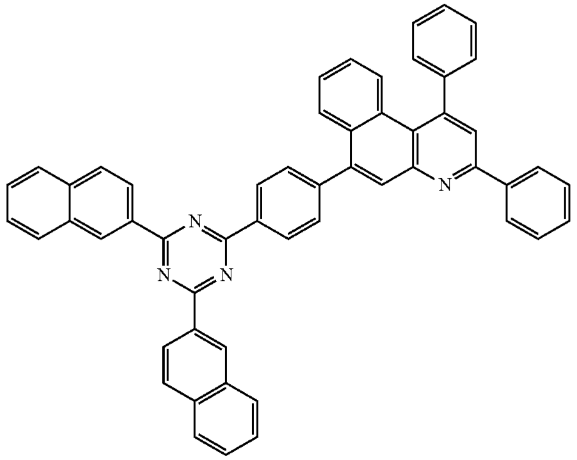

657

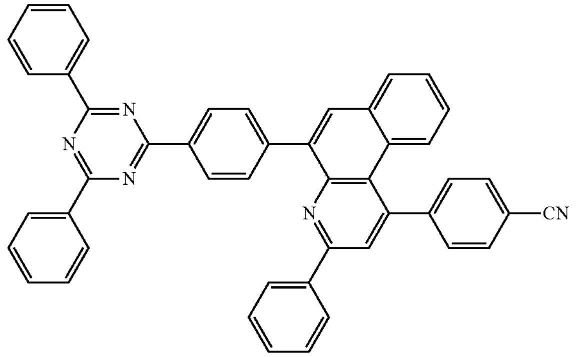

658

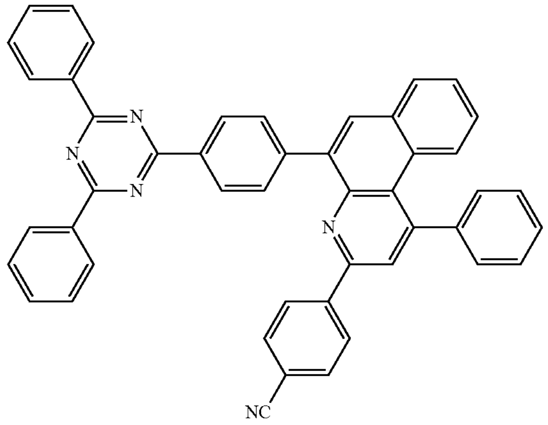

-continued

659

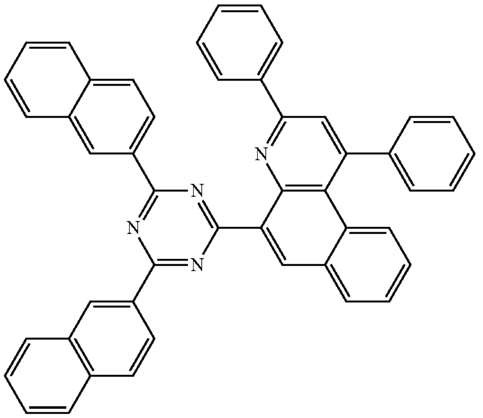

660

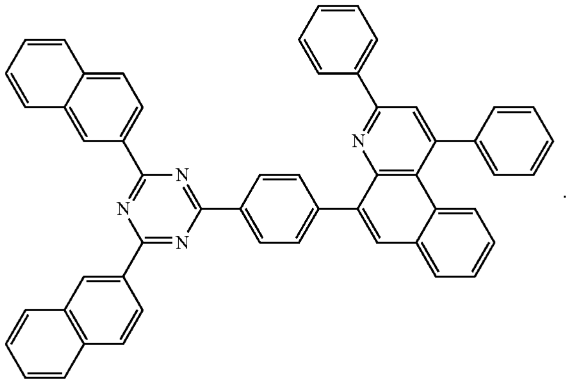

5. An organic light emitting device comprising:

a first electrode;

a second electrode; and one or more organic material layers provided between the first electrode and the second electrode, wherein one or more layers of the organic material layers comprise the heterocyclic compound of claim 1.

6. The organic light emitting device of claim 5, wherein the organic material layer comprises an electron transfer layer, and the electron transfer layer comprises the heterocyclic compound.

7. The organic light emitting device of claim 5, wherein the organic material layer comprises one or more hole blocking layers, and the hole blocking layer comprises the heterocyclic compound.

8. The organic light emitting device of claim 5, comprising:

a first stack provided on the first electrode and comprising a first light emitting layer;

a charge generation layer provided on the first stack;

a second stack provided on the charge generation layer and comprising a second light emitting layer; and the second electrode provided on the second stack.

9. The organic light emitting device of claim 8, wherein the charge generation layer comprises the heterocyclic compound.

* * * * *